US012774281B2

(12) United States Patent
Reynolds et al.

(10) Patent No.: US 12,774,281 B2
(45) Date of Patent: Oct. 27, 2026

(54) HETEROCYCLIC AMIDES AND THEIR USE FOR MODULATING SPLICING

(71) Applicant: REMIX THERAPEUTICS INC., Cambridge, MA (US)

(72) Inventors: Dominic Reynolds, Stoneham, MA (US); Michael W. Seiler, Belmont, MA (US); Anant A. Agrawal, Waltham, MA (US); Frederic Vaillancourt, Newton, MA (US); Peter Smith, Arlington, MA (US)

(73) Assignee: REMIX THERAPEUTICS INC., Watertown, MA (US)

( * ) Notice: Subject to any disclaimer, the term of this patent is extended or adjusted under 35 U.S.C. 154(b) by 928 days.

(21) Appl. No.: 17/802,719

(22) PCT Filed: Feb. 28, 2021

(86) PCT No.: PCT/US2021/020154
§ 371 (c)(1),
(2) Date: Aug. 26, 2022

(87) PCT Pub. No.: WO2021/174165
PCT Pub. Date: Sep. 2, 2021

(65) Prior Publication Data
US 2023/0365566 A1 Nov. 16, 2023

Related U.S. Application Data

(60) Provisional application No. 63/126,492, filed on Dec. 16, 2020, provisional application No. 63/072,790, filed on Aug. 31, 2020, provisional application No. 63/040,484, filed on Jun. 17, 2020, provisional application No. 63/007,333, filed on Apr. 8, 2020,
(Continued)

(51) Int. Cl.

| | |
|---|---|
| *C07D 487/04* | (2006.01) |
| *A61K 31/496* | (2006.01) |
| *A61K 31/498* | (2006.01) |
| *A61K 31/502* | (2006.01) |
| *A61K 31/5025* | (2006.01) |
| *A61K 31/53* | (2006.01) |
| *A61K 31/55* | (2006.01) |
| *A61P 5/00* | (2006.01) |
| *A61P 9/00* | (2006.01) |
| *A61P 11/00* | (2006.01) |
| *A61P 25/00* | (2006.01) |
| *A61P 25/28* | (2006.01) |
| *A61P 31/00* | (2006.01) |
| *A61P 35/00* | (2006.01) |
| *A61P 37/00* | (2006.01) |
| *C07D 401/14* | (2006.01) |
| *C07D 403/04* | (2006.01) |
| *C07D 403/12* | (2006.01) |
| *C07D 405/12* | (2006.01) |
| *C07D 413/12* | (2006.01) |
| *C07D 417/12* | (2006.01) |
| *C07D 471/04* | (2006.01) |
| *C07D 471/08* | (2006.01) |
| *C07D 487/10* | (2006.01) |
| *C07D 519/00* | (2006.01) |

(52) U.S. Cl.
CPC .......... *C07D 487/04* (2013.01); *A61K 31/496* (2013.01); *A61K 31/498* (2013.01); *A61K 31/502* (2013.01); *A61K 31/5025* (2013.01); *A61K 31/53* (2013.01); *A61K 31/55* (2013.01); *C07D 401/14* (2013.01); *C07D 403/04* (2013.01); *C07D 403/12* (2013.01); *C07D 405/12* (2013.01); *C07D 413/12* (2013.01); *C07D 417/12* (2013.01); *C07D 471/04* (2013.01); *C07D 519/00* (2013.01)

(58) Field of Classification Search
None
See application file for complete search history.

(56) References Cited

U.S. PATENT DOCUMENTS 8,772,505 B2 7/2014 Chen et al.
2007/0073054 A1 3/2007 Kimura et al.
(Continued)

FOREIGN PATENT DOCUMENTS

CA 3105174 A1 1/2020
CN 102020643 A 4/2011
(Continued)

OTHER PUBLICATIONS

STN, ACS CAS 627894-60-4 Registry, Dec. 19, 2003 (Year: 2003).*
(Continued)

*Primary Examiner* — Kortney L. Klinkel
*Assistant Examiner* — Alison Azar Hastings
(74) *Attorney, Agent, or Firm* — Lando & Anastasi, LLP

(57) ABSTRACT

The present disclosure features compounds of formula (I-a) and related compositions that, inter alia, modulate nucleic acid splicing e.g., splicing of a pre-mRNA, as well as methods of use thereof.

(I-a)

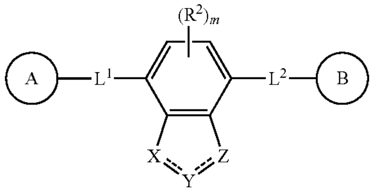

22 Claims, No Drawings

Specification includes a Sequence Listing.

Related U.S. Application Data provisional application No. 62/983,541, filed on Feb. 28, 2020.

(56) References Cited

U.S. PATENT DOCUMENTS

| | | | |
|---|---|---|---|
| 2007/0254894 A1 | 11/2007 | Kane et al. | |
| 2010/0105667 A1 | 4/2010 | Furet et al. | |
| 2011/0288089 A1 | 11/2011 | Renold et al. | |
| 2013/0164258 A1 | 6/2013 | Chen et al. | |
| 2014/0256706 A1 | 9/2014 | Wang et al. | |
| 2018/0118748 A1 | 5/2018 | Slaugenhaupt et al. | |
| 2019/0119236 A1 | 4/2019 | Pandey et al. | |
| 2019/0233440 A1 | 8/2019 | Planken et al. | |

FOREIGN PATENT DOCUMENTS

| | | | | |
|---|---|---|---|---|
| CN | 102036963 A | 4/2011 | | |
| CN | 102958930 A | 3/2013 | | |
| CN | 105377851 A | 3/2016 | | |
| CN | 104341403 B | 6/2016 | | |
| CN | 106220644 A | 12/2016 | | |
| CN | 109180690 A | 1/2019 | | |
| EP | 2481739 A1 | 8/2012 | | |
| EP | 3287463 A1 * | 2/2018 | | A61K 31/517 |
| EP | 3476848 A1 | 5/2019 | | |
| JP | 2012-028440 A | 2/2012 | | |
| KR | 2014-0125061 A | 10/2014 | | |
| WO | 2008/003958 A2 | 1/2008 | | |
| WO | 2008/019124 A1 | 2/2008 | | |
| WO | 2008/040951 A1 | 4/2008 | | |
| WO | 2009/108838 A1 | 9/2009 | | |
| WO | 2009/133136 A1 | 11/2009 | | |
| WO | 2009/141386 A1 | 11/2009 | | |
| WO | 2011/148922 A1 | 12/2011 | | |
| WO | 2012/000595 A1 | 1/2012 | | |
| WO | 2013/169622 A1 | 11/2013 | | |
| WO | 2014/085210 A1 | 6/2014 | | |
| WO | 2014/209841 A2 | 12/2014 | | |
| WO | 2016/004254 A1 | 1/2016 | | |
| WO | 2016/049524 A1 | 3/2016 | | |
| WO | 2016/061043 A1 | 4/2016 | | |
| WO | 2016/169504 A1 | 10/2016 | | |
| WO | 2016/196386 A1 | 12/2016 | | |
| WO | 2017/147328 A1 | 8/2017 | | |
| WO | 2018/140512 A1 | 8/2018 | | |
| WO | 2018/226622 A1 | 12/2018 | | |
| WO | 2019/028440 A1 | 2/2019 | | |
| WO | 2019/079649 A1 | 4/2019 | | |
| WO | 2019/232244 A2 | 12/2019 | | |
| WO | 2020/005873 A1 | 1/2020 | | |
| WO | WO-2020018610 A1 * | 1/2020 | | C07D 413/04 |
| WO | 2020/123395 A1 | 6/2020 | | |
| WO | 2020/132459 A1 | 6/2020 | | |
| WO | 2020/216190 A1 | 10/2020 | | |
| WO | 2021/007378 A1 | 1/2021 | | |

OTHER PUBLICATIONS

WO2020004521A1_ English (Year: 2020).*

Pais et al., "Preparation and pH-switching of fluorescent borylated arylisoquinolines for multilevel molecular logic" The Journal of Organic Chemistry, 2013, vol. 78, No. 16, pp. 7949-7961.

Lu et al., "Arylazolyl(azinyl)thioacetanilides. Part 20: Discovery of novel purinylthioacetanilides derivatives as potent HIV-1 NNRTIs via a structure-based bioisosterism approach" Bioorganic & Medicinal Chemistry, 2016, vol. 24, No. 18, pp. 4424-4433.

Havens et al., "Targeting RNA splicing for disease therapy" Wiley Interdisciplinary Reviews: RNA, 2013, vol. 4, No. 3, pp. 247-266.

International search report and written opinion for application No. PCT/US2021/020153 mailed Jul. 28, 2021.

Pawellek et al., "Identification of small molecule inhibitors of pre-mRNA splicing" Journal of Biological Chemistry, 2014, vol. 289, No. 50, pp. 34683-34698.

International search report and written opinion for application No. PCT/US2021/020154 mailed Jul. 7, 2021.

Reed et al., "Discovery of VU6027459: A first-in-class selective and CNS penetrant mGlu7 positive allosteric modulator tool compound" ACS Medicinal Chemistry Letters, 2020, vol. 11, No. 9, pp. 1773-1779.

Smits et al., "Ligand based design of novel histamine H4 receptor antagonists; fragment optimization and analysis of binding kinetics" Bioorganic & Medicinal Chemistry Letters, 2011, vol. 22, No. 1, pp. 461-467.

Schoffmann et al., "Efficient modulation of g-Aminobutyric acid type A receptors by piperine derivatives" Journal of Medicinal Chemistry, 2014, vol. 57, No. 13, pp. 5602-5619.

International search report and written opinion for application No. PCT/US2021/020152 mailed Jun. 25, 2021.

Srivastava et al., "Syntheses and antifilarial profile of 5-Amino and 5,8-Diamino-Isoquinoline derivatives: A new class of antifilarial agents" Bioorganic & Medicinal Chemistry Letters, 1996, vol. 6, No. 22, pp. 2623-2628.

Pais et al., "Preparation and pH-switching of fluorescent borylated arylisoquinolines for multilevel molecular logic" Journal of Organic Chemistry, 2013, vol. 78, No. 16, pp. 7949-7961.

Lu et al., "Arylazolyl(azinyl)thioacetanilides, Part 20: Discovery of novel purinylthioacetanilides derivatives as potent HIV-1 NNRTIs via a structure-based bioisoterism approach" Bioorganic & Medicinal Chemistry, 2016, vol. 24, No. 18, pp. 4424-4433.

Database accession No. 2307382-78-9, "quinoline derivatives", Database Registry [Online] Chemical Abstract Service, Columbus, Ohio, US; May 12, 2019.

Pawellek et al., "Identification of small molecule inhibitors of Pre-mRNA splicing" The Journal of Biological Chemistry, 2014, vol. 289, No. 50, pp. 34683-34698.

Campagne et al., "Structual basis of a small molecule targeting RNA for a specific correction" Nature Chemical Biology, Dec. 2019, vol. 15, No. 12, pp. 1191-1198.

Suzuki et al., "Preparation, properties, and X-ray structures of 5,5'-bi(8-aminoquinoxalyl)s: novel Wurster-type electron donors with a heterobiaryl skeleton" Tetrahedron Letters. vol. 45. 2004. pp 329-333.

Barsu et al., "Site-selective C—H bond carbonylation with CO2 and cobalt-catalysis", Catalysis Science & Technology, 2018. pp 5963-5969.

CAS Registry No. 1625630-02-05, entered on Sep. 24, 2014.

CAS Registry No. 1003225-26-0, entered on Feb. 13, 2008.

STN, ACS CAS 627894-60-4 Registry, Dec. 19, 2003.

Pinard et al., "Discovery of a Novel Class of Survival Motor Neuron 2 Splicing Modifiers for the Treatment of Spinal Muscular Atrophy", Journal of Medicinal Chemistry, 2017, vol. 60, pp. 4444-4457.

* cited by examiner

HETEROCYCLIC AMIDES AND THEIR USE FOR MODULATING SPLICING

CLAIM OF PRIORITY

This application is a U.S. National Phase Application under 35 U.S.C. § 371 of International Application No. PCT/US2021/020154, filed Feb. 28, 2021, which claims priority to U.S. Application No. 62/983,541, filed Feb. 28, 2020; U.S. Application No. 63/007,333, filed Apr. 8, 2020; U.S. Application No. 63/040,484, filed Jun. 17, 2020; U.S. Application No. 63/072,790, filed Aug. 31, 2020; and U.S. Application No. 63/126,492, filed Dec. 16, 2020. The disclosure of each of the foregoing applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 17, 2021, is named R2103-7014WO-_SL.txt and is 1,386,978 bytes in size.

BACKGROUND

Alternative splicing is a major source of protein diversity in higher eukaryotes and is frequently regulated in a tissue-specific or development stage-specific manner. Disease associated alternative splicing patterns in pre-mRNAs are often mapped to changes in splice site signals or sequence motifs and regulatory splicing factors (Faustino and Cooper (2003), *Genes Dev* 17(4):419-37). Current therapies to modulate RNA expression involve oligonucleotide targeting and gene therapy; however, each of these modalities exhibit unique challenges as currently presented. As such, there is a need for new technologies to modulate RNA expression, including the development of small molecule compounds that target splicing.

SUMMARY

The present disclosure features compounds and related compositions that, inter alia, modulate nucleic acid splicing, e.g., splicing of a pre-mRNA, as well as methods of use thereof. In an embodiment, the compounds described herein are compounds of Formula (I) (e.g., a compound of Formulas (I-a), (I-b), (I-c), (I-d), (I-e), (I-f), or (I-g)) and pharmaceutically acceptable salts, solvates, hydrates, tautomers, or stereoisomers thereof. The present disclosure additionally provides methods of using the compounds of the invention (e.g., compounds of Formulas (I), (I-a), (I-b), (I-c), (I-d), (I-e), (I-f), (I-g), or (I-h), and pharmaceutically acceptable salts, solvates, hydrates, tautomers, stereoisomers thereof), and compositions thereof, e.g., to target, and in embodiments bind or form a complex with, a nucleic acid (e.g., a pre-mRNA or nucleic acid component of a small nuclear ribonucleoprotein (snRNP) or spliceosome), a protein (e.g., a protein component of an snRNP or spliceosome, e.g., a member of the splicing machinery, e.g., one or more of the U1, U2, U4, U5, U6, U11, U12, U4atac, U6atac snRNPs), or a combination thereof. In another aspect, the compounds described herein may be used to alter the composition or structure of a nucleic acid (e.g., a pre-mRNA or mRNA (e.g., a pre-mRNA and the mRNA which arises from the pre-mRNA), e.g., by increasing or decreasing splicing at a splice site. In some embodiments, increasing or decreasing splicing results in modulating the level of a gene product (e.g., an RNA or protein) produced.

In another aspect, the compounds described herein may be used for the prevention and/or treatment of a disease, disorder, or condition, e.g., a disease, disorder or condition associated with splicing, e.g., alternative splicing. In some embodiments, the compounds described herein (e.g., compounds of Formulas (I), (I-a), (I-b), (I-c), (I-d), (I-e), (I-f), (I-g), or (I-h), and pharmaceutically acceptable salts, solvates, hydrates, tautomers, stereoisomers thereof) and compositions thereof are used for the prevention and/or treatment of a proliferative disease, disorder, or condition (e.g., a disease, disorder, or condition characterized by unwanted cell proliferation, e.g., a cancer or a benign neoplasm) in a subject. In some embodiments, the compounds described herein (e.g., compounds of Formulas (I), (I-a), (I-b), (I-c), (I-d), (I-e), (I-f), (I-g), or (I-h), and pharmaceutically acceptable salts, solvates, hydrates, tautomers, stereoisomers thereof) and compositions thereof are used for the prevention and/or treatment of a non-proliferative disease, disorder, or condition. In some embodiments, the compounds described herein (e.g., compounds of Formulas (I), (I-a), (I-b), (I-c), (I-d), (I-e), (I-f), (I-g), or (I-h), and pharmaceutically acceptable salts, solvates, hydrates, tautomers, stereoisomers thereof) and compositions thereof are used for the prevention and/or treatment of a neurological disease or disorder, an autoimmune disease or disorder, immunodeficiency disease or disorder, a lysosomal storage disease or disorder, a cardiovascular disease or disorder, a metabolic disease or disorder, a respiratory disease or disorder, a renal disease or disorder, or an infectious disease in a subject.

In another aspect, the present disclosure features a compound of Formula (I-a):

(I-a)

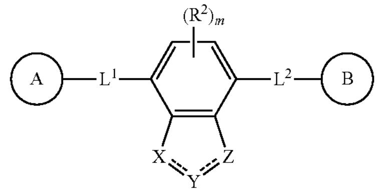

or a pharmaceutically acceptable salt, solvate, hydrate, tautomer, or stereoisomer thereof, wherein A and B are each independently cycloalkyl, heterocyclyl, aryl, or heteroaryl, each of which is optionally substituted with one or more $R^1$; X, Y, and Z are each independently $C(R^{3a})$, $C(R^{3a})(R^{3b})$, N, $N(R^{3c})$, or O, wherein at least one of X, Y, and Z is N, $N(R^{3c})$, or O, and the bonds in the ring comprising X, Y, and Z may be single or double bonds as valency permits; each of $L^1$ and $L^2$ is independently absent, $C_1$-$C_6$-alkylene, $C_1$-$C_6$-heteroalkylene, —O—, —C(O)—, —$N(R^4)$—, —$N(R^4)$C(O)—, or —C(O)$N(R^4)$—, wherein each alkylene and heteroalkylene is optionally substituted with one or more $R^5$; each $R^1$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, $C_1$-$C_6$ alkylene-aryl, $C_1$-$C_6$ alkenylene-aryl, $C_1$-$C_6$ alkylene-heteroaryl, heteroaryl, halo, cyano, oxo, —$OR^A$, —$NR^BR^C$, —$NR^B$C(O)$R^D$, —$NO_2$, —C(O)$NR^BR^C$, —C(O)$R^D$, —C(O)$OR^D$, —$SR^E$, or —$S(O)_xR^D$, wherein each alkyl, alkylene, alkenyl, alkynyl, heteroalkyl, haloalkyl, cycloalkyl, heterocyclyl, aryl, and heteroaryl is optionally substituted with one or more $R^6$; or two $R^1$ groups, together with the atoms to which they are attached, form a 3-7-membered cycloalkyl, heterocyclyl, aryl, or heteroaryl, wherein each cycloalkyl, heterocyclyl, aryl, and heteroaryl is optionally substituted with one or more $R^6$; each $R^2$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, halo, cyano, or —$OR^A$; $R^{3a}$ and $R^{3b}$ are each independently hydrogen, $C_1$-$C_6$-alkyl, $C_1$-$C_6$-heteroalkyl, $C_1$-$C_6$-haloalkyl, halo, cyano, —$OR^A$, —$NR^BR^C$, —$C(O)R^D$, or —$C(O)OR^D$; or each of $R^{3a}$ and $R^{3b}$, together with the carbon atom to which they are attached, form an oxo group; $R^{3c}$ is hydrogen or $C_1$-$C_6$-alkyl; each $R^4$ is independently hydrogen, $C_1$-$C_6$-alkyl, or $C_1$-$C_6$-haloalkyl; each $R^5$ is independently hydrogen, $C_1$-$C_6$-alkyl, $C_1$-$C_6$-heteroalkyl, $C_1$-$C_6$-haloalkyl, cycloalkyl, halo, cyano, oxo, —$OR^A$, —$NR^BR^C$, —$C(O)R^D$, or —$C(O)OR^D$; each $R^6$ is independently $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkenyl, alkynyl, heteroalkyl, haloalkyl, cycloalkyl, heterocyclyl, aryl, and heteroaryl is optionally substituted with one or more $R^{11}$; each $R^7$ is $C_1$-$C_6$-alkyl, halo, cyano, oxo, or —$OR^{A1}$; each $R^{11}$ is independently $C_1$-$C_6$-alkyl, $C_1$-$C_6$-heteroalkyl, $C_1$-$C_6$-haloalkyl, cycloalkyl, heterocyclyl, aryl, heteroaryl, halo, cyano, oxo, or —$OR^A$; each $R^A$ is independently hydrogen, $C_1$-$C_6$ alkyl, $C_1$-$C_6$ haloalkyl, aryl, heteroaryl, $C_1$-$C_6$ alkylene-aryl, $C_1$-$C_6$ alkylene-heteroaryl, —$C(O)R^D$, or —$S(O)_xR^D$; each of $R^B$ and $R^C$ is independently hydrogen, $C_1$-$C_6$ alkyl, $C_1$-$C_6$ heteroalkyl, cycloalkyl, heterocyclyl, or —$OR^A$; or $R^B$ and $R^C$ together with the atom to which they are attached form a 3-7-membered heterocyclyl ring optionally substituted with one or more $R^7$; each $R^D$ and $R^E$ is independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, heteroaryl, $C_1$-$C_6$ alkylene-aryl, or $C_1$-$C_6$ alkylene-heteroaryl; each $R^{A1}$ is hydrogen or $C_1$-$C_6$-alkyl; m is 0, 1, or 2; and x is 0, 1, or 2.

In another aspect, the present invention provides pharmaceutical compositions comprising a compound of Formula (I) (e.g., a compound of Formulas (I-a), (I-b), (I-c), (I-d), (I-e), (I-f), (I-g), (I-h), or (I-i)), or a pharmaceutically acceptable salt, solvate, hydrate, tautomer, or stereoisomer thereof, and optionally a pharmaceutically acceptable excipient. In an embodiment, the pharmaceutical compositions described herein include an effective amount (e.g., a therapeutically effective amount) of a compound of Formula (I) (e.g., a compound of Formulas (I), (I-a), (I-b), (I-c), (I-d), (I-e), (I-f), (I-g), or (I-h)), or a pharmaceutically acceptable salt, solvate, hydrate, tautomer, or stereoisomer thereof.

In another aspect, the present disclosure provides methods for modulating splicing, e.g., splicing of a nucleic acid (e.g., a DNA or RNA, e.g., a pre-mRNA) with a compound of Formula (I) (e.g., a compound of Formulas (I), (I-a), (I-b), (I-c), (I-d), (I-e), (I-f), (I-g), or (I-h)) or a pharmaceutically acceptable salt, solvate, hydrate, tautomer, or stereoisomer thereof. In another aspect, the present disclosure provides compositions for use in modulating splicing, e.g., splicing of a nucleic acid (e.g., a DNA or RNA, e.g., a pre-mRNA) with a compound of Formula (I) (e.g., a compound of Formulas (I), (I-a), (I-b), (I-c), (I-d), (I-e), (I-f), (I-g), or (I-h)) or a pharmaceutically acceptable salt, solvate, hydrate, tautomer, or stereoisomer thereof. Modulation of splicing may comprise impacting any step involved in splicing and may include an event upstream or downstream of a splicing event. For example, in some embodiments, the compound of Formula (I) binds to a target, e.g., a target nucleic acid (e.g., DNA or RNA, e.g., a precursor RNA, e.g., a pre-mRNA), a target protein, or combination thereof (e.g., an snRNP and a pre-mRNA). A target may include a splice site in a pre-mRNA or a component of the splicing machinery, such as the U1 snRNP. In some embodiments, the compound of Formula (I) alters a target nucleic acid (e.g., DNA or RNA, e.g., a precursor RNA, e.g., a pre-mRNA), target protein, or combination thereof. In some embodiments, the compound of Formula (I) increases or decreases splicing at a splice site on a target nucleic acid (e.g., an RNA, e.g., a precursor RNA, e.g., a pre-mRNA) by about 0.5% or more (e.g., about 1%, 2%, 3%, 4%, 5%, 10%, 20%, 30%, 40%, 50%, 75%, 90%, 95%, or more), relative to a reference (e.g., the absence of a compound of Formula (I), e.g., in a healthy or diseased cell or tissue). In some embodiments, the presence of a compound of Formula (I) results an increase or decrease of transcription of a target nucleic acid (e.g., an RNA) by about 0.5% or more (e.g., about 1%, 2%, 3%, 4%, 5%, 10%, 20%, 30%, 40%, 50%, 75%, 90%, 95%, or more), relative to a reference (e.g., the absence of a compound of Formula (I), e.g., in a healthy or diseased cell or tissue).

In another aspect, the present disclosure provides methods for preventing and/or treating a disease, disorder, or condition in a subject by administering a compound of Formula (I) (e.g., a compound of Formulas (I), (I-a), (I-b), (I-c), (I-d), (I-e), (1-f), (I-g), or (I-h)) or a pharmaceutically acceptable salt, solvate, hydrate, tautomer, or stereoisomer thereof, or related compositions. In some embodiments, the disease or disorder entails unwanted or aberrant splicing. In some embodiments, the disease or disorder is a proliferative disease, disorder, or condition. Exemplary proliferative diseases include cancer, a benign neoplasm, or angiogenesis. In other embodiments, the present disclosure provides methods for treating and/or preventing a non-proliferative disease, disorder, or condition. In still other embodiments, the present disclosure provides methods for treating and/or preventing a neurological disease or disorder, autoimmune disease or disorder, immunodeficiency disease or disorder, lysosomal storage disease or disorder, cardiovascular disease or disorder, metabolic disease or disorder, respiratory disease or disorder, renal disease or disorder, or infectious disease.

In another aspect, the present disclosure provides methods of down-regulating the expression of (e.g., the level of or the rate of production of) a target protein with a compound of Formula (I) (e.g., a compound of Formulas (I), (I-a), (I-b), (I-c), (I-d), (I-e), (I-f), (I-g), or (I-h)) or a pharmaceutically acceptable salt, solvate, hydrate, tautomer, or stereoisomer thereof in a biological sample or subject. In another aspect, the present disclosure provides methods of up-regulating the expression of (e.g., the level of or the rate of production of) a target protein with a compound of Formula (I) (e.g., a compound of Formulas (I), (I-a), (I-b), (I-c), (I-d), (I-e), (I-f), (I-g), or (I-h)) or a pharmaceutically acceptable salt, solvate, hydrate, tautomer, or stereoisomer thereof in a biological sample or subject. In another aspect, the present disclosure provides methods of altering the isoform of a target protein with a compound of Formula (I) (e.g., a compound of Formulas (I), (I-a), (I-b), (I-c), (I-d), (I-e), (I-f), (I-g), or (I-h))) or a pharmaceutically acceptable salt, solvate, hydrate, tautomer, or stereoisomer thereof in a biological sample or subject. Another aspect of the disclosure relates to methods of inhibiting the activity of a target protein in a biological sample or subject. In some embodiments, administration of a compound of Formula (I) to a biological sample, a cell, or a subject comprises inhibition of cell growth or induction of cell death.

In another aspect, the present disclosure provides compositions for use in preventing and/or treating a disease, disorder, or condition in a subject by administering a compound of Formula (I) (e.g., a compound of Formulas (I), (I-a), (I-b), (I-c), (I-d), (I-e), (I-f), (I-g), or (I-h)) or a pharmaceutically acceptable salt, solvate, hydrate, tautomer, or stereoisomer thereof, or related compositions. In some embodiments, the disease or disorder entails unwanted or aberrant splicing. In some embodiments, the disease or disorder is a proliferative disease, disorder, or condition. Exemplary proliferative diseases include cancer, a benign neoplasm, or angiogenesis. In other embodiments, the present disclosure provides methods for treating and/or preventing a non-proliferative disease, disorder, or condition. In still other embodiments, the present disclosure provides methods for treating and/or preventing a neurological disease or disorder, autoimmune disease or disorder, immunodeficiency disease or disorder, lysosomal storage disease or disorder, cardiovascular disease or disorder, metabolic disease or disorder, respiratory disease or disorder, renal disease or disorder, or infectious disease.

In another aspect, the present disclosure provides compositions for use in down-regulating the expression of (e.g., the level of or the rate of production of) a target protein with a compound of Formula (I) (e.g., a compound of Formulas (I), (I-a), (I-b), (I-c), (I-d), (I-e), (I-f), (I-g), or (I-h)) or a pharmaceutically acceptable salt, solvate, hydrate, tautomer, or stereoisomer thereof in a biological sample or subject. In another aspect, the present disclosure provides compositions for use in up-regulating the expression of (e.g., the level of or the rate of production of) a target protein with a compound of Formula (I) (e.g., a compound of Formulas (I), (I-a), (I-b), (I-c), (I-d), (I-e), (I-f), (I-g), or (I-h)) or a pharmaceutically acceptable salt, solvate, hydrate, tautomer, or stereoisomer thereof in a biological sample or subject. In another aspect, the present disclosure provides compositions for use in altering the isoform of a target protein with a compound of Formula (I) (e.g., a compound of Formulas (I), (I-a), (I-b), (I-c), (I-d), (I-e), (I-f), (I-g), or (I-h))) or a pharmaceutically acceptable salt, solvate, hydrate, tautomer, or stereoisomer thereof in a biological sample or subject. Another aspect of the disclosure relates to compositions for use in inhibiting the activity of a target protein in a biological sample or subject. In some embodiments, administration of a compound of Formula (I) to a biological sample, a cell, or a subject comprises inhibition of cell growth or induction of cell death.

In another aspect, the present disclosure features kits comprising a container with a compound of Formula (I) (e.g., a compound of Formulas (I), (I-a), (I-b), (I-c), (I-d), (I-e), (I-f), (I-g), or (I-h)), or a pharmaceutically acceptable salt, solvate, hydrate, tautomer, stereoisomer thereof, or a pharmaceutical composition thereof. In certain embodiments, the kits described herein further include instructions for administering the compound of Formula (I) or the pharmaceutically acceptable salt, solvate, hydrate, tautomer, stereoisomer thereof, or the pharmaceutical composition thereof.

In any and all aspects of the present disclosure, in some embodiments, the compound, target nucleic acid (e.g., DNA, RNA, e.g., pre-mRNA), or target protein described herein is a compound, target nucleic acid (e.g., DNA, RNA, e.g., pre-mRNA), or target protein other than a compound, target nucleic acid (e.g., DNA, RNA, e.g., pre-mRNA), or target protein described one of U.S. Pat. No. 8,729,263, U.S. Publication No. 2015/0005289, WO 2014/028459, WO 2016/128343, WO 2016/196386, WO 2017/100726, WO 2018/232039, WO 2018/098446, WO 2019/028440, WO 2019/060917, and WO 2019/199972. In some embodiments, the compound, target nucleic acid (e.g., DNA, RNA, e.g., pre-mRNA), or target protein described herein is a compound, target nucleic acid (e.g., DNA, RNA, e.g., pre-mRNA), or target protein described one of U.S. Pat. No. 8,729,263, U.S. Publication No. 2015/0005289, WO 2014/028459, WO 2016/128343, WO 2016/196386, WO 2017/100726, WO 2018/232039, WO 2018/098446, WO 2019/028440, WO 2019/060917, and WO 2019/199972, each of which is incorporated herein by reference in its entirety.

The details of one or more embodiments of the invention are set forth herein. Other features, objects, and advantages of the invention will be apparent from the Detailed Description, the Examples, and the Claims.

DETAILED DESCRIPTION

Selected Chemical Definitions

Definitions of specific functional groups and chemical terms are described in more detail below. The chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, *March's Advanced Organic Chemistry,* 5$^{th}$ Edition, John Wiley & Sons, Inc., New York, 2001; Larock, Comprehensive Organic Transformations, VCH Publishers, Inc., New York, 1989; and Carruthers, *Some Modern Methods of Organic Synthesis,* 3$^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The following terms are intended to have the meanings presented therewith below and are useful in understanding the description and intended scope of the present invention.

As used herein, "alkyl" refers to a radical of a straight-chain or branched saturated hydrocarbon group having from 1 to 24 carbon atoms ("$C_1$-$C_{24}$ alkyl"). In some embodiments, an alkyl group has 1 to 12 carbon atoms ("$C_1$-$C_{12}$ alkyl"). In some embodiments, an alkyl group has 1 to 8 carbon atoms ("$C_1$-$C_8$ alkyl"). In some embodiments, an alkyl group has 1 to 6 carbon atoms ("$C_1$-$C_6$ alkyl"). In some embodiments, an alkyl group has 2 to 6 carbon atoms ("$C_2$-$C_6$ alkyl"). In some embodiments, an alkyl group has 1 carbon atom ("$C_1$ alkyl"). Examples of $C_1$-$C_6$alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_1$-$C_{10}$ alkyl (e.g., —$CH_3$). In certain embodiments, the alkyl group is substituted $C_1$-$C_6$ alkyl.

As used herein, "alkenyl" refers to a radical of a straight-chain or branched hydrocarbon group having from 2 to 24 carbon atoms, one or more carbon-carbon double bonds, and no triple bonds ("$C_2$-$C_{24}$ alkenyl"). In some embodiments, an alkenyl group has 2 to 10 carbon atoms ("$C_2$-$C_{10}$ alkenyl"). In some embodiments, an alkenyl group has 2 to 8 carbon atoms ("$C_2$-$C_8$ alkenyl"). In some embodiments, an alkenyl group has 2 to 6 carbon atoms ("$C_2$-$C_6$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_1$-$C_{10}$ alkenyl. In certain embodiments, the alkenyl group is substituted $C_2$-$C_6$ alkenyl.

As used herein, the term "alkynyl" refers to a radical of a straight-chain or branched hydrocarbon group having from 2 to 24 carbon atoms, one or more carbon-carbon triple bonds ("$C_2$-$C_{24}$ alkenyl"). In some embodiments, an alkynyl group has 2 to 10 carbon atoms ("$C_2$-$C_{10}$ alkynyl"). In some embodiments, an alkynyl group has 2 to 8 carbon atoms ("$C_2$-$C_8$ alkynyl"). In some embodiments, an alkynyl group has 2 to 6 carbon atoms ("$C_2$-$C_6$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include ethynyl ($C_2$), 1-propynyl ($C_3$), 2-propynyl ($C_3$), 1-butynyl ($C_4$), 2-butynyl ($C_4$), and the like. Each instance of an alkynyl group may be independently optionally substituted, i.e., unsubstituted (an "unsubstituted alkynyl") or substituted (a "substituted alkynyl") with one or more substituents e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-6}$ alkynyl.

As used herein, the term "haloalkyl," refers to a non-cyclic stable straight or branched chain, or combinations thereof, including at least one carbon atom and at least one halogen selected from the group consisting of F, Cl, Br, and I. The halogen(s) F, Cl, Br, and I may be placed at any position of the haloalkyl group. Exemplary haloalkyl groups include, but are not limited to: —$CF_3$, —$CCl_3$, —$CH_2$—$CF_3$, —$CH_2$—$CCl_3$, —$CH_2$—$CBr_3$, —$CH_2$—$CI_3$, —$CH_2$—$CH_2$—$CH(CF_3)$—$CH_3$, —$CH_2$—$CH_2$—CH(Br)—$CH_3$, and —$CH_2$—CH═CH—$CH_2$—$CF_3$. Each instance of a haloalkyl group may be independently optionally substituted, i.e., unsubstituted (an "unsubstituted haloalkyl") or substituted (a "substituted haloalkyl") with one or more substituents e.g., for instance from 1 to 5 substituents, 1 to 3 substituents, or 1 substituent As used herein, the term "heteroalkyl," refers to a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any position of the heteroalkyl group. Exemplary heteroalkyl groups include, but are not limited to: —$CH_2$—$CH_2$—O—$CH_3$, —$CH_2$—$CH_2$—NH—$CH_3$, —$CH_2$—$CH_2$—$N(CH_3)$—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH═CHO—$CH_3$, —$Si(CH_3)_3$, —$CH_2$—CH═N—$OCH_3$, —CH═CH—$N(CH_3)$—$CH_3$, —O—$CH_3$, and —O—$CH_2$—$CH_3$. Up to two or three heteroatoms may be consecutive, such as, for example, —$CH_2$—NH—$OCH_3$ and —$CH_2$—O—$Si(CH_3)_3$. Where "heteroalkyl" is recited, followed by recitations of specific heteroalkyl groups, such as —$CH_2O$, —$NR^CR^D$, or the like, it will be understood that the terms heteroalkyl and —$CH_2O$ or —$NR^CR^D$ are not redundant or mutually exclusive. Rather, the specific heteroalkyl groups are recited to add clarity. Thus, the term "heteroalkyl" should not be interpreted herein as excluding specific heteroalkyl groups, such as —$CH_2O$, —$NR^CR^D$, or the like. Each instance of a heteroalkyl group may be independently optionally substituted, i.e., unsubstituted (an "unsubstituted heteroalkyl") or substituted (a "substituted heteroalkyl") with one or more substituents e.g., for instance from 1 to 5 substituents, 1 to 3 substituents, or 1 substituent As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents. In certain embodiments, the aryl group is unsubstituted $C_6$-$C_{14}$ aryl. In certain embodiments, the aryl group is substituted $C_6$-$C_{14}$ aryl.

As used herein, "heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety. Each instance of a heteroaryl group may be independently optionally substituted, i.e., unsubstituted (an "unsubstituted heteroaryl") or substituted (a "substituted heteroaryl") with one or more substituents e.g., for instance from 1 to 5 substituents, 1 to 3 substituents, or 1 substituent Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl.

Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Other exemplary heteroaryl groups include heme and heme derivatives.

As used herein, "cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$ cycloalkyl"). In some embodiments, a cycloalkyl group has 3 to 6 ring carbon atoms ("$C_3$-$C_6$ cycloalkyl"). In some embodiments, a cycloalkyl group has 3 to 6 ring carbon atoms ("$C_3$-$C_6$ cycloalkyl"). In some embodiments, a cycloalkyl group has 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_5$), bicyclo[2.2.2]octanyl ($C_8$), bicyclo [2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is a substituted $C_3$-$C_{10}$ cycloalkyl.

"Heterocyclyl" as used herein refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl (e.g., 2,2,6,6-tetramethylpiperidinyl), tetrahydropyranyl, dihydropyridinyl, pyridinonyl (e.g., 1-methylpyridin2-onyl), and thianyl. Exemplary 6-membered heterocyclyl groups containing two heteroatoms include, without limitation, piperazinyl, morpholinyl, pyridazinonyl (2-methylpyridazin-3-onyl), pyrimidinonyl (e.g., 1-methylpyrimidin-2-onyl, 3-methylpyrimidin-4-onyl), dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclyl ring) include, without limitation, indolinyl, isoindolinyl, dihydrobenzofuranyl, dihydrobenzothienyl, benzoxazolinonyl, and the like. Exemplary 5-membered heterocyclyl groups fused to a heterocyclyl ring (also referred to herein as a 5,5-bicyclic heterocyclyl ring) include, without limitation, octahydropyrrolopyrrolyl (e.g., octahydropyrrolo[3,4-c]pyrrolyl), and the like. Exemplary 6-membered heterocyclyl groups fused to a heterocyclyl ring (also referred to as a 4,6-membered heterocyclyl ring) include, without limitation, diazaspirononanyl (e.g., 2,7-diazaspiro[3.5]nonanyl). Exemplary 6-membered heterocyclyl groups fused to an aryl ring (also referred to herein as a 6,6-bicyclic heterocyclyl ring) include, without limitation, tetrahydroquinolinyl, tetrahydroisoquinolinyl, and the like. Exemplary 6-membered heterocyclyl groups fused to a cycloalkyl ring (also referred to herein as a 6,7-bicyclic heterocyclyl ring) include, without limitation, azabicyclooctanyl (e.g., (1,5)-8-azabicyclo[3.2.1]octanyl). Exemplary 6-membered heterocyclyl groups fused to a cycloalkyl ring (also referred to herein as a 6,8-bicyclic heterocyclyl ring) include, without limitation, azabicyclononanyl (e.g., 9-azabicyclo[3.3.1]nonanyl).

The terms "alkylene," "alkenylene," "alkynylene," "haloalkylene," "heteroalkylene," "cycloalkylene," or "heterocyclylene," alone or as part of another substituent, mean, unless otherwise stated, a divalent radical derived from an alkyl, alkenyl, alkynyl, haloalkylene, heteroalkylene, cycloalkyl, or heterocyclyl respectively. For example, the term "alkenylene," by itself or as part of another substituent, means, unless otherwise stated, a divalent radical derived from an alkene. An alkylene, alkenylene, alkynylene, haloalkylene, heteroalkylene, cycloalkylene, or heterocyclylene group may be described as, e.g., a $C_1$-$C_6$-membered alkylene, $C_2$-$C_6$-membered alkenylene, $C_2$-$C_6$-membered alkynylene, $C_1$-$C_6$-membered haloalkylene, $C_1$-$C_6$-membered heteroalkylene, $C_3$-$C_8$-membered cycloalkylene, or $C_3$-$C_8$-membered heterocyclylene, wherein the term "membered" refers to the non-hydrogen atoms within the moiety. In the case of heteroalkylene and heterocyclylene groups, heteroatoms can also occupy either or both of the chain termini (e.g., alkyleneoxy, alkylenedioxy, alkyleneamino, alkylenediamino, and the like). Still further, no orientation of the linking group is implied by the direction in which the formula of the linking group is written. For example, the formula —$C(O)_2R'$— may represent both —$C(O)_2R'$- and —$R'C(O)_2$—.

As used herein, the terms "cyano" or "—CN" refer to a substituent having a carbon atom joined to a nitrogen atom by a triple bond, e.g., C≡N.

As used herein, the terms "halogen" or "halo" refer to fluorine, chlorine, bromine or iodine.

As used herein, the term "hydroxy" refers to —OH.

As used herein, the term "nitro" refers to a substitutent having two oxygen atoms bound to a nitrogen atom, e.g., —$NO_2$.

As used herein, the term "nucleobase" as used herein, is a nitrogen-containing biological compounds found linked to a sugar within a nucleoside—the basic building blocks of deoxyribonucleic acid (DNA) and ribonucleic acid (RNA). The primary, or naturally occurring, nucleobases are cytosine (DNA and RNA), guanine (DNA and RNA), adenine (DNA and RNA), thymine (DNA) and uracil (RNA), abbreviated as C, G, A, T, and U, respectively. Because A, G, C, and T appear in the DNA, these molecules are called DNA-bases; A, G, C, and U are called RNA-bases. Adenine and guanine belong to the double-ringed class of molecules called purines (abbreviated as R). Cytosine, thymine, and uracil are all pyrimidines. Other nucleobases that do not function as normal parts of the genetic code, are termed non-naturally occurring. In an embodiment, a nucleobase may be chemically modified, for example, with an alkyl (e.g., methyl), halo, —O-alkyl, or other modification.

As used herein, the term "nucleic acid" refers to deoxyribonucleic acids (DNA) or ribonucleic acids (RNA) and polymers thereof in either single- or double-stranded form. The term "nucleic acid" includes a gene, cDNA, pre-mRNA, or an mRNA. In one embodiment, the nucleic acid molecule is synthetic (e.g., chemically synthesized) or recombinant. Unless specifically limited, the term encompasses nucleic acids containing analogues or derivatives of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementarity sequences as well as the sequence explicitly indicated.

As used herein, "oxo" refers to a carbonyl, i.e., —C(O)—.

The symbol "∿∿" as used herein in relation to a compound of Formula (I) refers to an attachment point to another moiety or functional group within the compound.

Alkyl, alkenyl, alkynyl, haloalkyl, heteroalkyl, cycloalkyl, heterocyclyl, aryl, and heteroaryl groups, as defined herein, are optionally substituted. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present disclosure contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

The compounds provided herein may exist in one or more particular geometric, optical, enantiomeric, diasteriomeric, epimeric, stereoisomeric, tautomeric, conformational, or anomeric forms, including but not limited to: cis- and trans-forms; E- and Z-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half chair-forms; and combinations thereof, hereinafter collectively referred to as “isomers” (or “isomeric forms”).

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. In an embodiment, the stereochemistry depicted in a compound is relative rather than absolute. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, Stereochemistry of Carbon Compounds (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). This disclosure additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess). In other words, an “S” form of the compound is substantially free from the “R” form of the compound and is, thus, in enantiomeric excess of the “R” form. The term “enantiomerically pure” or “pure enantiomer” denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising an enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising an enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound.

In some embodiments, a diastereomerically pure compound can be present with other active or inactive ingredients. For example, a pharmaceutical composition comprising a diastereometerically pure exo compound can comprise, for example, about 90% excipient and about 10% diastereometerically pure exo compound. In certain embodiments, the diastereometerically pure exo compound in such compositions can, for example, comprise, at least about 95% by weight exo compound and at most about 5% by weight endo compound, by total weight of the compound. For example, a pharmaceutical composition comprising a diastereometerically pure endo compound can comprise, for example, about 90% excipient and about 10% diastereometerically pure endo compound. In certain embodiments, the diastereometerically pure endo compound in such compositions can, for example, comprise, at least about 95% by weight endo compound and at most about 5% by weight exo compound, by total weight of the compound.

In some embodiments, an isomerically pure compound can be present with other active or inactive ingredients. For example, a pharmaceutical composition comprising a isomerically pure exo compound can comprise, for example, about 90% excipient and about 10% isomerically pure exo compound. In certain embodiments, the isomerically pure exo compound in such compositions can, for example, comprise, at least about 95% by weight exo compound and at most about 5% by weight endo compound, by total weight of the compound. For example, a pharmaceutical composition comprising an isomerically pure endo compound can comprise, for example, about 90% excipient and about 10% isomerically pure endo compound. In certain embodiments, the isomerically pure endo compound in such compositions can, for example, comprise, at least about 95% by weight endo compound and at most about 5% by weight exo compound, by total weight of the compound.

In certain embodiments, the active ingredient can be formulated with little or no excipient or carrier.

Compound described herein may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$, and $^{14}C$; O may be in any isotopic form, including $^{16}O$ and $^{18}O$; N may be in any isotopic form, including $^{14}N$ and $^{15}N$; F may be in any isotopic form, including $^{18}F$, $^{19}F$, and the like.

The term “pharmaceutically acceptable salt” is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al, *Journal of Pharmaceutical Science* 66: 1-19 (1977)). Certain specific compounds of the present invention contain both basic and acidic functionalities that allow the compounds to be converted into either base or acid addition salts. These salts may be prepared by methods known to those skilled in the art. Other pharmaceutically acceptable carriers known to those of skill in the art are suitable for the present invention.

In addition to salt forms, the present disclosure provides compounds in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomer" refers to compounds that are interchangeable forms of a particular compound structure, and that vary in the displacement of hydrogen atoms and electrons. Thus, two structures may be in equilibrium through the movement of $\pi$ electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base. Tautomeric forms may be relevant to the attainment of the optimal chemical reactivity and biological activity of a compound of interest.

Other Definitions

The following definitions are more general terms used throughout the present disclosure.

The articles "a" and "an" refer to one or more than one (e.g., to at least one) of the grammatical object of the article. By way of example, "an element" means one element or more than one element. The term "and/or" means either "and" or "or" unless indicated otherwise.

The term "about" is used herein to mean within the typical ranges of tolerances in the art. For example, "about" can be understood as about 2 standard deviations from the mean. In certain embodiments, about means±10%. In certain embodiments, about means±5%. When about is present before a series of numbers or a range, it is understood that "about" can modify each of the numbers in the series or range.

"Acquire" or "acquiring" as used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., performing an analytical method or protocol) to obtain the value or physical entity. "Indirectly acquiring" refers to receiving the value or physical entity from another party or source (e.g., a third-party laboratory that directly acquired the physical entity or value). Directly acquiring a value or physical entity includes performing a process that includes a physical change in a physical substance or the use of a machine or device. Examples of directly acquiring a value include obtaining a sample from a human subject. Directly acquiring a value includes performing a process that uses a machine or device, e.g., mass spectrometer to acquire mass spectrometry data.

The terms "administer," "administering," or "administration," as used herein refers to implanting, absorbing, ingesting, injecting, inhaling, or otherwise introducing an inventive compound, or a pharmaceutical composition thereof.

As used herein, the terms "condition," "disease," and "disorder" are used interchangeably.

An "effective amount" of a compound of Formula (I) refers to an amount sufficient to elicit the desired biological response, i.e., treating the condition. As will be appreciated by those of ordinary skill in this art, the effective amount of a compound of Formula (I) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formula (I) is an amount sufficient to provide a therapeutic benefit in the treatment of a condition or to delay or minimize one or more symptoms associated with the condition. In some embodiments, a therapeutically effective amount is an amount sufficient to provide a therapeutic benefit in the treatment of a condition or to minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprised therein. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types.

"Prevention," "prevent," and "preventing" as used herein refers to a treatment that comprises administering a therapy, e.g., administering a compound described herein (e.g., a compound of Formula (I)) prior to the onset of a disease, disorder, or condition in order to preclude the physical manifestation of said disease, disorder, or condition. In some embodiments, "prevention," "prevent," and "preventing" require that signs or symptoms of the disease, disorder, or condition have not yet developed or have not yet been observed. In some embodiments, treatment comprises prevention and in other embodiments it does not.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

As used herein, the terms "treatment," "treat," and "treating" refer to reversing, alleviating, delaying the onset of, or inhibiting the progress of one or more of a symptom, manifestation, or underlying cause of a disease, disorder, or condition (e.g., as described herein), e.g., by administering a therapy, e.g., administering a compound described herein (e.g., a compound of Formula (I)). In an embodiment, treating comprises reducing, reversing, alleviating, delaying the onset of, or inhibiting the progress of a symptom of a disease, disorder, or condition. In an embodiment, treating comprises reducing, reversing, alleviating, delaying the onset of, or inhibiting the progress of a manifestation of a disease, disorder, or condition. In an embodiment, treating comprises reducing, reversing, alleviating, reducing, or delaying the onset of, an underlying cause of a disease, disorder, or condition. In some embodiments, "treatment," "treat," and "treating" require that signs or symptoms of the disease, disorder, or condition have developed or have been observed. In other embodiments, treatment may be administered in the absence of signs or symptoms of the disease or condition, e.g., in preventive treatment. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence. Treatment may also be continued after symptoms have resolved, for example, to delay or prevent recurrence. In some embodiments, treatment comprises prevention and in other embodiments it does not.

A "proliferative disease" refers to a disease that occurs due to abnormal extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); 4) the pathological angiogenesis as in proliferative retinopathy and tumor metastasis; or 5) evasion of host immune surveillance and elimination of neoplastic cells. Exemplary proliferative diseases include cancers (i.e., "malignant neoplasms"), benign neoplasms, and angiogenesis.

A "non-proliferative disease" refers to a disease that does not primarily extend through the abnormal multiplication of cells. A non-proliferative disease may be associated with any cell type or tissue type in a subject. Exemplary non-proliferative diseases include neurological diseases or disorders (e.g., a repeat expansion disease); autoimmune disease or disorders; immunodeficiency diseases or disorders; lysosomal storage diseases or disorders; inflammatory diseases or disorders; cardiovascular conditions, diseases, or disorders; metabolic diseases or disorders; respiratory conditions, diseases, or disorders; renal diseases or disorders; and infectious diseases.

Compounds

The present disclosure features a compound of Formula (I):

(I)

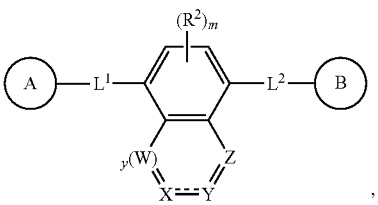

, or a pharmaceutically acceptable salt, solvate, hydrate, tautomer, or stereoisomer thereof, wherein A and B are each independently cycloalkyl, heterocyclyl, aryl, or heteroaryl, each of which is optionally substituted with one or more $R^1$;

W is N, C, or $C(R^{3a})$; X, Y, and Z are each independently $C(R^{3a})$, $C(R^{3a})(R^{3b})$, N, $N(R^{3c})$, or O, wherein the bonds in the ring comprising X, Y, and Z may be single or double bonds as valency permits; $L^1$ and $L^2$ are each independently absent, $C_1$-$C_6$-alkylene, $C_1$-$C_6$-heteroalkylene, —O—, —C(O)—, —$N(R^4)$—, —$N(R^4)C(O)$—, or —$C(O)N(R^4)$—, wherein each alkylene and heteroalkylene is optionally substituted with one or more $R^5$; each $R^1$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, $C_1$-$C_6$alkylene-aryl, $C_1$-$C_6$ alkenylene-aryl, $C_1$-$C_6$ alkylene-heteroaryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkylene, alkenyl, alkynyl, heteroalkyl, haloalkyl, cycloalkyl, heterocyclyl, aryl, and heteroaryl is optionally substituted with one or more $R^6$; or two $R^1$ groups, together with the atoms to which they are attached, form a 3-7-membered cycloalkyl, heterocyclyl, aryl, or heteroaryl, wherein each cycloalkyl, heterocyclyl, aryl, and heteroaryl is optionally substituted with one or more $R^6$; each $R^2$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, halo, cyano, or —$OR^A$; $R^{3a}$ and $R^{3b}$ are each independently hydrogen, $C_1$-$C_6$-alkyl, $C_1$-$C_6$-heteroalkyl, $C_1$-$C_6$-haloalkyl, halo, cyano, —$OR^A$, —$NR^BR^C$, —$C(O)R^D$, or —$C(O)OR^D$; or each of $R^{3a}$ and $R^{3b}$, together with the carbon atom to which they are attached, form an oxo group; $R^{3c}$ is hydrogen or $C_1$-$C_6$-alkyl; each $R^4$ is independently hydrogen, $C_1$-$C_6$-alkyl, or $C_1$-$C_6$-haloalkyl; each $R^5$ is independently hydrogen, $C_1$-$C_6$-alkyl, $C_1$-$C_6$-heteroalkyl, $C_1$-$C_6$-haloalkyl, cycloalkyl, halo, cyano, oxo, —$OR^A$, —$NR^BR^C$, —$C(O)R^D$, or —$C(O)OR^D$; each $R^6$ is independently $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkenyl, alkynyl, heteroalkyl, haloalkyl, cycloalkyl, heterocyclyl, aryl, and heteroaryl is optionally substituted with one or more $R^{11}$; each $R^7$ is $C_1$-$C_6$-alkyl, halo, cyano, oxo, or —$OR^{A1}$; each $R^{11}$ is independently $C_1$-$C_6$-alkyl, $C_1$-$C_6$-heteroalkyl, $C_1$-$C_6$-haloalkyl, cycloalkyl, heterocyclyl, aryl, heteroaryl, halo, cyano, oxo, or —$OR^A$; each $R^A$ is independently hydrogen, $C_1$-$C_6$ alkyl, $C_1$-$C_6$ haloalkyl, aryl, heteroaryl, $C_1$-$C_6$ alkylene-aryl, $C_1$-$C_6$ alkylene-heteroaryl, —$C(O)R^D$, or —$S(O)_xR^D$; each of $R^B$ and $R^C$ is independently hydrogen, $C_1$-$C_6$ alkyl, $C_1$-$C_6$ heteroalkyl, cycloalkyl, heterocyclyl, or —$OR^A$; or $R^B$ and $R^C$ together with the atom to which they are attached form a 3-7-membered heterocyclyl ring optionally substituted with one or more $R^7$; each $R^D$ and $R^E$ is independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, heteroaryl, $C_1$-$C_6$ alkylene-aryl, or $C_1$-$C_6$ alkylene-heteroaryl; each $R^{A1}$ is hydrogen or $C_1$-$C_6$-alkyl; m is 0, 1, or 2; x is 0, 1, or 2; and y is 0 or 1.

As generally described herein, A and B, are each independently cycloalkyl, heterocyclyl, aryl, or heteroaryl, each of which is optionally substituted with one or more $R^1$.

In some embodiments, each of A and B are independently a monocyclic ring, e.g., monocyclic cycloalkyl, monocyclic heterocyclyl, monocyclic aryl, or monocyclic heteroaryl. The monocyclic ring may be saturated, partially unsaturated, or fully unsaturated (e.g., aromatic). In some embodiments, A or B are independently a monocyclic ring comprising between 3 and 10 ring atoms (e.g., 3, 4, 5, 6, 7, 8, 9, or 10 ring atoms). In some embodiments, A is a 4-membered monocyclic ring. In some embodiments, B is a 4-membered monocyclic ring. In some embodiments, A is a 5-membered monocyclic ring. In some embodiments, B is a 5-membered monocyclic ring. In some embodiments, A is a 6-membered monocyclic ring. In some embodiments, B is a 6-membered monocyclic ring. In some embodiments, A is a 7-membered monocyclic ring. In some embodiments, B is a 7-membered monocyclic ring. In some embodiments, A is an 8-membered monocyclic ring. In some embodiments, B is an 8-membered monocyclic ring. In some embodiments, A or B are independently a monocyclic ring optionally substituted with one or more $R^1$.

In some embodiments, A or B are independently a bicyclic ring, e.g., bicyclic cycloalkyl, bicyclic heterocyclyl, bicyclic aryl, or bicyclic heteroaryl. The bicyclic ring may be saturated, partially unsaturated, or fully unsaturated (e.g., aromatic). In some embodiments, A or B are independently a bicyclic ring comprising a fused, bridged, or spiro ring system. In some embodiments, A or B are independently a bicyclic ring comprising between 4 and 18 ring atoms (e.g., 4, 5, 6, 7, 8, 9, 10, 11, 12, 13, 14, 15, 16, 17, or 18 ring atoms). In some embodiments, A is a 6-membered bicyclic ring. In some embodiments, B is a 6-membered bicyclic ring. In some embodiments, A is a 7-membered bicyclic ring. In some embodiments, B is a 7-membered bicyclic ring. In some embodiments, A is an 8-membered bicyclic ring. In some embodiments, B is an 8-membered bicyclic ring. In some embodiments, A is a 9-membered bicyclic ring. In some embodiments, B is a 9-membered bicyclic ring. In some embodiments, A is a 10-membered bicyclic ring. In some embodiments, B is a 10-membered bicyclic ring. In some embodiments, A is an 11-membered bicyclic ring. In some embodiments, B is an 11-membered bicyclic ring. In some embodiments, A is a 12-membered bicyclic ring. In some embodiments, B is a 12-membered bicyclic ring. In some embodiments, A or B are independently a bicyclic ring optionally substituted with one or more $R^1$.

In some embodiments, A or B are independently a tricyclic ring, e.g., tricyclic cycloalkyl, tricyclic heterocyclyl, tricyclic aryl, or tricyclic heteroaryl. The tricyclic ring may be saturated, partially unsaturated, or fully unsaturated (e.g., aromatic). In some embodiments, A or B are independently a tricyclic ring that comprises a fused, bridged, or spiro ring system, or a combination thereof. In some embodiments, A or B are independently a tricyclic ring comprising between 6 and 24 ring atoms (e.g., 6, 7, 8, 9, 10, 11, 12, 13, 14, 15, 16, 17, 18, 19, 20, 21, 22, 23, or 24 ring atoms). In some embodiments, A is an 8-membered tricyclic ring. In some embodiments, B is an 8-membered tricyclic ring. In some embodiments, A is a 9-membered tricyclic ring. In some embodiments, B is a 9-membered tricyclic ring. In some embodiments, A is a 10-membered tricyclic ring. In some embodiments, B is a 10-membered tricyclic ring. In some embodiments, A or B are independently a tricyclic ring optionally substituted with one or more $R^1$.

In some embodiments, A or B are independently monocyclic cycloalkyl, monocyclic heterocyclyl, monocyclic aryl, or monocyclic heteroaryl. In some embodiments, A or B are independently bicyclic cycloalkyl, bicyclic heterocyclyl, bicyclic aryl, or bicyclic heteroaryl. In some embodiments, A or B are independently tricyclic cycloalkyl, tricyclic heterocyclyl, tricyclic aryl, or tricyclic heteroaryl. In some embodiments, A is monocyclic heterocyclyl. In some embodiments, B is monocyclic heterocyclyl. In some embodiments, A is bicyclic heterocyclyl. In some embodiments, B is bicyclic heterocyclyl. In some embodiments, A is monocyclic heteroaryl. In some embodiments, B is monocyclic heteroaryl. In some embodiments, A is bicyclic heteroaryl. In some embodiments, B is bicyclic heteroaryl.

In some embodiments, A or B are independently a nitrogen-containing heterocyclyl, e.g., heterocyclyl comprising one or more nitrogen atom. The one or more nitrogen atom of the nitrogen-containing heterocyclyl may be at any position of the ring. In some embodiments, the nitrogen-containing heterocyclyl is monocyclic, bicyclic, or tricyclic. In some embodiments, A or B are independently heterocyclyl comprising at least 1, at least 2, at least 3, at least 4, at least 5, or at least 6 nitrogen atoms. In some embodiments, A is heterocyclyl comprising 1 nitrogen atom. In some embodiments, B is heterocyclyl comprising 1 nitrogen atom. In some embodiments, A is heterocyclyl comprising 2 nitrogen atoms. In some embodiments, B is heterocyclyl comprising 2 nitrogen atoms. In some embodiments, A is heterocyclyl comprising 3 nitrogen atoms. In some embodiments, B is heterocyclyl comprising 3 nitrogen atoms. In some embodiments, A is heterocyclyl comprising 4 nitrogen atoms. In some embodiments, B is heterocyclyl comprising 4 nitrogen atoms. In some embodiments, A or B are independently a nitrogen-containing heterocyclyl comprising one or more additional heteroatoms, e.g., one or more of oxygen, sulfur, boron, silicon, or phosphorus. In some embodiments, the one or more nitrogen of the nitrogen-containing heterocyclyl is substituted, e.g., with $R^1$.

In some embodiments, A or B are independently a nitrogen-containing heteroaryl, e.g., heteroaryl comprising one or more nitrogen atom. The one or more nitrogen atom of the nitrogen-containing heteroaryl may be at any position of the ring. In some embodiments, the nitrogen-containing heteroaryl is monocyclic, bicyclic, or tricyclic. In some embodiments, A or B are independently heteroaryl comprising at least 1, at least 2, at least 3, at least 4, at least 5, or at least 6 nitrogen atoms. In some embodiments, A is heteroaryl comprising 1 nitrogen atom. In some embodiments, B is heteroaryl comprising 1 nitrogen atom. In some embodiments, A is heteroaryl comprising 2 nitrogen atoms. In some embodiments, B is heteroaryl comprising 2 nitrogen atoms. In some embodiments, A is heteroaryl comprising 3 nitrogen atoms. In some embodiments, B is heteroaryl comprising 3 nitrogen atoms. In some embodiments, A is heteroaryl comprising 4 nitrogen atoms. In some embodiments, B is heteroaryl comprising 4 nitrogen atoms. In some embodiments, A or B are independently a nitrogen-containing heteroaryl comprising one or more additional heteroatoms, e.g., one or more of oxygen, sulfur, boron, silicon, or phosphorus. In some embodiments, the one or more nitrogen of the nitrogen-containing heteroaryl is substituted, e.g., with $R^1$.

In some embodiments, A is a 6-membered nitrogen-containing heterocyclyl, e.g., a 6-membered heterocyclyl comprising one or more nitrogen. In some embodiments, A is a 6-membered heterocyclyl comprising 1 nitrogen atom. In some embodiments, A is a 6-membered heterocyclyl comprising 2 nitrogen atoms. In some embodiments, A is a 6-membered heterocyclyl comprising 3 nitrogen atoms. In some embodiments, A is a 6-membered heterocyclyl comprising 4 nitrogen atoms. The one or more nitrogen atom of the 6-membered nitrogen-containing heterocyclyl may be at any position of the ring. In some embodiments, A is a 6-membered nitrogen-containing heterocyclyl optionally substituted with one or more $R^1$. In some embodiments, the one or more nitrogen of the 6-membered nitrogen-containing heterocyclyl is substituted, e.g., with $R^1$. In some embodiments, A is a 6-membered nitrogen-containing heterocyclyl comprising one or more additional heteroatoms, e.g., one or more of oxygen, sulfur, boron, silicon, or phosphorus.

In some embodiments, B is a 5-membered nitrogen-containing heterocyclyl or heteroaryl, e.g., a 5-membered heterocyclyl or heteroaryl comprising one or more nitrogen. In some embodiments, B is a 5-membered heterocyclyl comprising 1 nitrogen atom. In some embodiments, B is a 5-membered heteroaryl comprising 1 nitrogen atom. In some embodiments, B is a 5-membered heterocyclyl comprising 2 nitrogen atoms. In some embodiments, B is a 5-membered heteroaryl comprising 2 nitrogen atoms. In some embodiments, B is a 5-membered heterocyclyl comprising 3 nitrogen atoms. In some embodiments, B is a 5-membered heteroaryl comprising 3 nitrogen atoms. The one or more nitrogen atom of the 5-membered nitrogen-containing heterocyclyl or heteroaryl may be at any position of the ring. In some embodiments, B is a 5-membered nitrogen-containing heterocyclyl optionally substituted with one or more $R^1$. In some embodiments, B is a 5-membered nitrogen-containing heteroaryl optionally substituted with one or more $R^1$. In some embodiments, the one or more nitrogen of the 5-membered nitrogen-containing heterocyclyl or heteroaryl is substituted, e.g., with $R^1$. In some embodiments, B is a 5-membered nitrogen-containing heterocyclyl or heteroaryl comprising one or more additional heteroatoms, e.g., one or more of oxygen, sulfur, boron, silicon, or phosphorus.

In some embodiments, B is a nitrogen-containing bicyclic heteroaryl (e.g., a 9-membered nitrogen-containing bicyclic heteroaryl), that is optionally substituted with one or more $R^1$. In some embodiments, B is a 9-membered bicyclic heteroaryl comprising 1 nitrogen atom. In some embodiments, B is a 9-membered bicyclic heteroaryl comprising 2 nitrogen atoms. In some embodiments, B is a 9-membered bicyclic heteroaryl comprising 3 nitrogen atoms. In some embodiments, B is a 9-membered bicyclic heteroaryl comprising 4 nitrogen atoms. The one or more nitrogen atom of the 9-membered bicyclic heteroaryl may be at any position of the ring. In some embodiments, B is a 9-membered bicyclic heteroaryl substituted with one or more $R^1$.

In some embodiments, each of A and B are independently selected from:

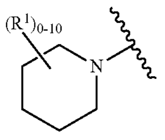
,
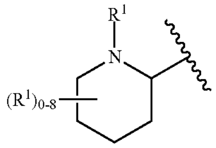
,
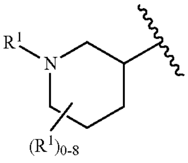
,
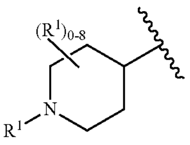
,
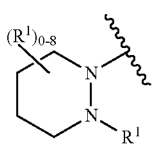
,
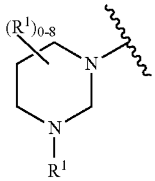
,

-continued
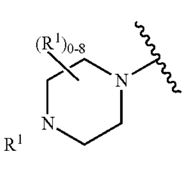, 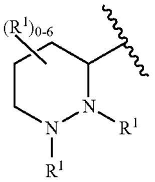,
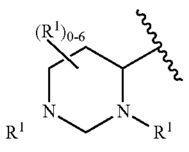, 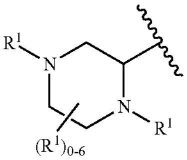,
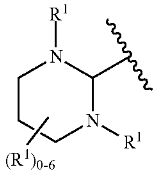, 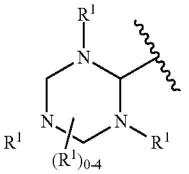,
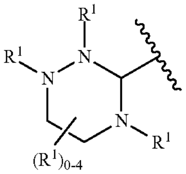, 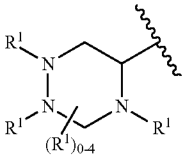,
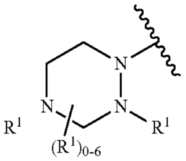, 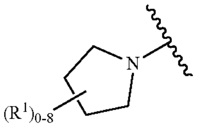,
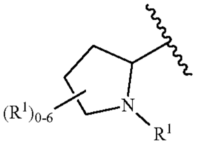, 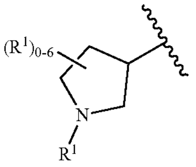,
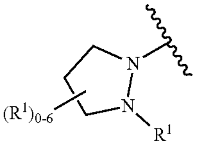, 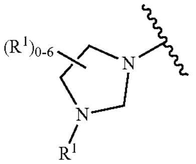,
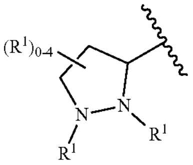, 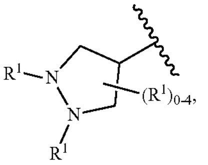
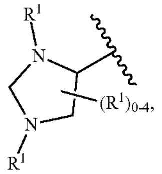 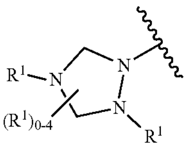,
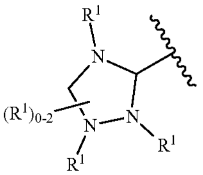, 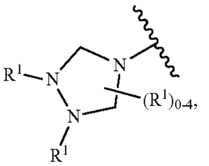
-continued
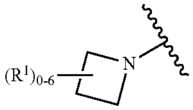, 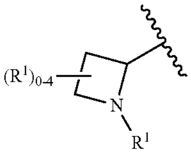,
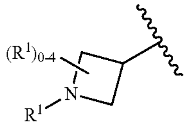, 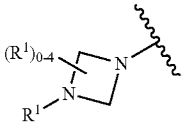,
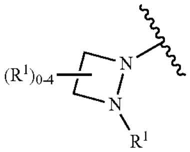, 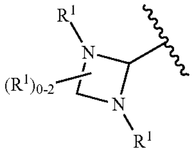,
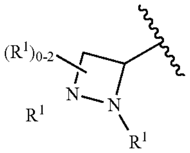, 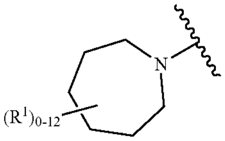,
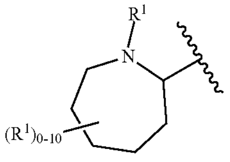, 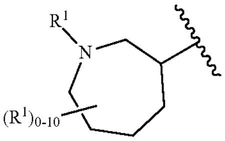,
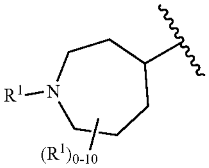, 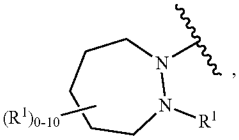,
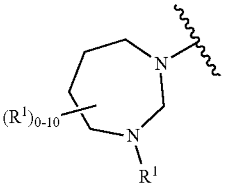, 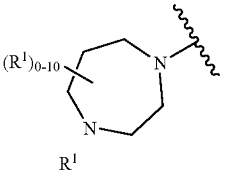,
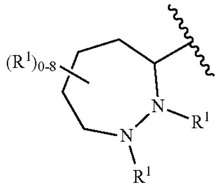, 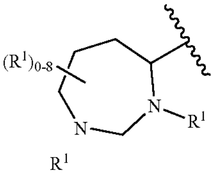,
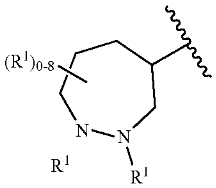, 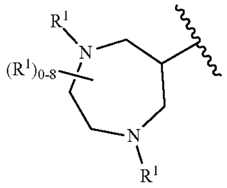
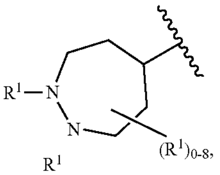 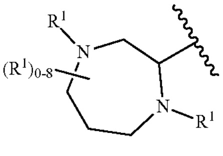, -continued
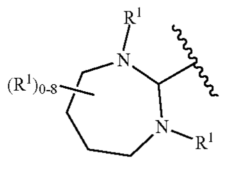,
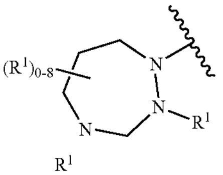,
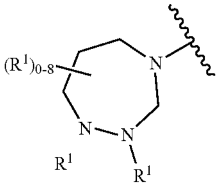,
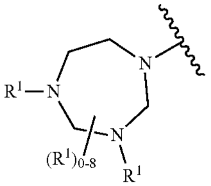,
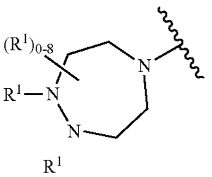,
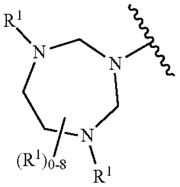,
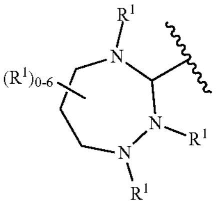,
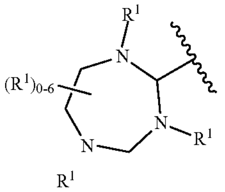,
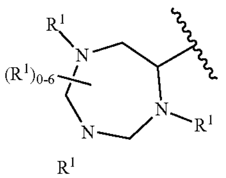,
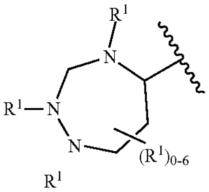,
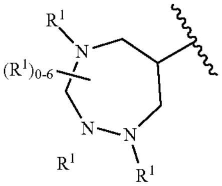,
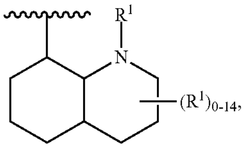
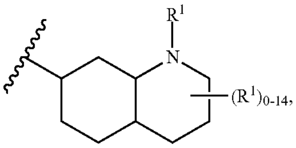
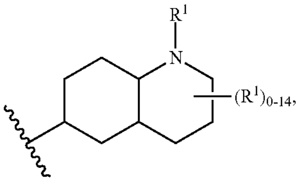
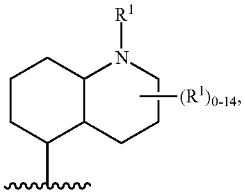
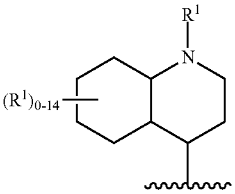,
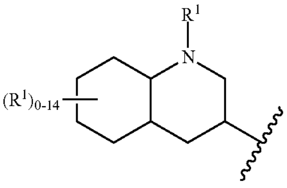,
-continued
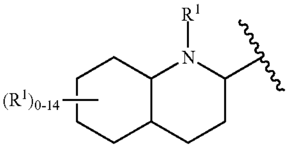,
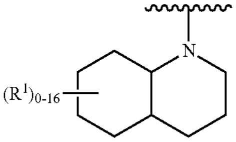,
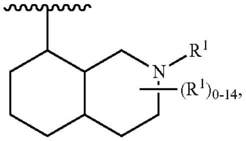
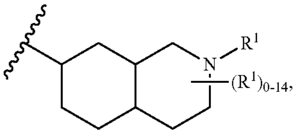
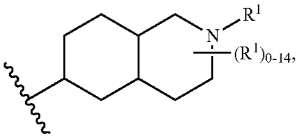
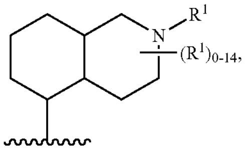
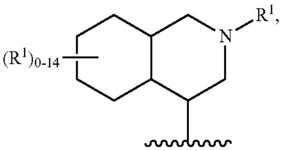
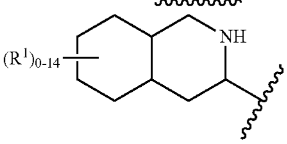,
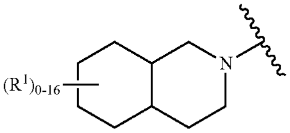,
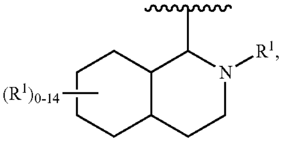
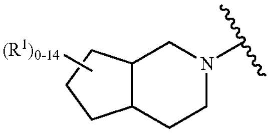,
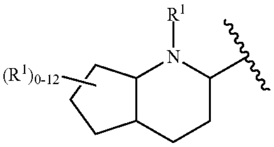,
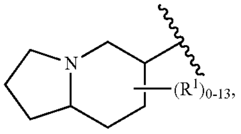
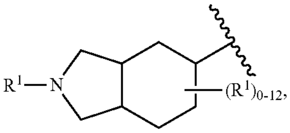
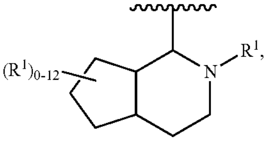
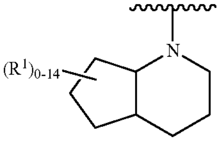,
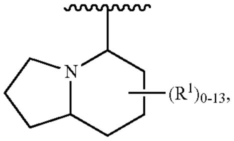
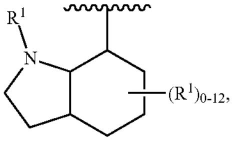

-continued
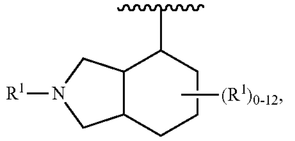
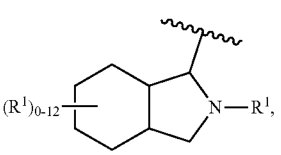
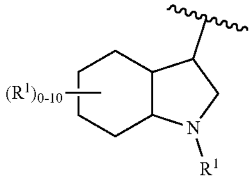
,
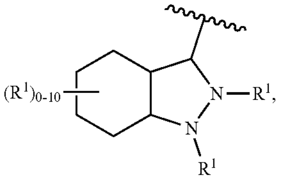
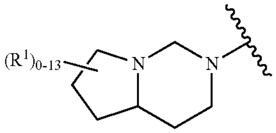
,
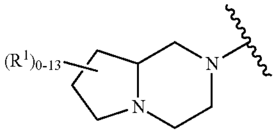
,
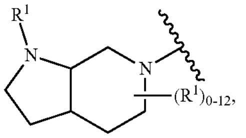
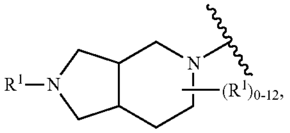
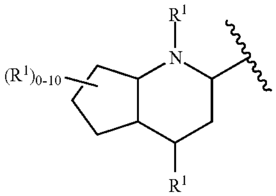
,
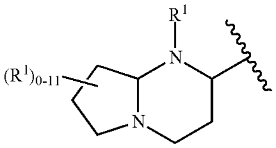
,
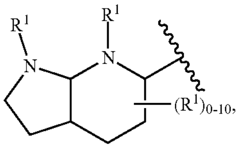
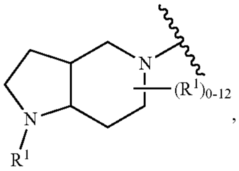
,
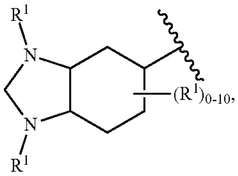
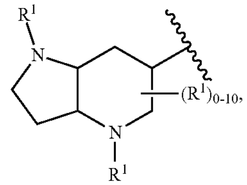
-continued
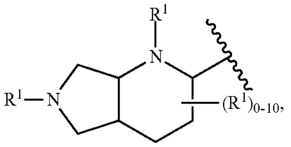
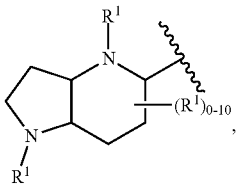
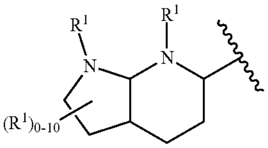
,
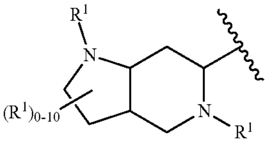
,
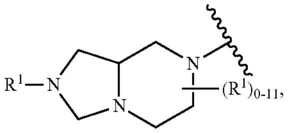
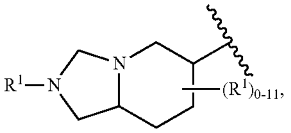
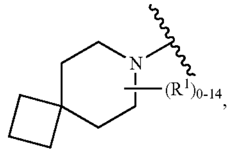
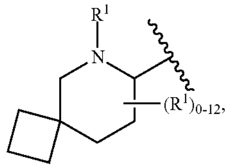
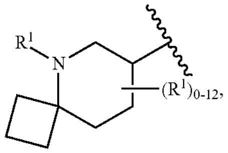
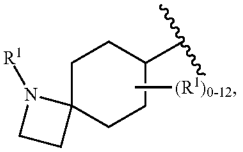
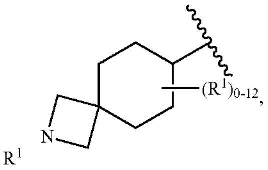
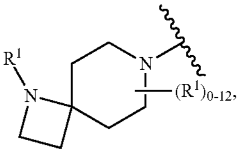
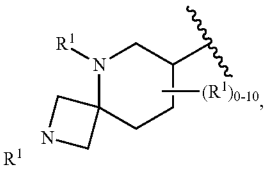
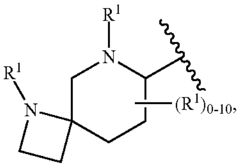
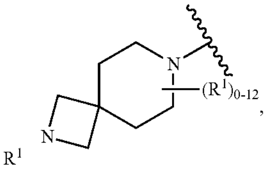
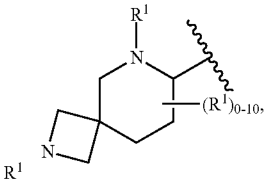
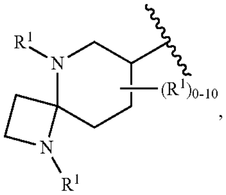

-continued
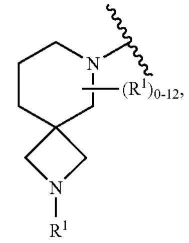
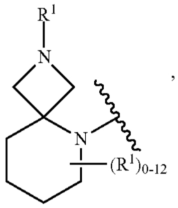
,
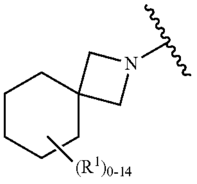
,
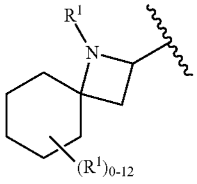
,
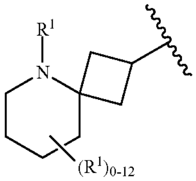
,
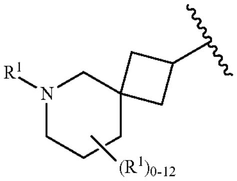
,
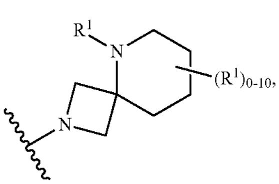
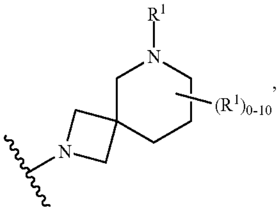
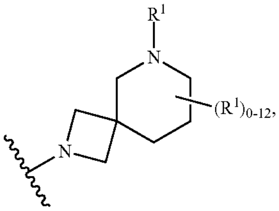
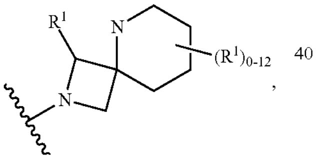
,
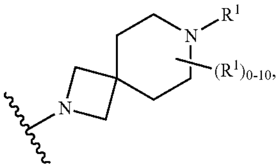
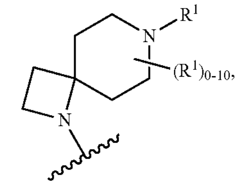
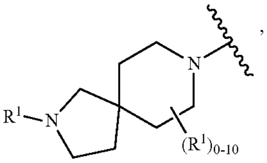
,
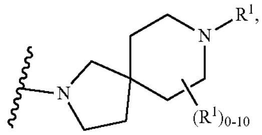
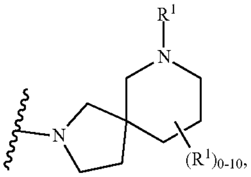
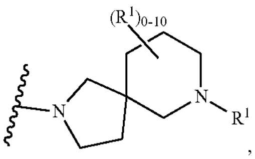
,
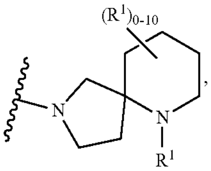
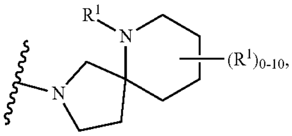
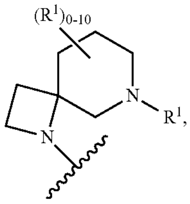
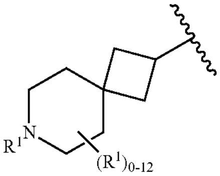
,
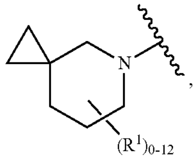
,
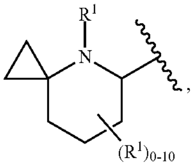
,
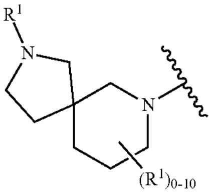
,
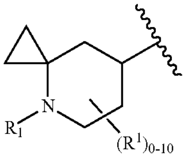
,
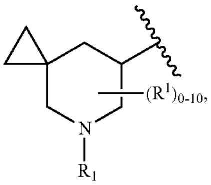
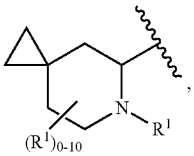
,
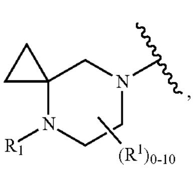
,
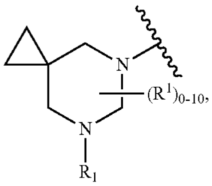
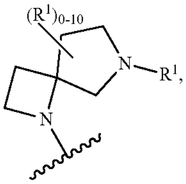
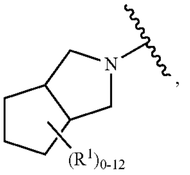
,
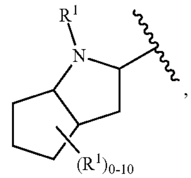
,
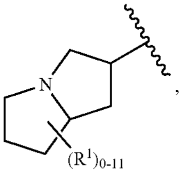
,
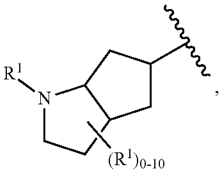
,
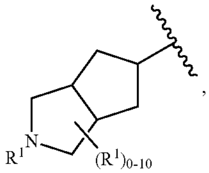
, -continued
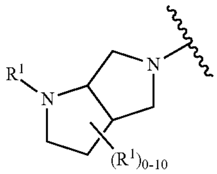,
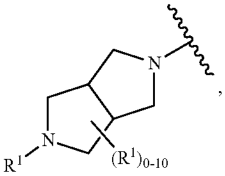,
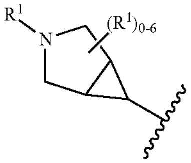,
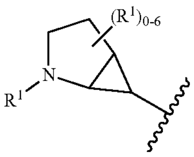,
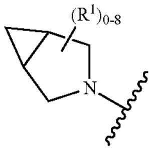,
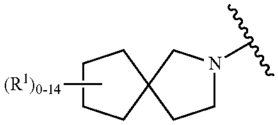,
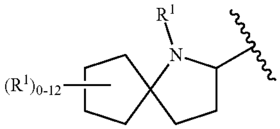,
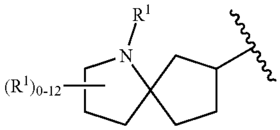,
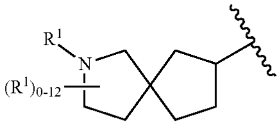,
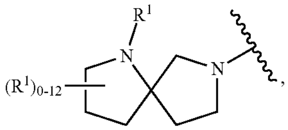,
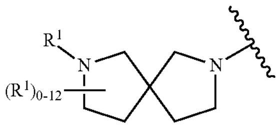,
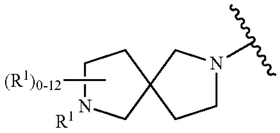,
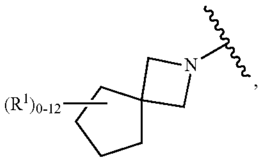,
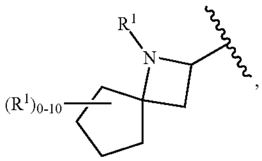,
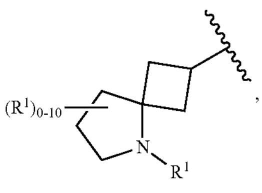,
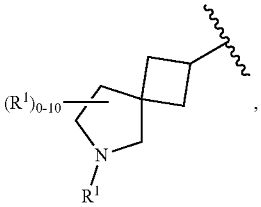,
-continued
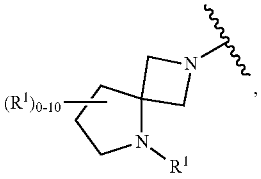,
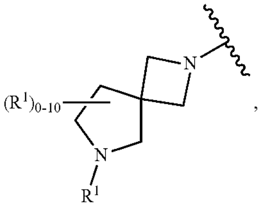,
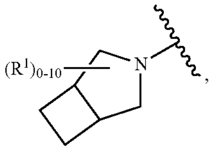,
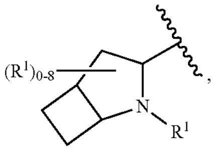,
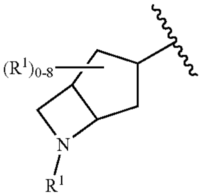,
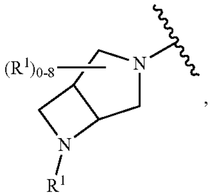,
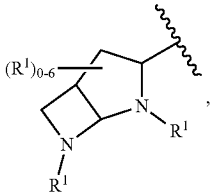,
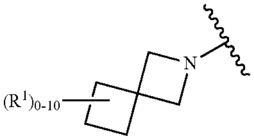,
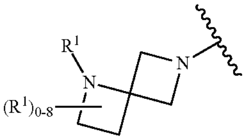,
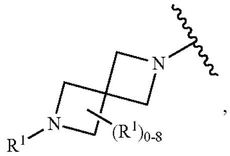,
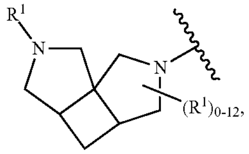
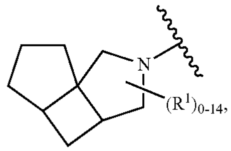
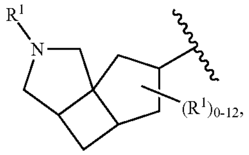
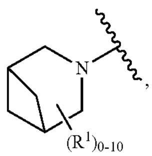,
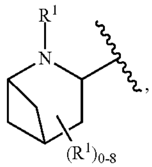,
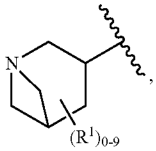,
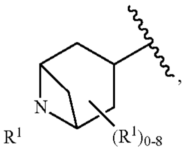,
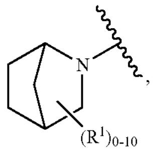,
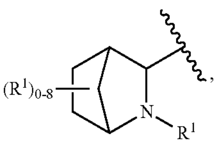,
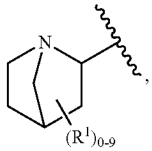, -continued
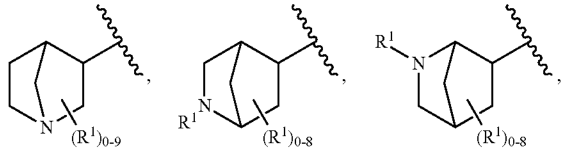
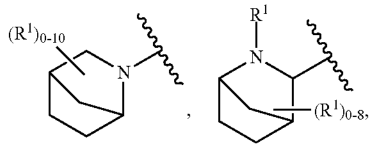
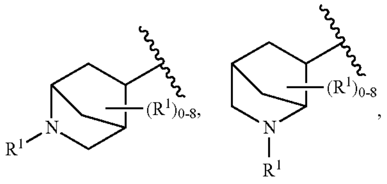
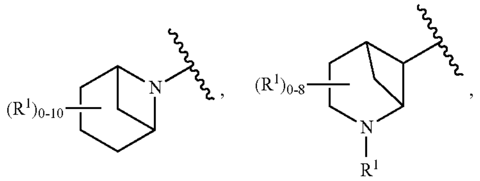
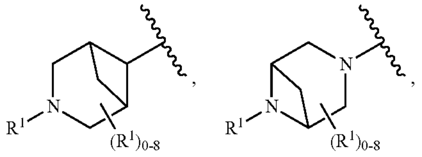
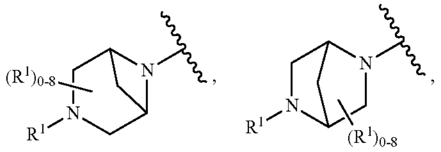
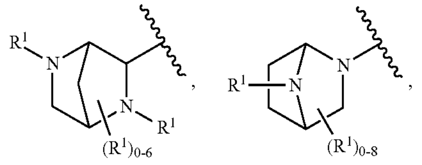
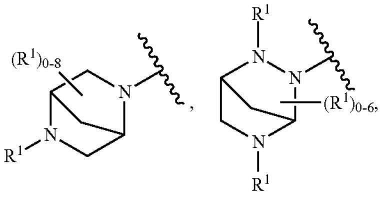
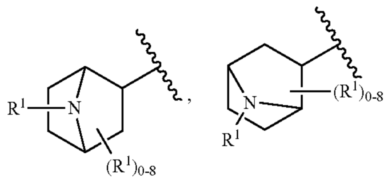
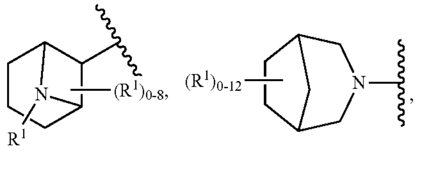
-continued
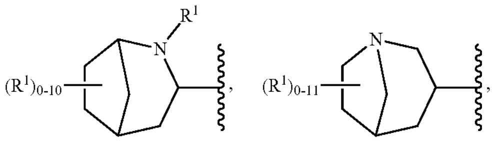
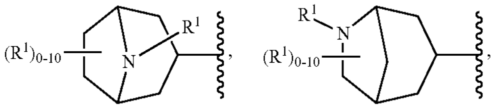
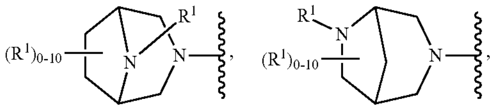
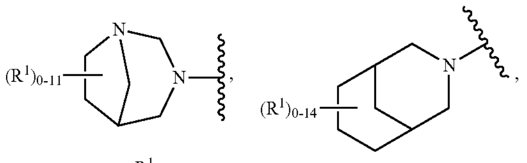
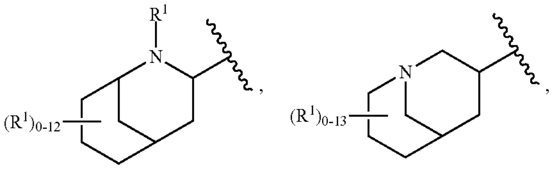
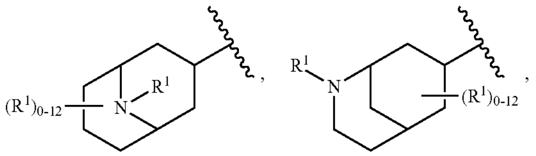
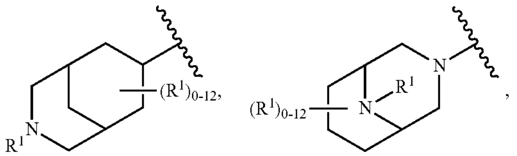
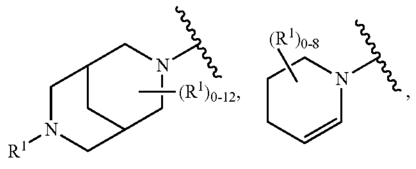
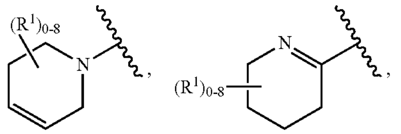
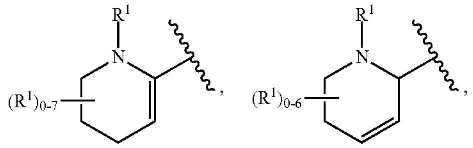
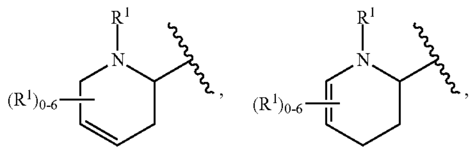
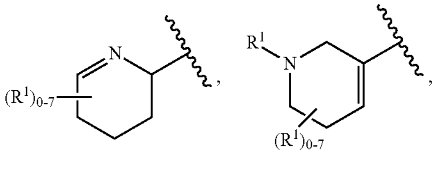

-continued
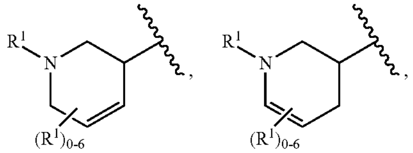
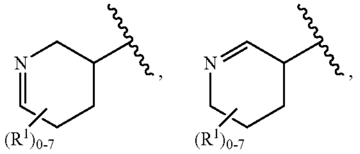
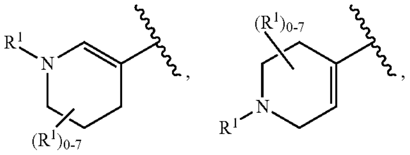
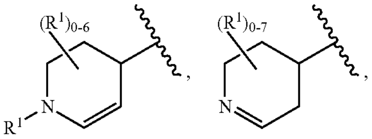
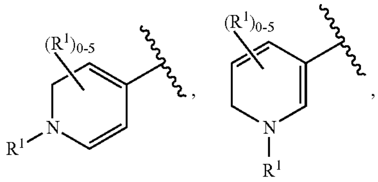
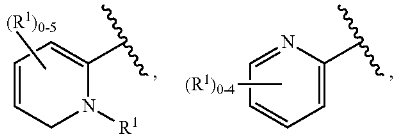
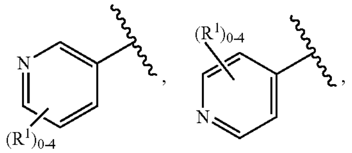
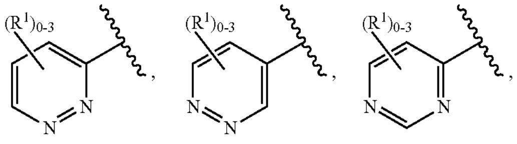
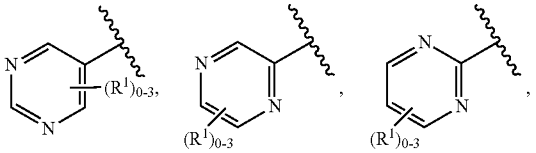
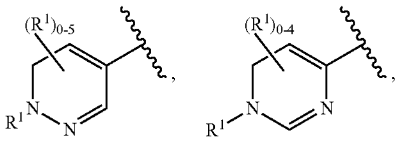
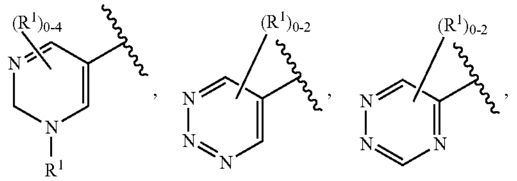
-continued
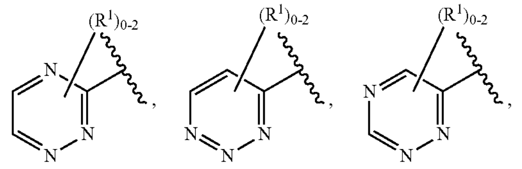
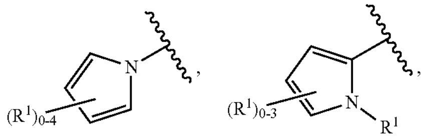
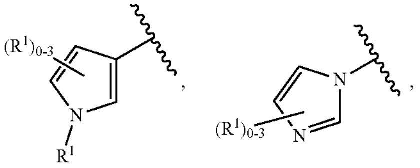
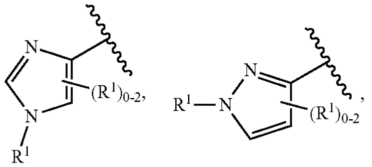
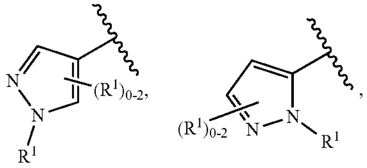
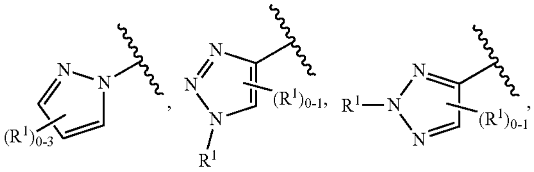
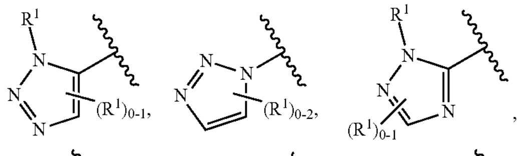
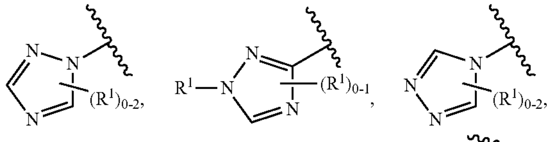
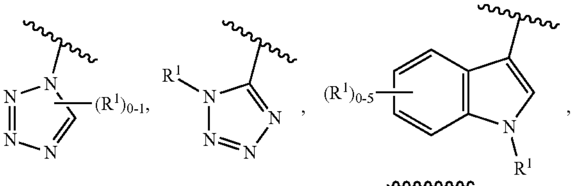
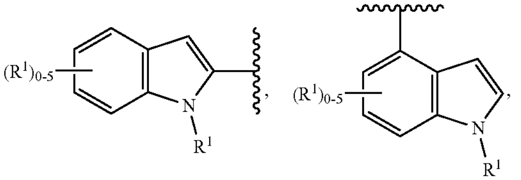

-continued
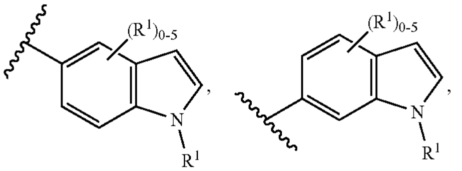
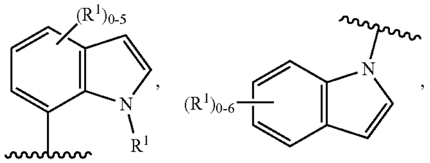
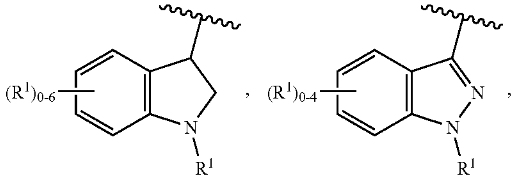
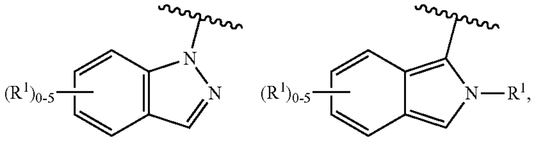
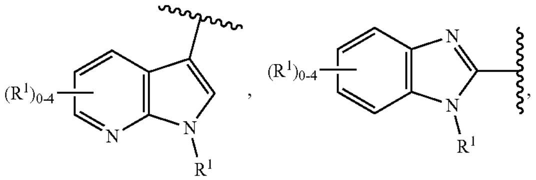
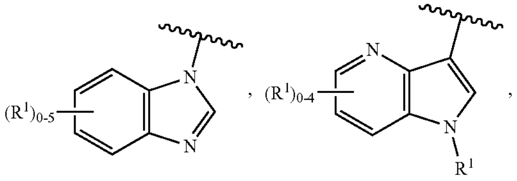
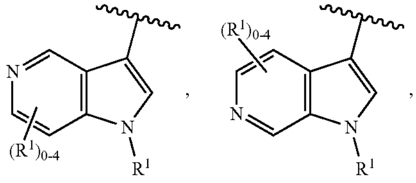
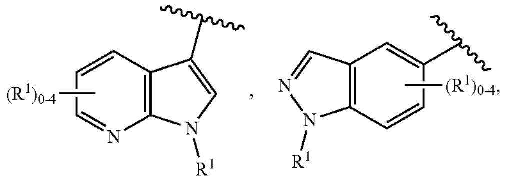
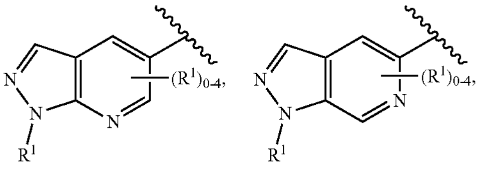
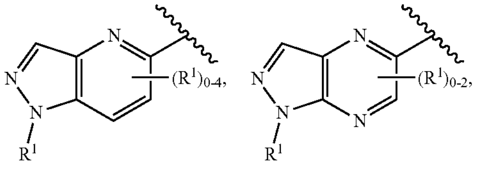
-continued
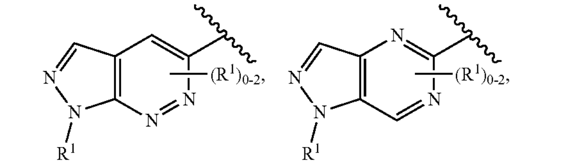
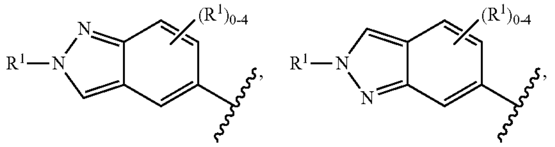
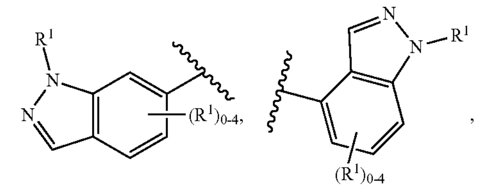
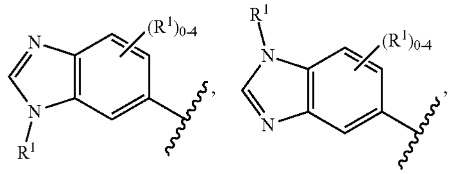
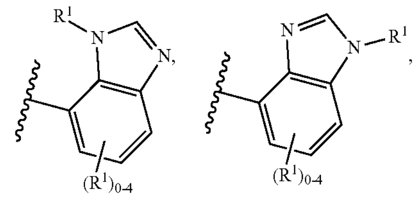
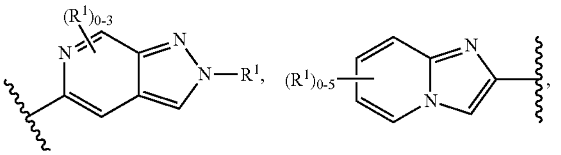
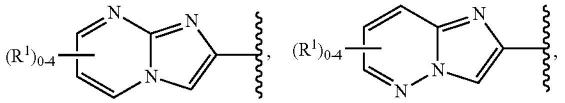
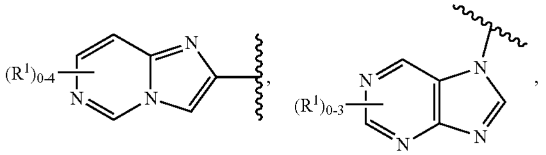
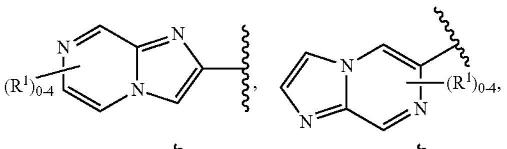
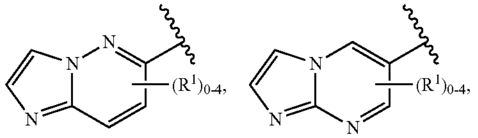
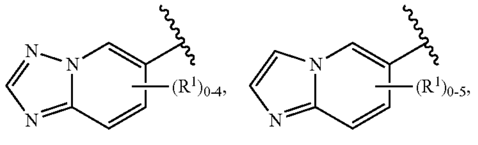

-continued

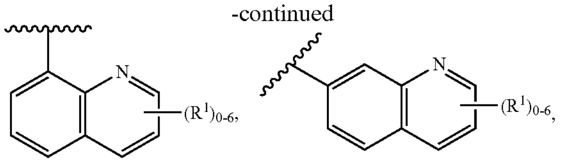

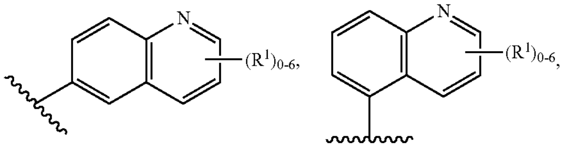

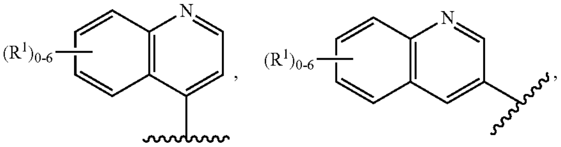

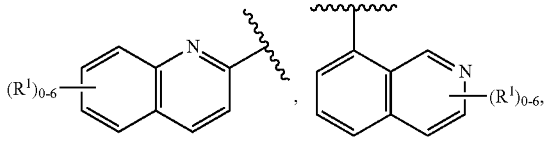

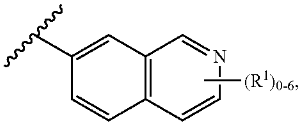

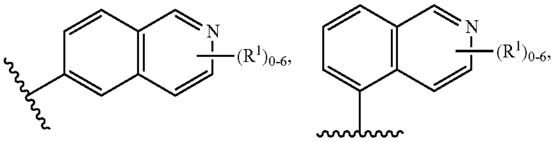

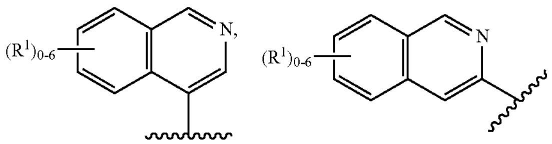

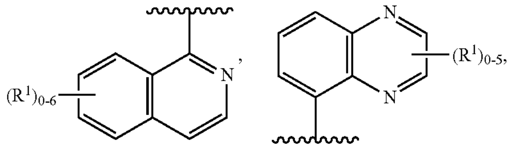

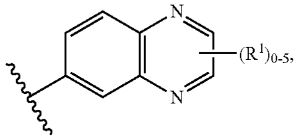

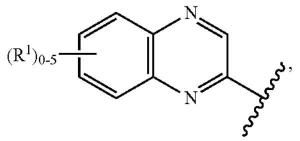

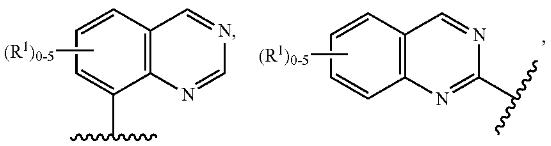

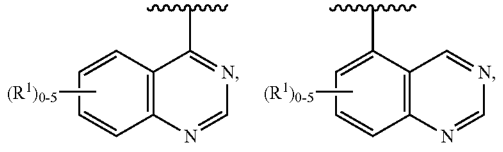

-continued

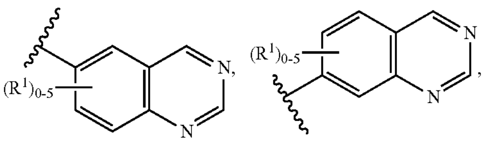

and

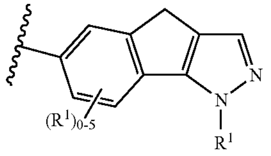

wherein each $R^1$ is as defined herein. In an embodiment, A and B are each independently a saturated, partially saturated, or unsaturated (e.g., aromatic) derivative of one of the rings described above. In an embodiment, A and B are each independently a stereoisomer of one of the rings described above.

In some embodiments, each of A and B are independently selected from:

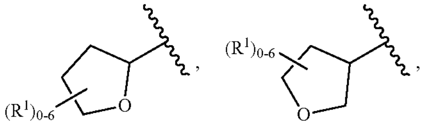

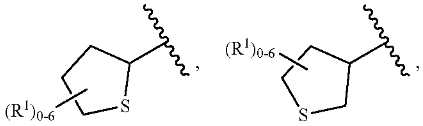

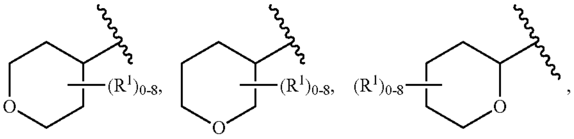

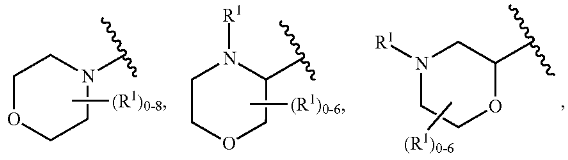

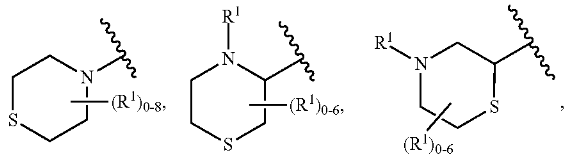

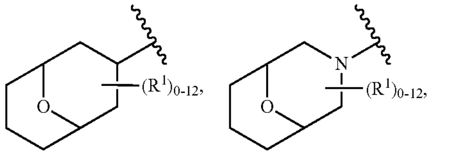

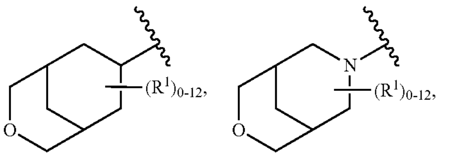

-continued
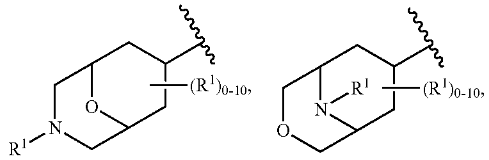
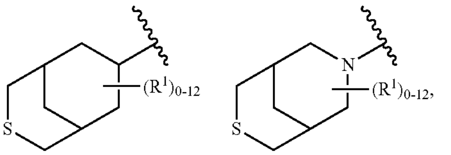
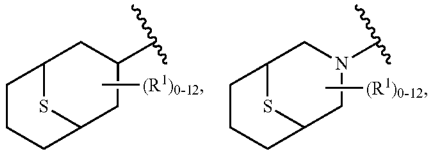
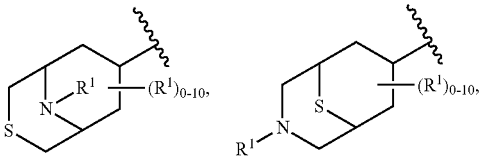
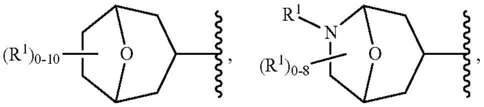
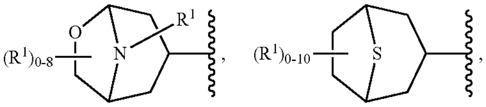
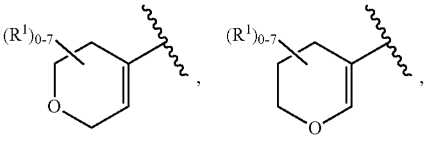
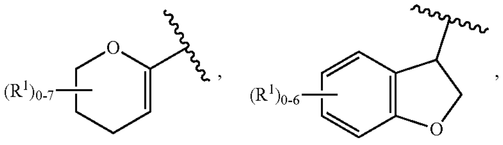
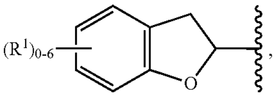
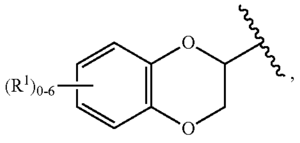
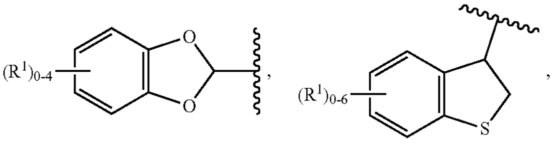
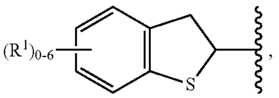
-continued
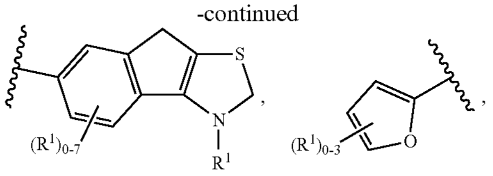
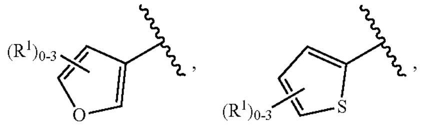
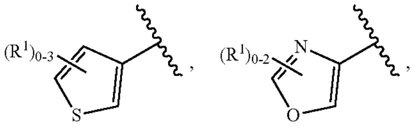
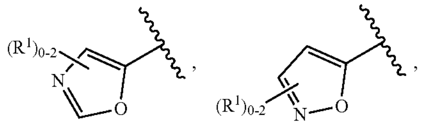
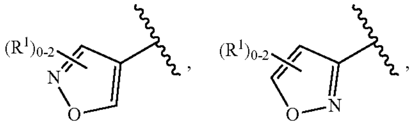
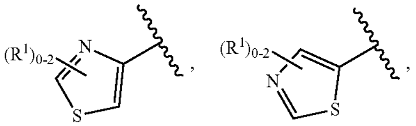
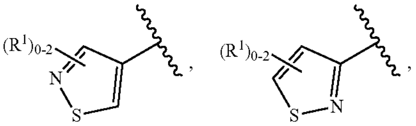
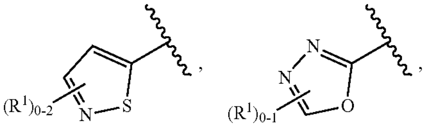
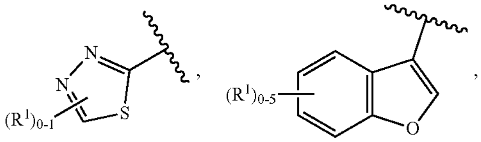
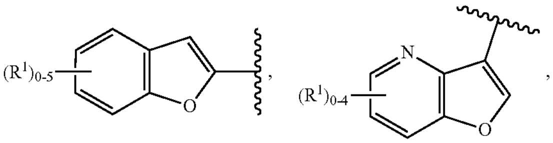
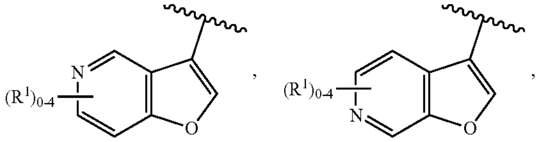
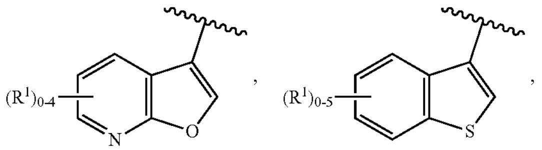
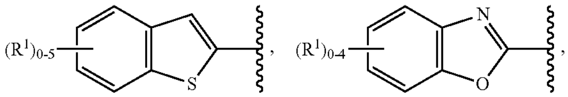

-continued

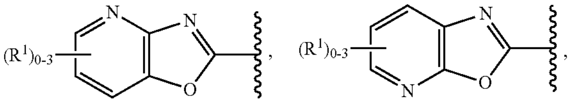

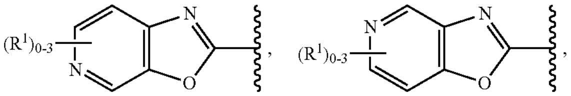

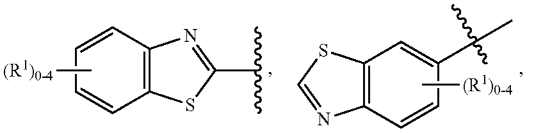

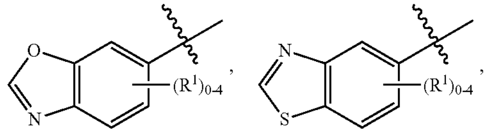

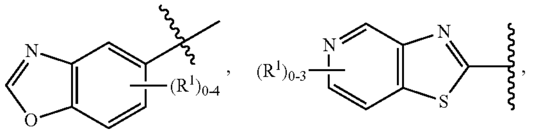

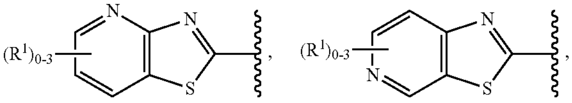

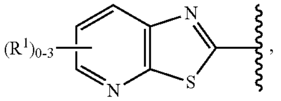

and

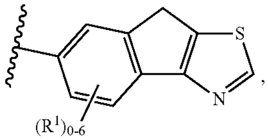

wherein each $R^1$ is as defined herein. In an embodiment, A and B are each independently a saturated, partially saturated, or unsaturated (e.g., aromatic) derivative of one of the rings described above. In an embodiment, A and B are each independently a stereoisomer of one of the rings described above.

In some embodiments, A is selected from

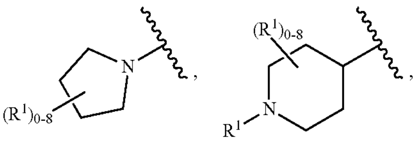

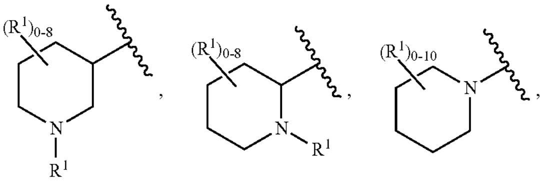

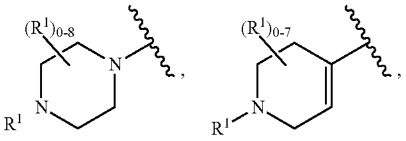

-continued

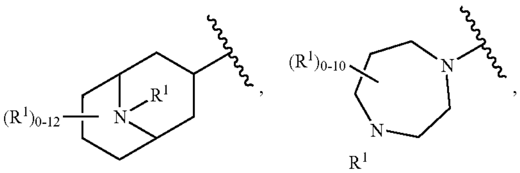

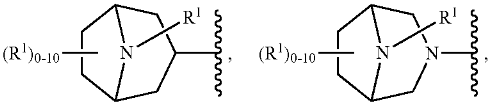

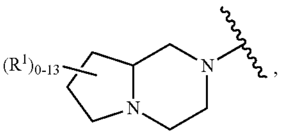

and

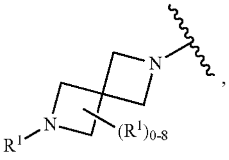

wherein $R^1$ is as defined herein.

In some embodiments, A is selected from

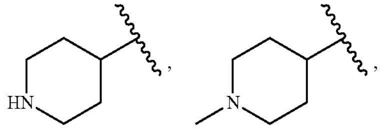

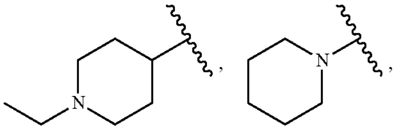

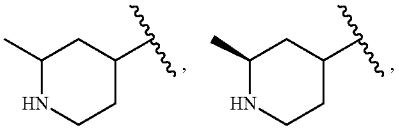

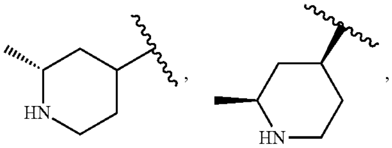

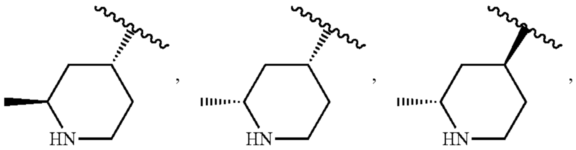

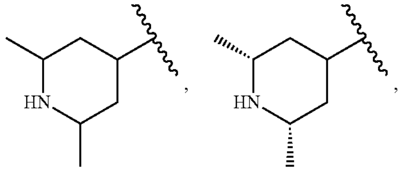

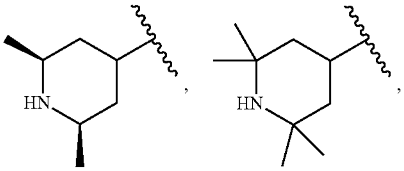

-continued
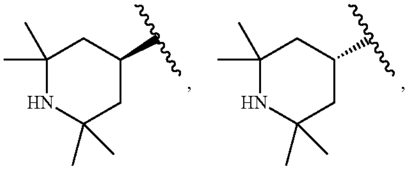
, ,
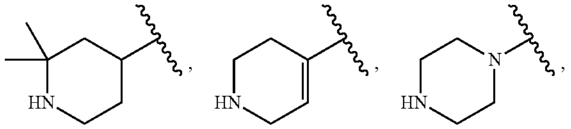
, , ,
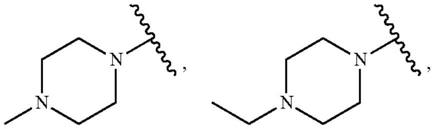
, ,
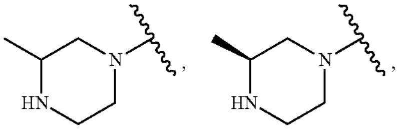
, ,
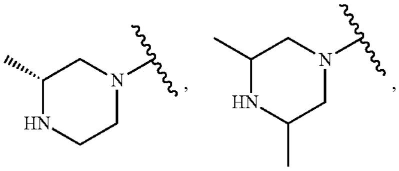
, ,
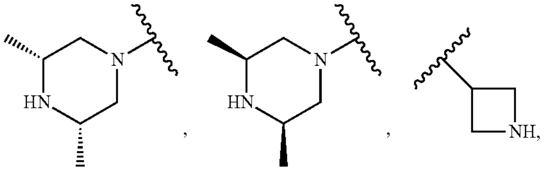
, ,
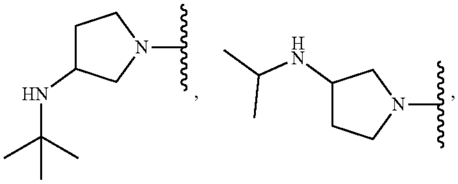
, ,
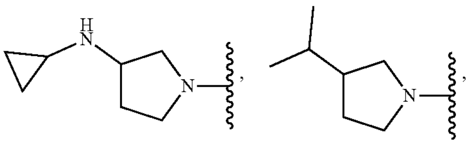
, ,
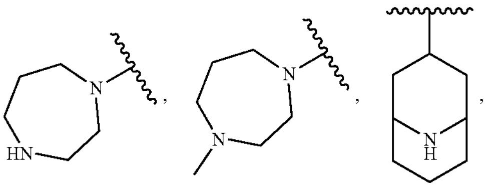
, , ,
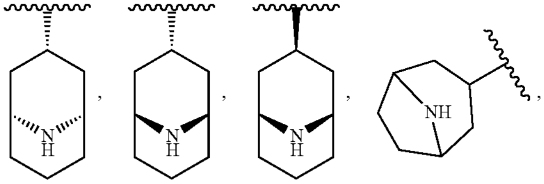
, , , ,
-continued
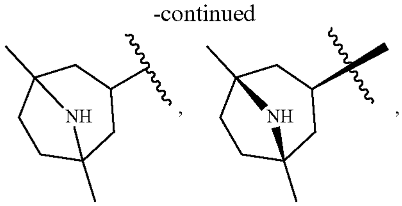
, ,
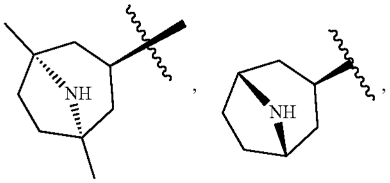
, ,
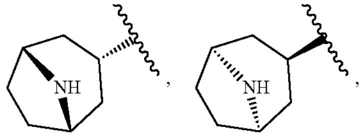
, ,
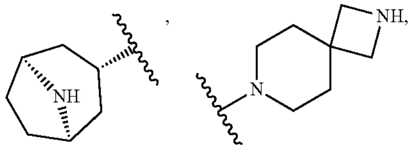
, ,
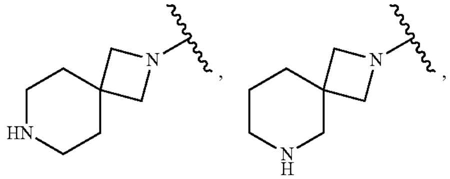
, ,
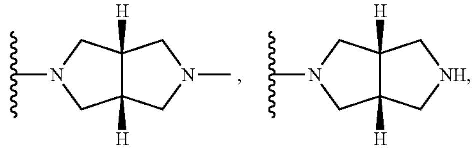
, ,
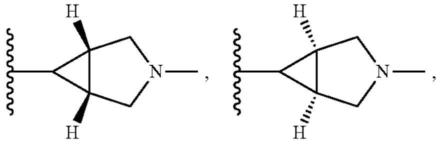
, ,
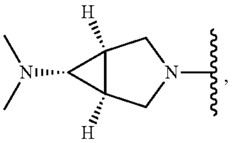
,
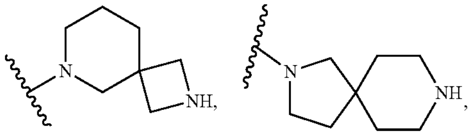
, ,
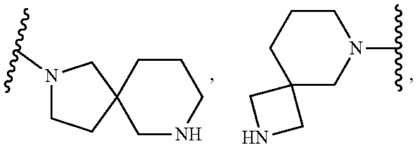
, ,
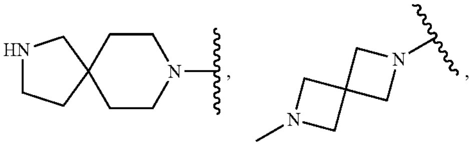
, , -continued
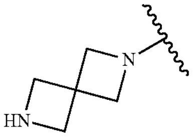, and 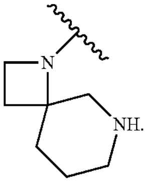
In some embodiments, A is selected from
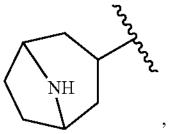, 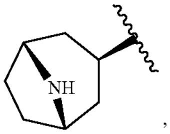, 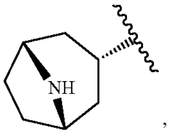, 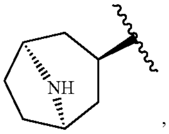, 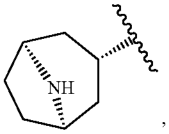, 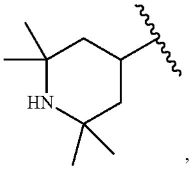, 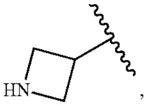, 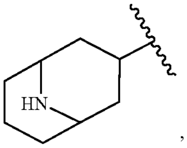, 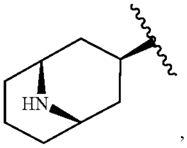, 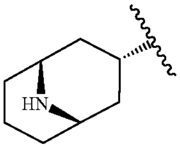, 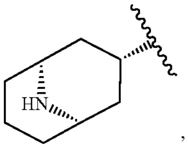, 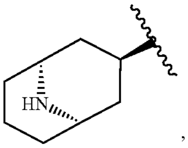, 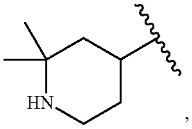, 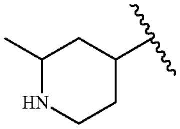, 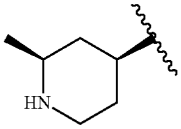, 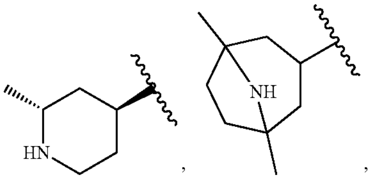, 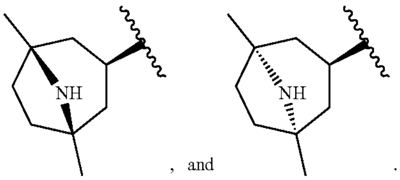.
In some embodiments, A is selected from
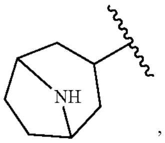, 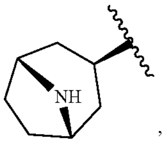, 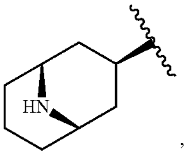,
-continued
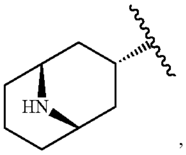, 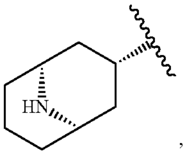, 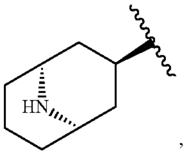, and 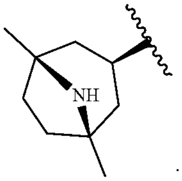.
In some embodiments, A is selected from wherein A is selected from
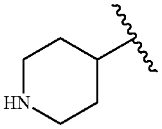, 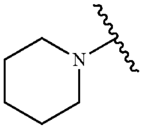, 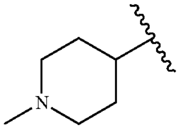, 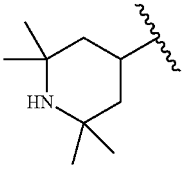, 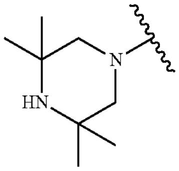, 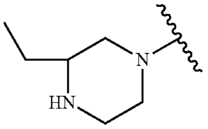, 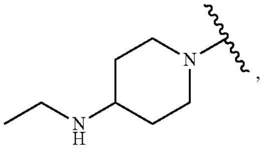, 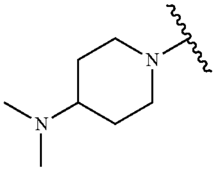, 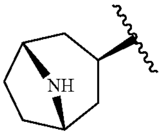, 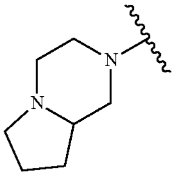, 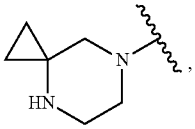, 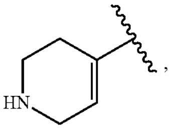, 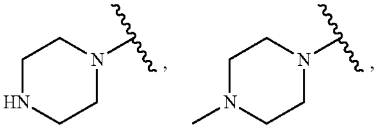, 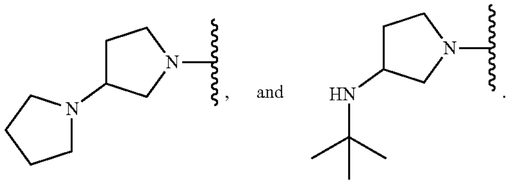.

In some embodiments, A is
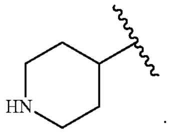
In some embodiments, A is
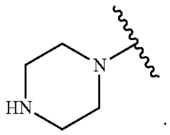
In some embodiments, A is
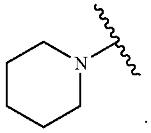 [SMILES: *N1CCCCC1]
In some embodiments, A is
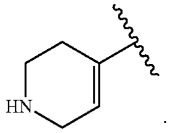
In some embodiments, A is
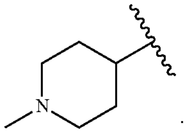
In some embodiments, A is
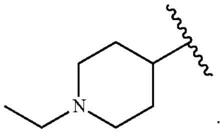 [SMILES: *C1CCN(CC)CC1]
In some embodiments, A is
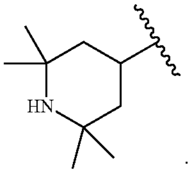 [SMILES: *C1CC(C)(C)NC(C)(C)C1]
In some embodiments, A is
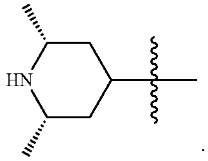
In some embodiments, A is
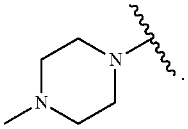 [SMILES: *N1CCN(C)CC1]
In some embodiments, A is
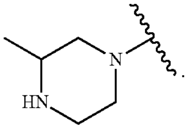 [SMILES: *N1CCNC(C)C1]
In some embodiments, A is
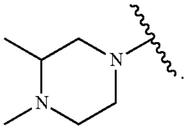 [SMILES: *N1CCN(C)C(C)C1]
In some embodiments, A is
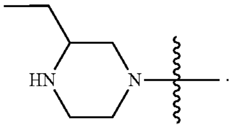 [SMILES: *N1CCNC(CC)C1]
In some embodiments, A is
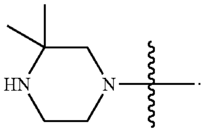

In some embodiments, A is
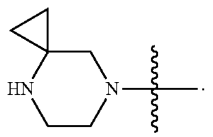 [SMILES: *N1CCNC2(CC2)C1]
In some embodiments, A is
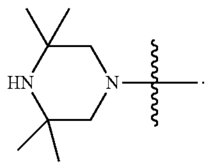 [SMILES: *N1CC(C)(C)NC(C)(C)C1]
In some embodiments, A is
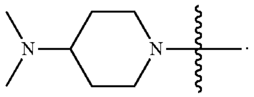 [SMILES: *N1CCC(N(C)C)CC1]
In some embodiments, A is
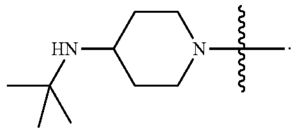 [SMILES: *N1CCC(NC(C)(C)C)CC1]
In some embodiments, A is
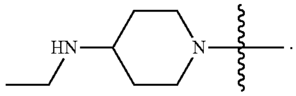 [SMILES: *N1CCC(NCC)CC1]
In some embodiments, A is
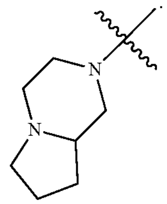 [SMILES: *N1CCN2CCCC2C1]
In some embodiments, A is
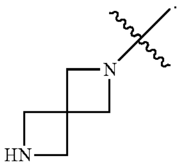
In some embodiments, A is
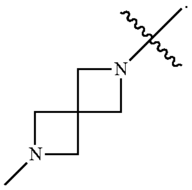 [SMILES: *N1CC2(C1)CN(C)C2]
In some embodiments, A is
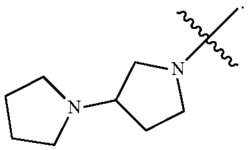 [SMILES: *N1CCC(N2CCCC2)C1]
In some embodiments, A is
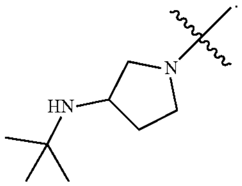 [SMILES: *N1CCC(NC(C)(C)C)C1]
In some embodiments, A is
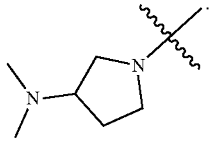 [SMILES: *N1CCC(N(C)C)C1]
In some embodiments, A is
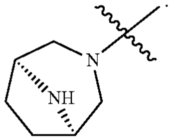 [SMILES: *N1C[C@H]2CC[C@@H](C1)N2]

In some embodiments, A is
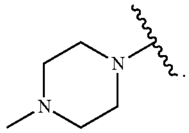 [SMILES: *N1CCN(C)CC1]
In some embodiments, A is
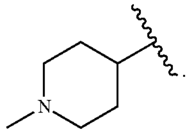 [SMILES: *C1CCN(C)CC1]
In some embodiments, A is
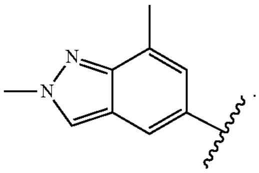 [SMILES: *c1cc(C)c2nn(C)cc2c1]
In some embodiments, A is
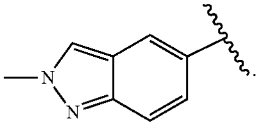 [SMILES: *c1ccc2nn(C)cc2c1]
In some embodiments, B is selected from
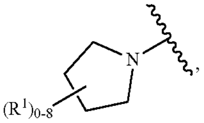 , 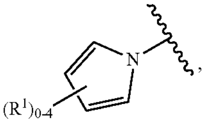 , 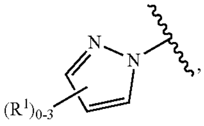 , and 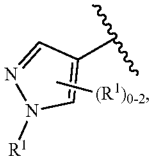 ,
wherein $R^1$ is as defined herein. In some embodiments, B is selected from
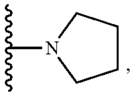 , 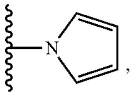 ,
-continued
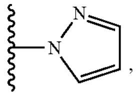 , and 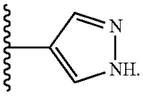
In some embodiments, B is selected from
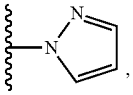 , 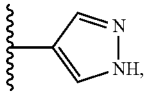 , 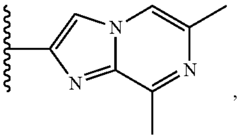 ,
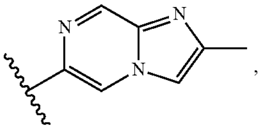 , 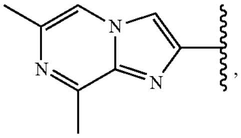 ,
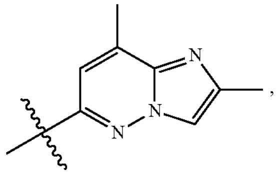 , 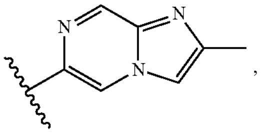 ,
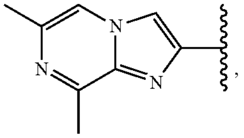 , 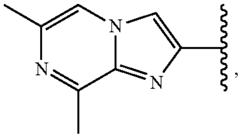 ,
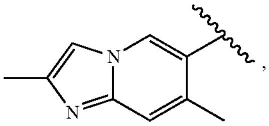 , 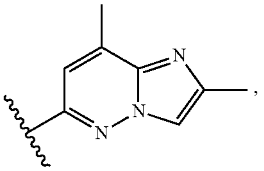 ,
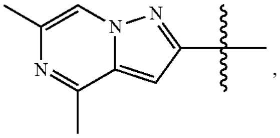 , 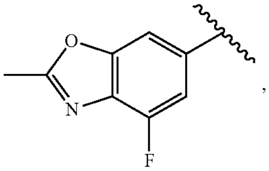 ,
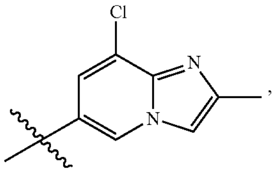 , 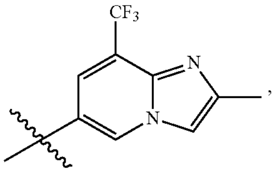 ,
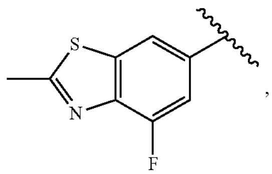 , 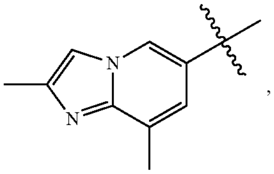 ,
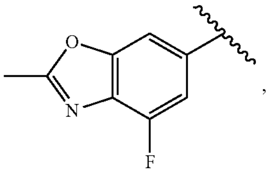 , 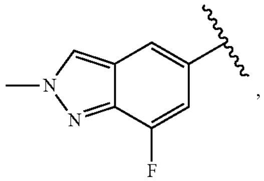 , -continued
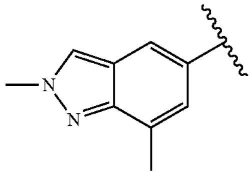
, and
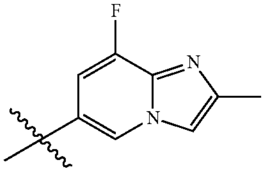
.
In some embodiments, B is selected from
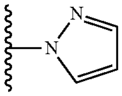
,
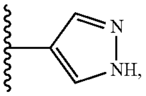
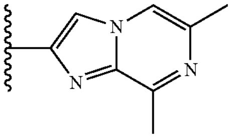
,
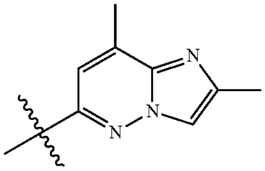
,
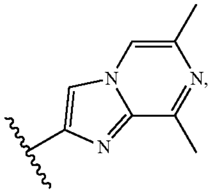
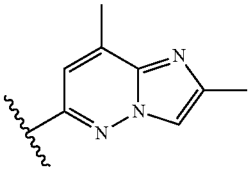
,
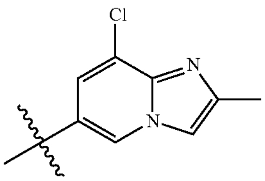
,
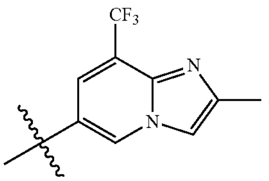
, and
-continued
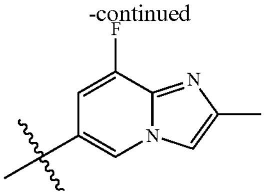
.
In some embodiments, B is
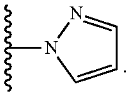
.
In some embodiments, B is
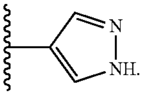 [SMILES: *c1cn[nH]c1]
In some embodiments, B is
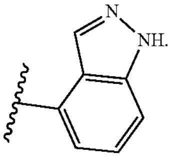 [SMILES: *c1cccc2[nH]ncc12]
In some embodiments, B is
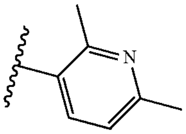
.
In some embodiments, B is
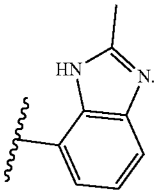 [SMILES: *c1cccc2nc(C)[nH]c12]
In some embodiments, B is
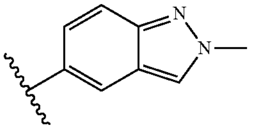
.

In some embodiments, B is
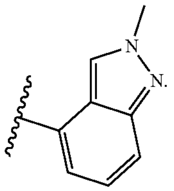 [SMILES: *c1cccc2nn(C)cc12]
In some embodiments, B is
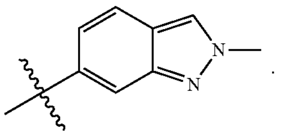 [SMILES: *c1ccc2cn(C)nc2c1]
In some embodiments, B is
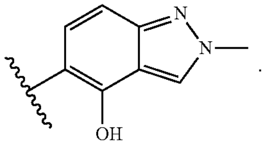 [SMILES: *c1ccc2nn(C)cc2c1O]
In some embodiments, B is
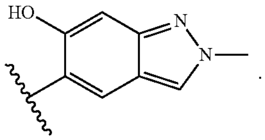 [SMILES: *c1cc2cn(C)nc2cc1O]
In some embodiments, B is
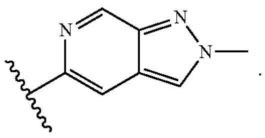 [SMILES: *c1cc2cn(C)nc2cn1]
In some embodiments, B is
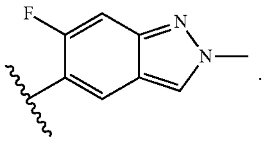 [SMILES: *c1cc2cn(C)nc2cc1F]
In some embodiments, B is
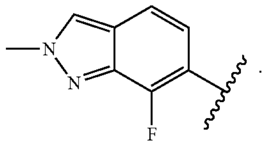 [SMILES: *c1ccc2cn(C)nc2c1F]
In some embodiments, B is
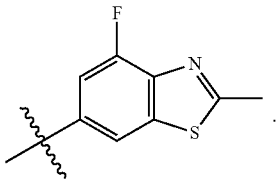 [SMILES: *c1cc(F)c2nc(C)sc2c1]
In some embodiments, B is
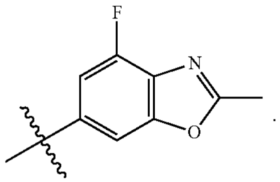 [SMILES: *c1cc(F)c2nc(C)oc2c1]
In some embodiments, B is selected is
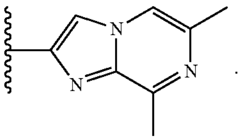
In some embodiments, B is
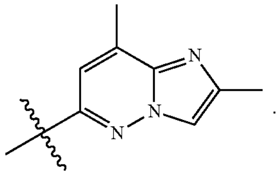 [SMILES: *c1cc(C)c2nc(C)cn2n1]
In some embodiments, B is
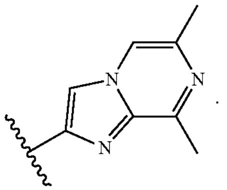 [SMILES: *c1cn2cc(C)nc(C)c2n1]

In some embodiments, B is

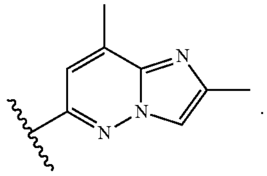 [SMILES: *c1cc(C)c2nc(C)cn2n1]

.

In some embodiments, B is

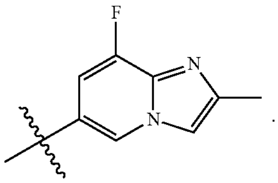 [SMILES: *c1cc(F)c2nc(C)cn2c1]

.

In some embodiments, B is a structure of Formula (A) or Formula (B):

(A)

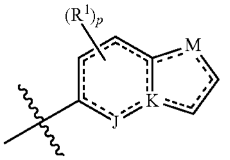

or (B)

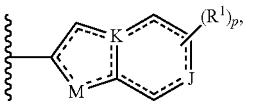

wherein each of J, K, and M is selected from N and C(R'); $R^1$ is as defined above; R' is hydrogen, halo (e.g., fluoro), or $C_1$-$C_6$-alkyl (e.g., methyl); and p is 0, 1, 2, 3, or 4; wherein at least one of J, K, and M is N; and the bonds in the ring comprising J, K, and M may be single or double bonds as valency permits.

In some embodiments, J, K, and M are each independently N. In some embodiments, J is C(R') and K and M are each independently M. In some embodiments, p is 0. In some embodiments, p is 1. In some embodiments, p is 2. In some embodiments, p is 3. In some embodiments, p is 4.

In some embodiments, B is selected from

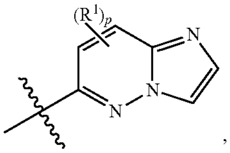

,

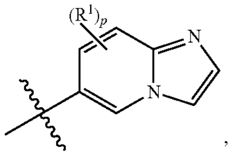

,

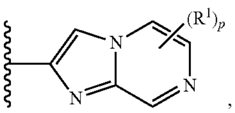

,

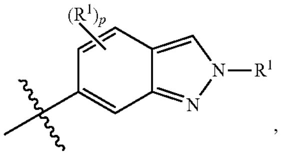

,

-continued

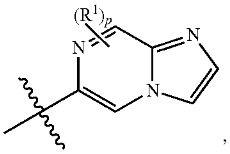

,

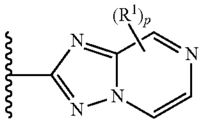

,

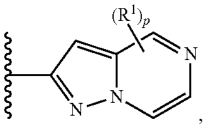

,

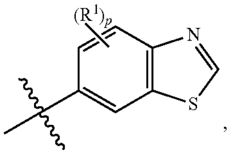

, and

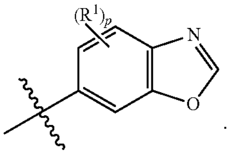

.

In some embodiments, B is

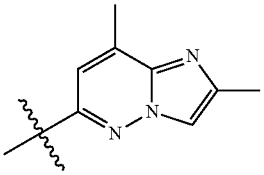

.

In some embodiments, B is

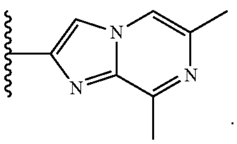 [SMILES: *c1cn2cc(C)nc(C)c2n1]

.

In some embodiments, B is

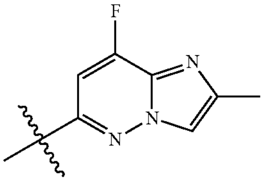

.

In some embodiments, B is

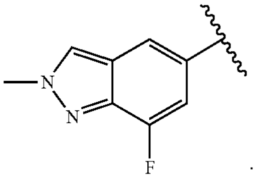 [SMILES: *c1cc(F)c2nn(C)cc2c1]

.

In some embodiments, B is

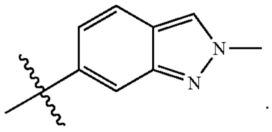 [SMILES: *c1ccc2cn(C)nc2c1]

.

In some embodiments, B is

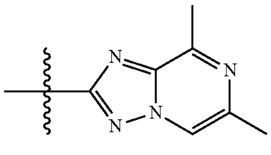

.

In some embodiments, B is

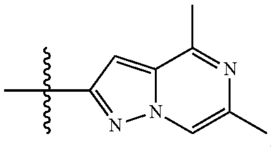

.

In some embodiments, B is

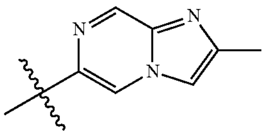

.

In some embodiments, B is

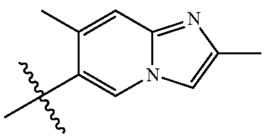

.

In some embodiments, B is

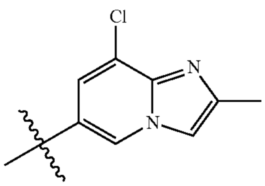

.

In some embodiments, B is

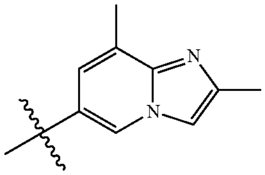

.

In some embodiments, B is

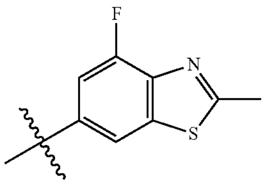

.

In some embodiments, B is

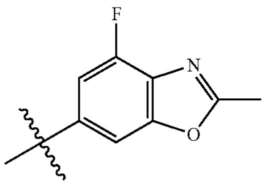

.

As generally described herein, $L^1$ and $L^2$ each independently may be absent or refer to a $C_1$-$C_6$-alkylene, $C_1$-$C_6$-heteroalkylene, —O—, —C(O)—, —N($R^4$)—, —N($R^4$)C(O)—, or —C(O)N($R^4$)— group, wherein each alkylene and heteroalkylene is optionally substituted with one or more $R^5$.

In some embodiments, $L^1$ is absent. In some embodiments, $L^1$ is $C_1$-$C_6$-alkylene (e.g., $C_1$-alkylene, $C_2$-alkylene, $C_3$-alkylene, $C_4$-alkylene, $C_5$-alkylene, or $C_6$-alkylene). In some embodiments, $L^1$ is unsubstituted $C_1$-$C_6$ alkylene. In some embodiments, $L^1$ is substituted $C_1$-$C_6$-alkylene, e.g., $C_1$-$C_6$ alkylene substituted with one or more $R^5$. In some embodiments, $L^1$ is $C_1$-alkylene substituted with one $R^5$. In some embodiments, $L^1$ is —$CH_2$— (or methylene). In some embodiments, $L^1$ is —C(O)— (or carbonyl).

In some embodiments, $L^1$ is absent, $C_1$-$C_6$-alkylene, $C_1$-$C_6$-heteroalkylene, —N($R^4$)C(O)—, or —C(O)N($R^4$)—, wherein each alkylene and heteroalkylene is optionally substituted with one or more $R^5$.

In some embodiments, $L^1$ is $C_1$-$C_6$ heteroalkylene (e.g., $C_1$-heteroalkylene, $C_2$-heteroalkylene, $C_3$-heteroalkylene, $C_4$-heteroalkylene, $C_5$-heteroalkylene, or $C_6$-heteroalkylene). In some embodiments, $L^1$ is unsubstituted $C_1$-$C_6$ heteroalkylene. In some embodiments, $L^1$ is substituted heteroalkylene, e.g., $C_1$-$C_6$ heteroalkylene substituted with one or more $R^5$. In some embodiments, the heteroalkylene comprises 1 or more heteroatoms. In some embodiments, the heteroalkylene comprises one or more of oxygen, sulfur, nitrogen, boron, silicon, or phosphorus. In some embodiments, $L^1$ is —N($R^4$)C(O)—. In some embodiments, $L^1$ is —C(O)N($R^4$)—. In some embodiments, $L^1$ is —C(O)N(H)—.

In some embodiments, $L^1$ is oxygen. In some embodiments, $L^1$ is nitrogen which is optionally substituted with $R^4$.

In some embodiments, $L^1$ is nitrogen substituted with $R^4$. In some embodiments, $L^1$ is —$N(R^4)$—, e.g., —$N(CH_3)$—. In some embodiments, $L^1$ is —NH—. In some embodiments, $L^1$ is —O—.

In some embodiments, $L^2$ is absent, $C_1$-$C_6$-alkylene, $C_1$-$C_6$-heteroalkylene, —$N(R^4)C(O)$—, or —$C(O)N(R^4)$—, wherein each alkylene and heteroalkylene is optionally substituted with one or more $R^5$. In some embodiments, $L^2$ is unsubstituted $C_1$-$C_6$ heteroalkylene. In some embodiments, $L^2$ is substituted heteroalkylene, e.g., $C_1$-$C_6$ heteroalkylene substituted with one or more $R^5$. In some embodiments, the heteroalkylene comprises 1 or more heteroatoms. In some embodiments, the heteroalkylene comprises one or more of oxygen, sulfur, nitrogen, boron, silicon, or phosphorus. In some embodiments, $L^2$ is —$N(R^4)C(O)$—. In some embodiments, $L^2$ is —$C(O)N(R^4)$—. In some embodiments, $L^2$ is —C(O)N(H)—.

In some embodiments, $L^2$ is nitrogen which is optionally substituted with $R^4$. In some embodiments, $L^2$ is nitrogen substituted with $R^4$. In some embodiments, $L^2$ is —$N(R^4)$—, e.g., —$N(CH_3)$—. In some embodiments, $L^2$ is —NH—.

As generally described herein, X, Y, and Z each independently refer to $C(R^{3a})$, $C(R^{3a})(R^{3b})$, N, or $N(R^{3c})$, or O, and W refers to $C(R^{3a})$, $C(R^{3a})(R^{3b})$, N, or $N(R^{3c})$. In some embodiments, at least one of X, Y, and Z is either N or $N(R^{3c})$. In some embodiments, at least one of X, Y, and Z is O. In some embodiments, at least two of X, Y, and Z is N or $N(R^{3c})$. In some embodiments, X is N. In some embodiments, X is $N(R^{3c})$. In some embodiments, X is O. In some embodiments, X is $C(R^{3a})$ (e.g., CH). In some embodiments, X is $C(R^{3a})(R^{3b})$. In some embodiments, Y is N. In some embodiments, Y is $N(R^{3c})$. In some embodiments, Y is $C(R^{3a})$ (e.g., CH). In some embodiments, Y is $C(R^{3a})C(R^{3b})$. In some embodiments, Z is N. In some embodiments, Z is $N(R^{3c})$. In some embodiments, Z is $C(R^{3a})$ (e.g., CH). In some embodiments, Z is $C(R^{3a})C(R^{3b})$. In some embodiments, two of X, Y, and Z are N, and the other of X, Y, and Z is $C(R^{3a})$ (e.g., CH). In some embodiments, one of X, Y, and Z is $C(R^{3a})$ (e.g., CH), and the others of X, Y, and Z are each independently N. In some embodiments, X and Y are each independently N, and Z is $C(R^{3a})$ (e.g., CH). In some embodiments, X is $C(R^{3a})$ (e.g., CH), and Y and Z are each independently N.

In some embodiments, X, Y, and Z are each independently N or $C(R^{3a})$, wherein at least one of X, Y, and Z is N and the bonds in the ring comprising X, Y, and Z may be single or double bonds as valency permits.

In some embodiments, X is $C(R^{3a})$, Y is $C(R^{3a})$, and Z is O. In some embodiments, X is $C(R^{3a})$, Y is $C(R^{3a})$, Z is O, and y is 0. In some embodiments, X is $C(R^{3a})$, Y is $C(R^{3a})$, Z is O, and the bond between X and Y is a double bond. In some embodiments, X is $C(R^{3a})$, Y is $C(R^{3a})$, Z is O, and the bond between Y and Z is a single bond.

In some embodiments, y is 0.

In some embodiments, $R^1$ is hydrogen. In some embodiments, $R^1$ is $C_1$-$C_6$-alkyl. In some embodiments, $R^1$ is $C_2$-$C_6$-alkenyl. In some embodiments, $R^1$ is $C_2$-$C_6$-alkynyl. In some embodiments, $R^1$ is $C_1$-$C_6$-heteroalkyl. In some embodiments, $R^1$ is $C_1$-$C_6$-haloalkyl (e.g., —$CF_3$). In some embodiments, $R^1$ is $C_1$-alkyl (e.g., methyl). In some embodiments, $R^1$ is unsubstituted $C_1$-$C_6$-alkyl, unsubstituted $C_2$-$C_6$-alkenyl, unsubstituted $C_2$-$C_6$-alkynyl, unsubstituted $C_1$-$C_6$-heteroalkyl, or unsubstituted $C_1$-$C_6$-haloalkyl. In some embodiments, $R^1$ is $C_1$-$C_6$-alkyl substituted with one or more $R^6$. In some embodiments, $R^1$ is $C_2$-$C_6$-alkenyl substituted with one or more $R^6$. In some embodiments, $R^1$ is $C_2$-$C_6$-alkynyl substituted with one or more $R^6$. In some embodiments, $R^1$ is $C_1$-$C_6$-heteroalkyl substituted with one or more $R^6$. In some embodiments, $R^1$ is $C_1$-$C_6$-haloalkyl substituted with one or more $R^6$. In some embodiments, R, is methyl.

In some embodiments, $R^1$ is cycloalkyl (e.g., 3-7 membered cycloalkyl). In some embodiments, $R^1$ is heterocyclyl (e.g., 3-7 membered heterocyclyl). In some embodiments, $R^1$ is aryl. In some embodiments, $R^1$ is $C_1$-$C_6$ alkylene-aryl (e.g., benzyl). In some embodiments, $R^1$ is $C_1$-$C_6$ alkenylene-aryl. In some embodiments, $R^1$ is $C_1$-$C_6$ alkylene-heteroaryl. In some embodiments, $R^1$ is heteroaryl. In some embodiments, $R^1$ is unsubstituted cycloalkyl, unsubstituted heterocyclyl, unsubstituted aryl, unsubstituted $C_1$-$C_6$ alkylene-aryl, unsubstituted $C_1$-$C_6$ alkenylene-aryl, unsubstituted $C_1$-$C_6$ alkylene-heteroaryl, or unsubstituted heteroaryl. In some embodiments, $R^1$ is cycloalkyl substituted with one or more $R^6$. In some embodiments, $R^1$ is heterocyclyl substituted with one or more $R^6$. In some embodiments, $R^1$ is aryl substituted with one or more $R^6$. In some embodiments, $R^1$ is $C_1$-$C_6$ alkylene-aryl substituted with one or more $R^6$. In some embodiments, $R^1$ is $C_1$-$C_6$ alkenylene-aryl substituted with one or more $R^6$. In some embodiments, $R^1$ is $C_1$-$C_6$ alkylene-heteroaryl substituted with one or more $R^6$. In some embodiments, $R^1$ is heteroaryl substituted with one or more $R^6$.

In some embodiments, $R^1$ is —$OR^A$. In some embodiments, $R^1$ is —$NR^BR^C$ (e.g., $NH_2$ or $NMe_2$). In some embodiments, $R^1$ is —$NR^BC(O)R^D$. In some embodiments, $R^1$ is-$C(O)NR^BR^C$. In some embodiments, $R^1$ is —$C(O)R^D$. In some embodiments, $R^1$ is —$C(O)OR^D$. In some embodiments, $R^1$ is —$SR^E$. In some embodiments, $R^1$ is —$S(O)_x R^D$. In some embodiments, $R^1$ is halo, e.g., fluoro, chloro, bromo, or iodo. In some embodiments, $R^1$ is cyano. In some embodiments, $R^1$ is nitro (—$NO_2$). In some embodiments, $R^1$ is oxo.

In some embodiments, two $R^1$ groups, together with the atoms to which they are attached, form a 3-7-membered cycloalkyl. In some embodiments, two $R^1$ groups, together with the atoms to which they are attached, form a 3-7-membered heterocyclyl. In some embodiments, two R, groups, together with the atoms to which they are attached, form a 5- or 6-membered aryl. In some embodiments, two $R^1$ groups, together with the atoms to which they are attached, form a 5-or 6-membered heteroaryl. The cycloalkyl, heterocyclyl, aryl, or heteroaryl may be substituted with one or more $R^6$.

In some embodiments, $R^2$ is hydrogen. In some embodiments, $R^2$ is halo (e.g., fluoro, chloro, bromo, or iodo). In some embodiments, $R^2$ is cyano. In some embodiments, $R^2$ is $C_1$-$C_6$-alkyl. In some embodiments, $R^2$ is $C_2$-$C_6$-alkenyl. In some embodiments, $R^2$ is $C_2$-$C_6$-alkynyl.

In some embodiments, $R^2$ is —$OR^A$ (e.g., —OH). In some embodiments, $R^{3a}$, $R^{3b}$, or both are independently hydrogen, $C_1$-$C_6$-alkyl, $C_1$-$C_6$-heteroalkyl, $C_1$-$C_6$-haloalkyl, halo, cyano, —$OR^A$, —$NR^BR^C$, —$C(O)R^D$, or —$C(O)OR^D$. In some embodiments, $R^{3a}$ and $R^{3b}$ are each independently hydrogen or $C_1$-$C_6$-alkyl. In some embodiments, $R^{3a}$ is hydrogen. In some embodiments, $R^{3b}$ is hydrogen. In some embodiments, $R^{3a}$ is $C_1$-$C_6$-alkyl (e.g., methyl). In some embodiments, $R^{3b}$ is $C_1$-$C_6$-alkyl (e.g., methyl). In some embodiments, $R^{3a}$ is halo (e.g., fluoro, chloro, bromo, or iodo). In some embodiments, $R^{3b}$ is halo (e.g., fluoro, chloro, bromo, or iodo). In some embodiments, $R^{3a}$ is cyano. In some embodiments, $R^{3b}$ is cyano. In some embodiments, $R^{3a}$ is —$OR^A$ (e.g., —OH). In some embodiments, $R^{3b}$ is —$OR^A$ (e.g., —OH). In some embodiments, $R^{3a}$ is —$NR^B R^C$. In some embodiments, $R^{3b}$ is —$NR^BR^C$. In some embodiments, $R^{3a}$ is —$C(O)R^D$. In some embodiments, $R^{3b}$ is —C(O)$R^D$. In some embodiments, $R^{3a}$ is —C(O)O$R^D$. In some embodiments, $R^{3b}$ is —C(O)O$R^D$.

In some embodiments, each of $R^{3a}$ and $R^{3b}$, together with the carbon atom to which they are attached, form an oxo group.

In some embodiments, $R^{3c}$ is hydrogen. In some embodiments, $R^{3c}$ is $C_1$-$C_6$-alkyl. In some embodiments, $R^{3c}$ is methyl.

In some embodiments, $R^4$ is hydrogen. In some embodiments, $R^4$ is $C_1$-$C_6$ alkyl. In some embodiments, $R^4$ is $C_1$-$C_6$ haloalkyl (e.g., —$CF_3$ or —$CHF_2$). In some embodiments, $R^4$ is methyl.

In some embodiments, $R^5$ is hydrogen. In some embodiments, $R^5$ is $C_1$-$C_6$-alkyl. In some embodiments, $R^5$ is $C_1$-$C_6$-heteroalkyl. In some embodiments, $R^5$ is $C_1$-$C_6$-haloalkyl. In some embodiments, $R^5$ is cycloalkyl. In some embodiments, $R^5$ is halo (e.g., fluoro, chloro, bromo, or iodo). In some embodiments, $R^5$ is cyano. In some embodiments, $R^5$ is oxo. In some embodiments, $R^5$ is —O$R^A$. In some embodiments, $R^5$ is —N$R^B$$R^C$. In some embodiments, $R^5$ is —C(O)$R^D$ or —C(O)O$R^D$.

In some embodiments, $R^6$ is $C_1$-$C_6$-alkyl. In some embodiments, $R^6$ is $C_2$-$C_6$-alkenyl. In some embodiments, $R^6$ is $C_2$-$C_6$-alkynyl. In some embodiments, $R^6$ is $C_1$-$C_6$-heteroalkyl. In some embodiments, $R^6$ is $C_1$-$C_6$-haloalkyl. In some embodiments, $R^6$ is unsubstituted $C_1$-$C_6$-alkyl, unsubstituted $C_2$-$C_6$-alkenyl, unsubstituted $C_2$-$C_6$-alkynyl, unsubstituted $C_1$-$C_6$-haloalkyl, or unsubstituted $C_1$-$C_6$-heteroalkyl. In some embodiments, $R^6$ is $C_1$-$C_6$-alkyl substituted with one or more $R^{11}$. In some embodiments, $R^6$ is $C_2$-$C_6$-alkenyl substituted with one or more $R^{11}$. In some embodiments, $R^6$ is $C_2$-$C_6$-alkynyl substituted with one or more $R^{11}$. In some embodiments, $R^6$ is $C_1$-$C_6$-haloalkyl substituted with one or more $R^{11}$. In some embodiments, $R^6$ is $C_1$-$C_6$-heteroalkyl substituted with one or more $R^{11}$.

In some embodiments, $R^6$ is cycloalkyl. In some embodiments, $R^6$ is heterocyclyl. In some embodiments, $R^6$ is aryl. In some embodiments, $R^6$ is heteroaryl. In some embodiments, $R^6$ is unsubstituted cycloalkyl, unsubstituted heterocyclyl, unsubstituted aryl, or unsubstituted heteroaryl. In some embodiments, $R^6$ is cycloalkyl substituted with one or more $R^{11}$. In some embodiments, $R^6$ is heterocyclyl substituted with one or more $R^{11}$. In some embodiments, $R^6$ is aryl substituted with one or more $R^{11}$. In some embodiments, $R^6$ is heteroaryl substituted with one or more $R^{11}$.

In some embodiments, $R^6$ is halo (e.g., fluoro, chloro, bromo, or iodo). In some embodiments, $R^6$ is cyano. In some embodiments, $R^6$ is oxo. In some embodiments, $R^6$ is —O$R^A$. In some embodiments, $R^6$ is —N$R^B$$R^C$. In some embodiments, $R^6$ is —N$R^B$C(O)$R^D$. In some embodiments, $R^6$ is —$NO_2$. In some embodiments, $R^6$ is —C(O)N$R^B$$R^C$. In some embodiments, $R^6$ is —C(O)$R^D$. In some embodiments, $R^6$ is —C(O)O$R^D$. In some embodiments, $R^6$ is —S$R^E$. In some embodiments, $R^6$ is —$S(O)_x$$R^D$.

In some embodiments, $R^7$ is $C_1$-$C_6$-alkyl. In some embodiments, $R^7$ is halo (e.g., fluoro, chloro, bromo, or iodo). In some embodiments, $R^7$ is cyano. In some embodiments, $R^7$ is oxo. In some embodiments, $R^7$ is —O$R^{A1}$ (e.g., —OH).

In some embodiments, $R^{11}$ is $C_1$-$C_6$-alkyl. In some embodiments, $R^{11}$ is $C_1$-$C_6$-heteroalkyl. In some embodiments, $R^{11}$ is $C_1$-$C_6$-haloalkyl (e.g., —$CF_3$). In some embodiments, $R^{11}$ is cycloalkyl. In some embodiments, $R^{11}$ is heterocyclyl. In some embodiments, $R^{11}$ is aryl. In some embodiments, $R^{11}$ is heteroaryl. In some embodiments, $R^{11}$ is halo. In some embodiments, $R^{11}$ is cyano. In some embodiments, $R^{11}$ is oxo. In some embodiments, $R^{11}$ is —O$R^A$.

In some embodiments, $R^A$ is hydrogen. In some embodiments, $R^A$ is $C_1$-$C_6$ alkyl (e.g., methyl). In some embodiments, $R^A$ is $C_1$-$C_6$ haloalkyl. In some embodiments, $R^A$ is aryl. In some embodiments, $R^A$ is heteroaryl. In some embodiments, $R^A$ is $C_1$-$C_6$ alkylene-aryl (e.g., benzyl). In some embodiments, $R^A$ is $C_1$-$C_6$ alkylene-heteroaryl. In some embodiments, $R^A$ is C(O)$R^D$. In some embodiments, $R^A$ is —$S(O)_x$$R^D$.

In some embodiments, $R^B$, $R^C$, or both are independently hydrogen, $C_1$-$C_6$-alkyl, $C_1$-$C_6$-heteroalkyl, cycloalkyl, heterocyclyl, or —O$R^A$. In some embodiments, each of $R^B$ and $R^C$ is independently hydrogen. In some embodiments, each of $R^B$ and $R^C$ is independently $C_1$-$C_6$ alkyl. In some embodiments, one of $R^B$ and $R^C$ is hydrogen, and the other of $R^B$ and $R^C$ is $C_1$-$C_6$ alkyl. In some embodiments, $R^B$ and $R^C$ together with the atom to which they are attached form a 3-7-membered heterocyclyl ring optionally substituted with one or more of $R^7$.

In some embodiments, $R^D$, $R^E$, or both are independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, heteroaryl, $C_1$-$C_6$ alkylene-aryl (e.g., benzyl), or $C_1$-$C_6$ alkylene-heteroaryl. In some embodiments, each of $R^D$ and $R^E$ is independently hydrogen. In some embodiments, each of $R^D$ and $R^E$ is independently $C_1$-$C_6$ alkyl. In some embodiments, $R^D$ is hydrogen. In some embodiments, $R^E$ is hydrogen. In some embodiments, $R^D$ is $C_1$-$C_6$ alkyl (e.g., methyl). In some embodiments, $R^E$ is $C_1$-$C_6$ alkyl (e.g., methyl). In some embodiments, $R^D$ is $C_1$-$C_6$ heteroalkyl. In some embodiments, $R^E$ is $C_1$-$C_6$ heteroalkyl. In some embodiments, $R^D$ is $C_1$-$C_6$ haloalkyl. In some embodiments, $R^E$ is $C_1$-$C_6$ haloalkyl. In some embodiments, $R^D$ is cycloalkyl. In some embodiments, $R^E$ is cycloalkyl. In some embodiments, $R^D$ is heterocyclyl. In some embodiments, $R^E$ is heterocyclyl. In some embodiments, $R^D$ is aryl. In some embodiments, $R^E$ is aryl. In some embodiments, $R^D$ is heteroaryl. In some embodiments, $R^E$ is heteroaryl. In some embodiments, $R^D$ is $C_1$-$C_6$ alkylene-aryl (e.g., benzyl). In some embodiments, $R^E$ is $C_1$-$C_6$ alkylene-aryl (e.g., benzyl). In some embodiments, $R^D$ is $C_1$-$C_6$ alkylene-heteroaryl. In some embodiments, $R^E$ is $C_1$-$C_6$ alkylene-heteroaryl.

In some embodiments, $R^{A1}$ is hydrogen. In some embodiments, $R^{A1}$ is $C_1$-$C_6$-alkyl (e.g., methyl).

In some embodiments, m is 0, 1, or 2. In some embodiments, m is 0. In some embodiments, m is 1. In some embodiments, m is 2. In some embodiments, x is 0, 1, or 2. In some embodiments, x is 0. In some embodiments, x is 1. In some embodiments, x is 2. In some embodiments y is 0 or 1. In some embodiments, y is 0.

In some embodiments, the compound of Formula (I) is a compound of Formula (I-a):

(I-a)

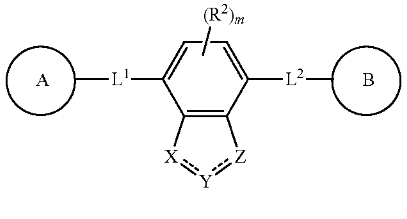

or a pharmaceutically acceptable salt, solvate, hydrate, tautomer, or stereoisomer thereof, wherein:

A and B are each independently cycloalkyl, heterocyclyl, aryl, or heteroaryl, each of which is optionally substituted with one or more $R^1$;

X, Y, and Z are each independently $C(R^{3a})$, $C(R^{3a})(R^{3b})$, N, $N(R^{3c})$, or O, wherein at least one of X, Y, and Z is N, $N(R^{3c})$, or O, and the bonds in the ring comprising X, Y, and Z may be single or double bonds as valency permits;

each of $L^1$ and $L^2$ is independently absent, $C_1$-$C_6$-alkylene, $C_1$-$C_6$-heteroalkylene, —O—, —C(O)—, —$N(R^4)$—, —$N(R^4)C(O)$—, or —$C(O)N(R^4)$—, wherein each alkylene and heteroalkylene is optionally substituted with one or more R;

each $R^1$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, $C_1$-$C_6$ alkylene-aryl, $C_1$-$C_6$ alkenylene-aryl, $C_1$-$C_6$ alkylene-heteroaryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkylene, alkenyl, alkynyl, heteroalkyl, haloalkyl, cycloalkyl, heterocyclyl, aryl, and heteroaryl is optionally substituted with one or more $R^6$; or two $R^1$ groups, together with the atoms to which they are attached, form a 3-7-membered cycloalkyl, heterocyclyl, aryl, or heteroaryl, wherein each cycloalkyl, heterocyclyl, aryl, and heteroaryl is optionally substituted with one or more $R^6$;

each $R^2$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, halo, cyano, or —$OR^A$;

$R^{3a}$ and $R^{3b}$ are each independently hydrogen, $C_1$-$C_6$-alkyl, $C_1$-$C_6$-heteroalkyl, $C_1$-$C_6$-haloalkyl, halo, cyano, —$OR^A$, —$NR^BR^C$, —$C(O)R^D$, or —$C(O)OR^D$; or each of $R^{3a}$ and $R^{3b}$, together with the carbon atom to which they are attached, form an oxo group;

$R^{3c}$ is hydrogen or $C_1$-$C_6$-alkyl;

each $R^4$ is independently hydrogen, $C_1$-$C_6$-alkyl, or $C_1$-$C_6$-haloalkyl;

each $R^5$ is independently hydrogen, $C_1$-$C_6$-alkyl, $C_1$-$C_6$-heteroalkyl, $C_1$-$C_6$-haloalkyl, cycloalkyl, halo, cyano, oxo, —$OR^A$, —$NR^BR^C$, —$C(O)R^D$, or —$C(O)OR^D$;

each $R^6$ is independently $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkenyl, alkynyl, heteroalkyl, haloalkyl, cycloalkyl, heterocyclyl, aryl, and heteroaryl is optionally substituted with one or more $R^{11}$;

each $R^7$ is $C_1$-$C_6$-alkyl, halo, cyano, oxo, or —$OR^{A1}$;

each $R^{11}$ is independently $C_1$-$C_6$-alkyl, $C_1$-$C_6$-heteroalkyl, $C_1$-$C_6$-haloalkyl, cycloalkyl, heterocyclyl, aryl, heteroaryl, halo, cyano, oxo, or —$OR^A$;

each $R^A$ is independently hydrogen, $C_1$-$C_6$ alkyl, $C_1$-$C_6$ haloalkyl, aryl, heteroaryl, $C_1$-$C_6$ alkylene-aryl, $C_1$-$C_6$ alkylene-heteroaryl, —$C(O)R^D$, or —$S(O)_xR^D$;

each of $R^B$ and $R^C$ is independently hydrogen, $C_1$-$C_6$ alkyl, $C_1$-$C_6$ heteroalkyl, cycloalkyl, heterocyclyl, or —$OR^A$; or $R^B$ and $R^C$ together with the atom to which they are attached form a 3-7-membered heterocyclyl ring optionally substituted with one or more $R^7$;

each $R^D$ and $R^E$ is independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, heteroaryl, $C_1$-$C_6$ alkylene-aryl, or $C_1$-$C_6$ alkylene-heteroaryl;

each $R^{A1}$ is hydrogen or $C_1$-$C_6$-alkyl;

m is 0, 1, or 2; and x is 0, 1, or 2.

In some embodiments, A is selected from

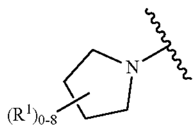, 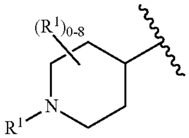,

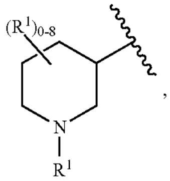, 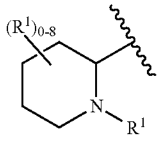, 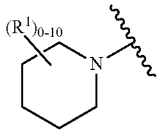,

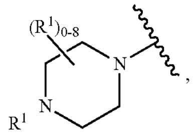, 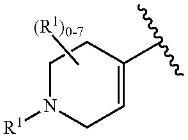,

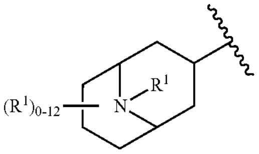, 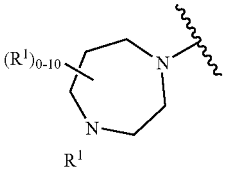,

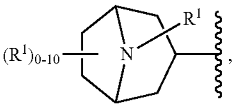, 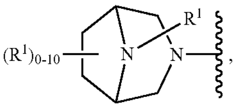,

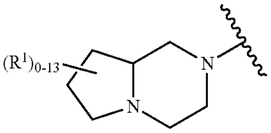, and 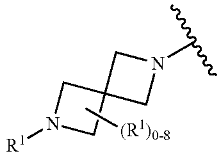, wherein $R^1$ is as defined herein.

In some embodiments, A is selected from

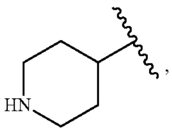, 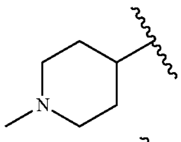,

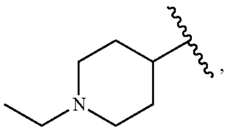, 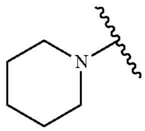,

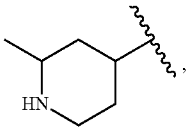, 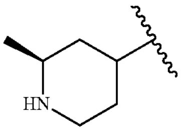,

-continued
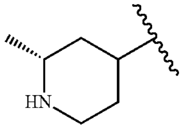
,
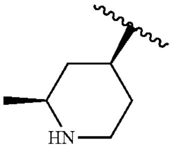
,
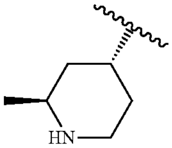
,
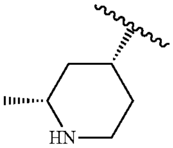
,
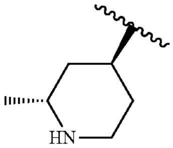
,
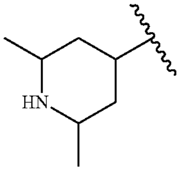
,
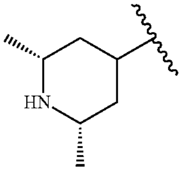
,
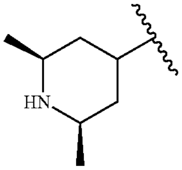
,
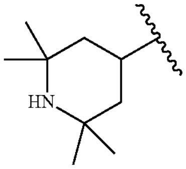
,
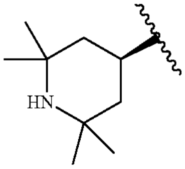
,
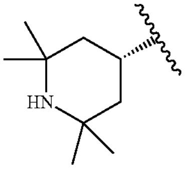
,
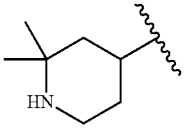
,
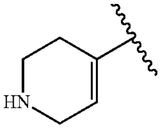
,
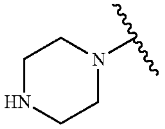
,
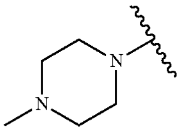
,
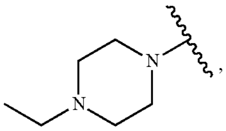
,
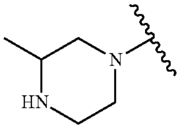
,
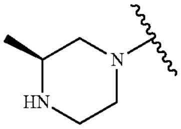
,
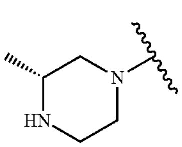
,
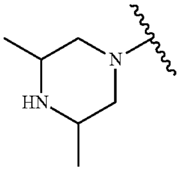
,
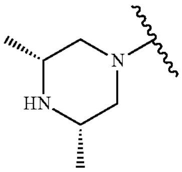
,
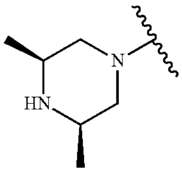
,
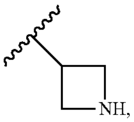
,
-continued
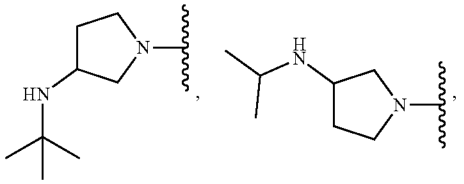
, ,
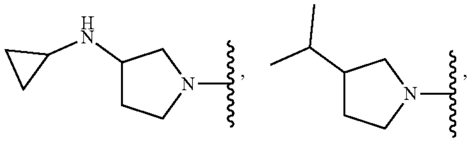
, ,
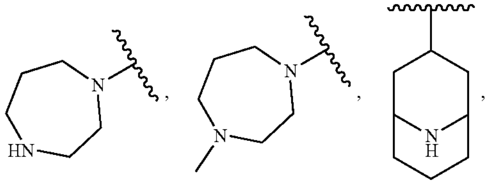
, , ,
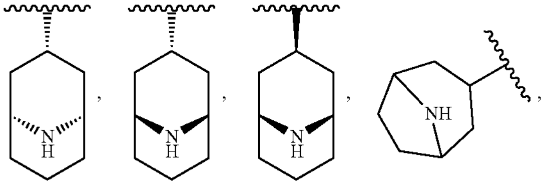
, , , ,
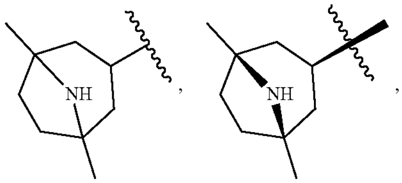
, ,
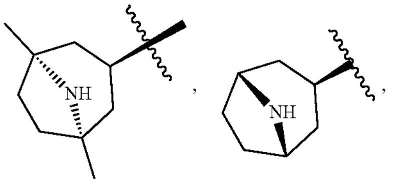
, ,
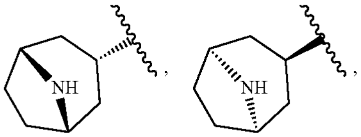
, ,
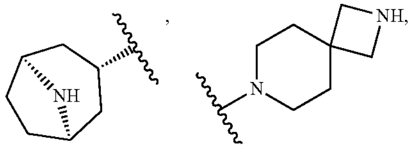
, ,
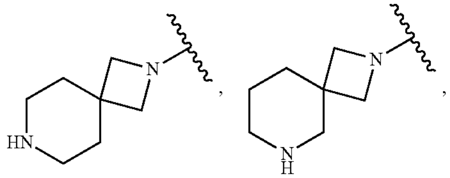
, ,
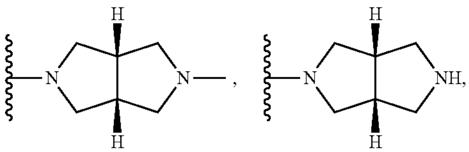
, , -continued
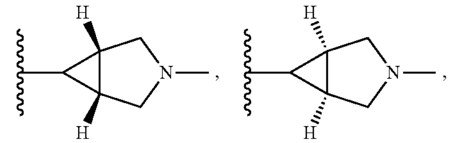,
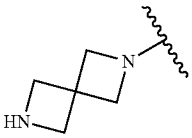,
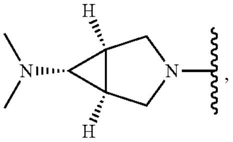
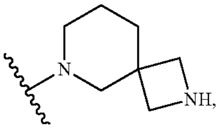,
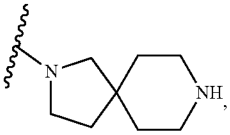,
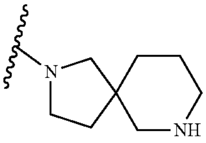,
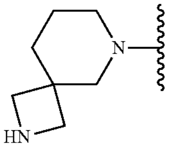,
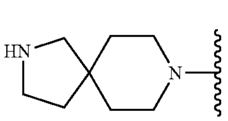,
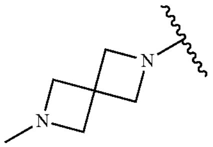, and 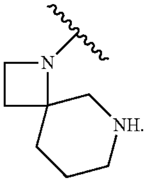.
In some embodiments, A is selected from
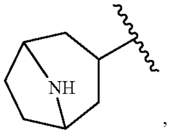, 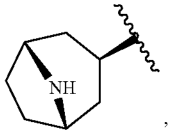, 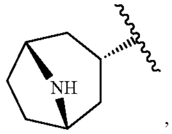,
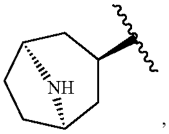, 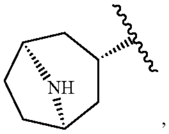, 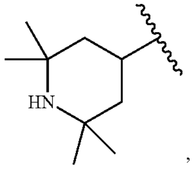,
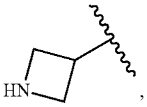, 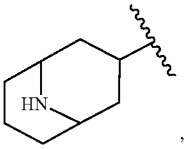, 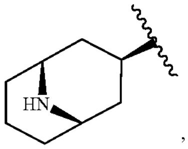,
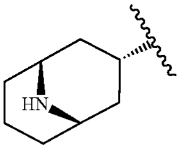, 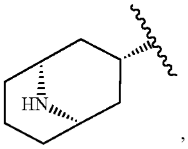, 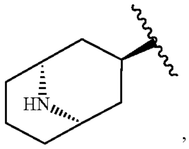,
-continued
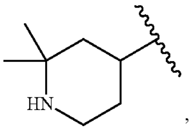, 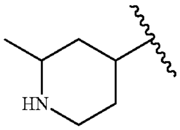, 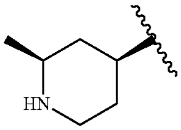,
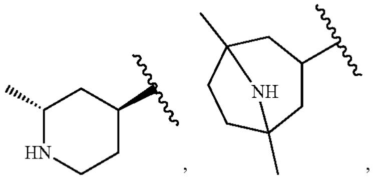,
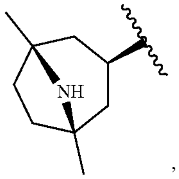, and 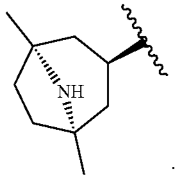.
In some embodiments, A is selected from wherein A is selected from
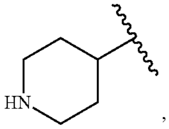, 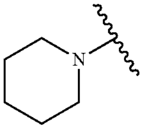, 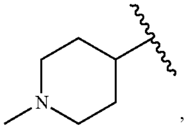,
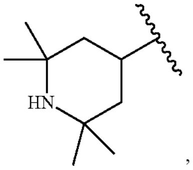, 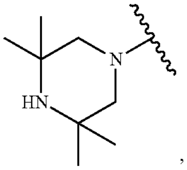,
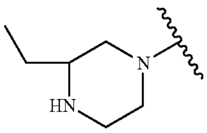, 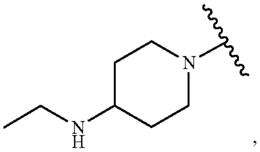,
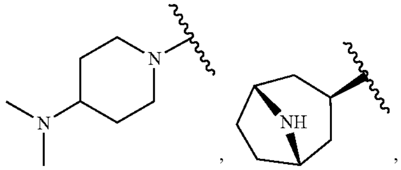,
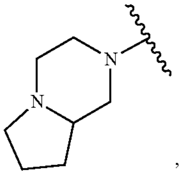, 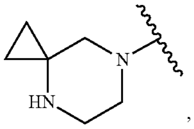, 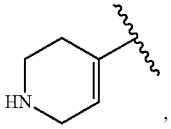,
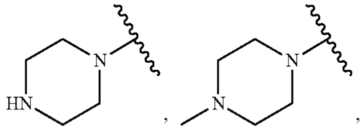, -continued
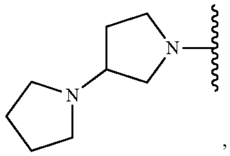
, and
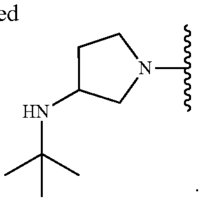
In some embodiments, A is
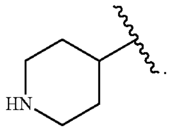
In some embodiments, A is
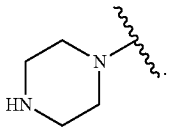
In some embodiments, A is
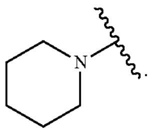 [SMILES: *N1CCCCC1]
In some embodiments, A is
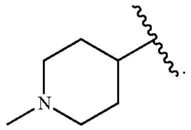 [SMILES: *C1CCN(C)CC1]
In some embodiments, A is
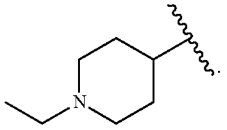 [SMILES: *C1CCN(CC)CC1]
In some embodiments, A is
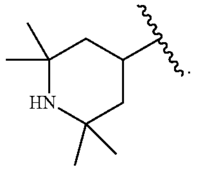 [SMILES: *C1CC(C)(C)NC(C)(C)C1]
In some embodiments, A is
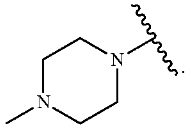 [SMILES: *N1CCN(C)CC1]
In some embodiments, A is
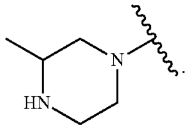 [SMILES: *N1CCNC(C)C1]
In some embodiments, A is
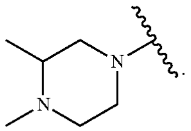 [SMILES: *N1CCN(C)C(C)C1]
In some embodiments, A is
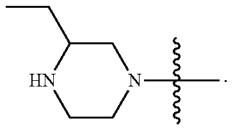 [SMILES: *N1CCNC(CC)C1]
In some embodiments, A is
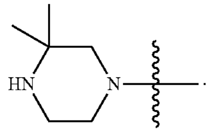 [SMILES: *N1CCNC(C)(C)C1]
In some embodiments, A is
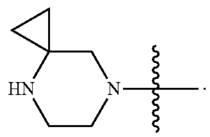 [SMILES: *N1CCNC2(CC2)C1]
In some embodiments, A is
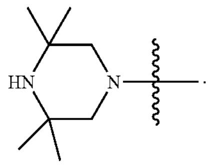 [SMILES: *N1CC(C)(C)NC(C)(C)C1]

In some embodiments, A is
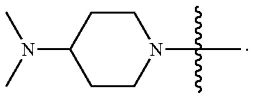 [SMILES: *N1CCC(N(C)C)CC1]
In some embodiments, A is
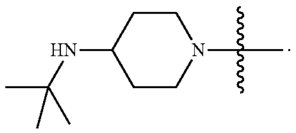 [SMILES: *N1CCC(NC(C)(C)C)CC1]
In some embodiments, A is
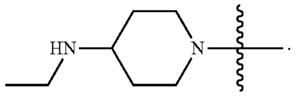 [SMILES: *N1CCC(NCC)CC1]
In some embodiments, A is
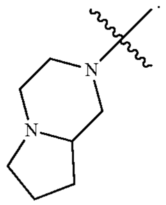 [SMILES: *N1CCN2CCCC2C1]
In some embodiments, A is
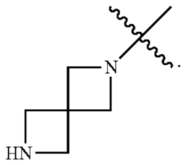 [SMILES: *N1CC2(CNC2)C1]
In some embodiments, A is
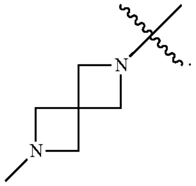 [SMILES: *N1CC2(C1)CN(C)C2]
In some embodiments, A is
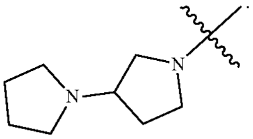 [SMILES: *N1CCC(N2CCCC2)C1]
In some embodiments, A is
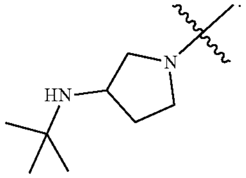 [SMILES: *N1CCC(NC(C)(C)C)C1]
In some embodiments, A is
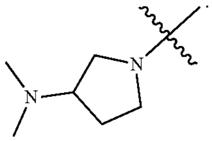 [SMILES: *N1CCC(N(C)C)C1]
In some embodiments, A is
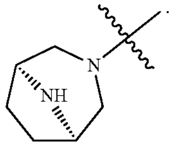 [SMILES: *N1C[C@H]2CC[C@@H](C1)N2]
In some embodiments, A is
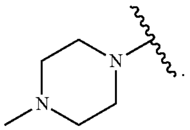 [SMILES: *N1CCN(C)CC1]
In some embodiments, A is
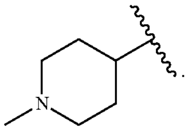 [SMILES: *C1CCN(C)CC1]

In some embodiments, A is
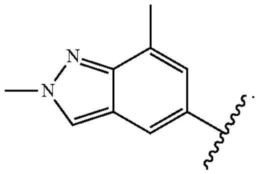 [SMILES: *c1cc(C)c2nn(C)cc2c1].
In some embodiments, A is
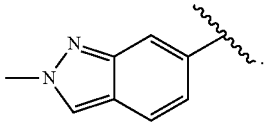 [SMILES: *c1ccc2cn(C)nc2c1].
In some embodiments, B is selected from
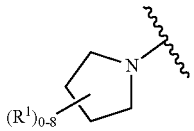, 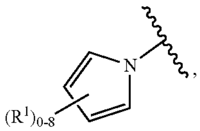, 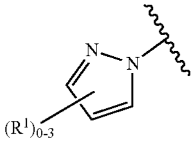, and 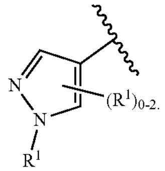.
In some embodiments, B is selected from
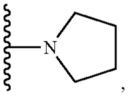, 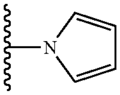, 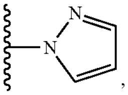, and 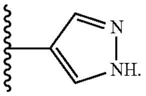.
In some embodiments, B is selected from
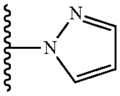, 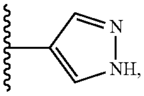, 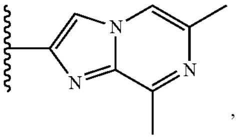, 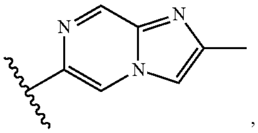, 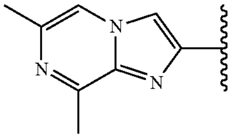,
-continued
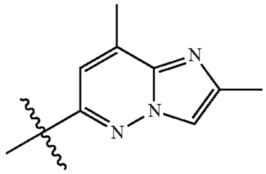, 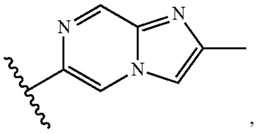, 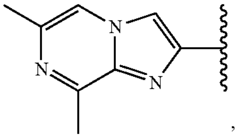, 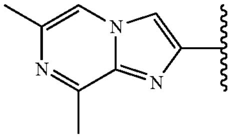, 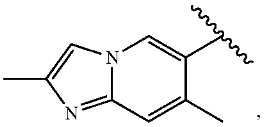, 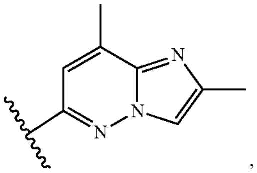, 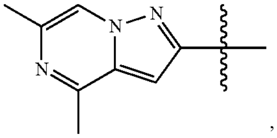, 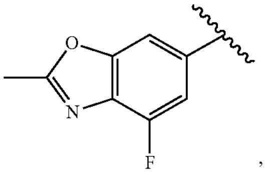, 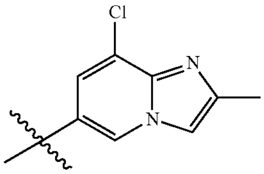, 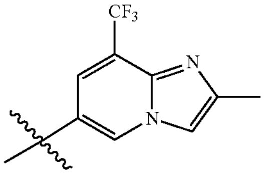, 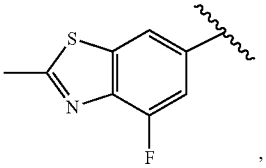, 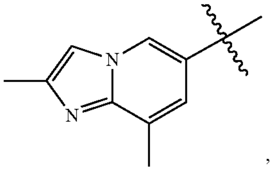, 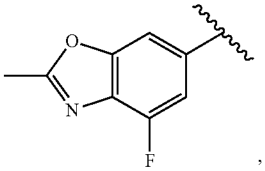, 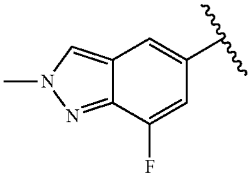, 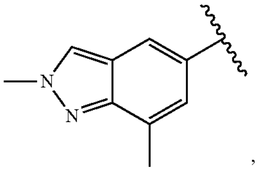, and 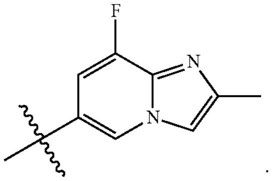.
In some embodiments, B is selected from
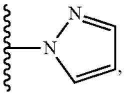, 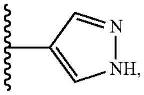, 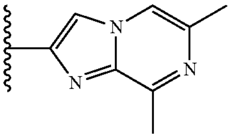, -continued

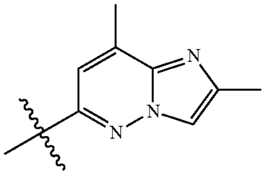

,

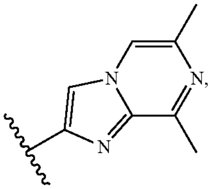

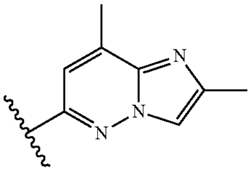

,

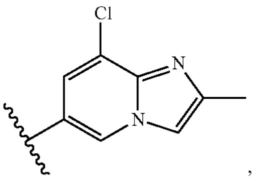

,

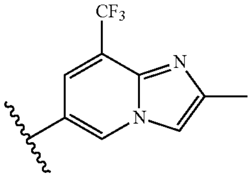

, and

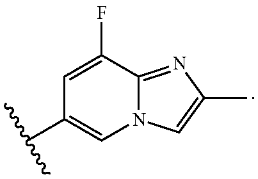

In some embodiments, B is selected is

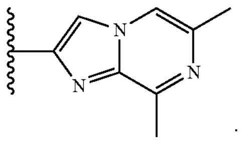 [SMILES: *c1cn2cc(C)nc(C)c2n1]

In some embodiments, B is

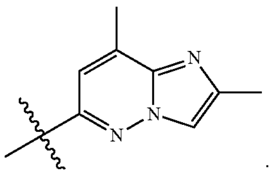 [SMILES: *c1cc(C)c2nc(C)cn2n1]

In some embodiments, B is

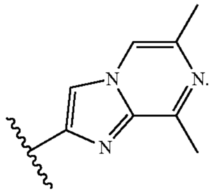 [SMILES: *c1cn2cc(C)nc(C)c2n1]

In some embodiments, B is

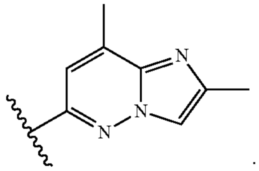 [SMILES: *c1cc(C)c2nc(C)cn2n1]

In some embodiments, B is

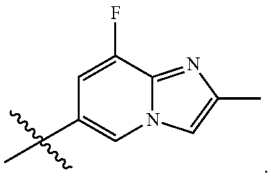 [SMILES: *c1cc(F)c2nc(C)cn2c1]

In some embodiments, X is N. In some embodiments, X is O. In some embodiments, X is $C(R^{3a})$. In some embodiments, Y is N. In some embodiments, Y is $C(R^{3a})$. In some embodiments, Z is $C(R^{3a})$ (e.g., CH). In some embodiments, Z is N. In some embodiments, Z is O. In some embodiments, X and Y are each independently N or $N(R^{3c})$, and Z is $C(R^{3a})$ (e.g., CH). In some embodiments, Y and Z are each independently N or $N(R^{3c})$, and X is $C(R^{3a})$ (e.g., CH). In some embodiments, X is $C(R^{3a})$, Y is $C(R^{3a})$, and Z is O. In some embodiments, Y is $C(R^{3a})$, Z is $C(R^{3a})$, and X is O.

In some embodiments,

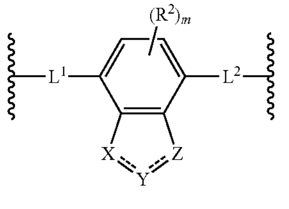

is selected from

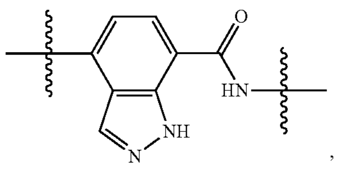

,

-continued

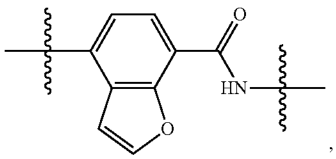

,

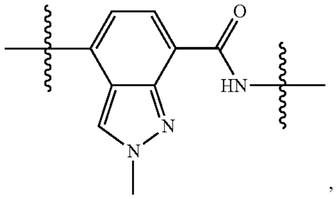

,

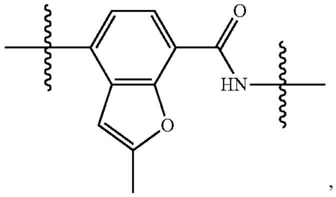

,

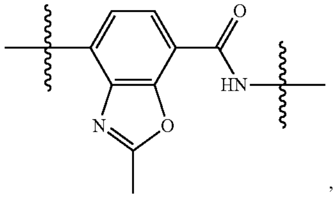

,

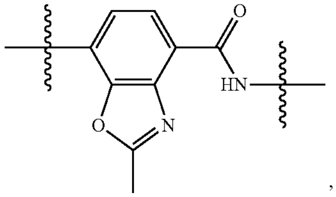

,

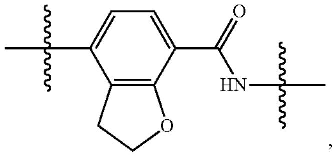

, and

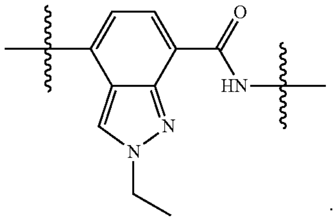

.

In some embodiments,

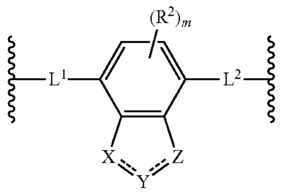

is

-continued

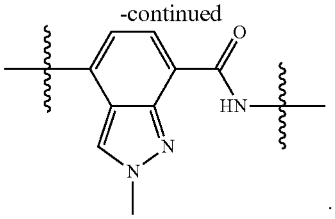

.

In some embodiments,

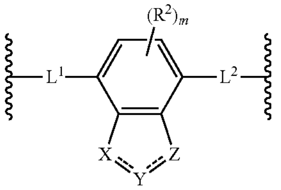

is

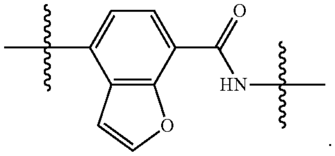

.

In some embodiments, $L^1$ and $L^2$ are each independently absent, —O—, —N($R^4$)—, —N($R^4$)C(O)—, or —C(O)N($R^4$)—. In some embodiments, $L^1$ and $L^2$ are each independently absent. In some embodiments, $L^1$ is absent or —N($R^4$)—. In some embodiments, $L^2$ is absent, —N($R^4$)C(O)—, or —C(O)N($R^4$)—. In some embodiments, $L^2$ is —C(O)N($R^4$)—.

In some embodiments, the compound of Formula (I) is a compound of Formula (I-b):

(I-b)

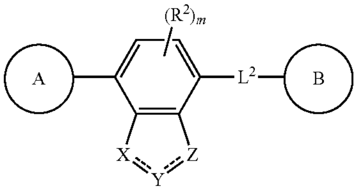

or a pharmaceutically acceptable salt, solvate, hydrate, tautomer, or stereoisomer thereof, wherein:

A and B are each independently cycloalkyl, heterocyclyl, aryl, or heteroaryl, each of which is optionally substituted with one or more $R^1$;

X, Y, and Z are each independently C($R^{3a}$), C($R^{3a}$)($R^{3b}$), N, N($R^{3c}$), or O, wherein at least one of X, Y, and Z is N, N($R^{3c}$), or O, and the bonds in the ring comprising X, Y, and Z may be single or double bonds as valency permits;

$L^2$ is absent, $C_1$-$C_6$-alkylene, $C_1$-$C_6$-heteroalkylene, —O—, —C(O)—, —N($R^4$)—, —N($R^4$)C(O)—, or —C(O)N($R^4$)—, wherein each alkylene and heteroalkylene is optionally substituted with one or more $R^5$;

each $R^1$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, $C_1$-$C_6$ alkylene-aryl, $C_1$-$C_6$ alkenylene-aryl, $C_1$-$C_6$ alkylene-heteroaryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkylene, alkenyl, alkynyl, heteroalkyl, haloalkyl, cycloalkyl, heterocyclyl, aryl, and heteroaryl is optionally substituted with one or more $R^6$; or two $R^1$ groups, together with the atoms to which they are attached, form a 3-7-membered cycloalkyl, heterocyclyl, aryl, or heteroaryl, wherein each cycloalkyl, heterocyclyl, aryl, and heteroaryl is optionally substituted with one or more $R^6$;

each $R^2$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, halo, cyano, or —$OR^A$;

$R^{3a}$ and $R^{3b}$ are each independently hydrogen, $C_1$-$C_6$-alkyl, $C_1$-$C_6$-heteroalkyl, $C_1$-$C_6$-haloalkyl, halo, cyano, —$OR^A$, —$NR^BR^C$, —$C(O)R^D$, or —$C(O)OR^D$; or each of $R^{3a}$ and $R^{3b}$, together with the carbon atom to which they are attached, form an oxo group;

$R^{3c}$ is hydrogen or $C_1$-$C_6$-alkyl;

each $R^4$ is independently hydrogen, $C_1$-$C_6$-alkyl, or $C_1$-$C_6$-haloalkyl;

each $R^5$ is independently hydrogen, $C_1$-$C_6$-alkyl, $C_1$-$C_6$-heteroalkyl, $C_1$-$C_6$-haloalkyl, cycloalkyl, halo, cyano, oxo, —$OR^A$, —$NR^BR^C$, —$C(O)R^D$, or —$C(O)OR^D$;

each $R^6$ is independently $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkenyl, alkynyl, heteroalkyl, haloalkyl, cycloalkyl, heterocyclyl, aryl, and heteroaryl is optionally substituted with one or more $R^1$;

each $R^7$ is $C_1$-$C_6$-alkyl, halo, cyano, oxo, or —$OR^{A1}$;

each $R^{11}$ is independently $C_1$-$C_6$-alkyl, $C_1$-$C_6$-heteroalkyl, $C_1$-$C_6$-haloalkyl, cycloalkyl, heterocyclyl, aryl, heteroaryl, halo, cyano, oxo, or —$OR^A$;

each $R^A$ is independently hydrogen, $C_1$-$C_6$ alkyl, $C_1$-$C_6$ haloalkyl, aryl, heteroaryl, $C_1$-$C_6$ alkylene-aryl, $C_1$-$C_6$ alkylene-heteroaryl, —$C(O)R^D$, or —$S(O)_xR^D$;

each of $R^B$ and $R^C$ is independently hydrogen, $C_1$-$C_6$ alkyl, $C_1$-$C_6$ heteroalkyl, cycloalkyl, heterocyclyl, or —$OR^A$; or $R^B$ and $R^C$ together with the atom to which they are attached form a 3-7-membered heterocyclyl ring optionally substituted with one or more $R^7$;

each $R^D$ and $R^E$ is independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, heteroaryl, $C_1$-$C_6$ alkylene-aryl, or $C_1$-$C_6$ alkylene-heteroaryl;

each $R^{A1}$ is hydrogen or $C_1$-$C_6$-alkyl;

m is 0, 1, or 2; and x is 0, 1, or 2.

In some embodiments, A is heterocyclyl optionally substituted with one or more $R^1$. In some embodiments, A is bicyclic heterocyclyl. In some embodiments, A is monocyclic nitrogen-containing heterocyclyl. In some embodiments, A is bicyclic nitrogen-containing heterocyclyl. In some embodiments, A is optionally substituted piperidinyl. In some embodiments, A is optionally substituted piperazinyl. In some embodiments, A is R

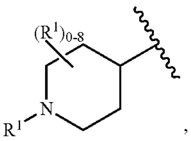
, wherein each $R^1$ is independently hydrogen or $C_1$-$C_6$-alkyl. In some embodiments, A is

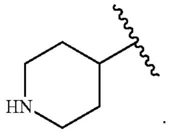
.

In some embodiments, A is

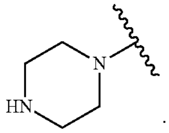
.

In some embodiments, $L^2$ is absent. In some embodiments, $L^2$ is $C_1$-$C_6$-heteroalkylene, that is optionally substituted with one or more $R^5$. In some embodiments, $L^2$ is —$C(O)N(R^4)$—. In some embodiments, $L^2$ is —$C(O)N(H)$—.

In some embodiments, X is N. In some embodiments, X is O. In some embodiments, X is $C(R^{3a})$. In some embodiments, Y is N. In some embodiments, Y is $C(R^{3a})$. In some embodiments, Z is $C(R^{3a})$ (e.g., CH). In some embodiments, Z is N. In some embodiments, Z is O. In some embodiments, X and Y are each independently N or $N(R^{3c})$, and Z is $C(R^{3a})$ (e.g., CH). In some embodiments, Y and Z are each independently N or $N(R^{3c})$, and X is $C(R^{3a})$ (e.g., CH). In some embodiments, X is $C(R^{3a})$, Y is $C(R^{3a})$, and Z is O. In some embodiments, Y is $C(R^{3a})$, Z is $C(R^{3a})$, and X is O.

In some embodiments, A is selected from

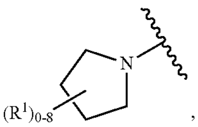
,
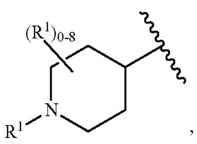
,
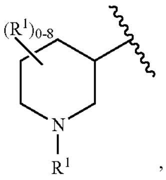
,
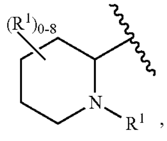
,
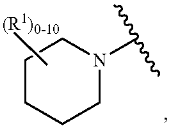
,
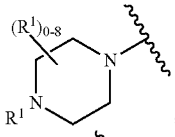
,
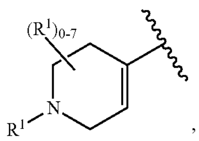
,
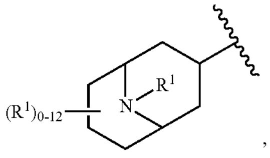
, -continued
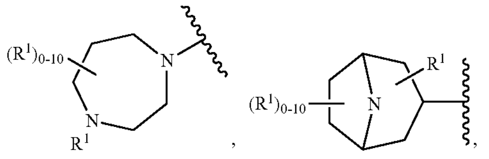
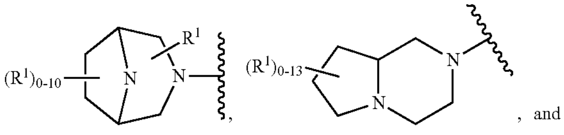
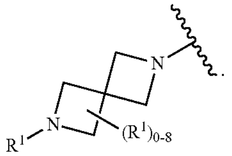
wherein $R^1$ is as defined herein.
In some embodiments, A is selected from
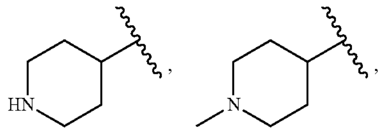
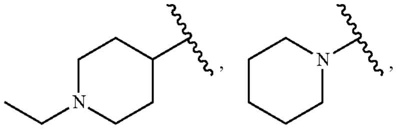
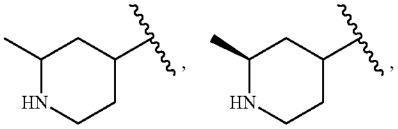
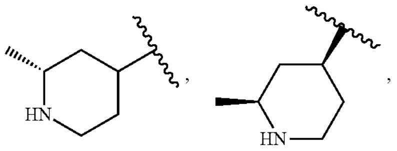
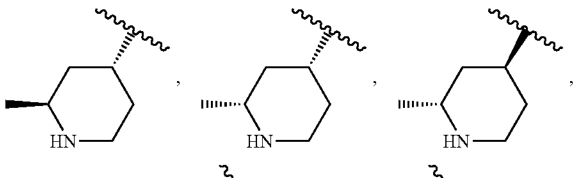
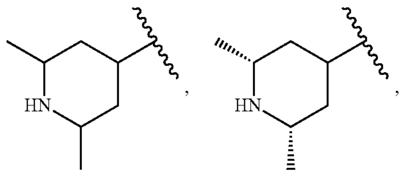
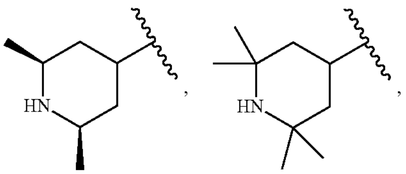
-continued
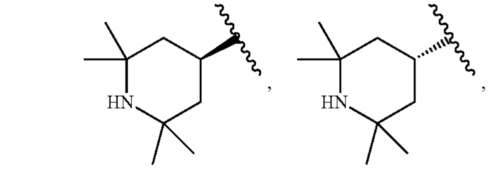
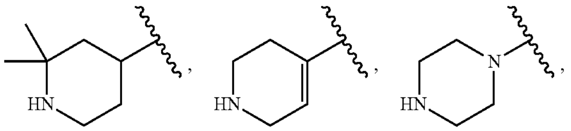
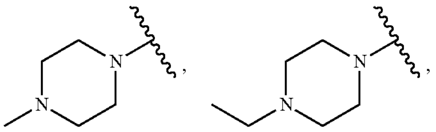
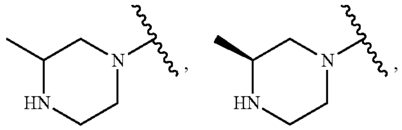
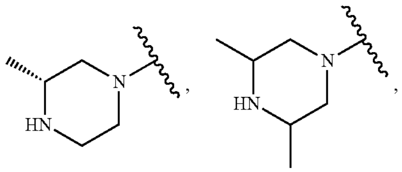
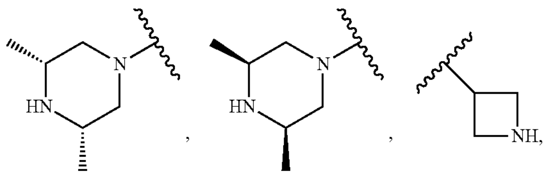
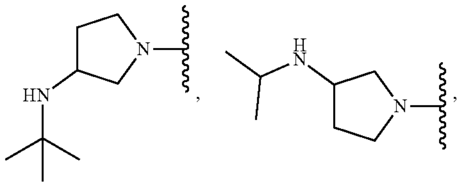
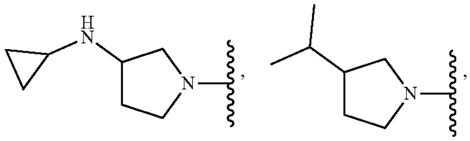
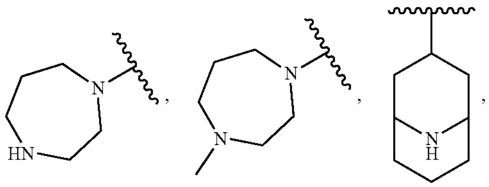
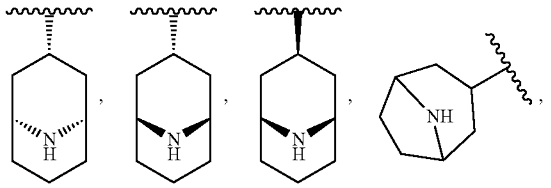

-continued
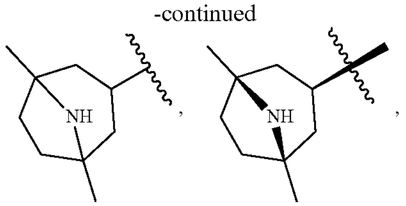
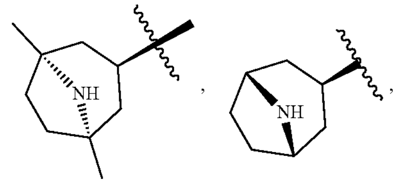
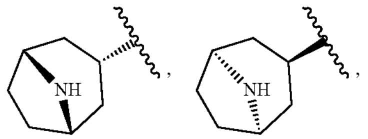
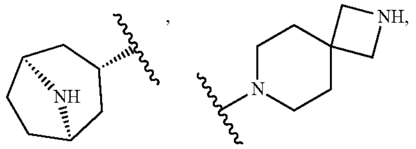
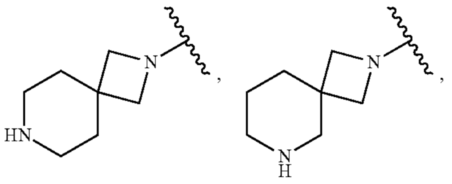
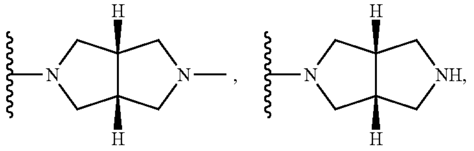
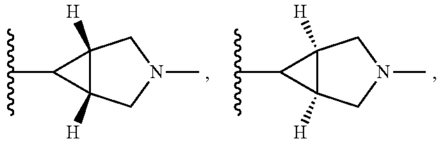
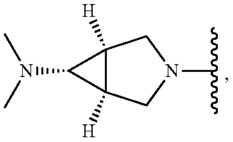
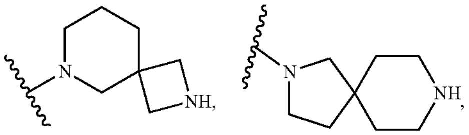
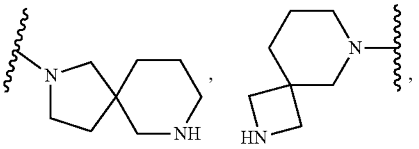
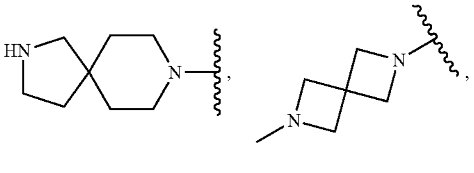
-continued
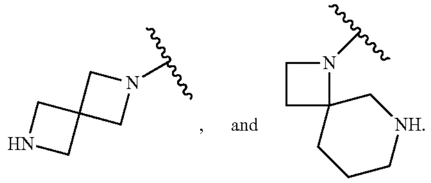
In some embodiments, A is selected from
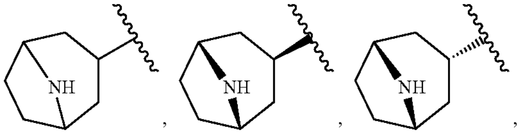
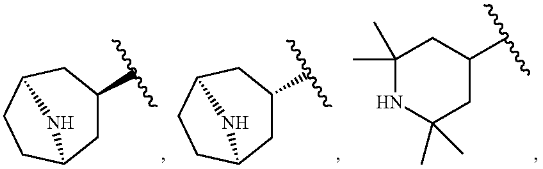
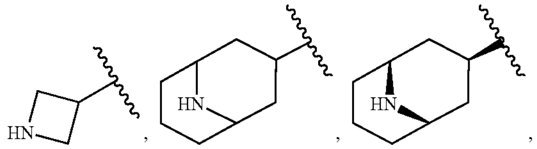
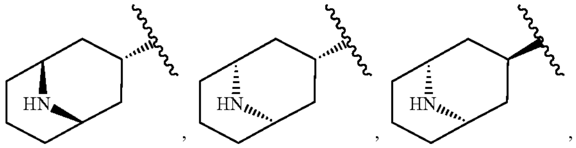
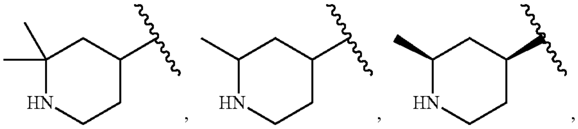
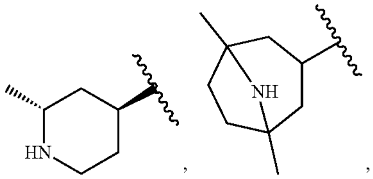
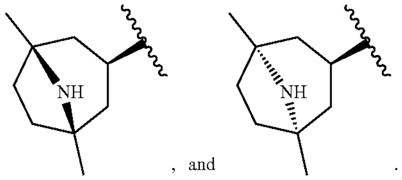
In some embodiments, A is selected from
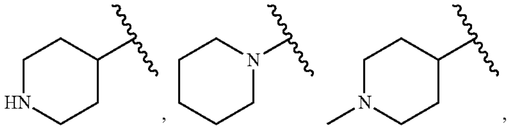

-continued
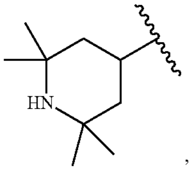,
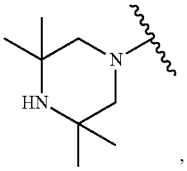,
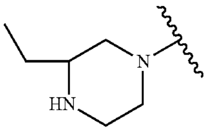,
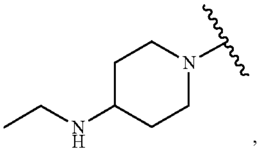,
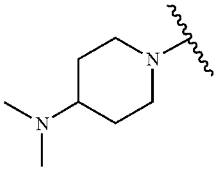,
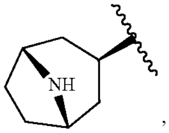,
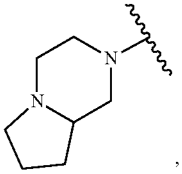,
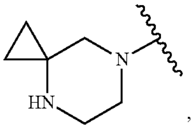,
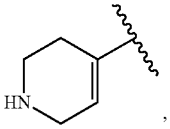,
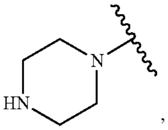,
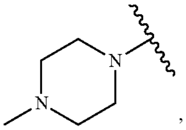,
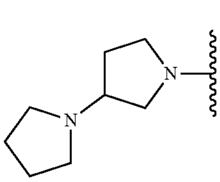, and
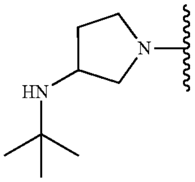.
In some embodiments, A is
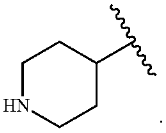.
In some embodiments, A is
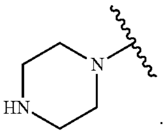.
In some embodiments, A is
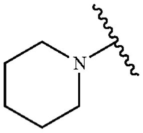.
In some embodiments, A is
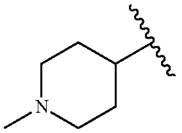.
In some embodiments, A is
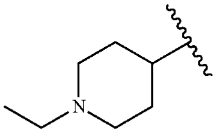.
In some embodiments, A is
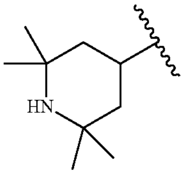.
In some embodiments, A is
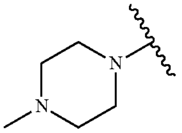.
In some embodiments, A is
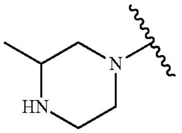.
In some embodiments, A is
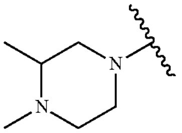.

In some embodiments, A is
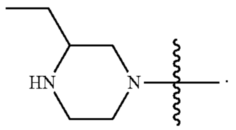 [SMILES: *N1CCNC(CC)C1]
In some embodiments, A is
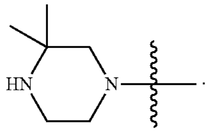
In some embodiments, A is
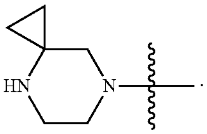
In some embodiments, A is
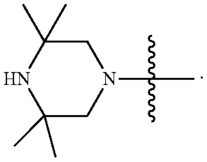
In some embodiments, A is
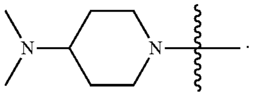
In some embodiments, A is
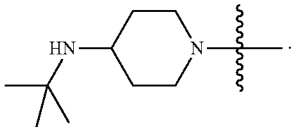
In some embodiments, A is
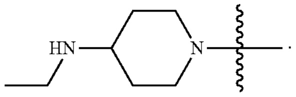
In some embodiments, A is
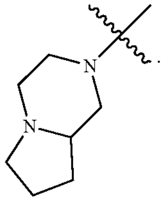
In some embodiments, A is
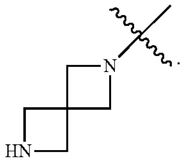
In some embodiments, A is
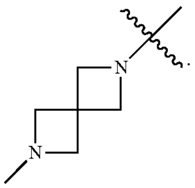 [SMILES: *N1CC2(C1)CN(C)C2]
In some embodiments, A is
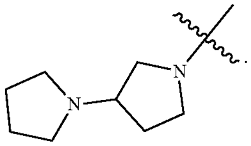 [SMILES: *N1CCC(N2CCCC2)C1]
In some embodiments, A is
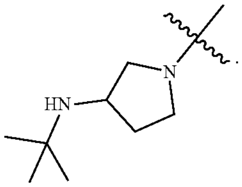 [SMILES: *N1CCC(NC(C)(C)C)C1]
In some embodiments, A is
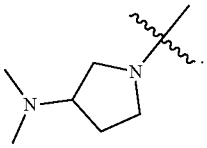 [SMILES: *N1CCC(N(C)C)C1]

In some embodiments, A is
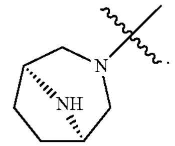 [SMILES: *N1C[C@H]2CC[C@@H](C1)N2]
In some embodiments, A is
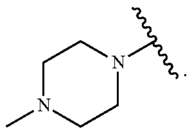 [SMILES: *N1CCN(C)CC1]
In some embodiments, A is
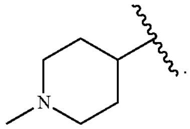 [SMILES: *C1CCN(C)CC1]
In some embodiments, A is
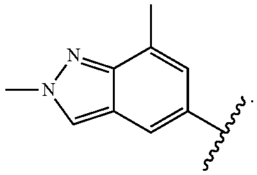 [SMILES: *c1cc(C)c2nn(C)cc2c1]
In some embodiments, A is
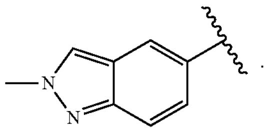 [SMILES: *c1ccc2nn(C)cc2c1]
In some embodiments, B is selected from
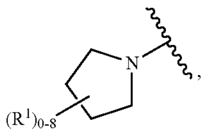, 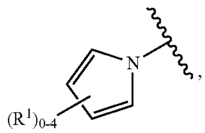, 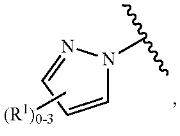, and 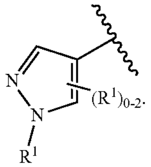
In some embodiments, B is selected from
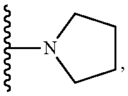, 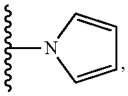, 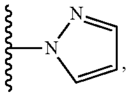, and 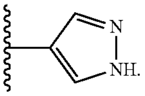
In some embodiments, B is selected from
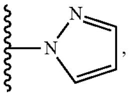, 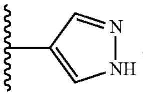, 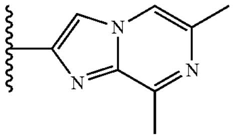, 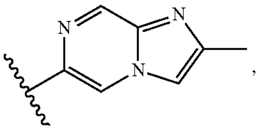, 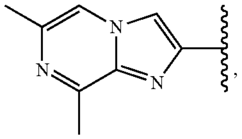, 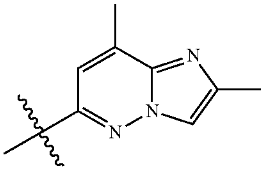, 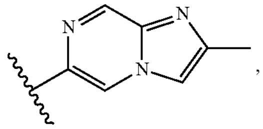, 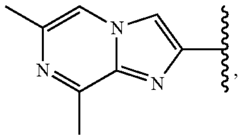, 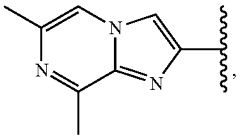, 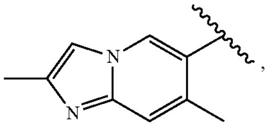, 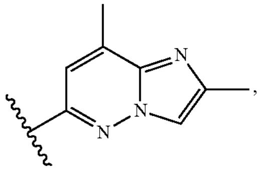, 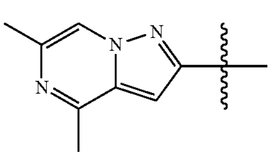, 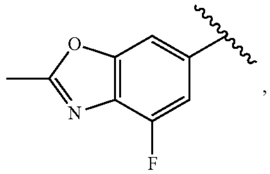, 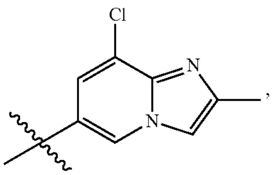, 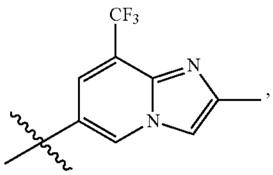, 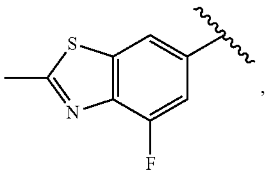, 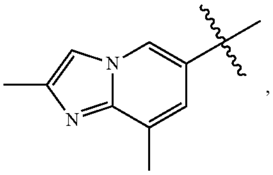, -continued
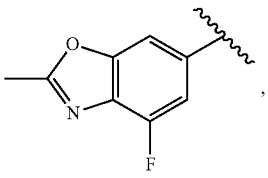
,
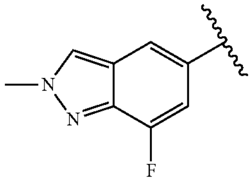
,
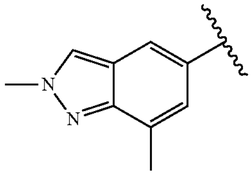
, and
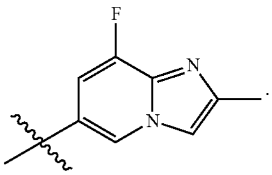
.
In some embodiments, B is selected from
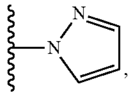
,
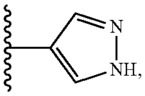
,
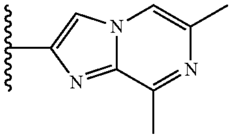
,
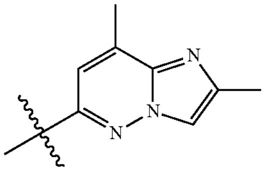
,
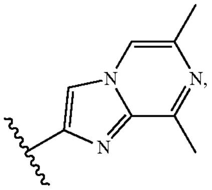
,
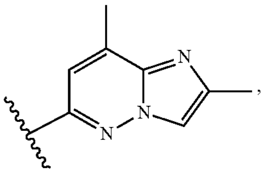
,
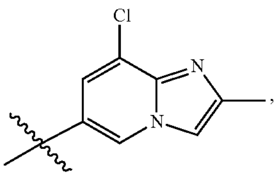
,
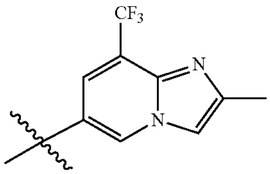
, and
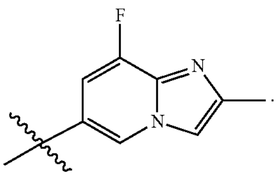
.
In some embodiments, B is selected is
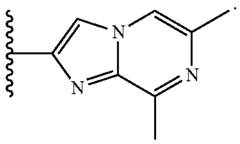 [SMILES: *c1cn2cc(C)nc(C)c2n1]
.
In some embodiments, B is
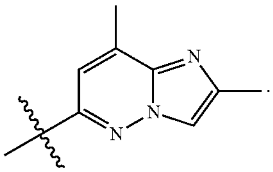 [SMILES: *c1cc(C)c2nc(C)cn2n1]
.
In some embodiments, B is
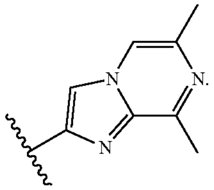 [SMILES: *c1cn2cc(C)nc(C)c2n1]
.
In some embodiments, B is
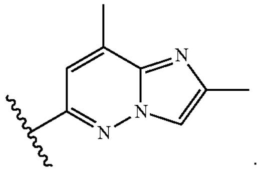 [SMILES: *c1cc(C)c2nc(C)cn2n1]
.
In some embodiments, B is
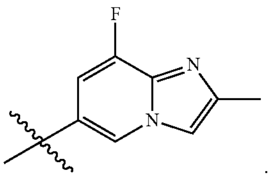 [SMILES: *c1cc(F)c2nc(C)cn2c1]
.
In some embodiments,
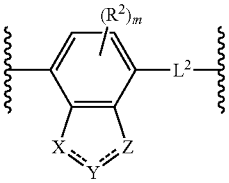
is selected from

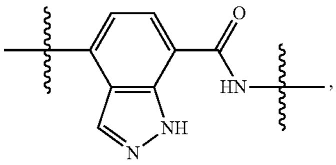,

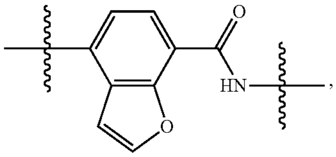,

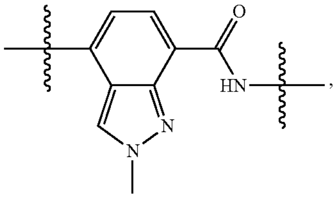,

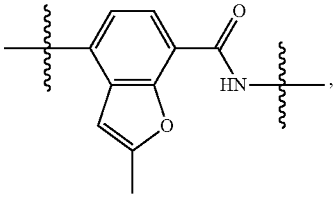,

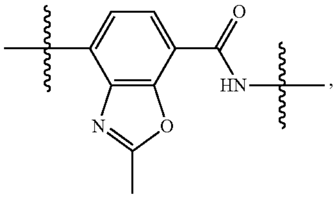,

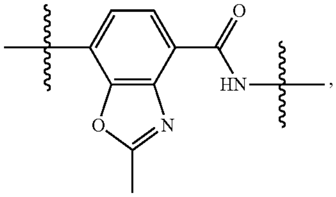,

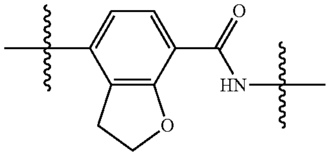, and

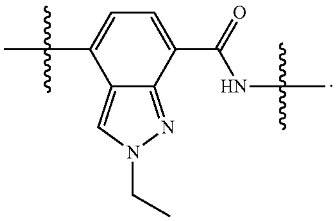.

In some embodiments,

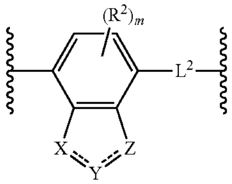

is

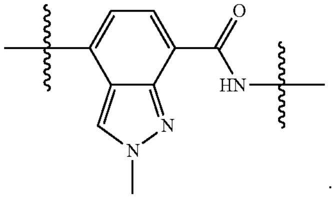.

In some embodiments,

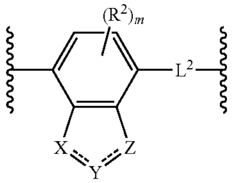

is

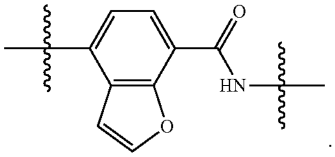.

In some embodiments, the compound of Formula (I) is a compound of Formula (I-c):

(I-c)

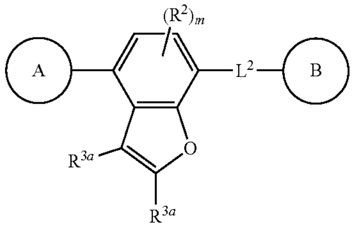

or a pharmaceutically acceptable salt, solvate, hydrate, tautomer, or stereoisomer thereof, wherein:

A and B are each independently cycloalkyl, heterocyclyl, aryl, or heteroaryl, each of which is optionally substituted with one or more $R^1$;

$L^2$ is absent, $C_1$-$C_6$-alkylene, $C_1$-$C_6$-heteroalkylene, —O—, —C(O)—, —$N(R^4)$—, —$N(R^4)C(O)$—, or —$C(O)N(R^4)$—, wherein each alkylene and heteroalkylene is optionally substituted with one or more $R^5$;

each $R^1$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, $C_1$-$C_6$ alkylene-aryl, $C_1$-$C_6$ alkenylene-aryl, $C_1$-$C_6$ alkylene-heteroaryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkylene, alkenyl, alkynyl, heteroalkyl, haloalkyl, cycloalkyl, heterocyclyl, aryl, and heteroaryl is optionally substituted with one or more $R^6$; or two $R^1$ groups, together with the atoms to which they are attached, form a 3-7-membered cycloalkyl, heterocyclyl, aryl, or heteroaryl, wherein each cycloalkyl, heterocyclyl, aryl, and heteroaryl is optionally substituted with one or more $R^6$;

each $R^2$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, halo, cyano, or —$OR^A$;

each $R^{3a}$ is independently hydrogen, $C_1$-$C_6$-alkyl, $C_1$-$C_6$-heteroalkyl, $C_1$-$C_6$-haloalkyl, halo, cyano, —$OR^A$, —$NR^BR^C$, —$C(O)R^D$, or —$C(O)OR^D$;

each $R^4$ is independently hydrogen, $C_1$-$C_6$-alkyl, or $C_1$-$C_6$-haloalkyl;

each $R^5$ is independently hydrogen, $C_1$-$C_6$-alkyl, $C_1$-$C_6$-heteroalkyl, $C_1$-$C_6$-haloalkyl, cycloalkyl, halo, cyano, oxo, —$OR^A$, —$NR^BR^C$, —$C(O)R^D$, or —$C(O)OR^D$;

each $R^6$ is independently $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkenyl, alkynyl, heteroalkyl, haloalkyl, cycloalkyl, heterocyclyl, aryl, and heteroaryl is optionally substituted with one or more $R^{11}$;

each $R^7$ is $C_1$-$C_6$-alkyl, halo, cyano, oxo, or —$OR^{A1}$;

each $R^{11}$ is independently $C_1$-$C_6$-alkyl, $C_1$-$C_6$-heteroalkyl, $C_1$-$C_6$-haloalkyl, cycloalkyl, heterocyclyl, aryl, heteroaryl, halo, cyano, oxo, or —$OR^A$;

each $R^A$ is independently hydrogen, $C_1$-$C_6$ alkyl, $C_1$-$C_6$ haloalkyl, aryl, heteroaryl, $C_1$-$C_6$ alkylene-aryl, $C_1$-$C_6$ alkylene-heteroaryl, —$C(O)R^D$, or —$S(O)_xR^D$;

each of $R^B$ and $R^C$ is independently hydrogen, $C_1$-$C_6$ alkyl, $C_1$-$C_6$ heteroalkyl, cycloalkyl, heterocyclyl, or —$OR^A$; or $R^B$ and $R^C$ together with the atom to which they are attached form a 3-7-membered heterocyclyl ring optionally substituted with one or more $R^7$;

each $R^D$ and $R^E$ is independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, heteroaryl, $C_1$-$C_6$ alkylene-aryl, or $C_1$-$C_6$ alkylene-heteroaryl;

each $R^{A1}$ is hydrogen or $C_1$-$C_6$-alkyl;

m is 0, 1, or 2; and x is 0, 1, or 2.

In some embodiments, A is heterocyclyl optionally substituted with one or more $R^1$. In some embodiments, A is bicyclic heterocyclyl. In some embodiments, A is monocyclic nitrogen-containing heterocyclyl. In some embodiments, A is bicyclic nitrogen-containing heterocyclyl. In some embodiments, A is optionally substituted piperidinyl. In some embodiments, A is optionally substituted piperazinyl. In some embodiments, A is

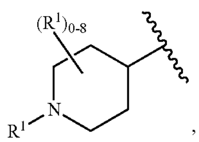

, wherein each $R^1$ is independently hydrogen or $C_1$-$C_6$-alkyl. In some embodiments, A is

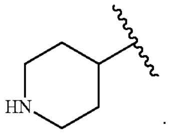

.

In some embodiments, A is

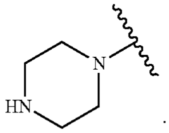 [SMILES: *N1CCNCC1]

.

In some embodiments, $L^2$ is absent. In some embodiments, $L^2$ is $C_1$-$C_6$-heteroalkylene, that is optionally substituted with one or more $R^5$. In some embodiments, $L^2$ is —$C(O)N(R^4)$—. In some embodiments, $L^2$ is —C(O)N(H)—.

In some embodiments, each $R^{3a}$ is independently hydrogen or $C_1$-$C_6$-alkyl (e.g., $CH_3$). In some embodiments, each $R^{3a}$ is independently hydrogen. In some embodiments, each $R^{3a}$ is independently $C_1$-$C_6$-alkyl (e.g., $CH_3$).

In some embodiments, B is heteroaryl optionally substituted with one or more $R^1$. In some embodiments, B is monocyclic heteroaryl. In some embodiments, B is bicyclic heteroaryl. In some embodiments, B is monocyclic nitrogen-containing heteroaryl. In some embodiments, B is bicyclic nitrogen-containing heteroaryl. In some embodiments, B is optionally substituted pyrazolyl. In some embodiments, B is selected from

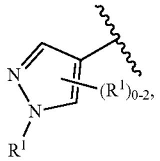

,

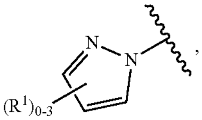

,

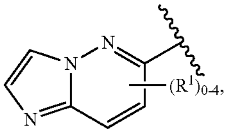

,

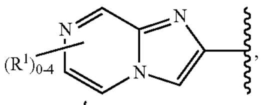

, and

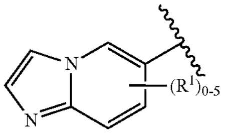

wherein each $R^1$ is as defined above. In some embodiments, B is

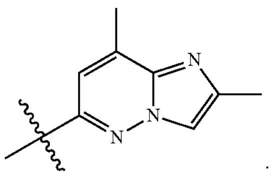 [SMILES: *c1cc(C)c2nc(C)cn2n1]

.

In some embodiments, B is
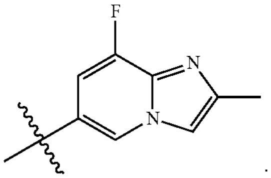 [SMILES: *c1cc(F)c2nc(C)cn2c1]
.
In some embodiments, $R^2$ is $C_1$-$C_6$-alkyl. In some embodiments, $R^2$ is halo (e.g., fluoro). In some embodiments, $R^2$ is —$OR^A$ (e.g., —OH). In some embodiments, $R^{3a}$ is hydrogen. In some embodiments, m is 0.
In some embodiments, A is selected from
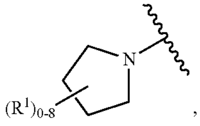
,
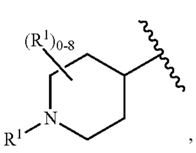
,
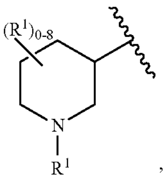
,
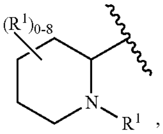
,
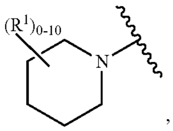
,
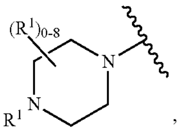
,
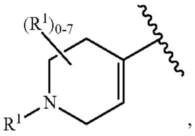
,
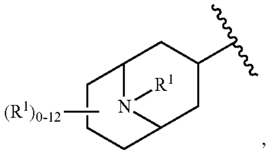
,
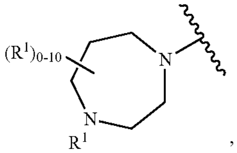
,
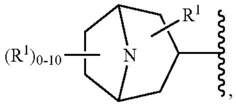
,
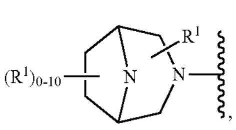
,
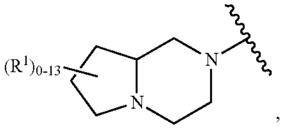
, and
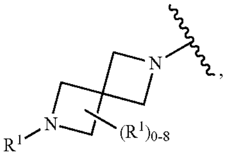
,
wherein $R^1$ is as defined herein.
In some embodiments, A is selected from
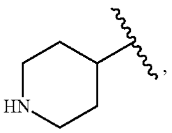
,
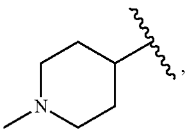
,
-continued
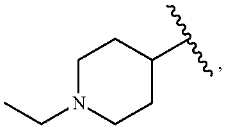
,
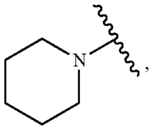
,
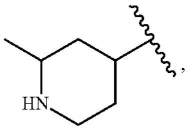
,
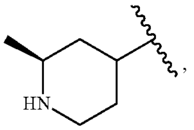
,
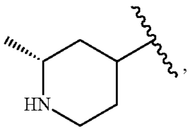
,
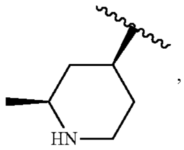
,
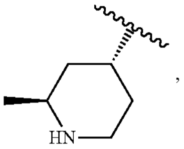
,
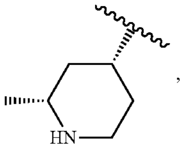
,
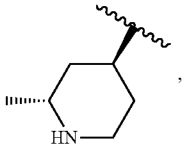
,
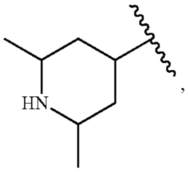
,
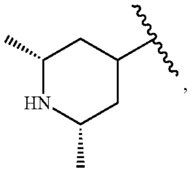
,
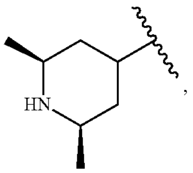
,
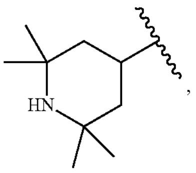
,
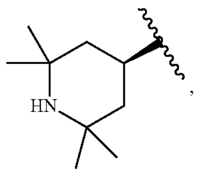
,
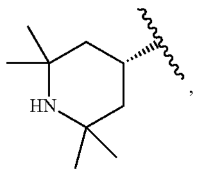
,
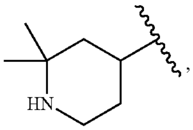
,
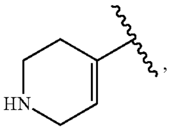
,
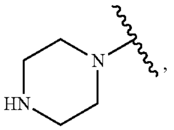
,
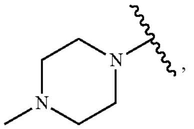
,
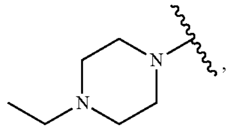
,
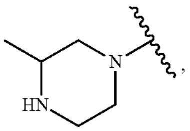
,
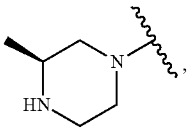
,
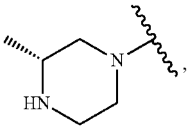
,
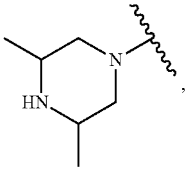
, -continued
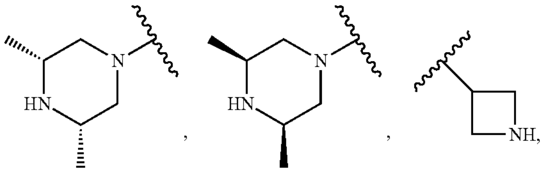
, , 
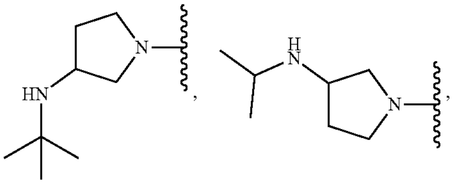
, ,
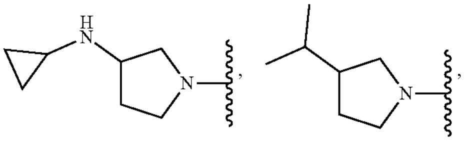
, ,
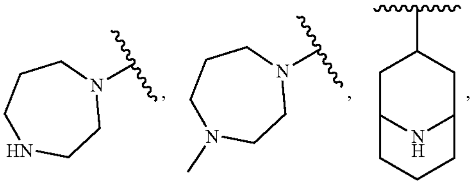
, , ,
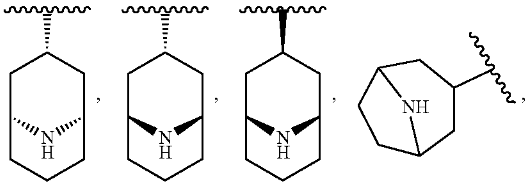
, , , ,
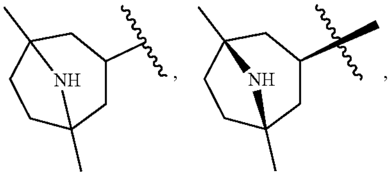
, ,
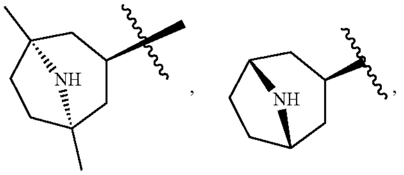
, ,
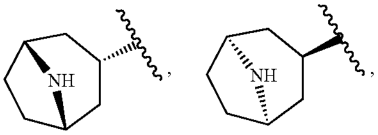
, ,
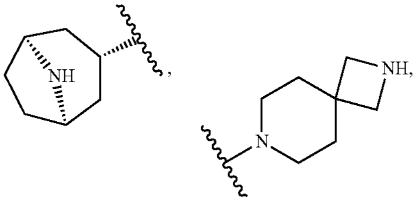
,
-continued
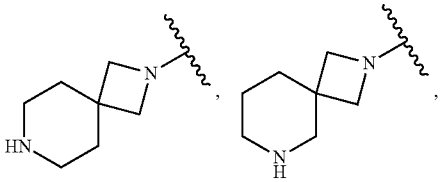
, ,
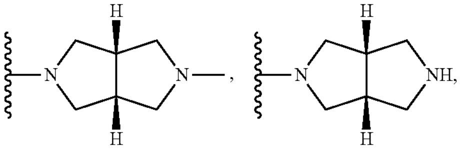
, 
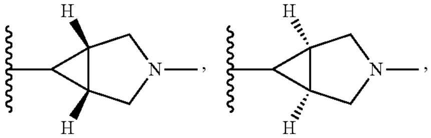
, ,
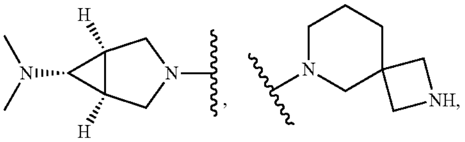
, 
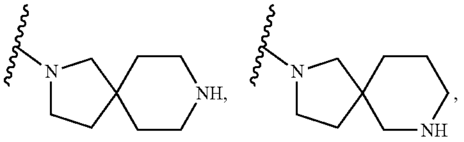
, ,
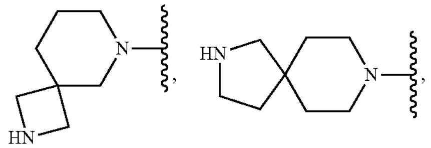
, ,
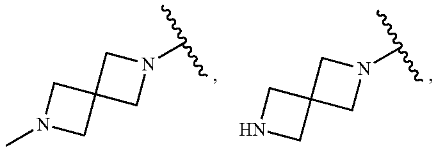
, , and
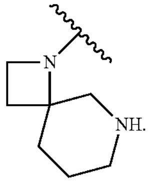
In some embodiments, A is selected from
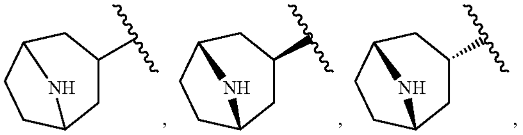
, , ,
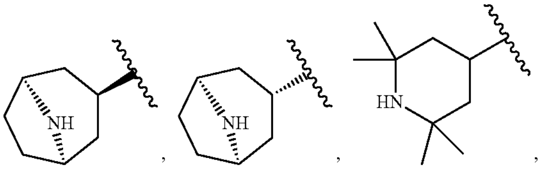
, , , -continued
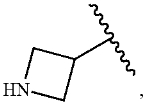, 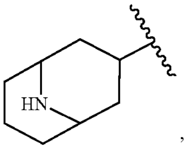, 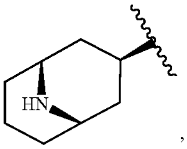,
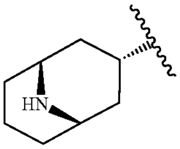, 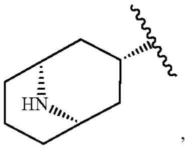, 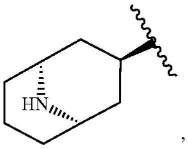,
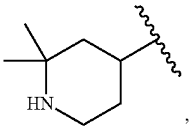, 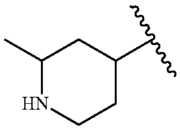, 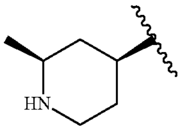,
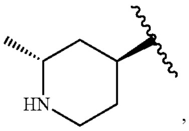, 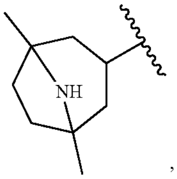,
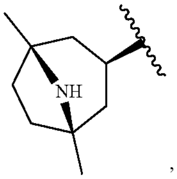, and 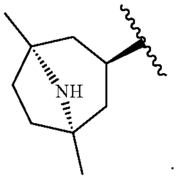.
In some embodiments, A is selected from
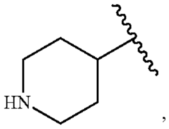, 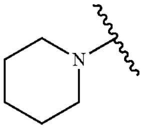, 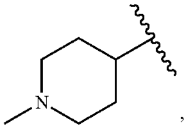,
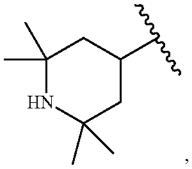, 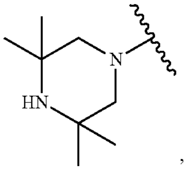,
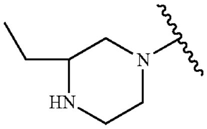, 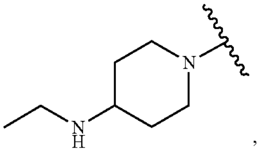,
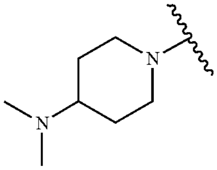, 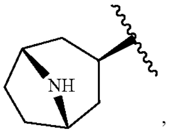,
-continued
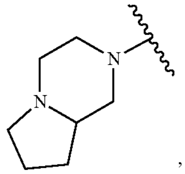, 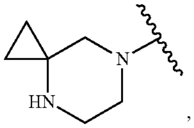, 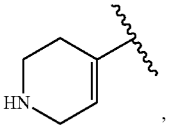,
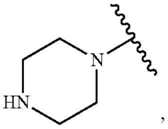, 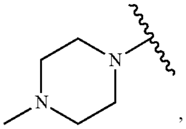,
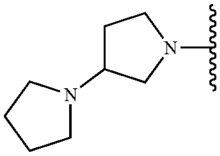, and 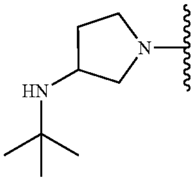.
In some embodiments, A is
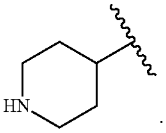.
In some embodiments, A is
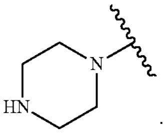 [SMILES: *N1CCNCC1].
In some embodiments, A is
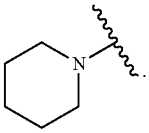 [SMILES: *N1CCCCC1].
In some embodiments, A is
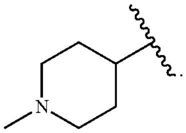.

In some embodiments, A is
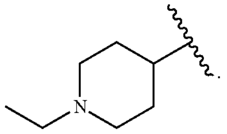 [SMILES: *C1CCN(CC)CC1]
In some embodiments, A is
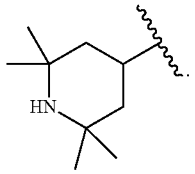 [SMILES: *C1CC(C)(C)NC(C)(C)C1]
In some embodiments, A is
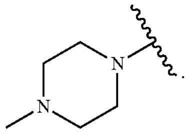
In some embodiments, A is
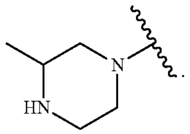 [SMILES: *N1CCNC(C)C1]
In some embodiments, A is
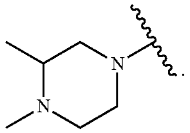
In some embodiments, A is
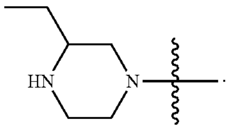 [SMILES: *N1CCNC(CC)C1]
In some embodiments, A is
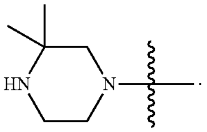
In some embodiments, A is
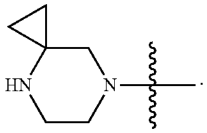
In some embodiments, A is
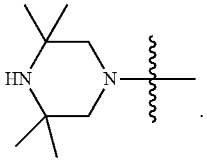 [SMILES: *N1CC(C)(C)NC(C)(C)C1]
In some embodiments, A is
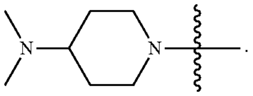 [SMILES: *N1CCC(N(C)C)CC1]
In some embodiments, A is
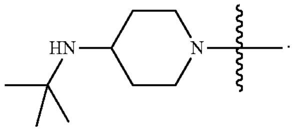 [SMILES: *N1CCC(NC(C)(C)C)CC1]
In some embodiments, A is
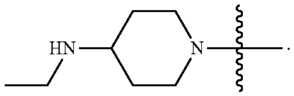 [SMILES: *N1CCC(NCC)CC1]
In some embodiments, A is
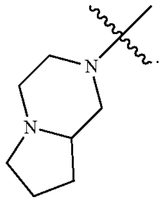 [SMILES: *N1CCN2CCCC2C1]
In some embodiments, A is
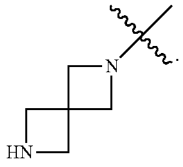

In some embodiments, A is
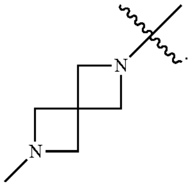 [SMILES: *N1CC2(C1)CN(C)C2]
In some embodiments, A is
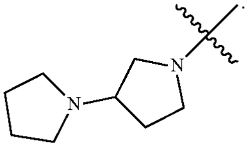 [SMILES: *N1CCC(N2CCCC2)C1]
In some embodiments, A is
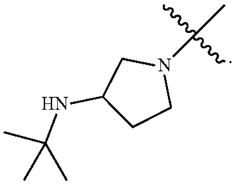 [SMILES: *N1CCC(NC(C)(C)C)C1]
In some embodiments, A is
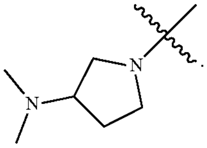 [SMILES: *N1CCC(N(C)C)C1]
In some embodiments, A is
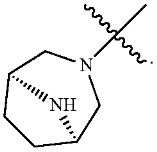 [SMILES: *N1C[C@H]2CC[C@@H](C1)N2]
In some embodiments, A is
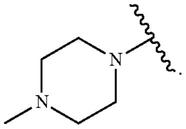 [SMILES: *N1CCN(C)CC1]
In some embodiments, A is
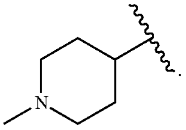 [SMILES: *C1CCN(C)CC1]
In some embodiments, A is
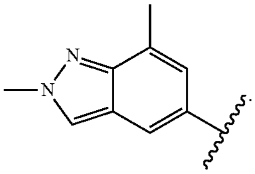 [SMILES: *c1cc(C)c2nn(C)cc2c1]
In some embodiments, A is
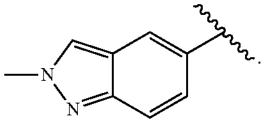 [SMILES: *c1ccc2nn(C)cc2c1]
In some embodiments, B is selected from
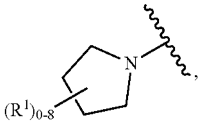, 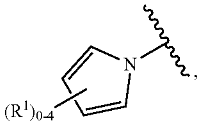, 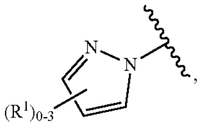, and 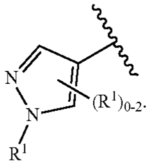
In some embodiments, B is selected from
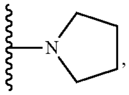, 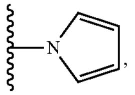, 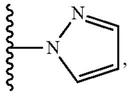, and 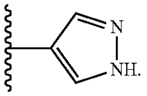
In some embodiments, B is selected from
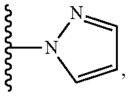, 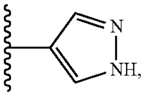, 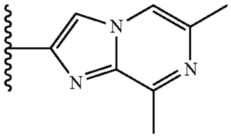, -continued
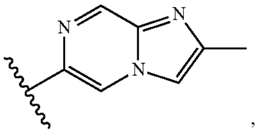,
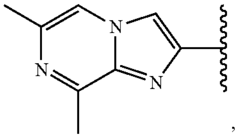,
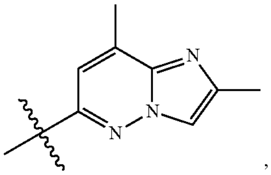,
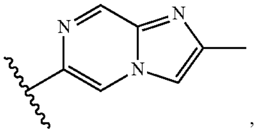,
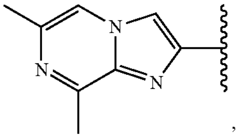,
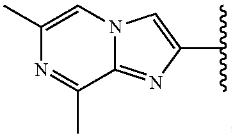,
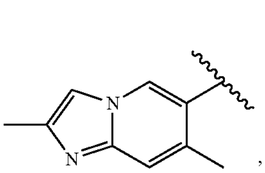,
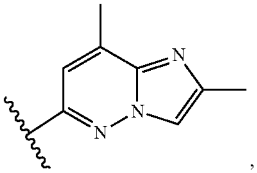,
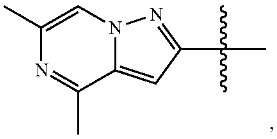,
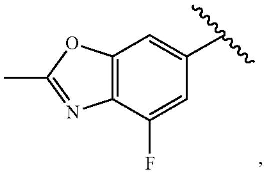,
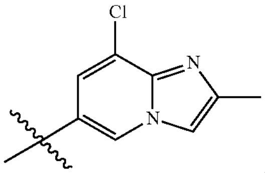,
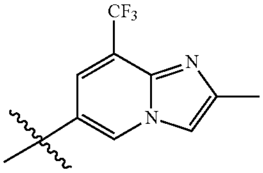,
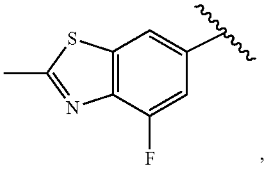,
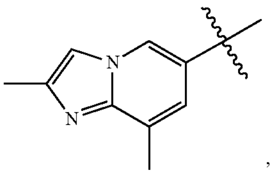,
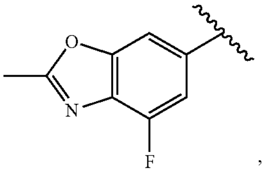,
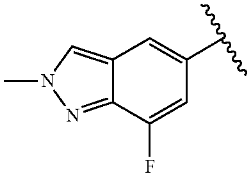,
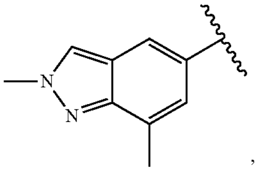, and
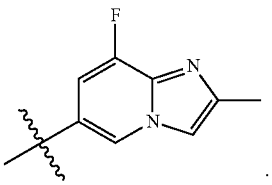.
In some embodiments, B is selected from
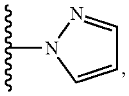,
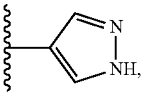
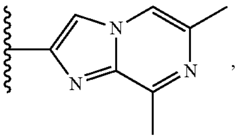,
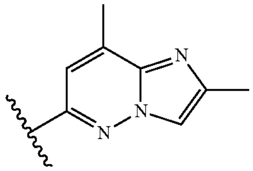,
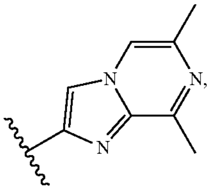
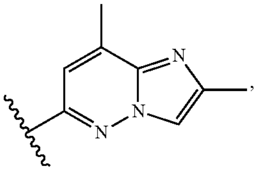,
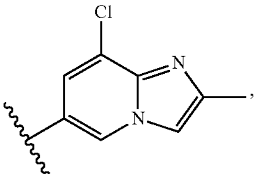,
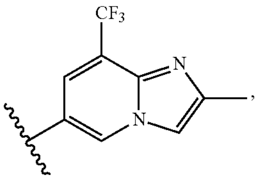, and
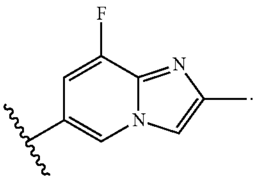.
In some embodiments, B is selected is
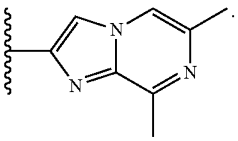 [SMILES: *c1cn2cc(C)nc(C)c2n1].
In some embodiments, B is
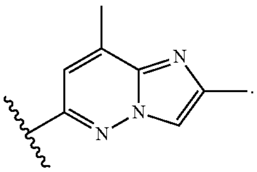 [SMILES: *c1cc(C)c2nc(C)cn2n1].
In some embodiments, B is
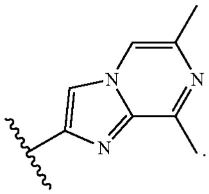 [SMILES: *c1cn2cc(C)nc(C)c2n1].

In some embodiments, B is

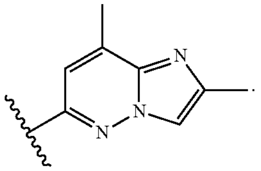 [SMILES: *c1cc(C)c2nc(C)cn2n1]

In some embodiments, B is

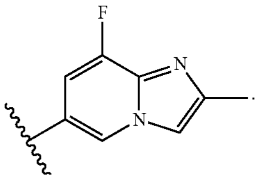 [SMILES: *c1cc(F)c2nc(C)cn2c1]

In some embodiments, the compound of Formula (I) is a compound of Formula (I-d):

(I-d)

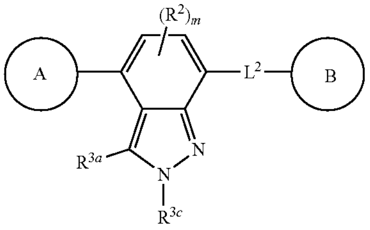

or a pharmaceutically acceptable salt, solvate, hydrate, tautomer, or stereoisomer thereof, wherein:

A and B are each independently cycloalkyl, heterocyclyl, aryl, or heteroaryl, each of which is optionally substituted with one or more $R^1$;

$L^2$ is absent, $C_1$-$C_6$-alkylene, $C_1$-$C_6$-heteroalkylene, —O—, —C(O)—, —N($R^4$)—, —N($R^4$)C(O)—, or —C(O)N($R^4$)—, wherein each alkylene and heteroalkylene is optionally substituted with one or more $R^5$;

each $R^1$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, $C_1$-$C_6$ alkylene-aryl, $C_1$-$C_6$ alkenylene-aryl, $C_1$-$C_6$ alkylene-heteroaryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkylene, alkenyl, alkynyl, heteroalkyl, haloalkyl, cycloalkyl, heterocyclyl, aryl, and heteroaryl is optionally substituted with one or more $R^6$; or two $R^1$ groups, together with the atoms to which they are attached, form a 3-7-membered cycloalkyl, heterocyclyl, aryl, or heteroaryl, wherein each cycloalkyl, heterocyclyl, aryl, and heteroaryl is optionally substituted with one or more $R^6$;

each $R^2$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, halo, cyano, or —$OR^A$;

$R^{3a}$ is hydrogen, $C_1$-$C_6$-alkyl, $C_1$-$C_6$-heteroalkyl, $C_1$-$C_6$-haloalkyl, halo, cyano, —$OR^A$, —$NR^BR^C$, —$C(O)R^D$, or —$C(O)OR^D$;

$R^{3c}$ is hydrogen, $C_1$-$C_6$-alkyl, $C_1$-$C_6$-heteroalkyl, $C_1$-$C_6$-haloalkyl, halo, cyano, or —$C(O)R^D$;

each $R^4$ is independently hydrogen, $C_1$-$C_6$-alkyl, or $C_1$-$C_6$-haloalkyl;

each $R^5$ is independently hydrogen, $C_1$-$C_6$-alkyl, $C_1$-$C_6$-heteroalkyl, $C_1$-$C_6$-haloalkyl, cycloalkyl, halo, cyano, oxo, —$OR^A$, —$NR^BR^C$, —$C(O)R^D$, or —$C(O)OR^D$;

each $R^6$ is independently $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkenyl, alkynyl, heteroalkyl, haloalkyl, cycloalkyl, heterocyclyl, aryl, and heteroaryl is optionally substituted with one or more $R^{11}$;

each $R^7$ is $C_1$-$C_6$-alkyl, halo, cyano, oxo, or —$OR^{A1}$;

each $R^{11}$ is independently $C_1$-$C_6$-alkyl, $C_1$-$C_6$-heteroalkyl, $C_1$-$C_6$-haloalkyl, cycloalkyl, heterocyclyl, aryl, heteroaryl, halo, cyano, oxo, or —$OR^A$;

each $R^A$ is independently hydrogen, $C_1$-$C_6$ alkyl, $C_1$-$C_6$ haloalkyl, aryl, heteroaryl, $C_1$-$C_6$ alkylene-aryl, $C_1$-$C_6$ alkylene-heteroaryl, —$C(O)R^D$, or —$S(O)_xR^D$;

each of $R^B$ and $R^C$ is independently hydrogen, $C_1$-$C_6$ alkyl, $C_1$-$C_6$ heteroalkyl, cycloalkyl, heterocyclyl, or —$OR^A$; or $R^B$ and $R^C$ together with the atom to which they are attached form a 3-7-membered heterocyclyl ring optionally substituted with one or more $R^7$;

each $R^D$ and $R^E$ is independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, heteroaryl, $C_1$-$C_6$ alkylene-aryl, or $C_1$-$C_6$ alkylene-heteroaryl;

each $R^{A1}$ is hydrogen or $C_1$-$C_6$-alkyl;

m is 0, 1, or 2; and x is 0, 1, or 2.

In some embodiments, A is heterocyclyl optionally substituted with one or more $R^1$. In some embodiments, A is bicyclic heterocyclyl. In some embodiments, A is monocyclic nitrogen-containing heterocyclyl. In some embodiments, A is bicyclic nitrogen-containing heterocyclyl. In some embodiments, A is optionally substituted piperidinyl. In some embodiments, A is optionally substituted piperazinyl. In some embodiments, A is

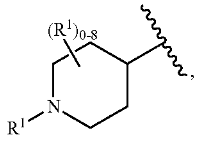

wherein each $R^1$ is independently hydrogen or $C_1$-$C_6$-alkyl. In some embodiments, A is

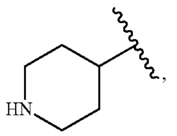 [SMILES: *C1CCNCC1]

In some embodiments, A is

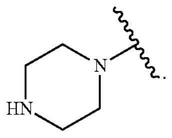 [SMILES: *N1CCNCC1]

In some embodiments, $L^2$ is absent. In some embodiments, $L^2$ is $C_1$-$C_6$-heteroalkylene, that is optionally substituted with one or more $R^5$. In some embodiments, $L^2$ is —C(O)N($R^4$)—. In some embodiments, $L^2$ is —C(O)N(H)—.

In some embodiments, $R^{3a}$ is independently hydrogen or $C_1$-$C_6$-alkyl (e.g., $CH_3$). In some embodiments, $R^{3a}$ is independently hydrogen. In some embodiments, $R^{3a}$ is independently $C_1$-$C_6$-alkyl (e.g., $CH_3$).

In some embodiments, $R^{3c}$ is independently hydrogen or $C_1$-$C_6$-alkyl (e.g., $CH_3$). In some embodiments, $R^{3c}$ is independently hydrogen. In some embodiments, $R^{3c}$ is independently $C_1$-$C_6$-alkyl (e.g., $CH_3$).

In some embodiments, B is heteroaryl optionally substituted with one or more $R^1$. In some embodiments, B is monocyclic heteroaryl. In some embodiments, B is bicyclic heteroaryl. In some embodiments, B is monocyclic nitrogen-containing heteroaryl. In some embodiments, B is bicyclic nitrogen-containing heteroaryl. In some embodiments, B is optionally substituted pyrazolyl. In some embodiments, B is selected from

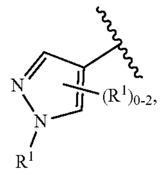 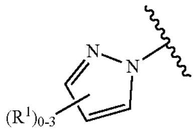, 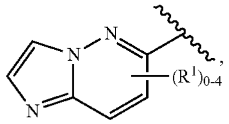, 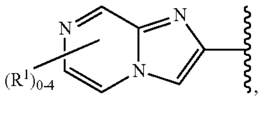, and 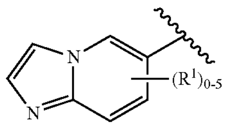

wherein each $R^1$ is as defined above. In some embodiments, B is

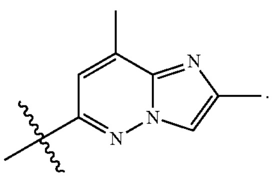 [SMILES: *c1cc(C)c2nc(C)cn2n1]

In some embodiments, B is

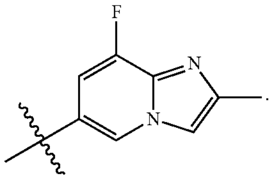 [SMILES: *c1cc(F)c2nc(C)cn2c1]

In some embodiments, A is selected from

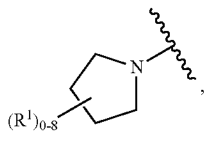, 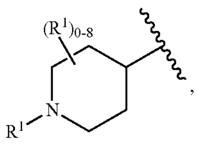, 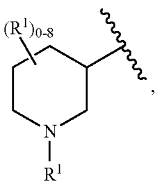, 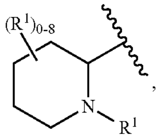, 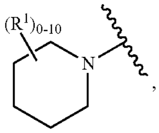, 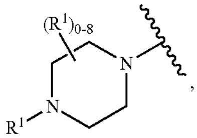, 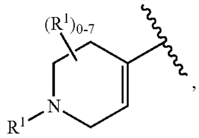, 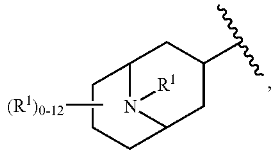, 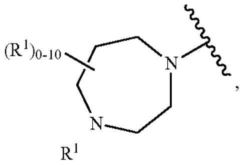, 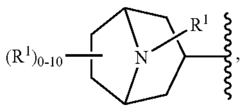, 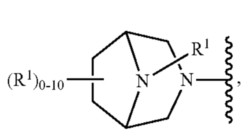, 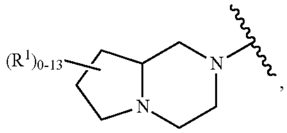, and 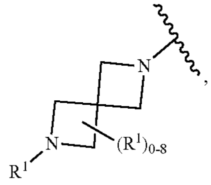, wherein $R^1$ is as defined herein.

In some embodiments, A is selected from

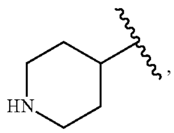, 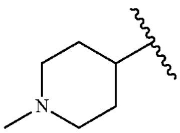, 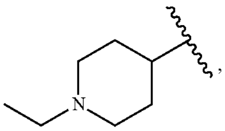, 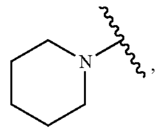,

-continued
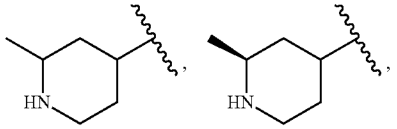
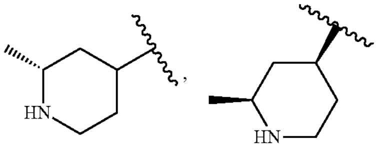
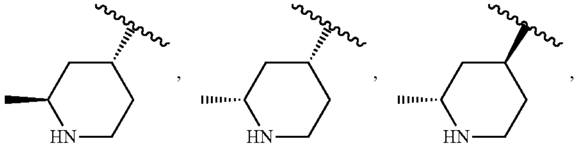
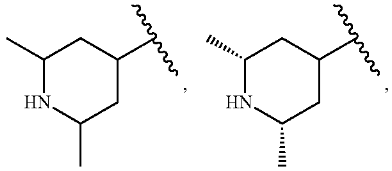
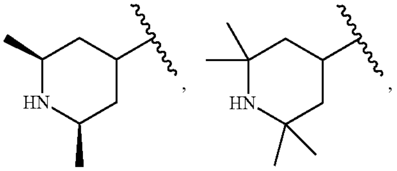
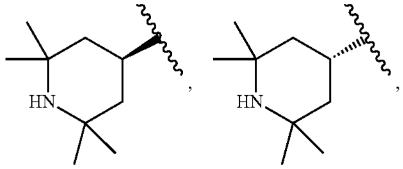
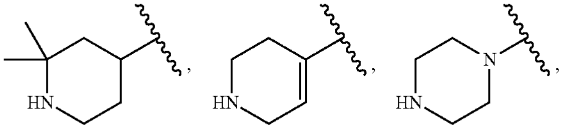
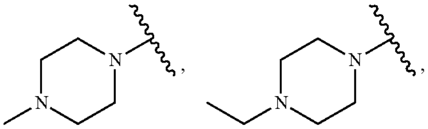
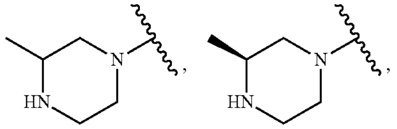
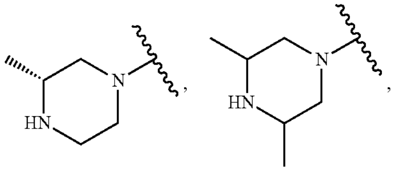
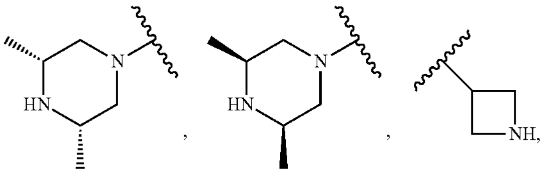
-continued
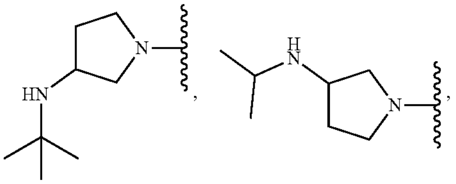
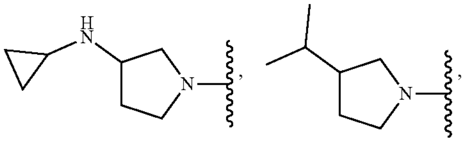
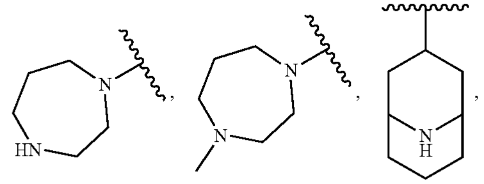
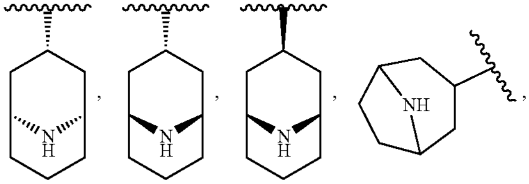
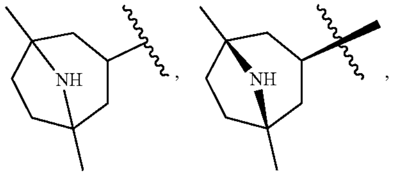
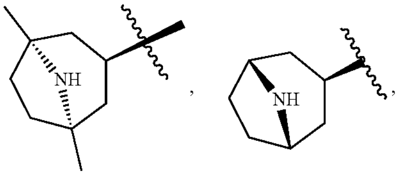
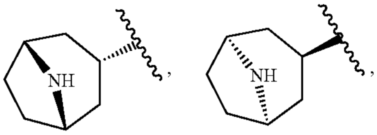
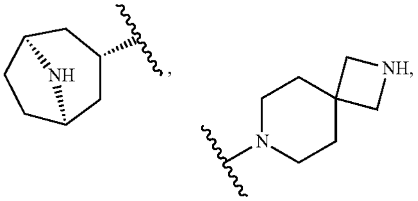
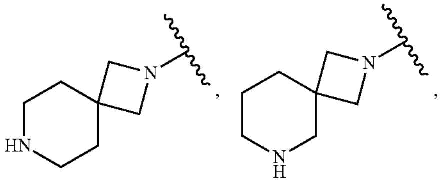
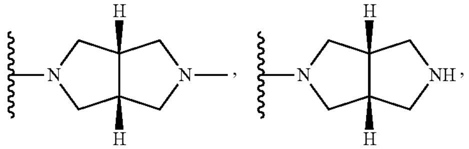

-continued
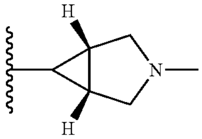, 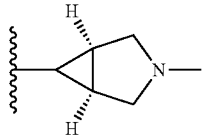,
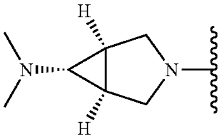, 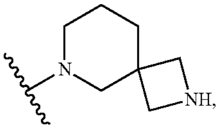,
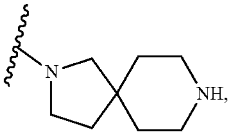, 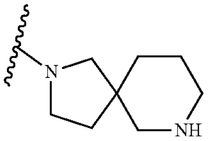,
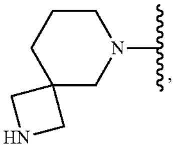, 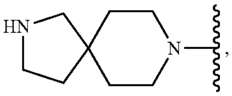,
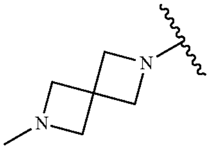, 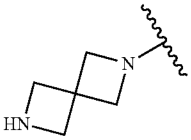, and
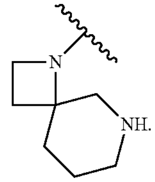.
In some embodiments, A is selected from
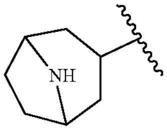, 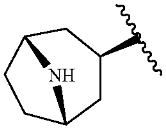, 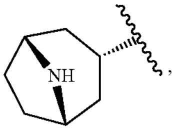,
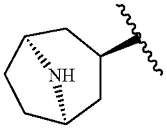, 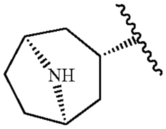, 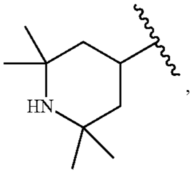,
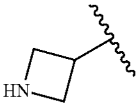, 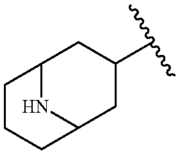, 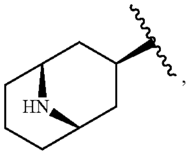,
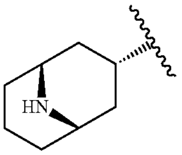, 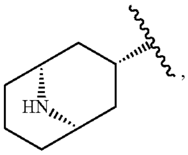,
-continued
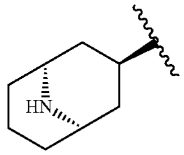, 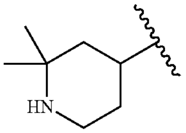,
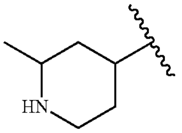, 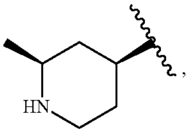,
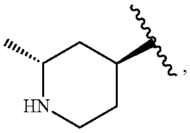, 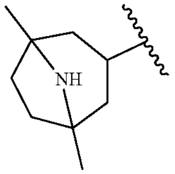,
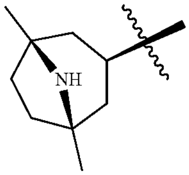, and 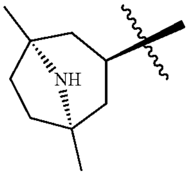.
In some embodiments, A is selected from
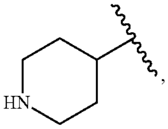, 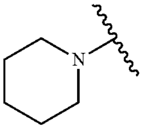, 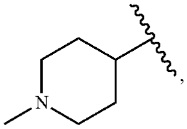,
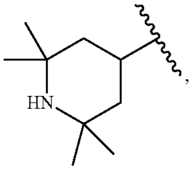, 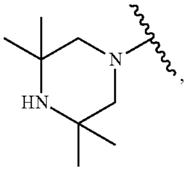,
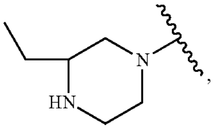, 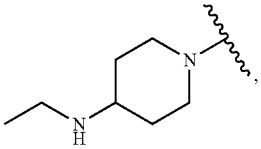,
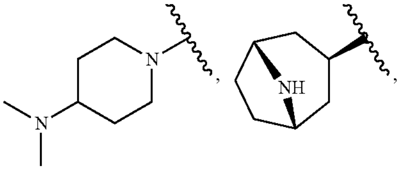,
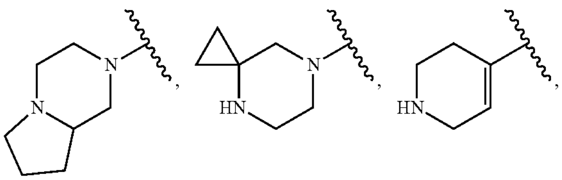,
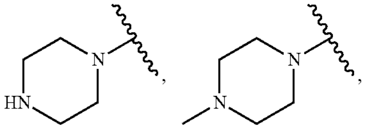, -continued
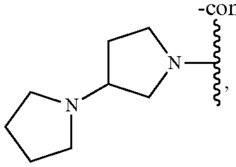
, and
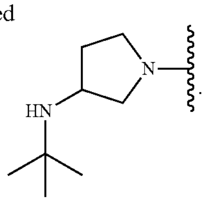
In some embodiments, A is
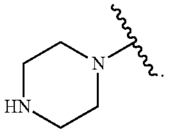
In some embodiments, A is
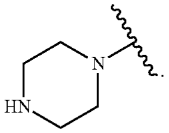 [SMILES: *N1CCNCC1]
In some embodiments, A is
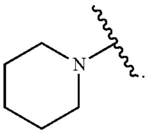 [SMILES: *N1CCCCC1]
In some embodiments, A is
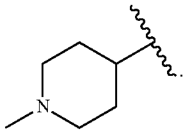
In some embodiments, A is
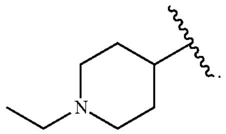 [SMILES: *C1CCN(CC)CC1]
In some embodiments, A is
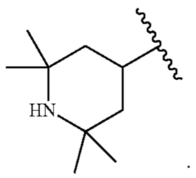 [SMILES: *C1CC(C)(C)NC(C)(C)C1]
In some embodiments, A is
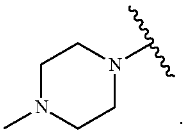 [SMILES: *N1CCN(C)CC1]
In some embodiments, A is
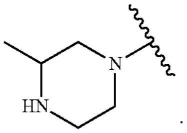
In some embodiments, A is
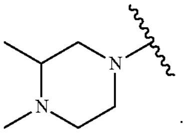 [SMILES: *N1CCN(C)C(C)C1]
In some embodiments, A is
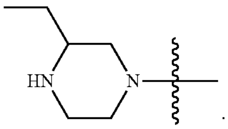 [SMILES: *N1CCNC(CC)C1]
In some embodiments, A is
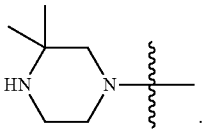 [SMILES: *N1CCNC(C)(C)C1]
In some embodiments, A is
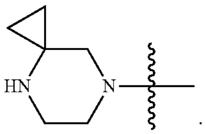
In some embodiments, A is
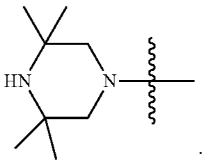 [SMILES: *N1CC(C)(C)NC(C)(C)C1]

In some embodiments, A is
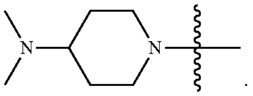 [SMILES: *N1CCC(N(C)C)CC1]
In some embodiments, A is
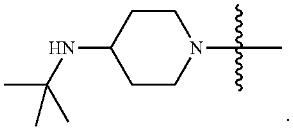 [SMILES: *N1CCC(NC(C)(C)C)CC1]
In some embodiments, A is
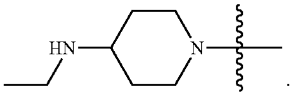 [SMILES: *N1CCC(NCC)CC1]
In some embodiments, A is
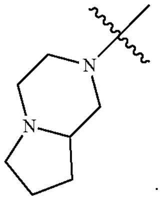 [SMILES: *N1CCN2CCCC2C1]
In some embodiments, A is
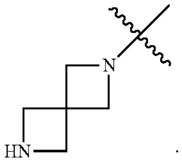 [SMILES: *N1CC2(CNC2)C1]
In some embodiments, A
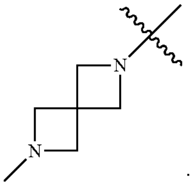 [SMILES: *N1CC2(C1)CN(C)C2]
In some embodiments, A is
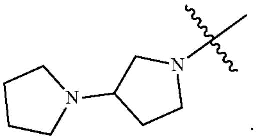 [SMILES: *N1CCC(N2CCCC2)C1]
In some embodiments, A is
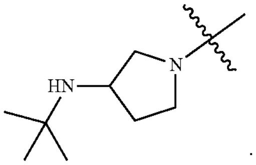 [SMILES: *N1CCC(NC(C)(C)C)C1]
In some embodiments, A is
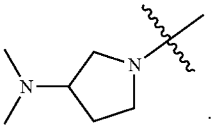 [SMILES: *N1CCC(N(C)C)C1]
In some embodiments, A is
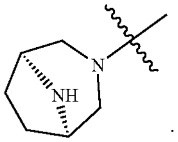 [SMILES: *N1C[C@H]2CC[C@@H](C1)N2]
In some embodiments, A is
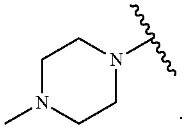 [SMILES: *N1CCN(C)CC1]
In some embodiments, A is
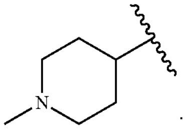 [SMILES: *C1CCN(C)CC1]
In some embodiments, A is
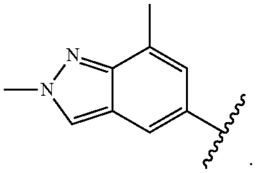 [SMILES: *c1cc(C)c2nn(C)cc2c1]

In some embodiments, A is
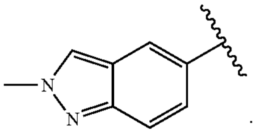 [SMILES: *c1ccc2nn(C)cc2c1].
In some embodiments, B is selected from
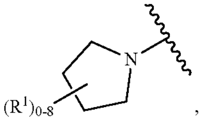, 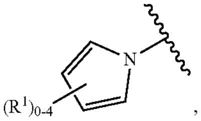,
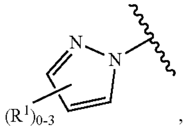, and 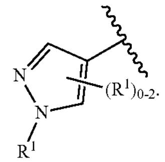.
In some embodiments, B is selected from
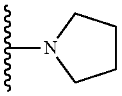, 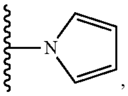, 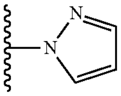, and
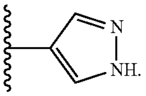
In some embodiments, B is selected from
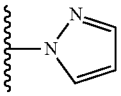, 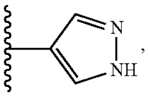, 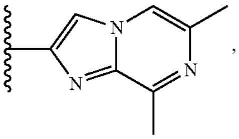,
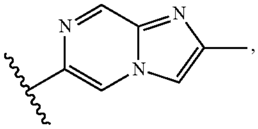, 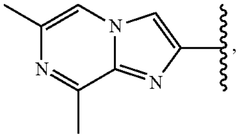,
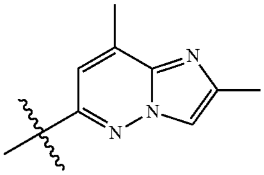, 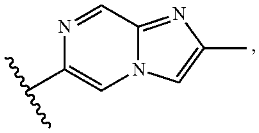,
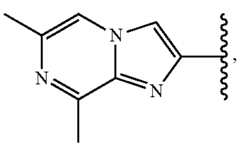, 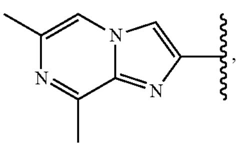,
-continued
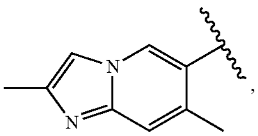, 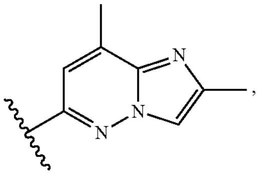,
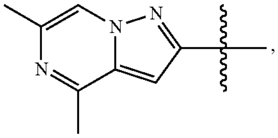, 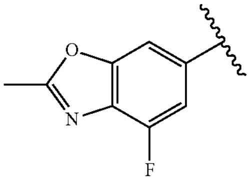
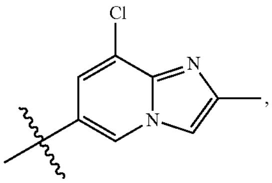, 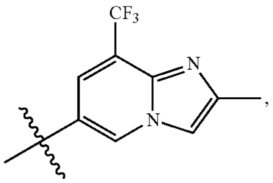,
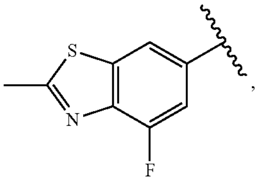, 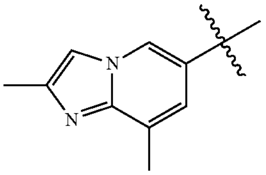,
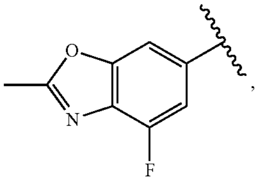, 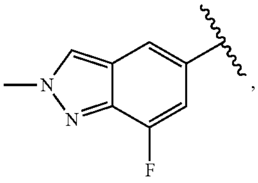,
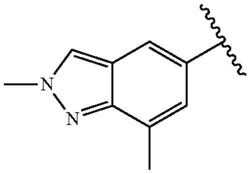, and
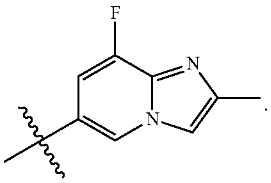.
In some embodiments, B is selected from
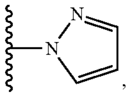, 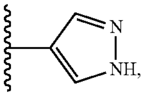, 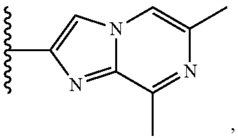 [SMILES: *c1cn2cc(C)nc(C)c2n1], -continued

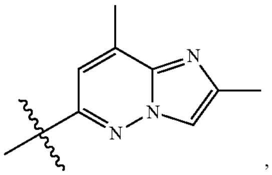

,

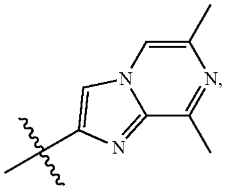

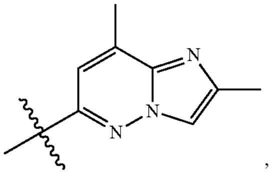 [SMILES: *c1cc(C)c2nc(C)cn2n1]

,

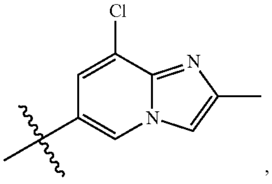

,

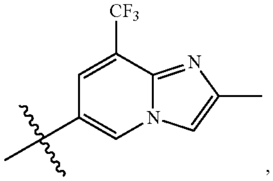

, and

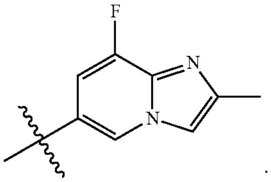

.

In some embodiments, B is selected is

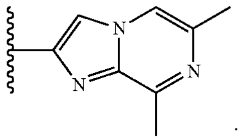

.

In some embodiments, B is

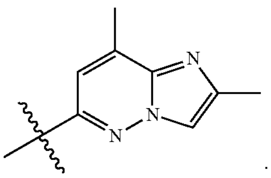

.

In some embodiments, B is

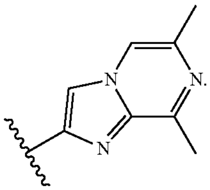 [SMILES: *c1cn2cc(C)nc(C)c2n1]

In some embodiments, B is

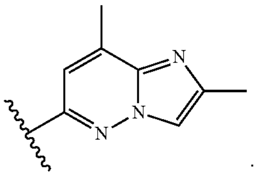 [SMILES: *c1cc(C)c2nc(C)cn2n1]

.

In some embodiments, B is

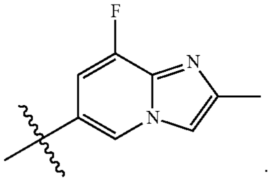 [SMILES: *c1cc(F)c2nc(C)cn2c1]

.

In some embodiments, $R^2$ is $C_1$-$C_6$-alkyl. In some embodiments, $R^2$ is halo (e.g., fluoro). In some embodiments, $R^2$ is —$OR^A$ (e.g., —OH). In some embodiments, $R^{3a}$ is hydrogen. In some embodiments, $R^{3c}$ is hydrogen. In some embodiments, m is 0.

In some embodiments, the compound of Formula (I) is a compound of Formula (I-e):

(I-e)

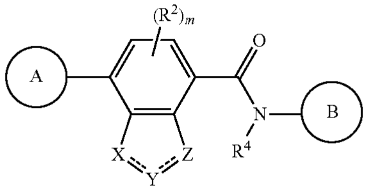

or a pharmaceutically acceptable salt, solvate, hydrate, tautomer, or stereoisomer thereof, wherein:

A and B are each independently cycloalkyl, heterocyclyl, aryl, or heteroaryl, each of which is optionally substituted with one or more $R^1$;

X, Y, and Z are each independently $C(R^{3a})$, $C(R^{3a})(R^{3b})$, N, $N(R^{3c})$, or O, wherein at least one of X, Y, and Z is N, $N(R^{3c})$, or O, and the bonds in the ring comprising X, Y, and Z may be single or double bonds as valency permits;

each $R^1$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, $C_1$-$C_6$ alkylene-aryl, $C_1$-$C_6$ alkenylene-aryl, $C_1$-$C_6$ alkylene-heteroaryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkylene, alkenyl, alkynyl, heteroalkyl, haloalkyl, cycloalkyl, heterocyclyl, aryl, and heteroaryl is optionally substituted with one or more $R^6$; or two $R^1$ groups, together with the atoms to which they are attached, form a 3-7-membered cycloalkyl, heterocyclyl, aryl, or heteroaryl, wherein each cycloalkyl, heterocyclyl, aryl, and heteroaryl is optionally substituted with one or more $R^6$;

each $R^2$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, halo, cyano, or —$OR^A$;

$R^{3a}$ and $R^{3b}$ are each independently hydrogen, $C_1$-$C_6$-alkyl, $C_1$-$C_6$-heteroalkyl, $C_1$-$C_6$-haloalkyl, halo, cyano, —$OR^A$, —$NR^BR^C$, —$C(O)R^D$, or —$C(O)OR^D$; or each of $R^{3a}$ and $R^{3b}$, together with the carbon atom to which they are attached, form an oxo group;

$R^{3c}$ is hydrogen or $C_1$-$C_6$-alkyl;

each $R^4$ is independently hydrogen, $C_1$-$C_6$-alkyl, or $C_1$-$C_6$-haloalkyl;

each $R^6$ is independently $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkenyl, alkynyl, heteroalkyl, haloalkyl, cycloalkyl, heterocyclyl, aryl, and heteroaryl is optionally substituted with one or more $R^1$;

each $R^7$ is $C_1$-$C_6$-alkyl, halo, cyano, oxo, or —$OR^{A1}$;

each $R^{11}$ is independently $C_1$-$C_6$-alkyl, $C_1$-$C_6$-heteroalkyl, $C_1$-$C_6$-haloalkyl, cycloalkyl, heterocyclyl, aryl, heteroaryl, halo, cyano, oxo, or —$OR^A$;

each $R^A$ is independently hydrogen, $C_1$-$C_6$ alkyl, $C_1$-$C_6$ haloalkyl, aryl, heteroaryl, $C_1$-$C_6$ alkylene-aryl, $C_1$-$C_6$ alkylene-heteroaryl, —$C(O)R^D$, or —$S(O)_xR^D$;

each of $R^B$ and $R^C$ is independently hydrogen, $C_1$-$C_6$ alkyl, $C_1$-$C_6$ heteroalkyl, cycloalkyl, heterocyclyl, or —$OR^A$; or $R^B$ and $R^C$ together with the atom to which they are attached form a 3-7-membered heterocyclyl ring optionally substituted with one or more $R^7$;

each $R^D$ and $R^E$ is independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, heteroaryl, $C_1$-$C_6$ alkylene-aryl, or $C_1$-$C_6$ alkylene-heteroaryl;

each $R^{A1}$ is hydrogen or $C_1$-$C_6$-alkyl;

m is 0, 1, or 2; and x is 0, 1, or 2.

In some embodiments, A is selected from

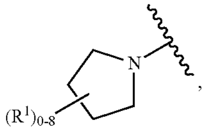,
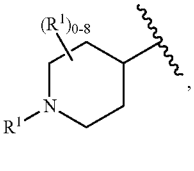,
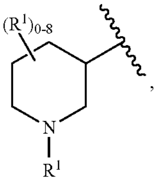,
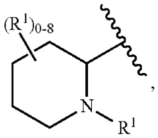,
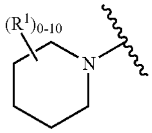,
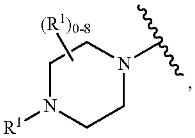,
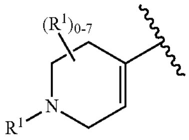,
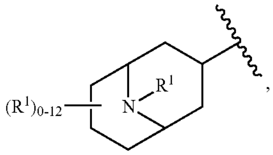,
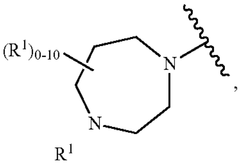,
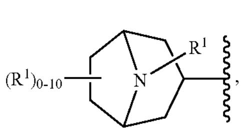, -continued

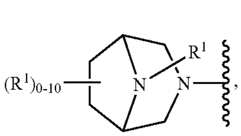,
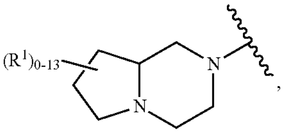, and
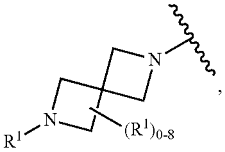, wherein $R^1$ is as defined herein.

In some embodiments, A is selected from

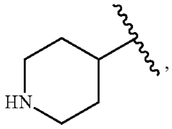,
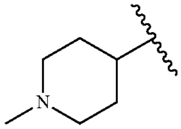,
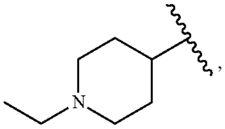,
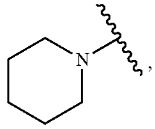,
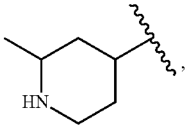,
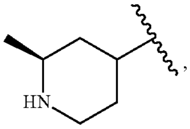,
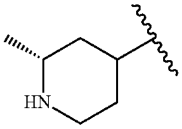,
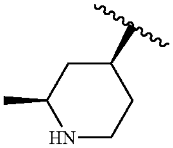,
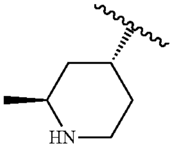,
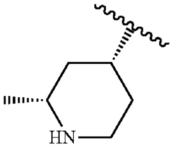,
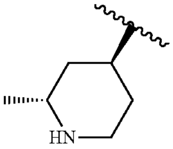,
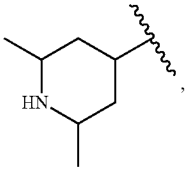,
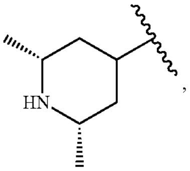,
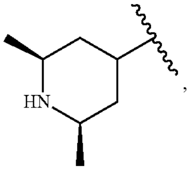,
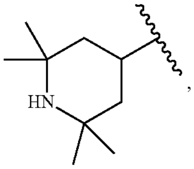,
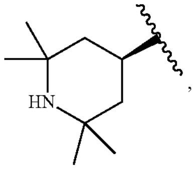,
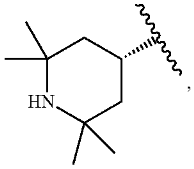, -continued
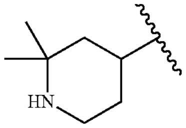, 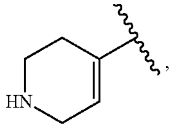, 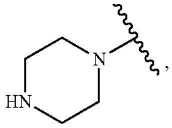,
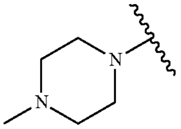, 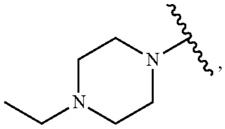,
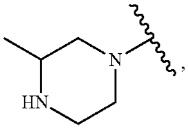, 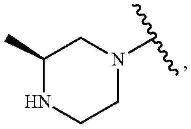,
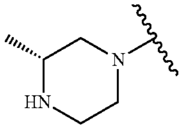, 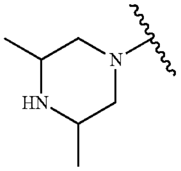,
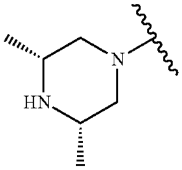, 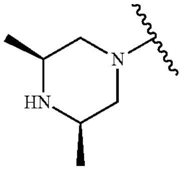, 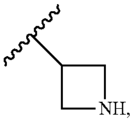,
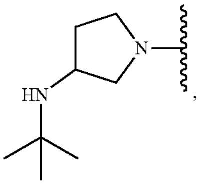, 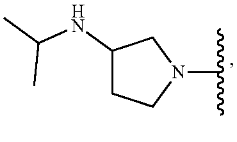,
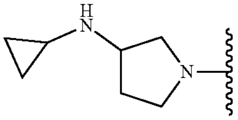, 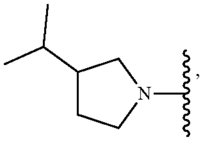,
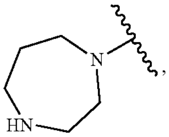, 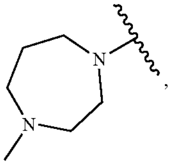, 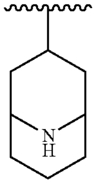,
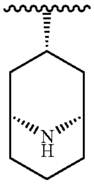, 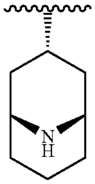, 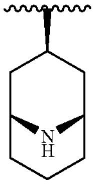, 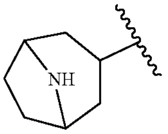,
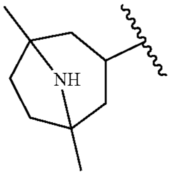, 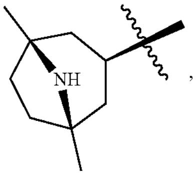,
-continued
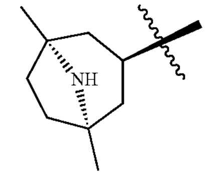, 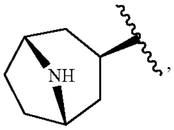,
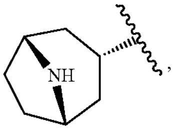, 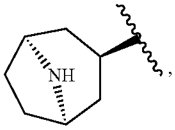,
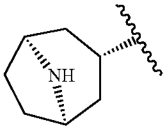, 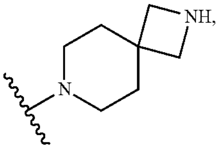,
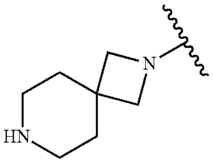, 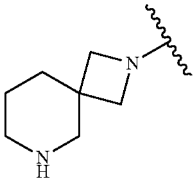,
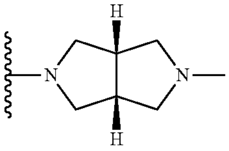, 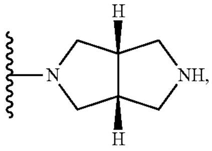,
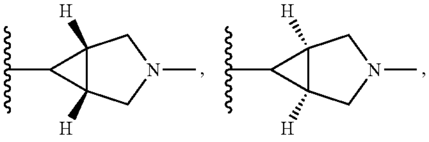,
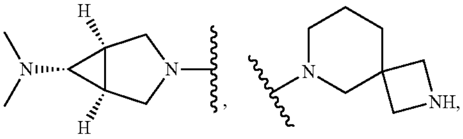,
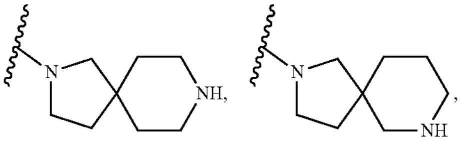,
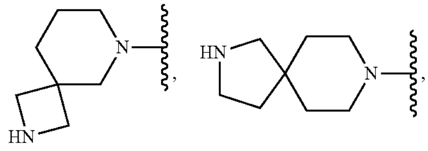,
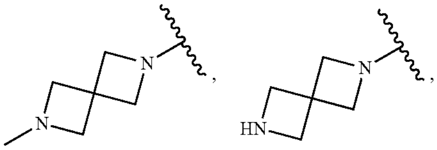, and -continued
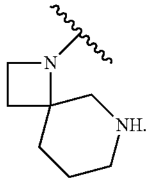
In some embodiments, A is selected from
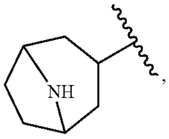, 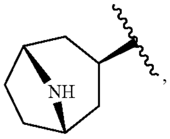, 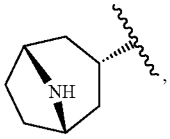,
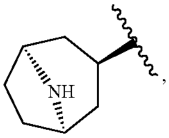, 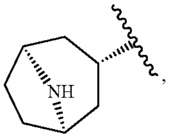, 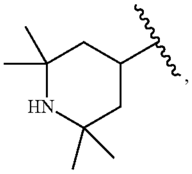,
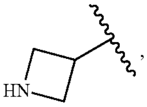, 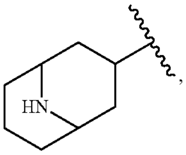, 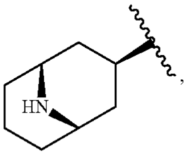,
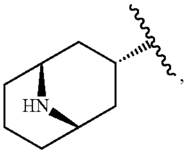, 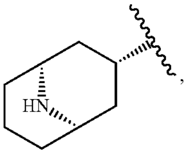, 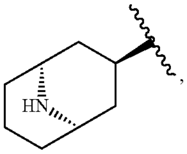,
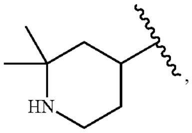, 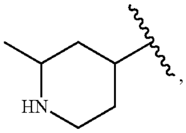, 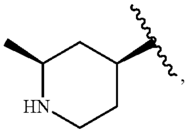,
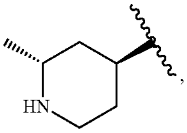, 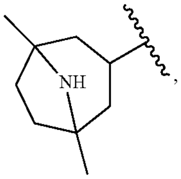,
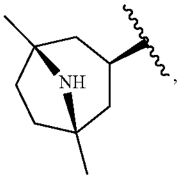, and 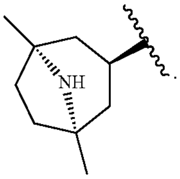.
In some embodiments, A is selected from
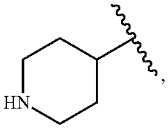, 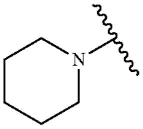, 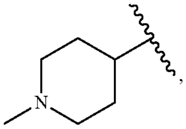,
-continued
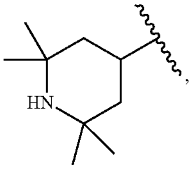, 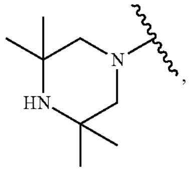,
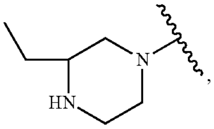, 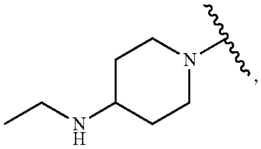,
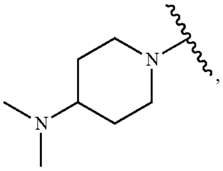, 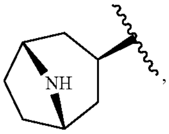,
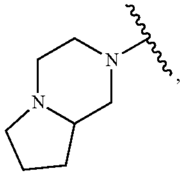, 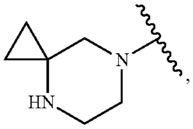, 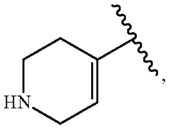,
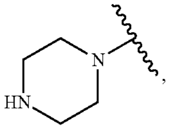, 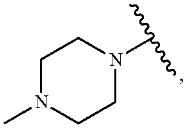,
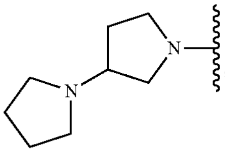, and 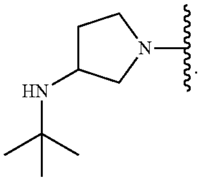.
In some embodiments, A is
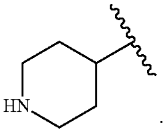.
In some embodiments, A is
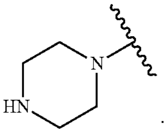.

In some embodiments, A is
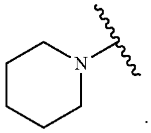 [SMILES: *N1CCCCC1]
.
In some embodiments, A is
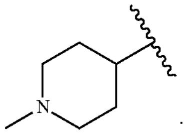 [SMILES: *C1CCN(C)CC1]
.
In some embodiments, A is
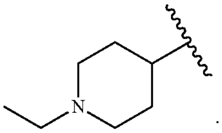 [SMILES: *C1CCN(CC)CC1]
.
In some embodiments, A is
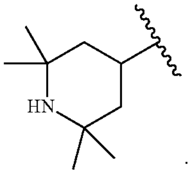 [SMILES: *C1CC(C)(C)NC(C)(C)C1]
.
In some embodiments, A is
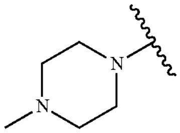
.
In some embodiments, A is
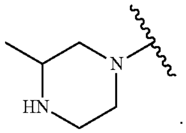 [SMILES: *N1CCNC(C)C1]
.
In some embodiments, A is
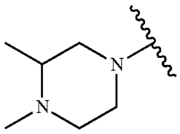
.
In some embodiments, A is
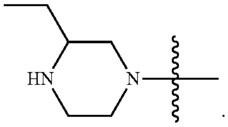 [SMILES: *N1CCNC(CC)C1]
.
In some embodiments, A is
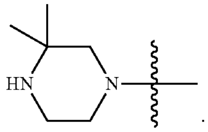 [SMILES: *N1CCNC(C)(C)C1]
.
In some embodiments, A is
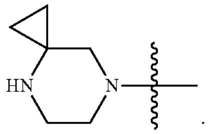 [SMILES: *N1CCNC2(CC2)C1]
.
In some embodiments, A is
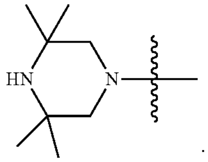 [SMILES: *N1CC(C)(C)NC(C)(C)C1]
.
In some embodiments, A is
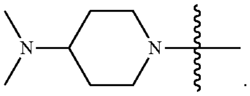 [SMILES: *N1CCC(N(C)C)CC1]
.
In some embodiments, A is
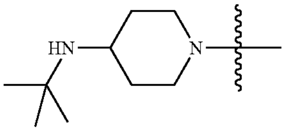
.
In some embodiments, A is
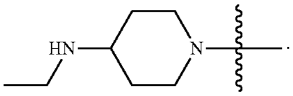 [SMILES: *N1CCC(NCC)CC1]
.

In some embodiments, A is

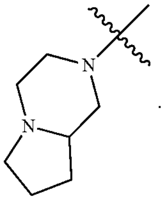 [SMILES: *N1CCN2CCCC2C1]

In some embodiments, A is

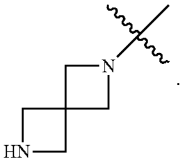

In some embodiments, A is

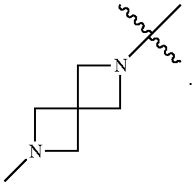 [SMILES: *N1CC2(C1)CN(C)C2]

In some embodiments, A is

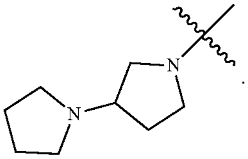 [SMILES: *N1CCC(N2CCCC2)C1]

In some embodiments, A is

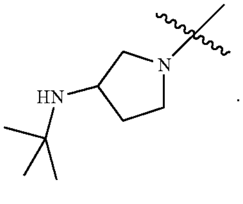 [SMILES: *N1CCC(NC(C)(C)C)C1]

In some embodiments, A is

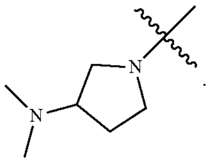 [SMILES: *N1CCC(N(C)C)C1]

In some embodiments, A is

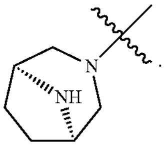 [SMILES: *N1C[C@H]2CC[C@@H](C1)N2]

In some embodiments, A is

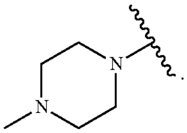 [SMILES: *N1CCN(C)CC1]

In some embodiments, A is

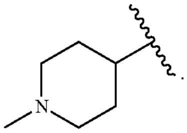 [SMILES: *C1CCN(C)CC1]

In some embodiments, A is

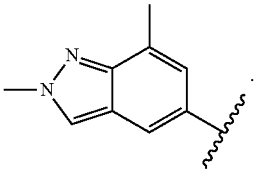 [SMILES: *c1cc(C)c2nn(C)cc2c1]

In some embodiments, A is

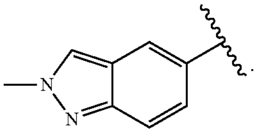

In some embodiments, X is N. In some embodiments, X is O. In some embodiments, X is C($R^{3a}$). In some embodiments, Y is N. In some embodiments, Y is C($R^{3a}$). In some embodiments, Z is C($R^{3a}$) (e.g., CH). In some embodiments, Z is N. In some embodiments, Z is O. In some embodiments, X and Y are each independently N or N($R^{3c}$), and Z is C($R^{3a}$) (e.g., CH). In some embodiments, Y and Z are each independently N or N($R^{3c}$), and X is C($R^{3a}$) (e.g., CH). In some embodiments, X is C($R^{3a}$), Y is C($R^{3a}$), and Z is O. In some embodiments, Y is C($R^{3a}$), Z is C($R^{3a}$), and X is O.

In some embodiments, B is selected from
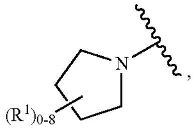, 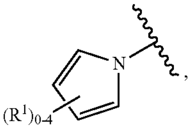, 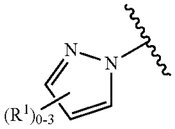, and 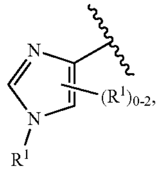
In some embodiments, B is selected from
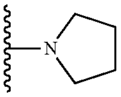, 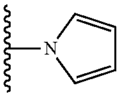, 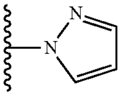, and 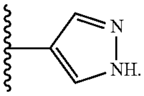
In some embodiments, B is selected from
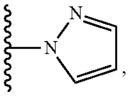, 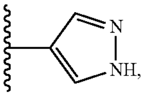 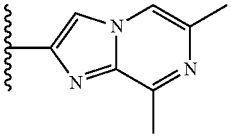, 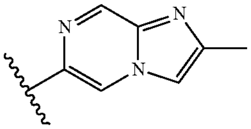, 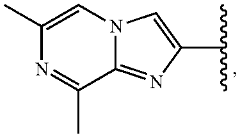 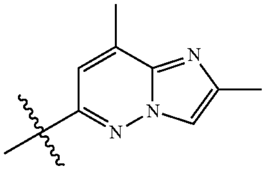, 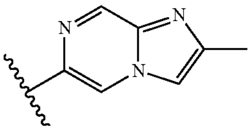, 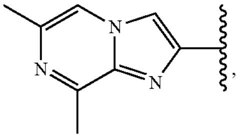 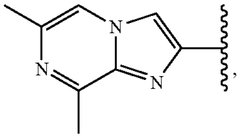 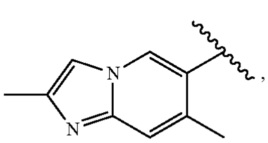, 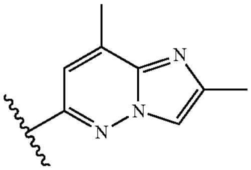, 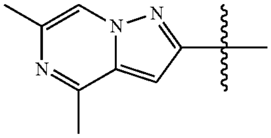, 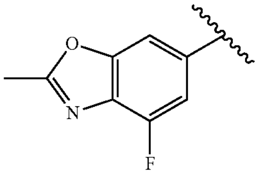,
-continued
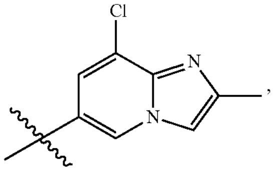, 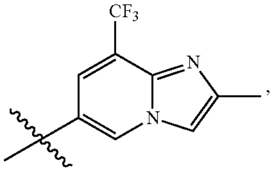, 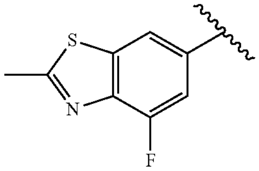, 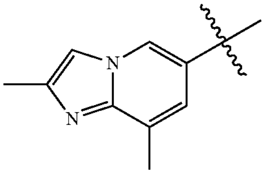, 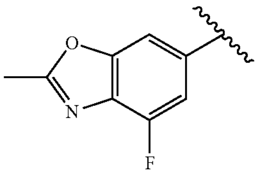, 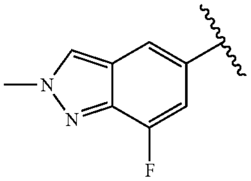, 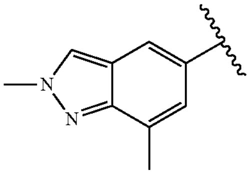, and 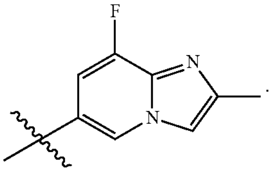.
In some embodiments, B is selected from
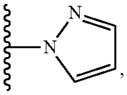, 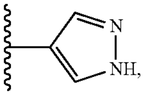 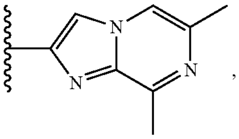, 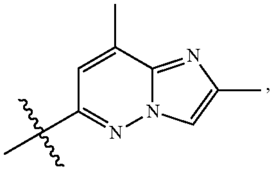, 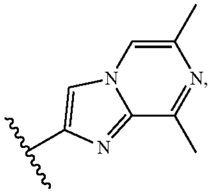 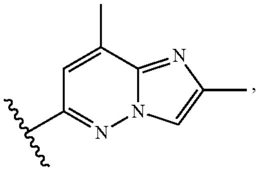, 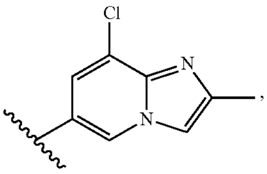, 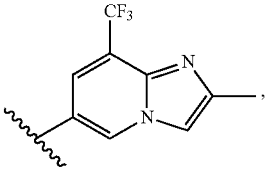, and -continued

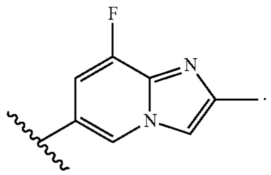

In some embodiments, B is selected is

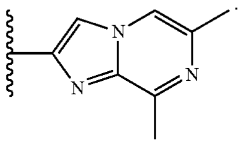 [SMILES: *c1cn2cc(C)nc(C)c2n1]

In some embodiments, B is

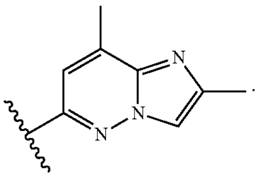 [SMILES: *c1cc(C)c2nc(C)cn2n1]

In some embodiments, B is

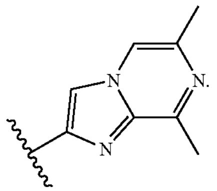 [SMILES: *c1cn2cc(C)nc(C)c2n1]

In some embodiments, B is

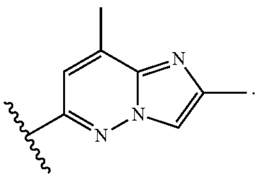 [SMILES: *c1cc(C)c2nc(C)cn2n1]

In some embodiments, B is

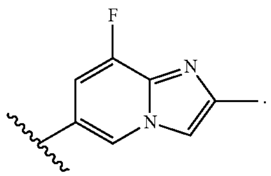 [SMILES: *c1cc(F)c2nc(C)cn2c1]

In some embodiments, the compound of Formula (I) is a compound of Formula (I-f):

(I-f)

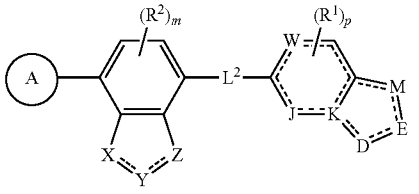

or a pharmaceutically acceptable salt, solvate, hydrate, tautomer, or stereoisomer thereof, wherein:

A and B are each independently cycloalkyl, heterocyclyl, aryl, or heteroaryl, each of which is optionally substituted with one or more $R^1$;

X, Y, and Z are each independently $C(R^{3a})$, $C(R^{3a})(R^{3b})$, N, $N(R^{3c})$, or O, wherein at least one of X, Y, and Z is N, $N(R^{3c})$, or O, and the bonds in the ring comprising X, Y, and Z may be single or double bonds as valency permits;

$L^2$ is absent, $C_1$-$C_6$-alkylene, $C_1$-$C_6$-heteroalkylene, —O—, —C(O)—, —$N(R^4)$—, —$N(R^4)C(O)$—, or —$C(O)N(R^4)$—, wherein each alkylene and heteroalkylene is optionally substituted with one or more $R^5$;

D, E, J, K, M, and W are each independently N and C(R'), wherein at least one of D, E, J, K, M, and W is N; and the bonds in the rings comprising D, E, J, K, M, and W may be single or double bonds as valency permits;

each $R^1$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, $C_1$-$C_6$ alkylene-aryl, $C_1$-$C_6$ alkenylene-aryl, $C_1$-$C_6$ alkylene-heteroaryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkylene, alkenyl, alkynyl, heteroalkyl, haloalkyl, cycloalkyl, heterocyclyl, aryl, and heteroaryl is optionally substituted with one or more $R^6$; or two $R^1$ groups, together with the atoms to which they are attached, form a 3-7-membered cycloalkyl, heterocyclyl, aryl, or heteroaryl, wherein each cycloalkyl, heterocyclyl, aryl, and heteroaryl is optionally substituted with one or more $R^6$;

R' is hydrogen, $C_1$-$C_6$-alkyl, or halo;

each $R^2$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, halo, cyano, or —$OR^A$;

$R^{3a}$ and $R^{3b}$ are each independently hydrogen, $C_1$-$C_6$-alkyl, $C_1$-$C_6$-heteroalkyl, $C_1$-$C_6$-haloalkyl, halo, cyano, —$OR^A$, —$NR^BR^C$, —$C(O)R^D$, or —$C(O)OR^D$; or each of $R^{3a}$ and $R^{3b}$, together with the carbon atom to which they are attached, form an oxo group;

$R^{3c}$ is hydrogen or $C_1$-$C_6$-alkyl;

each $R^4$ is independently hydrogen, $C_1$-$C_6$-alkyl, or $C_1$-$C_6$-haloalkyl;

each $R^5$ is independently hydrogen, $C_1$-$C_6$-alkyl, $C_1$-$C_6$-heteroalkyl, $C_1$-$C_6$-haloalkyl, cycloalkyl, halo, cyano, oxo, —$OR^A$, —$NR^BR^C$, —$C(O)R^D$, or —$C(O)OR^D$;

each $R^6$ is independently $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkenyl, alkynyl, heteroalkyl, haloalkyl, cycloalkyl, heterocyclyl, aryl, and heteroaryl is optionally substituted with one or more $R^{11}$;

each $R^7$ is $C_1$-$C_6$-alkyl, halo, cyano, oxo, or —$OR^{A1}$;

each $R^{11}$ is independently $C_1$-$C_6$-alkyl, $C_1$-$C_6$-heteroalkyl, $C_1$-$C_6$-haloalkyl, cycloalkyl, heterocyclyl, aryl, heteroaryl, halo, cyano, oxo, or —$OR^A$;

each $R^A$ is independently hydrogen, $C_1$-$C_6$ alkyl, $C_1$-$C_6$ haloalkyl, aryl, heteroaryl, $C_1$-$C_6$ alkylene-aryl, $C_1$-$C_6$ alkylene-heteroaryl, —$C(O)R^D$, or —$S(O)_xR^D$;

each of $R^B$ and $R^C$ is independently hydrogen, $C_1$-$C_6$ alkyl, $C_1$-$C_6$ heteroalkyl, cycloalkyl, heterocyclyl, or —$OR^A$; or $R^B$ and $R^C$ together with the atom to which they are attached form a 3-7-membered heterocyclyl ring optionally substituted with one or more $R^7$;

each $R^D$ and $R^E$ is independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, heteroaryl, $C_1$-$C_6$ alkylene-aryl, or $C_1$-$C_6$ alkylene-heteroaryl;

each $R^{A1}$ is hydrogen or $C_1$-$C_6$-alkyl;

m is 0, 1, or 2;

p is 0, 1, 2, 3, or 4; and x is 0, 1, or 2.

In some embodiments, the compound of Formula (I) is a compound of Formula (I-g):

(I-g)

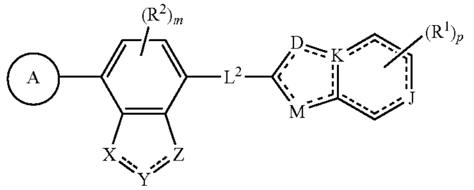

or a pharmaceutically acceptable salt, solvate, hydrate, tautomer, or stereoisomer thereof, wherein:

A and B are each independently cycloalkyl, heterocyclyl, aryl, or heteroaryl, each of which is optionally substituted with one or more $R^1$;

X, Y, and Z are each independently $C(R^{3a})$, $C(R^{3a})(R^{3b})$, N, $N(R^{3c})$, or O, wherein at least one of X, Y, and Z is N, $N(R^{3c})$, or O, and the bonds in the ring comprising X, Y, and Z may be single or double bonds as valency permits;

$L^2$ is absent, $C_1$-$C_6$-alkylene, $C_1$-$C_6$-heteroalkylene, —O—, —C(O)—, —$N(R^4)$—, —$N(R^4)C(O)$—, or —$C(O)N(R^4)$—, wherein each alkylene and heteroalkylene is optionally substituted with one or more $R^5$;

D, J, K, and M are each independently N and C(R'), wherein at least one of D, J, K, and M is N; and the bonds in the rings comprising D, E, J, K, M, and W may be single or double bonds as valency permits;

each $R^1$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, $C_1$-$C_6$ alkylene-aryl, $C_1$-$C_6$ alkenylene-aryl, $C_1$-$C_6$ alkylene-heteroaryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkylene, alkenyl, alkynyl, heteroalkyl, haloalkyl, cycloalkyl, heterocyclyl, aryl, and heteroaryl is optionally substituted with one or more $R^6$; or two $R^1$ groups, together with the atoms to which they are attached, form a 3-7-membered cycloalkyl, heterocyclyl, aryl, or heteroaryl, wherein each cycloalkyl, heterocyclyl, aryl, and heteroaryl is optionally substituted with one or more $R^6$;

R' is hydrogen, $C_1$-$C_6$-alkyl, or halo;

each $R^2$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, halo, cyano, or —$OR^A$;

$R^{3a}$ and $R^{3b}$ are each independently hydrogen, $C_1$-$C_6$-alkyl, $C_1$-$C_6$-heteroalkyl, $C_1$-$C_6$-haloalkyl, halo, cyano, —$OR^A$, —$NR^BR^C$, —$C(O)R^D$, or —$C(O)OR^D$; or each of $R^{3a}$ and $R^{3b}$, together with the carbon atom to which they are attached, form an oxo group;

$R^{3c}$ is hydrogen or $C_1$-$C_6$-alkyl;

each $R^4$ is independently hydrogen, $C_1$-$C_6$-alkyl, or $C_1$-$C_6$-haloalkyl;

each $R^5$ is independently hydrogen, $C_1$-$C_6$-alkyl, $C_1$-$C_6$-heteroalkyl, $C_1$-$C_6$-haloalkyl, cycloalkyl, halo, cyano, oxo, —$OR^A$, —$NR^BR^C$, —$C(O)R^D$, or —$C(O)OR^D$;

each $R^6$ is independently $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkenyl, alkynyl, heteroalkyl, haloalkyl, cycloalkyl, heterocyclyl, aryl, and heteroaryl is optionally substituted with one or more $R^{11}$;

each $R^7$ is $C_1$-$C_6$-alkyl, halo, cyano, oxo, or —$OR^{A1}$;

each $R^{11}$ is independently $C_1$-$C_6$-alkyl, $C_1$-$C_6$-heteroalkyl, $C_1$-$C_6$-haloalkyl, cycloalkyl, heterocyclyl, aryl, heteroaryl, halo, cyano, oxo, or —$OR^A$;

each $R^A$ is independently hydrogen, $C_1$-$C_6$ alkyl, $C_1$-$C_6$ haloalkyl, aryl, heteroaryl, $C_1$-$C_6$ alkylene-aryl, $C_1$-$C_6$ alkylene-heteroaryl, —$C(O)R^D$, or —$S(O)_xR^D$;

each of $R^B$ and $R^C$ is independently hydrogen, $C_1$-$C_6$ alkyl, $C_1$-$C_6$ heteroalkyl, cycloalkyl, heterocyclyl, or —$OR^A$; or $R^B$ and $R^C$ together with the atom to which they are attached form a 3-7-membered heterocyclyl ring optionally substituted with one or more $R^7$;

each $R^D$ and $R^E$ is independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, heteroaryl, $C_1$-$C_6$ alkylene-aryl, or $C_1$-$C_6$ alkylene-heteroaryl;

each $R^{A1}$ is hydrogen or $C_1$-$C_6$-alkyl;

m is 0, 1, or 2;

p is 0, 1, 2, 3, or 4; and x is 0, 1, or 2.

In some embodiments, the compound of Formula (I) is a compound of Formula (I-h):

(I-h)

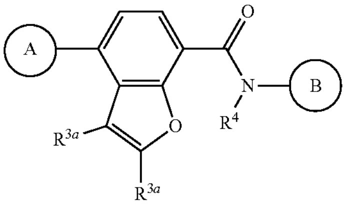

or a pharmaceutically acceptable salt, solvate, hydrate, tautomer, or stereoisomer thereof, wherein:

A and B are each independently cycloalkyl, heterocyclyl, aryl, or heteroaryl, each of which is optionally substituted with one or more $R^1$;

each $R^1$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, $C_1$-$C_6$ alkylene-aryl, $C_1$-$C_6$ alkenylene-aryl, $C_1$-$C_6$ alkylene-heteroaryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkylene, alkenyl, alkynyl, heteroalkyl, haloalkyl, cycloalkyl, heterocyclyl, aryl, and heteroaryl is optionally substituted with one or more $R^6$; or two $R^1$ groups, together with the atoms to which they are attached, form a 3-7-membered cycloalkyl, heterocyclyl, aryl, or heteroaryl, wherein each cycloalkyl, heterocyclyl, aryl, and heteroaryl is optionally substituted with one or more $R^6$;

each $R^2$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, halo, cyano, or —$OR^A$;

each $R^{3a}$ is independently hydrogen, $C_1$-$C_6$-alkyl, $C_1$-$C_6$-heteroalkyl, $C_1$-$C_6$-haloalkyl, halo, cyano, —$OR^A$, —$NR^BR^C$, —$C(O)R^D$, or —$C(O)OR^D$;

each $R^4$ is independently hydrogen, $C_1$-$C_6$-alkyl, or $C_1$-$C_6$-haloalkyl;

each $R^6$ is independently $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkenyl, alkynyl, heteroalkyl, haloalkyl, cycloalkyl, heterocyclyl, aryl, and heteroaryl is optionally substituted with one or more $R^1$;

each $R^7$ is $C_1$-$C_6$-alkyl, halo, cyano, oxo, or —$OR^{A1}$;

each $R^{11}$ is independently $C_1$-$C_6$-alkyl, $C_1$-$C_6$-heteroalkyl, $C_1$-$C_6$-haloalkyl, cycloalkyl, heterocyclyl, aryl, heteroaryl, halo, cyano, oxo, or —$OR^A$;

each $R^A$ is independently hydrogen, $C_1$-$C_6$ alkyl, $C_1$-$C_6$ haloalkyl, aryl, heteroaryl, $C_1$-$C_6$ alkylene-aryl, $C_1$-$C_6$ alkylene-heteroaryl, —$C(O)R^D$, or —$S(O)_xR^D$;

each of $R^B$ and $R^C$ is independently hydrogen, $C_1$-$C_6$ alkyl, $C_1$-$C_6$ heteroalkyl, cycloalkyl, heterocyclyl, or —$OR^A$; or $R^B$ and $R^C$ together with the atom to which they are attached form a 3-7-membered heterocyclyl ring optionally substituted with one or more $R^7$;

each $R^D$ and $R^E$ is independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, heteroaryl, $C_1$-$C_6$ alkylene-aryl, or $C_1$-$C_6$ alkylene-heteroaryl;

each $R^{A1}$ is hydrogen or $C_1$-$C_6$-alkyl;

m is 0, 1, or 2; and x is 0, 1, or 2.

In some embodiments, A is heterocyclyl optionally substituted with one or more $R^1$. In some embodiments, A is bicyclic heterocyclyl. In some embodiments, A is monocyclic nitrogen-containing heterocyclyl. In some embodiments, A is bicyclic nitrogen-containing heterocyclyl. In some embodiments, A is optionally substituted piperidinyl. In some embodiments, A is optionally substituted piperazinyl. In some embodiments, A is

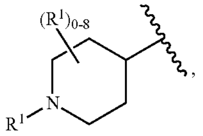

wherein each $R^1$ is independently hydrogen or $C_1$-$C_6$-alkyl. In some embodiments, A is

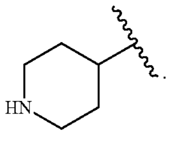

In some embodiments, A is

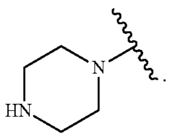

In some embodiments, each $R^{3a}$ is independently hydrogen or $C_1$-$C_6$-alkyl (e.g., $CH_3$). In some embodiments, each $R^{3a}$ is independently hydrogen. In some embodiments, each $R^{3a}$ is independently $C_1$-$C_6$-alkyl (e.g., $CH_3$).

In some embodiments, B is heteroaryl optionally substituted with one or more $R^1$. In some embodiments, B is monocyclic heteroaryl. In some embodiments, B is bicyclic heteroaryl. In some embodiments, B is monocyclic nitrogen-containing heteroaryl. In some embodiments, B is bicyclic nitrogen-containing heteroaryl. In some embodiments, B is optionally substituted pyrazolyl. In some embodiments, B is selected from

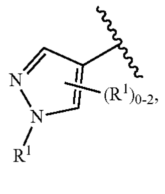

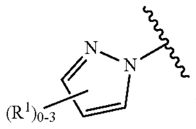
,

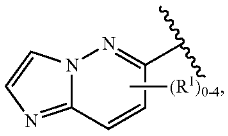

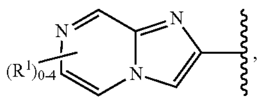
, and

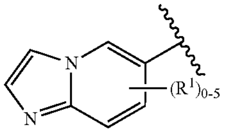

wherein each $R^1$ is as defined above. In some embodiments, B is
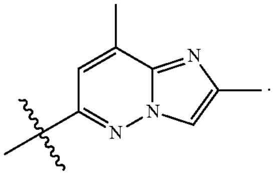 [SMILES: *c1cc(C)c2nc(C)cn2n1]
In some embodiments, B is
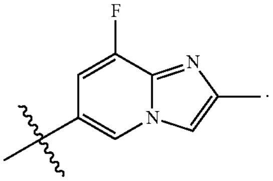 [SMILES: *c1cc(F)c2nc(C)cn2c1]
In some embodiments, A is selected from
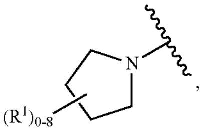, 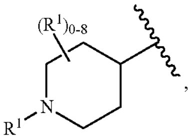, 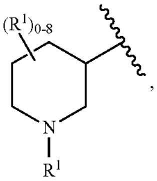, 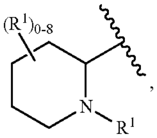, 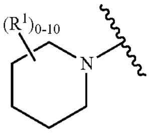, 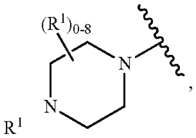, 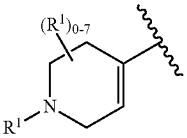, 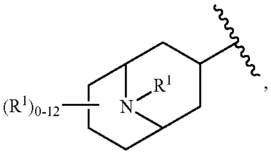, 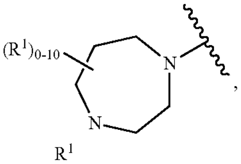, 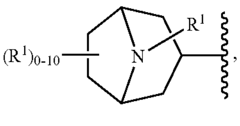, 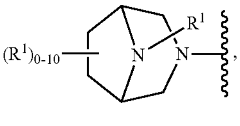, 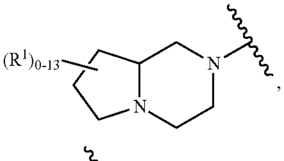, and
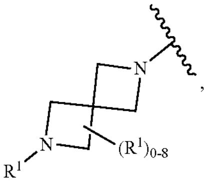,
wherein $R^1$ is as defined herein.
In some embodiments, A is selected from
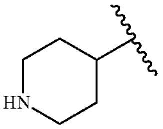, 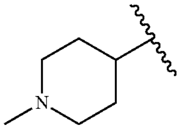, 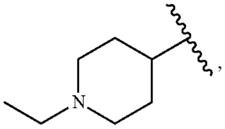, 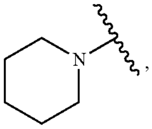, 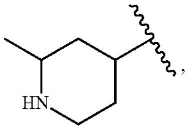, 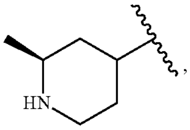, 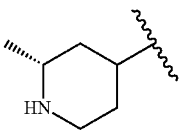, 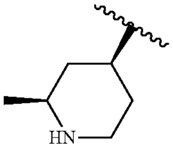, 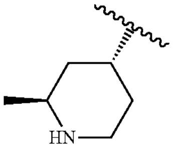, 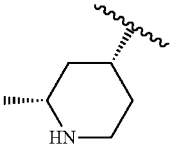, 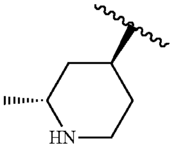, 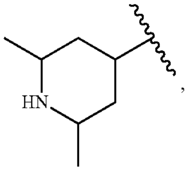, 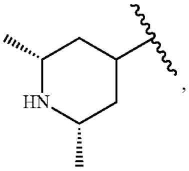, 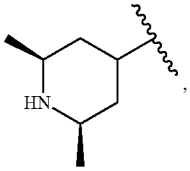, 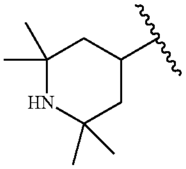, 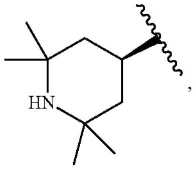, 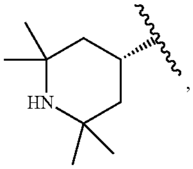, 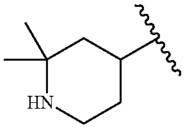, 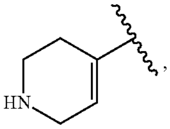, 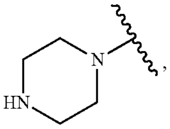, 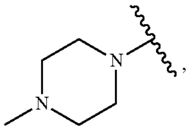, 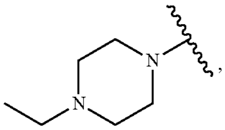, 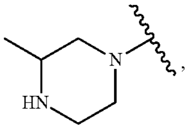, 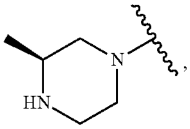, -continued
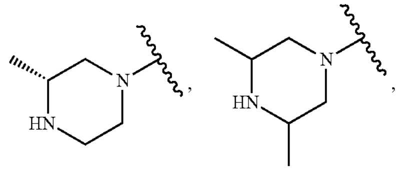
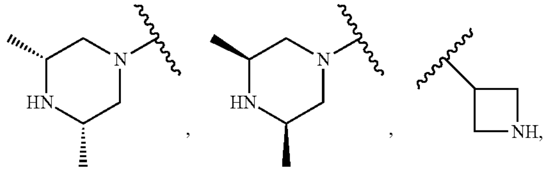
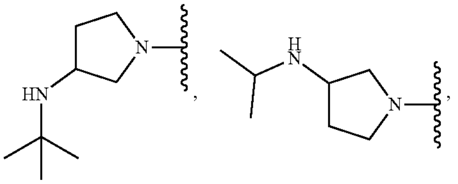
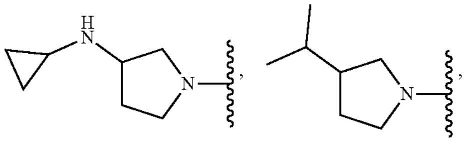
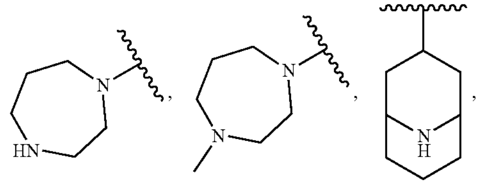
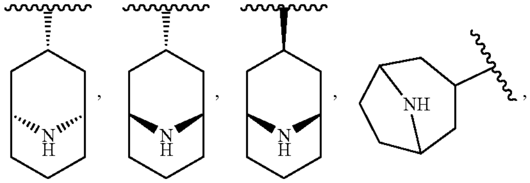
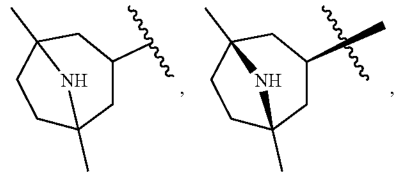
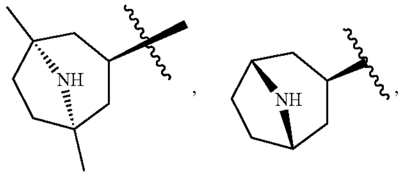
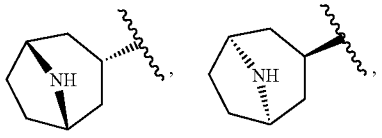
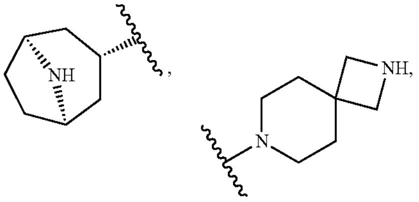
-continued
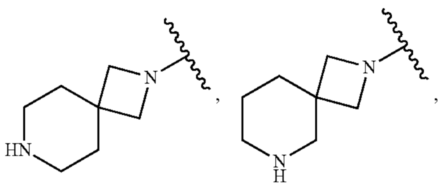
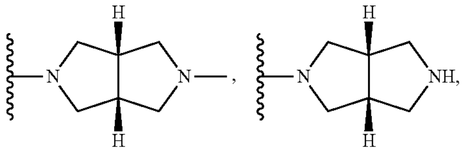
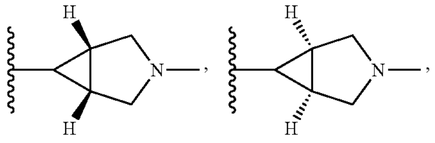
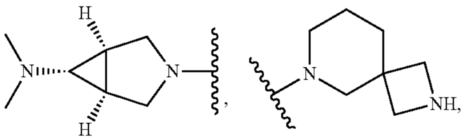
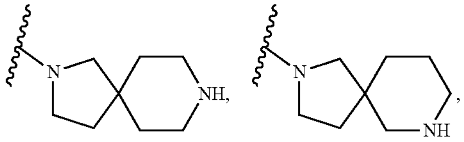
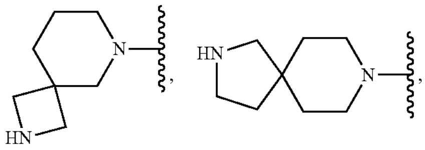
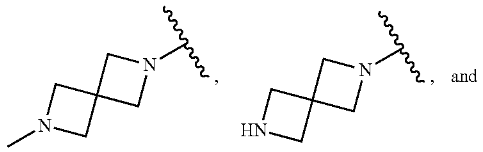
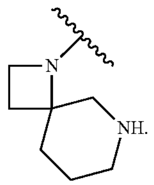
In some embodiments, A is selected from
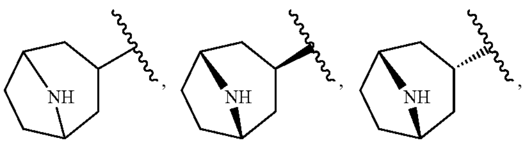
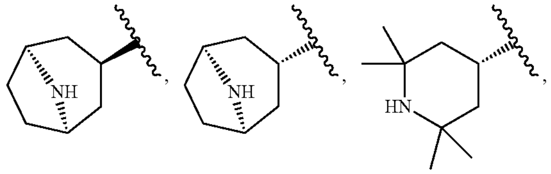

-continued
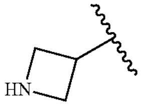, 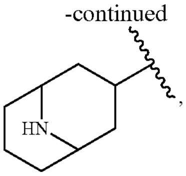, 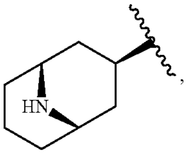,
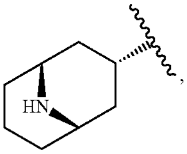, 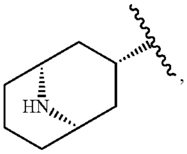, 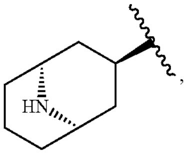,
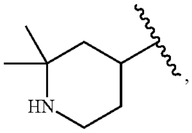, 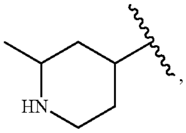, 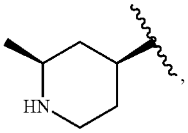,
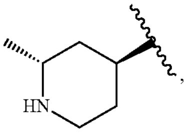, 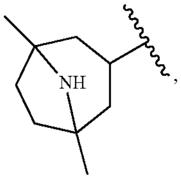,
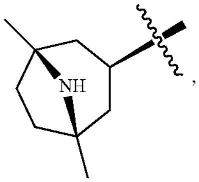, and 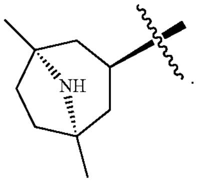.
In some embodiments, A is selected from
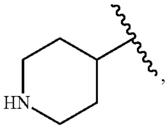, 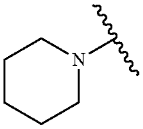 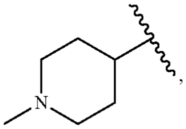,
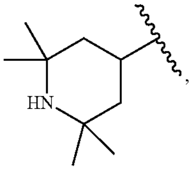, 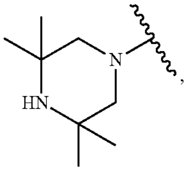,
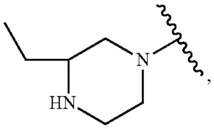, 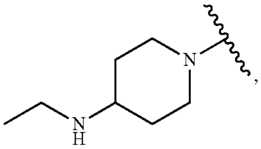,
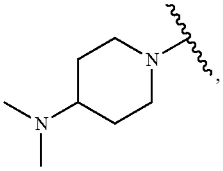, 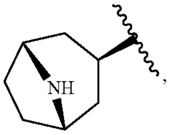,
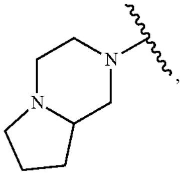, 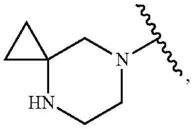, 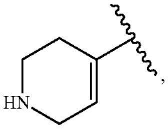,
-continued
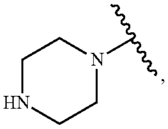, 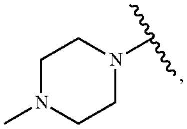,
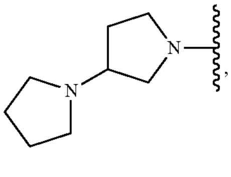, and 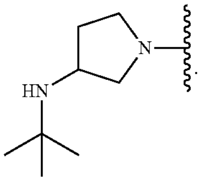.
In some embodiments, A is
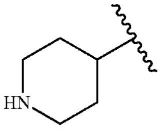.
In some embodiments, A is
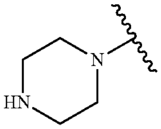.
In some embodiments, A is
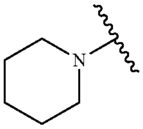.
In some embodiments, A is
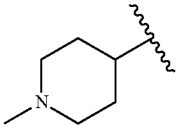.
In some embodiments, A is
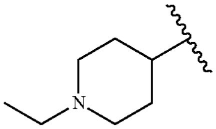.

In some embodiments, A is
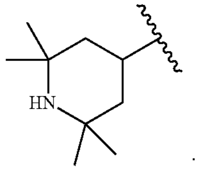 [SMILES: *C1CC(C)(C)NC(C)(C)C1]
In some embodiments, A is
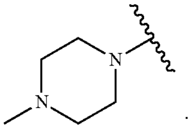 [SMILES: *N1CCN(C)CC1]
In some embodiments, A is
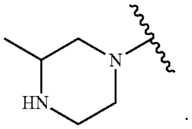 [SMILES: *N1CCNC(C)C1]
In some embodiments, A is
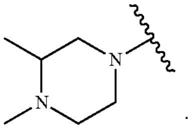 [SMILES: *N1CCN(C)C(C)C1]
In some embodiments, A is
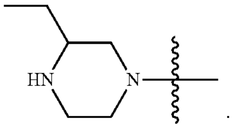
In some embodiments, A is
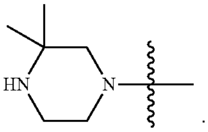 [SMILES: *N1CCNC(C)(C)C1]
In some embodiments, A is
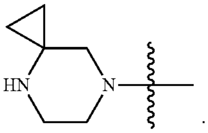 [SMILES: *N1CCNC2(CC2)C1]
In some embodiments, A is
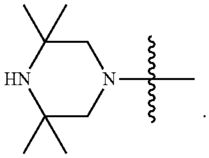 [SMILES: *N1CC(C)(C)NC(C)(C)C1]
In some embodiments, A is
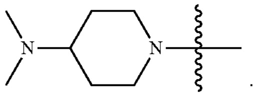
In some embodiments, A is
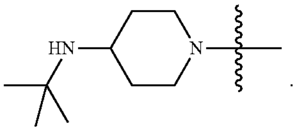 [SMILES: *N1CCC(NC(C)(C)C)CC1]
In some embodiments, A is
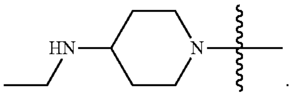
In some embodiments, A is
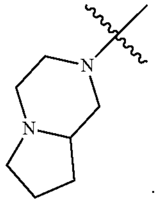 [SMILES: *N1CCN2CCCC2C1]
In some embodiments, A is
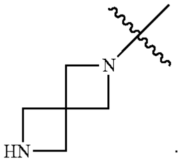 [SMILES: *N1CC2(CNC2)C1]
In some embodiments, A is
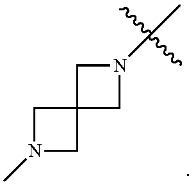 [SMILES: *N1CC2(C1)CN(C)C2]

In some embodiments, A is
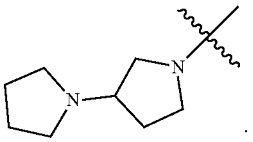 [SMILES: *N1CCC(N2CCCC2)C1]
In some embodiments, A is
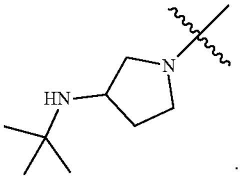 [SMILES: *N1CCC(NC(C)(C)C)C1]
In some embodiments, A is
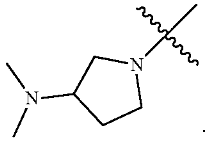 [SMILES: *N1CCC(N(C)C)C1]
In some embodiments, A is
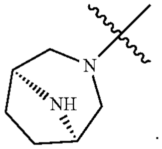 [SMILES: *N1C[C@H]2CC[C@@H](C1)N2]
In some embodiments, A is
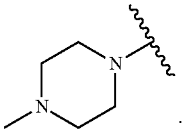 [SMILES: *N1CCN(C)CC1]
In some embodiments, A is
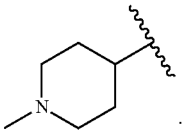 [SMILES: *C1CCN(C)CC1]
In some embodiments, A is
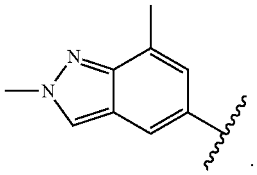 [SMILES: *c1cc(C)c2nn(C)cc2c1]
In some embodiments, A is
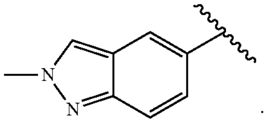 [SMILES: *c1ccc2nn(C)cc2c1]
In some embodiments, B is selected from
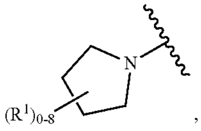, 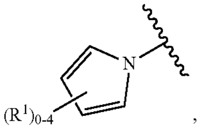,
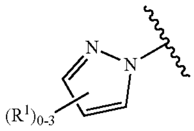, and 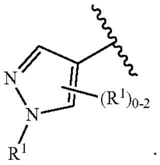.
In some embodiments, B is selected from
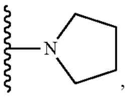, 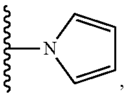, 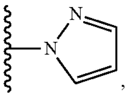, and
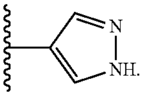
In some embodiments, B is selected from
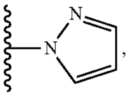, 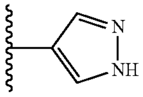, 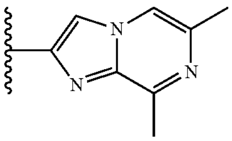,
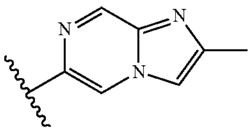, 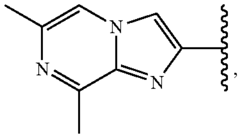, -continued
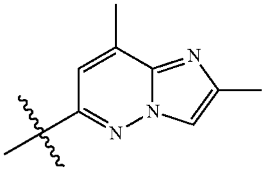,
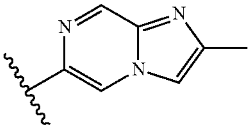,
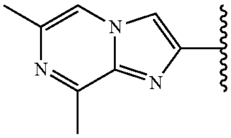,
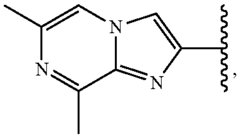,
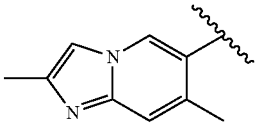,
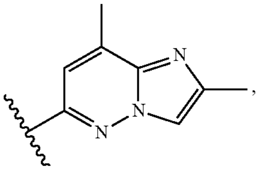,
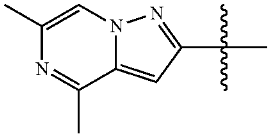,
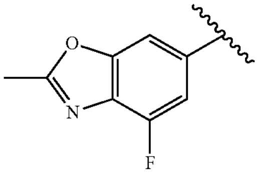,
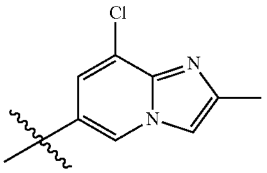,
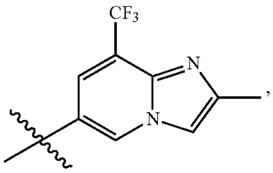,
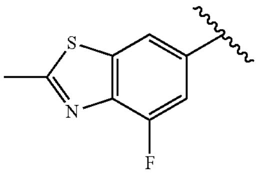,
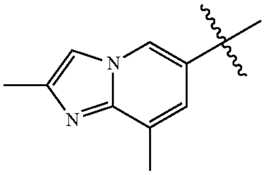,
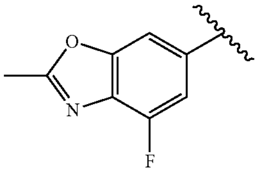,
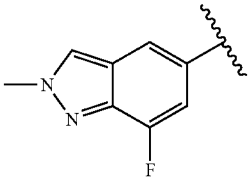,
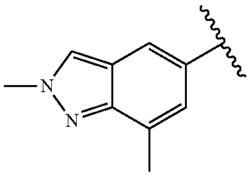, and
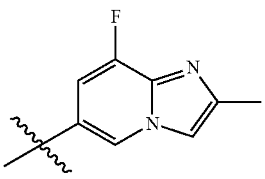.
In some embodiments, B is selected from
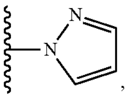,
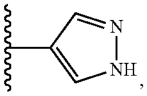,
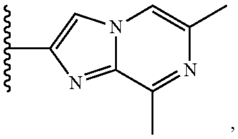,
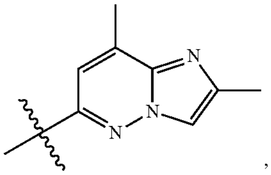,
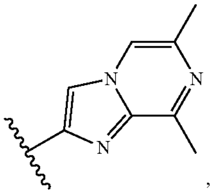,
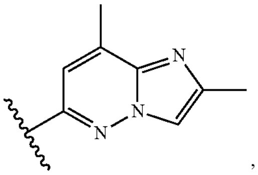,
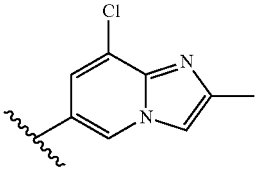,
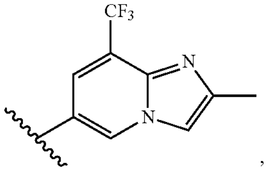, and
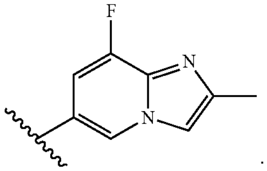.
In some embodiments, B is selected is
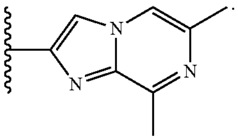 [SMILES: *c1cn2cc(C)nc(C)c2n1].
In some embodiments, B is
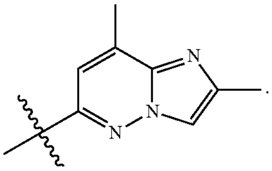 [SMILES: *c1cc(C)c2nc(C)cn2n1].

In some embodiments, B is
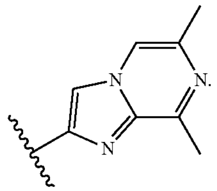 [SMILES: *c1cn2cc(C)nc(C)c2n1]
In some embodiments, B is
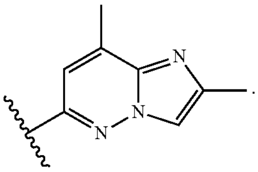 [SMILES: *c1cc(C)c2nc(C)cn2n1]
In some embodiments, B is
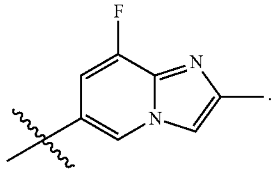 [SMILES: *c1cc(F)c2nc(C)cn2c1]
In some embodiments, the compound of Formula (I) is selected from a compound in Table 1, or a pharmaceutically acceptable salt, solvate, hydrate, tautomer, or stereoisomer thereof.
TABLE 1
| Exemplary compounds of Formula (I) | |
|---|---|
| Compound No. | Structure |
| 118 | 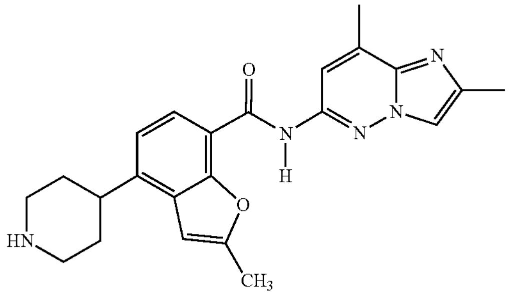 [SMILES: Cc1cn2nc(NC(=O)c3ccc(C4CCNCC4)c4cc(C)oc34)cc(C)c2n1] |
| 119 | 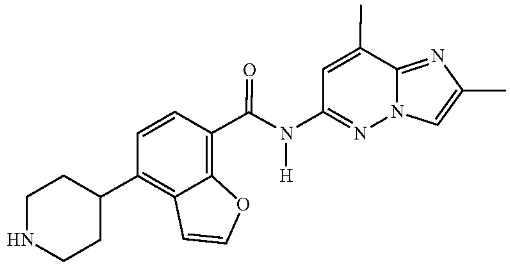 |
| 140 | 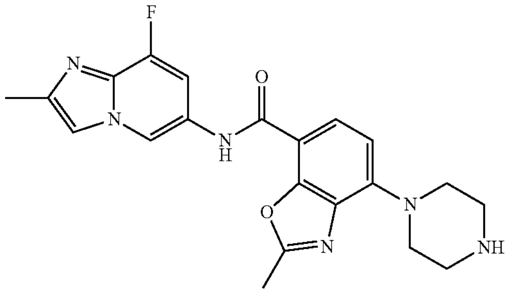 [SMILES: Cc1cn2cc(NC(=O)c3ccc(N4CCNCC4)c4nc(C)oc34)cc(F)c2n1] |

TABLE 1-continued
| Exemplary compounds of Formula (I) | |
| --- | --- |
| Compound No. | Structure |
| 141 | 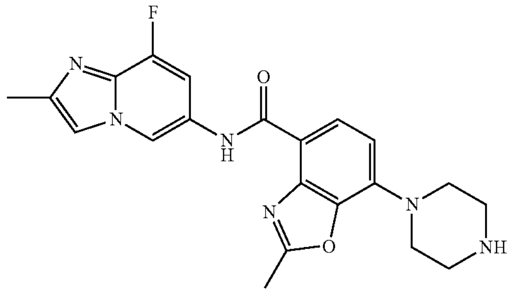 [SMILES: Cc1cn2cc(NC(=O)c3ccc(N4CCNCC4)c4oc(C)nc34)cc(F)c2n1] |
| 142 | 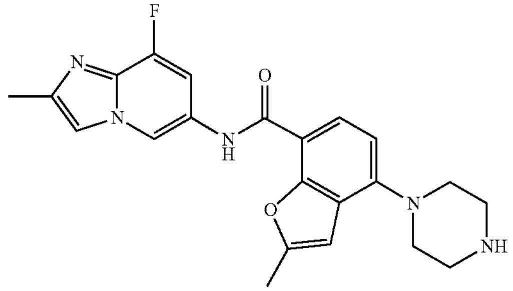 [SMILES: Cc1cn2cc(NC(=O)c3ccc(N4CCNCC4)c4cc(C)oc34)cc(F)c2n1] |
| 143 | 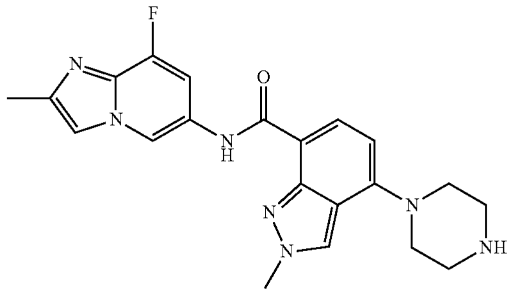 [SMILES: Cc1cn2cc(NC(=O)c3ccc(N4CCNCC4)c4cn(C)nc34)cc(F)c2n1] |
| 145 | 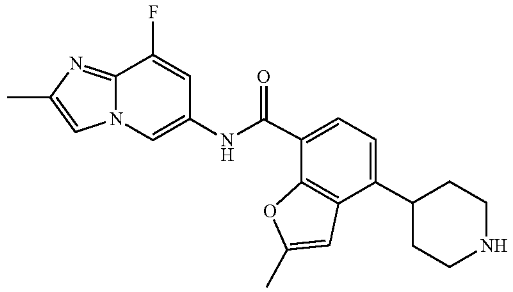 [SMILES: Cc1cn2cc(NC(=O)c3ccc(C4CCNCC4)c4cc(C)oc34)cc(F)c2n1] |
| 146 | 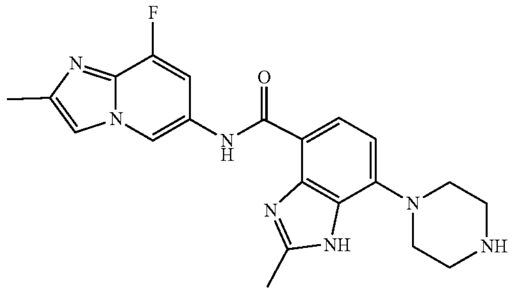 [SMILES: Cc1cn2cc(NC(=O)c3ccc(N4CCNCC4)c4[nH]c(C)nc34)cc(F)c2n1] |

TABLE 1-continued
| Exemplary compounds of Formula (I) | |
|---|---|
| Compound No. | Structure |
| 147 | 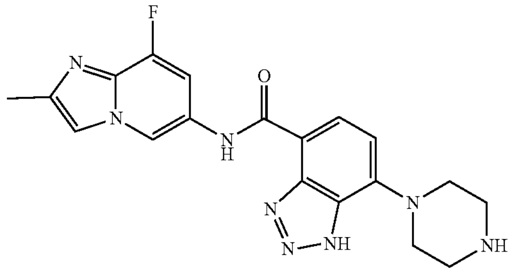 [SMILES: Cc1cn2cc(NC(=O)c3ccc(N4CCNCC4)c4[nH]nnc34)cc(F)c2n1] |
| 148 | 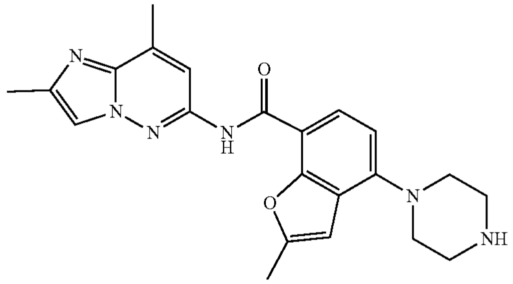 [SMILES: Cc1cn2nc(NC(=O)c3ccc(N4CCNCC4)c4cc(C)oc34)cc(C)c2n1] |
| 149 | 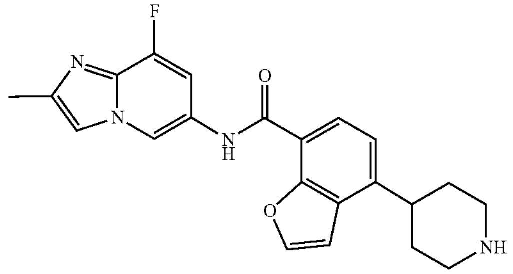 [SMILES: Cc1cn2cc(NC(=O)c3ccc(C4CCNCC4)c4ccoc34)cc(F)c2n1] |
| 150 | 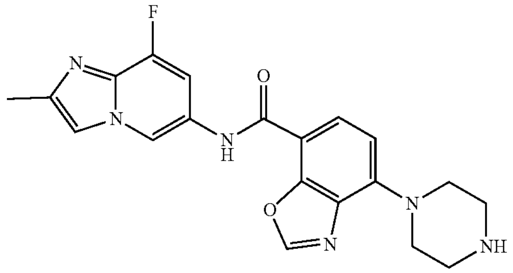 [SMILES: Cc1cn2cc(NC(=O)c3ccc(N4CCNCC4)c4ncoc34)cc(F)c2n1] |
| 187 | 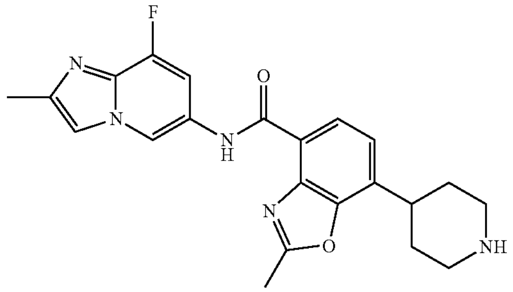 [SMILES: Cc1cn2cc(NC(=O)c3ccc(C4CCNCC4)c4oc(C)nc34)cc(F)c2n1] |

TABLE 1-continued
| Compound No. | Structure |
| --- | --- |
| Exemplary compounds of Formula (I) | |
| 188 | 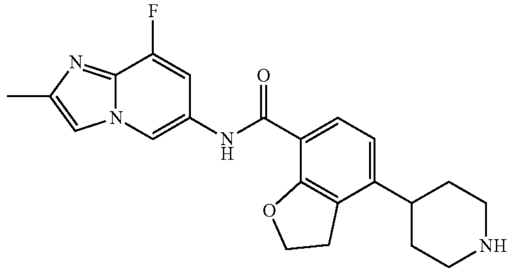 [SMILES: Cc1cn2cc(NC(=O)c3ccc(C4CCNCC4)c4c3OCC4)cc(F)c2n1] |
| 189 | 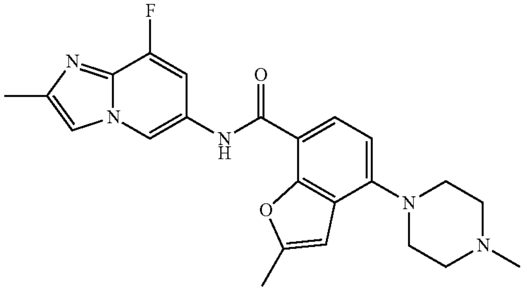 |
| 190 | 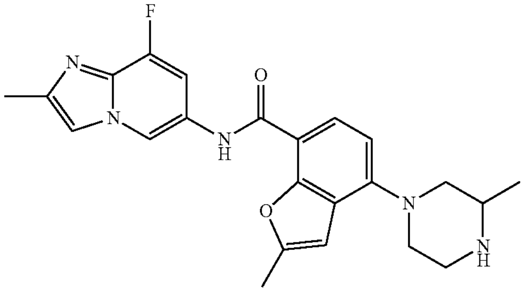 |
| 191 | 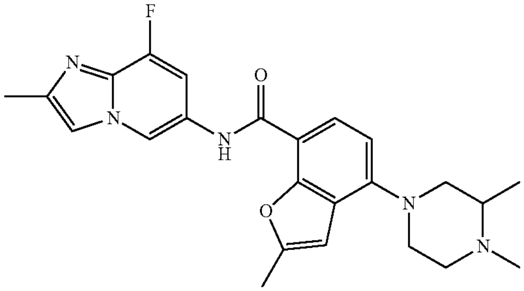 |
| 192 | 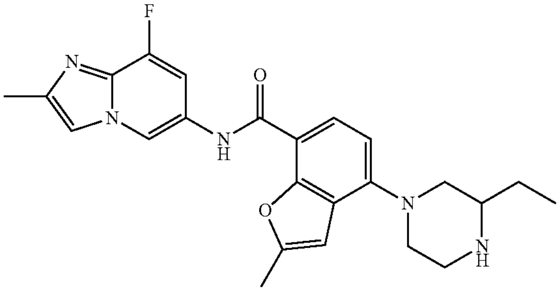 [SMILES: CCC1CN(c2ccc(C(=O)Nc3cc(F)c4nc(C)cn4c3)c3oc(C)cc23)CCN1] |

TABLE 1-continued
| Exemplary compounds of Formula (I) | |
|---|---|
| Compound No. | Structure |
| 193 | 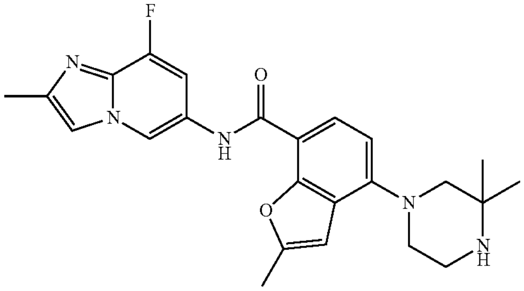 |
| 194 | 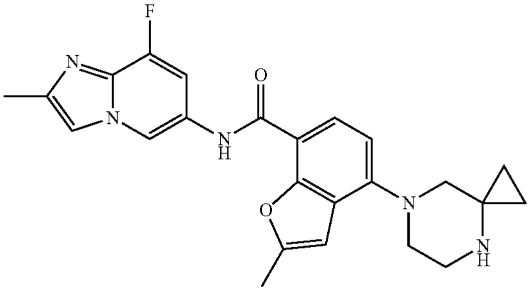 [SMILES: Cc1cn2cc(NC(=O)c3ccc(N4CCNC5(CC5)C4)c4cc(C)oc34)cc(F)c2n1] |
| 195 | 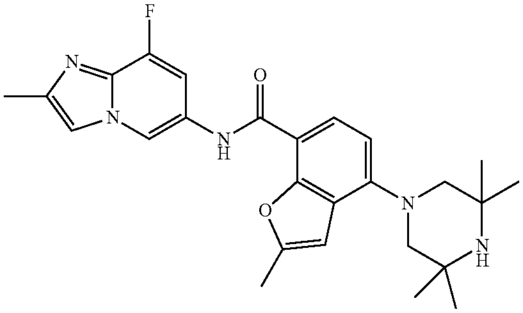 |
| 196 | 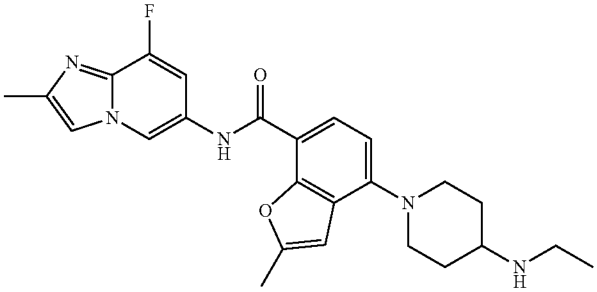 [SMILES: CCNC1CCN(c2ccc(C(=O)Nc3cc(F)c4nc(C)cn4c3)c3oc(C)cc23)CC1] |
| 197 | 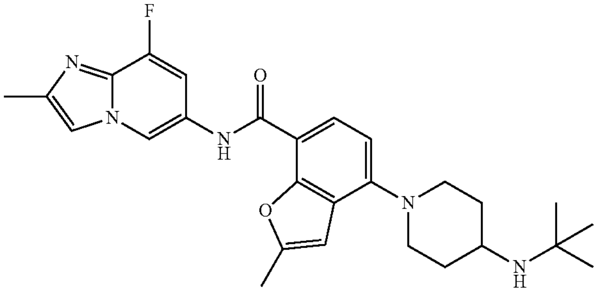 [SMILES: Cc1cn2cc(NC(=O)c3ccc(N4CCC(NC(C)(C)C)CC4)c4cc(C)oc34)cc(F)c2n1] |

TABLE 1-continued
| Compound No. | Structure |
| --- | --- |
| | Exemplary compounds of Formula (I) |
| 198 | 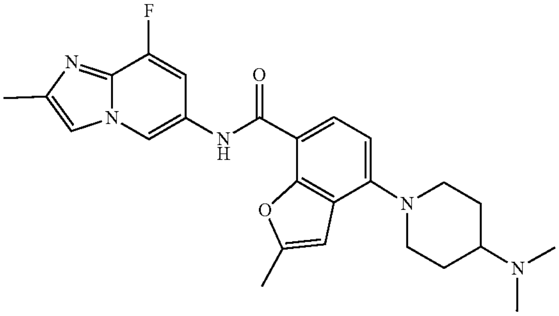 |
| 199 | 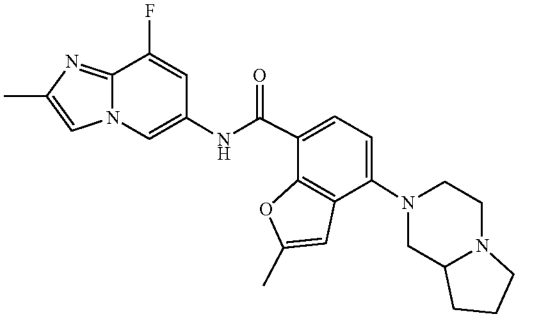 [SMILES: Cc1cn2cc(NC(=O)c3ccc(N4CCN5CCCC5C4)c4cc(C)oc34)cc(F)c2n1] |
| 200 | 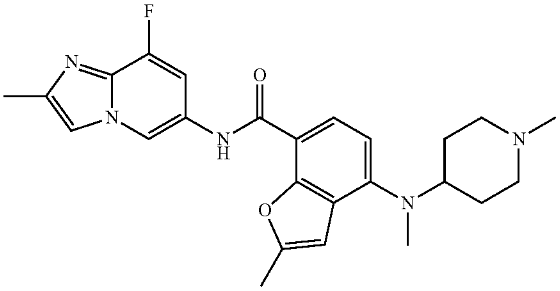 |
| 201 | 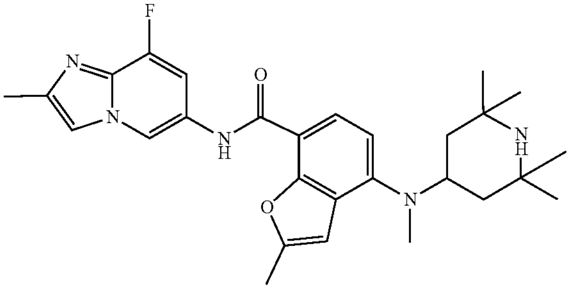 [SMILES: CCC1(C)CC(N(C)c2ccc(C(=O)Nc3cc(F)c4nc(C)cn4c3)c3oc(C)cc23)CC(C)(C)N1] |
| 202 | 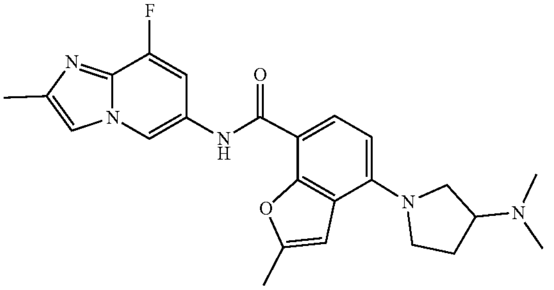 |

TABLE 1-continued
| Exemplary compounds of Formula (I) | |
|---|---|
| Compound No. | Structure |
| 203 | 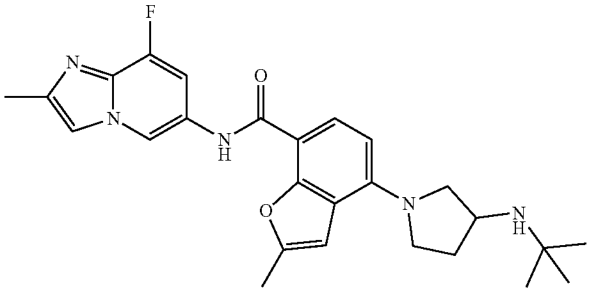 [SMILES: Cc1cn2cc(NC(=O)c3ccc(N4CCC(NC(C)(C)C)C4)c4cc(C)oc34)cc(F)c2n1] |
| 204 | 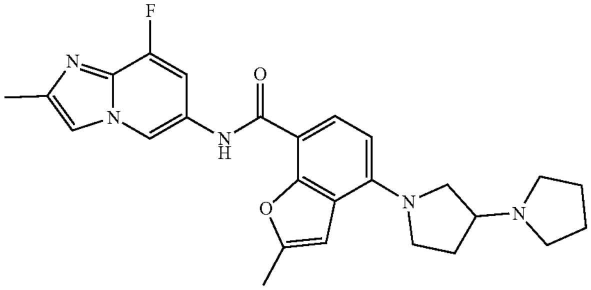 [SMILES: Cc1cn2cc(NC(=O)c3ccc(N4CCC(N5CCCC5)C4)c4cc(C)oc34)cc(F)c2n1] |
| 205 | 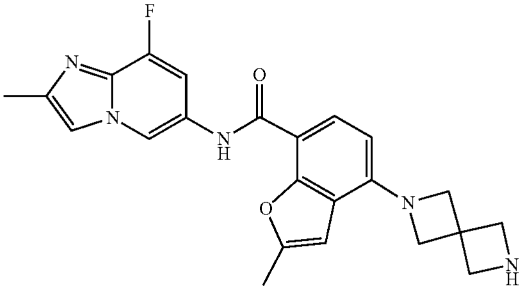 [SMILES: Cc1cn2cc(NC(=O)c3ccc(N4CC5(CNC5)C4)c4cc(C)oc34)cc(F)c2n1] |
| 206 | 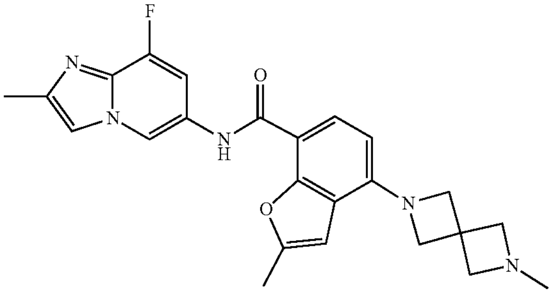 |
| 207 | 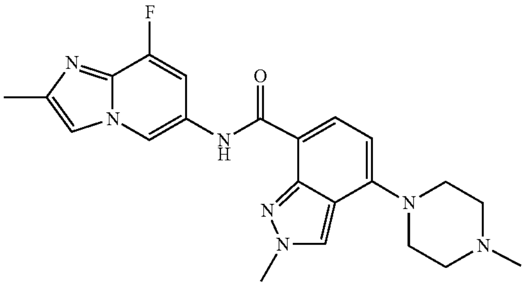 |

TABLE 1-continued
| Exemplary compounds of Formula (I) | |
|---|---|
| Compound No. | Structure |
| 208 | 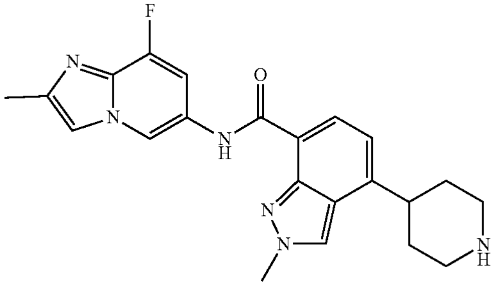 |
| 209 | 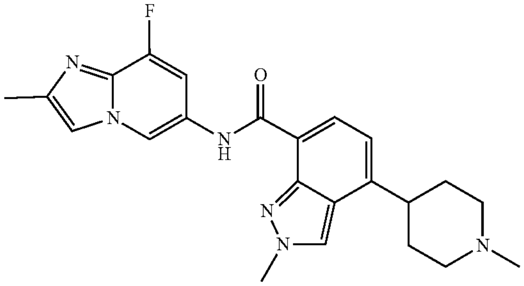 |
| 210 | 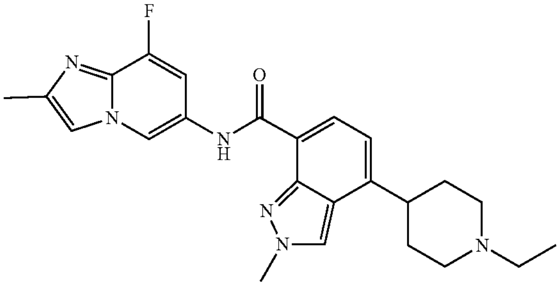 |
| 211 | 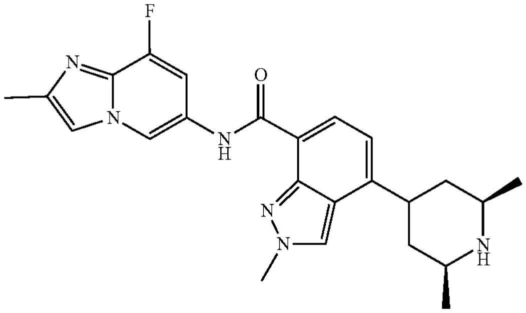 |
| 212 | 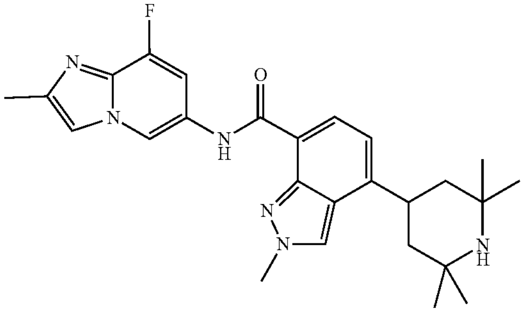 |

TABLE 1-continued
| Exemplary compounds of Formula (I) | |
|---|---|
| Compound No. | Structure |
| 217 | 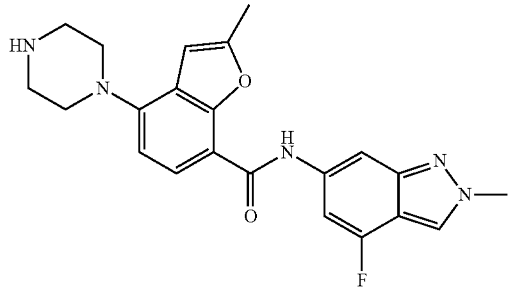 [SMILES: Cc1cc2c(N3CCNCC3)ccc(C(=O)Nc3cc(F)c4cn(C)nc4c3)c2o1] |
| 218 | 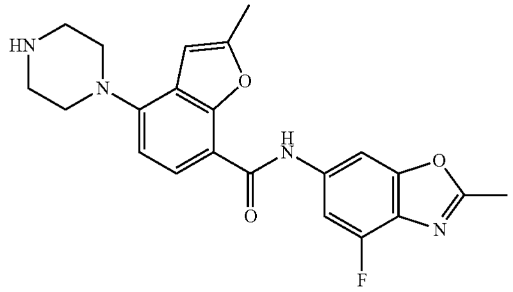 [SMILES: Cc1cc2c(N3CCNCC3)ccc(C(=O)Nc3cc(F)c4nc(C)oc4c3)c2o1] |
| 219 | 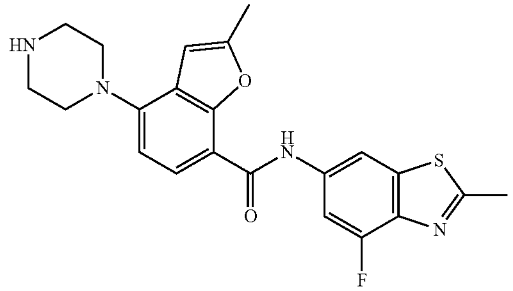 [SMILES: Cc1cc2c(N3CCNCC3)ccc(C(=O)Nc3cc(F)c4nc(C)sc4c3)c2o1] |
| 228 | 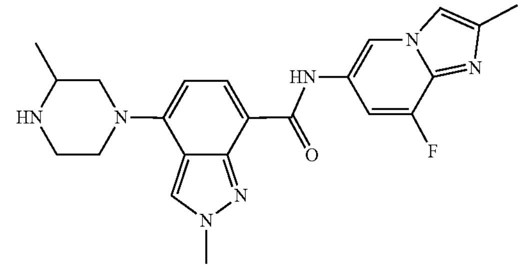 [SMILES: Cc1cn2cc(NC(=O)c3ccc(N4CCNC(C)C4)c4cn(C)nc34)cc(F)c2n1] |
| 229 | 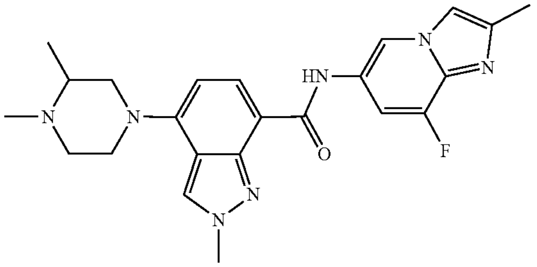

TABLE 1-continued
| Exemplary compounds of Formula (I) | |
|---|---|
| Compound No. | Structure |
| 230 | 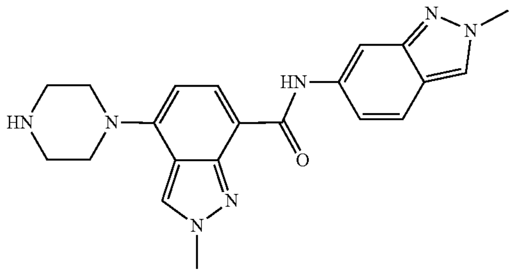 [SMILES: Cn1cc2ccc(NC(=O)c3ccc(N4CCNCC4)c4cn(C)nc34)cc2n1] |
| 231 | 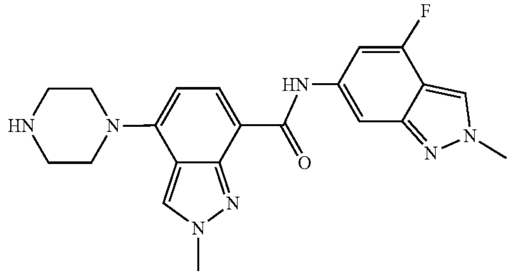 [SMILES: Cn1cc2c(F)cc(NC(=O)c3ccc(N4CCNCC4)c4cn(C)nc34)cc2n1] |
| 234 | 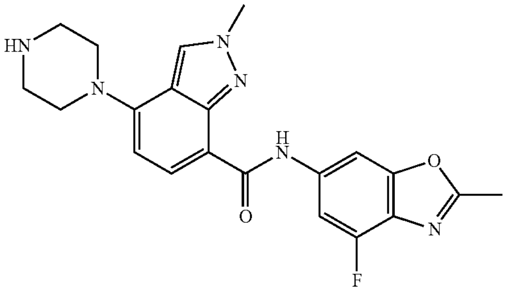 [SMILES: Cc1nc2c(F)cc(NC(=O)c3ccc(N4CCNCC4)c4cn(C)nc34)cc2o1] |
| 235 | 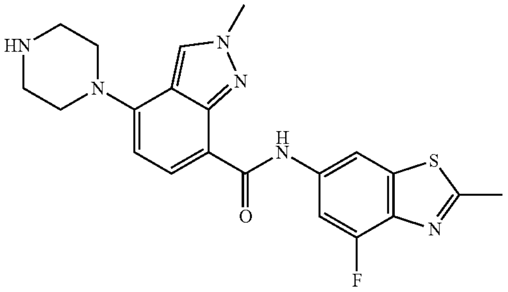 [SMILES: Cc1nc2c(F)cc(NC(=O)c3ccc(N4CCNCC4)c4cn(C)nc34)cc2s1] |
| 237 | 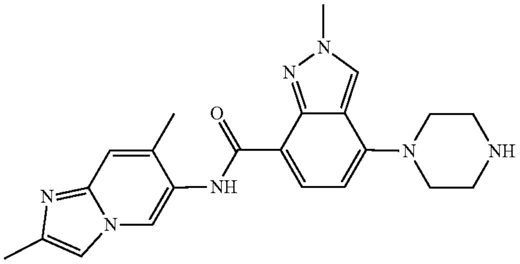 [SMILES: Cc1cn2cc(NC(=O)c3ccc(N4CCNCC4)c4cn(C)nc34)c(C)cc2n1] |

TABLE 1-continued
| Exemplary compounds of Formula (I) | |
|---|---|
| Compound No. | Structure |
| 238 | 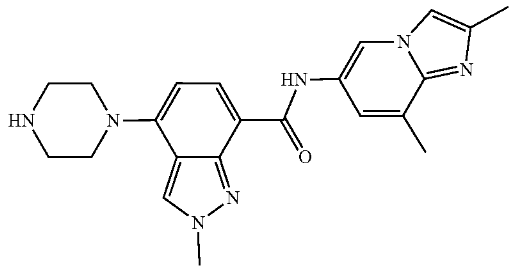 [SMILES: Cc1cn2cc(NC(=O)c3ccc(N4CCNCC4)c4cn(C)nc34)cc(C)c2n1] |
| 239 | 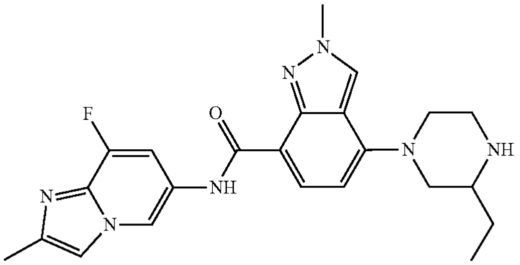 [SMILES: CCC1CN(c2ccc(C(=O)Nc3cc(F)c4nc(C)cn4c3)c3nn(C)cc23)CCN1] |
| 240 | 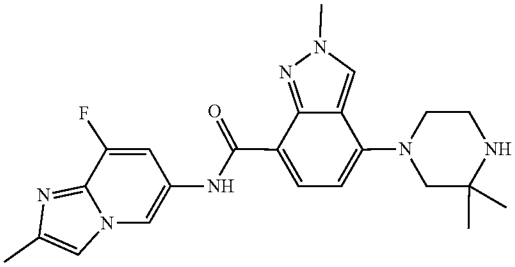 |
| 241 | 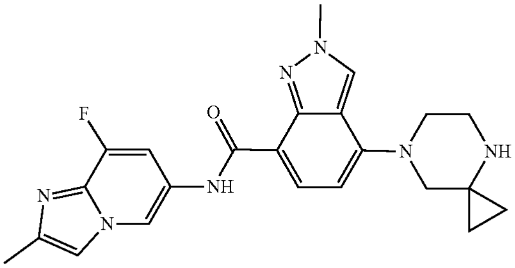 [SMILES: Cc1cn2cc(NC(=O)c3ccc(N4CCNC5(CC5)C4)c4cn(C)nc34)cc(F)c2n1] |
| 242 | 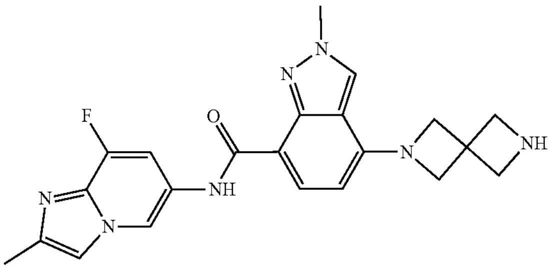 [SMILES: Cc1cn2cc(NC(=O)c3ccc(N4CC5(CNC5)C4)c4cn(C)nc34)cc(F)c2n1] |

TABLE 1-continued
| Exemplary compounds of Formula (I) | |
|---|---|
| Compound No. | Structure |
| 243 | 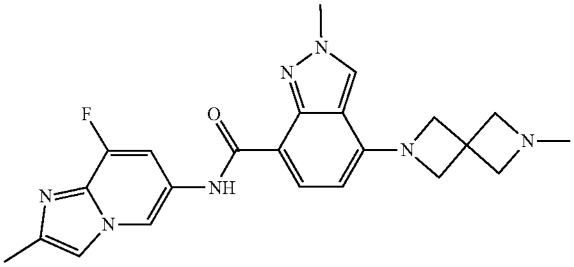 |
| 244 | 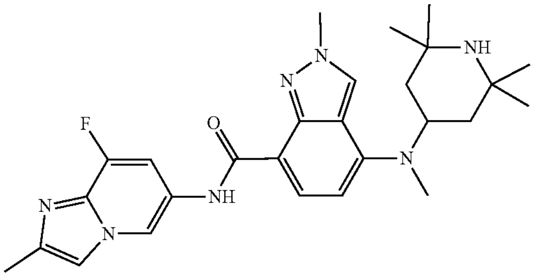 |
| 245 | 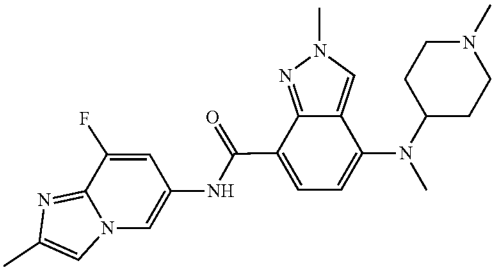 |
| 246 | 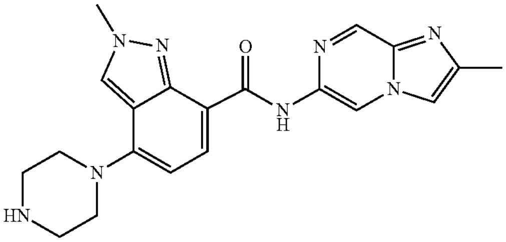 [SMILES: Cc1cn2cc(NC(=O)c3ccc(N4CCNCC4)c4cn(C)nc34)ncc2n1] |
| 247 | 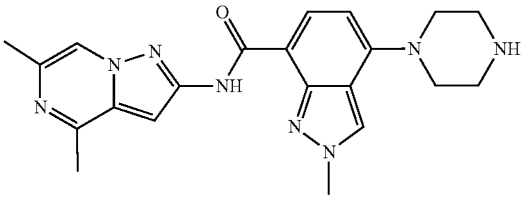 [SMILES: Cc1cn2nc(NC(=O)c3ccc(N4CCNCC4)c4cn(C)nc34)cc2c(C)n1] |

TABLE 1-continued
| Exemplary compounds of Formula (I) | |
|---|---|
| Compound No. | Structure |
| 249 | 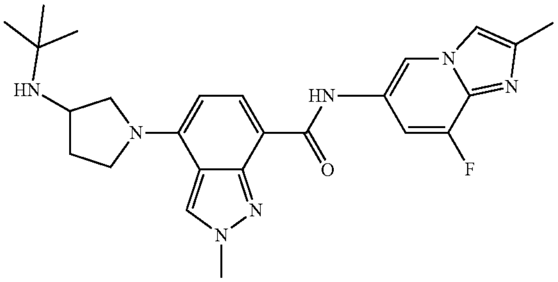 [SMILES: Cc1cn2cc(NC(=O)c3ccc(N4CCC(NC(C)(C)C)C4)c4cn(C)nc34)cc(F)c2n1] |
| 250 | 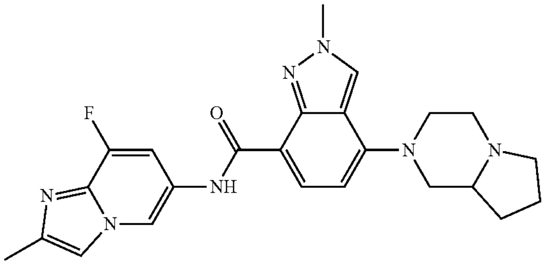 [SMILES: Cc1cn2cc(NC(=O)c3ccc(N4CCN5CCCC5C4)c4cn(C)nc34)cc(F)c2n1] |
| 251 | 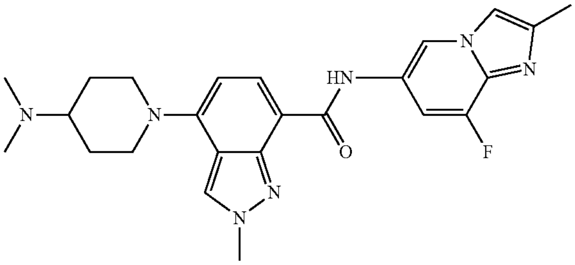 |
| 252 | 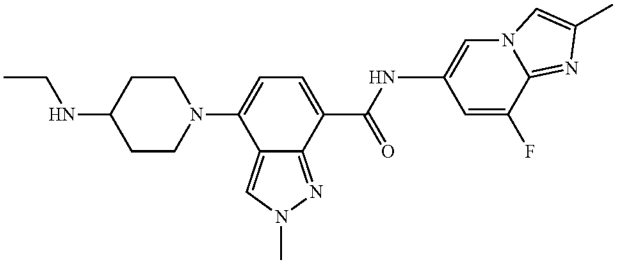 [SMILES: CCNC1CCN(c2ccc(C(=O)Nc3cc(F)c4nc(C)cn4c3)c3nn(C)cc23)CC1] |
| 253 | 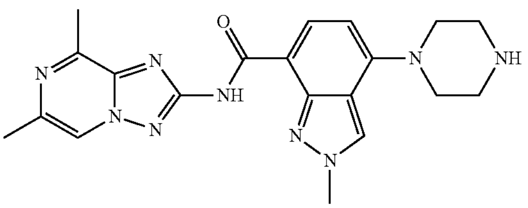 [SMILES: Cc1cn2nc(NC(=O)c3ccc(N4CCNCC4)c4cn(C)nc34)nc2c(C)n1] |

TABLE 1-continued
| Exemplary compounds of Formula (I) | |
|---|---|
| Compound No. | Structure |
| 255 | 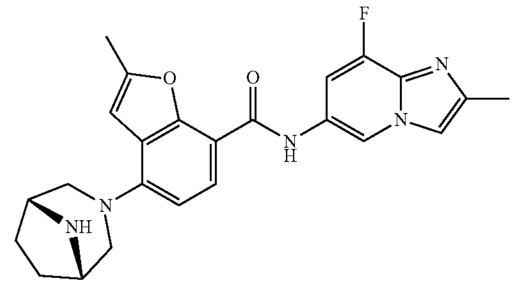 [SMILES: Cc1cn2cc(NC(=O)c3ccc(N4C[C@H]5CC[C@@H](C4)N5)c4cc(C)oc34)cc(F)c2n1] |
| 256 | 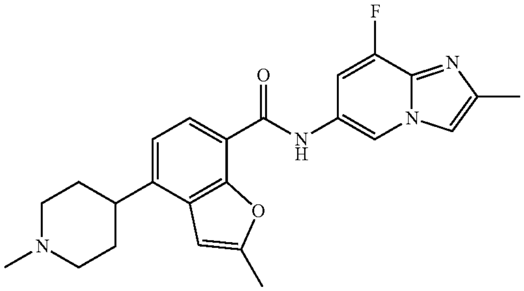 |
| 257 | 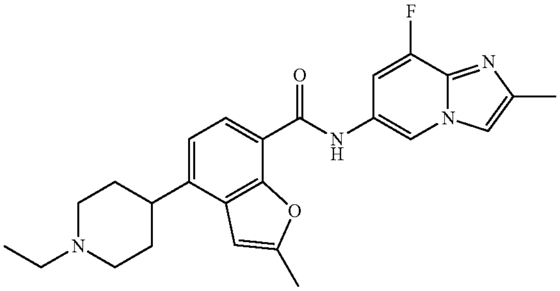 [SMILES: CCN1CCC(c2ccc(C(=O)Nc3cc(F)c4nc(C)cn4c3)c3oc(C)cc23)CC1] |
| 258 | 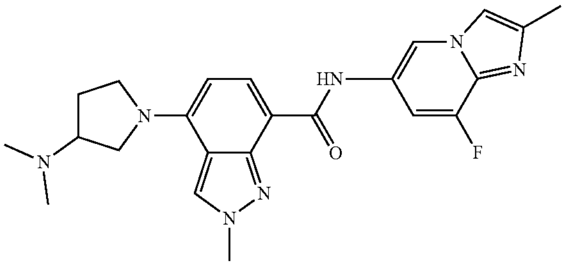 |
| 259 | 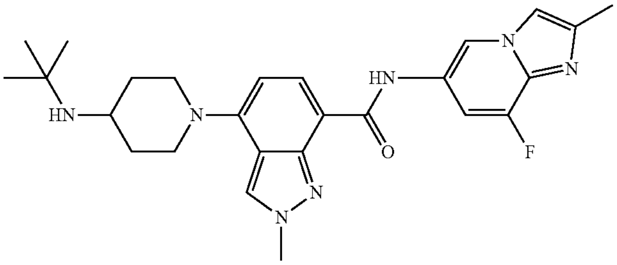 [SMILES: Cc1cn2cc(NC(=O)c3ccc(N4CCC(NC(C)(C)C)CC4)c4cn(C)nc34)cc(F)c2n1] |

TABLE 1-continued
| Exemplary compounds of Formula (I) | |
|---|---|
| Compound No. | Structure |
| 260 | 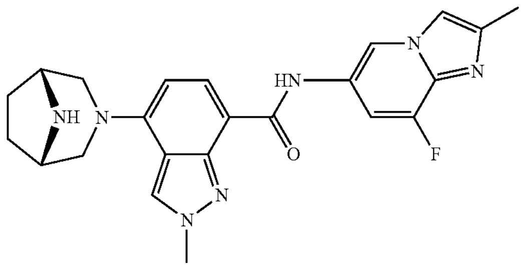 [SMILES: Cc1cn2cc(NC(=O)c3ccc(N4C[C@H]5CC[C@@H](C4)N5)c4cn(C)nc34)cc(F)c2n1] |
| 261 | 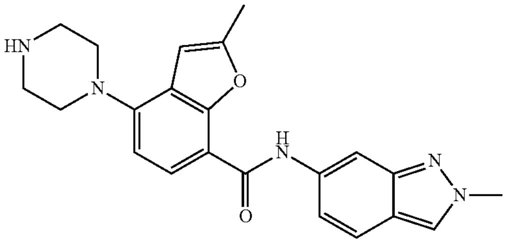 [SMILES: Cc1cc2c(N3CCNCC3)ccc(C(=O)Nc3ccc4cn(C)nc4c3)c2o1] |
| 262 | 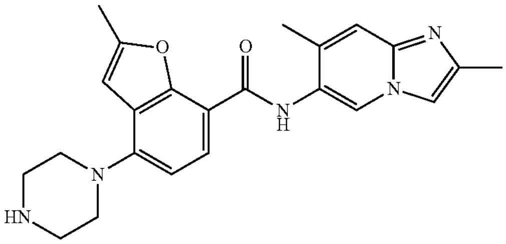 [SMILES: Cc1cn2cc(NC(=O)c3ccc(N4CCNCC4)c4cc(C)oc34)c(C)cc2n1] |
| 263 | 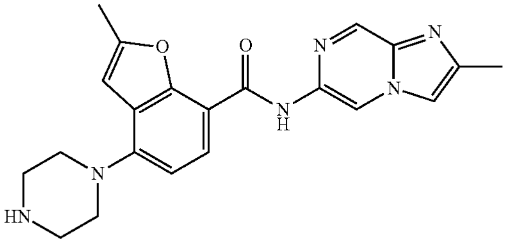 [SMILES: Cc1cn2cc(NC(=O)c3ccc(N4CCNCC4)c4cc(C)oc34)ncc2n1] |
| 264 | 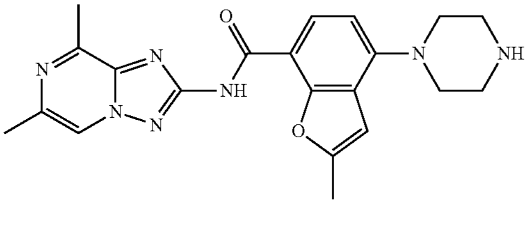 [SMILES: Cc1cn2nc(NC(=O)c3ccc(N4CCNCC4)c4cc(C)oc34)nc2c(C)n1] |
| 265 | 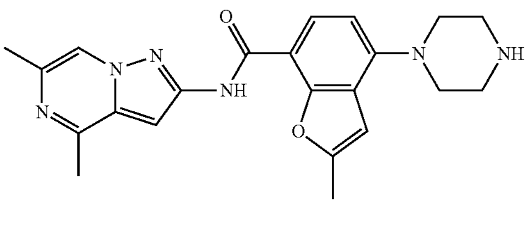 [SMILES: Cc1cn2nc(NC(=O)c3ccc(N4CCNCC4)c4cc(C)oc34)cc2c(C)n1] |

TABLE 1-continued
| Exemplary compounds of Formula (I) | |
|---|---|
| Compound No. | Structure |
| 266 | 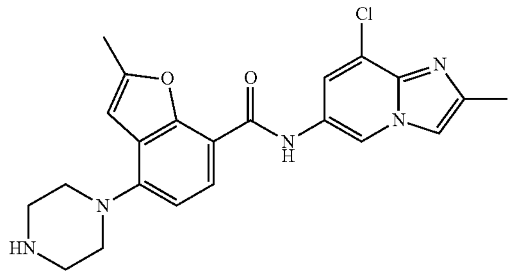 [SMILES: Cc1cn2cc(NC(=O)c3ccc(N4CCNCC4)c4cc(C)oc34)cc(Cl)c2n1] |
| 267 | 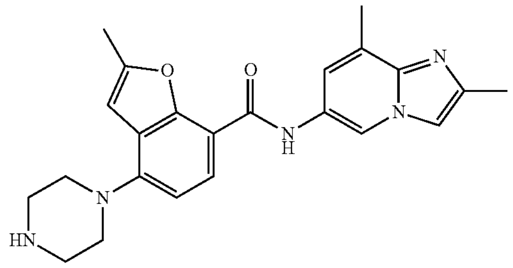 [SMILES: Cc1cn2cc(NC(=O)c3ccc(N4CCNCC4)c4cc(C)oc34)cc(C)c2n1] |
| 268 | 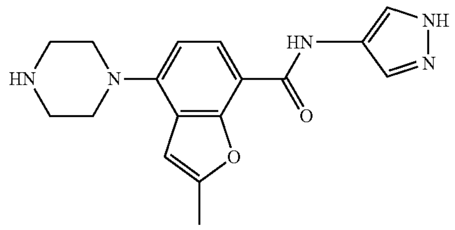 [SMILES: Cc1cc2c(N3CCNCC3)ccc(C(=O)Nc3cn[nH]c3)c2o1] |
| 269 | 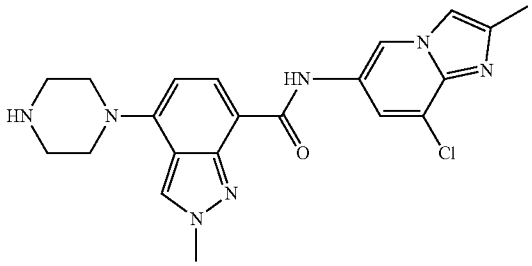 [SMILES: Cc1cn2cc(NC(=O)c3ccc(N4CCNCC4)c4cn(C)nc34)cc(Cl)c2n1] |
| 270 | 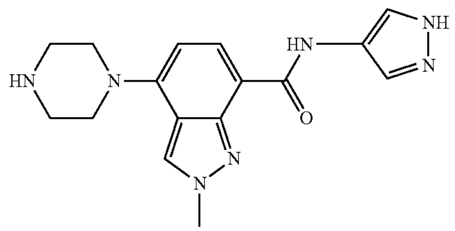 [SMILES: Cn1cc2c(N3CCNCC3)ccc(C(=O)Nc3cn[nH]c3)c2n1] |

TABLE 1-continued
| Exemplary compounds of Formula (I) | |
|---|---|
| Compound No. | Structure |
| 271 | 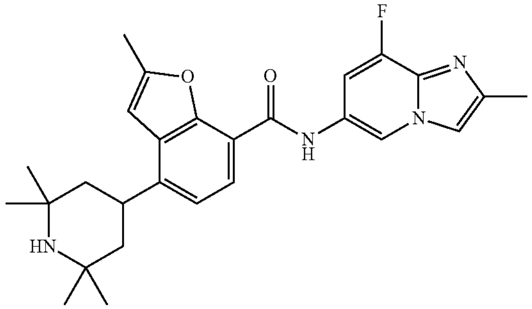 |
| 272 | 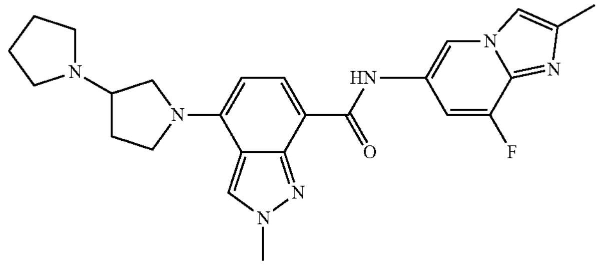 [SMILES: Cc1cn2cc(NC(=O)c3ccc(N4CCC(N5CCCC5)C4)c4cn(C)nc34)cc(F)c2n1] |
| 273 | 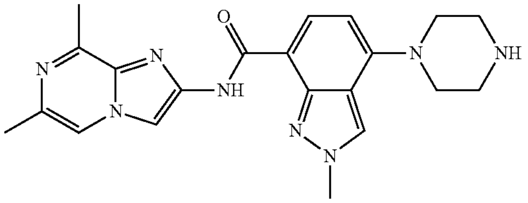 [SMILES: Cc1cn2cc(NC(=O)c3ccc(N4CCNCC4)c4cn(C)nc34)nc2c(C)n1] |
| 274 | 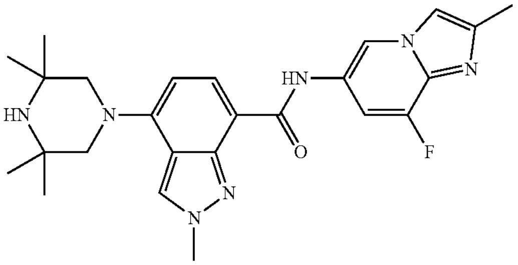 |
| 275 | 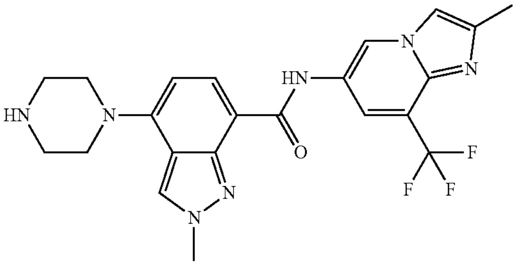 [SMILES: Cc1cn2cc(NC(=O)c3ccc(N4CCNCC4)c4cn(C)nc34)cc(C(F)(F)F)c2n1] |

TABLE 1-continued
| Exemplary compounds of Formula (I) | |
|---|---|
| Compound No. | Structure |
| 277 | 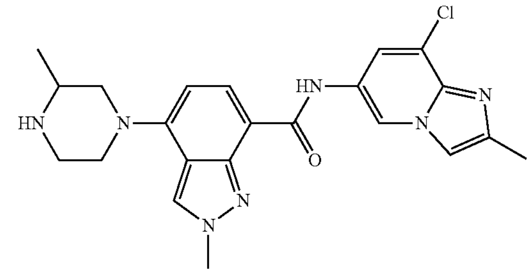 [SMILES: Cc1cn2cc(NC(=O)c3ccc(N4CCNC(C)C4)c4cn(C)nc34)cc(Cl)c2n1] |
| 278 | 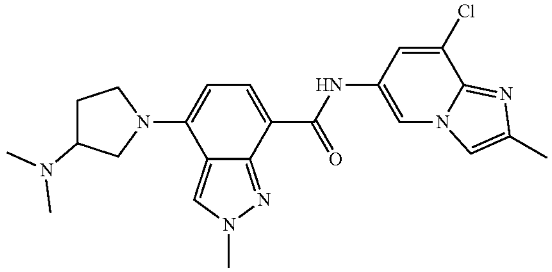 |
| 279 | 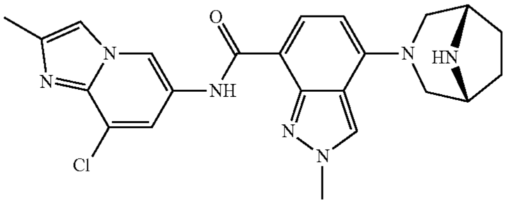 [SMILES: Cc1cn2cc(NC(=O)c3ccc(N4C[C@H]5CC[C@@H](C4)N5)c4cn(C)nc34)cc(Cl)c2n1] |
| 280 | 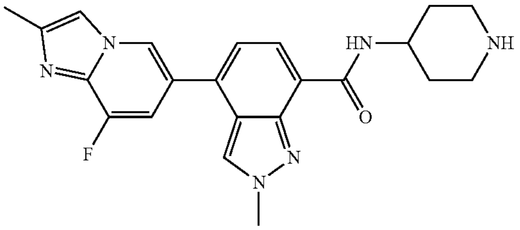 [SMILES: Cc1cn2cc(-c3ccc(C(=O)NC4CCNCC4)c4nn(C)cc34)cc(F)c2n1] |
| 281 | 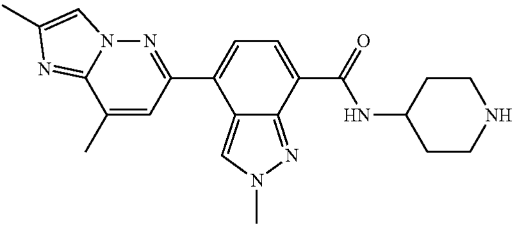 [SMILES: Cc1cn2nc(-c3ccc(C(=O)NC4CCNCC4)c4nn(C)cc34)cc(C)c2n1] |
| 282 | 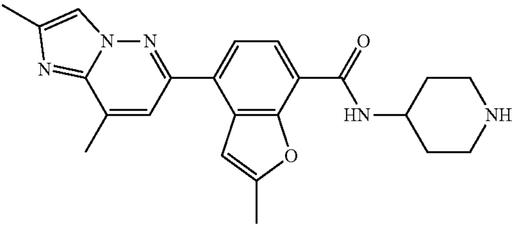 [SMILES: Cc1cn2nc(-c3ccc(C(=O)NC4CCNCC4)c4oc(C)cc34)cc(C)c2n1] |

TABLE 1-continued

| Exemplary compounds of Formula (I) | |
|---|---|
| Compound No. | Structure |
| 283 | 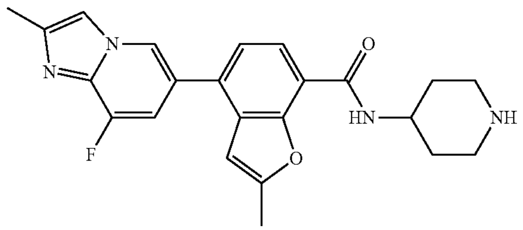 [SMILES: Cc1cn2cc(-c3ccc(C(=O)NC4CCNCC4)c4oc(C)cc34)cc(F)c2n1] |
| 284 | 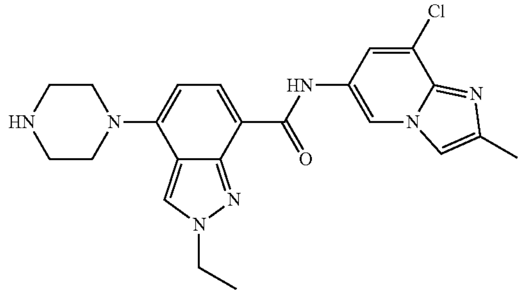 [SMILES: CCn1cc2c(N3CCNCC3)ccc(C(=O)Nc3cc(Cl)c4nc(C)cn4c3)c2n1] |
| 285 | 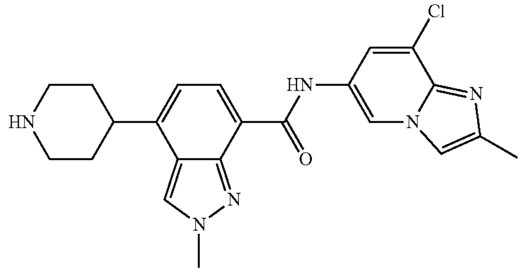 [SMILES: Cc1cn2cc(NC(=O)c3ccc(C4CCNCC4)c4cn(C)nc34)cc(Cl)c2n1] |
| 286 | 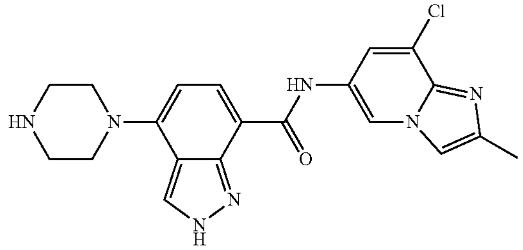 [SMILES: Cc1cn2cc(NC(=O)c3ccc(N4CCNCC4)c4c[nH]nc34)cc(Cl)c2n1] |
| 287 | 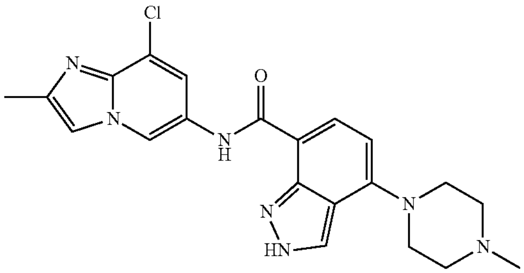 |

In some embodiments, for Formula (I), A is monocyclic heterocyclyl (e.g., piperidinyl); B is bicyclic heteroaryl (e.g., imidazo[1,2-b]pyridazinyl); $L^2$ is —C(O)N($R^4$)— (e.g., —C(O)N(H)—); X is C($R^{3a}$) (e.g., CH); Y is C($R^{3a}$) (e.g., C($CH_3$)); Z is O; y is 0; and m is 0. In some embodiments, the compound of Formulas (I), (I-d), (I-e), and (I-f) is Compound 118, or a pharmaceutically acceptable salt, solvate, hydrate, tautomer, or stereoisomer thereof.

In some embodiments, for Formula (I), A is monocyclic heterocyclyl (e.g., piperidinyl); B is bicyclic heteroaryl (e.g., imidazo[1,2-b]pyridazinyl); $L^2$ is —C(O)N($R^4$)— (e.g., —C(O)N(H)—); X and Y are each independently C($R^{3a}$) (e.g., CH); Z is O; y is 0; and m is 0. In some embodiments, the compound of Formulas (I), (I-d), (I-e), and I-f) is Compound 119, or a pharmaceutically acceptable salt, solvate, hydrate, tautomer, or stereoisomer thereof. In some embodiments, the compound of Formulas (I), (I-a), (I-e) and II-f) is one of Compounds 140-150.

In some embodiments, for Formula (I), A is monocyclic heterocyclyl (e.g., piperidinyl); B is bicyclic heteroaryl (e.g., imidazo[1,2-b]pyridazinyl); $L^1$ is absent or —$N(R^4)$—; and $L^2$ is absent or —$C(O)N(R^4)$— (e.g., —C(O)N(H)—). In some embodiments, for Formula (I), the compound is selected from Compound 118, 141, 228, 229, 242, 243, 269, and 277.

Pharmaceutical Compositions, Kits, and Administration

The present invention provides pharmaceutical compositions comprising a compound of Formula (I), e.g., a compound of Formula (I) or a pharmaceutically acceptable salt, solvate, hydrate, tautomer, or stereoisomer, as described herein, and optionally a pharmaceutically acceptable excipient. In certain embodiments, the pharmaceutical composition described herein comprises a compound of Formula (I) or a pharmaceutically acceptable salt thereof, and optionally a pharmaceutically acceptable excipient. In certain embodiments, the compound of Formula (I) or a pharmaceutically acceptable salt, solvate, hydrate, tautomer, or stereoisomer thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I) (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

The term "pharmaceutically acceptable excipient" refers to a non-toxic carrier, adjuvant, diluent, or vehicle that does not destroy the pharmacological activity of the compound with which it is formulated. Pharmaceutically acceptable excipients useful in the manufacture of the pharmaceutical compositions of the invention are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally, or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Alternatively, pharmaceutically acceptable compositions of this invention may be administered in the form of suppositories for rectal administration. Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

For ophthalmic use, provided pharmaceutically acceptable compositions may be formulated as micronized suspensions or in an ointment such as petrolatum.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form, e.g., single unit dosage form, for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating a proliferative disease or a non-proliferative disease, e.g., as described herein. The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one-unit dosage form.

Thus, in one aspect, provided are kits including a first container comprising a compound described herein, or a pharmaceutically acceptable salt, solvate, hydrate, tautomer, or stereoisomer thereof, or a pharmaceutical composition thereof. In certain embodiments, the kit of the disclosure includes a first container comprising a compound described herein, or a pharmaceutically acceptable salt thereof, or a pharmaceutical composition thereof. In certain embodiments, the kits are useful in preventing and/or treating a disease, disorder, or condition described herein in a subject (e.g., a proliferative disease or a non-proliferative disease). In certain embodiments, the kits further include instructions for administering the compound, or a pharmaceutically acceptable salt, solvate, hydrate, tautomer, or stereoisomer thereof, or a pharmaceutical composition thereof, to a subject to prevent and/or treat a proliferative disease or a non-proliferative disease.

Methods of Use

Described herein are compounds useful for modulating splicing. In some embodiments, a compound of Formula (I) may be used to alter the amount, structure, or composition of a nucleic acid (e.g., a precursor RNA, e.g., a pre-mRNA, or the resulting mRNA) by increasing or decreasing splicing at a splice site. In some embodiments, increasing or decreasing splicing results in modulating the level or structure of a gene product (e.g., an RNA or protein) produced. In some embodiments, a compound of Formula (I) may modulate a component of the splicing machinery, e.g., by modulating the interaction with a component of the splicing machinery with another entity (e.g., nucleic acid, protein, or a combination thereof). The splicing machinery as referred to herein comprises one or more spliceosome components. Spliceosome components may comprise, for example, one or more of major spliceosome members (U1, U2, U4, U5, U6 snRNPs), or minor spliceosome members (U11, U12, U4atac, U6atac snRNPs) and their accessory splicing factors.

In another aspect, the present disclosure features a method of modifying of a target (e.g., a precursor RNA, e.g., a pre-mRNA) through inclusion of a splice site in the target, wherein the method comprises providing a compound of Formula (I). In some embodiments, inclusion of a splice site in a target (e.g., a precursor RNA, e.g., a pre-mRNA, or the resulting mRNA) results in addition or deletion of one or more nucleic acids to the target (e.g., a new exon, e.g. a skipped exon). Addition or deletion of one or more nucleic acids to the target may result in an increase in the levels of a gene product (e.g., RNA, e.g., mRNA, or protein).

In another aspect, the present disclosure features a method of modifying a target (e.g., a precursor RNA, e.g., a pre-mRNA, or the resulting mRNA) through exclusion of a splice site in the target, wherein the method comprises providing a compound of Formula (I). In some embodiments, exclusion of a splice site in a target (e.g., a precursor RNA, e.g., a pre-mRNA) results in deletion or addition of one or more nucleic acids from the target (e.g., a skipped exon, e.g. a new exon). Deletion or addition of one or more nucleic acids from the target may result in a decrease in the levels of a gene product (e.g., RNA, e.g., mRNA, or protein). In other embodiments, the methods of modifying a target (e.g., a precursor RNA, e.g., a pre-mRNA, or the resulting mRNA) comprise suppression of splicing at a splice site or enhancement of splicing at a splice site (e.g., by more than about 0.5%, e.g., 1%, 5%, 10%, 15%, 20%, 25%, 30%, 35%, 40%, 45%, 50%, 55%, 60%, 65%, 70%, 75%, 80%, 85%, 90%, 95%, 99%, or more), e.g., as compared to a reference (e.g., the absence of a compound of Formula (I), or in a healthy or diseased cell or tissue).

The methods described herein can be used to modulate splicing, e.g., of a nucleic acid comprising a particular sequence (e.g., a target sequence). Exemplary genes encoding a target sequence (e.g., a target sequence comprising DNA or RNA, e.g., pre-mRNA) include, inter alia, ABCA4, ABCA9, ABCB1, ABCB5, ABCC9, ABCD1, ACADL, ACADM, ACADSB, ACSS2, ACTB, ACTG2, ADA, ADAL, ADAM10, ADAM15, ADAM22, ADAM32, ADAMTS12, ADAMTS13, ADAMTS20, ADAMTS6, ADAMTS9, ADAR, ADCY3, ADCY10, ADCY8, ADNP, ADRBK2, AFP, AGL, AGT, AHCTF1, AHR, AKAP10, AKAP3, AKNA, ALAS1, ALS2CL, ALB, ALDH3A2, ALG6, AMBRA1, ANK3, ANTXR2, ANXA10, ANXA11, ANGPTL3, AP2A2, AP4E1, APC, APOA1, APOB, APOC3, APOH, AR, ARID2, ARID3A, ARID3B, ARFGEF1, ARFGEF2, ARHGAP1, ARHGAP8, ARHGAP18, ARHGAP26, ARHGEF18, ARHGEF2, ARPC3, ARS2, ASHIL, ASHIL-IT1, ASNSD1, ASPM, ATADS, ATF1, ATG4A, ATG16L2, ATM, ATN1, ATP11C, ATP6V1G3, ATP13A5, ATP7A, ATP7B, ATR, ATXN2, ATXN3, ATXN7, ATXN10, AXIN1, B2M, B4GALNT3, BBS4, BCL2, BCL2L1, BCL2-like 11 (BIM), BCL1B, BBOX1, BCS1L, BEAN1, BHLHE40, BMPR2, BMP2K, BPTF, BRAF, BRCA1, BRCA2, BRCC3, BRSK1, BRSK2, BTAF1, BTK, C2orf55, C4orf29, C6orf118, C9orf43, C9orf72, C10orf137, C11orf30, C11orf65, C11orf70, C11orf87, C2orf51, C13orf1, C13orf15, C14orf101, C14orf118, C15orf29, C15orf42, C15orf60, C16orf33, C16orf38, C16orf48, C18orf8, C19orf42, C1 orf107, C1 orf114, C1 orf130, C1orf149, C1orf27, C1orf71, C1orf94, C1R, C20orf74, C21orf70, C3orf23, C4orf18, C5orf34, C8B, C8orf33, C9orf114, C9orf86, C9orf98, C3, CA11, CAB39, CACHD, CACNAA, CACNA1B, CACNA1C, CACNA2D1, CACNA1G, CACNA1H, CALCA, CALCOCO2, CAMK1D, CAMKK1, CAPN3, CAPN9, CAPSL, CARD11, CARKD, CASZ1, CAT, CBLB, CBX1, CBX3, CCDC102B, CCDC11, CCDC15, CCDC18, CCDC5, CCDC81, CCDC131, CCDC146, CD4, CD274, CD1B, CDC14A, CDC16, CDC2L5, CDC42BPB, CDCA8, CDH10, CDH11, CDH24, CDH8, CDH9, CDK5RAP2, CDK6, CDK8, CDK11B, CD33, CD46, CDH1, CDH23, CDK6, CDK11B, CDK13, CEBPZ, CEL, CELSR3, CENPA, CENP1, CENPT, CENTB2, CENTG2, CEP110, CEP170, CEP192, CETP, CFB, CFTR, CFH, CGN, CGNL1, CHAF1A, CHD9, CHIC2, CHL1, CHN1, CHM, CLEC16A, CL1C2, CLCN1, CLINT1, CLK1, CLPB, CLPTM1, CMIP, CMYAS, CNGA3, CNOT1, CNOT7, CNTN6, COG3, COL11A1, COL11A2, COL12A1, COL14A1, COL15A1, COL17A1, COL19A1, COL1A1, COL1A2, COL2A1, COL3A1, COL4A1, COL4A2, COL4A5, COL4A6, COL5A2, COL6A1, COL7A1, COL9A1, COL9A2, COL22A1, COL24A1, COL25A1, COL29A1, COLQ, COMTD1, COPA, COPB2, COPS7B, COPZ2, CPSF2, CPXM2, CR1, CRBN, CRYZ, CREBBP, CRKRS, CSE1L, CSTB, CSTF3, CT45-6, CTNNB1, CUBN, CUL4B, CUL5, CXorf41, CXXC1, CYBB, CYFIP2, CYP3A4, CYP3A43, CYP3A5, CYP4F2, CYP4F3, CYP17, CYP19, CYP24A1, CYP27A1, DAB1, DAZ2, DCBLD1, DCC, DCTN3, DCUNID4, DDA1, DDEF1, DDX1, DDX24, DDX4, DENND2D, DEPDC2, DES, DGAT2, DHFR, DHRS7, DHRS9, DHX8, DIP2A, DMD, DMTF1, DNAH3, DNAH8, DNAI1, DNAJA4, DNAJC13, DNAJC7, DNMT1, DNTTIP2, DOCK4, DOCK5, DOCK10, DOCK11, DOT1L, DPP3, DPP4, DPY19L2P2, DR1, DSCC1, DVL3, DUX4, DYNC1H1, DYSF, E2F1, E2F3, E2F8, E4F1, EBF1, EBF3, ECM2, EDEM3, EFCAB3, EFCAB4B, EFNA4, EFTUD2, EGFR, EIF3A, ELA1, ELA2A, ELF2, ELF3, ELF4, EMCN, EMD, EMLS, ENO3, ENPP3, EP300, EPAS1, EPB41L5, EPHA3, EPHA4, EPHB1, EPHB2, EPHB3, EPS15, ERBB4, ERCC1, ERCC8, ERGIC3, ERMN, ERMP1, ERN1, ERN2, ESR1, ESRRG, ETS2, ETV3, ETV4, ETV5, ETV6, EVC2, EWSR1, EXO1, EXOC4, F3, F11, F13A1, F5, F7, F8, FAH, FAM13A1, FAM13B1, FAM13C1, FAM134A, FAM161A, FAM176B, FAM184A, FAM19A1, FAM20A, FAM23B, FAM65C, FANCA, FANCC, FANCG, FANCM, FANK1, FAR2, FBN1, FBXO15, FBXO18, FBXO38, FCGBP, FECH, FEZ2, FGA, FGD6, FGFR2, FGFR1OP, FGFR1OP2, FGFR2, FGG, FGR, FIX, FKBP3, FLI1, FLJ35848, FLJ36070, FLNA, FN1, FNBP1L, FOLH1, FOSL1, FOSL2, FOXK1, FOXM1, FOXO1, FOXP4, FRAS1, FUT9, FXN, FZD3, FZD6, GAB1, GABPA, GALC, GALNT3, GAPDH, GART, GAS2L3, GATA3, GATAD2A, GBA, GBGT1, GCG, GCGR, GCK, GFI1, GFM1, GH1, GHR, GHV, GJA1, GLA, GLT8D1, GNA11, GNAQ, GNAS, GNB5, GOLGB1, GOLT1A, GOLT1B, GPATCH1, GPR158, GPR160, GPX4, GRAMD3, GRHL1, GRHL2, GRHPR, GRIA1, GRIA3, GRIA4, GRIN2B, GRM3, GRM4, GRN, GSDMB, GSTCD, GSTO2, GTF21, GTPBP4, HADHA, HAND2, HBA2, HBB, HCK, HDAC3, HDACS, HDX, HEPACAM2, HERC1, HES7, HEXA, HEXB, HHEX, HIPK3, HLA-DPB1, HLA-G, HLCS, HLTF, HMBS, HMGA1, HMGCL, HNF1A, HNF1B, HNF4A, HNF4G, HNRNPH1, HOXC10, HP1BP3, HPGD, HPRT1, HPRT2, HSF1, HSF4, HSF2BP, HSPA9, HSPG2, HTT, HXA, ICA1, IDH1, IDS, IFI44L, IKBKAP, IKZF1, IKZF3, IL1R2, ILSRA, IL7RA, IMMT, INPPSD, INSR, INTS3, INTU, IPO4, IP08, IQGAP2, IRF2, IRF4, IRF8, IRX3, ISL1, ISL2, ITFG1, ITGA6, ITGAL, ITGB1, ITGB2, 1TGB3, ITGB4, ITIH1, ITPR2, IWS1, JAK1, JAK2, JAG1, JMJDIC, JPH3, KALRN, KAT6A, KATNAL2, KCNN2, KCNT2, KDM2A, KIAA0256, KIAA0528, KIAA0564, KIAA0586, KIAA1033, KIAA1166, KIAA1219, KIAA1409, KIAA1622, KIAA1787, KIF3B, KIF15, KIF16B, KIF5A, KIFSB, KIF9, KIN, KIR2DL5B, KIR3DL2, KIR3DL3, KIT, KLF3, KLFS, KLF7, KLF10, KLF12, KLF16, KLHL20, KLK12, KLKB1, KMT2A, KMT2B, KPNAS, KRAS, KREMEN1, KRIT1, KRTS, KRTCAP2, KYNU, LICAM, L3MBTL, L3MBTL2, LACE1, LAMA1, LAMA2, LAMA3, LAMB1, LARP7, LDLR, LEF1, LENG1, LGALS3, LGMN, LHCGR, LHX3, LHX6, LIMCH1, LIMK2, LIN28B, LIN54, LMBRD1, LMBRD2, LMLN, LMNA, LMO2, LMO7, LOC389634, LOC390110, LPA, LPCAT2, LPL, LRP4, LRPPRC, LRRK2, LRRC19, LRRC42, LRWD1, LUM, LVRN, LYN, LYST, MADD, MAGI1, MAGT1, MALT1, MAP2K1, MAP4K4, MAPK8IP3, MAPK9, MAPT, MARC1, MARCH5, MATN2, MBD3, MCF2L2, MCM6, MDGA2, MDM4, ASXL1, FUS, SPR54, MECOM, MEF2C, MEF2D, MEGF10, MEGFI1, MEMO1, MET, MGA, MGAM, MGAT4A, MGAT5, MGC16169, MGC34774, MKKS, MIB1, MIER2, MITF, MKL2, MLANA, MLH1, MLLS, MLX, MME, MPDZ, MP1, MRAP2, MRPL11, MRPL39, MRPS28, MRPS35, MS4A13, MSH2, MSH3, MSMB, MST1R, MTDH, MTERF3, MTF1, MTF2, MTIF2, MTHFR, MUC2, MUT, MVK, MYB, MYBL2, MYC, MYCBP2, MYH2, MYRF, MYT1, MYO19, MYO3A, MYO9B, MYOM2, MYOM3, NAG, NARG1, NARG2, NCOA1, NDC80, NDFIP2, NEB, NEDD4, NEK1, NEKS, NEK11, NF1, NF2, NFATC2, NFE2L2, NFIA, NFIB, NFIX, NFKB1, NFKB2, NFKBIL2, NFRKB, NFYA, NFYB, NIPA2, NKAIN2, NKAP, NLRC3, NLRCS, NLRP3, NLRP7, NLRP8, NLRP13, NME1, NME1-NME2, NME2, NME7, NOL10, NOP561, NOS1, NOS2A, NOTCH1, NPAS4, NPM1, NR1D1, NR1H3, NR1H4, NR4A3, NR5A1, NRXN1, NSMAF, NSMCE2, NTSC, NT5C2, NT5C3, NUBP1, NUBPL, NUDTS, NUMA1, NUP88, NUP98, NUP160, NUPL1, OAT, OAZ1, OBFC2A, OBFC2B, OLIG2, OMA1, OPA1, OPN4, OPTN, OSBPLI1, OSBPL8, OSGEPL1, OTC, OTX2, OVOL2, OXT, PA2G4, PADI4, PAH, PAN2, PAOX, PAPOLG, PARD3, PARP1, PARVB, PAWR, PAX3, PAX8, PBGD, PBRM1, PBX2, PCBP4, PCCA, PCGF2, PCNX, PCOTH, PDCD4, PDE4D, PDE8B, PDE10A, PD1A3, PDH1, PDLIMS, PDXK, PDZRN3, PELI2, PDK4, PDSSA, PDSSB, PGK1, PGM2, PHACTR4, PHEX, PHKB, PHLDB2, PHOX2B, PHTF, PIAS1, PIEZO1, PIGF, PIGN, PIGT, PIK3C2G, PIK3CA, PIK3CD, PIK3CG, PIK3R1, PIPSK1A, PITRM1, PIWIL3, PKD1, PKHD1L1, PKD2, PKIB, PKLR, PKM1, PKM2, PLAGL2, PLCB1, PLCB4, PLCG1, PLD1, PLEKHA5, PLEKHA7, PLEKHM1, PLKR, PLXNC1, PMFBP1, POLN, POLR3D, POMT2, POSTN, POU2AF1, POU2F2, POU2F3, PPARA, PPFIA2, PPP1R12A, PPP3CB, PPP4C, PPP4R1L, PPP4R2, PRAME, PRC1, PRDM1, PREX1, PREX2, PRIM1, PRIM2, PRKARIA, PRKCA, PRKG1, PRMT7, PROC, PROCR, PROSC, PRODH, PROX1, PRPF40B, PRPF4B, PRRG2, PRUNE2, PSD3, PSEN1, PSMAL, PTCH1, PTEN, PTK2, PTK2B, PTPN2, PTPN3, PTPN4, PTPN11, PTPN22, PTPRD, PTPRK, PTPRM, PTPRN2, PTPRT, PUS10, PVRL2, PYGM, QRSL1, RABIIFIP2, RAB23, RAF1, RALBP1, RALGDS, RB1CC1, RBL2, RBM39, RBM45, RBPJ, RBSN, REC8, RELB, RFC4, RFT1, RFTN1, RHOA, RHPN2, RIF1, RIT1, RLN3, RMNDSB, RNFI1, RNF32, RNFT1, RNGTT, ROCK1, ROCK2, ROR$^{4}$, RP1, RP6KA3, RP11-265F1, RP13-36C9, RPAP3, RPN1, RPGR, RPL22, RPL22L1, RPS6KA6, RREB1, RRM1, RRP1B, RSK2, RTEL1, RTF1, RUFY1, RUNX1, RUNX2, RXRA, RYR3, SAAL1, SAE1, SALL4, SAT1, SATB2, SBCAD, SCN1A, SCN2A, SCN3A, SCN4A, SCNSA, SCN8A, SCNA, SCN11A, SCO1, SCYL3, SDC1, SDK1, SDK2, SEC24A, SEC24D, SEC31A, SELIL, SENP3, SENP6, SENP7, SERPINA1, SETD3, SETD4, SETDB1, SEZ6, SFRS12, SGCE, SGOL2, SGPL1, SH2DA, SH3BGRL2, SH3PXD2A, SH3PXD2B, SH3RF2, SH3TC2, SHOC2, SIPAIL2, SIPAIL3, SIVA1, SKAP1, SKIV2L2, SLC6A11, SLC6A13, SLC6A6, SLC7A2, SLC12A3, SLC13A1, SLC22A17, SLC25A14, SLC28A3, SLC33A1, SLC35F6, SLC38A1, SLC38A4, SLC39A10, SLC4A2, SLC6A8, SMARCA1, SMARCA2, SMARCA5, SMARCC2, SMCS, SMN2, SMOX, SMS, SMTN, SNCAIP, SNORD86, SNRK, SNRP70, SNX5, SNX6, SOD1, SOD10, SOS, SOS2, SOX5, SOX6, SOX8, SP1, SP2, SP3, SP110, SPAG9, SPATA13, SPATA4, SPATS1, SPECC1L, SPDEF, SP11, SPINKS, SPP2, SPTA1, SRF, SRM, SRP72, SSX3, SSX5, SSX9, STAG1, STAG2, STAMBPL1, STARD6, STAT1, STAT3, STAT5A, STATSB, STAT6, STK17B, STX3, STXBP1, SUCLG2, SULF2, SUPT6H, SUPT16H, SV2C, SYCP2, SYT6, SYCP1, SYTL3, SYTLS, TAF2, TARDBP, TBC1D3G, TBC1D8B, TBC1D26, TBC1D29, TBCEL, TBK1, TBP, TBPL1, TBR1, TBX, TCEB3, TCF3, TCF4, TCF7L2, TCFLS, TCF12, TCP11L2, TDRD3, TEAD1, TEAD3, TEAD4, TECTB, TEK, TERF1, TERF2, TET2, TFAP2A, TFAP2B, TFAP2C, TFAP4, TFDP1, TFRC, TG, TGM7, TGS1, THAP7, THAP12, THOC2, TIAL1, TIAM2, TIMM50, TLK2, TM4SF20, TM6SF1, TMEM27, TMEM77, TMEM156, TMEM194A, TMF1, TMPRSS6, TNFRSFI0A, TNFRSFI0B, TNFRSF8, TNK2, TNKS, TNKS2, TOM1L1, TOM1L2, TOP2B, TP53, TP53INP1, TP53BP2, TP53I3, TP63, TRAF3IP3, TRAPPC2, TRIM44, TRIM65, TRIML1, TRIML2, TRPM3, TRPMS, TRPM7, TRPS1, TSC1, TSC2, TSHB, TSPAN7, TTC17, TTF1, TTLL5, TTLL9, TTN, TTPAL, TTR, TUSC3, TXNDC10, UBE3A, UCKI, UGT1A1, UHRFIBP1, UNC45B, UNCSC, USH2A, USF2, USP1, USP6, USP18, USP38, USP39, UTP20, UTP15, UTP18, UTRN, UTX, UTY, UVRAG, UXT, VAPA, VEGFA, VPS29, VPS35, VPS39, VTIA, VT11B, VWA3B, WDFY2, WDR16, WDR17, WDR26, WDR44, WDR67, WDTC1, WRN, WRNIP1, WT1, WWC3, XBP1, XRN1, XRN2, XX-FW88277, YAP1, YARS, YBX1, YGM, YY1, ZBTB18, ZBTB20, ZC3HAV1, ZC3HC1, ZC3H7A, ZDHHC19, ZEB1, ZEB2, ZFPM1, ZFYVE1, ZFX, ZIC2, ZNF37A, ZNF91, ZNF114, ZNF155, ZNF169, ZNF205, ZNF236, ZNF317, ZNF320, ZNF326, ZNF335, ZNF365, ZNF367, ZNF407, ZNF468, ZNF506, ZNF511, ZNF511-PRAP1, ZNF519, ZNF521, ZNF592, ZNF618, ZNF763, and ZWINT.

Additional exemplary genes encoding a target sequence (e.g., a target sequence comprising DNA or RNA, e.g., pre-mRNA) include genes include A1CF, A4GALT, AAR2, ABAT, ABCA11P, ZNF721, ABCA5, ABHD10, ABHD13, ABHD2, ABHD6, AC000120.3, KRIT1, AC004076.1, ZNF772, AC004076.9, ZNF772, AC004223.3, RAD51D, AC004381.6, AC006486.1, ERF, AC007390.5, AC007780.1, PRKAR1A, AC007998.2, IN080C, AC009070.1, CMC2, AC009879.2, AC009879.3, ADHFE1, AC010487.3, ZNF816-ZNF321P, ZNF816, AC010328.3, AC010522.1, ZNF587B, AC010547.4, ZNF19, AC012313.3, ZNF497, AC012651.1, CAPN3, AC013489.1, DET1, AC016747.4, C2orf74, AC020907.6, FXYD3, AC021087.5, PDCD6, AHRR, AC022137.3, ZNF761, AC025283.3, NAA60, AC027644.4, RABGEF1, AC055811.2, FLCN, AC069368.3, ANKDD1A, AC073610.3, ARF3, AC074091.1, GPN1, AC079447.1, LIPT1, AC092587.1, AC079594.2, TRIM59, AC091060.1, C18orf21, AC092143.3, MC1R, AC093227.2, ZNF607, AC093512.2, ALDOA, AC098588.1, ANAPC10, AC107871.1, CALML4, AC114490.2, ZMYM6, AC138649.1, NIPA1, AC138894.1, CLN3, AC139768.1, AC242426.2, CHD1L, ACADM, ACAP3, ACKR2, RP11-141M3.5, KRBOX1, ACMSD, ACOT9, ACPS, ACPL2, ACSBG1, ACSF2, ACSF3, ACSL1, ACSL3, ACVR1, ADAL, ADAM29, ADAMTS10, ADAMTSLS, ADARB1, ADAT2, ADCK3, ADD3, ADGRG1, ADGRG2, ADH1B, ADIPOR1, ADNP, ADPRH, AGBLS, AGPAT1, AGPAT3, AGR2, AGTR1, AHDC1, AHI1, AHNAK, AIFM1, AIFM3, AIMP2, AK4, AKAP1, AKNAD1, CLCC1, AKR1A1, AKT1, AKT1S1, AKT2, AL139011.2, PEX19, AL157935.2, ST6GALNAC6, AL358113.1, TJP2, AL441992.2, KYAT1, AL449266.1, CLCC1, AL590556.3, LINC00339, CDC42, ALAS1, ALB, ALDH16A1, ALDHIB1, ALDH3A1, ALDH3B2, ALDOA, ALKBH2, ALPL, AMD1, AMICA1, AMN1, AMOTL2, AMY1B, AMY2B, ANAPC10, ANAPC11, ANAPC15, ANG, RNASE4, AL163636.2, ANGEL2, ANGPTL1, ANKMY1, ANKRDI1, ANKRD28, ANKRD46, ANKRD9, ANKS3, ANKS3, RP11-127I20.7, ANKS6, ANKZF1, ANPEP, ANXA11, ANXA2, ANXA8L2, AL603965.1, AOC3, AP000304.12, CRYZL1, AP000311.1, CRYZL1, AP000893.2, RAB30, AP001267.5, ATP5MG, AP002495.2, AP003175.1, OR2AT4, AP003419.1, CLCF1, AP005263.1, ANKRD12, AP006621.5, AP006621.1, AP1G1, AP3M1, AP3M2, APBA2, APBB1, APLP2, APOA2, APOL1, APOL3, APTX, ARAP1, STARD10, ARF4, ARFIP1, ARFIP2, ARFRP1, ARHGAPIIA, ARHGAP33, ARHGAP4, ARHGEF10, ARHGEF3, ARHGEF35, OR2A1-AS1, ARHGEF35, OR2A1-AS1, ARHGEF34P, ARID1B, ARHGEF35, OR2A20P, OR2A1-AS1, ARHGEF9, ARL1, ARL13B, ARL16, ARL6, ARMC6, ARMC8, ARMCX2, ARMCX5, RP4-769N13.6, ARMCX5-GPRASP2, BHLHB9, ARMCX5-GPRASP2, GPRASP1, ARMCX5-GPRASP2, GPRASP2, ARMCX6, ARNT2, ARPP19, ARRB2, ARSA, ART3, ASB3, GPR75-ASB3, ASCC2, ASNS, ASNS, AC079781.5, ASPSCR1, ASS1, ASUN, ATE1, ATF1, ATF7IP2, ATG13, ATG4D, ATG7, ATG9A, ATM, ATOX1, ATP1B3, ATP2C1, ATP5F1 A, ATP5G2, ATPSJ, ATPSMD, ATPSPF, ATP6AP2, ATP6VOB, ATP6ViC1, ATP6V1D, ATP7B, ATXN1, ATXN1L, IST1, ATXN3, ATXN7L1, AURKA, AURKB, AXDND1, B3GALNT1, B3GALT5, AF064860.1, B3GALT5, AF064860.5, B3GNT5, B4GALT3, B4GALT4, B9D1, BACH1, BAIAP2, BANF1, BANF2, BAX, BAZ2A, BBIP1, BCHE, BCL2L14, BCL6, BCL9L, BCS1L, BDH1, BDKRB2, AL355102.2, BEST1, BEST3, BEX4, BHLHB9, BID, BIN3, BIRC2, BIVM, BIVM-ERCCS, BIVM, BLCAP, BLK, BLOCIS1, RP11-644F5.10, BLOCIS6, AC090527.2, BLOC1S6, RP11-96020.4, BLVRA, BMF, BOLA1, BORCS8-MEF2B, BORCS8, BRCA1, BRD1, BRDT, BRINP3, BROX, BTBD10, BTBD3, BTBD9, BTD, BTF3L4, BTNL9, BUB1B-PAK6, PAK6, BUB3, C10orf68, C11orf1, C11orf48, C11orf54, C11orf54, AP001273.2, C11orf57, C11orf63, C11orf82, C12orf23, C12orf4, C12orf65, C12orf79, C14orf159, C14orf93, C17orf62, C18orj21, C19orf12, C19orf40, C19orf47, C19orf48, C19orf54, CID, C1GALT, C1 QB, C1QTNF, CIS, C1orf101, C1orf112, C1orf116, C1orf159, C1orf63, C2, C2, CFB, C20orf27, C21 orf58, C2CD4D, C2orf15, LIPT1, MRPL30, C2orf80, C2orf81, C3orf14, C3orf17, C3orf18, C3orf22, C3orf33, AC04472.3, C4orf33, C5orf28, C5orf34, C6orf118, C6orf203, C6orf211, C6orf48, C7orf50, C7orf55, C7orf55-LUC7L2, LUC7L2, C8orf44-SGK3, C8orf44, C8orf59, C9, DAB2, C9orf153, C9orf9, CA5BP1, CA5B, CABYR, CALCA, CALCOCO1, CALCOCO2, CALM1, CALM3, CALML4, RP11-315D16.2, CALN, CALU, CANT1, CANX, CAP1, CAPN12, CAPS2, CARD8, CAR-HSP1, CARNS1, CASC1, CASP3, CASP7, CBFA2T2, CBS, CBY1, CCBL1, CCBL2, RBMXL1, CCDC12, CCDC126, CCDC14, CCDC149, CCDC150, CCDC169-SOHLH2, CCDC169, CCDC171, CCDC37, CCDC41, CCDC57, CCDC63, CCDC7, CCDC74B, CCDC77, CCDC82, CCDC90B, CCDC91, CCDC92, CCNE1, CCHCR1, CCL28, CCNBIIP1, CCNC, CCND3, CCNG1, CCP110, CCR9, CCT7, CCT8, CD151, CD1D, CD200, CD22, CD226, CD276, CD36, CD59, CDC26, CDC42, CDC42SE1, CDC42SE2, CDHR3, CDK10, CDK16, CDK4, CDKAL1, CDKL3, CTD-2410N18.4, CDKN1A, CDKN2A, CDNF, CEBPZOS, CELF1, CEMIP, CENPK, CEP170B, CEP250, CEP57, CEP57L1, CEP63, CERS4, CFL1, CFL2, CFLAR, CGNL1, CHCHD7, CHDIL, CHD8, CHFR, ZNF605, CHIA, CHID1, CHL1, CHM, CHMPIA, CHMP3, RNF103-CHMP3, CHRNA2, CIDEC, CIRBP, CITED1, CKLF-CMTM1, CMTM1, CKMTIB, CLDN12, CTB-13L3.1, CLDND1, AC021660.3, CLDND1, CPOX, CLHC1, CLIP1, CLUL1, CMC4, MTCP1, CNDP2, CNFN, CNOT1, CNOT6, CNOT7, CNOT8, CNR1, CNR2, CNTFR, CNTRL, COA1, COASY, COCH, COL8A1, COLCA1, COLEC11, COMMD3-BMI1, BMI1, COPSS, COPS7B, COQ8A, COR06, COTL1, COX14, RP4-60503.4, COX7A2, COX7A2L, COX7B2, CPA4, CPAS, CPEB1, CPNE1, AL109827.1, RBM12, CPNE1, RP1-

309K20.6, RBM12, CPNE3, CPSF3L, CPT1C, CREB3L2, CREM, CRP, CRYZ, CS, AC073896.1, CS, RP11-977G19.10, CSAD, CSDE1, CSF2RA, CSGALNACT1, CSK, CSNK2A1, CSRNP2, CT45A4, CT45A4, CT45A5, CT45A6, CTBP2, CTCFL, CTD-2116N17.1, KIAA0101, CTD-2349B8.1, SYT17, CTD-2528L19.4, ZNF607, CTD-2619J13.8, ZNF497, CTNNA1, CTNNBIP1, CTNND1, CTPS2, CTSB, CTSL, CTTN, CUL2, CUL9, CWC15, CXorf40B, CYB561A3, CYBC1, CYLD, CYP11A1, CYP2R1, CYP4B1, CYP4F22, DAG1, DAGLB, KDELR2, DARS, DBNL, DCAF11, DCAF8, PEX19, DCLRE1C, DCTD, DCTN1, DCTN4, DCUNID2, DDR1, DDX11, DDX19B, AC012184.2, DDX19B, RP1-529KL.3, DDX25, DDX39B, ATP6V1G2-DDX39B, SNORD84, DDX42, DDX60L, DEDD, DEDD2, DEFA1, DEFA1B, DEFA1B, DEFA3, DENND1C, DENND2A, DENND4B, DET1, DGKA, DGKZ, DGLUCY, DHRS4L2, DHRS9, DHX40, DIABLO, AC048338.1, DIAPH1, DICER1, DKKL1, DLG1, DLG3, DLST, DMC1, DMKN, DMTF1, DMTN, DNAJC14, DNAJC19, DNAL1, DNASE1L1, DNMT3A, DOC2A, DOCK8, DOK1, DOPEY1, DPAGT1, DPP8, DRAM2, DRD2, DROSHA, DSN1, DTNA, DTX2, DTX3, DUOX1, DUOXA1, DUS2, DUSP10, DUSP13, DUSP18, DUSP22, DYDC1, DYDC2, DYNLL1, DYNLT1, DYRK1A, DYRK2, DYRK4, RP11-500M8.7, DZIP1L, E2F6, ECHDC1, ECSIT, ECT2, EDC3, EDEM1, EDEM2, MMP24-AS1, RP4-61404.11, EEF1AKNMT, EEF1D, EFEMP1, EFHC1, EGFL7, EHF, EI24, EIFIAD, EIF2B5, EIF4G1, EIF2B5, POLR2H, EIF3E, EIF3K, EIF4E3, EIF4G1, ELF1, ELMO2, ELMOD1, AP000889.3, ELMOD3, ELOC, ELOF1, ELOVL1, ELOVL7, ELP1, ELP6, EML3, EMP3, ENC1, ENDOV, ENO1, ENPPS, ENTHD2, ENTPD6, EP400NL, EPB41L1, EPDR1, NME8, EPHX1, EPM2A, EPN1, EPN2, EPN3, EPS8L2, ERBB3, ERC1, ERCC1, ERG, ERI2, ERI2, DCUNID3, ERLIN2, ERMARD, ERRFI1, ESR2, RP11-544I20.2, ESRRA, ESRRB, ESRRG, ETFA, ETFRF1, ETV1, ETV4, ETV7, EVAIA, EVC2, EVX1, EXD2, EXOS, EXOC1, EXOC2, FAAP24, FABP6, FADS1, FADS2, FAHD2B, FAM107B, FAM111A, FAM111B, FAM114A1, FAM114A2, FAM115C, FAM115C, FAM115D, FAM120B, FAM133B, FAM135A, FAM153A, FAM153B, FAM154B, FAM156A, FAM156B, FAM168B, FAM172A, FAM182B, FAM192A, FAM19A2, FAM200B, FAM220A, FAM220A, AC009412.1, FAM222B, FAM227B, FAM234A, AC004754.1, FAM3C, FAM45A, FAM49B, FAM60A, FAM63A, FAM81A, FAM86B1, FAM86B2, FANC1, FANK1, FAR2, FAXC, FAXDC2, FBF1, FBH1, FBXL4, FBXO18, FBXO22, FBXO31, FBXO41, FBXO44, FBXO45, FBXW9, FCHO1, FCHSD2, FDFT1, FDPS, FER, FETUB, FGD4, FGF1, FGFR1, FGFRL1, FGL1, FHL2, FIBCD1, FIGNL1, FIGNL1, DDC, FKBPS, FKRP, FLRT2, FLRT3, FMC1, LUC7L2, FMC1-LUC7L2, FNDC3B, FOLH1, FOLR1, FOXP1, FOXK1, FOXM1, FOXO1, FOXP4, AC097634.4, FOXRED1, FPR1, FPR2, FRG1B, FRS2, FTO, FTSJ1, FUK, FUT10, FUT3, FUT6, FXYD3, FZD3, G2E3, GAA, GABARAPL1, GABPB1, GABRAS, GAL3ST1, GALE, GALNT11, GALNT14, GALNT6, GAPVD1, GARNL3, GAS2L3, GAS8, GATA1, GATA2, GATA4, GBA, GCNT1, GDPD2, GDPDS, GEMIN7, MARK4, GEMIN8, GGA3, GGACT, AL356966.1, GGPS1, GHRL, GID8, GIGYF2, GIMAP8, GIPC1, GJB1, GJB6, GLB1L, GLI1, GLT8D1, GMFG, GMPR2, GNAI2, GNAQ, GNB1, GNB2, GNE, GNG2, GNGT2, GNPDA1, GNPDA2, GOLGA3, CHFR, GOLGA4, GOLPH3L, GOLT1B, GPBP1L1, GPER1, GPR116, GPR141, EPDR1, GPR155, GPR161, GPR56, GPR63, GPR75-ASB3, ASB3, GPR85, GPSM2, GRAMD1B, GRB10, GRB7, GREM2, GRIA2, GSDMB, GSE1, GSN, GSTA4, GSTZ1, GTDC1, GTF2H1, GTF2H4, VARS2, GTF3C2, GUCYIA3, GUCYIB3, GUK1, GULP1, GYPC, GYS1, GZF1, HAGH, HAO2, HAPLN3, HAVCR1, HAX1, HBG2, AC104389.4, HBG2, AC104389.4, HBE1, HBG2, AC104389.4, HBE1, OR51B5, HBG2, HBE1, AC104389.28, HBS1L, HCFC1R1, HCK, HDAC2, HDAC6, HDAC7, HDLBP, HEATR4, HECTD4, HEXIM2, HHAT, HHATL, CCDC13, HINFP, HIRA, C22orf39, HIVEP3, HJV, HKR1, HLF, HMBOX1, HMGA1, HMGB3, HMGCR, HMGN4, HMOX2, HNRNPC, HNRNPD, HNRNPH1, HNRNPH3, HNRNPR, HOMER3, HOPX, HOXA3, HOXB3, HOXB3, HOXB4, HOXC4, HOXD3, HOXD3, HOXD4, HPCAL1, HPS4, HPS5, HRH1, HS3ST3A1, HSH2D, HSP90AA1, HSPD1, HTT, HUWE1, HYOU1, IAH1, ICA1L, ICAM2, ICE2, ICK, IDH2, IDH3G, IDS, IFI27, IFI44, IFT20, IFT22, IFT88, IGF2, INS-IGF2, IGF2BP3, IGFBP6, IKBKAP, IKBKB, ILI1, IL18BP, IL18RAP, ILIRAP, ILIRL1, IL18R1, IL1RN, IL32, IL4I1, NUP62, AC011452.1, IL4I1, NUP62, CTC-326K19.6, IL6ST, ILVBL, IMMPIL, IMPDH1, INCA1, ING1, INIP, INPP1, INPPSJ, INPPSK, INSIG2, INTSI1, INTS12, INTS14, IP6K2, IP6K3, IPOI1, LRRC70, IQCE, IQGAP3, IRAK4, IRF3, IRF5, IRF6, ISG20, IST1, ISYNA1, ITFG2, ITGBIBP1, ITGB7, ITIH4, RP5-966M1.6, ITPRIPL1, JADE1, JAK2, JARID2, JDP2, KANK1, KANK1, RP11-31F19.1, KANK2, KANSLIL, KAT6A, KBTBD2, KBTBD3, KCNAB2, KCNE3, KCNG1, KCNJ16, KCNJ9, KCNMB2, AC117457.1, LINC01014, KCTD20, KCTD7, RABGEF1, KDM1B, KDM4A, AL451062.3, KHNYN, KIAA0040, KIAA0125, KIAA0196, KIAA0226L, PPP1R2P4, KIAA0391, KIAA0391, AL121594.1, KIAA0391, PSMA6, KIAA0753, KIAA0895, KIAA0895L, KIAA1191, KIAA1407, KIAA1841, C2orf74, KIF12, KIF14, KIF27, KIF9, KIFC3, KIN, KIRREL1, KITLG, KLC1, APOPT1, AL139300.1, KLC4, KLHDC4, KLHDC8A, KLHL13, KLHL18, KLHL2, KLHL24, KLHL7, KLKI1, KLK2, KLKS, KLK6, KLK7, KNOP1, KRBA2, AC135178.2, KRBA2, RP11-849F2.7, KRIT1, KRT15, KRT8, KTN1, KXD1, KYAT3, RBMXL1, KYNU, L3MBTL1, LACC1, LARGE, LARP4, LARP7, LAT2, LBHD1, LCA5, LCASL, LCTL, LEP-ROTL1, LGALS8, LGALS9C, LGMN, LHFPL2, LIG4, LIMCH1, LIMK2, LIMS2, LINC00921, ZNF263, LIPF, LLGL2, LMAN2L, LMCD1, LMF1, RP11-161M6.2, LMO1, LMO3, LOXHD1, LPAR1, LPAR2, LPAR4, LPARS, LPAR6, LPHN1, LPIN2, LPIN3, LPP, LRFNS, LRIF1, LRMP, LRRC14, LRRC20, LRRC24, C8orf82, LRRC39, LRRC42, LRRC48, LRRC4C, LRRC8A, LRRC8B, LRRD1, LRTOMT, LRTOMT, AP000812.5, LSM7, LTB4R, LTBP3, LUC7L2, FMC1-LUC7L2, LUC7L3, LUZP1, LYG1, LYL1, LYPD4, LYPD6B, LYRM1, LYRMS, LYSMD4, MACC1, MAD1L1, MAD1L1, AC069288.1, MAEA, MAFF, MAFG, MAFK, MAGEA12, CSAG4, MAGEA2, MAGEA2B, MAGEA4, MAGEB1, MAGOHB, MAN2A2, MANBAL, MAOB, MAP2K3, MAP3K7CL, MAP3K8, MAP7, MAP9, MAPK6, MAPK7, MAPK8, MAPKAP1, 10-Mar, 7-Mar, 8-Mar, MARK2, MASP1, MATK, MATR3, MATR3, SNHG4, MB, MBDS, MBNL1, MBOAT7, MCC, MCFD2, MCM9, MCOLN3, MCRS1, MDC1, MDGA2, MDH2, MDM2, ME1, MEAK7, MECR, MED4, MEF2A, MEF2B, BORCS8-MEF2B, MEF2BNB-MEF2B, MEF2B, MEF2BNB, MEF2C, MEF2D, MEGF10, ME11, MEIS2, MELK, MET, METTL13, METTL23, MFF, MFN2, MFSD2A, MGST3, MIB2, MICAL1, MICAL3, MICOS10, NBL1, MICOS10-NBL1, MID1, MINA, MINOS1-NBL1, MINOS1, MIOS, MIPOL1, MIS12, MKLN1, MKNK1, MKNK1, MOB3C, MLF2, MLH1, MMP17, MOBP, MOCS1, MOGS, MOK, MORF4L1, MPC1, MPC2, MPG, MP1, MPP1, MPP2, MPPE1, MPST, MRAS, MRO, MROH1, MROH7-TTC4, MROH7, MRPL14, MRPL24, MRPL33, BABAM2, MRPL33, BRE, MRPL47, MRPL48, MRPL55, MRRF, MRTFA, MRTFB, MRVI1, MS4A1, MS4A15, MS4A3, MS4A6E, MS4A7, MS4A14, MSANTD3, MSANTD4, MSH5, MSH5-SAPCD1, MSL2, MSRB3, MSS51, MTCP1, CMC4, MTERF, MTERF1, MTERF3, MTERFD2, MTERFD3, MTF2, MTG2, MTHFD2, MTHFD2L, MTIF2, MTIF3, MTMR10, MTRF1, MTRR, MTUS2, MUTYH, MVK, MX1, MX2, MYH10, MYL12A, MYB, MYD88, MYL5, MYLIP, MYNN, MYO15A, MYO1B, MYOM2, MZF, N4BP2L2, NAA60, NAB1, NAE, NAGK, NAP1L1, NAPIL4, NAPG, NARFL, NARG2, NAT1, NAT10, NBPF11, WI2-3658N16.1, NBPF12, NBPF15, NBPF24, NBPF6, NBPF9, NBR1, NCAPG2, NCBP2, NCEH1, NCOA1, NCOA4, NDC1, NDRG1, NDRG2, NDRG4, NDST1, NDUFAF6, NDUFB2, NDUFC1, NDUFS1, NDUFS8, NDUFV1, NEDD1, NEIL1, NEIL2, NEK10, NEK11, NEK6, NEK9, NELFA, NEU4, NFATS, NFE2, NFE2L2, AC019080.1, NFRKB, NFYA, NFYC, NIF3L1, NIPA2, NKIRAS1, NKX2-1, NLRC3, NME1, NME1-NME2, NME2, NME1-NME2, NME2, NME4, NME6, NME9, NOD1, NOL10, NOL8, NONO, NPAS1, NPIPA8, RP11-1212A22.1, NPIPB3, NPIPB4, NPIPB9, NPL, NPM1, NPPA, NQO2, NR1H3, NR2C2, NR2F2, NR4A1, NRDC, NREP, NRF, NRG4, NRIP1, NSD2, NSDHL, NSG1, NSMCE2, NSRP1, NT5C2, NTF4, NTMT1, NTNG2, NUBP2, NUCB2, NUDT1, NUDT2, NUDT4, NUF2, NUMBL, NUP50, NUP54, NUP85, NVL, NXF1, NXPE1, NXPE3, OARD1, OAT, OAZ2, OCIAD1, OCLN, ODF2, OGDHL, OGFOD2, AC026362.1, OGFOD2, RP11-197N18.2, OLA1, OPRL1, OPTN, OR2H1, ORAI2, ORMDL1, ORMDL2, ORMDL3, OSBPL2, OSBPL3, OSBPLS, OSBPL9, OSER1, OSGIN1, OSR2, P2RX4, P2RY2, P2RY6, P4HA2, PABPC1, PACRGL, PACSIN3, PADI1, PAIP2, PAK1, PAK3, PAK4, PAK7, PALB2, PANK2, PAQR6, PARP11, PARVG, PASK, PAX6, PBRM1, PBXIP1, PCBP3, PCBP4, AC115284.1, PCBP4, RP11-155D18.14, RP11-155D18.12, PCGF3, PCGFS, PCNP, PCSK9, PDCD10, PDCD6, AHRR, PDDC1, PDGFRB, PDIA6, PDIK1L, PDLIM7, PDP1, PDPK1, PDPN, PDZD11, PEA15, PEX2, PEX5, PEXSL, PFKM, PFN4, PGAP2, PGAP2, AC090587.2, PGAP3, PGM3, PGPEP1, PHB, PHC2, PHF20, PHF21A, PHF23, PHKB, PHLDB1, PHOSPHO1, PHOSPHO2, KLHL23, PI4 KB, PIAS2, PICALM, PIF1, PIGN, PIGO, PIGT, PIK3CD, PILRB, STAG3L5P-PVRIG2P-PILRB, PIPSKIB, PIR, PISD, PIWIL4, FUT4, PKD2, PKIA, PKIG, PKM, PKN2, PLAlA, PLA2G2A, PLA2G5, PLA2G7, PLAC8, PLAGL1, PLD1, PLD3, PLEKHA1, PLEKHA2, PLEKHA6, PLEKHGS, PLIN1, PLS1, PLS3, PLSCR1, PLSCR2, PLSCR4, PLXNB1, PLXNB2, PMP22, PMS1, PNISR, PNKP, AKTIS1, PNMT, PNPLA4, PNPLA8, PNPO, PNRC1, POCiB, POFUT1, POLB, POLD1, POLH, POL1, POLL, POLRIB, POM121, POM121C, AC006014.7, POM121C, AC211429.1, POMC, POMT1, POP1, PORCN, POUSF1, PSORS1C3, PPARD, PPARG, PPHLN1, PPIL3, PPIL4, PPM1A, PPMIB, AC013717.1, PPP1CB, PPP1R11, PPP1R13L, PPP1R26, PPP1R9A, PPP2R2B, PPP3CA, PPP6R1, PPP6R3, PPT2, PPT2-EGFL8, EGFL8, PPWD1, PRDM2, PRDM8, PRELID3A, PREPL, PRICKLE1, PRKAG1, PRMT2, PRMTS, PRMT7, PROM1, PRPS1, PRPSAP2, PRR14L, PRR15L, PRR5, PRRS-ARHGAP8, PRRSL, PRR7, PRRC2B, PRRT4, PRSS50, PRSS45, PRSS44, PRUNE, PRUNE1, PSEN1, PSMA2, PSMF1, PSORS1C1, PSPH, PSRC1, PTBP3, PTHLH, PTK2, PTPDC1, PTPRM, PUF60, PUM2, PUS1, PUS10, PXN, PXYLP1, PYCR1, QRICH1, R3HCC1L, R3HDM2, RAB17, RAB23, RAB3A, RAB3D, TMEM205, RAB4B-EGLN2, EGLN2, AC008537.1, RAB5B, RAB7L1, RABL2A, RABL2B, RABL5, RACGAP1, RAD17, RAD51L3-RFFL, RAD51D, RAD52, RAE1, RAI14, RAI2, RALBP1, RAN, RANGAP1, RAP1A, RAPiB, RAP1GAP, RAPGEF4, RAPGEFL1, RASGRP2, RASSF1, RBCK1, RBM12B, RBM14, RBM4, RBM14-RBM4, RBM23, RBM4, RBM14-RBM4, RBM47, RBM7, AP002373.1, RBM7, RP11-212D19.4, RBMS2, RBMY1E, RBPJ, RBPMS, RBSN, RCBTB2, RCC1, RCC1, SNHG3, RCCD1, RECQL, RELL2, REPIN1, AC073111.3, REPIN1, ZNF775, RER1, RERE, RFWD3, RFX3, RGL2, RGMB, RGS11, RGS3, RGS5, AL592435.1, RHBDD1, RHNO1, TULP3, RHOC, AL603832.3, RHOC, RP11-426L16.10, RHOH, RIC8B, RIMKLB, RIN1, RIPK2, RIT1, RLIM, RNASE4, ANG, AL163636.6, RNASEK, RNASEK-C17orf49, RNF111, RNF123, RNF13, RNF14, RNF185, RNF216, RNF24, RNF32, RNF34, RNF38, RNF4, RNF44, RNH1, RNMT, RNPS1, RO60, ROPN1, ROPN1B, ROR2, RP1-102H19.8, C6orf163, RP1-283E3.8, CDK11A, RP11-120M18.2, PRKAR1A, RP11-133K10.2, PAK6, RP11-164J13.1, CAPN3, RP11-21J18.1, ANKRD12, RP11-322E11.6, INO80C, RP1-337C18.10, CHD1L, RP11-432B6.3, TRIM59, RP11-468E2.4, IRF9, RP11-484M3.5, UPK1B, RP11-517H2.6, CCR6, RP11-613M10.9, SLC25A51, RP11-659G9.3, RAB30, RP11-691N7.6, CTNND1, RP11-849H4.2, RP11-896J10.3, NKX2-1, RP11-96020.4, SQRDL, RP1-986E7.7, SERPINA3, RP4-769N13.6, GPRASP1, RP4-769N13.6, GPRASP2, RP4-798P15.3, SEC16B, RP5-1021I20.4, ZNF410, RP6-109B7.3, FLJ27365, RPE, RPH3AL, RPL15, RPL17, RPL17-C18orf32, RPL17, RPL23A, RPL36, HSD11B1L, RPP38, RPS20, RPS27A, RPS3A, RPS6KA3, RPS6KC1, RPS6KL1, RPUSD1, RRAGD, RRAS2, RRBP1, RSLiD1, RSRC2, RSRP1, RUBCNL, RUNXIT1, RUVBL2, RWDD1, RWDD4, S100A13, AL162258.1, S100A13, RP1-178F15.5, S100A16, S100A4, S100A3, S100A6, S100PBP, SAA1, SACM1L, SAMD4B, SAR1A, SARAF, SARNP, RP11-762I7.5, SCAMPS, SCAP, SCAPER, SCFD1, SCGB3A2, SCIN, SCML1, SCNNID, SC02, SCOC, SCRN1, SDC2, SDC4, SECi3, SECi4L1, SECi4L2, SEC22C, SEC23B, SEC24C, SEC61G, SEMA4A, SEMA4C, SEMA4D, SEMA6C, SENP7, SEPP1, ii-Sep, 2-Sep, SERGEF, AC055860.1, SERP1, SERPINA1, SER-PINAS, SERPINB6, SERPING1, SERPINH1, SERTAD3, SETD5, SFMBT1, AC096887.1, SFTPA1, SFTPA2, SFXN2, SGCD, SGCE, SGK3, SGK3, C8orf44, SH2B1, SH2D6, SH3BP1, Z83844.3, SH3BP2, SH3BP5, SH3D19, SH3YL1, SHC1, SHISAS, SHMT1, SHMT2, SHOC2, SHROOM1, SIGLEC5, SIGLEC14, SIL1, SIN3A, SIRT2, SIRT6, SKP1, STAT4, AC104109.3, SLAIN1, SLC10A3, SLC12A9, SLC14A1, SLC16A6, SLC1A2, SLC1A6, SLC20A2, SLC25A18, SLC25A19, SLC25A22, SLC25A25, SLC25A29, SLC25A30, SLC25A32, SLC25A39, SLC25A44, SLC25A45, SLC25A53, SLC26A11, SLC26A4, SLC28A1, SLC29A1, SLC2A14, SLC2A5, SLC2A8, SLC35B2, SLC35B3, SLC35C2, SLC37A1, SLC38A1, SLC38A11, SLC39A13, SLC39A14, SLC41A3, SLC44A3, SLC4A7, SLC4A8, SLC5A10, SLC5A11, SLC6A1, SLC6A12, SLC6A9, SLC7A2, SLC7A6, SLC7A7, SLCO1A2, SLCO1C1, SLCO2B1, SLFN11, SLFN12, SLFNL1, SLMO1, SLTM, SLU7, SMAD2, SMAP2, SMARCA2, SMARCE1, AC073508.2, SMARCE1, KRT222, SMC6, SMG7, SMIM22, SMOX, SMPDL3A, SMTN, SMU1, SMUG1, SNAP25, SNCA, SNRK, SNRPC, SNRPD1, SNRPD2, SNRPN, SNRPN, SNURF, SNUPN, SNX11, SNX16, SNX17, SOAT1, SOHLH2, CCDC169-SOHLH2, CCDC169, SORBS1, SORBS2, SOX5, SP2, SPART, SPATA20, SPATA21, SPATS2, SPATS2L, SPDYE2, SPECC1, SPECC1L, SPECC1L-ADORA2A, SPECC1L-ADORA2A, ADORA2A, SPEG, SPG20, SPG21, SPIDR, SPIN1, SPOCD1, SPOP, SPRR2A, SPRR2B, SPRR2E, SPRR2B, SPRR2F, SPRR2D, SPRR3, SPRYi, SPRY4, SPTBN2, SRC, SRGAP1, SRP68, SRSF11, SSX1, SSX2IP, ST3GAL4, ST3GAL6, STS, ST6GALNAC6, ST7L, STAC3, STAG1, STAG2, STAMBP, STAMBPL1, STARD3NL, STAT6, STAU1, STAU2, AC022826.2, STAU2, RP11-463D19.2, STEAP2, STEAP3, ST1L, STK25, STK33, STK38L, STK40, STMN1, STON1, STON1-GTF2AiL, STRAP, STRBP, STRC, AC011330.5, STRC, CATSPER2, STRC, CATSPER2, AC011330.5, STRC, STRCP1, STT3A, STX16-NPEPL1, NPEPL1, STX5, STX6, STX8, STXBP6, STYK1, SULTIA1, SUL-TIA2, SUMF2, SUN, SUN2, SUN2, DNAL4, SUOX, SUPT6H, SUV39H2, SV2B, SYBU, SYNCR1P, SYNJ2, SYT1, SYTL4, TAB2, TACC1, TADA2B, TAFiC, TAF6, AC073842.2, TAF6, RP11-506M12.1, TAF9, TAGLN, TANK, TAPSAR1, PSMB9, TAPT1, TATDN1, TAZ, TBC1D1, TBC1D12, HELLS, TBC1D15, TBCID3H, TBCID3G, TBC1D5, TBC1D5, SATB1, TBCA, TBCEL, TBCEL, AP000646.1, TBL1XR1, TBP, TBX5, TBXAS1, TCAF1, TCEA2, TCEAL4, TCEAL8, TCEAL9, TCEANC, TCEB1, TCF19, TCF25, TCF4, TCP1, TCP10L, AP000275.65, TCP11, TCP11L2, TCTN1, TDG, TDP1, TDRD7, TEAD2, TECR, TENC1, TENT4A, TEX264, TEX30, TEX37, TFDP1, TFDP2, TFEB, TFG, TFP1, TF, TFP1, TGIF1, THAP6, THBS3, THOCS, THRAP3, THUMPD3, TIAL1, TIMM9, TIMP1, TIRAP, TJAP1, TJP2, TK2, TLDC1, TLE3, TLE6, TLN1, TLR10, TM9SF1, TMBIM1, TMBIM4, TMBIM6, TMC6, TMCC1, TMCO4, TMEM126A, TMEM139, TMEM150B, TMEM155, TMEM161B, TMEM164, TMEM168, TMEM169, TMEM175, TMEM176B, TMEM182, TMEM199, CTB-96E2.3, TMEM216, TMEM218, TMEM230, TMEM263, TMEM45A, TMEM45B, TMEM62, TMEM63B, TMEM66, TMEM68, TMEM98, TMEM9B, TMPRSSIID, TMPRSSS, TMSB15B, TMTC4, TMUB2, TMX2-CTNND1, RP11-691N7.6, CTNND1, TNFAIP2, TNFAIP8L2, SCNM1, TNFRSFIOC, TNFRSF19, TNFRSF8, TNFSF12-TNFSF13, TNFSF12, TNFSF13, TNFSF12-TNFSF13, TNFSF13, TNIP1, TNK2, TNNT1, TNRC18, TNS3, TOB2, TOM1L, TOP1MT, TOP3B, TOX2, TP53, RP11-199F1.2, TP53I1, TP53INP2, TPCN1, TPM3P9, AC022137.3, TPT1, TRA2B, TRAF2, TRAF3, TRAPPC12, TRAPPC3, TREH, TREX1, TREX2, TRIB2, TRIM3, TRIM36, TRIM39, TRIM46, TRIM6, TRIM6-TRIM34, TRIM6-TRIM34, TRIM34, TRIM66, TRIM73, TRIT1, TRMTIOB, TRMT2B, TRMT2B-AS1, TRNT1, TRO, TROVE2, TRPS1, TRPT1, TSC2, TSGA10, TSPAN14, TSPAN3, TSPAN4, TSPAN5, TSPAN6, TSPAN9, TSPO, TTC12, TTC23, TTC3, TTC39A, TTC39C, TTLL1, TTLL7, TTPAL, TUBD1, TWNK, TXNL4A, TXNL4B, TXNRD1, TYK2, U2AF1, UBA2, UBA52, UBAP2, UBE2D2, UBE2D3, UBE2E3, UBE21, UBE2J2, UBE3A, UBL7, UBXNI1, UBXN7, UGDH, UGGT1, UGP2, UMAD1, ACO007161.3, UNC45A, UQCC1, URGCP-MRPS24, URGCP, USMGS, USP16, USP21, USP28, USP3, USP33, USP35, USP54, USP9Y, USPL1, UTP15, VARS2, VASH2, VAV3, VDAC1, VDAC2, VDR, VEZT, VGF, VIL1, VILL, VIPR1, VPS29, VPS37C, VPS8, VPS9D1, VRK2, VWA1, VWASA, WARS, WASF1, WASHCS, WBPS, WDHD1, WDPCP, WDR37, WDR53, WDR6, WDR72, WDR74, WDR81, WDR86, WDYHV1, WFDC3, WHSC1, WIPF1, WSCD2, WWP2, XAGE1A, XAGEIB, XKR9, XPNPEP1, XRCC3, XRN2, XXYLT1, YIF1A, YIF1B, YIPF1, YIPFS, YPELS, YWHAB, YWHAZ, YYIAP1, ZBTB1, ZBTB14, ZBTB18, ZBTB20, ZBTB21, ZBTB25, ZBTB33, ZBTB34, ZBTB38, ZBTB43, ZBTB49, ZBTB7B, ZBTB7C, ZBTB8OS, ZC3H11A, ZBED6, ZC3H13, ZCCHC17, ZCCHC7, ZDHHC11, ZDHHC13, ZEB2, ZFANDS, ZFAND6, ZFP1, ZFP62, ZFX, ZFYVE16, ZFYVE19, ZFYVE20, ZFYVE27, ZHX2, AC016405.1, ZHX3, ZIK1, ZIM2, PEG3, ZKSCAN1, ZKSCAN3, ZKSCAN8, ZMAT3, ZMATS, ZMIZ2, ZMYM6, ZMYND11, ZNF10, AC026786.1, ZNF133, ZNF146, ZNF16, ZNF177, ZNF18, ZNF200, ZNF202, ZNF211, ZNF219, ZNF226, ZNF227, ZNF23, AC010547.4, ZNF23, AC010547.9, ZNF239, ZNF248, ZNF25, ZNF253, ZNF254, ZNF254, AC092279.1, ZNF263, ZNF274, ZNF275, ZNF28, ZNF468, ZNF283, ZNF287, ZNF3, ZNF320, ZNF322, ZNF324B, ZNF331, ZNF334, ZNF34, ZNF350, ZNF385A, ZNF395, FBX016, ZNF415, ZNF418, ZNF43, ZNF433-AS1, AC008770.4, ZNF438, ZNF444, ZNF445, ZNF467, ZNF480, ZNF493, ZNF493, CTD-2561J22.3, ZNF502, ZNF507, ZNF512, AC074091.1, ZNF512, RP11-158I13.2, ZNF512B, ZNF512B, SAMD10, ZNF521, ZNF532, ZNF544, AC020915.5, ZNF544, CTD-3138B18.4, ZNF559, ZNF177, ZNF562, ZNF567, ZNF569, ZNF570, ZNF571-AS1, ZNF540, ZNF577, ZNF580, ZNF581, ZNF580, ZNF581, CCDC106, ZNF600, ZNF611, ZNF613, ZNF615, ZNF619, ZNF620, ZNF639, ZNF652, ZNF665, ZNF667, ZNF668, ZNF671, ZNF682, ZNF687, ZNF691, ZNF696, ZNF701, ZNF706, ZNF707, ZNF714, ZNF717, ZNF718, ZNF720, ZNF721, ZNF730, ZNF763, ZNF780B, AC005614.5, ZNF782, ZNF786, ZNF79, ZNF791, ZNF81, ZNF83, ZNF837, ZNF839, ZNF84, ZNF845, ZNF846, ZNF865, ZNF91, ZNF92, ZNHIT3, ZSCAN21, ZSCAN25, ZSCAN30, and ZSCAN32.

In some embodiments, the gene encoding a target sequence comprises the HTT gene.

Exemplary genes that may be modulated by the compounds of Formula (I) described herein may also include, inter alia, AC005258.1, AC005943.1, AC007849.1, AC008770.2, AC010487.3, AC011477.4, AC012651.1, AC012531.3, AC034102.2, AC073896.4, AC104472.3, AL109811.3, AL133342.1, AL137782.1, AL157871.5, AF241726.2, AL355336.1, AL358113.1, AL360181.3, AL445423.2, AL691482.3, AP001267.5, RF01169, and RF02271.

The compounds described herein may further be used to modulate a sequence comprising a particular splice site sequence, e.g., an RNA sequence (e.g., a pre-mRNA sequence). In some embodiments, the splice site sequence comprises a 5' splice site sequence. In some embodiments, the splice site sequence comprises a 3' splice site sequence. Exemplary gene sequences and splice site sequences (e.g., 5' splice site sequences) include AAAgcaaguu (SEQ ID NO: 1), AAAguaaaaa (SEQ ID NO: 2), AAAguaaaau (SEQ ID NO: 3), AAAguaaagu (SEQ ID NO: 4), AAAguaaaua (SEQ ID NO: 5), AAAguaaaug (SEQ ID NO: 6), AAAguaaauu (SEQ ID NO: 7), AAAguaacac (SEQ ID NO: 8), AAAguaacca (SEQ ID NO: 9), AAAguaacuu (SEQ ID NO: 10), AAAguaagaa (SEQ ID NO: 11), AAAguaagac (SEQ ID NO: 12), AAAguaagag (SEQ ID NO: 13), AAAguaagau (SEQ ID NO: 14), AAAguaagca (SEQ ID NO: 15), AAAguaagcc (SEQ ID NO: 16), AAAguaagcu (SEQ ID NO: 17), AAAguaagga (SEQ ID NO: 18), AAAguaaggg (SEQ ID NO: 19), AAAguaaggu (SEQ ID NO: 20), AAAguaagua (SEQ ID NO: 21), AAAguaaguc (SEQ ID NO: 22), AAAguaagug (SEQ ID NO: 23), AAAguaaguu (SEQ ID NO: 24), AAAguaaucu (SEQ ID NO: 25), AAAguaauua (SEQ ID NO: 26), AAAguacaaa (SEQ ID NO: 27), AAAguaccgg (SEQ ID NO: 28), AAAguacuag (SEQ ID NO: 29), AAAguacugg (SEQ ID NO: 30), AAAguacuuc (SEQ ID NO: 31), AAAguacuug (SEQ ID NO: 32), AAAguagcuu (SEQ ID NO: 33), AAAguaggag (SEQ ID NO: 34), AAAguaggau (SEQ ID NO: 35), AAAguagggg (SEQ ID NO: 36), AAAguaggua (SEQ ID NO: 37), AAAguaguaa (SEQ ID NO: 38), AAAguauauu (SEQ ID NO: 39), AAAguauccu (SEQ ID NO: 40), AAAguaucuc (SEQ ID NO: 41), AAAguaugga (SEQ ID NO: 42), AAAguaugua (SEQ ID NO: 43), AAAguaugug (SEQ ID NO: 44), AAAguauguu (SEQ ID NO: 45), AAAguauugg (SEQ ID NO: 46), AAAguauuuu (SEQ ID NO: 47), AAAgucagau (SEQ ID NO: 48), AAAgucugag (SEQ ID NO: 49), AAAgugaaua (SEQ ID NO: 50), AAAgugagaa (SEQ ID NO: 51), AAAgugagac (SEQ ID NO: 52), AAAgugagag (SEQ ID NO: 53), AAAgugagau (SEQ ID NO: 54), AAAgugagca (SEQ ID NO: 55), AAAgugagcu (SEQ ID NO: 56), AAAgugaggg (SEQ ID NO: 57), AAAgugagua (SEQ ID NO: 58), AAAgugaguc (SEQ ID NO: 59), AAAgugagug (SEQ ID NO: 60), AAAgugaguu (SEQ ID NO: 61), AAAgugcguc (SEQ ID NO: 62), AAAgugcuga (SEQ ID NO: 63), AAAgugggu c (SEQ ID NO: 64), AAAguggguu (SEQ ID NO: 65), AAAgugguaa (SEQ ID NO: 66), AAAguguaug (SEQ ID NO: 67), AAAgugugug (SEQ ID NO: 68), AAAguguguu (SEQ ID NO: 69), AAAguuaagu (SEQ ID NO: 70), AAAguuacuu (SEQ ID NO: 71), AAAguuagug (SEQ ID NO: 72), AAAguuaugu (SEQ ID NO: 73), AAAguugagu (SEQ ID NO: 74), AAAguuugua (SEQ ID NO: 75), AACguaaaac (SEQ ID NO: 76), AACguaaagc (SEQ ID NO: 77), AACguaaagg (SEQ ID NO: 78), AACguaagca (SEQ ID NO: 79), AACguaaggg (SEQ ID NO: 80), AACguaaguc (SEQ ID NO: 81), AACguaagug (SEQ ID NO: 82), AACguaaugg (SEQ ID NO: 83), AACguaguga (SEQ ID NO: 84), AACguaugua (SEQ ID NO: 85), AACguauguu (SEQ ID NO: 86), AACgugagca (SEQ ID NO: 87), AACgugagga (SEQ ID NO: 88), AACgugauuu (SEQ ID NO: 89), AACgugggau (SEQ ID NO: 90), AACgugggua (SEQ ID NO: 91), AACguguguu (SEQ ID NO: 92), AACguuggua (SEQ ID NO: 93), AAGgcaaauu (SEQ ID NO: 94), AAGgcaagag (SEQ ID NO: 95), AAGgcaagau (SEQ ID NO: 96), AAGgcaagcc (SEQ ID NO: 97), AAGgcaagga (SEQ ID NO: 98), AAGgcaaggg (SEQ ID NO: 99), AAGgcaagug (SEQ ID NO: 100), AAGgcaaguu (SEQ ID NO: 101), AAGgcacugc (SEQ ID NO: 102), AAGgcagaaa (SEQ ID NO: 103), AAGgcaggau (SEQ ID NO: 104), AAGgcaggca (SEQ ID NO: 105), AAGgcaggga (SEQ ID NO: 106), AAGgcagggg (SEQ ID NO: 107), AAGgcaggua (SEQ ID NO: 108), AAGgcaggug (SEQ ID NO: 109), AAGgcaucuc (SEQ ID NO: 110), AAGgcaugcu (SEQ ID NO: 111), AAGgcaugga (SEQ ID NO: 112), AAGgcauguu (SEQ ID NO: 113), AAGgcauuau (SEQ ID NO: 114), AAGgcgagcu (SEQ ID NO: 115), AAGgcgaguc (SEQ ID NO: 116), AAGgcgaguu (SEQ ID NO: 117), AAGgcuagcc (SEQ ID NO: 118), AAGguaaaaa (SEQ ID NO: 119), AAGguaaaac (SEQ ID NO: 120), AAGguaaaag (SEQ ID NO: 121), AAGguaaaau (SEQ ID NO: 122), AAGguaaaca (SEQ ID NO: 123), AAGguaaacc (SEQ ID NO: 124), AAGguaaacu (SEQ ID NO: 125), AAGguaaaga (SEQ ID NO: 126), AAGguaaagc (SEQ ID NO: 127), AAGguaaagg (SEQ ID NO: 128), AAGguaaagu (SEQ ID NO: 129), AAGguaaaua (SEQ ID NO: 130), AAGguaaauc (SEQ ID NO: 131), AAGguaaaug (SEQ ID NO: 132), AAGguaaauu (SEQ ID NO: 133), AAGguaacaa (SEQ ID NO: 134), AAGguaacau (SEQ ID NO: 135), AAGguaaccc (SEQ ID NO: 136), AAGguaacua (SEQ ID NO: 137), AAGguaacuc (SEQ ID NO: 138), AAGguaacug (SEQ ID NO: 139), AAGguaacuu (SEQ ID NO: 140), AAGguaagaa (SEQ ID NO: 141), AAGguaagac (SEQ ID NO: 142), AAGguaagag (SEQ ID NO: 143), AAGguaagau (SEQ ID NO: 144), AAGguaagca (SEQ ID NO: 145), AAGguaagcc (SEQ ID NO: 146), AAGguaagcg (SEQ ID NO: 147), AAGguaagcu (SEQ ID NO: 148), AAGguaagga (SEQ ID NO: 149), AAGguaaggc (SEQ ID NO: 150), AAGguaaggg (SEQ ID NO: 151), AAGguaaggu (SEQ ID NO: 152), AAGguaagua (SEQ ID NO: 153), AAGguaaguc (SEQ ID NO: 154), AAGguaagug (SEQ ID NO: 155), AAGguaaguu (SEQ ID NO: 156), AAGguaauaa (SEQ ID NO: 157), AAGguaauac (SEQ ID NO: 158), AAGguaauag (SEQ ID NO: 159), AAGguaauau (SEQ ID NO: 160), AAGguaauca (SEQ ID NO: 161), AAGguaaucc (SEQ ID NO: 162), AAGguaaucu (SEQ ID NO: 163), AAGguaauga (SEQ ID NO: 164), AAGguaaugc (SEQ ID NO: 165), AAGguaaugg (SEQ ID NO: 166), AAGguaaugu (SEQ ID NO: 167), AAGguaauua (SEQ ID NO: 168), AAGguaauuc (SEQ ID NO: 169), AAGguaauug (SEQ ID NO: 170), AAGguaauuu (SEQ ID NO: 171), AAGguacaaa (SEQ ID NO: 172), AAGguacaag (SEQ ID NO: 173), AAGguacaau (SEQ ID NO: 174), AAGguacacc (SEQ ID NO: 175), AAGguacacu (SEQ ID NO: 176), AAGguacagg (SEQ ID NO: 177), AAGguacagu (SEQ ID NO: 178), AAGguacaua (SEQ ID NO: 179), AAGguacaug (SEQ ID NO: 180), AAGguacauu (SEQ ID NO: 181), AAGguaccaa (SEQ ID NO: 182), AAGguaccag (SEQ ID NO: 183), AAGguaccca (SEQ ID NO: 184), AAGguacccu (SEQ ID NO: 185), AAGguaccuc (SEQ ID NO: 186), AAGguaccug (SEQ ID NO: 187), AAGguaccuu (SEQ ID NO: 188), AAGguacgaa (SEQ ID NO: 189), AAGguacggg (SEQ ID NO: 190), AAGguacggu (SEQ ID NO: 191), AAGguacguc (SEQ ID NO: 192), AAGguacguu (SEQ ID NO: 193), AAGguacuaa (SEQ ID NO: 194), AAGguacuau (SEQ ID NO: 195), AAGguacucu (SEQ ID NO: 196), AAGguacuga (SEQ ID NO: 197), AAGguacugc (SEQ ID NO: 198), AAGguacugu (SEQ ID NO: 199), AAGguacuuc (SEQ ID NO: 200), AAGguacuug (SEQ ID NO: 201), AAGguacuuu (SEQ ID NO: 202), AAGguagaaa (SEQ ID NO: 203), AAGguagaac (SEQ ID NO: 204), AAGguagaca (SEQ ID NO: 205), AAGguagacc (SEQ ID NO: 206), AAGguagacu (SEQ ID NO: 207), AAGguagagu (SEQ ID NO: 208), AAGguagaua (SEQ ID NO: 209), AAGguagcaa (SEQ ID NO: 210), AAGguagcag (SEQ ID NO: 211), AAGguagcca (SEQ ID NO: 212), AAGguagccu (SEQ ID NO: 213), AAGguagcua (SEQ ID NO: 214), AAGguagcug (SEQ ID NO: 215), AAGguagcuu (SEQ ID NO: 216), AAGguaggaa (SEQ ID NO: 217), AAGguaggag (SEQ ID NO: 218), AAGguaggau (SEQ ID NO: 219), AAGguaggca (SEQ ID NO: 220), AAGguaggcc (SEQ ID NO: 221), AAGguaggcu (SEQ ID NO: 222), AAGguaggga (SEQ ID NO: 223), AAGguagggc (SEQ ID NO: 224), AAGguagggg (SEQ ID NO: 225), AAGguagggu (SEQ ID NO: 226), AAGguaggua (SEQ ID NO: 227), AAGguagguc (SEQ ID NO: 228), AAGguaggug (SEQ ID NO: 229), AAGguagguu (SEQ ID NO: 230), AAGguaguaa (SEQ ID NO: 231), AAGguaguag (SEQ ID NO: 232), AAGguagucu (SEQ ID NO: 233), AAGguagugc (SEQ ID NO: 234), AAGguagugg (SEQ ID NO: 235), AAGguaguuc (SEQ ID NO: 236), AAGguaguuu (SEQ ID NO: 237), AAGguauaaa (SEQ ID NO: 238), AAGguauaau (SEQ ID NO: 239), AAGguauaca (SEQ ID NO: 240), AAGguauacu (SEQ ID NO: 241), AAGguauaua (SEQ ID NO: 242), AAGguauauc (SEQ ID NO: 243), AAGguauaug (SEQ ID NO: 244), AAGguauauu (SEQ ID NO: 245), AAGguaucac (SEQ ID NO: 246), AAGguaucag (SEQ ID NO: 247), AAGguauccc (SEQ ID NO: 248), AAGguauccu (SEQ ID NO: 249), AAGguaucuc (SEQ ID NO: 250), AAGguaucug (SEQ ID NO: 251), AAGguaucuu (SEQ ID NO: 252), AAGguaugaa (SEQ ID NO: 253), AAGguaugac (SEQ ID NO: 254), AAGguaugag (SEQ ID NO: 255), AAGguaugau (SEQ ID NO: 256), AAGguaugca (SEQ ID NO: 257), AAGguaugcc (SEQ ID NO: 258), AAGguaugcu (SEQ ID NO: 259), AAGguaugga (SEQ ID NO: 260), AAGguauggc (SEQ ID NO: 261), AAGguauggg (SEQ ID NO: 262), AAGguaugua (SEQ ID NO: 263), AAGguauguc (SEQ ID NO: 264), AAGguaugug (SEQ ID NO: 265), AAGguauguu (SEQ ID NO: 266), AAGguauuaa (SEQ ID NO: 267), AAGguauuac (SEQ ID NO: 268), AAGguauuag (SEQ ID NO: 269), AAGguauuau (SEQ ID NO: 270), AAGguauucc (SEQ ID NO: 271), AAGguauuga (SEQ ID NO: 272), AAGguauugu (SEQ ID NO: 273), AAGguauuua (SEQ ID NO: 274), AAGguauuuc (SEQ ID NO: 275), AAGguauuug (SEQ ID NO: 276), AAGguauuuu (SEQ ID NO: 277), AAGgucaaau (SEQ ID NO: 278), AAGgucaaga (SEQ ID NO: 279), AAGgucaagu (SEQ ID NO: 280), AAGgucacag (SEQ ID NO: 281), AAGgucagaa (SEQ ID NO: 282), AAGgucagac (SEQ ID NO: 283), AAGgucagag (SEQ ID NO: 284), AAGgucagca (SEQ ID NO: 285), AAGgucagcc (SEQ ID NO: 286), AAGgucagcg (SEQ ID NO: 287), AAGgucagcu (SEQ ID NO: 288), AAGgucagga (SEQ ID NO: 289), AAGgucaggc (SEQ ID NO: 290), AAGgucaggg (SEQ ID NO: 291), AAGgucaggu (SEQ ID NO: 292), AAGgucagua (SEQ ID NO: 293), AAGgucaguc (SEQ ID NO: 294), AAGgucagug (SEQ ID NO: 295), AAGgucaguu (SEQ ID NO: 296), AAGgucauag (SEQ ID NO: 297), AAGgucaucu (SEQ ID NO: 298), AAGguccaca (SEQ ID NO: 299), AAGguccaga (SEQ ID NO: 300), AAGguccaua (SEQ ID NO: 301), AAGgucccag (SEQ ID NO: 302), AAGgucccuc (SEQ ID NO: 303), AAGguccuuc (SEQ ID NO: 304), AAGgucgagg (SEQ ID NO: 305), AAGgucuaau (SEQ ID NO: 306), AAGgucuacc (SEQ ID NO: 307), AAGgucuaua (SEQ ID NO: 308), AAGgucuccu (SEQ ID NO: 309), AAGgucucug (SEQ ID NO: 310), AAGgucucuu (SEQ ID NO: 311), AAGgucugaa (SEQ ID NO: 312), AAGgucugag (SEQ ID NO: 313), AAGgucugga (SEQ ID NO: 314), AAGgucuggg (SEQ ID NO: 315), AAGgucugua (SEQ ID NO: 316), AAGgucuguu (SEQ ID NO: 317), AAGgucuucu (SEQ ID NO: 318), AAGgucuuuu (SEQ ID NO: 319), AAGgugaaac (SEQ ID NO: 320), AAGgugaaag (SEQ ID NO: 321), AAGgugaaau (SEQ ID NO: 322), AAGgugaacu (SEQ ID NO: 323), AAGgugaagc (SEQ ID NO: 324), AAGgugaagg (SEQ ID NO: 325), AAGgugaagu (SEQ ID NO: 326), AAGgugaaua (SEQ ID NO: 327), AAGgugaaug (SEQ ID NO: 328), AAGgugaauu (SEQ ID NO: 329), AAGgugacaa (SEQ ID NO: 330), AAGgugacag (SEQ ID NO: 331), AAGgugacau (SEQ ID NO: 332), AAGgugacug (SEQ ID NO: 333), AAGgugacuu (SEQ ID NO: 334), AAGgugagaa (SEQ ID NO: 335), AAGgugagac (SEQ ID NO: 336), AAGgugagag (SEQ ID NO: 337), AAGgugagau (SEQ ID NO: 338), AAGgugagca (SEQ ID NO: 339), AAGgugagcc (SEQ ID NO: 340), AAGgugagcg (SEQ ID NO: 341), AAGgugagcu (SEQ ID NO: 342), AAGgugagga (SEQ ID NO: 343), AAGgugaggc (SEQ ID NO: 344), AAGgugaggg (SEQ ID NO: 345), AAGgugaggu (SEQ ID NO: 346), AAGgugagua (SEQ ID NO: 347), AAGgugaguc (SEQ ID NO: 348), AAGgugagug (SEQ ID NO: 349), AAGgugaguu (SEQ ID NO: 350), AAGgugauaa (SEQ ID NO: 351), AAGgugauca (SEQ ID NO: 352), AAGgugaucc (SEQ ID NO: 353), AAGgugauga (SEQ ID NO: 354), AAGgugaugc (SEQ ID NO: 355), AAGgugaugu (SEQ ID NO: 356), AAGgugauua (SEQ ID NO: 357), AAGgugauug (SEQ ID NO: 358), AAGgugauuu (SEQ ID NO: 359), AAGgugcaca (SEQ ID NO: 360), AAGgugcauc (SEQ ID NO: 361), AAGgugcccu (SEQ ID NO: 362), AAGgugccug (SEQ ID NO: 363), AAGgugcgug (SEQ ID NO: 364), AAGgugcguu (SEQ ID NO: 365), AAGgugcucc (SEQ ID NO: 366), AAGgugcuga (SEQ ID NO: 367), AAGgugcugc (SEQ ID NO: 368), AAGgugcugg (SEQ ID NO: 369), AAGgugcuua (SEQ ID NO: 370), AAGgugcuuu (SEQ ID NO: 371), AAGguggaua (SEQ ID NO: 372), AAGguggcua (SEQ ID NO: 373), AAGguggcug (SEQ ID NO: 374), AAGguggcuu (SEQ ID NO: 375), AAGgugggaa (SEQ ID NO: 376), AAGgugggag (SEQ ID NO: 377), AAGgugggau (SEQ ID NO: 378), AAGgugggca (SEQ ID NO: 379), AAGgugggcc (SEQ ID NO: 380), AAGgugggcg (SEQ ID NO: 381), AAGgugggga (SEQ ID NO: 382), AAGguggggu (SEQ ID NO: 383), AAGgugggua (SEQ ID NO: 384), AAGgugggug (SEQ ID NO: 385), AAGguggguu (SEQ ID NO: 386), AAGgugguaa (SEQ ID NO: 387), AAGgugguac (SEQ ID NO: 388), AAGgugguau (SEQ ID NO: 389), AAGguggugg (SEQ ID NO: 390), AAGgugguua (SEQ ID NO: 391), AAGgugguuc (SEQ ID NO: 392), AAGgugguuu (SEQ ID NO: 393), AAGguguaag (SEQ ID NO: 394), AAGgugucaa (SEQ ID NO: 395), AAGgugucag (SEQ ID NO: 396), AAGgugucug (SEQ ID NO: 397), AAGgugugaa (SEQ ID NO: 398), AAGgugugag (SEQ ID NO: 399), AAGgugugca (SEQ ID NO: 400), AAGgugugga (SEQ ID NO: 401), AAGguguggu (SEQ ID NO: 402), AAGgugugua (SEQ ID NO: 403), AAGguguguc (SEQ ID NO: 404), AAGgugugug (SEQ ID NO: 405), AAGguguguu (SEQ ID NO: 406), AAGguguucu (SEQ ID NO: 407), AAGguguugc (SEQ ID NO: 408), AAGguguugg (SEQ ID NO: 409), AAGguguuug (SEQ ID NO: 410), AAGguuaaaa (SEQ ID NO: 411), AAGguuaaca (SEQ ID NO: 412), AAGguuaagc (SEQ ID NO: 413), AAGguuaauu (SEQ ID NO: 414), AAGguuacau (SEQ ID NO: 415), AAGguuagaa (SEQ ID NO: 416), AAGguuagau (SEQ ID NO: 417), AAGguuagca (SEQ ID NO: 418), AAGguuagcc (SEQ ID NO: 419), AAGguuagga (SEQ ID NO: 420), AAGguuaggc (SEQ ID NO: 421), AAGguuagua (SEQ ID NO: 422), AAGguuaguc (SEQ ID NO: 423), AAGguuagug (SEQ ID NO: 424), AAGguuaguu (SEQ ID NO: 425), AAGguuauag (SEQ ID NO: 426), AAGguuauga (SEQ ID NO: 427), AAGguucaaa (SEQ ID NO: 428), AAGguucaag (SEQ ID NO: 429), AAGguuccuu (SEQ ID NO: 430), AAGguucggc (SEQ ID NO: 431), AAGguucguu (SEQ ID NO: 432), AAGguucuaa (SEQ ID NO: 433), AAGguucuga (SEQ ID NO: 434), AAGguucuua (SEQ ID NO: 435), AAGguugaau (SEQ ID NO: 436), AAGguugacu (SEQ ID NO: 437), AAGguugagg (SEQ ID NO: 438), AAGguugagu (SEQ ID NO: 439), AAGguugaua (SEQ ID NO: 440), AAGguugcac (SEQ ID NO: 441), AAGguugcug (SEQ ID NO: 442), AAGguuggaa (SEQ ID NO: 443), AAGguuggca (SEQ ID NO: 444), AAGguuggga (SEQ ID NO: 445), AAGguugggg (SEQ ID NO: 446), AAGguuggua (SEQ ID NO: 447), AAGguugguc (SEQ ID NO: 448), AAGguuggug (SEQ ID NO: 449), AAGguugguu (SEQ ID NO: 450), AAGguuguaa (SEQ ID NO: 451), AAGguugucc (SEQ ID NO: 452), AAGguugugc (SEQ ID NO: 453), AAGguuguua (SEQ ID NO: 454), AAGguuuacc (SEQ ID NO: 455), AAGguuuaua (SEQ ID NO: 456), AAGguuuauu (SEQ ID NO: 457), AAGguuuccu (SEQ ID NO: 458), AAGguuucgu (SEQ ID NO: 459), AAGguuugag (SEQ ID NO: 460), AAGguuugca (SEQ ID NO: 461), AAGguuugcc (SEQ ID NO: 462), AAGguuugcu (SEQ ID NO: 463), AAGguuugga (SEQ ID NO: 464), AAGguuuggu (SEQ ID NO: 465), AAGguuugua (SEQ ID NO: 466), AAGguuuguc (SEQ ID NO: 467), AAGguuugug (SEQ ID NO: 468), AAGguuuuaa (SEQ ID NO: 469), AAGguuuuca (SEQ ID NO: 470), AAGguuuucg (SEQ ID NO: 471), AAGguuuugc (SEQ ID NO: 472), AAGguuuugu (SEQ ID NO: 473), AAGguuuuuu (SEQ ID NO: 474), AAUgcaagua (SEQ ID NO: 475), AAUgcaaguc (SEQ ID NO: 476), AAUguaaaca (SEQ ID NO: 477), AAUguaaaua (SEQ ID NO: 478), AAUguaaauc (SEQ ID NO: 479), AAUguaaaug (SEQ ID NO: 480), AAUguaaauu (SEQ ID NO: 481), AAUguaacua (SEQ ID NO: 482), AAUguaagaa (SEQ ID NO: 483), AAUguaagag (SEQ ID NO: 484), AAUguaagau (SEQ ID NO: 485), AAUguaagcc (SEQ ID NO: 486), AAUguaagcu (SEQ ID NO: 487), AAUguaagga (SEQ ID NO: 488), AAUguaagua (SEQ ID NO: 489), AAUguaaguc (SEQ ID NO: 490), AAUguaagug (SEQ ID NO: 491), AAUguaaguu (SEQ ID NO: 492), AAUguaauca (SEQ ID NO: 493), AAUguaauga (SEQ ID NO: 494), AAUguaaugu (SEQ ID NO: 495), AAUguacauc (SEQ ID NO: 496), AAUguacaug (SEQ ID NO: 497), AAUguacgau (SEQ ID NO: 498), AAUguacgua (SEQ ID NO: 499), AAUguacguc (SEQ ID NO: 500), AAUguacgug (SEQ ID NO: 501), AAUguacucu (SEQ ID NO: 502), AAUguaggca (SEQ ID NO: 503), AAUguagguu (SEQ ID NO: 504), AAUguaucua (SEQ ID NO: 505), AAUguaugaa (SEQ ID NO: 506), AAUguaugua (SEQ ID NO: 507), AAUguaugug (SEQ ID NO: 508), AAUguauguu (SEQ ID NO: 509), AAUgucagag (SEQ ID NO: 510), AAUgucagau (SEQ ID NO: 511), AAUgucagcu (SEQ ID NO: 512), AAUgucagua (SEQ ID NO: 513), AAUgucaguc (SEQ ID NO: 514), AAUgucagug (SEQ ID NO: 515), AAUgucaguu (SEQ ID NO: 516), AAUgucggua (SEQ ID NO: 517), AAUgucuguu (SEQ ID NO: 518), AAUgugagaa (SEQ ID NO: 519), AAUgugagca (SEQ ID NO: 520), AAUgugagcc (SEQ ID NO: 521), AAUgugagga (SEQ ID NO: 522), AAUgugagua (SEQ ID NO: 523), AAUgugaguc (SEQ ID NO: 524), AAUgugagug (SEQ ID NO: 525), AAUgugaguu (SEQ ID NO: 526), AAUgugauau (SEQ ID NO: 527), AAUgugcaua (SEQ ID NO: 528), AAUgugcgua (SEQ ID NO: 529), AAUgugcguc (SEQ ID NO: 530), AAUgugggac (SEQ ID NO: 531), AAUgugggguc (SEQ ID NO: 532), AAUgugggug (SEQ ID NO: 533), AAUgugguuu (SEQ ID NO: 534), AAUgugugua (SEQ ID NO: 535), AAUguuaagu (SEQ ID NO: 536), AAUguuagaa (SEQ ID NO: 537), AAUguuagau (SEQ ID NO: 538), AAUguuagua (SEQ ID NO: 539), AAUguuggug (SEQ ID NO: 540), ACAgcaagua (SEQ ID NO: 541), ACAguaaaua (SEQ ID NO: 542), ACAguaaaug (SEQ ID NO: 543), ACAguaagaa (SEQ ID NO: 544), ACAguaagca (SEQ ID NO: 545), ACAguaagua (SEQ ID NO: 546), ACAguaaguc (SEQ ID NO: 547), ACAguaagug (SEQ ID NO: 548), ACAguaaguu (SEQ ID NO: 549), ACAguacgua (SEQ ID NO: 550), ACAguaggug (SEQ ID NO: 551), ACAguauaac (SEQ ID NO: 552), ACAguaugua (SEQ ID NO: 553), ACAgucaguu (SEQ ID NO: 554), ACAgugagaa (SEQ ID NO: 555), ACAgugagcc (SEQ ID NO: 556), ACAgugagcu (SEQ ID NO: 557), ACAgugagga (SEQ ID NO: 558), ACAgugaggu (SEQ ID NO: 559), ACAgugagua (SEQ ID NO: 560), ACAgugaguc (SEQ ID NO: 561), ACAgugagug (SEQ ID NO: 562), ACAgugaguu (SEQ ID NO: 563), ACAgugggua (SEQ ID NO: 564), ACAgugguu (SEQ ID NO: 565), ACAguguaaa (SEQ ID NO: 566), ACAguuaagc (SEQ ID NO: 567), ACAguuaagu (SEQ ID NO: 568), ACAguuaugu (SEQ ID NO: 569), ACAguugagu (SEQ ID NO: 570), ACAguuguga (SEQ ID NO: 571), ACCguaagua (SEQ ID NO: 572), ACCgugagaa (SEQ ID NO: 573), ACCgugagca (SEQ ID NO: 574), ACCgugaguu (SEQ ID NO: 575), ACCgugggug (SEQ ID NO: 576), ACGguaaaac (SEQ ID NO: 577), ACGguaacua (SEQ ID NO: 578), ACGguaagua (SEQ ID NO: 579), ACGguaagug (SEQ ID NO: 580), ACGguaaguu (SEQ ID NO: 581), ACGguaauua (SEQ ID NO: 582), ACGguaauuu (SEQ ID NO: 583), ACGguacaau (SEQ ID NO: 584), ACGguacagu (SEQ ID NO: 585), ACGguaccag (SEQ ID NO: 586), ACGguacggu (SEQ ID NO: 587), ACGguacgua (SEQ ID NO: 588), ACGguaggaa (SEQ ID NO: 589), ACGguaggag (SEQ ID NO: 590), ACGguaggug (SEQ ID NO: 591), ACGguaguaa (SEQ ID NO: 592), ACGguauaau (SEQ ID NO: 593), ACGguaugac (SEQ ID NO: 594), ACGguaugcg (SEQ ID NO: 595), ACGguaugua (SEQ ID NO: 596), ACGguauguc (SEQ ID NO: 597), ACGgugaaac (SEQ ID NO: 598), ACGgugaagu (SEQ ID NO: 599), ACGgugaauc (SEQ ID NO: 600), ACGgugacag (SEQ ID NO: 601), ACGgugacca (SEQ ID NO: 602), ACGgugagaa (SEQ ID NO: 603), ACGgugagau (SEQ ID NO: 604), ACGgugagcc (SEQ ID NO: 605), ACGgugagua (SEQ ID NO: 606), ACGgugagug (SEQ ID NO: 607), ACGgugaguu (SEQ ID NO: 608), ACGgugcgug (SEQ ID NO: 609), ACGguggcac (SEQ ID NO: 610), ACGguggggc (SEQ ID NO: 611), ACGgugggug (SEQ ID NO: 612), ACGguguagu (SEQ ID NO: 613), ACGgugucac (SEQ ID NO: 614), ACGgugugua (SEQ ID NO: 615), ACGguguguu (SEQ ID NO: 616), ACGguuagug (SEQ ID NO: 617), ACGguuaguu (SEQ ID NO: 618), ACGguucaau (SEQ ID NO: 619), ACUguaaaua (SEQ ID NO: 620), ACUguaagaa (SEQ ID NO: 621), ACUguaagac (SEQ ID NO: 622), ACUguaagca (SEQ ID NO: 623), ACUguaagcu (SEQ ID NO: 624), ACUguaagua (SEQ ID NO: 625), ACUguaaguc (SEQ ID NO: 626), ACUguaaguu (SEQ ID NO: 627), ACUguacguu (SEQ ID NO: 628), ACUguacugc (SEQ ID NO: 629), ACUguaggcu (SEQ ID NO: 630), ACUguaggua (SEQ ID NO: 631), ACUguauauu (SEQ ID NO: 632), ACUguaugaa (SEQ ID NO: 633), ACUguaugcu (SEQ ID NO: 634), ACUguaugug (SEQ ID NO: 635), ACUguauucc (SEQ ID NO: 636), ACUgucagcu (SEQ ID NO: 637), ACUgucagug (SEQ ID NO: 638), ACUgugaacg (SEQ ID NO: 639), ACUgugagca (SEQ ID NO: 640), ACUgugagcg (SEQ ID NO: 641), ACUgugagcu (SEQ ID NO: 642), ACUgugagua (SEQ ID NO: 643), ACUgugaguc (SEQ ID NO: 644), ACUgugagug (SEQ ID NO: 645), ACUgugaguu (SEQ ID NO: 646), ACUgugggua (SEQ ID NO: 647), ACUgugugug (SEQ ID NO: 648), ACUguuaagu (SEQ ID NO: 649), AGAgcaagua (SEQ ID NO: 650), AGAguaaaac (SEQ ID NO: 651), AGAguaaacg (SEQ ID NO: 652), AGAguaaaga (SEQ ID NO: 653), AGAguaaagu (SEQ ID NO: 654), AGAguaaauc (SEQ ID NO: 655), AGAguaaaug (SEQ ID NO: 656), AGAguaacau (SEQ ID NO: 657), AGAguaacua (SEQ ID NO: 658), AGAguaagaa (SEQ ID NO: 659), AGAguaagac (SEQ ID NO: 660), AGAguaagag (SEQ ID NO: 661), AGAguaagau (SEQ ID NO: 662), AGAguaagca (SEQ ID NO: 663), AGAguaagcu (SEQ ID NO: 664), AGAguaagga (SEQ ID NO: 665), AGAguaaggc (SEQ ID NO: 666), AGAguaaggg (SEQ ID NO: 667), AGAguaaggu (SEQ ID NO: 668), AGAguaaguc (SEQ ID NO: 669), AGAguaagug (SEQ ID NO: 670), AGAguaaguu (SEQ ID NO: 671), AGAguaauaa (SEQ ID NO: 672), AGAguaaugu (SEQ ID NO: 673), AGAguaauuc (SEQ ID NO: 674), AGAguaauuu (SEQ ID NO: 675), AGAguacacc (SEQ ID NO: 676), AGAguaccug (SEQ ID NO: 677), AGAguacgug (SEQ ID NO: 678), AGAguacucu (SEQ ID NO: 679), AGAguacuga (SEQ ID NO: 680), AGAguacuuu (SEQ ID NO: 681), AGAguagcug (SEQ ID NO: 682), AGAguaggaa (SEQ ID NO: 683), AGAguaggga (SEQ ID NO: 684), AGAguagggu (SEQ ID NO: 685), AGAguagguc (SEQ ID NO: 686), AGAguaggug (SEQ ID NO: 687), AGAguagguu (SEQ ID NO: 688), AGAguauaua (SEQ ID NO: 689), AGAguauauu (SEQ ID NO: 690), AGAguaugaa (SEQ ID NO: 691), AGAguaugac (SEQ ID NO: 692), AGAguaugau (SEQ ID NO: 693), AGAguauguc (SEQ ID NO: 694), AGAguaugug (SEQ ID NO: 695), AGAguauguu (SEQ ID NO: 696), AGAguauuaa (SEQ ID NO: 697), AGAguauuau (SEQ ID NO: 698), AGAgucagug (SEQ ID NO: 699), AGAgugagac (SEQ ID NO: 700), AGAgugagag (SEQ ID NO: 701), AGAgugagau (SEQ ID NO: 702), AGAgugagca (SEQ ID NO: 703), AGAgugagua (SEQ ID NO: 704), AGAgugaguc (SEQ ID NO: 705), AGAgugagug (SEQ ID NO: 706), AGAgugaguu (SEQ ID NO: 707), AGAgugcguc (SEQ ID NO: 708), AGAgugggga (SEQ ID NO: 709), AGAguggggug (SEQ ID NO: 710), AGAgugugug (SEQ ID NO: 711), AGAguguuuc (SEQ ID NO: 712), AGAguuagua (SEQ ID NO: 713), AGAguugaga (SEQ ID NO: 714), AGAguugagu (SEQ ID NO: 715), AGAguugguu (SEQ ID NO: 716), AGAguuugau (SEQ ID NO: 717), AGCguaagcu (SEQ ID NO: 718), AGCguaagug (SEQ ID NO: 719), AGCgugagcc (SEQ ID NO: 720), AGCgugagug (SEQ ID NO: 721), AGCguuguuc (SEQ ID NO: 722), AGGgcagagu (SEQ ID NO: 723), AGGgcagccu (SEQ ID NO: 724), AGGgcuagua (SEQ ID NO: 725), AGGguaaaga (SEQ ID NO: 726), AGGguaaaua (SEQ ID NO: 727), AGGguaaauc (SEQ ID NO: 728), AGGguaaauu (SEQ ID NO: 729), AGGguaacca (SEQ ID NO: 730), AGGguaacug (SEQ ID NO: 731), AGGguaacuu (SEQ ID NO: 732), AGGguaagaa (SEQ ID NO: 733), AGGguaagag (SEQ ID NO: 734), AGGguaagau (SEQ ID NO: 735), AGGguaagca (SEQ ID NO: 736), AGGguaagga (SEQ ID NO: 737), AGGguaaggc (SEQ ID NO: 738), AGGguaaggg (SEQ ID NO: 739), AGGguaagua (SEQ ID NO: 740), AGGguaaguc (SEQ ID NO: 741), AGGguaagug (SEQ ID NO: 742), AGGguaaguu (SEQ ID NO: 743), AGGguaauac (SEQ ID NO: 744), AGGguaauga (SEQ ID NO: 745), AGGguaauua (SEQ ID NO: 746), AGGguaauuu (SEQ ID NO: 747), AGGguacacc (SEQ ID NO: 748), AGGguacagu (SEQ ID NO: 749), AGGguacggu (SEQ ID NO: 750), AGGguaggac (SEQ ID NO: 751), AGGguaggag (SEQ ID NO: 752), AGGguaggca (SEQ ID NO: 753), AGGguaggcc (SEQ ID NO: 754), AGGguaggga (SEQ ID NO: 755), AGGguagggu (SEQ ID NO: 756), AGGguagguc (SEQ ID NO: 757), AGGguaggug (SEQ ID NO: 758), AGGguagguu (SEQ ID NO: 759), AGGguauaua (SEQ ID NO: 760), AGGguaugac (SEQ ID NO: 761), AGGguaugag (SEQ ID NO: 762), AGGguaugau (SEQ ID NO: 763), AGGguaugca (SEQ ID NO: 764), AGGguaugcu (SEQ ID NO: 765), AGGguauggg (SEQ ID NO: 766), AGGguauggu (SEQ ID NO: 767), AGGguaugua (SEQ ID NO: 768), AGGguauguc (SEQ ID NO: 769), AGGguaugug (SEQ ID NO: 770), AGGguauuac (SEQ ID NO: 771), AGGguauucu (SEQ ID NO: 772), AGGguauuuc (SEQ ID NO: 773), AGGgucagag (SEQ ID NO: 774), AGGgucagca (SEQ ID NO: 775), AGGgucagga (SEQ ID NO: 776), AGGgucaggg (SEQ ID NO: 777), AGGgucagug (SEQ ID NO: 778), AGGgucaguu (SEQ ID NO: 779), AGGguccccu (SEQ ID NO: 780), AGGgucggga (SEQ ID NO: 781), AGGgucugca (SEQ ID NO: 782), AGGgucuguu (SEQ ID NO: 783), AGGgugaaga (SEQ ID NO: 784), AGGgugacua (SEQ ID NO: 785), AGGgugagaa (SEQ ID NO: 786), AGGgugagac (SEQ ID NO: 787), AGGgugagag (SEQ ID NO: 788), AGGgugagca (SEQ ID NO: 789), AGGgugagcc (SEQ ID NO: 790), AGGgugagcu (SEQ ID NO: 791), AGGgugagga (SEQ ID NO: 792), AGGgugaggg (SEQ ID NO: 793), AGGgugaggu (SEQ ID NO: 794), AGGgugagua (SEQ ID NO: 795), AGGgugaguc (SEQ ID NO: 796), AGGgugagug (SEQ ID NO: 797), AGGgugaguu (SEQ ID NO: 798), AGGgugggga (SEQ ID NO: 799), AGGgugggggu (SEQ ID NO: 800), AGGgugggua (SEQ ID NO: 801), AGGgugggug (SEQ ID NO: 802), AGGgugugua (SEQ ID NO: 803), AGGgugugug (SEQ ID NO: 804), AGGguuaaug (SEQ ID NO: 805), AGGguuagaa (SEQ ID NO: 806), AGGguuaguu (SEQ ID NO: 807), AGGguuggug (SEQ ID NO: 808), AGGguuugug (SEQ ID NO: 809), AGGguuuguu (SEQ ID NO: 810), AGUguaaaag (SEQ ID NO: 811), AGUguaaaua (SEQ ID NO: 812), AGUguaaauu (SEQ ID NO: 813), AGUguaagaa (SEQ ID NO: 814), AGUguaagag (SEQ ID NO: 815), AGUguaagau (SEQ ID NO: 816), AGUguaagca (SEQ ID NO: 817), AGUguaagcc (SEQ ID NO: 818), AGUguaagua (SEQ ID NO: 819), AGUguaagug (SEQ ID NO: 820), AGUguaaguu (SEQ ID NO: 821), AGUguaauug (SEQ ID NO: 822), AGUguaggac (SEQ ID NO: 823), AGUguagguc (SEQ ID NO: 824), AGUguaugag (SEQ ID NO: 825), AGUguaugua (SEQ ID NO: 826), AGUguauguu (SEQ ID NO: 827), AGUguauugu (SEQ ID NO: 828), AGUguauuua (SEQ ID NO: 829), AGUgucaguc (SEQ ID NO: 830), AGUgugagag (SEQ ID NO: 831), AGUgugagca (SEQ ID NO: 832), AGUgugagcc (SEQ ID NO: 833), AGUgugagcu (SEQ ID NO: 834), AGUgugagua (SEQ ID NO: 835), AGUgugaguc (SEQ ID NO: 836), AGUgugagug (SEQ ID NO: 837), AGUgugaguu (SEQ ID NO: 838), AGUgugggua (SEQ ID NO: 839), AGUgugggug (SEQ ID NO: 840), AGUgugugua (SEQ ID NO: 841), AGUguuccua (SEQ ID NO: 842), AGUguugggg (SEQ ID NO: 843), AGUguuucag (SEQ ID NO: 844), AUAguaaaua (SEQ ID NO: 845), AUAguaagac (SEQ ID NO: 846), AUAguaagau (SEQ ID NO: 847), AUAguaagca (SEQ ID NO: 848), AUAguaagua (SEQ ID NO: 849), AUAguaagug (SEQ ID NO: 850), AUAguaaguu (SEQ ID NO: 851), AUAguaggua (SEQ ID NO: 852), AUAguauguu (SEQ ID NO: 853), AUAgucucac (SEQ ID NO: 854), AUAgugagac (SEQ ID NO: 855), AUAgugagag (SEQ ID NO: 856), AUAgugagau (SEQ ID NO: 857), AUAgugagcc (SEQ ID NO: 858), AUAgugaggc (SEQ ID NO: 859), AUAgugagua (SEQ ID NO: 860), AUAgugaguc (SEQ ID NO: 861), AUAgugagug (SEQ ID NO: 862), AUAgugcguc (SEQ ID NO: 863), AUAgugugua (SEQ ID NO: 864), AUAguucagu (SEQ ID NO: 865), AUCguaagcc (SEQ ID NO: 866), AUCguaaguu (SEQ ID NO: 867), AUCguauucc (SEQ ID NO: 868), AUCgugagua (SEQ ID NO: 869), AUGgcaagcg (SEQ ID NO: 870), AUGgcaagga (SEQ ID NO: 871), AUGgcaaguu (SEQ ID NO: 872), AUGgcaggua (SEQ ID NO: 873), AUGgcaugug (SEQ ID NO: 874), AUGgcgccau (SEQ ID NO: 875), AUGgcuugug (SEQ ID NO: 876), AUGguaaaac (SEQ ID NO: 877), AUGguaaaau (SEQ ID NO: 878), AUGguaaacc (SEQ ID NO: 879), AUGguaaaga (SEQ ID NO: 880), AUGguaaaua (SEQ ID NO: 881), AUGguaaaug (SEQ ID NO: 882), AUGguaaauu (SEQ ID NO: 883), AUGguaacag (SEQ ID NO: 884), AUGguaacau (SEQ ID NO: 885), AUGguaacua (SEQ ID NO: 886), AUGguaacuc (SEQ ID NO: 887), AUGguaacuu (SEQ ID NO: 888), AUGguaagaa (SEQ ID NO: 889), AUGguaagac (SEQ ID NO: 890), AUGguaagag (SEQ ID NO: 891), AUGguaagau (SEQ ID NO: 892), AUGguaagca (SEQ ID NO: 893), AUGguaagcc (SEQ ID NO: 894), AUGguaagcu (SEQ ID NO: 895), AUGguaagga (SEQ ID NO: 896), AUGguaaggg (SEQ ID NO: 897), AUGguaagua (SEQ ID NO: 898), AUGguaaguc (SEQ ID NO: 899), AUGguaagug (SEQ ID NO: 900), AUGguaaguu (SEQ ID NO: 901), AUGguaauaa (SEQ ID NO: 902), AUGguaauau (SEQ ID NO: 903), AUGguaauga (SEQ ID NO: 904), AUGguaaugg (SEQ ID NO: 905), AUGguaauug (SEQ ID NO: 906), AUGguaauuu (SEQ ID NO: 907), AUGguacagc (SEQ ID NO: 908), AUGguacauc (SEQ ID NO: 909), AUGguaccag (SEQ ID NO: 910), AUGguaccug (SEQ ID NO: 911), AUGguacgag (SEQ ID NO: 912), AUGguacggu (SEQ ID NO: 913), AUGguagauc (SEQ ID NO: 914), AUGguagcag (SEQ ID NO: 915), AUGguagcug (SEQ ID NO: 916), AUGguaggaa (SEQ ID NO: 917), AUGguaggau (SEQ ID NO: 918), AUGguaggca (SEQ ID NO: 919), AUGguaggcu (SEQ ID NO: 920), AUGguagggg (SEQ ID NO: 921), AUGguagggu (SEQ ID NO: 922), AUGguaggua (SEQ ID NO: 923), AUGguaggug (SEQ ID NO: 924), AUGguaguuu (SEQ ID NO: 925), AUGguauagu (SEQ ID NO: 926), AUGguauaua (SEQ ID NO: 927), AUGguaucag (SEQ ID NO: 928), AUGguaucuu (SEQ ID NO: 929), AUGguaugau (SEQ ID NO: 930), AUGguaugca (SEQ ID NO: 931), AUGguaugcc (SEQ ID NO: 932), AUGguaugcg (SEQ ID NO: 933), AUGguaugcu (SEQ ID NO: 934), AUGguaugga (SEQ ID NO: 935), AUGguauggc (SEQ ID NO: 936), AUGguaugug (SEQ ID NO: 937), AUGguauguu (SEQ ID NO: 938), AUGguauuau (SEQ ID NO: 939), AUGguauuga (SEQ ID NO: 940), AUGguauuug (SEQ ID NO: 941), AUGgucaggg (SEQ ID NO: 942), AUGgucaguc (SEQ ID NO: 943), AUGgucagug (SEQ ID NO: 944), AUGgucauuu (SEQ ID NO: 945), AUGgugaaaa (SEQ ID NO: 946), AUGgugaaac (SEQ ID NO: 947), AUGgugaaau (SEQ ID NO: 948), AUGgugaacu (SEQ ID NO: 949), AUGgugaaga (SEQ ID NO: 950), AUGgugacgu (SEQ ID NO: 951), AUGgugagaa (SEQ ID NO: 952), AUGgugagac (SEQ ID NO: 953), AUGgugagag (SEQ ID NO: 954), AUGgugagca (SEQ ID NO: 955), AUGgugagcc (SEQ ID NO: 956), AUGgugagcg (SEQ ID NO: 957), AUGgugagcu (SEQ ID NO: 958), AUGgugaggc (SEQ ID NO: 959), AUGgugaggg (SEQ ID NO: 960), AUGgugagua (SEQ ID NO: 961), AUGgugaguc (SEQ ID NO: 962), AUGgugagug (SEQ ID NO: 963), AUGgugaguu (SEQ ID NO: 964), AUGgugauuu (SEQ ID NO: 965), AUGgugcgau (SEQ ID NO: 966), AUGgugcgug (SEQ ID NO: 967), AUGgugggua (SEQ ID NO: 968), AUGgugggug (SEQ ID NO: 969), AUGgugugguu (SEQ ID NO: 970), AUGgugguua (SEQ ID NO: 971), AUGguguaag (SEQ ID NO: 972), AUGgugugaa (SEQ ID NO: 973), AUGgugugua (SEQ ID NO: 974), AUGgugugug (SEQ ID NO: 975), AUGguuacuc (SEQ ID NO: 976), AUGguuagca (SEQ ID NO: 977), AUGguuaguc (SEQ ID NO: 978), AUGguuagug (SEQ ID NO: 979), AUGguuaguu (SEQ ID NO: 980), AUGguucagu (SEQ ID NO: 981), AUGguucguc (SEQ ID NO: 982), AUGguuggua (SEQ ID NO: 983), AUGguugguc (SEQ ID NO: 984), AUGguugguu (SEQ ID NO: 985), AUGguuguuu (SEQ ID NO: 986), AUGguuugca (SEQ ID NO: 987), AUGguuugua (SEQ ID NO: 988), AUUgcaagua (SEQ ID NO: 989), AUUguaaaua (SEQ ID NO: 990), AUUguaagau (SEQ ID NO: 991), AUUguaagca (SEQ ID NO: 992), AUUguaagga (SEQ ID NO: 993), AUUguaaggc (SEQ ID NO: 994), AUUguaagua (SEQ ID NO: 995), AUUguaaguc (SEQ ID NO: 996), AUUguaaguu (SEQ ID NO: 997), AUUguaauua (SEQ ID NO: 998), AUUguaauuu (SEQ ID NO: 999), AUUguacaaa (SEQ ID NO: 1000), AUUguaccuc (SEQ ID NO: 1001), AUUguacgug (SEQ ID NO: 1002), AUUguacuug (SEQ ID NO: 1003), AUUguaggua (SEQ ID NO: 1004), AUUguaugag (SEQ ID NO: 1005), AUUguaugua (SEQ ID NO: 1006), AUUgucuguu (SEQ ID NO: 1007), AUUgugagcu (SEQ ID NO: 1008), AUUgugagua (SEQ ID NO: 1009), AUUgugaguc (SEQ ID NO: 1010), AUUgugaguu (SEQ ID NO: 1011), AUUgugcgug (SEQ ID NO: 1012), AUUgugggug (SEQ ID NO: 1013), AUUguuagug (SEQ ID NO: 1014), CAAguaaaaa (SEQ ID NO: 1015), CAAguaaaua (SEQ ID NO: 1016), CAAguaaauc (SEQ ID NO: 1017), CAAguaaaug (SEQ ID NO: 1018), CAAguaaccc (SEQ ID NO: 1019), CAAguaacua (SEQ ID NO: 1020), CAAguaacug (SEQ ID NO: 1021), CAAguaagaa (SEQ ID NO: 1022), CAAguaagac (SEQ ID NO: 1023), CAAguaagau (SEQ ID NO: 1024), CAAguaaggu (SEQ ID NO: 1025), CAAguaagua (SEQ ID NO: 1026), CAAguaaguc (SEQ ID NO: 1027), CAAguaagug (SEQ ID NO: 1028), CAAguaaguu (SEQ ID NO: 1029), CAAguaaucc (SEQ ID NO: 1030), CAAguaaucu (SEQ ID NO: 1031), CAAguaauua (SEQ ID NO: 1032), CAAguaauuc (SEQ ID NO: 1033), CAAguaauug (SEQ ID NO: 1034), CAAguaauuu (SEQ ID NO: 1035), CAAguacaca (SEQ ID NO: 1036), CAAguacguu (SEQ ID NO: 1037), CAAguacuuu (SEQ ID NO: 1038), CAAguagcug (SEQ ID NO: 1039), CAAguaggau (SEQ ID NO: 1040), CAAguaggua (SEQ ID NO: 1041), CAAguagguc (SEQ ID NO: 1042), CAAguaggug (SEQ ID NO: 1043), CAAguagguu (SEQ ID NO: 1044), CAAguaguuu (SEQ ID NO: 1045), CAAguauaac (SEQ ID NO: 1046), CAAguauaug (SEQ ID NO: 1047), CAAguaucuu (SEQ ID NO: 1048), CAAguaugag (SEQ ID NO: 1049), CAAguaugua (SEQ ID NO: 1050), CAAguauguc (SEQ ID NO: 1051), CAAguaugug (SEQ ID NO: 1052), CAAguauguu (SEQ ID NO: 1053), CAAguauuga (SEQ ID NO: 1054), CAAguauuuc (SEQ ID NO: 1055), CAAgucagac (SEQ ID NO: 1056), CAAgucagua (SEQ ID NO: 1057), CAAgucuaua (SEQ ID NO: 1058), CAAgucugau (SEQ ID NO: 1059), CAAgugacuu (SEQ ID NO: 1060), CAAgugagaa (SEQ ID NO: 1061), CAAgugagac (SEQ ID NO: 1062), CAAgugagca (SEQ ID NO: 1063), CAAgugaggc (SEQ ID NO: 1064), CAAgugaggg (SEQ ID NO: 1065), CAAgugagua (SEQ ID NO: 1066), CAAgugaguc (SEQ ID NO: 1067), CAAgugagug (SEQ ID NO: 1068), CAAgugaucc (SEQ ID NO: 1069), CAAgugaucu (SEQ ID NO: 1070), CAAgugauuc (SEQ ID NO: 1071), CAAgugauug (SEQ ID NO: 1072), CAAgugauuu (SEQ ID NO: 1073), CAAgugccuu (SEQ ID NO: 1074), CAAguggua (SEQ ID NO: 1075), CAAgugggguc (SEQ ID NO: 1076), CAAgugggug (SEQ ID NO: 1077), CAAgugugag (SEQ ID NO: 1078), CAAguuaaaa (SEQ ID NO: 1079), CAAguuaagu (SEQ ID NO: 1080), CAAguuaauc (SEQ ID NO: 1081), CAAguuagaa (SEQ ID NO: 1082), CAAguuaguu (SEQ ID NO: 1083), CAAguucaag (SEQ ID NO: 1084), CAAguuccgu (SEQ ID NO: 1085), CAAguuggua (SEQ ID NO: 1086), CAAguuuagu (SEQ ID NO: 1087), CAAguuucca (SEQ ID NO: 1088), CAAguuuguu (SEQ ID NO: 1089), CACguaagag (SEQ ID NO: 1090), CACguaagca (SEQ ID NO: 1091), CACguaauug (SEQ ID NO: 1092), CACguaggac (SEQ ID NO: 1093), CACguaucga (SEQ ID NO: 1094), CACgucaguu (SEQ ID NO: 1095), CACgugagcu (SEQ ID NO: 1096), CACgugaguc (SEQ ID NO: 1097), CACgugagug (SEQ ID NO: 1098), CAGgcaagaa (SEQ ID NO: 1099), CAGgcaagac (SEQ ID NO: 1100), CAGgcaagag (SEQ ID NO: 1101), CAGgcaagga (SEQ ID NO: 1102), CAGgcaagua (SEQ ID NO: 1103), CAGgcaagug (SEQ ID NO: 1104), CAGgcaaguu (SEQ ID NO: 1105), CAGgcacgca (SEQ ID NO: 1106), CAGgcagagg (SEQ ID NO: 1107), CAGgcaggug (SEQ ID NO: 1108), CAGgcaucau (SEQ ID NO: 1109), CAGgcaugaa (SEQ ID NO: 1110), CAGgcaugag (SEQ ID NO: 1111), CAGgcaugca (SEQ ID NO: 1112), CAGgcaugcg (SEQ ID NO: 1113), CAGgcaugug (SEQ ID NO: 1114), CAGgcgagag (SEQ ID NO: 1115), CAGgcgccug (SEQ ID NO: 1116), CAGgcgugug (SEQ ID NO: 1117), CAGguaaaaa (SEQ ID NO: 1118), CAGguaaaag (SEQ ID NO: 1119), CAGguaaaca (SEQ ID NO: 1120), CAGguaaacc (SEQ ID NO: 1121), CAGguaaaga (SEQ ID NO: 1122), CAGguaaagc (SEQ ID NO: 1123), CAGguaaagu (SEQ ID NO: 1124), CAGguaaaua (SEQ ID NO: 1125), CAGguaaauc (SEQ ID NO: 1126), CAGguaaaug (SEQ ID NO: 1127), CAGguaaauu (SEQ ID NO: 1128), CAGguaacag (SEQ ID NO: 1129), CAGguaacau (SEQ ID NO: 1130), CAGguaacca (SEQ ID NO: 1131), CAGguaaccg (SEQ ID NO: 1132), CAGguaacgu (SEQ ID NO: 1133), CAGguaacua (SEQ ID NO: 1134), CAGguaacuc (SEQ ID NO: 1135), CAGguaacug (SEQ ID NO: 1136), CAGguaacuu (SEQ ID NO: 1137), CAGguaagaa (SEQ ID NO: 1138), CAGguaagac (SEQ ID NO: 1139), CAG-guaagag (SEQ ID NO: 1140), CAGguaagau (SEQ ID NO: 1141), CAGguaagcc (SEQ ID NO: 1142), CAGguaagga (SEQ ID NO: 1143), CAGguaaggc (SEQ ID NO: 1144), CAGguaaggg (SEQ ID NO: 1145), CAGguaaggu (SEQ ID NO: 1146), CAGguaagua (SEQ ID NO: 1147), CAG-guaagug (SEQ ID NO: 1148), CAGguaaguu (SEQ ID NO: 1149), CAGguaauaa (SEQ ID NO: 1150), CAGguaauau (SEQ ID NO: 1151), CAGguaaucc (SEQ ID NO: 1152), CAGguaaugc (SEQ ID NO: 1153), CAGguaaugg (SEQ ID NO: 1154), CAGguaaugu (SEQ ID NO: 1155), CAG-guaauua (SEQ ID NO: 1156), CAGguaauuc (SEQ ID NO: 1157), CAGguaauug (SEQ ID NO: 1158), CAGguaauuu (SEQ ID NO: 1159), CAGguacaaa (SEQ ID NO: 1160), CAGguacaag (SEQ ID NO: 1161), CAGguacaau (SEQ ID NO: 1162), CAGguacaca (SEQ ID NO: 1163), CAGguacacg (SEQ ID NO: 1164), CAGguacaga (SEQ ID NO: 1165), CAGguacagg (SEQ ID NO: 1166), CAGguacagu (SEQ ID NO: 1167), CAGguacaua (SEQ ID NO: 1168), CAGgua-caug (SEQ ID NO: 1169), CAGguacauu (SEQ ID NO: 1170), CAGguaccac (SEQ ID NO: 1171), CAGguaccca (SEQ ID NO: 1172), CAGguacccg (SEQ ID NO: 1173), CAGguacccu (SEQ ID NO: 1174), CAGguaccgc (SEQ ID NO: 1175), CAGguaccgg (SEQ ID NO: 1176), CAGguac-cuc (SEQ ID NO: 1177), CAGguaccug (SEQ ID NO: 1178), CAGguaccuu (SEQ ID NO: 1179), CAGguacgag (SEQ ID NO: 1180), CAGguacgca (SEQ ID NO: 1181), CAGguacgcc (SEQ ID NO: 1182), CAGguacggu (SEQ ID NO: 1183), CAGguacgua (SEQ ID NO: 1184), CAGguacgug (SEQ ID NO: 1185), CAGguacuaa (SEQ ID NO: 1186), CAGguac-uag (SEQ ID NO: 1187), CAGguacuau (SEQ ID NO: 1188), CAGguacucc (SEQ ID NO: 1189), CAGguacucu (SEQ ID NO: 1190), CAGguacuga (SEQ ID NO: 1191), CAGgua-cugc (SEQ ID NO: 1192), CAGguacugu (SEQ ID NO: 1193), CAGguacuua (SEQ ID NO: 1194), CAGguacuuu (SEQ ID NO: 1195), CAGguagaaa (SEQ ID NO: 1196), CAGguagaac (SEQ ID NO: 1197), CAGguagaag (SEQ ID NO: 1198), CAGguagaca (SEQ ID NO: 1199), CAGguagacc (SEQ ID NO: 1200), CAGguagaga (SEQ ID NO: 1201), CAGguagauu (SEQ ID NO: 1202), CAGguagcaa (SEQ ID NO: 1203), CAGguagcac (SEQ ID NO: 1204), CAG-guagcag (SEQ ID NO: 1205), CAGguagcca (SEQ ID NO: 1206), CAGguagcgu (SEQ ID NO: 1207), CAGguagcua (SEQ ID NO: 1208), CAGguagcuc (SEQ ID NO: 1209), CAGguagcug (SEQ ID NO: 1210), CAGguagcuu (SEQ ID NO: 1211), CAGguaggaa (SEQ ID NO: 1212), CAG-guaggac (SEQ ID NO: 1213), CAGguaggag (SEQ ID NO: 1214), CAGguaggca (SEQ ID NO: 1215), CAGguaggga (SEQ ID NO: 1216), CAGguagggc (SEQ ID NO: 1217), CAGguagggg (SEQ ID NO: 1218), CAGguagggu (SEQ ID NO: 1219), CAGguaggua (SEQ ID NO: 1220), CAGguag-guc (SEQ ID NO: 1221), CAGguaggug (SEQ ID NO: 1222), CAGguagguu (SEQ ID NO: 1223), CAGguaguaa (SEQ ID NO: 1224), CAGguaguau (SEQ ID NO: 1225), CAGgua-guca (SEQ ID NO: 1226), CAGguagucc (SEQ ID NO: 1227), CAGguaguga (SEQ ID NO: 1228), CAGguagugu (SEQ ID NO: 1229), CAGguaguuc (SEQ ID NO: 1230), CAGguaguug (SEQ ID NO: 1231), CAGguaguuu (SEQ ID NO: 1232), CAGguauaag (SEQ ID NO: 1233), CAG-guauaca (SEQ ID NO: 1234), CAGguauaga (SEQ ID NO: 1235), CAGguauauc (SEQ ID NO: 1236), CAGguauaug (SEQ ID NO: 1237), CAGguauauu (SEQ ID NO: 1238), CAGguaucag (SEQ ID NO: 1239), CAGguaucau (SEQ ID NO: 1240), CAGguauccu (SEQ ID NO: 1241), CAG-guaucga (SEQ ID NO: 1242), CAGguaucgc (SEQ ID NO: 1243), CAGguaucua (SEQ ID NO: 1244), CAGguaucug (SEQ ID NO: 1245), CAGguaucuu (SEQ ID NO: 1246), CAGguaugaa (SEQ ID NO: 1247), CAGguaugac (SEQ ID NO: 1248), CAGguaugag (SEQ ID NO: 1249), CAG-guaugau (SEQ ID NO: 1250), CAGguaugca (SEQ ID NO: 1251), CAGguaugcc (SEQ ID NO: 1252), CAGguaugcg (SEQ ID NO: 1253), CAGguaugcu (SEQ ID NO: 1254), CAGguaugga (SEQ ID NO: 1255), CAGguauggg (SEQ ID NO: 1256), CAGguauggu (SEQ ID NO: 1257), CAGguau-gua (SEQ ID NO: 1258), CAGguauguc (SEQ ID NO: 1259), CAGguaugug (SEQ ID NO: 1260), CAGguauguu (SEQ ID NO: 1261), CAGguauuau (SEQ ID NO: 1262), CAG-guauuca (SEQ ID NO: 1263), CAGguauucu (SEQ ID NO: 1264), CAGguauuga (SEQ ID NO: 1265), CAGguauugg (SEQ ID NO: 1266), CAGguauugu (SEQ ID NO: 1267), CAGguauuua (SEQ ID NO: 1268), CAGguauuuc (SEQ ID NO: 1269), CAGguauuug (SEQ ID NO: 1270), CAG-guauuuu (SEQ ID NO: 1271), CAGgucaaca (SEQ ID NO: 1272), CAGgucaaug (SEQ ID NO: 1273), CAGgucacgu (SEQ ID NO: 1274), CAGgucagaa (SEQ ID NO: 1275), CAGgucagac (SEQ ID NO: 1276), CAGgucagca (SEQ ID NO: 1277), CAGgucagcc (SEQ ID NO: 1278), CAGgu-cagcg (SEQ ID NO: 1279), CAGgucagga (SEQ ID NO: 1280), CAGgucagua (SEQ ID NO: 1281), CAGgucaguc (SEQ ID NO: 1282), CAGgucagug (SEQ ID NO: 1283), CAGgucaguu (SEQ ID NO: 1284), CAGgucaucc (SEQ ID NO: 1285), CAGgucaugc (SEQ ID NO: 1286), CAGgu-cauua (SEQ ID NO: 1287), CAGgucauuu (SEQ ID NO: 1288), CAGguccacc (SEQ ID NO: 1289), CAGguccacu (SEQ ID NO: 1290), CAGguccagu (SEQ ID NO: 1291), CAGguccauc (SEQ ID NO: 1292), CAGguccauu (SEQ ID NO: 1293), CAGgucccag (SEQ ID NO: 1294), CAGgucc-cug (SEQ ID NO: 1295), CAGguccuga (SEQ ID NO: 1296), CAGguccugc (SEQ ID NO: 1297), CAGguccugg (SEQ ID NO: 1298), CAGgucggcc (SEQ ID NO: 1299), CAGgucg-gug (SEQ ID NO: 1300), CAGgucguug (SEQ ID NO: 1301), CAGgucucuc (SEQ ID NO: 1302), CAGgucucuu (SEQ ID NO: 1303), CAGgucugag (SEQ ID NO: 1304), CAGgucugcc (SEQ ID NO: 1305), CAGgucugcg (SEQ ID NO: 1306), CAGgucugga (SEQ ID NO: 1307), CAGgu-cuggu (SEQ ID NO: 1308), CAGgucugua (SEQ ID NO: 1309), CAGgucuguc (SEQ ID NO: 1310), CAGgucugug (SEQ ID NO: 1311), CAGgucuguu (SEQ ID NO: 1312), CAGgucuucc (SEQ ID NO: 1313), CAGgucuuuc (SEQ ID NO: 1314), CAGgugaaag (SEQ ID NO: 1315), CAG-gugaaau (SEQ ID NO: 1316), CAGgugaaca (SEQ ID NO: 1317), CAGgugaaga (SEQ ID NO: 1318), CAGgugaagg (SEQ ID NO: 1319), CAGgugaaua (SEQ ID NO: 1320), CAGgugaauc (SEQ ID NO: 1321), CAGgugaauu (SEQ ID NO: 1322), CAGgugacaa (SEQ ID NO: 1323), CAGguga-cau (SEQ ID NO: 1324), CAGgugacca (SEQ ID NO: 1325), CAGgugaccc (SEQ ID NO: 1326), CAGgugaccg (SEQ ID NO: 1327), CAGgugaccu (SEQ ID NO: 1328), CAG-gugacgg (SEQ ID NO: 1329), CAGgugacua (SEQ ID NO: 1330), CAGgugacuc (SEQ ID NO: 1331), CAGgugacug (SEQ ID NO: 1332), CAGgugagaa (SEQ ID NO: 1333), CAGgugagac (SEQ ID NO: 1334), CAGgugagag (SEQ ID NO: 1335), CAGgugagau (SEQ ID NO: 1336), CAG-gugagca (SEQ ID NO: 1337), CAGgugagcc (SEQ ID NO: 1338), CAGgugagcg (SEQ ID NO: 1339), CAGgugagcu (SEQ ID NO: 1340), CAGgugagga (SEQ ID NO: 1341), CAGgugaggc (SEQ ID NO: 1342), CAGgugaggg (SEQ ID NO: 1343), CAGgugaggu (SEQ ID NO: 1344), CAGgugagua (SEQ ID NO: 1345), CAGgugaguc (SEQ ID NO: 1346), CAGgugagug (SEQ ID NO: 1347), CAGgugaguu (SEQ ID NO: 1348), CAGgugauaa (SEQ ID NO: 1349), CAGgugaucc (SEQ ID NO: 1350), CAGgugaucu (SEQ ID NO: 1351), CAGgugaugc (SEQ ID NO: 1352), CAGgugaugg (SEQ ID NO: 1353), CAGgugaugu (SEQ ID NO: 1354), CAGgugauua (SEQ ID NO: 1355), CAGgugauuc (SEQ ID NO: 1356), CAGgugauug (SEQ ID NO: 1357), CAGgugauuu (SEQ ID NO: 1358), CAGgugcaaa (SEQ ID NO: 1359), CAGgugcaag (SEQ ID NO: 1360), CAGgugcaca (SEQ ID NO: 1361), CAGgugcacg (SEQ ID NO: 1362), CAGgugcaga (SEQ ID NO: 1363), CAGgugcagg (SEQ ID NO: 1364), CAGgugcaua (SEQ ID NO: 1365), CAGgugcauc (SEQ ID NO: 1366), CAGgugcaug (SEQ ID NO: 1367), CAGgugccaa (SEQ ID NO: 1368), CAGgugccca (SEQ ID NO: 1369), CAGgugcccc (SEQ ID NO: 1370), CAGgugcccg (SEQ ID NO: 1371), CAGgugccua (SEQ ID NO: 1372), CAGgugccug (SEQ ID NO: 1373), CAGgugcgaa (SEQ ID NO: 1374), CAGgugcgca (SEQ ID NO: 1375), CAGgugcgcc (SEQ ID NO: 1376), CAGgugcgcg (SEQ ID NO: 1377), CAGgugcgga (SEQ ID NO: 1378), CAGgugcggu (SEQ ID NO: 1379), CAGgugcgua (SEQ ID NO: 1380), CAGgugcguc (SEQ ID NO: 1381), CAGgugcgug (SEQ ID NO: 1382), CAGgugcuag (SEQ ID NO: 1383), CAGgugcuau (SEQ ID NO: 1384), CAGgugcuca (SEQ ID NO: 1385), CAGgugcucc (SEQ ID NO: 1386), CAGgugcucg (SEQ ID NO: 1387), CAGgugcugc (SEQ ID NO: 1388), CAGgugcugg (SEQ ID NO: 1389), CAGgugcuua (SEQ ID NO: 1390), CAGgugcuuc (SEQ ID NO: 1391), CAGgugcuug (SEQ ID NO: 1392), CAGguggaac (SEQ ID NO: 1393), CAGguggaag (SEQ ID NO: 1394), CAGguggaau (SEQ ID NO: 1395), CAGguggaga (SEQ ID NO: 1396), CAGguggagu (SEQ ID NO: 1397), CAGguggauu (SEQ ID NO: 1398), CAGguggcca (SEQ ID NO: 1399), CAGguggcuc (SEQ ID NO: 1400), CAGguggcug (SEQ ID NO: 1401), CAGgugggaa (SEQ ID NO: 1402), CAGgugggac (SEQ ID NO: 1403), CAGgugggag (SEQ ID NO: 1404), CAGgugggau (SEQ ID NO: 1405), CAGgugggca (SEQ ID NO: 1406), CAGgugggcc (SEQ ID NO: 1407), CAGgugggcu (SEQ ID NO: 1408), CAGgugggga (SEQ ID NO: 1409), CAGgugggc (SEQ ID NO: 1410), CAGgugggg (SEQ ID NO: 1411), CAGgugggu (SEQ ID NO: 1412), CAGgugggua (SEQ ID NO: 1413), CAGguggguc (SEQ ID NO: 1414), CAGgugggug (SEQ ID NO: 1415), CAGguggguu (SEQ ID NO: 1416), CAGguggucu (SEQ ID NO: 1417), CAGguggugg (SEQ ID NO: 1418), CAGgugguug (SEQ ID NO: 1419), CAGguguaca (SEQ ID NO: 1420), CAGguguagg (SEQ ID NO: 1421), CAGguguauc (SEQ ID NO: 1422), CAGgugucac (SEQ ID NO: 1423), CAGgugucag (SEQ ID NO: 1424), CAGgugucca (SEQ ID NO: 1425), CAGguguccu (SEQ ID NO: 1426), CAGgugucua (SEQ ID NO: 1427), CAGgugucuc (SEQ ID NO: 1428), CAGgugucug (SEQ ID NO: 1429), CAGgugugaa (SEQ ID NO: 1430), CAGgugugac (SEQ ID NO: 1431), CAGgugugag (SEQ ID NO: 1432), CAGgugugau (SEQ ID NO: 1433), CAGgugugca (SEQ ID NO: 1434), CAGgugugcc (SEQ ID NO: 1435), CAGgugugcg (SEQ ID NO: 1436), CAGgugugcu (SEQ ID NO: 1437), CAGgugugga (SEQ ID NO: 1438), CAGguguggc (SEQ ID NO: 1439), CAGgugugua (SEQ ID NO: 1440), CAGguguguc (SEQ ID NO: 1441), CAGgugugug (SEQ ID NO: 1442), CAGguguguu (SEQ ID NO: 1443), CAGguguuua (SEQ ID NO: 1444), CAGguuaaaa (SEQ ID NO: 1445), CAGguuaaua (SEQ ID NO: 1446), CAGguuaauc (SEQ ID NO: 1447), CAGguuaccu (SEQ ID NO: 1448), CAGguuagaa (SEQ ID NO: 1449), CAGguuagag (SEQ ID NO: 1450), CAGguuagau (SEQ ID NO: 1451), CAGguuagcc (SEQ ID NO: 1452), CAGguuaggg (SEQ ID NO: 1453), CAGguuaggu (SEQ ID NO: 1454), CAGguuagua (SEQ ID NO: 1455), CAGguuaguc (SEQ ID NO: 1456), CAGguuagug (SEQ ID NO: 1457), CAGguuaguu (SEQ ID NO: 1458), CAGguuauca (SEQ ID NO: 1459), CAGguuaugu (SEQ ID NO: 1460), CAGguuauua (SEQ ID NO: 1461), CAGguuauug (SEQ ID NO: 1462), CAGguucaaa (SEQ ID NO: 1463), CAGguucaac (SEQ ID NO: 1464), CAGguucaag (SEQ ID NO: 1465), CAGguucaca (SEQ ID NO: 1466), CAGguucacg (SEQ ID NO: 1467), CAGguucagg (SEQ ID NO: 1468), CAGguucaug (SEQ ID NO: 1469), CAGguuccag (SEQ ID NO: 1470), CAGguuccca (SEQ ID NO: 1471), CAGguucccg (SEQ ID NO: 1472), CAGguucgaa (SEQ ID NO: 1473), CAGguucgag (SEQ ID NO: 1474), CAGguucuau (SEQ ID NO: 1475), CAGguucugc (SEQ ID NO: 1476), CAGguucuua (SEQ ID NO: 1477), CAGguucuuc (SEQ ID NO: 1478), CAGguucuuu (SEQ ID NO: 1479), CAGguugaac (SEQ ID NO: 1480), CAGguugaag (SEQ ID NO: 1481), CAGguugagu (SEQ ID NO: 1482), CAGguugaua (SEQ ID NO: 1483), CAGguuggag (SEQ ID NO: 1484), CAGguuggca (SEQ ID NO: 1485), CAGguuggcc (SEQ ID NO: 1486), CAGguugguc (SEQ ID NO: 1487), CAGguuggug (SEQ ID NO: 1488), CAGguugguu (SEQ ID NO: 1489), CAGguuguaa (SEQ ID NO: 1490), CAGguuguac (SEQ ID NO: 1491), CAGguuguau (SEQ ID NO: 1492), CAGguuguca (SEQ ID NO: 1493), CAGguuguga (SEQ ID NO: 1494), CAGguuguug (SEQ ID NO: 1495), CAGguuuaag (SEQ ID NO: 1496), CAGguuuacc (SEQ ID NO: 1497), CAGguuuagc (SEQ ID NO: 1498), CAGguuuagu (SEQ ID NO: 1499), CAGguuucuu (SEQ ID NO: 1500), CAGguuugaa (SEQ ID NO: 1501), CAGguuugag (SEQ ID NO: 1502), CAGguuugau (SEQ ID NO: 1503), CAGguuugcc (SEQ ID NO: 1504), CAGguuugcu (SEQ ID NO: 1505), CAGguuuggg (SEQ ID NO: 1506), CAGguuuggu (SEQ ID NO: 1507), CAGguuugua (SEQ ID NO: 1508), CAGguuugug (SEQ ID NO: 1509), CAGguuuguu (SEQ ID NO: 1510), CAGguuuucu (SEQ ID NO: 1511), CAGguuuugg (SEQ ID NO: 1512), CAGguuuuuc (SEQ ID NO: 1513), CAGguuuuuu (SEQ ID NO: 1514), CAUgcagguu (SEQ ID NO: 1515), CAUguaaaac (SEQ ID NO: 1516), CAUguaacua (SEQ ID NO: 1517), CAUguaagaa (SEQ ID NO: 1518), CAUguaagag (SEQ ID NO: 1519), CAUguaagau (SEQ ID NO: 1520), CAUguaagcc (SEQ ID NO: 1521), CAUguaagua (SEQ ID NO: 1522), CAUguaagug (SEQ ID NO: 1523), CAUguaaguu (SEQ ID NO: 1524), CAUguaauua (SEQ ID NO: 1525), CAUguacaua (SEQ ID NO: 1526), CAUguaccac (SEQ ID NO: 1527), CAUguacguu (SEQ ID NO: 1528), CAUguaggua (SEQ ID NO: 1529), CAUguaggug (SEQ ID NO: 1530), CAUguagguu (SEQ ID NO: 1531), CAUguaugaa (SEQ ID NO: 1532), CAUguaugua (SEQ ID NO: 1533), CAUguaugug (SEQ ID NO: 1534), CAUguauguu (SEQ ID NO: 1535), CAUgugagaa (SEQ ID NO: 1536), CAUgugagca (SEQ ID NO: 1537), CAUgugagcu (SEQ ID NO: 1538), CAUgugagua (SEQ ID NO: 1539), CAUgugaguc (SEQ ID NO: 1540), CAUgugagug (SEQ ID NO: 1541), CAUgugaguu (SEQ ID NO: 1542), CAUgugcgua (SEQ ID NO: 1543), CAUguggaa (SEQ ID NO: 1544), CAUguggguu (SEQ ID NO: 1545), CAUgugugug (SEQ ID NO: 1546), CAUguguguu (SEQ ID NO: 1547), CAUguuaaua (SEQ ID NO: 1548), CAUguuagcc (SEQ ID NO: 1549), CCAguaagau (SEQ ID NO: 1550), CCAguaagca (SEQ ID NO: 1551), CCAguaagcc (SEQ ID NO: 1552), CCAguaagcu (SEQ ID NO: 1553), CCAguaagga (SEQ ID NO: 1554), CCAguaagua (SEQ ID NO: 1555), CCAguaaguc (SEQ ID NO: 1556), CCAguaagug (SEQ ID NO: 1557), CCAguaaguu (SEQ ID NO: 1558), CCAguaauug (SEQ ID NO: 1559), CCAguacggg (SEQ ID NO: 1560), CCAguagguc (SEQ ID NO: 1561), CCAguauugu (SEQ ID NO: 1562), CCAgugaggc (SEQ ID NO: 1563), CCAgugagua (SEQ ID NO: 1564), CCAgugagug (SEQ ID NO: 1565), CCAguggguc (SEQ ID NO: 1566), CCAguuaguu (SEQ ID NO: 1567), CCAguugagu (SEQ ID NO: 1568), CCCguaagau (SEQ ID NO: 1569), CCCguauguc (SEQ ID NO: 1570), CCCguauguu (SEQ ID NO: 1571), CCCguccugc (SEQ ID NO: 1572), CCCgugagug (SEQ ID NO: 1573), CCGguaaaga (SEQ ID NO: 1574), CCGguaagau (SEQ ID NO: 1575), CCGguaagcc (SEQ ID NO: 1576), CCGguaagga (SEQ ID NO: 1577), CCGguaaggc (SEQ ID NO: 1578), CCGguaaugg (SEQ ID NO: 1579), CCGguacagu (SEQ ID NO: 1580), CCGguacuga (SEQ ID NO: 1581), CCGguauucc (SEQ ID NO: 1582), CCGgucagug (SEQ ID NO: 1583), CCGgugaaaa (SEQ ID NO: 1584), CCGgugagaa (SEQ ID NO: 1585), CCGgugaggg (SEQ ID NO: 1586), CCGgugagug (SEQ ID NO: 1587), CCGgugaguu (SEQ ID NO: 1588), CCGgugcgcg (SEQ ID NO: 1589), CCGgugggcg (SEQ ID NO: 1590), CCGguuggUc (SEQ ID NO: 1591), CCUguaaaug (SEQ ID NO: 1592), CCUguaaauu (SEQ ID NO: 1593), CCUguaagaa (SEQ ID NO: 1594), CCUguaagac (SEQ ID NO: 1595), CCUguaagag (SEQ ID NO: 1596), CCUguaagca (SEQ ID NO: 1597), CCUguaagcg (SEQ ID NO: 1598), CCUguaagga (SEQ ID NO: 1599), CCUguaaguu (SEQ ID NO: 1600), CCUguaggua (SEQ ID NO: 1601), CCUguaggug (SEQ ID NO: 1602), CCUguaucuu (SEQ ID NO: 1603), CCUguauggu (SEQ ID NO: 1604), CCUguaugug (SEQ ID NO: 1605), CCUgugagaa (SEQ ID NO: 1606), CCUgugagca (SEQ ID NO: 1607), CCUgugaggg (SEQ ID NO: 1608), CCUgugaguc (SEQ ID NO: 1609), CCUgugagug (SEQ ID NO: 1610), CCUgugaguu (SEQ ID NO: 1611), CCUguggcuc (SEQ ID NO: 1612), CCUgugggua (SEQ ID NO: 1613), CCUgugugua (SEQ ID NO: 1614), CCUguuagaa (SEQ ID NO: 1615), CGAguaaggg (SEQ ID NO: 1616), CGAguaaggu (SEQ ID NO: 1617), CGAguagcug (SEQ ID NO: 1618), CGAguaggug (SEQ ID NO: 1619), CGAguagguu (SEQ ID NO: 1620), CGAgugagca (SEQ ID NO: 1621), CGCguaagag (SEQ ID NO: 1622), CGGgcaggca (SEQ ID NO: 1623), CGGguaagcc (SEQ ID NO: 1624), CGGguaagcu (SEQ ID NO: 1625), CGGguaaguu (SEQ ID NO: 1626), CGGguaauuc (SEQ ID NO: 1627), CGGguaauuu (SEQ ID NO: 1628), CGGguacagu (SEQ ID NO: 1629), CGGguacggg (SEQ ID NO: 1630), CGGguaggag (SEQ ID NO: 1631), CGGguaggcc (SEQ ID NO: 1632), CGGguaggug (SEQ ID NO: 1633), CGGguauuua (SEQ ID NO: 1634), CGGgucugag (SEQ ID NO: 1635), CGGgugaccg (SEQ ID NO: 1636), CGGgugacuc (SEQ ID NO: 1637), CGGgugagaa (SEQ ID NO: 1638), CGGgugaggg (SEQ ID NO: 1639), CGGgugaggu (SEQ ID NO: 1640), CGGgugagua (SEQ ID NO: 1641), CGGgugagug (SEQ ID NO: 1642), CGGgugaguu (SEQ ID NO: 1643), CGGgugauuu (SEQ ID NO: 1644), CGGgugccuu (SEQ ID NO: 1645), CGGguggag (SEQ ID NO: 1646), CGGgugggug (SEQ ID NO: 1647), CGGgugggUu (SEQ ID NO: 1648), CGGgugugUc (SEQ ID NO: 1649), CGGgugugug (SEQ ID NO: 1650), CGGguguguu (SEQ ID NO: 1651), CGGguucaag (SEQ ID NO: 1652), CGGguucaug (SEQ ID NO: 1653), CGGguuugcu (SEQ ID NO: 1654), CGUguagggu (SEQ ID NO: 1655), CGUguaugca (SEQ ID NO: 1656), CGUguaugua (SEQ ID NO: 1657), CGUgucugua (SEQ ID NO: 1658), CGUgugagug (SEQ ID NO: 1659), CGUguuuucu (SEQ ID NO: 1660), CUAguaaaug (SEQ ID NO: 1661), CUAguaagcg (SEQ ID NO: 1662), CUAguaagcu (SEQ ID NO: 1663), CUAguaagua (SEQ ID NO: 1664), CUAguaaguc (SEQ ID NO: 1665), CUAguaagug (SEQ ID NO: 1666), CUAguaaguu (SEQ ID NO: 1667), CUAguaauuu (SEQ ID NO: 1668), CUAguaggua (SEQ ID NO: 1669), CUAguagguu (SEQ ID NO: 1670), CUAguaugua (SEQ ID NO: 1671), CUAguauguu (SEQ ID NO: 1672), CUAgugagua (SEQ ID NO: 1673), CUCguaagca (SEQ ID NO: 1674), CUCguaagug (SEQ ID NO: 1675), CUCguaaguu (SEQ ID NO: 1676), CUCguaucug (SEQ ID NO: 1677), CUCgucugug (SEQ ID NO: 1678), CUCgugaaua (SEQ ID NO: 1679), CUCgugagua (SEQ ID NO: 1680), CUCgugauua (SEQ ID NO: 1681), CUGguaaaaa (SEQ ID NO: 1682), CUGguaaaau (SEQ ID NO: 1683), CUGguaaacc (SEQ ID NO: 1684), CUGguaaacg (SEQ ID NO: 1685), CUGguaaagc (SEQ ID NO: 1686), CUGguaaaua (SEQ ID NO: 1687), CUGguaaauc (SEQ ID NO: 1688), CUGguaaaug (SEQ ID NO: 1689), CUGguaaauu (SEQ ID NO: 1690), CUGguaacac (SEQ ID NO: 1691), CUGguaacag (SEQ ID NO: 1692), CUGguaaccc (SEQ ID NO: 1693), CUGguaaccg (SEQ ID NO: 1694), CUGguaacug (SEQ ID NO: 1695), CUGguaacuu (SEQ ID NO: 1696), CUGguaagaa (SEQ ID NO: 1697), CUGguaagag (SEQ ID NO: 1698), CUGguaagau (SEQ ID NO: 1699), CUGguaagca (SEQ ID NO: 1700), CUGguaagcc (SEQ ID NO: 1701), CUGguaagcu (SEQ ID NO: 1702), CUGguaagga (SEQ ID NO: 1703), CUGguaaggc (SEQ ID NO: 1704), CUGguaaggg (SEQ ID NO: 1705), CUGguaaggu (SEQ ID NO: 1706), CUGguaagua (SEQ ID NO: 1707), CUGguaagug (SEQ ID NO: 1708), CUGguaaguu (SEQ ID NO: 1709), CUGguaauga (SEQ ID NO: 1710), CUGguaaugc (SEQ ID NO: 1711), CUGguaauuc (SEQ ID NO: 1712), CUGguaauuu (SEQ ID NO: 1713), CUGguacaac (SEQ ID NO: 1714), CUGguacaau (SEQ ID NO: 1715), CUGguacaga (SEQ ID NO: 1716), CUGguacaua (SEQ ID NO: 1717), CUGguacauu (SEQ ID NO: 1718), CUGguaccau (SEQ ID NO: 1719), CUGguacguu (SEQ ID NO: 1720), CUGguacuaa (SEQ ID NO: 1721), CUGguacuug (SEQ ID NO: 1722), CUGguacuuu (SEQ ID NO: 1723), CUGguagaga (SEQ ID NO: 1724), CUGguagaua (SEQ ID NO: 1725), CUGguagcgu (SEQ ID NO: 1726), CUGguaggau (SEQ ID NO: 1727), CUGguaggca (SEQ ID NO: 1728), CUGguaggua (SEQ ID NO: 1729), CUGguagguc (SEQ ID NO: 1730), CUGguaggug (SEQ ID NO: 1731), CUGguaucaa (SEQ ID NO: 1732), CUGguaugau (SEQ ID NO: 1733), CUGguauggc (SEQ ID NO: 1734), CUGguauggu (SEQ ID NO: 1735), CUGguaugua (SEQ ID NO: 1736), CUGguaugug (SEQ ID NO: 1737), CUGguauguu (SEQ ID NO: 1738), CUGguauuga (SEQ ID NO: 1739), CUGguauuuc (SEQ ID NO: 1740), CUGguauuuu (SEQ ID NO: 1741), CUGgucaaca (SEQ ID NO: 1742), CUGgucagag (SEQ ID NO: 1743), CUGgucccgc (SEQ ID NO: 1744), CUGgucggua (SEQ ID NO: 1745), CUGgucuggg (SEQ ID NO: 1746), CUGgugaagu (SEQ ID NO: 1747), CUGgugaaua (SEQ ID NO: 1748), CUGgugaauu (SEQ ID NO: 1749), CUGgugacua (SEQ ID NO: 1750), CUGgugagaa (SEQ ID NO: 1751), CUGgugagac (SEQ ID NO: 1752), CUGgugagca (SEQ ID NO: 1753), CUGgugagcu (SEQ ID NO: 1754), CUGgugagga (SEQ ID NO: 1755), CUGgugaggc (SEQ ID NO: 1756), CUGgugaggg (SEQ ID NO: 1757), CUGgugaggu (SEQ ID NO: 1758), CUGgugagua (SEQ ID NO: 1759), CUGgugaguc (SEQ ID NO: 1760), CUGgugagug (SEQ ID NO: 1761), CUGgugaguu (SEQ ID NO: 1762), CUGgugauua (SEQ ID NO: 1763), CUGgugauuu (SEQ ID NO: 1764), CUGgugcaga (SEQ ID NO: 1765), CUGgugcgcu (SEQ ID NO: 1766), CUGgugcgug (SEQ ID NO: 1767), CUGgugcuga (SEQ ID NO: 1768), CUGgugggag (SEQ ID NO: 1769), CUGgugggga (SEQ ID NO: 1770), CUGgugggua (SEQ ID NO: 1771), CUGguggguc (SEQ ID NO: 1772), CUGguggug (SEQ ID NO: 1773), CUGgugggUu (SEQ ID NO:

1774), CUGgugugaa (SEQ ID NO: 1775), CUGgugugca (SEQ ID NO: 1776), CUGgugugcu (SEQ ID NO: 1777), CUGguguggu (SEQ ID NO: 1778), CUGgugugug (SEQ ID NO: 1779), CUGguguguu (SEQ ID NO: 1780), CUGguuagcu (SEQ ID NO: 1781), CUGguuagug (SEQ ID NO: 1782), CUGguucgug (SEQ ID NO: 1783), CUGguuggcu (SEQ ID NO: 1784), CUGguuguuu (SEQ ID NO: 1785), CUGguuugua (SEQ ID NO: 1786), CUGguuuguc (SEQ ID NO: 1787), CUGguuugug (SEQ ID NO: 1788), CUUguaaaug (SEQ ID NO: 1789), CUUguaagcu (SEQ ID NO: 1790), CUUguaagga (SEQ ID NO: 1791), CUUguaaggc (SEQ ID NO: 1792), CUUguaagua (SEQ ID NO: 1793), CUUguaagug (SEQ ID NO: 1794), CUUguaaguu (SEQ ID NO: 1795), CUUguacguc (SEQ ID NO: 1796), CUUguacgug (SEQ ID NO: 1797), CUUguaggua (SEQ ID NO: 1798), CUUguagugc (SEQ ID NO: 1799), CUUguauagg (SEQ ID NO: 1800), CUUgucagua (SEQ ID NO: 1801), CUUgugagua (SEQ ID NO: 1802), CUUgugaguc (SEQ ID NO: 1803), CUUgugaguu (SEQ ID NO: 1804), CUUguggguu (SEQ ID NO: 1805), CUUgugugua (SEQ ID NO: 1806), CUUguuagug (SEQ ID NO: 1807), CUUguuugag (SEQ ID NO: 1808), GAAguaaaac (SEQ ID NO: 1809), GAAguaaagc (SEQ ID NO: 1810), GAAguaaagu (SEQ ID NO: 1811), GAAguaaaua (SEQ ID NO: 1812), GAAguaaauu (SEQ ID NO: 1813), GAAguaagaa (SEQ ID NO: 1814), GAAguaagcc (SEQ ID NO: 1815), GAAguaagcu (SEQ ID NO: 1816), GAAguaagga (SEQ ID NO: 1817), GAAguaagua (SEQ ID NO: 1818), GAAguaagug (SEQ ID NO: 1819), GAAguaaguu (SEQ ID NO: 1820), GAAguaauau (SEQ ID NO: 1821), GAAguaaugc (SEQ ID NO: 1822), GAAguaauua (SEQ ID NO: 1823), GAAguaauuu (SEQ ID NO: 1824), GAAguaccau (SEQ ID NO: 1825), GAAguacgua (SEQ ID NO: 1826), GAAguacguc (SEQ ID NO: 1827), GAAguaggca (SEQ ID NO: 1828), GAAguagguc (SEQ ID NO: 1829), GAAguauaaa (SEQ ID NO: 1830), GAAguaugcu (SEQ ID NO: 1831), GAAguaugug (SEQ ID NO: 1832), GAAguauguu (SEQ ID NO: 1833), GAAguauuaa (SEQ ID NO: 1834), GAAgucagug (SEQ ID NO: 1835), GAAgugagag (SEQ ID NO: 1836), GAAgugagcg (SEQ ID NO: 1837), GAAgugaggu (SEQ ID NO: 1838), GAAgugaguc (SEQ ID NO: 1839), GAAgugagug (SEQ ID NO: 1840), GAAgugaguu (SEQ ID NO: 1841), GAAgugauaa (SEQ ID NO: 1842), GAAgugauuc (SEQ ID NO: 1843), GAAgugcgug (SEQ ID NO: 1844), GAAguguggg (SEQ ID NO: 1845), GAAgugugüc (SEQ ID NO: 1846), GAAguuggug (SEQ ID NO: 1847), GACguaaagu (SEQ ID NO: 1848), GACguaagcu (SEQ ID NO: 1849), GACguaagua (SEQ ID NO: 1850), GACguaaugg (SEQ ID NO: 1851), GACguaugcc (SEQ ID NO: 1852), GACguauguu (SEQ ID NO: 1853), GACgugagcc (SEQ ID NO: 1854), GACgugagug (SEQ ID NO: 1855), GAGgcaaaug (SEQ ID NO: 1856), GAGgcaagag (SEQ ID NO: 1857), GAGgcaagua (SEQ ID NO: 1858), GAGgcaagug (SEQ ID NO: 1859), GAGgcaaguu (SEQ ID NO: 1860), GAGgcacgag (SEQ ID NO: 1861), GAGgcaggga (SEQ ID NO: 1862), GAGgcaugug (SEQ ID NO: 1863), GAGgcgaagg (SEQ ID NO: 1864), GAGguaaaaa (SEQ ID NO: 1865), GAGguaaaac (SEQ ID NO: 1866), GAGguaaaag (SEQ ID NO: 1867), GAGguaaaau (SEQ ID NO: 1868), GAGguaaacc (SEQ ID NO: 1869), GAGguaaaga (SEQ ID NO: 1870), GAGguaaagc (SEQ ID NO: 1871), GAGguaaagu (SEQ ID NO: 1872), GAGguaaaua (SEQ ID NO: 1873), GAGguaaauc (SEQ ID NO: 1874), GAGguaaaug (SEQ ID NO: 1875), GAGguaaauu (SEQ ID NO: 1876), GAGguaacaa (SEQ ID NO: 1877), GAGguaacag (SEQ ID NO: 1878), GAGguaacca (SEQ ID NO: 1879), GAGguaaccu (SEQ ID NO: 1880), GAGguaacuu (SEQ ID NO: 1881), GAGguaagaa (SEQ ID NO: 1882), GAGguaagag (SEQ ID NO: 1883), GAGguaagau (SEQ ID NO: 1884), GAGguaagca (SEQ ID NO: 1885), GAGguaagcc (SEQ ID NO: 1886), GAGguaagcg (SEQ ID NO: 1887), GAGguaagcu (SEQ ID NO: 1888), GAGguaagga (SEQ ID NO: 1889), GAGguaaggc (SEQ ID NO: 1890), GAGguaaggg (SEQ ID NO: 1891), GAGguaaggu (SEQ ID NO: 1892), GAGguaagua (SEQ ID NO: 1893), GAGguaaguc (SEQ ID NO: 1894), GAGguaauaa (SEQ ID NO: 1895), GAGguaauac (SEQ ID NO: 1896), GAGguaauau (SEQ ID NO: 1897), GAGguaauca (SEQ ID NO: 1898), GAGguaaucu (SEQ ID NO: 1899), GAGguaaugg (SEQ ID NO: 1900), GAGguaaugu (SEQ ID NO: 1901), GAGguaauug (SEQ ID NO: 1902), GAGguaauuu (SEQ ID NO: 1903), GAGguacaaa (SEQ ID NO: 1904), GAGguacaac (SEQ ID NO: 1905), GAGguacaga (SEQ ID NO: 1906), GAGguacagc (SEQ ID NO: 1907), GAGguacagu (SEQ ID NO: 1908), GAGguacaua (SEQ ID NO: 1909), GAGguacauu (SEQ ID NO: 1910), GAGguaccag (SEQ ID NO: 1911), GAGguaccga (SEQ ID NO: 1912), GAGguaccug (SEQ ID NO: 1913), GAGguaccuu (SEQ ID NO: 1914), GAGguacuag (SEQ ID NO: 1915), GAGguacuau (SEQ ID NO: 1916), GAGguacucc (SEQ ID NO: 1917), GAGguacugc (SEQ ID NO: 1918), GAGguacugg (SEQ ID NO: 1919), GAGguacugu (SEQ ID NO: 1920), GAGguacuug (SEQ ID NO: 1921), GAGguacuuu (SEQ ID NO: 1922), GAGguagaag (SEQ ID NO: 1923), GAGguagaga (SEQ ID NO: 1924), GAGguagagg (SEQ ID NO: 1925), GAGguagagu (SEQ ID NO: 1926), GAGguagauc (SEQ ID NO: 1927), GAGguagcua (SEQ ID NO: 1928), GAGguagcug (SEQ ID NO: 1929), GAGguaggaa (SEQ ID NO: 1930), GAGguaggag (SEQ ID NO: 1931), GAGguaggca (SEQ ID NO: 1932), GAGguaggcu (SEQ ID NO: 1933), GAGguaggga (SEQ ID NO: 1934), GAGguagggc (SEQ ID NO: 1935), GAGguagggg (SEQ ID NO: 1936), GAGguaggua (SEQ ID NO: 1937), GAGguaggug (SEQ ID NO: 1938), GAGguagguu (SEQ ID NO: 1939), GAGguaguaa (SEQ ID NO: 1940), GAGguaguag (SEQ ID NO: 1941), GAGguaguau (SEQ ID NO: 1942), GAGguagucu (SEQ ID NO: 1943), GAGguagugc (SEQ ID NO: 1944), GAGguagugg (SEQ ID NO: 1945), GAGguaguua (SEQ ID NO: 1946), GAGguaguug (SEQ ID NO: 1947), GAGguauaag (SEQ ID NO: 1948), GAGguauacu (SEQ ID NO: 1949), GAGguauagc (SEQ ID NO: 1950), GAGguauaug (SEQ ID NO: 1951), GAGguauauu (SEQ ID NO: 1952), GAGguaucau (SEQ ID NO: 1953), GAGguaucug (SEQ ID NO: 1954), GAGguaucuu (SEQ ID NO: 1955), GAGguaugaa (SEQ ID NO: 1956), GAGguaugac (SEQ ID NO: 1957), GAGguaugag (SEQ ID NO: 1958), GAGguaugcc (SEQ ID NO: 1959), GAGguaugcg (SEQ ID NO: 1960), GAGguaugcu (SEQ ID NO: 1961), GAGguaugga (SEQ ID NO: 1962), GAGguauggg (SEQ ID NO: 1963), GAGguauggu (SEQ ID NO: 1964), GAGguaugua (SEQ ID NO: 1965), GAGguauguc (SEQ ID NO: 1966), GAGguaugug (SEQ ID NO: 1967), GAGguauguu (SEQ ID NO: 1968), GAGguauucc (SEQ ID NO: 1969), GAGguauuga (SEQ ID NO: 1970), GAGguauugu (SEQ ID NO: 1971), GAGguauuua (SEQ ID NO: 1972), GAGguauuuc (SEQ ID NO: 1973), GAGguauuug (SEQ ID NO: 1974), GAGguauuuu (SEQ ID NO: 1975), GAGgucaaca (SEQ ID NO: 1976), GAGgucaagg (SEQ ID NO: 1977), GAGgucaaug (SEQ ID NO: 1978), GAGgucacug (SEQ ID NO: 1979), GAGgucagaa (SEQ ID NO: 1980), GAGgucagag (SEQ ID NO: 1981), GAGgucagcu (SEQ ID NO: 1982), GAGgucagga (SEQ ID NO: 1983), GAGgucaggc (SEQ ID NO: 1984), GAGgucaggg (SEQ ID NO: 1985), GAGgucaggu (SEQ ID NO: 1986), GAGgucagua (SEQ ID NO: 1987), GAGgucauau (SEQ ID NO: 1988), GAGgucaugu (SEQ ID NO: 1989), GAGgucauuu (SEQ ID NO: 1990), GAGguccaua (SEQ ID NO: 1991), GAGguccauc (SEQ ID NO: 1992), GAGguccggg (SEQ ID NO: 1993), GAGguccggu (SEQ ID NO: 1994), GAGguccuug (SEQ ID NO: 1995), GAGgucgggg (SEQ ID NO: 1996), GAGgucucgu (SEQ ID NO: 1997), GAGgucugag (SEQ ID NO: 1998), GAGgucuggu (SEQ ID NO: 1999), GAGgucuguc (SEQ ID NO: 2000), GAGgucuguu (SEQ ID NO: 2001), GAGgucuuuu (SEQ ID NO: 2002), GAGgugaaaa (SEQ ID NO: 2003), GAGgugaaau (SEQ ID NO: 2004), GAGgugaaca (SEQ ID NO: 2005), GAGgugaagg (SEQ ID NO: 2006), GAGgugaaua (SEQ ID NO: 2007), GAGgugaauu (SEQ ID NO: 2008), GAGgugacau (SEQ ID NO: 2009), GAGgugacca (SEQ ID NO: 2010), GAGgugaccu (SEQ ID NO: 2011), GAGgugacua (SEQ ID NO: 2012), GAGgugacuu (SEQ ID NO: 2013), GAGgugagaa (SEQ ID NO: 2014), GAGgugagac (SEQ ID NO: 2015), GAGgugagag (SEQ ID NO: 2016), GAGgugagau (SEQ ID NO: 2017), GAGgugagca (SEQ ID NO: 2018), GAGgugagcc (SEQ ID NO: 2019), GAGgugagcg (SEQ ID NO: 2020), GAGgugagcu (SEQ ID NO: 2021), GAGgugagga (SEQ ID NO: 2022), GAGgugaggc (SEQ ID NO: 2023), GAGgugaggg (SEQ ID NO: 2024), GAGgugagua (SEQ ID NO: 2025), GAGgugagug (SEQ ID NO: 2026), GAGgugaguu (SEQ ID NO: 2027), GAGgugauau (SEQ ID NO: 2028), GAGgugaucc (SEQ ID NO: 2029), GAGgugaucu (SEQ ID NO: 2030), GAGgugauga (SEQ ID NO: 2031), GAGgugaugg (SEQ ID NO: 2032), GAGgugaugu (SEQ ID NO: 2033), GAGgugauuc (SEQ ID NO: 2034), GAGgugcaca (SEQ ID NO: 2035), GAGgugcaga (SEQ ID NO: 2036), GAGgugcagc (SEQ ID NO: 2037), GAGgugcagg (SEQ ID NO: 2038), GAGgugccag (SEQ ID NO: 2039), GAGgugccca (SEQ ID NO: 2040), GAGgugccuu (SEQ ID NO: 2041), GAGgugcggg (SEQ ID NO: 2042), GAGgugcgug (SEQ ID NO: 2043), GAGgugcucc (SEQ ID NO: 2044), GAGgugcugg (SEQ ID NO: 2045), GAGgugcuua (SEQ ID NO: 2046), GAGgugcuug (SEQ ID NO: 2047), GAGguggaaa (SEQ ID NO: 2048), GAGguggaau (SEQ ID NO: 2049), GAGguggacc (SEQ ID NO: 2050), GAGguggacg (SEQ ID NO: 2051), GAGguggagg (SEQ ID NO: 2052), GAGguggcug (SEQ ID NO: 2053), GAGgugggaa (SEQ ID NO: 2054), GAGgugggag (SEQ ID NO: 2055), GAGgugggau (SEQ ID NO: 2056), GAGgugggca (SEQ ID NO: 2057), GAGgugggcg (SEQ ID NO: 2058), GAGgugggcu (SEQ ID NO: 2059), GAGguggggga (SEQ ID NO: 2060), GAGguggggc (SEQ ID NO: 2061), GAGgugggggg (SEQ ID NO: 2062), GAGgugggua (SEQ ID NO: 2063), GAGguggguc (SEQ ID NO: 2064), GAGgugggug (SEQ ID NO: 2065), GAGguggguu (SEQ ID NO: 2066), GAGgugguau (SEQ ID NO: 2067), GAGgugguuc (SEQ ID NO: 2068), GAGgugucau (SEQ ID NO: 2069), GAGgugugag (SEQ ID NO: 2070), GAGgugugau (SEQ ID NO: 2071), GAGgugugca (SEQ ID NO: 2072), GAGgugugcu (SEQ ID NO: 2073), GAGgugugga (SEQ ID NO: 2074), GAGguguggg (SEQ ID NO: 2075), GAGguguggu (SEQ ID NO: 2076), GAGgugugua (SEQ ID NO: 2077), GAGgugugug (SEQ ID NO: 2078), GAGguuaaau (SEQ ID NO: 2079), GAGguuaaga (SEQ ID NO: 2080), GAGguuaaua (SEQ ID NO: 2081), GAGguuaccg (SEQ ID NO: 2082), GAGguuagaa (SEQ ID NO: 2083), GAGguuagac (SEQ ID NO: 2084), GAGguuagag (SEQ ID NO: 2085), GAGguuaggu (SEQ ID NO: 2086), GAGguuagua (SEQ ID NO: 2087), GAGguuaguc (SEQ ID NO: 2088), GAGguuagug (SEQ ID NO: 2089), GAGguuaguu (SEQ ID NO: 2090), GAGguuaugu (SEQ ID NO: 2091), GAGguuauuc (SEQ ID NO: 2092), GAGguucaaa (SEQ ID NO: 2093), GAGguucaua (SEQ ID NO: 2094), GAGguucuga (SEQ ID NO: 2095), GAGguugaag (SEQ ID NO: 2096), GAGguugcag (SEQ ID NO: 2097), GAGguugcug (SEQ ID NO: 2098), GAGguuggaa (SEQ ID NO: 2099), GAGguuggag (SEQ ID NO: 2100), GAGguuggau (SEQ ID NO: 2101), GAGguuggua (SEQ ID NO: 2102), GAGguugguc (SEQ ID NO: 2103), GAGguugguu (SEQ ID NO: 2104), GAGguuguag (SEQ ID NO: 2105), GAGguuucug (SEQ ID NO: 2106), GAGguuugag (SEQ ID NO: 2107), GAGguuugga (SEQ ID NO: 2108), GAGguuuggg (SEQ ID NO: 2109), GAGguuugua (SEQ ID NO: 2110), GAGguuuguu (SEQ ID NO: 2111), GAGguuuuca (SEQ ID NO: 2112), GAGguuuuga (SEQ ID NO: 2113), GAGguuuugg (SEQ ID NO: 2114), GAGguuuuua (SEQ ID NO: 2115), GAGguuuuuc (SEQ ID NO: 2116), GAUguaaaau (SEQ ID NO: 2117), GAUguaagca (SEQ ID NO: 2118), GAUguaagcc (SEQ ID NO: 2119), GAUguaaggu (SEQ ID NO: 2120), GAUguaagua (SEQ ID NO: 2121), GAUguaagug (SEQ ID NO: 2122), GAUguaaguu (SEQ ID NO: 2123), GAUguacauc (SEQ ID NO: 2124), GAUguaggua (SEQ ID NO: 2125), GAUguauggc (SEQ ID NO: 2126), GAUguaugua (SEQ ID NO: 2127), GAUguauguu (SEQ ID NO: 2128), GAUgucagug (SEQ ID NO: 2129), GAUgugagag (SEQ ID NO: 2130), GAUgugagcc (SEQ ID NO: 2131), GAUgugagcu (SEQ ID NO: 2132), GAUgugagga (SEQ ID NO: 2133), GAUgugaguc (SEQ ID NO: 2134), GAUgugagug (SEQ ID NO: 2135), GAUgugaguu (SEQ ID NO: 2136), GAUguggggua (SEQ ID NO: 2137), GAUgugggug (SEQ ID NO: 2138), GAUguguguu (SEQ ID NO: 2139), GAUguuagcu (SEQ ID NO: 2140), GAUguucagu (SEQ ID NO: 2141), GAUguucgug (SEQ ID NO: 2142), GAUguuuguu (SEQ ID NO: 2143), GCAguaaagg (SEQ ID NO: 2144), GCAguaagaa (SEQ ID NO: 2145), GCAguaagga (SEQ ID NO: 2146), GCAguaagua (SEQ ID NO: 2147), GCAguaaguc (SEQ ID NO: 2148), GCAguaaguu (SEQ ID NO: 2149), GCAguagaug (SEQ ID NO: 2150), GCAguaggua (SEQ ID NO: 2151), GCAguaugug (SEQ ID NO: 2152), GCAguauguu (SEQ ID NO: 2153), GCAgucagua (SEQ ID NO: 2154), GCAgucagug (SEQ ID NO: 2155), GCAguccggu (SEQ ID NO: 2156), GCAgugacuu (SEQ ID NO: 2157), GCAgugagcc (SEQ ID NO: 2158), GCAgugagcg (SEQ ID NO: 2159), GCAgugagcu (SEQ ID NO: 2160), GCAgugagua (SEQ ID NO: 2161), GCAgugagug (SEQ ID NO: 2162), GCAgugaguu (SEQ ID NO: 2163), GCAgugggua (SEQ ID NO: 2164), GCAguuaagu (SEQ ID NO: 2165), GCAguugagu (SEQ ID NO: 2166), GCCguaaguc (SEQ ID NO: 2167), GCCgugagua (SEQ ID NO: 2168), GCGguaaagc (SEQ ID NO: 2169), GCGguaaaua (SEQ ID NO: 2170), GCGguaagcu (SEQ ID NO: 2171), GCGguaaggg (SEQ ID NO: 2172), GCGguaagug (SEQ ID NO: 2173), GCGguaauca (SEQ ID NO: 2174), GCGguacgua (SEQ ID NO: 2175), GCGguacuug (SEQ ID NO: 2176), GCGguagggu (SEQ ID NO: 2177), GCGguagugu (SEQ ID NO: 2178), GCGgugagca (SEQ ID NO: 2179), GCGgugagcu (SEQ ID NO: 2180), GCGgugaguu (SEQ ID NO: 2181), GCGguggcuc (SEQ ID NO: 2182), GCGgugugca (SEQ ID NO: 2183), GCGguguguu (SEQ ID NO: 2184), GCGguuaagu (SEQ ID NO: 2185), GCGguuugca (SEQ ID NO: 2186), GCUgcuguaa (SEQ ID NO: 2187), GCUguaaaua (SEQ ID NO: 2188), GCUguaagac (SEQ ID NO: 2189), GCUguaagag (SEQ ID NO: 2190), GCUguaagca (SEQ ID NO: 2191), GCUguaagga (SEQ ID NO: 2192), GCUguaagua (SEQ ID NO: 2193), GCUguaaguc (SEQ ID NO: 2194), GCUguaagug (SEQ ID NO: 2195), GCUguaaguu (SEQ ID NO: 2196), GCUguaggug (SEQ ID NO: 2197), GCUguauggu (SEQ ID NO: 2198), GCUgucagug (SEQ ID NO: 2199), GCUguccuug (SEQ ID NO: 2200), GCUgugagaa (SEQ ID NO: 2201), GCUgugagcc (SEQ ID NO:

2202), GCUgugagga (SEQ ID NO: 2203), GCUgugagua (SEQ ID NO: 2204), GCUgugaguc (SEQ ID NO: 2205), GCUgugagug (SEQ ID NO: 2206), GCUgugaguu (SEQ ID NO: 2207), GCUguggguu (SEQ ID NO: 2208), GGAguaagag (SEQ ID NO: 2209), GGAguaagca (SEQ ID NO: 2210), GGAguaagcc (SEQ ID NO: 2211), GGAguaagcu (SEQ ID NO: 2212), GGAguaagga (SEQ ID NO: 2213), GGAguaagug (SEQ ID NO: 2214), GGAguaaguu (SEQ ID NO: 2215), GGAguaauuu (SEQ ID NO: 2216), GGAguacugu (SEQ ID NO: 2217), GGAguaggaa (SEQ ID NO: 2218), GGAguaggua (SEQ ID NO: 2219), GGAguagguu (SEQ ID NO: 2220), GGAguaguau (SEQ ID NO: 2221), GGAguaugac (SEQ ID NO: 2222), GGAguauggu (SEQ ID NO: 2223), GGAgucaagu (SEQ ID NO: 2224), GGAgugaggg (SEQ ID NO: 2225), GGAgugagua (SEQ ID NO: 2226), GGAgugaguc (SEQ ID NO: 2227), GGAgugagug (SEQ ID NO: 2228), GGAgugaguu (SEQ ID NO: 2229), GGAgugcuuu (SEQ ID NO: 2230), GGAgugggca (SEQ ID NO: 2231), GGAgugggug (SEQ ID NO: 2232), GGAguuaagg (SEQ ID NO: 2233), GGAguugaga (SEQ ID NO: 2234), GGCguaagcc (SEQ ID NO: 2235), GGCguaggua (SEQ ID NO: 2236), GGCguaggug (SEQ ID NO: 2237), GGCgugagcc (SEQ ID NO: 2238), GGCgugaguc (SEQ ID NO: 2239), GGGguaaaca (SEQ ID NO: 2240), GGGguaaacc (SEQ ID NO: 2241), GGGguaaacu (SEQ ID NO: 2242), GGGguaagaa (SEQ ID NO: 2243), GGGguaagag (SEQ ID NO: 2244), GGGguaagau (SEQ ID NO: 2245), GGGguaagca (SEQ ID NO: 2246), GGGguaagcc (SEQ ID NO: 2247), GGGguaagcu (SEQ ID NO: 2248), GGGguaagga (SEQ ID NO: 2249), GGGguaaggg (SEQ ID NO: 2250), GGGguaagua (SEQ ID NO: 2251), GGGguaagug (SEQ ID NO: 2252), GGGguaaguu (SEQ ID NO: 2253), GGGguagaca (SEQ ID NO: 2254), GGGguaggag (SEQ ID NO: 2255), GGGguaggcc (SEQ ID NO: 2256), GGGguaggga (SEQ ID NO: 2257), GGGguaggua (SEQ ID NO: 2258), GGGguaggug (SEQ ID NO: 2259), GGGguagguu (SEQ ID NO: 2260), GGGguagugc (SEQ ID NO: 2261), GGGguaucug (SEQ ID NO: 2262), GGGguaugac (SEQ ID NO: 2263), GGGguaugga (SEQ ID NO: 2264), GGGguaugua (SEQ ID NO: 2265), GGGguauguc (SEQ ID NO: 2266), GGGguaugug (SEQ ID NO: 2267), GGGguauguu (SEQ ID NO: 2268), GGGgucagua (SEQ ID NO: 2269), GGGguccgug (SEQ ID NO: 2270), GGGgucggag (SEQ ID NO: 2271), GGGgucugug (SEQ ID NO: 2272), GGGgugaaca (SEQ ID NO: 2273), GGGgugaaga (SEQ ID NO: 2274), GGGgugagaa (SEQ ID NO: 2275), GGGgugagau (SEQ ID NO: 2276), GGGgugagcc (SEQ ID NO: 2277), GGGgugagcg (SEQ ID NO: 2278), GGGgugagcu (SEQ ID NO: 2279), GGGgugagga (SEQ ID NO: 2280), GGGgugaggc (SEQ ID NO: 2281), GGGgugaggg (SEQ ID NO: 2282), GGGgugaguc (SEQ ID NO: 2283), GGGgugagug (SEQ ID NO: 2284), GGGgugaguu (SEQ ID NO: 2285), GGGgugcgua (SEQ ID NO: 2286), GGGguggggu (SEQ ID NO: 2287), GGGgugggua (SEQ ID NO: 2288), GGGgugggug (SEQ ID NO: 2289), GGGguggguu (SEQ ID NO: 2290), GGGgugugcg (SEQ ID NO: 2291), GGGgugugua (SEQ ID NO: 2292), GGGguguguc (SEQ ID NO: 2293), GGGgugugug (SEQ ID NO: 2294), GGGguuacag (SEQ ID NO: 2295), GGGguuggac (SEQ ID NO: 2296), GGGguuggga (SEQ ID NO: 2297), GGGguuugcc (SEQ ID NO: 2298), GGGguuugua (SEQ ID NO: 2299), GGUguaagaa (SEQ ID NO: 2300), GGUguaagau (SEQ ID NO: 2301), GGUguaagca (SEQ ID NO: 2302), GGUguaagcc (SEQ ID NO: 2303), GGUguaagcg (SEQ ID NO: 2304), GGUguaaguc (SEQ ID NO: 2305), GGUguaagug (SEQ ID NO: 2306), GGUguagguc (SEQ ID NO: 2307), GGUguaggug (SEQ ID NO: 2308), GGUguagguu (SEQ ID NO: 2309), GGUguccgua (SEQ ID NO: 2310), GGUgugagag (SEQ ID NO: 2311), GGUgugagcc (SEQ ID NO: 2312), GGUgugagcu (SEQ ID NO: 2313), GGUgugagua (SEQ ID NO: 2314), GGUgugaguc (SEQ ID NO: 2315), GGUgugcuuc (SEQ ID NO: 2316), GGUguggcug (SEQ ID NO: 2317), GGUguggUga (SEQ ID NO: 2318), GGUgugucug (SEQ ID NO: 2319), GGUguugaaa (SEQ ID NO: 2320), GGUguugcug (SEQ ID NO: 2321), GUAguaagau (SEQ ID NO: 2322), GUAguaagua (SEQ ID NO: 2323), GUAguaagug (SEQ ID NO: 2324), GUAguagcuu (SEQ ID NO: 2325), GUAguaggua (SEQ ID NO: 2326), GUAgucagua (SEQ ID NO: 2327), GUAgugagua (SEQ ID NO: 2328), GUAguggugg (SEQ ID NO: 2329), GUAguuaagu (SEQ ID NO: 2330), GUAguuucug (SEQ ID NO: 2331), GUCguaagug (SEQ ID NO: 2332), GUCgugagug (SEQ ID NO: 2333), GUCgugaguu (SEQ ID NO: 2334), GUGgcaagua (SEQ ID NO: 2335), GUGgcuugua (SEQ ID NO: 2336), GUGguaaaau (SEQ ID NO: 2337), GUGguaaaga (SEQ ID NO: 2338), GUGguaaauu (SEQ ID NO: 2339), GUGguaacau (SEQ ID NO: 2340), GUGguaacua (SEQ ID NO: 2341), GUGguaagaa (SEQ ID NO: 2342), GUGguaagac (SEQ ID NO: 2343), GUGguaagag (SEQ ID NO: 2344), GUGguaagau (SEQ ID NO: 2345), GUGguaagca (SEQ ID NO: 2346), GUGguaagcg (SEQ ID NO: 2347), GUGguaagcu (SEQ ID NO: 2348), GUGguaagga (SEQ ID NO: 2349), GUGguaaggc (SEQ ID NO: 2350), GUGguaagua (SEQ ID NO: 2351), GUGguaaguc (SEQ ID NO: 2352), GUGguaagug (SEQ ID NO: 2353), GUGguaaguu (SEQ ID NO: 2354), GUGguaauga (SEQ ID NO: 2355), GUGguaauuc (SEQ ID NO: 2356), GUGguaauuu (SEQ ID NO: 2357), GUGguacaug (SEQ ID NO: 2358), GUGguacgau (SEQ ID NO: 2359), GUGguacuau (SEQ ID NO: 2360), GUGguacuug (SEQ ID NO: 2361), GUGguagaua (SEQ ID NO: 2362), GUGguagcgc (SEQ ID NO: 2363), GUGguaggga (SEQ ID NO: 2364), GUGguagguc (SEQ ID NO: 2365), GUGguaggug (SEQ ID NO: 2366), GUGguagguu (SEQ ID NO: 2367), GUGguauaaa (SEQ ID NO: 2368), GUGguaucuc (SEQ ID NO: 2369), GUGguaugaa (SEQ ID NO: 2370), GUGguaugau (SEQ ID NO: 2371), GUGguaugca (SEQ ID NO: 2372), GUGguaugua (SEQ ID NO: 2373), GUGguauguu (SEQ ID NO: 2374), GUGguccgug (SEQ ID NO: 2375), GUGgucuggc (SEQ ID NO: 2376), GUGgugaaac (SEQ ID NO: 2377), GUGgugagaa (SEQ ID NO: 2378), GUGgugagau (SEQ ID NO: 2379), GUGgugagca (SEQ ID NO: 2380), GUGgugagcu (SEQ ID NO: 2381), GUGgugagga (SEQ ID NO: 2382), GUGgugaggc (SEQ ID NO: 2383), GUGgugagug (SEQ ID NO: 2384), GUGgugaguu (SEQ ID NO: 2385), GUGgugauua (SEQ ID NO: 2386), GUGgugauuc (SEQ ID NO: 2387), GUGgugcgau (SEQ ID NO: 2388), GUGgugcuua (SEQ ID NO: 2389), GUGgugggaa (SEQ ID NO: 2390), GUGgugggua (SEQ ID NO: 2391), GUGguggguc (SEQ ID NO: 2392), GUGguguccg (SEQ ID NO: 2393), GUGguuagca (SEQ ID NO: 2394), GUGguuaggu (SEQ ID NO: 2395), GUGguuagug (SEQ ID NO: 2396), GUGguuugca (SEQ ID NO: 2397), GUGguuugua (SEQ ID NO: 2398), GUUguaaggu (SEQ ID NO: 2399), GUUguaagua (SEQ ID NO: 2400), GUUguaaguc (SEQ ID NO: 2401), GUUguaaguu (SEQ ID NO: 2402), GUUguaccac (SEQ ID NO: 2403), GUUguagcgu (SEQ ID NO: 2404), GUUguaugug (SEQ ID NO: 2405), GUUguauguu (SEQ ID NO: 2406), GUUgucugug (SEQ ID NO: 2407), GUUgugagcu (SEQ ID NO: 2408), GUUgugagug (SEQ ID NO: 2409), GUUgugaguu (SEQ ID NO: 2410), GUUgugggua (SEQ ID NO: 2411), GUUguggguu (SEQ ID NO: 2412), UAAguaaaug (SEQ ID NO: 2413), UAAguaacua (SEQ ID NO: 2414), UAAguaagaa (SEQ ID NO: 2415), UAAguaagag (SEQ ID NO: 2416), UAAguaagau (SEQ ID NO: 2417), UAAguaagca (SEQ ID NO: 2418), UAAguaagcu (SEQ ID NO: 2419), UAAguaagga (SEQ ID NO: 2420), UAAguaaggu (SEQ ID NO: 2421), UAAguaagua (SEQ ID NO: 2422), UAAguaaguc (SEQ ID NO: 2423), UAAguaagug (SEQ ID NO: 2424), UAAguaaguu (SEQ ID NO: 2425), UAAguaauaa (SEQ ID NO: 2426), UAAguacuag (SEQ ID NO: 2427), UAAguaguuu (SEQ ID NO: 2428), UAAguauaaa (SEQ ID NO: 2429), UAAguauaca (SEQ ID NO: 2430), UAAguaugua (SEQ ID NO: 2431), UAAguauuau (SEQ ID NO: 2432), UAAguauuuu (SEQ ID NO: 2433), UAAgucuuuu (SEQ ID NO: 2434), UAAgugagac (SEQ ID NO: 2435), UAAgugagga (SEQ ID NO: 2436), UAAgugaggg (SEQ ID NO: 2437), UAAgugagua (SEQ ID NO: 2438), UAAgugaguc (SEQ ID NO: 2439), UAAgugagug (SEQ ID NO: 2440), UAAgugaguu (SEQ ID NO: 2441), UAAgugaucc (SEQ ID NO: 2442), UAAgugauuc (SEQ ID NO: 2443), UAAgugcgug (SEQ ID NO: 2444), UAAguuaagu (SEQ ID NO: 2445), UAAguuccag (SEQ ID NO: 2446), UAAguucuuu (SEQ ID NO: 2447), UAAguuguaa (SEQ ID NO: 2448), UAAguuguau (SEQ ID NO: 2449), UAAguuuguu (SEQ ID NO: 2450), UACguaacug (SEQ ID NO: 2451), UACguaagaa (SEQ ID NO: 2452), UACguaagau (SEQ ID NO: 2453), UACguaagua (SEQ ID NO: 2454), UACguaagug (SEQ ID NO: 2455), UACguauccu (SEQ ID NO: 2456), UACgucuggc (SEQ ID NO: 2457), UACgugacca (SEQ ID NO: 2458), UAGgcaagac (SEQ ID NO: 2459), UAGgcaaguc (SEQ ID NO: 2460), UAGgcagguc (SEQ ID NO: 2461), UAGgcgugug (SEQ ID NO: 2462), UAGguaaaaa (SEQ ID NO: 2463), UAGguaaaac (SEQ ID NO: 2464), UAGguaaaag (SEQ ID NO: 2465), UAGguaaaau (SEQ ID NO: 2466), UAGguaaaca (SEQ ID NO: 2467), UAGguaaaga (SEQ ID NO: 2468), UAGguaaaua (SEQ ID NO: 2469), UAGguaaauc (SEQ ID NO: 2470), UAGguaaaug (SEQ ID NO: 2471), UAGguaaauu (SEQ ID NO: 2472), UAGguaacac (SEQ ID NO: 2473), UAGguaacag (SEQ ID NO: 2474), UAGguaacau (SEQ ID NO: 2475), UAGguaacca (SEQ ID NO: 2476), UAGguaacgg (SEQ ID NO: 2477), UAGguaacua (SEQ ID NO: 2478), UAGguaacuc (SEQ ID NO: 2479), UAGguaacug (SEQ ID NO: 2480), UAGguaacuu (SEQ ID NO: 2481), UAGguaagac (SEQ ID NO: 2482), UAGguaagag (SEQ ID NO: 2483), UAGguaagau (SEQ ID NO: 2484), UAGguaagca (SEQ ID NO: 2485), UAGguaagcc (SEQ ID NO: 2486), UAGguaagcu (SEQ ID NO: 2487), UAGguaagga (SEQ ID NO: 2488), UAGguaaggc (SEQ ID NO: 2489), UAGguaaggg (SEQ ID NO: 2490), UAGguaagua (SEQ ID NO: 2491), UAGguaaguc (SEQ ID NO: 2492), UAGguaagug (SEQ ID NO: 2493), UAGguaaguu (SEQ ID NO: 2494), UAGguaauag (SEQ ID NO: 2495), UAGguaauau (SEQ ID NO: 2496), UAGguaaucu (SEQ ID NO: 2497), UAGguaauga (SEQ ID NO: 2498), UAGguaaugg (SEQ ID NO: 2499), UAGguaaugu (SEQ ID NO: 2500), UAGguaauua (SEQ ID NO: 2501), UAGguaauuc (SEQ ID NO: 2502), UAGguaauuu (SEQ ID NO: 2503), UAGguacagc (SEQ ID NO: 2504), UAGguacagu (SEQ ID NO: 2505), UAGguacauu (SEQ ID NO: 2506), UAGguaccag (SEQ ID NO: 2507), UAGguaccua (SEQ ID NO: 2508), UAGguaccuu (SEQ ID NO: 2509), UAGguacgag (SEQ ID NO: 2510), UAGguacgua (SEQ ID NO: 2511), UAGguacguu (SEQ ID NO: 2512), UAGguacuau (SEQ ID NO: 2513), UAGguacuga (SEQ ID NO: 2514), UAGguacugg (SEQ ID NO: 2515), UAGguacuuc (SEQ ID NO: 2516), UAGguacuuu (SEQ ID NO: 2517), UAGguagcgg (SEQ ID NO: 2518), UAGguaggaa (SEQ ID NO: 2519), UAGguaggac (SEQ ID NO: 2520), UAGguaggau (SEQ ID NO: 2521), UAGguaggga (SEQ ID NO: 2522), UAGguagggg (SEQ ID NO: 2523), UAGguaggua (SEQ ID NO: 2524), UAGguagguc (SEQ ID NO: 2525), UAGguaggug (SEQ ID NO: 2526), UAGguagguu (SEQ ID NO: 2527), UAGguaguaa (SEQ ID NO: 2528), UAGguagucu (SEQ ID NO: 2529), UAGguagugg (SEQ ID NO: 2530), UAGguagugu (SEQ ID NO: 2531), UAGguaguuu (SEQ ID NO: 2532), UAGguauaaa (SEQ ID NO: 2533), UAGguauaac (SEQ ID NO: 2534), UAGguauaag (SEQ ID NO: 2535), UAGguauaau (SEQ ID NO: 2536), UAGguauaca (SEQ ID NO: 2537), UAGguauacu (SEQ ID NO: 2538), UAGguauaua (SEQ ID NO: 2539), UAGguauauc (SEQ ID NO: 2540), UAGguauauu (SEQ ID NO: 2541), UAGguaucag (SEQ ID NO: 2542), UAGguaucua (SEQ ID NO: 2543), UAGguaucuc (SEQ ID NO: 2544), UAGguaugaa (SEQ ID NO: 2545), UAGguaugag (SEQ ID NO: 2546), UAGguaugca (SEQ ID NO: 2547), UAGguaugga (SEQ ID NO: 2548), UAGguauggc (SEQ ID NO: 2549), UAGguauggu (SEQ ID NO: 2550), UAGguaugua (SEQ ID NO: 2551), UAGguauguc (SEQ ID NO: 2552), UAGguaugug (SEQ ID NO: 2553), UAGguauguu (SEQ ID NO: 2554), UAGguauuaa (SEQ ID NO: 2555), UAGguauuac (SEQ ID NO: 2556), UAGguauuau (SEQ ID NO: 2557), UAGguauuca (SEQ ID NO: 2558), UAGguauucc (SEQ ID NO: 2559), UAGguauucu (SEQ ID NO: 2560), UAGguauuga (SEQ ID NO: 2561), UAGguauuua (SEQ ID NO: 2562), UAGguauuuc (SEQ ID NO: 2563), UAGguauuuu (SEQ ID NO: 2564), UAGgucacuc (SEQ ID NO: 2565), UAGgucagcu (SEQ ID NO: 2566), UAGgucaggu (SEQ ID NO: 2567), UAGgucagua (SEQ ID NO: 2568), UAGgucagug (SEQ ID NO: 2569), UAGgucaguu (SEQ ID NO: 2570), UAGgucaucu (SEQ ID NO: 2571), UAGgucauug (SEQ ID NO: 2572), UAGguccaau (SEQ ID NO: 2573), UAGguccugu (SEQ ID NO: 2574), UAGgucucaa (SEQ ID NO: 2575), UAGgucucgc (SEQ ID NO: 2576), UAGgucuggc (SEQ ID NO: 2577), UAGgucuguc (SEQ ID NO: 2578), UAGgucugug (SEQ ID NO: 2579), UAGgugaagu (SEQ ID NO: 2580), UAGgugaaua (SEQ ID NO: 2581), UAGgugaaug (SEQ ID NO: 2582), UAGgugaauu (SEQ ID NO: 2583), UAGgugacau (SEQ ID NO: 2584), UAGgugacca (SEQ ID NO: 2585), UAGgugacua (SEQ ID NO: 2586), UAGgugagaa (SEQ ID NO: 2587), UAGgugagac (SEQ ID NO: 2588), UAGgugagag (SEQ ID NO: 2589), UAGgugagau (SEQ ID NO: 2590), UAGgugagcc (SEQ ID NO: 2591), UAGgugagcu (SEQ ID NO: 2592), UAGgugagga (SEQ ID NO: 2593), UAGgugaggc (SEQ ID NO: 2594), UAGgugaggu (SEQ ID NO: 2595), UAGgugagua (SEQ ID NO: 2596), UAGgugaguc (SEQ ID NO: 2597), UAGgugagug (SEQ ID NO: 2598), UAGgugauca (SEQ ID NO: 2599), UAGgugauuc (SEQ ID NO: 2600), UAGgugauuu (SEQ ID NO: 2601), UAGgugcaua (SEQ ID NO: 2602), UAGgugcauc (SEQ ID NO: 2603), UAGgugccgu (SEQ ID NO: 2604), UAGgugccug (SEQ ID NO: 2605), UAGgugcgca (SEQ ID NO: 2606), UAGgugcgua (SEQ ID NO: 2607), UAGgugcgug (SEQ ID NO: 2608), UAGgugcuga (SEQ ID NO: 2609), UAGguggaua (SEQ ID NO: 2610), UAGgugggaa (SEQ ID NO: 2611), UAGgugggac (SEQ ID NO: 2612), UAGgugggag (SEQ ID NO: 2613), UAGgugggau (SEQ ID NO: 2614), UAGgugggcc (SEQ ID NO: 2615), UAGgugggcu (SEQ ID NO: 2616), UAGguggguu (SEQ ID NO: 2617), UAGguggugu (SEQ ID NO: 2618), UAGguguaaa (SEQ ID NO: 2619), UAGgugugaa (SEQ ID NO: 2620), UAGgugugag (SEQ ID NO: 2621), UAGgugugca (SEQ ID NO: 2622), UAGgugugcc (SEQ ID NO: 2623), UAGgugugcg (SEQ ID NO: 2624), UAGguguggu (SEQ ID NO: 2625), UAGgugugua (SEQ ID NO: 2626), UAGgugugug (SEQ ID NO: 2627), UAGguguugg (SEQ ID NO: 2628), UAGguuaagc (SEQ ID NO: 2629), UAGguuagac (SEQ ID NO: 2630), UAGguuagcc (SEQ ID NO: 2631), UAGguuaggc (SEQ ID NO: 2632), UAGguuagua (SEQ ID NO: 2633), UAGguuaguc (SEQ ID NO: 2634), UAGguuagug (SEQ ID NO: 2635), UAGguucccc (SEQ ID NO: 2636), UAGguucuac (SEQ ID NO: 2637), UAGguuggua (SEQ ID NO: 2638), UAGguugguu (SEQ ID NO: 2639), UAGguugucc (SEQ ID NO: 2640), UAGguuuauu (SEQ ID NO: 2641), UAGguuugcc (SEQ ID NO: 2642), UAGguuugua (SEQ ID NO: 2643), UAGguuuguc (SEQ ID NO: 2644), UAGguuugug (SEQ ID NO: 2645), UAGguuuguu (SEQ ID NO: 2646), UAGguuuuuc (SEQ ID NO: 2647), UAGguuuuug (SEQ ID NO: 2648), UAUguaagaa (SEQ ID NO: 2649), UAUguaagau (SEQ ID NO: 2650), UAUguaagca (SEQ ID NO: 2651), UAUguaagcc (SEQ ID NO: 2652), UAUguaagua (SEQ ID NO: 2653), UAUguaaguc (SEQ ID NO: 2654), UAUguaagug (SEQ ID NO: 2655), UAUguaaguu (SEQ ID NO: 2656), UAUguacgug (SEQ ID NO: 2657), UAUguacguu (SEQ ID NO: 2658), UAUguagguc (SEQ ID NO: 2659), UAUguagguu (SEQ ID NO: 2660), UAUguauccu (SEQ ID NO: 2661), UAUguaucuc (SEQ ID NO: 2662), UAUguaugua (SEQ ID NO: 2663), UAUguauguc (SEQ ID NO: 2664), UAUguaugug (SEQ ID NO: 2665), UAUguauuau (SEQ ID NO: 2666), UAUgucagaa (SEQ ID NO: 2667), UAUgucugua (SEQ ID NO: 2668), UAUgugaaua (SEQ ID NO: 2669), UAUgugacag (SEQ ID NO: 2670), UAUgugagua (SEQ ID NO: 2671), UAUgugagug (SEQ ID NO: 2672), UAUgugaguu (SEQ ID NO: 2673), UAUgugggca (SEQ ID NO: 2674), UAUgugugua (SEQ ID NO: 2675), UAUguguuua (SEQ ID NO: 2676), UAUguuuugu (SEQ ID NO: 2677), UCAgcgacau (SEQ ID NO: 2678), UCAguaaaau (SEQ ID NO: 2679), UCAguaaaua (SEQ ID NO: 2680), UCAguaacug (SEQ ID NO: 2681), UCAguaagaa (SEQ ID NO: 2682), UCAguaagag (SEQ ID NO: 2683), UCAguaagau (SEQ ID NO: 2684), UCAguaagca (SEQ ID NO: 2685), UCAguaagcc (SEQ ID NO: 2686), UCAguaagcu (SEQ ID NO: 2687), UCAguaaggg (SEQ ID NO: 2688), UCAguaagua (SEQ ID NO: 2689), UCAguaaguc (SEQ ID NO: 2690), UCAguaagug (SEQ ID NO: 2691), UCAguaaguu (SEQ ID NO: 2692), UCAguaucuu (SEQ ID NO: 2693), UCAguaugga (SEQ ID NO: 2694), UCAguauggu (SEQ ID NO: 2695), UCAgucccca (SEQ ID NO: 2696), UCAgugagca (SEQ ID NO: 2697), UCAgugagcu (SEQ ID NO: 2698), UCAgugagua (SEQ ID NO: 2699), UCAgugagug (SEQ ID NO: 2700), UCAgugaguu (SEQ ID NO: 2701), UCAgugauug (SEQ ID NO: 2702), UCAguggugug (SEQ ID NO: 2703), UCAguugagc (SEQ ID NO: 2704), UCAguugauu (SEQ ID NO: 2705), UCAguuuagu (SEQ ID NO: 2706), UCCguaagca (SEQ ID NO: 2707), UCCguaagcu (SEQ ID NO: 2708), UCCguaaguc (SEQ ID NO: 2709), UCCguaagug (SEQ ID NO: 2710), UCCguaauag (SEQ ID NO: 2711), UCCguacuua (SEQ ID NO: 2712), UCCguaugua (SEQ ID NO: 2713), UCCguauguu (SEQ ID NO: 2714), UCCgugagau (SEQ ID NO: 2715), UCCgugaguc (SEQ ID NO: 2716), UCGguaaauu (SEQ ID NO: 2717), UCGguaagag (SEQ ID NO: 2718), UCGguaagcu (SEQ ID NO: 2719), UCGguacauc (SEQ ID NO: 2720), UCGguacucc (SEQ ID NO: 2721), UCGguagacc (SEQ ID NO: 2722), UCGguagguu (SEQ ID NO: 2723), UCGguaguaa (SEQ ID NO: 2724), UCGguaugug (SEQ ID NO: 2725), UCGguauguu (SEQ ID NO: 2726), UCGguauuga (SEQ ID NO: 2727), UCGgucagua (SEQ ID NO: 2728), UCGgucuuag (SEQ ID NO: 2729), UCGgugaagu (SEQ ID NO: 2730), UCGgugagaa (SEQ ID NO: 2731), UCGgugagca (SEQ ID NO: 2732), UCGgugaggc (SEQ ID NO: 2733), UCGgugagua (SEQ ID NO: 2734), UCGgugcgcu (SEQ ID NO: 2735), UCGgugcuuu (SEQ ID NO: 2736), UCGgugguuu (SEQ ID NO: 2737), UCGguuagcu (SEQ ID NO: 2738), UCUguaaaag (SEQ ID NO: 2739), UCUguaagaa (SEQ ID NO: 2740), UCUguaagau (SEQ ID NO: 2741), UCUguaagca (SEQ ID NO: 2742), UCUguaagcu (SEQ ID NO: 2743), UCUguaagua (SEQ ID NO: 2744), UCUguaaguc (SEQ ID NO: 2745), UCUguaagug (SEQ ID NO: 2746), UCUguaaguu (SEQ ID NO: 2747), UCUguaauaa (SEQ ID NO: 2748), UCUguaauga (SEQ ID NO: 2749), UCUguaaugu (SEQ ID NO: 2750), UCUguaggua (SEQ ID NO: 2751), UCUguagguu (SEQ ID NO: 2752), UCUguauaua (SEQ ID NO: 2753), UCUguaugac (SEQ ID NO: 2754), UCUguaugua (SEQ ID NO: 2755), UCUguccucg (SEQ ID NO: 2756), UCUgugagag (SEQ ID NO: 2757), UCUgugagcu (SEQ ID NO: 2758), UCUgugagga (SEQ ID NO: 2759), UCUgugagua (SEQ ID NO: 2760), UCUgugaguc (SEQ ID NO: 2761), UCUgugagug (SEQ ID NO: 2762), UCUgugaguu (SEQ ID NO: 2763), UCUgugcgua (SEQ ID NO: 2764), UCUgugugag (SEQ ID NO: 2765), UGAguaacuu (SEQ ID NO: 2766), UGAguaagau (SEQ ID NO: 2767), UGAguaagca (SEQ ID NO: 2768), UGAguaagcu (SEQ ID NO: 2769), UGAguaaggc (SEQ ID NO: 2770), UGAguaaggu (SEQ ID NO: 2771), UGAguaagua (SEQ ID NO: 2772), UGAguaaguc (SEQ ID NO: 2773), UGAguaagug (SEQ ID NO: 2774), UGAguaaguu (SEQ ID NO: 2775), UGAguaaucc (SEQ ID NO: 2776), UGAguaauua (SEQ ID NO: 2777), UGAguacagu (SEQ ID NO: 2778), UGAguacgua (SEQ ID NO: 2779), UGAguacguu (SEQ ID NO: 2780), UGAguacugu (SEQ ID NO: 2781), UGAguagcug (SEQ ID NO: 2782), UGAguaggua (SEQ ID NO: 2783), UGAguauaaa (SEQ ID NO: 2784), UGAguaugcu (SEQ ID NO: 2785), UGAguaugga (SEQ ID NO: 2786), UGAguaugua (SEQ ID NO: 2787), UGAguauguc (SEQ ID NO: 2788), UGAguauguu (SEQ ID NO: 2789), UGAgucagag (SEQ ID NO: 2790), UGAgucuacg (SEQ ID NO: 2791), UGAgugaaua (SEQ ID NO: 2792), UGAgugaauu (SEQ ID NO: 2793), UGAgugagaa (SEQ ID NO: 2794), UGAgugagau (SEQ ID NO: 2795), UGAgugagca (SEQ ID NO: 2796), UGAgugagcc (SEQ ID NO: 2797), UGAgugagga (SEQ ID NO: 2798), UGAgugagua (SEQ ID NO: 2799), UGAgugagug (SEQ ID NO: 2800), UGAgugaguu (SEQ ID NO: 2801), UGAgugggaa (SEQ ID NO: 2802), UGAguuaaga (SEQ ID NO: 2803), UGAguuaaug (SEQ ID NO: 2804), UGAguuacgg (SEQ ID NO: 2805), UGAguuaggu (SEQ ID NO: 2806), UGAguucuau (SEQ ID NO: 2807), UGAguugguu (SEQ ID NO: 2808), UGAguuguag (SEQ ID NO: 2809), UGAguuuauc (SEQ ID NO: 2810), UGCguaaguc (SEQ ID NO: 2811), UGCguaagug (SEQ ID NO: 2812), UGCguacggc (SEQ ID NO: 2813), UGCguacggg (SEQ ID NO: 2814), UGCguaugua (SEQ ID NO: 2815), UGGgcaaguc (SEQ ID NO: 2816), UGGgcaagug (SEQ ID NO: 2817), UGGgcacauc (SEQ ID NO: 2818), UGGgccacgu (SEQ ID NO: 2819), UGGgccccgg (SEQ ID NO: 2820), UGGguaaaau (SEQ ID NO: 2821), UGGguaaagc (SEQ ID NO: 2822), UGGguaaagg (SEQ ID NO: 2823), UGGguaaagu (SEQ ID NO: 2824), UGGguaaaua (SEQ ID NO: 2825), UGGguaaaug (SEQ ID NO: 2826), UGGguaaauu (SEQ ID NO: 2827), UGGguaacag (SEQ ID NO: 2828), UGGguaacau (SEQ ID NO: 2829), UGGguaacua (SEQ ID NO: 2830), UGGguaacuu (SEQ ID NO: 2831), UGGguaagaa (SEQ ID NO: 2832), UGGguaagac (SEQ ID NO: 2833), UGGguaagag (SEQ ID NO: 2834), UGGguaagau (SEQ ID NO: 2835), UGGguaagca (SEQ ID NO: 2836), UGGguaagcc (SEQ ID NO: 2837), UGGguaagcu (SEQ ID NO: 2838), UGGguaaggg (SEQ ID NO: 2839), UGGguaaggu (SEQ ID NO: 2840), UGGguaagua (SEQ ID NO: 2841), UGGguaaguc (SEQ ID NO: 2842), UGGguaagug (SEQ ID NO: 2843), UGGguaaguu (SEQ ID NO: 2844), UGGguaaugu (SEQ ID NO: 2845), UGGguaauua (SEQ ID NO: 2846), UGGguaauuu (SEQ ID NO: 2847), UGGguacaaa (SEQ ID NO: 2848), UGGguacagu (SEQ ID NO: 2849), UGGguacuac (SEQ ID NO: 2850), UGGguaggga (SEQ ID NO: 2851), UGGguagguc (SEQ ID NO: 2852), UGGguaggug (SEQ ID NO: 2853), UGGguagguu (SEQ ID NO: 2854), UGGguaguua (SEQ ID NO: 2855), UGGguauagu (SEQ ID NO: 2856), UGGguaugaa (SEQ ID NO: 2857), UGGguaugac (SEQ ID NO: 2858), UGGguaugag (SEQ ID NO: 2859), UGGguaugua (SEQ ID NO: 2860), UGGguauguc (SEQ ID NO: 2861), UGGguaugug (SEQ ID NO: 2862), UGGguauguu (SEQ ID NO: 2863), UGGguauuug (SEQ ID NO: 2864), UGGgucuuug (SEQ ID NO: 2865), UGGgugaccu (SEQ ID NO: 2866), UGGgugacua (SEQ ID NO: 2867), UGGgugagac (SEQ ID NO: 2868), UGGgugagag (SEQ ID NO: 2869), UGGgugagca (SEQ ID NO: 2870), UGGgugagcc (SEQ ID NO: 2871), UGGgugagga (SEQ ID NO: 2872), UGGgugaggc (SEQ ID NO: 2873), UGGgugaggg (SEQ ID NO: 2874), UGGgugagua (SEQ ID NO: 2875), UGGgugaguc (SEQ ID NO: 2876), UGGgugagug (SEQ ID NO: 2877), UGGgugaguu (SEQ ID NO: 2878), UGGgugcgug (SEQ ID NO: 2879), UGGguggagg (SEQ ID NO: 2880), UGGguggcuu (SEQ ID NO: 2881), UGGguggggg (SEQ ID NO: 2882), UGGgugggua (SEQ ID NO: 2883), UGGguggguc (SEQ ID NO: 2884), UGGgugggug (SEQ ID NO: 2885), UGGguggguu (SEQ ID NO: 2886), UGGgugugga (SEQ ID NO: 2887), UGGgugugc (SEQ ID NO: 2888), UGGgugugug (SEQ ID NO: 2889), UGGguguguu (SEQ ID NO: 2890), UGGguguuua (SEQ ID NO: 2891), UGGguuaaug (SEQ ID NO: 2892), UGGguuaguc (SEQ ID NO: 2893), UGGguuagug (SEQ ID NO: 2894), UGGguuaguu (SEQ ID NO: 2895), UGGguucaag (SEQ ID NO: 2896), UGGguucgua (SEQ ID NO: 2897), UGGguuggug (SEQ ID NO: 2898), UGGguuuaag (SEQ ID NO: 2899), UGGguuugua (SEQ ID NO: 2900), UGUgcaagua (SEQ ID NO: 2901), UGUguaaaua (SEQ ID NO: 2902), UGUguaagaa (SEQ ID NO: 2903), UGUguaagac (SEQ ID NO: 2904), UGUguaagag (SEQ ID NO: 2905), UGUguaaggu (SEQ ID NO: 2906), UGUguaagua (SEQ ID NO: 2907), UGUguaaguc (SEQ ID NO: 2908), UGUguaaguu (SEQ ID NO: 2909), UGUguacuuc (SEQ ID NO: 2910), UGUguaggcg (SEQ ID NO: 2911), UGUguaggua (SEQ ID NO: 2912), UGUguaguua (SEQ ID NO: 2913), UGUguaugug (SEQ ID NO: 2914), UGUgucagua (SEQ ID NO: 2915), UGUgucugua (SEQ ID NO: 2916), UGUgucuguc (SEQ ID NO: 2917), UGUgugaccc (SEQ ID NO: 2918), UGUgugagau (SEQ ID NO: 2919), UGUgugagca (SEQ ID NO: 2920), UGUgugagcc (SEQ ID NO: 2921), UGUgugagua (SEQ ID NO: 2922), UGUgugaguc (SEQ ID NO: 2923), UGUgugagug (SEQ ID NO: 2924), UGUgugcgug (SEQ ID NO: 2925), UGUgugggug (SEQ ID NO: 2926), UGUguggguu (SEQ ID NO: 2927), UGUgugugag (SEQ ID NO: 2928), UGUguguucu (SEQ ID NO: 2929), UGUguuuaga (SEQ ID NO: 2930), UUAguaaaua (SEQ ID NO: 2931), UUAguaagaa (SEQ ID NO: 2932), UUAguaagua (SEQ ID NO: 2933), UUAguaagug (SEQ ID NO: 2934), UUAguaaguu (SEQ ID NO: 2935), UUAguaggug (SEQ ID NO: 2936), UUAgugagca (SEQ ID NO: 2937), UUAgugaguu (SEQ ID NO: 2938), UUAguuaagu (SEQ ID NO: 2939), UUCguaaguc (SEQ ID NO: 2940), UUCguaaguu (SEQ ID NO: 2941), UUCguaauua (SEQ ID NO: 2942), UUCgugagua (SEQ ID NO: 2943), UUCgugaguu (SEQ ID NO: 2944), UUGgcaagug (SEQ ID NO: 2945), UUGgccgagu (SEQ ID NO: 2946), UUGguaaaaa (SEQ ID NO: 2947), UUGguaaaau (SEQ ID NO: 2948), UUGguaaaga (SEQ ID NO: 2949), UUGguaaagg (SEQ ID NO: 2950), UUGguaaagu (SEQ ID NO: 2951), UUGguaaauc (SEQ ID NO: 2952), UUGguaaaug (SEQ ID NO: 2953), UUGguaaauu (SEQ ID NO: 2954), UUGguaacug (SEQ ID NO: 2955), UUGguaacuu (SEQ ID NO: 2956), UUGguaagaa (SEQ ID NO: 2957), UUGguaagag (SEQ ID NO: 2958), UUGguaagcu (SEQ ID NO: 2959), UUGguaagga (SEQ ID NO: 2960), UUGguaaggg (SEQ ID NO: 2961), UUGguaagua (SEQ ID NO: 2962), UUGguaagug (SEQ ID NO: 2963), UUGguaaguu (SEQ ID NO: 2964), UUGguaauac (SEQ ID NO: 2965), UUGguaauca (SEQ ID NO: 2966), UUGguaaugc (SEQ ID NO: 2967), UUGguaaugu (SEQ ID NO: 2968), UUGguaauug (SEQ ID NO: 2969), UUGguaauuu (SEQ ID NO: 2970), UUGguacaua (SEQ ID NO: 2971), UUGguacgug (SEQ ID NO: 2972), UUGguagagg (SEQ ID NO: 2973), UUGguaggac (SEQ ID NO: 2974), UUGguaggcg (SEQ ID NO: 2975), UUGguaggcu (SEQ ID NO: 2976), UUGguaggga (SEQ ID NO: 2977), UUGguaggua (SEQ ID NO: 2978), UUGguagguc (SEQ ID NO: 2979), UUGguaggug (SEQ ID NO: 2980), UUGguauaaa (SEQ ID NO: 2981), UUGguauaca (SEQ ID NO: 2982), UUGguauauu (SEQ ID NO: 2983), UUGguaucua (SEQ ID NO: 2984), UUGguaucuc (SEQ ID NO: 2985), UUGguaugca (SEQ ID NO: 2986), UUGguaugua (SEQ ID NO: 2987), UUGguaugug (SEQ ID NO: 2988), UUGguauguu (SEQ ID NO: 2989), UUGguauugu (SEQ ID NO: 2990), UUGguauuua (SEQ ID NO: 2991), UUGguauuuu (SEQ ID NO: 2992), UUGgucagaa (SEQ ID NO: 2993), UUGgucagua (SEQ ID NO: 2994), UUGgucucug (SEQ ID NO: 2995), UUGgucugca (SEQ ID NO: 2996), UUGgugaaaa (SEQ ID NO: 2997), UUGgugacug (SEQ ID NO: 2998), UUGgugagac (SEQ ID NO: 2999), UUGgugagau (SEQ ID NO: 3000), UUGgugagca (SEQ ID NO: 3001), UUGgugagga (SEQ ID NO: 3002), UUGgugaggg (SEQ ID NO: 3003), UUGgugagua (SEQ ID NO: 3004), UUGgugaguc (SEQ ID NO: 3005), UUGgugagug (SEQ ID NO: 3006), UUGgugaguu (SEQ ID NO: 3007), UUGgugaugg (SEQ ID NO: 3008), UUGgugauua (SEQ ID NO: 3009), UUGgugauug (SEQ ID NO: 3010), UUGgugcaca (SEQ ID NO: 3011), UUGgugggaa (SEQ ID NO: 3012), UUGgugggc (SEQ ID NO: 3013), UUGgugggua (SEQ ID NO: 3014), UUGguggguc (SEQ ID NO: 3015), UUGgugggug (SEQ ID NO: 3016), UUGguggguu (SEQ ID NO: 3017), UUGgugguggu (SEQ ID NO: 3018), UUGgugugc (SEQ ID NO: 3019), UUGgugugug (SEQ ID NO: 3020), UUGguguguu (SEQ ID NO: 3021), UUGguuaagu (SEQ ID NO: 3022), UUGguuagca (SEQ ID NO: 3023), UUGguuagug (SEQ ID NO: 3024), UUGguuaguu (SEQ ID NO: 3025), UUGguuggga (SEQ ID NO: 3026), UUGguugguu (SEQ ID NO: 3027), UUGguuugua (SEQ ID NO: 3028), UUGguuuguc (SEQ ID NO: 3029), UUUgcaagug (SEQ ID NO: 3030), UUUguaaaua (SEQ ID NO: 3031), UUUguaaaug (SEQ ID NO: 3032), UUUguaagaa (SEQ ID NO: 3033), UUUguaagac (SEQ ID NO: 3034), UUUguaagag (SEQ ID NO: 3035), UUUguaagca (SEQ ID NO: 3036), UUUguaaggu (SEQ ID NO: 3037), UUUguaagua (SEQ ID NO: 3038), UUUguaaguc (SEQ ID NO: 3039), UUUguaagug (SEQ ID NO: 3040), UUUguaaguu (SEQ ID NO: 3041), UUUguaauuu (SEQ ID NO: 3042), UUUguacagg (SEQ ID NO: 3043), UUUguacgug (SEQ ID NO: 3044), UUUguacuag (SEQ ID NO: 3045), UUUguacugu (SEQ ID NO: 3046), UUUguagguu (SEQ ID NO: 3047), UUUguauccu (SEQ ID NO: 3048), UUUguauguu (SEQ ID NO: 3049), UUUgugagca (SEQ ID NO: 3050), UUUgugagug (SEQ ID NO: 3051), UUUgugcguc (SEQ ID NO: 3052), UUUguguguc (SEQ ID NO: 3053), and uGGguaccug (SEQ ID NO: 3054).

Additional exemplary gene sequences and splice site sequences (e.g., 5' splice site sequences) include AAGgcaagau (SEQ ID NO: 96), AUGguaugug (SEQ ID NO: 937), GGGgugaggc (SEQ ID NO: 2281), CAGguaggug (SEQ ID NO: 1222), AAGgucagua (SEQ ID NO: 293), AAGguuagag (SEQ ID NO: 3055), AUGgcacuua (SEQ ID NO: 3056), UAAguaaguc (SEQ ID NO: 2423), UGG-gugagcu (SEQ ID NO: 3057), CGAgcugggc (SEQ ID NO: 3058), AAAgcacccc (SEQ ID NO: 3059), UAGguggggg (SEQ ID NO: 3060), AGAguaacgu (SEQ ID NO: 3061), UCGgugaugu (SEQ ID NO: 3062), AAUgucaguu (SEQ ID NO: 516), AGGgucugag (SEQ ID NO: 3063), GAGgugacug (SEQ ID NO: 3064), AUGguagguu (SEQ ID NO: 3065), GAGgucuguc (SEQ ID NO: 2000), CAGguaugug (SEQ ID NO: 1260), CAAguacugc (SEQ ID NO: 3066), CACgugcgua (SEQ ID NO: 3067), CCGgugagcu (SEQ ID NO: 3068), CAGguacuuc (SEQ ID NO: 3069), CAGgcgagag (SEQ ID NO: 1115), GAAgcaagua (SEQ ID NO: 3070), AGGgugagca (SEQ ID NO: 789), CAGgcaaguc (SEQ ID NO: 3071), AAGgugaggc (SEQ ID NO: 344), CAGguaagua (SEQ ID NO: 1147), CCAguugggu (SEQ ID NO: 3072), AAGguguggg (SEQ ID NO: 3073), CAGguug-gag (SEQ ID NO: 1484), CCGguaugaa (SEQ ID NO: 3074), UGGguaaugu (SEQ ID NO: 2845), CAGgugaggu (SEQ ID NO: 1344), AGAguaauag (SEQ ID NO: 3075), CAG-guaugag (SEQ ID NO: 1249), AUGguaaguu (SEQ ID NO: 901), UUGgugggcc (SEQ ID NO: 3015), UUUguaagca (SEQ ID NO: 3036), CUCguaugcc (SEQ ID NO: 3076), UAGguaagag (SEQ ID NO: 2483), UAGgcaaguu (SEQ ID NO: 3077), GGAguuaagu (SEQ ID NO: 3078), GAG-guaugcc (SEQ ID NO: 1959), AAGguguggu (SEQ ID NO: 402), CAGguggggug (SEQ ID NO: 1415), UUAguaagua (SEQ ID NO: 2933), AAGguuggcu (SEQ ID NO: 3079), UGAguaugug (SEQ ID NO: 3080), CCAgccuucc (SEQ ID NO: 3081), CCUguacgug (SEQ ID NO: 3082), CCUguag-gua (SEQ ID NO: 1601), CAGguacgcu (SEQ ID NO: 3083), GAGguucuuc (SEQ ID NO: 3084), AAGguugccu (SEQ ID NO: 3085), CGUguucacu (SEQ ID NO: 3086), CGG-gugggga (SEQ ID NO: 3087), UAGgugggau (SEQ ID NO: 2614), CGGguaagga (SEQ ID NO: 3088), AAGguacuau (SEQ ID NO: 195), GGGguaagcu (SEQ ID NO: 2248), ACGguagagc (SEQ ID NO: 3089), CAGgugaaga (SEQ ID NO: 1318), GCGguaagag (SEQ ID NO: 3090), CAGgu-guugu (SEQ ID NO: 3091), GAAguuugug (SEQ ID NO: 3092), AUGgugagca (SEQ ID NO: 955), CGGguucgug (SEQ ID NO: 3093), AUUguccggc (SEQ ID NO: 3094), GAUgugugug (SEQ ID NO: 3095), AUGgucuguu (SEQ ID NO: 3096), AAGguaggau (SEQ ID NO: 219), CCGguaagau (SEQ ID NO: 1575), AAGguaaaga (SEQ ID NO: 126), GGGgugaguu (SEQ ID NO: 2285), AGGguuggug (SEQ ID NO: 808), GGAgugagug (SEQ ID NO: 2228), AGUguaagga (SEQ ID NO: 3097), UAGguaacug (SEQ ID NO: 2480), AAGgugaaga (SEQ ID NO: 3098), UGGguaagug (SEQ ID NO: 2843), CAGguaagag (SEQ ID NO: 1140), UAG-gugagcg (SEQ ID NO: 3099), GAGguaaaaa (SEQ ID NO: 1865), GCCguaaguu (SEQ ID NO: 3100), AAGguuuugu (SEQ ID NO: 473), CAGgugagga (SEQ ID NO: 1341), ACAgcccaug (SEQ ID NO: 3101), GCGgugagcc (SEQ ID NO: 3102), CAGguaugca (SEQ ID NO: 1251), AUGguac-cua (SEQ ID NO: 3103), CAAguaugua (SEQ ID NO: 1050), AUGgugggugc (SEQ ID NO: 3104), UAAguggcag (SEQ ID NO: 3105), UAGguauagu (SEQ ID NO: 3106), CUG-guauuua (SEQ ID NO: 3107), AGGguaaacg (SEQ ID NO: 3108), AUAguaagug (SEQ ID NO: 850), UUGguacuga (SEQ ID NO: 3109), GGUguaagcc (SEQ ID NO: 2303), GAGguggaua (SEQ ID NO: 3110), GAUguaagaa (SEQ ID NO: 3111), ACGgucaguu (SEQ ID NO: 3112), UAAguaaaca (SEQ ID NO: 3113), AAGguaucug (SEQ ID NO: 251), AGGguauuug (SEQ ID NO: 3114), AAGgugaaug (SEQ ID NO: 328), CUGgugaauu (SEQ ID NO: 1749), CAGguuuuuu (SEQ ID NO: 1514), CAUguaugug (SEQ ID NO: 1534), UUGguagagg (SEQ ID NO: 2973), AAGguaugcc (SEQ ID NO: 258), CAGgugccac (SEQ ID NO: 3115), UCGguauuga (SEQ ID NO: 2727), AAGguuugug (SEQ ID NO: 468), AAUguacagg (SEQ ID NO: 3116), CAUguggguu (SEQ ID NO: 1545), CAUgugaguu (SEQ ID NO: 1542), UUG-guaaugu (SEQ ID NO: 2968), AGUguaggug (SEQ ID NO: 3117), GAGguaacuc (SEQ ID NO: 3118), GAGguggcgc (SEQ ID NO: 3119), CUGguaauug (SEQ ID NO: 3120), GAGguuugcu (SEQ ID NO: 3121), UGUguacgug (SEQ ID NO: 3122), UAGguaaaga (SEQ ID NO: 2468), CUAguaggca (SEQ ID NO: 3123), UCUgugaguc (SEQ ID NO: 2761), UCUguaaggc (SEQ ID NO: 3124), CAGguuu-gug (SEQ ID NO: 1509), GAGguagggc (SEQ ID NO: 1935), AAGguaacca (SEQ ID NO: 3125), ACUgugaguu (SEQ ID NO: 646), UAGguaauag (SEQ ID NO: 2495), AAAguaagcu (SEQ ID NO: 17), AUGgugagug (SEQ ID NO: 963), UAGguuugug (SEQ ID NO: 2645), AACguaggac (SEQ ID NO: 3126), GUAgcaggua (SEQ ID NO: 3127), GAGgucagac (SEQ ID NO: 3128), AGGguaugaa (SEQ ID NO: 3129), GAGguuagug (SEQ ID NO: 2089), CAGgcacgug (SEQ ID NO: 3130), GGGgcaagac (SEQ ID NO: 3131), CAGgugugc (SEQ ID NO: 1441), CAG-guauuga (SEQ ID NO: 1265), CAGguauguc (SEQ ID NO: 1259), AAGgcaaggu (SEQ ID NO: 3132), UUGgugagaa (SEQ ID NO: 3133), AAGguaaaau (SEQ ID NO: 122), GGGguaagua (SEQ ID NO: 2251), AAGguaucuu (SEQ ID NO: 252), GACgugaguc (SEQ ID NO: 3134), UAUguaugcu (SEQ ID NO: 3135), AAGguacugu (SEQ ID NO: 199), CAGgugaacu (SEQ ID NO: 3136), CACguaaaug (SEQ ID NO: 3137), AAGgugugau (SEQ ID NO: 3138), GAAguauuug (SEQ ID NO: 3139), AAGgucugug (SEQ ID NO: 3140), AAGguggagg (SEQ ID NO: 3141), AAG-guauaug (SEQ ID NO: 244), CAGguucuua (SEQ ID NO: 1477), AGGguaacca (SEQ ID NO: 730), CAGgugucac (SEQ ID NO: 1423), AAAguucugu (SEQ ID NO: 3142), UUGgugaguu (SEQ ID NO: 3007), CAAgugaguc (SEQ ID NO: 1067), UAGguagguc (SEQ ID NO: 2525), GCG-gugagcu (SEQ ID NO: 2180), AUUgugagga (SEQ ID NO: 3143), CAGgugcaca (SEQ ID NO: 1361), CAGguuggaa (SEQ ID NO: 3144), CUGgucacuu (SEQ ID NO: 3145), GGAguaagug (SEQ ID NO: 2214), GAGgugggcu (SEQ ID NO: 2059), AAGguacuug (SEQ ID NO: 201), AGGguaggau (SEQ ID NO: 3146), AAUguguguu (SEQ ID NO: 3147), ACAguuaagu (SEQ ID NO: 568), GAGgugugug (SEQ ID NO: 2078), AAGgcgggcu (SEQ ID NO: 3148), AUAgca-agua (SEQ ID NO: 3149), AAGguuguua (SEQ ID NO: 454), CAAgcaaggc (SEQ ID NO: 3150), GUGguaauua (SEQ ID NO: 3151), UCUguucagu (SEQ ID NO: 3152), AGG-guaggcc (SEQ ID NO: 754), AAGguaucau (SEQ ID NO: 3153), UAGguaccuu (SEQ ID NO: 2509), AAGguaugac (SEQ ID NO: 254), GGAguaggua (SEQ ID NO: 2219), UAAguuggca (SEQ ID NO: 3154), AGUgugaggc (SEQ ID NO: 3155), GAGguuugug (SEQ ID NO: 3156), UGGgu-cugcu (SEQ ID NO: 3157), CAGgugaucc (SEQ ID NO: 1350), CAGgucagug (SEQ ID NO: 1283), AAGguaaggg (SEQ ID NO: 151), CAGgugcagu (SEQ ID NO: 3158), GAGgugggguc (SEQ ID NO: 2064), GCUgugagug (SEQ ID NO: 2206), AAGguggagu (SEQ ID NO: 3159), GGGgu-caguu (SEQ ID NO: 3160), AGCguaagug (SEQ ID NO: 719), AGAguaugaa (SEQ ID NO: 691), GGGguagggu (SEQ ID NO: 3161), AAGgccagca (SEQ ID NO: 3162), CGAguaugcc (SEQ ID NO: 3163), GUGgugagcg (SEQ ID NO: 3164), AAUguaaauu (SEQ ID NO: 481), CAGgugcgca (SEQ ID NO: 1375), GGUguaugaa (SEQ ID NO: 3165), CUUgugaguu (SEQ ID NO: 1804), AAGguaucuc (SEQ ID NO: 250), AGAguaagga (SEQ ID NO: 665), UAGguaagac (SEQ ID NO: 2482), GAGgugagug (SEQ ID NO: 2026), CAGguguguu (SEQ ID NO: 1443), UUGgugagua (SEQ ID NO: 3004), AGGgcgaguu (SEQ ID NO: 3166), CAG-guuuugc (SEQ ID NO: 3167), UUUgugaguu (SEQ ID NO: 3168), AGGguaagca (SEQ ID NO: 736), GAGguccucu (SEQ ID NO: 3169), CCAgcaggua (SEQ ID NO: 3170), GAGguucgcg (SEQ ID NO: 3171), CAGgugaucu (SEQ ID NO: 1351), ACUguaagua (SEQ ID NO: 625), AAGguaaauc (SEQ ID NO: 131), CAGgcaaaua (SEQ ID NO: 3172), GUGguaagca (SEQ ID NO: 2346), CAGguuaaau (SEQ ID NO: 3173), UUGguaauaa (SEQ ID NO: 3174), UAUguag-gua (SEQ ID NO: 3175), CAGguaguau (SEQ ID NO: 1225), AAGgugugcc (SEQ ID NO: 3176), UGGguaagag (SEQ ID NO: 2834), CAGgcaagca (SEQ ID NO: 3177), UUG-guaaggg (SEQ ID NO: 2961), AAGgcaggug (SEQ ID NO: 109), ACGguaaaug (SEQ ID NO: 3178), GCUgugagca (SEQ ID NO: 3179), AUGguacaca (SEQ ID NO: 3180), GUAguguguu (SEQ ID NO: 3181), ACUguaagag (SEQ ID NO: 3182), CCCgcagguc (SEQ ID NO: 3183), GAG-gugagcc (SEQ ID NO: 2019), GAGgugcugu (SEQ ID NO: 3184), UAAguaugcu (SEQ ID NO: 3185), GAGgccaucu (SEQ ID NO: 3186), UCAgugagug (SEQ ID NO: 2700), CAGgugcuac (SEQ ID NO: 3187), AAUgugggug (SEQ ID NO: 533), GAGgugugaa (SEQ ID NO: 3188), CUGguagguc (SEQ ID NO: 1730), GUGgcgcgcg (SEQ ID NO: 3189), CAGgugcaaa (SEQ ID NO: 1359), UAAguggagg (SEQ ID NO: 3190), CAUgugggua (SEQ ID NO: 3191), GAG-guagggu (SEQ ID NO: 3192), AAAgugaguu (SEQ ID NO: 61), AGGguucuag (SEQ ID NO: 3193), UGUgugagcu (SEQ ID NO: 3194), AGGgugaauc (SEQ ID NO: 3195), CAG-gucaggg (SEQ ID NO: 3196), AAGgucccug (SEQ ID NO: 3197), CUGguagagu (SEQ ID NO: 3198), UAGgucaguu (SEQ ID NO: 2570), AAAguaaggg (SEQ ID NO: 19), CAAguaugug (SEQ ID NO: 1052), CAGgugcuuu (SEQ ID NO: 3199), AAGguaauuc (SEQ ID NO: 169), GGGgugcacg (SEQ ID NO: 3200), ACUgugcuac (SEQ ID NO: 3201), CAGguaccua (SEQ ID NO: 3202), CAGguagcuu (SEQ ID NO: 1211), UGGgugaggc (SEQ ID NO: 2873), CUGgua-cauu (SEQ ID NO: 1718), AGGguaaucu (SEQ ID NO: 3203), CAGguacaag (SEQ ID NO: 1161), CAGguaauuc (SEQ ID NO: 1157), AGGgcacuug (SEQ ID NO: 3204), UAGgugagaa (SEQ ID NO: 2587), GAGguaaugc (SEQ ID NO: 3205), CCAgugaguu (SEQ ID NO: 3206), AAAguau-gug (SEQ ID NO: 44), CUGgugaauc (SEQ ID NO: 3207), UAUguaugua (SEQ ID NO: 2663), CCUgcaggug (SEQ ID NO: 3208), CAGguaucug (SEQ ID NO: 1245), GAG-gugaggu (SEQ ID NO: 3209), CUGguaaaac (SEQ ID NO: 3210), UGUgugugcu (SEQ ID NO: 3211), CAGguuaagu (SEQ ID NO: 3212), CAGguaaucc (SEQ ID NO: 1152), UAGguauuug (SEQ ID NO: 3213), UGGguagguc (SEQ ID NO: 2852), CAGguaacag (SEQ ID NO: 1129), AGCgugcgug (SEQ ID NO: 3214), AAGgucagga (SEQ ID NO: 289), GGUgugagcc (SEQ ID NO: 2312), CUGguaagua (SEQ ID NO: 1707), GGGgugggca (SEQ ID NO: 3215), AAGgugggaa (SEQ ID NO: 376), CAGgugagug (SEQ ID NO: 1347), CUGguuguua (SEQ ID NO: 3216), CAG-guaauag (SEQ ID NO: 3217), UAGgugaguu (SEQ ID NO: 3218), AGAguaaguu (SEQ ID NO: 671), UAGguaaucc (SEQ ID NO: 3219), CCGgugacug (SEQ ID NO: 3220), GUCgugauua (SEQ ID NO: 3221), CUUguaagug (SEQ ID NO: 1794), UAGguaguca (SEQ ID NO: 3222), CUGguaa-guc (SEQ ID NO: 3223), AGGgugagcg (SEQ ID NO: 3224), CAGguaugga (SEQ ID NO: 1255), AUUgugacca (SEQ ID NO: 3225), GUUgugggua (SEQ ID NO: 2411), AAGgua-caag (SEQ ID NO: 173), CUAgcaagug (SEQ ID NO: 3226), CUGgugagau (SEQ ID NO: 3227), CAGgugggca (SEQ ID NO: 1406), AUGgcucgag (SEQ ID NO: 3228), CUG-guacguu (SEQ ID NO: 1720), UUGgugugua (SEQ ID NO: 3229), GAGgugucug (SEQ ID NO: 3230), GAGgugggac (SEQ ID NO: 3231), GGGgugggag (SEQ ID NO: 3232), GCAgcgugag (SEQ ID NO: 3233), GAGguaaaga (SEQ ID NO: 1870), GAGguaugua (SEQ ID NO: 1965), AAGguga-gac (SEQ ID NO: 336), AAGguacaau (SEQ ID NO: 174), CUGguaugag (SEQ ID NO: 3234), AACguaaaau (SEQ ID NO: 3235), GUGguaggga (SEQ ID NO: 2364), CUGguau-gug (SEQ ID NO: 1737), CUUguaagca (SEQ ID NO: 3236), AAGguaggga (SEQ ID NO: 223), AUUguaagcc (SEQ ID NO: 3237), AUGguaagcu (SEQ ID NO: 895), CAGgugaauu (SEQ ID NO: 1322), UAGgugaaua (SEQ ID NO: 2581), CAAguaugga (SEQ ID NO: 3238), AUGguauggc (SEQ ID NO: 936), GAGgucaugc (SEQ ID NO: 3239), CAGguacccu (SEQ ID NO: 1174), ACAgugagac (SEQ ID NO: 3240), CAGgucugau (SEQ ID NO: 3241), GAAguugggu (SEQ ID NO: 3242), CUGgugcgug (SEQ ID NO: 1767), CAG-guacgag (SEQ ID NO: 1180), ACAgugagcc (SEQ ID NO: 556), AAGguaagua (SEQ ID NO: 153), GGAguaaggc (SEQ ID NO: 3243), GAGgugugua (SEQ ID NO: 2077), AAG-gucauuu (SEQ ID NO: 3244), CAGguagucu (SEQ ID NO: 3245), AUGguaucug (SEQ ID NO: 3246), AAGguaaacu (SEQ ID NO: 125), GAGguaggug (SEQ ID NO: 1938), CUGguaagca (SEQ ID NO: 1700), AGGguaagag (SEQ ID NO: 734), AAAguaaagc (SEQ ID NO: 3247), CAGguuugag (SEQ ID NO: 1502), GAGgcgggua (SEQ ID NO: 3248), CGAguacgau (SEQ ID NO: 3249), CAGguuguug (SEQ ID NO: 1495), AAAguauggg (SEQ ID NO: 3250), UAGgcug-guc (SEQ ID NO: 3251), AAGguaagga (SEQ ID NO: 149), AAGguuuccu (SEQ ID NO: 458), UUGguaaaac (SEQ ID NO: 3252), GAGguaagua (SEQ ID NO: 1893), CAGguu-caag (SEQ ID NO: 1465), UGGguuaugu (SEQ ID NO: 3253), GAGgugaguu (SEQ ID NO: 2027), ACGgugaaac (SEQ ID NO: 598), GAUguaacca (SEQ ID NO: 3254), AAGgugcggg (SEQ ID NO: 3255), CCGguacgug (SEQ ID NO: 3256), GAUgugagaa (SEQ ID NO: 3257), GUGgcg-guga (SEQ ID NO: 3258), CAGguauuag (SEQ ID NO: 3259), GAGguuggga (SEQ ID NO: 3260), AAGgcuagua (SEQ ID NO: 3261), AAGgugggcg (SEQ ID NO: 381), CAGgcaggga (SEQ ID NO: 3262), AAUguuaguu (SEQ ID NO: 3263), GAGguaaagg (SEQ ID NO: 3264), CAGgu-gugcu (SEQ ID NO: 1437), CUGguaugau (SEQ ID NO: 1733), AUGguuaguc (SEQ ID NO: 978), CUGgugagaa (SEQ ID NO: 1751), CAGgccggcg (SEQ ID NO: 3265), CAGgugacug (SEQ ID NO: 1332), AAAguaaggu (SEQ ID NO: 20), UAAguacuug (SEQ ID NO: 3266), AAGguaaagc (SEQ ID NO: 127), UCGguagggg (SEQ ID NO: 3267), CAGguaggaa (SEQ ID NO: 1212), AGUguaagca (SEQ ID NO: 817), CCCgugagau (SEQ ID NO: 3268), GUGguuguuu (SEQ ID NO: 3269), CAGguuugcc (SEQ ID NO: 1504), AGGguauggg (SEQ ID NO: 766), UAAguaagug (SEQ ID NO: 2424), GAGguaagac (SEQ ID NO: 3270), GAUguag-guc (SEQ ID NO: 3271), CAAguaggug (SEQ ID NO: 1043), AUAguaaaua (SEQ ID NO: 845), GAGguugggg (SEQ ID NO: 3272), GAGgcgagua (SEQ ID NO: 3273), CAG-guagugu (SEQ ID NO: 1229), GUGguaggug (SEQ ID NO: 2366), CAAgugagug (SEQ ID NO: 1068), AAGgugacaa (SEQ ID NO: 330), CCAgcguaau (SEQ ID NO: 3274), ACGgugaggu (SEQ ID NO: 3275), GGGguauauu (SEQ ID NO: 3276), CAGgugagua (SEQ ID NO: 1345), AAG-gugcgug (SEQ ID NO: 364), UAUguaaauu (SEQ ID NO: 3277), CAGgucagua (SEQ ID NO: 1281), ACGguacuua (SEQ ID NO: 3278), GAGgucagca (SEQ ID NO: 3279), UAAguaugua (SEQ ID NO: 2431), GGGgucagac (SEQ ID NO: 3280), AAUgugugag (SEQ ID NO: 3281), UCCgucagua (SEQ ID NO: 3282), CAGgugcuuc (SEQ ID NO: 1391), CCAguuagug (SEQ ID NO: 3283), CCGgugggcg (SEQ ID NO: 1590), AGGgugcaug (SEQ ID NO: 3284), GGGguaggau (SEQ ID NO: 3285), UAGgugggcc (SEQ ID NO: 2615), GAGguguucg (SEQ ID NO: 3286), UUGgcaagaa (SEQ ID NO: 3287), UCCguaagua (SEQ ID NO: 3288), CAGguguaag (SEQ ID NO: 3289), CUCgugagua (SEQ ID NO: 1680), GAGguguuuu (SEQ ID NO: 3290), GAGgugagca (SEQ ID NO: 2018), GAGguaaagu (SEQ ID NO: 1872), AAGguacguu (SEQ ID NO: 193), CAGguccagu (SEQ ID NO: 1291), AUGgugaaac (SEQ ID NO: 947), GUAgugagcu (SEQ ID NO: 3291), CAGgugaaaa (SEQ ID NO: 3292), AGGguacagg (SEQ ID NO: 3293), AAGguaacgc (SEQ ID NO: 3294), AAGguauacc (SEQ ID NO: 3295), CCUgugagau (SEQ ID NO: 3296), GGGguacgug (SEQ ID NO: 3297), GAGguauggu (SEQ ID NO: 1964), UAGguauuau (SEQ ID NO: 2557), GAAguaggag (SEQ ID NO: 3298), UCGguaaggg (SEQ ID NO: 3299), CCGguaagcg (SEQ ID NO: 3300), GAAguaauua (SEQ ID NO: 1823), CAGgugaguc (SEQ ID NO: 1346), AAGgucaaga (SEQ ID NO: 279), AUGguaaguc (SEQ ID NO: 899), CAGgugagcu (SEQ ID NO: 1340), CCAguuuuug (SEQ ID NO: 3301), CAGgugggag (SEQ ID NO: 1404), AAGguauuau (SEQ ID NO: 270), AAGguaaaua (SEQ ID NO: 130), AAGgugcugu (SEQ ID NO: 3302), AAAguacacc (SEQ ID NO: 3303), CUGguucgug (SEQ ID NO: 1783), UCAguaaguc (SEQ ID NO: 2690), GAAguacgug (SEQ ID NO: 3304), CAGgugacaa (SEQ ID NO: 1323), UGGguaagaa (SEQ ID NO: 2832), UGUguagggg (SEQ ID NO: 3305), GAGguaggca (SEQ ID NO: 1932), UUGgugaggc (SEQ ID NO: 3306), AUGgugugua (SEQ ID NO: 974), CAGguccucc (SEQ ID NO: 3307), UUGguaaaug (SEQ ID NO: 2953), GCUgugaguu (SEQ ID NO: 2207), AUGgucugua (SEQ ID NO: 3308), CAUgcaggug (SEQ ID NO: 3309), CUGguacacc (SEQ ID NO: 3310), CAGguccuua (SEQ ID NO: 3311), CAAguaaucu (SEQ ID NO: 1031), AUGgcagccu (SEQ ID NO: 3312), AAGgucagaa (SEQ ID NO: 282), AACgugaggc (SEQ ID NO: 3313), CAGgcacgca (SEQ ID NO: 1106), ACGguccagg (SEQ ID NO: 3314), UCUguacaua (SEQ ID NO: 3315), GAGgugauua (SEQ ID NO: 3316), ACGguaaaua (SEQ ID NO: 3317), AUGguaacug (SEQ ID NO: 3318), CAGgcgcguu (SEQ ID NO: 3319), CAGguauaga (SEQ ID NO: 1235), AAGguuuguu (SEQ ID NO: 3320), CAGguaugaa (SEQ ID NO: 1247), UAGguuggua (SEQ ID NO: 2638), CUGgugagac (SEQ ID NO: 1752), CAGguuagga (SEQ ID NO: 3321), AUGgugacug (SEQ ID NO: 3322), UUGguauccc (SEQ ID NO: 3323), CUUguaggac (SEQ ID NO: 3324), AAAguguguu (SEQ ID NO: 69), CAGguuucuu (SEQ ID NO: 1500), GGGguauggc (SEQ ID NO: 3325), GGGguaggac (SEQ ID NO: 3326), ACUguaaguc (SEQ ID NO: 626), AUCguaagcu (SEQ ID NO: 3327), UAGguucccc (SEQ ID NO: 2636), GGUgugagca (SEQ ID NO: 3328), CUGguuggua (SEQ ID NO: 3329), GGGguuaggg (SEQ ID NO: 3330), UGAguaagaa (SEQ ID NO: 3331), GAGguauucc (SEQ ID NO: 1969), UGGguuaguc (SEQ ID NO: 2893), CAGgcucgug (SEQ ID NO: 3332), UAGguagagu (SEQ ID NO: 3333), UAGgugcccu (SEQ ID NO: 3334), AAAgugagua (SEQ ID NO: 58), GAGguucaua (SEQ ID NO: 2094), UUGguaagag (SEQ ID NO: 2958), ACCgugugua (SEQ ID NO: 3335), UAUguaguau (SEQ ID NO: 3336), UGGguauag (SEQ ID NO: 3337), CAGgucugaa (SEQ ID NO: 3338), AAAguauaaa (SEQ ID NO: 3339), GUGgugaguc (SEQ ID NO: 3340), AGUgugauua (SEQ ID NO: 3341), UUGgugugug (SEQ ID NO: 3020), CAGgugaugg (SEQ ID NO: 1353), GCUgugagua (SEQ ID NO: 2204), CAGguacaug (SEQ ID NO: 1169), AAGguacagu (SEQ ID NO: 178), GAAguuguag (SEQ ID NO: 3342), CAGgugauua (SEQ ID NO: 1355), UAGgugaauu (SEQ ID NO: 2583), GGUguuaaua (SEQ ID NO: 3343), CAGguauuua (SEQ ID NO: 1268), CAAguacucg (SEQ ID NO: 3344), CAAguaagaa (SEQ ID NO: 1022), AAGguaccuu (SEQ ID NO: 188), ACGgugaggg (SEQ ID NO: 3345), UGAgcaggca (SEQ ID NO: 3346), GGGgugaccg (SEQ ID NO: 3347), GAGguaaaug (SEQ ID NO: 1875), CGGguuugug (SEQ ID NO: 3348), AAGgugagcg (SEQ ID NO: 341), GUGguaugga (SEQ ID NO: 3349), CUGguaagga (SEQ ID NO: 1703), GAGguaccag (SEQ ID NO: 1911), CCGgugagug (SEQ ID NO: 1587), AAGguuagaa (SEQ ID NO: 416), GAGguacuug (SEQ ID NO: 1921), AGAguaaaac (SEQ ID NO: 651), UCUgugagua (SEQ ID NO: 2760), AAGgcgggaa (SEQ ID NO: 3350), CAGguaugcg (SEQ ID NO: 1253), AGGguaaaac (SEQ ID NO: 3351), AAGgugacug (SEQ ID NO: 333), AGGguauguu (SEQ ID NO: 3352), AAGguaugua (SEQ ID NO: 263), CAGgucucuc (SEQ ID NO: 1302), CAGgcaugua (SEQ ID NO: 3353), CUGguaggua (SEQ ID NO: 1729), AAGgucaugc (SEQ ID NO: 3354), CAGguacaca (SEQ ID NO: 1163), GAUguacguu (SEQ ID NO: 3355), ACAguacgug (SEQ ID NO: 3356), ACGguaccca (SEQ ID NO: 3357), CAGguagugc (SEQ ID NO: 3358), ACAguaagag (SEQ ID NO: 3359), GGUgcacacc (SEQ ID NO: 3360), GAGguguaac (SEQ ID NO: 3361), AAGgugugua (SEQ ID NO: 403), UAGguacuua (SEQ ID NO: 3362), GCGguacugc (SEQ ID NO: 3363), UGGguaaguc (SEQ ID NO: 2842), CAUguaggua (SEQ ID NO: 1529), CAGguaggau (SEQ ID NO: 3364), CAGgucuggc (SEQ ID NO: 3365), GUGguuuuaa (SEQ ID NO: 3366), CAGgugggaa (SEQ ID NO: 1402), UGGgugagua (SEQ ID NO: 2875), CGAgugagcc (SEQ ID NO: 3367), AAGguauggc (SEQ ID NO: 261), AGUguuguca (SEQ ID NO: 3368), CAGgugauuu (SEQ ID NO: 1358), UAGguaucuc (SEQ ID NO: 2544), UAAguauguu (SEQ ID NO: 3369), AAGguugagc (SEQ ID NO: 3370), AGAguaaaga (SEQ ID NO: 653), GGUguaagua (SEQ ID NO: 3371), GGGgugagcu (SEQ ID NO: 2279), CAGguauaau (SEQ ID NO: 3372), GAGguacaaa (SEQ ID NO: 1904), AUGguaccaa (SEQ ID NO: 3373), UAGguagggg (SEQ ID NO: 2523), UGAgucagaa (SEQ ID NO: 3374), AAGgcaauua (SEQ ID NO: 3375), UUGguaagau (SEQ ID NO: 3376), CAGguacaga (SEQ ID NO: 1165), AGAguuagag (SEQ ID NO: 3377), CAGgugcguc (SEQ ID NO: 1381), GAGguauuac (SEQ ID NO: 3378), ACGguacaga (SEQ ID NO: 3379), CAGgucuucc (SEQ ID NO: 1313), AAGguaaggu (SEQ ID NO: 152), GAGguaauuu (SEQ ID NO: 1903), AGUguaggcu (SEQ ID NO: 3380), AAAguaagcg (SEQ ID NO: 3381), CCUguaagcc (SEQ ID NO: 3382), AGGgugauuu (SEQ ID NO: 3383), UGUguaugaa (SEQ ID NO: 3384), CUGguacaca (SEQ ID NO: 3385), AGGguagaga (SEQ ID NO: 3386), AUAguaagca (SEQ ID NO: 848), AGAguaugua (SEQ ID NO: 3387), UUGgucagca (SEQ ID NO: 3388), CAGgcaaguu (SEQ ID NO: 1105), AAGguauaua (SEQ ID NO: 242), AAGgucugga (SEQ ID NO: 314), CAGguacgca (SEQ ID NO: 1181), AGGgugcggg (SEQ ID NO: 3389), AUGguaagug (SEQ ID NO: 900), AAAgugauga (SEQ ID NO: 3390), UGCgugagua (SEQ ID NO: 3391), AGAguaggga (SEQ ID NO: 684), UGUguaggua (SEQ ID NO: 2912), UAGguaggau (SEQ ID NO: 2521), UAAgugagug (SEQ ID NO: 2440), GCUguaagua (SEQ ID NO: 2193), GAAguaagaa (SEQ ID NO: 1814), UCGgugaggc (SEQ ID NO: 2733), UAGguauuuu (SEQ ID NO: 2564), AAGguacaca (SEQ ID NO: 3392), AAGguaggua (SEQ ID NO: 227), UGGguagguu (SEQ ID NO: 2854), ACAgcaagua (SEQ ID NO: 541), GAGguaggag (SEQ ID NO: 1931), UGGgugaguu (SEQ ID NO: 2878), GCGgugagau (SEQ ID NO: 3393), CCUguagguu (SEQ ID NO: 3394), CAGgugugua (SEQ ID NO: 1440), CUGguaagcc (SEQ ID NO: 1701), AAGgugauuc (SEQ ID NO: 3395), CAGguagcua (SEQ ID NO: 1208), GUUguaagug (SEQ ID NO: 3396), AUGguaagca (SEQ ID NO: 893), AUAguaggga (SEQ ID NO: 3397), GGGguucgcu (SEQ ID NO: 3398), CCGgucagag (SEQ ID NO: 3399), GUAguaugag (SEQ ID NO: 3400), CGUguaagau (SEQ ID NO: 3401), UGAguaggca (SEQ ID NO: 3402), UCAguaugua (SEQ ID NO: 3403), GAGguaucug (SEQ ID NO: 1954), AGAguauuuu (SEQ ID NO: 3404), AAGguuguag (SEQ ID NO: 3405), AGUguaaguu (SEQ ID NO: 821), CGGguaaguu (SEQ ID NO: 1626), UCGgugcgga (SEQ ID NO: 3406), UAGguaagua (SEQ ID NO: 2491), GAAguuagau (SEQ ID NO: 3407), GCUgugagac (SEQ ID NO: 3408), CAGgcaggua (SEQ ID NO: 3409), CAGguagggg (SEQ ID NO: 1218), UAAguuaaga (SEQ ID NO: 3410), AUGguggguu (SEQ ID NO: 970), UAGguaaguu (SEQ ID NO: 2494), CUGguaaauu (SEQ ID NO: 1690), CCGguaagga (SEQ ID NO: 1577), GAGgcaggca (SEQ ID NO: 3411), CAUguaagug (SEQ ID NO: 1523), AAGgugccua (SEQ ID NO: 3412), UUGguaggga (SEQ ID NO: 2977), AAGguaaaca (SEQ ID NO: 123), CGGgugugag (SEQ ID NO: 3413), GGGgugugag (SEQ ID NO: 3414), UCCgugggue (SEQ ID NO: 3415), ACGguaaauc (SEQ ID NO: 3416), UCAguaggua (SEQ ID NO: 3417), CAGgucagcc (SEQ ID NO: 1278), CAGgcggugg (SEQ ID NO: 3418), CGAguaagcu (SEQ ID NO: 3419), CCCgugagca (SEQ ID NO: 3420), AAAguaauga (SEQ ID NO: 3421), CUGguaagcu (SEQ ID NO: 1702), CGGguaacca (SEQ ID NO: 3422), CAGgucgcac (SEQ ID NO: 3423), GAGguaggcc (SEQ ID NO: 3424), UAGgugagcc (SEQ ID NO: 2591), UAGguaggca (SEQ ID NO: 3425), GCGgugcgug (SEQ ID NO: 3426), AUGgugagua (SEQ ID NO: 961), GGGgugaggg (SEQ ID NO: 2282), GAGgucacac (SEQ ID NO: 3427), CAGguaggcc (SEQ ID NO: 3428), CAAgugcuga (SEQ ID NO: 3429), GUCgucuuca (SEQ ID NO: 3430), CAUguaagaa (SEQ ID NO: 1518), GUAguaagga (SEQ ID NO: 3431), UAGguuugua (SEQ ID NO: 2643), CAAguuagag (SEQ ID NO: 3432), AAGguagagu (SEQ ID NO: 208), AAGgugagau (SEQ ID NO: 338), AAAguaggua (SEQ ID NO: 37), ACAgugaauc (SEQ ID NO: 3433), CAGgugugcg (SEQ ID NO: 1436), CAGgucggcc (SEQ ID NO: 1299), AAGguaguau (SEQ ID NO: 3434), ACUgucaguc (SEQ ID NO: 3435), UCUgcagccu (SEQ ID NO: 3436), CGAguaagug (SEQ ID NO: 3437), AGAguaauua (SEQ ID NO: 3438), AGUgugagug (SEQ ID NO: 837), CCGgugagcg (SEQ ID NO: 3439), AAGguaaccu (SEQ ID NO: 3440), AAGguugugg (SEQ ID NO: 3441), AAGgcauggg (SEQ ID NO: 3442), AAGgucagag (SEQ ID NO: 284), ACGguaaggu (SEQ ID NO: 3443), GGGgugagca (SEQ ID NO: 3444), GAGguugcuu (SEQ ID NO: 3445), AAGguaucgc (SEQ ID NO: 3446), CCGguaaagg (SEQ ID NO: 3447), AAAguuaaug (SEQ ID NO: 3448), UAGguacgag (SEQ ID NO: 2510), ACCguaauua (SEQ ID NO: 3449), GGGguaagga (SEQ ID NO: 2249), CCGguaacgc (SEQ ID NO: 3450), CAGgucagaa (SEQ ID NO: 1275), AAGguacuga (SEQ ID NO: 197), GAGgugacca (SEQ ID NO: 2010), GGGgugagcc (SEQ ID NO: 2277), AAGguacagg (SEQ ID NO: 177), AUGguaauua (SEQ ID NO: 3451), CAGgugagag (SEQ ID NO: 1335), AAGgugacuc (SEQ ID NO: 3452), AUAguaagua (SEQ ID NO: 849), GAGguaaacc (SEQ ID NO: 1869), CAGgugggau (SEQ ID NO: 1405), CAGgugagaa (SEQ ID NO: 1333), AGGguaaaaa (SEQ ID NO: 3453), GAGgugugac (SEQ ID NO: 3454), CACguaagcu (SEQ ID NO: 3455), CAGguccccc (SEQ ID NO: 3456), CAGgucaggu (SEQ ID NO: 3457), CGGguaaguc (SEQ ID NO: 3458), ACGguauggg (SEQ ID NO: 3459), GAUguaaguu (SEQ ID NO: 2123), CAAguaauau (SEQ ID NO: 3460), CAGguugggg (SEQ ID NO: 3461), CCUgugcugg (SEQ ID NO: 3462), AAGguaugau (SEQ ID NO: 256), AGGguagagg (SEQ ID NO: 3463), AAGguggguu (SEQ ID NO: 386), CAGgugugaa (SEQ ID NO: 1430), UUGguaugug (SEQ ID NO: 2988), UUGguaucuc (SEQ ID NO: 2985), GGGgugagug (SEQ ID NO: 2284), CUGgugugug (SEQ ID NO: 1779), AGGguagggc (SEQ ID NO: 3464), GUGgugagua (SEQ ID NO: 3465), CAGguaugua (SEQ ID NO: 1258), AAGguacauu (SEQ ID NO: 181), UUAguaagug (SEQ ID NO: 2934), AAUguauauc (SEQ ID NO: 3466), CUUguaagua (SEQ ID NO: 1793), GAGguuagua (SEQ ID NO: 2087), CAGguaaggu (SEQ ID NO: 1146), CAGguaaugu (SEQ ID NO: 1155), AGGgugaggc (SEQ ID NO: 3467), CAGguauuuc (SEQ ID NO: 1269), CAGgucugga (SEQ ID NO: 1307), GGGgugugcu (SEQ ID NO: 3468), UAGgugagug (SEQ ID NO: 2598), AAUguaaccu (SEQ ID NO: 3469), UAAgugaguc (SEQ ID NO: 2439), CAGgugcacu (SEQ ID NO: 3470), ACGguaagua (SEQ ID NO: 579), GAGguauccu (SEQ ID NO: 3471), UCUguaaguc (SEQ ID NO: 2745), CAGguauuca (SEQ ID NO: 1263), UGUguaagug (SEQ ID NO: 3472), CCAgcaaggc (SEQ ID NO: 3473), GAGgugaagg (SEQ ID NO: 2006), AAUguggggu (SEQ ID NO: 3474), UCGgugcgug (SEQ ID NO: 3475), UUGguaaggc (SEQ ID NO: 3476), GAGguaagug (SEQ ID NO: 3477), AAAguaagau (SEQ ID NO: 14), UAGgucuuuu (SEQ ID NO: 3478), GAGgucugau (SEQ ID NO: 3479), CCAguuagag (SEQ ID NO: 3480), UGGgugaaaa (SEQ ID NO: 3481), AGAguaagau (SEQ ID NO: 662), CAGguaauug (SEQ ID NO: 1158), CAGgccgguc (SEQ ID NO: 3482), CCGguaagag (SEQ ID NO: 3483), GAGgugagcu (SEQ ID NO: 2021), CUGguaagac (SEQ ID NO: 3484), CAGgugagau (SEQ ID NO: 1336), CUGguuuguu (SEQ ID NO: 3485), UGGguaggua (SEQ ID NO: 3486), CAGguuagug (SEQ ID NO: 1457), CAGguguucg (SEQ ID NO: 3487), CGGguagguc (SEQ ID NO: 3488), GUGguacaua (SEQ ID NO: 3489), AAGguacuaa (SEQ ID NO: 194), GAUgugagua (SEQ ID NO: 3490), UGUguaagac (SEQ ID NO: 2904), GAGguagccg (SEQ ID NO: 3491), UAGgugaucu (SEQ ID NO: 3492), CAGguacgug (SEQ ID NO: 1185), CUUgucaguc (SEQ ID NO: 3493), GAGguaucac (SEQ ID NO: 3494), GAGguaauga (SEQ ID NO: 3495), AAGguaacac (SEQ ID NO: 3496), CAGguaaagc (SEQ ID NO: 1123), AAGgcaagua (SEQ ID NO: 3497), CGCgugagcc (SEQ ID NO: 3498), AGUgugcguu (SEQ ID NO: 3499), GAUguaagca (SEQ ID NO: 2118), AAGguaauag (SEQ ID NO: 159), GGAgcaguug (SEQ ID NO: 3500), AGCguaagau (SEQ ID NO: 3501), AAGgucaggc (SEQ ID NO: 290), GAGguauuca (SEQ ID NO: 3502), AAUguaaagu (SEQ ID NO: 3503), CAGguaacaa (SEQ ID NO: 3504), UCGguaggug (SEQ ID NO: 3505), AAAguaaguc (SEQ ID NO: 22), CGGgugcagu (SEQ ID NO: 3506), GGUgugugca (SEQ ID NO: 3507), UGAgugagaa (SEQ ID NO: 2794), CACguguaag (SEQ ID NO: 3508), GUGguuggua (SEQ ID NO: 3509), GCAgccuuga (SEQ ID NO: 3510), CGAgugugau (SEQ ID NO: 3511), CAGguauaua (SEQ ID NO: 3512), UAUguaugug (SEQ ID NO: 2665), CCCgugguca (SEQ ID NO: 3513), AUGguaagac (SEQ ID NO: 890), GAGgugugga (SEQ ID NO: 2074), AGUguauccu (SEQ ID NO: 3514), UGAgugugue (SEQ ID NO: 3515), UGGguaaucu (SEQ ID NO: 3516), AUGgcagguu (SEQ ID NO: 3517), GAGguaagau (SEQ ID NO: 1884), UCAgcagcgu (SEQ ID NO: 3518), AAGguggau (SEQ ID NO: 378), CGGgugcgcu (SEQ ID NO: 3519), CAGgugucug (SEQ ID NO: 1429), AGCgugguaa (SEQ ID NO: 3520), AAUgugaaug (SEQ ID NO: 3521), UCGgugagac (SEQ ID NO: 3522), UAGguaaagc (SEQ ID NO: 3523), CUGguaaaag (SEQ ID NO: 3524), CCGgugcgga (SEQ ID NO: 3525), CAGguacuca (SEQ ID NO: 3526), CAG-guagcaa (SEQ ID NO: 1203), GAAguugagu (SEQ ID NO: 3527), GAGguggagg (SEQ ID NO: 2052), AGGguaugag (SEQ ID NO: 762), UAGguaugcu (SEQ ID NO: 3528), UAGgugagac (SEQ ID NO: 2588), CAGguaauua (SEQ ID NO: 1156), CGUguaagcc (SEQ ID NO: 3529), CUU-guaaguu (SEQ ID NO: 1795), AAGguaacuu (SEQ ID NO: 140), UCGgcaaggc (SEQ ID NO: 3530), GAGguucucg (SEQ ID NO: 3531), GAGgugggcg (SEQ ID NO: 2058), AAGgcaugug (SEQ ID NO: 3532), CUGguauguu (SEQ ID NO: 1738), UAAgucauuu (SEQ ID NO: 3533), CAU-guaauua (SEQ ID NO: 1525), AAUguaaaga (SEQ ID NO: 3534), UAGgugcuca (SEQ ID NO: 3535), AAGguaaugg (SEQ ID NO: 166), GAGguacuga (SEQ ID NO: 3536), UGGguaagua (SEQ ID NO: 2841), UGGguaaaaa (SEQ ID NO: 3537), AAGgugagcu (SEQ ID NO: 342), UACgugaguu (SEQ ID NO: 3538), AGGgugagcc (SEQ ID NO: 790), CGGgugagga (SEQ ID NO: 3539), UGGgugagag (SEQ ID NO: 2869), GGUguaagcu (SEQ ID NO: 3540), CGGgugg-guu (SEQ ID NO: 1648), CCAgcuaagu (SEQ ID NO: 3541), AAGguuuguc (SEQ ID NO: 467), GAGguuagac (SEQ ID NO: 2084), GAGguaccuc (SEQ ID NO: 3542), UUU-guaaguu (SEQ ID NO: 3041), GAGguuagga (SEQ ID NO: 3543), CAGguaggga (SEQ ID NO: 1216), AGGguaauac (SEQ ID NO: 744), UGCgugugua (SEQ ID NO: 3544), CCAguaacca (SEQ ID NO: 3545), AGGgucuguc (SEQ ID NO: 3546), UGGguaugua (SEQ ID NO: 2860), GUG-guaagcu (SEQ ID NO: 2348), CAGguaaccu (SEQ ID NO: 3547), AAGgugaguu (SEQ ID NO: 350), UAGguucgug (SEQ ID NO: 3548), AAAguuagua (SEQ ID NO: 3549), UGGgcaaguc (SEQ ID NO: 2816), AAGgcacagu (SEQ ID NO: 3550), GUUguaaguc (SEQ ID NO: 2401), AAG-guuugcc (SEQ ID NO: 462), CUUgcauggg (SEQ ID NO: 3551), GCGgugagua (SEQ ID NO: 3552), GGGguaagcg (SEQ ID NO: 3553), GCCguaagaa (SEQ ID NO: 3554), GAGgucggga (SEQ ID NO: 3555), UUGguauugu (SEQ ID NO: 2990), AGUgugagac (SEQ ID NO: 3556), CUG-gugggga (SEQ ID NO: 1770), AGAguaaggu (SEQ ID NO: 668), CCGguggguc (SEQ ID NO: 3557), CAGguauucu (SEQ ID NO: 1264), UGGguaacgu (SEQ ID NO: 3558), UUGgugagag (SEQ ID NO: 3559), UAGguacccu (SEQ ID NO: 3560), GGGgugcguc (SEQ ID NO: 3561), AAGgcag-gag (SEQ ID NO: 3562), ACGguacauu (SEQ ID NO: 3563), GAGguaguua (SEQ ID NO: 1946), CAGguauggg (SEQ ID NO: 1256), UUUguguguc (SEQ ID NO: 3053), CAGguac-uua (SEQ ID NO: 1194), AUGguauacu (SEQ ID NO: 3564), AGUgugagcc (SEQ ID NO: 833), ACAguaacga (SEQ ID NO: 3565), CUGguaccca (SEQ ID NO: 3566), CAGguaaccc (SEQ ID NO: 3567), GGAguaagua (SEQ ID NO: 3568), GAGgugggug (SEQ ID NO: 2065), ACUguauguc (SEQ ID NO: 3569), ACGgugagua (SEQ ID NO: 606), CUGguaaugu (SEQ ID NO: 3570), AAGguaucag (SEQ ID NO: 247), CAGgugcccc (SEQ ID NO: 1370), AGUgucagug (SEQ ID NO: 3571), AAGguaggag (SEQ ID NO: 218), GGAguaugug (SEQ ID NO: 3572), UUGguauuuu (SEQ ID NO: 2992), CCUguuguga (SEQ ID NO: 3573), UUUguaagaa (SEQ ID NO: 3033), UAGguaacau (SEQ ID NO: 2475), CAG-guaagca (SEQ ID NO: 3574), CAGgucacag (SEQ ID NO: 3575), CAGgugugag (SEQ ID NO: 1432), UAGguuugcg (SEQ ID NO: 3576), CUGguaagaa (SEQ ID NO: 1697), ACGguuguau (SEQ ID NO: 3577), AAGguugggg (SEQ ID NO: 446), AAGgugaauu (SEQ ID NO: 329), GGGguuaguu (SEQ ID NO: 3578), ACGguaaggc (SEQ ID NO: 3579), CAGguuuaag (SEQ ID NO: 1496), CUGguaaguu (SEQ ID NO: 1709), GGGgugagag (SEQ ID NO: 3580), UGGgugg-guu (SEQ ID NO: 2886), GAGguuuguu (SEQ ID NO: 2111), UGGguaaaug (SEQ ID NO: 2826), CAGgcaggcc (SEQ ID NO: 3581), CACgugcagg (SEQ ID NO: 3582), AAGgugagcc (SEQ ID NO: 340), CAAguaagug (SEQ ID NO: 1028), CAGgucaguc (SEQ ID NO: 1282), GCG-guauaau (SEQ ID NO: 3583), UAGguaaagu (SEQ ID NO: 3584), UAGguggauu (SEQ ID NO: 3585), GAGgucugga (SEQ ID NO: 3586), UCGgucaguu (SEQ ID NO: 3587), UGGguaacug (SEQ ID NO: 3588), AAGguuugau (SEQ ID NO: 3589), UGUgcuggug (SEQ ID NO: 3590), UGUguac-cuc (SEQ ID NO: 3591), UGGguacagu (SEQ ID NO: 2849), AUCgucagcg (SEQ ID NO: 3592), CAGgucuugg (SEQ ID NO: 3593), GAAguuggua (SEQ ID NO: 3594), GAAguaaaga (SEQ ID NO: 3595), UUGguaagcu (SEQ ID NO: 2959), UAGguaccag (SEQ ID NO: 2507), AGGguau-cau (SEQ ID NO: 3596), CAGguaaaaa (SEQ ID NO: 1118), ACGguaauuu (SEQ ID NO: 583), AUUguaaguu (SEQ ID NO: 997), GAGguacagu (SEQ ID NO: 1908), CAGgugaaag (SEQ ID NO: 1315), UGGguuguuu (SEQ ID NO: 3597), GGGguaggug (SEQ ID NO: 2259), CAGgugccca (SEQ ID NO: 1369), AGCgugagau (SEQ ID NO: 3598), CCAgugagug (SEQ ID NO: 1565), AGGguagaug (SEQ ID NO: 3599), UGGguguguc (SEQ ID NO: 2888), AUCgcgugag (SEQ ID NO: 3600), AGGguaagcc (SEQ ID NO: 3601), AGGguagcag (SEQ ID NO: 3602), UUCguuuccg (SEQ ID NO: 3603), AAGguaagcg (SEQ ID NO: 147), UGGguaagcc (SEQ ID NO: 2837), CAGguauggc (SEQ ID NO: 3604), UGUguaagua (SEQ ID NO: 2907), AAGguagaga (SEQ ID NO: 3605), ACGguaauaa (SEQ ID NO: 3606), CUGguacggu (SEQ ID NO: 3607), GAGgu-cacag (SEQ ID NO: 3608), UAUguaaguu (SEQ ID NO: 2656), CUGguacgcc (SEQ ID NO: 3609), CAAguaagau (SEQ ID NO: 1024), CUAgugagua (SEQ ID NO: 1673), CCGguaaccg (SEQ ID NO: 3610), CUUguaaguc (SEQ ID NO: 3611), GUGgugagaa (SEQ ID NO: 2378), ACCguau-gua (SEQ ID NO: 3612), GUAguaagug (SEQ ID NO: 2324), UUGgugggua (SEQ ID NO: 3014), CGGguacuuu (SEQ ID NO: 3613), UGGguaaaua (SEQ ID NO: 2825), AGAgug-agua (SEQ ID NO: 704), AAGguagguu (SEQ ID NO: 230), AAGguaugcg (SEQ ID NO: 3614), CCUguaggcu (SEQ ID NO: 3615), ACAguagaaa (SEQ ID NO: 3616), CCGguu-agua (SEQ ID NO: 3617), CGGguaggcg (SEQ ID NO: 3618), GCAgugagug (SEQ ID NO: 2162), GAGgugaguc (SEQ ID NO: 3619), CUGguagccu (SEQ ID NO: 3620), CAUguaugua (SEQ ID NO: 1533), GAAguaacuu (SEQ ID NO: 3621), GAAguaagau (SEQ ID NO: 3622), AAGguua-gau (SEQ ID NO: 417), AAGguaauca (SEQ ID NO: 161), AAUguaugua (SEQ ID NO: 507), UGAguaagau (SEQ ID NO: 2767), AGAgugagca (SEQ ID NO: 703), GUAguucuau (SEQ ID NO: 3623), GAGguaauca (SEQ ID NO: 1898), UAGguaugga (SEQ ID NO: 2548), UAGgugggac (SEQ ID NO: 2612), GAGguacaug (SEQ ID NO: 3624), UGG-guaaggc (SEQ ID NO: 3625), CAGguacgcc (SEQ ID NO: 1182), CCAguuacgc (SEQ ID NO: 3626), ACUgugguga (SEQ ID NO: 3627), GAGguaaguc (SEQ ID NO: 1894), AUUguaggug (SEQ ID NO: 3628), ACCgucagug (SEQ ID NO: 3629), AAUgugaggg (SEQ ID NO: 3630), ACU-gugagug (SEQ ID NO: 645), UGGguguggu (SEQ ID NO: 3631), AAGguuggga (SEQ ID NO: 445), AAGguuugga (SEQ ID NO: 464), UCCgugagug (SEQ ID NO: 3632), CGGgugagug (SEQ ID NO: 1642), AGAguaagcu (SEQ ID NO: 664), CAGgcaagcu (SEQ ID NO: 3633), UAGguauauu (SEQ ID NO: 2541), AAAguagcag (SEQ ID NO: 3634), GAGguaaccu (SEQ ID NO: 1880), AAGgugggca (SEQ ID NO: 379), AGGgugagua (SEQ ID NO: 795), UGGguaaggu (SEQ ID NO: 2840), CUUgucagug (SEQ ID NO: 3635), UAGgugcgcu (SEQ ID NO: 3636), GAGgcaaauu (SEQ ID NO: 3637), AGGguaccuc (SEQ ID NO: 3638), CAAgugcgua (SEQ ID NO: 3639), AGAguaagac (SEQ ID NO: 660), GUGguaaaua (SEQ ID NO: 3640), GAUguaagcg (SEQ ID NO: 3641), GAGguaaagc (SEQ ID NO: 1871), UAGgugagua (SEQ ID NO: 2596), CAGguaacau (SEQ ID NO: 1130), CCUguacggc (SEQ ID NO: 3642), UAGguauguc (SEQ ID NO: 2552), UAGguccaua (SEQ ID NO: 3643), GAGgugaaaa (SEQ ID NO: 2003), AAAguacuga (SEQ ID NO: 3644), UUGguaagcg (SEQ ID NO: 3645), CAGgcaagcg (SEQ ID NO: 3646), UUUgcagguu (SEQ ID NO: 3647), CAGguuuaua (SEQ ID NO: 3648), CUGguaaagc (SEQ ID NO: 1686), AUGgugagcu (SEQ ID NO: 958), CAGgugguug (SEQ ID NO: 1419), GUAguaaguu (SEQ ID NO: 3649), CAGguaauac (SEQ ID NO: 3650), CAGgcaaggc (SEQ ID NO: 3651), AAGguaauuu (SEQ ID NO: 171), UUUguccgug (SEQ ID NO: 3652), GAGguagguu (SEQ ID NO: 1939), ACCgugagug (SEQ ID NO: 3653), CAAguaagcu (SEQ ID NO: 3654), ACAgugagua (SEQ ID NO: 560), UUGgugagau (SEQ ID NO: 3000), AAGguagucu (SEQ ID NO: 233), CAGguaaagg (SEQ ID NO: 3655), GGGguaugga (SEQ ID NO: 2264), UUUguaagug (SEQ ID NO: 3040), GUGguaagag (SEQ ID NO: 2344), AGUgugaguu (SEQ ID NO: 838), AAGgcaagcg (SEQ ID NO: 3656), UAAgugagua (SEQ ID NO: 2438), AGGgugagug (SEQ ID NO: 797), AGUguacgug (SEQ ID NO: 3657), AGGgugcgua (SEQ ID NO: 3658), GGCgugagcc (SEQ ID NO: 2238), CGAguuauga (SEQ ID NO: 3659), CAGguaaaga (SEQ ID NO: 1122), UUGgugaaga (SEQ ID NO: 3660), AGGguaaugg (SEQ ID NO: 3661), AAGguccaga (SEQ ID NO: 300), AGUgugaguc (SEQ ID NO: 836), CAGguaauuu (SEQ ID NO: 1159), CAGguaacgc (SEQ ID NO: 3662), CUGguacacu (SEQ ID NO: 3663), CUGguuagug (SEQ ID NO: 1782), CAGguacuug (SEQ ID NO: 3664), CACguaagua (SEQ ID NO: 3665), GUGgugcggc (SEQ ID NO: 3666), GAGgucaguu (SEQ ID NO: 3667), AUGguaugcc (SEQ ID NO: 932), AAGgugugug (SEQ ID NO: 405), CUGgugggucc (SEQ ID NO: 1772), CAGgugaggc (SEQ ID NO: 1342), AAGguuaguc (SEQ ID NO: 423), AAGguagcug (SEQ ID NO: 215), GAGgucagga (SEQ ID NO: 1983), GUUguaggua (SEQ ID NO: 3668), UGGguacaag (SEQ ID NO: 3669), AUGguaggug (SEQ ID NO: 924), GAGguaagcc (SEQ ID NO: 1886), AUGgcaagua (SEQ ID NO: 3670), AAGguauauu (SEQ ID NO: 245), GCGgugagag (SEQ ID NO: 3671), AAGgugcuuc (SEQ ID NO: 3672), UAGguacauc (SEQ ID NO: 3673), ACUgugguaa (SEQ ID NO: 3674), GAGguaggcu (SEQ ID NO: 1933), GAGguaugca (SEQ ID NO: 3675), AGGguaguuc (SEQ ID NO: 3676), CAGguauccu (SEQ ID NO: 1241), AGGguaaguc (SEQ ID NO: 741), AGGgucaguu (SEQ ID NO: 779), CAGguuggga (SEQ ID NO: 3677), CAGguggaua (SEQ ID NO: 3678), GGAguagguu (SEQ ID NO: 2220), GAGguaggau (SEQ ID NO: 3679), GGGguuugug (SEQ ID NO: 3680), UAGguaauug (SEQ ID NO: 3681), AAGguaaccc (SEQ ID NO: 136), ACGguaagaa (SEQ ID NO: 3682), GAGguagggg (SEQ ID NO: 1936), CGAguaggug (SEQ ID NO: 1619), UCCguaagug (SEQ ID NO: 2710), UCGguacagg (SEQ ID NO: 3683), CAAguaagcg (SEQ ID NO: 3684), AAGguccgcg (SEQ ID NO: 3685), AAUgugagua (SEQ ID NO: 523), CAGgugaaug (SEQ ID NO: 3686), GUGguaaggc (SEQ ID NO: 2350), AGAgugagug (SEQ ID NO: 706), UCUguauguc (SEQ ID NO: 3687), UGGgugaguc (SEQ ID NO: 2876), UCGguuagua (SEQ ID NO: 3688), GAUguaugca (SEQ ID NO: 3689), GAGguuggug (SEQ ID NO: 3690), GAGguggggc (SEQ ID NO: 2061), UGGgucaguc (SEQ ID NO: 3691), GCAgugagua (SEQ ID NO: 2161), CAGguugcuu (SEQ ID NO: 3692), AGGguagagu (SEQ ID NO: 3693), UAGgucaggu (SEQ ID NO: 2567), CGCguaugua (SEQ ID NO: 3694), GAGguauuaa (SEQ ID NO: 3695), CAGguaaacu (SEQ ID NO: 3696), AAAguaaguu (SEQ ID NO: 24), GGGgucuggc (SEQ ID NO: 3697), GCUguggggu (SEQ ID NO: 3698), UUGguaaguc (SEQ ID NO: 3699), AAGguagaag (SEQ ID NO: 3700), AAUgugaguc (SEQ ID NO: 524), AAGgucagcu (SEQ ID NO: 288), AAGguaagag (SEQ ID NO: 143), AUGgugagga (SEQ ID NO: 3701), AAGguacuuc (SEQ ID NO: 200), AAGguaagaa (SEQ ID NO: 141), CCGguacagc (SEQ ID NO: 3702), GCGgugcgga (SEQ ID NO: 3703), CAGguacaua (SEQ ID NO: 1168), CUGgugagga (SEQ ID NO: 1755), CUGguaggug (SEQ ID NO: 1731), AACguagguu (SEQ ID NO: 3704), AUGgugugug (SEQ ID NO: 975), UUGguacuau (SEQ ID NO: 3705), CAGgucggug (SEQ ID NO: 1300), CAGgcauggg (SEQ ID NO: 3706), AUGguaucuu (SEQ ID NO: 929), AAGguaacua (SEQ ID NO: 137), CAGgugggcg (SEQ ID NO: 3707), CACgugagga (SEQ ID NO: 3708), AAGgugguuc (SEQ ID NO: 392), UGGgcauucu (SEQ ID NO: 3709), AUGguaagcc (SEQ ID NO: 894), AGGgucagug (SEQ ID NO: 778), AGAguacgua (SEQ ID NO: 3710), AAGguaggca (SEQ ID NO: 220), AAGguauuca (SEQ ID NO: 3711), CAGguagauu (SEQ ID NO: 1202), GAGguauuua (SEQ ID NO: 1972), GAGgucuaca (SEQ ID NO: 3712), GUUguagguc (SEQ ID NO: 3713), CAGguacucg (SEQ ID NO: 3714), GUCguauguu (SEQ ID NO: 3715), AAGguacuuu (SEQ ID NO: 202), AGAgugagau (SEQ ID NO: 702), AGUguuggua (SEQ ID NO: 3716), AAUgugagug (SEQ ID NO: 525), AAGguagauu (SEQ ID NO: 3717), AUGguuugua (SEQ ID NO: 988), GAGgccccag (SEQ ID NO: 3718), AUGgucaguu (SEQ ID NO: 3719), UCUguaagga (SEQ ID NO: 3720), CAGgucgggc (SEQ ID NO: 3721), CAGguaagcc (SEQ ID NO: 1142), UAGgucagug (SEQ ID NO: 2569), AGAguaggaa (SEQ ID NO: 683), CUGguacuuc (SEQ ID NO: 3722), CUCguaagca (SEQ ID NO: 1674), CAGguaacua (SEQ ID NO: 1134), CAGguggcug (SEQ ID NO: 1401), UGGguccgua (SEQ ID NO: 3723), GAGguugugc (SEQ ID NO: 3724), CAGgugcgcg (SEQ ID NO: 1377), AAAguauggc (SEQ ID NO: 3725), UGAguacgua (SEQ ID NO: 2779), CUGguacgga (SEQ ID NO: 3726), CAAgugaccu (SEQ ID NO: 3727), AAGgugaugu (SEQ ID NO: 356), AAGgucugca (SEQ ID NO: 3728), AAAguuugua (SEQ ID NO: 75), AAGgugagca (SEQ ID NO: 339), GAUguaagcc (SEQ ID NO: 2119), CAAguaauuu (SEQ ID NO: 1035), CAGgugugug (SEQ ID NO: 1442), UGGgugaggg (SEQ ID NO: 2874), AAGgugaccu (SEQ ID NO: 3729), UAGgugugag (SEQ ID NO: 2621), CAGgcagguc (SEQ ID NO: 3730), UCAguaaguu (SEQ ID NO: 2692), UCAgcaguga (SEQ ID NO: 3731), AAGguaccac (SEQ ID NO: 3732), UAAguaggug (SEQ ID NO: 3733), AAGgucagcc (SEQ ID NO: 286), CAGguaacuc (SEQ ID NO: 1135), AAAguaagag (SEQ ID NO: 13), AAGguagaua (SEQ ID NO: 209), AAGgcaaggg (SEQ ID NO: 99), CAGgugucgg (SEQ ID NO: 3734), CAGguggcua (SEQ ID NO: 3735), GAGguugcca (SEQ ID NO: 3736), CAGgccgugg (SEQ ID NO: 3737), UUGguauaug (SEQ ID NO: 3738), GAGguugagu (SEQ ID NO: 3739), GAGguagguc (SEQ ID NO: 3740), GUGguaagac (SEQ ID NO: 2343), UAGguccuuc (SEQ ID NO: 3741), GAGgcaaguc (SEQ ID NO: 3742), GAGguaacau (SEQ ID NO: 3743), CAGguauauc (SEQ ID NO: 1236), UCGguugguu (SEQ ID NO: 3744), CAGgugaacc (SEQ ID NO: 3745), CAGgucuuuu (SEQ ID NO: 3746), CAGgcauggc (SEQ ID NO: 3747), AAAguacuug (SEQ ID NO: 32), CAGgugauuc (SEQ ID NO: 1356), UUGguagguu (SEQ ID NO: 3748), UAUgugagca (SEQ ID NO: 3749), CAGgugagcg (SEQ ID NO: 1339), AAUguaauaa (SEQ ID NO: 3750), AAAguaaggc (SEQ ID NO: 3751), UAGguuuguc (SEQ ID NO: 2644), UAGgugggag (SEQ ID NO: 2613), GAGguaaguu (SEQ ID NO: 3752), AAGguagccg (SEQ ID NO:

3753), CAGguggugc (SEQ ID NO: 3754), UGAgucaguu (SEQ ID NO: 3755), CUGguaggcc (SEQ ID NO: 3756), CAAguaagga (SEQ ID NO: 3757), CGGguaaggc (SEQ ID NO: 3758), AAGgcgagga (SEQ ID NO: 3759), CAG-guaguuc (SEQ ID NO: 1230), CAGguaagga (SEQ ID NO: 1143), CCUgugagug (SEQ ID NO: 1610), AAGguaaaug (SEQ ID NO: 132), CCGguaauua (SEQ ID NO: 3760), CAGguaaguu (SEQ ID NO: 1149), AAGgugguca (SEQ ID NO: 3761), CAGguaccuc (SEQ ID NO: 1177), AUCgua-agua (SEQ ID NO: 3762), CCGguacaua (SEQ ID NO: 3763), GCGgugagug (SEQ ID NO: 3764), GAGgugguau (SEQ ID NO: 2067), CUGgugugga (SEQ ID NO: 3765), GAGguaauuc (SEQ ID NO: 3766), CAAguacgua (SEQ ID NO: 3767), UCUguaagug (SEQ ID NO: 2746), AAU-guaagug (SEQ ID NO: 491), AGGgucuguu (SEQ ID NO: 783), GAGguacugc (SEQ ID NO: 1918), AGGguaaggc (SEQ ID NO: 738), AAGgcaagag (SEQ ID NO: 95), CAG-guggguu (SEQ ID NO: 1416), UAGguuagga (SEQ ID NO: 3768), UGAguaagcu (SEQ ID NO: 2769), AGAguaagag (SEQ ID NO: 661), AUGgcaggug (SEQ ID NO: 3769), UAGgcaagua (SEQ ID NO: 3770), AUGguaggua (SEQ ID NO: 923), GCAgcccgca (SEQ ID NO: 3771), ACGguaaacu (SEQ ID NO: 3772), AGGgugaguu (SEQ ID NO: 798), GUAguagucu (SEQ ID NO: 3773), GUGgcugaaa (SEQ ID NO: 3774), CAGguuaguc (SEQ ID NO: 1456), CUG-gugagca (SEQ ID NO: 1753), UCAguaagug (SEQ ID NO: 2691), AAAgugauug (SEQ ID NO: 3775), UAGgucugga (SEQ ID NO: 3776), GAGguguuuc (SEQ ID NO: 3777), AAGguaaauu (SEQ ID NO: 133), CAUguacauc (SEQ ID NO: 3778), AAGguuugaa (SEQ ID NO: 3779), CCAgcaagug (SEQ ID NO: 3780), UAGguaauaa (SEQ ID NO: 3781), GAGgcaagug (SEQ ID NO: 1859), CAAgugauuc (SEQ ID NO: 1071), CAGgucgugg (SEQ ID NO: 3782), GAAguaugcc (SEQ ID NO: 3783), UCG-gugcccu (SEQ ID NO: 3784), GAGgucaguc (SEQ ID NO: 3785), CAGgugagac (SEQ ID NO: 1334), UUUgucugua (SEQ ID NO: 3786), CAGguagaua (SEQ ID NO: 3787), UGGguaucag (SEQ ID NO: 3788), UAGgugggcu (SEQ ID NO: 2616), AUGgugagau (SEQ ID NO: 3789), CAG-guaacac (SEQ ID NO: 3790), CCGguauccu (SEQ ID NO: 3791), UAGguaagcu (SEQ ID NO: 2487), UCAguacauc (SEQ ID NO: 3792), UAGguuugcc (SEQ ID NO: 2642), AUGguaagaa (SEQ ID NO: 889), UUGguaagac (SEQ ID NO: 3793), CCGguuaguc (SEQ ID NO: 3794), GAG-guaagaa (SEQ ID NO: 1882), UGGguaaguu (SEQ ID NO: 2844), CCGgugagaa (SEQ ID NO: 1585), CCUgugaggg (SEQ ID NO: 1608), ACGguaggag (SEQ ID NO: 590), ACAguauguc (SEQ ID NO: 3795), CAGguauuaa (SEQ ID NO: 3796), CAGguggauc (SEQ ID NO: 3797), AGAgugcgua (SEQ ID NO: 3798), AAGgugaccg (SEQ ID NO: 3799), AGAguaggug (SEQ ID NO: 687), ACUguaugua (SEQ ID NO: 3800), UAGgucaauu (SEQ ID NO: 3801), AGUguguaag (SEQ ID NO: 3802), CGGguaccuu (SEQ ID NO: 3803), CUAgugaguu (SEQ ID NO: 3804), CUAguaagug (SEQ ID NO: 1666), CAGguacaac (SEQ ID NO: 3805), UAGgugugug (SEQ ID NO: 2627), CAU-guacggc (SEQ ID NO: 3806), AUGgugugag (SEQ ID NO: 3807), AGGguggaag (SEQ ID NO: 3808), CAGgugcgag (SEQ ID NO: 3809), UAGgugcucc (SEQ ID NO: 3810), AAGguguggg (SEQ ID NO: 390), AAGgucuguu (SEQ ID NO: 317), CAGgugggcc (SEQ ID NO: 1407), AAGgucaguc (SEQ ID NO: 294), CAGguuuuua (SEQ ID NO: 3811), AACgugaggu (SEQ ID NO: 3812), CGGguaagag (SEQ ID NO: 3813), UUUgucggua (SEQ ID NO: 3814), UAG-guuaagu (SEQ ID NO: 3815), GUGguaagaa (SEQ ID NO: 2342), CAGguauugg (SEQ ID NO: 1266), GCUguaaguu (SEQ ID NO: 2196), CUAguaagua (SEQ ID NO: 1664), UCGguaaaua (SEQ ID NO: 3816), CAGguaacuu (SEQ ID NO: 1137), CCUgugagua (SEQ ID NO: 3817), CAG-guuauau (SEQ ID NO: 3818), CUGgugaaca (SEQ ID NO: 3819), AAGguauaaa (SEQ ID NO: 238), GAGguaagca (SEQ ID NO: 1885), AAGgugaagc (SEQ ID NO: 324), CAGgugaguu (SEQ ID NO: 1348), UUUgugagua (SEQ ID NO: 3820), CUUguacgcc (SEQ ID NO: 3821), AGAguaagug (SEQ ID NO: 670), UGGguaggug (SEQ ID NO: 2853), UGAgcccugc (SEQ ID NO: 3822), UGUguau-gua (SEQ ID NO: 3823), AAGguagagg (SEQ ID NO: 3824), GAGgugggggg (SEQ ID NO: 2062), UAGguaauuc (SEQ ID NO: 2502), AAGgcauggu (SEQ ID NO: 3825), AGAguaagca (SEQ ID NO: 663), AAGguaggaa (SEQ ID NO: 217), CAAguaagua (SEQ ID NO: 1026), ACUguaauug (SEQ ID NO: 3826), CAGgucugug (SEQ ID NO: 1311), UCGguaccga (SEQ ID NO: 3827), CUGgugagag (SEQ ID NO: 3828), AAGguuugcu (SEQ ID NO: 463), AUGguaccac (SEQ ID NO: 3829), UAAguuaguu (SEQ ID NO: 3830), CAGguaggac (SEQ ID NO: 1213), AGAgugaggc (SEQ ID NO: 3831), CGAgucagua (SEQ ID NO: 3832), CAGgu-cugag (SEQ ID NO: 1304), GAGguggugg (SEQ ID NO: 3833), ACGguauugg (SEQ ID NO: 3834), GCUgcgagua (SEQ ID NO: 3835), CUGguaagug (SEQ ID NO: 1708), GUGgugagau (SEQ ID NO: 2379), GGGguuugau (SEQ ID NO: 3836), UCUgugagug (SEQ ID NO: 2762), CUUguc-agua (SEQ ID NO: 1801), GAGguaaaac (SEQ ID NO: 1866), UCUguaagau (SEQ ID NO: 2741), CCAguaaguu (SEQ ID NO: 1558), CAGguaaagu (SEQ ID NO: 1124), GCGgugagca (SEQ ID NO: 2179), UAAguaagag (SEQ ID NO: 2416), CUGgcaggug (SEQ ID NO: 3837), GAG-guaaggg (SEQ ID NO: 1891), UGAguaaguu (SEQ ID NO: 2775), GAGgugagac (SEQ ID NO: 2015), GCUgucuguu (SEQ ID NO: 3838), AAGguaacaa (SEQ ID NO: 134), GAGguaacgg (SEQ ID NO: 3839), CUGguauucu (SEQ ID NO: 3840), CAAguaacug (SEQ ID NO: 1021), AAG-gugggggu (SEQ ID NO: 383), UAGguauggc (SEQ ID NO: 2549), CAGguauuuu (SEQ ID NO: 1271), GUGguaaacu (SEQ ID NO: 3841), GAGgucugag (SEQ ID NO: 1998), CUGguaaggu (SEQ ID NO: 1706), CAAguaaguu (SEQ ID NO: 1029), AAGguagacc (SEQ ID NO: 206), GAGgcgagcg (SEQ ID NO: 3842), CUGguaaaua (SEQ ID NO: 1687), UGUguaagcg (SEQ ID NO: 3843), CAGguuaggg (SEQ ID NO: 1453), GGGgugagga (SEQ ID NO: 2280), ACAguau-gug (SEQ ID NO: 3844), CCGgugggga (SEQ ID NO: 3845), GAGgucagug (SEQ ID NO: 3846), AGGguaaggu (SEQ ID NO: 3847), ACAguaagua (SEQ ID NO: 546), GGUguaaggu (SEQ ID NO: 3848), GAGguaauaa (SEQ ID NO: 1895), CAGguauucc (SEQ ID NO: 3849), CUGguauaaa (SEQ ID NO: 3850), CCGgucugug (SEQ ID NO: 3851), CAG-guaacug (SEQ ID NO: 1136), GCAguaagua (SEQ ID NO: 2147), AAGguagggg (SEQ ID NO: 225), CAAguccacc (SEQ ID NO: 3852), CAAguuggug (SEQ ID NO: 3853), CAGgugcggu (SEQ ID NO: 1379), CAGguaaaau (SEQ ID NO: 3854), ACGguaagga (SEQ ID NO: 3855), UGG-guaauaa (SEQ ID NO: 3856), UAGguaagug (SEQ ID NO: 2493), CCGguagguu (SEQ ID NO: 3857), AGAguaugga (SEQ ID NO: 3858), CUCgugaguc (SEQ ID NO: 3859), AAAgccggug (SEQ ID NO: 3860), UUGguaauuu (SEQ ID NO: 2970), GAGguaaaag (SEQ ID NO: 1867), CCUgu-gugag (SEQ ID NO: 3861), AAAguaagga (SEQ ID NO: 18), UGAgugagug (SEQ ID NO: 2800), AAGguacaug (SEQ ID NO: 180), CCGguaaaug (SEQ ID NO: 3862), CAGgugaagc (SEQ ID NO: 3863), CAGguacccg (SEQ ID NO: 1173), GAGguaaggc (SEQ ID NO: 1890), UUUguauguu (SEQ ID NO: 3049), CAGgugcucc (SEQ ID NO: 1386), UCGguag-guc (SEQ ID NO: 3864), CGGgugaggc (SEQ ID NO: 3865), AAGguaauua (SEQ ID NO: 168), ACUgugaguc (SEQ ID NO: 644), AAGgucagca (SEQ ID NO: 285), GUGgugagug (SEQ ID NO: 2384), CAUguccacc (SEQ ID NO: 3866), AAGgugaccc (SEQ ID NO: 3867), CGGguuagua (SEQ ID NO: 3868), GCGguaguaa (SEQ ID NO: 3869), GCUguaggua (SEQ ID NO: 3870), CCUguugagu (SEQ ID NO: 3871), UAGgucuggc (SEQ ID NO: 2577), GAUgugagcc (SEQ ID NO: 2131), CUUgugagua (SEQ ID NO: 1802), CUGguguguu (SEQ ID NO: 1780), GAGgcaugug (SEQ ID NO: 1863), CAGgcaagag (SEQ ID NO: 1101), UUGguaagaa (SEQ ID NO: 2957), GAGguguggg (SEQ ID NO: 2075), GAGguauuuu (SEQ ID NO: 1975), CAGguaguaa (SEQ ID NO: 1224), AGGguaagac (SEQ ID NO: 3872), UUUguaggca (SEQ ID NO: 3873), AGGgugagau (SEQ ID NO: 3874), GAGguuugua (SEQ ID NO: 2110), AAGgugagug (SEQ ID NO: 349), GAGgugggag (SEQ ID NO: 2055), AAGgugagaa (SEQ ID NO: 335), CUGguaagag (SEQ ID NO: 1698), AUAguaaaga (SEQ ID NO: 3875), GAUgugaguc (SEQ ID NO: 2134), AAGgugcagg (SEQ ID NO: 3876), CAGgucuguc (SEQ ID NO: 1310), GAGgugauuu (SEQ ID NO: 3877), CAGguuggcu (SEQ ID NO: 3878), CGGguauggg (SEQ ID NO: 3879), AUGguccauc (SEQ ID NO: 3880), CCGguuggug (SEQ ID NO: 3881), GGAguaaguc (SEQ ID NO: 3882), AAUguaagga (SEQ ID NO: 488), CAGguuuguu (SEQ ID NO: 1510), UAGgugugua (SEQ ID NO: 2626), UAUgucuuug (SEQ ID NO: 3883), ACGguacuuc (SEQ ID NO: 3884), AAGgcacgcg (SEQ ID NO: 3885), CUGguaaacc (SEQ ID NO: 1684), CUUgugggua (SEQ ID NO: 3886), UGAguaaguc (SEQ ID NO: 2773), CUGguggggug (SEQ ID NO: 1773), GAGguggaga (SEQ ID NO: 3887), GUGguggcug (SEQ ID NO: 3888), GUGguaagug (SEQ ID NO: 2353), AACgugagua (SEQ ID NO: 3889), GAAgcuguaa (SEQ ID NO: 3890), CGGguaucuu (SEQ ID NO: 3891), CAGgugucag (SEQ ID NO: 1424), AAUguacgca (SEQ ID NO: 3892), CCGgugggua (SEQ ID NO: 3893), UGGgugaggu (SEQ ID NO: 3894), AAGguauguu (SEQ ID NO: 266), CAGguauguu (SEQ ID NO: 1261), CAGguuugcu (SEQ ID NO: 1505), UUGguaaguu (SEQ ID NO: 2964), CAGguaguug (SEQ ID NO: 1231), CCUgugaaua (SEQ ID NO: 3895), GCUgugugug (SEQ ID NO: 3896), CAAguaauuc (SEQ ID NO: 1033), AGGguaaugu (SEQ ID NO: 3897), GCUgugaguc (SEQ ID NO: 2205), ACCguaaguu (SEQ ID NO: 3898), CGUguaagua (SEQ ID NO: 3899), GGGguaaguc (SEQ ID NO: 3900), AAUguaugau (SEQ ID NO: 3901), AAUgugauua (SEQ ID NO: 3902), UCAguaagaa (SEQ ID NO: 2682), CAGguccguc (SEQ ID NO: 3903), GAAguauuga (SEQ ID NO: 3904), UUGguaagga (SEQ ID NO: 2960), CAGgucgguu (SEQ ID NO: 3905), UAGguuagug (SEQ ID NO: 2635), ACGguaaaac (SEQ ID NO: 577), AAGguagguc (SEQ ID NO: 228), UACgugagua (SEQ ID NO: 3906), UUGguaagca (SEQ ID NO: 3907), GCGgugaguc (SEQ ID NO: 3908), GAAguaaggg (SEQ ID NO: 3909), CGCgugaguu (SEQ ID NO: 3910), CAGguacccc (SEQ ID NO: 3911), UCUguaagac (SEQ ID NO: 3912), GAGgugggca (SEQ ID NO: 2057), AAUguaagac (SEQ ID NO: 3913), CAGgcaaggg (SEQ ID NO: 3914), CAAguaacua (SEQ ID NO: 1020), AAAguuuguc (SEQ ID NO: 3915), CAGguacugu (SEQ ID NO: 1193), AAGgucccuc (SEQ ID NO: 303), UCGguaaguc (SEQ ID NO: 3916), UGGgugagug (SEQ ID NO: 2877), CUUgugagau (SEQ ID NO: 3917), AGAgugagcu (SEQ ID NO: 3918), UAAgugggga (SEQ ID NO: 3919), UAGguaggga (SEQ ID NO: 2522), CAGguuagcc (SEQ ID NO: 1452), AGGguaauca (SEQ ID NO: 3920), AAGguucagc (SEQ ID NO: 3921), UGGgugggug (SEQ ID NO: 2885), CAGguuguga (SEQ ID NO: 1494), AAGguaagug (SEQ ID NO: 155), CAUgugcgua (SEQ ID NO: 1543), CCGguauauu (SEQ ID NO: 3922), ACCguaugug (SEQ ID NO: 3923), CAGguauagu (SEQ ID NO: 3924), CAGguauuac (SEQ ID NO: 3925), CAGgugcagg (SEQ ID NO: 1364), GUGgugagcu (SEQ ID NO: 2381), AAGguaacau (SEQ ID NO: 135), CUGgugaugg (SEQ ID NO: 3926), AUGguaaaug (SEQ ID NO: 882), CCGgugagca (SEQ ID NO: 3927), AAGguaaacc (SEQ ID NO: 124), AAGguacugg (SEQ ID NO: 3928), GCGgucagga (SEQ ID NO: 3929), CUGgucaggg (SEQ ID NO: 3930), AAAguacguu (SEQ ID NO: 3931), AGAguagguu (SEQ ID NO: 688), AGGguaagcu (SEQ ID NO: 3932), AUUgugagua (SEQ ID NO: 1009), CCGgccacca (SEQ ID NO: 3933), GAGguaacuu (SEQ ID NO: 1881), GAGguaugaa (SEQ ID NO: 1956), CAGgucagac (SEQ ID NO: 1276), UAGgcgugug (SEQ ID NO: 2462), AGGguaaguu (SEQ ID NO: 743), CAGgcaugag (SEQ ID NO: 1111), CAGguaacgu (SEQ ID NO: 1133), CAGgcgagca (SEQ ID NO: 3934), UAGguauggu (SEQ ID NO: 2550), AGAguaggau (SEQ ID NO: 3935), CUGguuucaa (SEQ ID NO: 3936), GAGguaaacu (SEQ ID NO: 3937), CAGgcaugca (SEQ ID NO: 1112), UUGguaaucu (SEQ ID NO: 3938), AGGgcagaau (SEQ ID NO: 3939), AUGguaaaac (SEQ ID NO: 877), GCUgcaggug (SEQ ID NO: 3940), GAAgcacgug (SEQ ID NO: 3941), CAUguaaaca (SEQ ID NO: 3942), UGGguaagau (SEQ ID NO: 2835), AGGguagcua (SEQ ID NO: 3943), AGGgugggu (SEQ ID NO: 800), CCUguaaguu (SEQ ID NO: 1600), UGAgugaguu (SEQ ID NO: 2801), GGAguaugua (SEQ ID NO: 3944), CAGgugaccu (SEQ ID NO: 1328), AAAguacgga (SEQ ID NO: 3945), GAGguacaga (SEQ ID NO: 1906), GAUguaggua (SEQ ID NO: 2125), GGGguaauug (SEQ ID NO: 3946), UAGgugggguu (SEQ ID NO: 2617), GUGguacgua (SEQ ID NO: 3947), AAGguacagc (SEQ ID NO: 3948), GAGgugaaga (SEQ ID NO: 3949), GGGguaagca (SEQ ID NO: 2246), UGAguagguc (SEQ ID NO: 3950), GGGguaaguu (SEQ ID NO: 2253), AUUgugaguu (SEQ ID NO: 1011), UCAguaagac (SEQ ID NO: 3951), AGUgugagcu (SEQ ID NO: 834), AAGgcaaaac (SEQ ID NO: 3952), CUGgugaguc (SEQ ID NO: 1760), AAGgucucug (SEQ ID NO: 310), GAGgcugugc (SEQ ID NO: 3953), AGAgugagac (SEQ ID NO: 700), GAGgugaugu (SEQ ID NO: 2033), AGAguauggu (SEQ ID NO: 3954), UGGgugggguc (SEQ ID NO: 2884), GCUgcugagc (SEQ ID NO: 3955), CAGguagcug (SEQ ID NO: 1210), UAGgucagaa (SEQ ID NO: 3956), CCGguaggug (SEQ ID NO: 3957), GCAguaugau (SEQ ID NO: 3958), CAGguuucag (SEQ ID NO: 3959), GAGguuugcc (SEQ ID NO: 3960), GGGgugggggg (SEQ ID NO: 3961), AAGguacaua (SEQ ID NO: 179), UGGguguguu (SEQ ID NO: 2890), AGAguaaggc (SEQ ID NO: 666), GCGguuagug (SEQ ID NO: 3962), AAGgugacuu (SEQ ID NO: 334), AUGguaagau (SEQ ID NO: 892), AUGguaguug (SEQ ID NO: 3963), CAUguaagac (SEQ ID NO: 3964), CUGguaugua (SEQ ID NO: 1736), UUCguaagga (SEQ ID NO: 3965), GAAguaugac (SEQ ID NO: 3966), CGGguaauuc (SEQ ID NO: 1627), UGGguaacuu (SEQ ID NO: 2831), CAGgugccua (SEQ ID NO: 1372), CAUguagggc (SEQ ID NO: 3967), ACCgucagga (SEQ ID NO: 3968), CGUguucgau (SEQ ID NO: 3969), GAGgcaggac (SEQ ID NO: 3970), UAGguaauau (SEQ ID NO: 2496), UCGguauacu (SEQ ID NO: 3971), UAGguugugc (SEQ ID NO: 3972), CCGgugaguc (SEQ ID NO: 3973), CAGgugccaa (SEQ ID NO: 1368), CAGgugaugc (SEQ ID NO: 1352), AAGgugagga (SEQ ID NO: 343), GUGgugaggg (SEQ ID NO: 3974), UGGgucagua (SEQ ID NO: 3975), GAGgucaggg (SEQ ID NO: 1985), UAGguacgua (SEQ ID NO: 2511), GAGgcaagag (SEQ ID NO: 1857), CCUguuggua (SEQ ID NO: 3976), GAGguaucca (SEQ ID NO: 3977), UAAguaagcu (SEQ ID NO: 2419), AAGgucaguu (SEQ ID NO: 296), AAAguuaaag (SEQ ID NO: 3978), GAGgugcuau (SEQ ID NO: 3979), ACGguaagu (SEQ ID NO: 581), CUGgugaggg (SEQ ID NO: 1757), GAGguuaugu (SEQ ID NO: 2091), CUUgugugca (SEQ ID NO: 3980), UGAgcugggg (SEQ ID NO: 3981), AAGguauagu (SEQ ID NO: 3982), UAGguaaaac (SEQ ID NO: 2464), GGGgugaggu (SEQ ID NO: 3983), GAGgcaagca (SEQ ID NO: 3984), GGAguaacgu (SEQ ID NO: 3985), AGAguaagua (SEQ ID NO: 3986), AAAguaagua (SEQ ID NO: 21), GAGgcaacca (SEQ ID NO: 3987), UGUguaaguu (SEQ ID NO: 2909), UAGgugaggc (SEQ ID NO: 2594), ACAguaagaa (SEQ ID NO: 544), UGAguaagug (SEQ ID NO: 2774), CAAgucagua (SEQ ID NO: 1057), AGGguaaaug (SEQ ID NO: 3988), AAGguaugca (SEQ ID NO: 257), GCUgugcgug (SEQ ID NO: 3989), GAGguucgcc (SEQ ID NO: 3990), AAGgcuugca (SEQ ID NO: 3991), CAGgcaagug (SEQ ID NO: 1104), AUAguaaguc (SEQ ID NO: 3992), UUGguaggua (SEQ ID NO: 2978), GCAgcaggua (SEQ ID NO: 3993), AAGguauauc (SEQ ID NO: 243), AGCguaagcc (SEQ ID NO: 3994), CUGguucgaa (SEQ ID NO: 3995), ACGgugggug (SEQ ID NO: 612), CUGgucauug (SEQ ID NO: 3996), CAGgucagga (SEQ ID NO: 1280), CAAgugagac (SEQ ID NO: 1062), GAGguacugg (SEQ ID NO: 1919), GAGguguagu (SEQ ID NO: 3997), GAGguguccu (SEQ ID NO: 3998), CAGgugcgua (SEQ ID NO: 1380), AGUgcccuga (SEQ ID NO: 3999), AUGgugaguc (SEQ ID NO: 962), UGUgugugua (SEQ ID NO: 4000), CAGguaugcu (SEQ ID NO: 1254), CUGguacagu (SEQ ID NO: 4001), UUGguacgua (SEQ ID NO: 4002), UCUguacgua (SEQ ID NO: 4003), UAAguaauuc (SEQ ID NO: 4004), CACguaugug (SEQ ID NO: 4005), CAGgcaagua (SEQ ID NO: 1103), UCGgugagug (SEQ ID NO: 4006), GGUgugaguc (SEQ ID NO: 2315), UCUguaagcu (SEQ ID NO: 2743), AAGguucaga (SEQ ID NO: 4007), AGGguacuuc (SEQ ID NO: 4008), GCGgcagguu (SEQ ID NO: 4009), GAGgcccgug (SEQ ID NO: 4010), CAGguauaaa (SEQ ID NO: 4011), AUGgucaagu (SEQ ID NO: 4012), AAGgugagua (SEQ ID NO: 347), GUGguuuguu (SEQ ID NO: 4013), AGAgugagga (SEQ ID NO: 4014), GAGguaugac (SEQ ID NO: 1957), UAGgcgugag (SEQ ID NO: 4015), AAGguacucc (SEQ ID NO: 4016), UGAgugagga (SEQ ID NO: 2798), GAGguaugau (SEQ ID NO: 4017), GGGgucggua (SEQ ID NO: 4018), ACGguaugca (SEQ ID NO: 4019), CAGguaccac (SEQ ID NO: 1171), UAAguaccug (SEQ ID NO: 4020), AGGgugggcu (SEQ ID NO: 4021), CUGgucuguu (SEQ ID NO: 4022), UAGgucagag (SEQ ID NO: 4023), AAGguguguu (SEQ ID NO: 406), CUGgucagug (SEQ ID NO: 4024), AAGgugggac (SEQ ID NO: 4025), GUGguaguag (SEQ ID NO: 4026), CUAguuuagg (SEQ ID NO: 4027), CCCgccccau (SEQ ID NO: 4028), GCUguacugc (SEQ ID NO: 4029), GAGguaauau (SEQ ID NO: 1897), UAGguuggug (SEQ ID NO: 4030), AAGguccaac (SEQ ID NO: 4031), UAGgugagga (SEQ ID NO: 2593), GUGguaaguu (SEQ ID NO: 2354), AGUgugagag (SEQ ID NO: 831), AAUguacaug (SEQ ID NO: 497), UUGgcaggug (SEQ ID NO: 4032), UAGguuauug (SEQ ID NO: 4033), CAGguacuga (SEQ ID NO: 1191), GCGguggguc (SEQ ID NO: 4034), UGUguaagau (SEQ ID NO: 4035), GAGgugagua (SEQ ID NO: 2025), GCAgccccgg (SEQ ID NO: 4036), CAGgugcuaa (SEQ ID NO: 4037), AGUguaagag (SEQ ID NO: 815), CAGguacauc (SEQ ID NO: 4038), CAGgugggac (SEQ ID NO: 1403), AGGguaaaua (SEQ ID NO: 727), UAAguaauua (SEQ ID NO: 4039), CAGguaaccg (SEQ ID NO: 1132), AAGguuugca (SEQ ID NO: 461), UAGgugguuu (SEQ ID NO: 4040), CAGgugaccg (SEQ ID NO: 1327), UGUguaagcu (SEQ ID NO: 4041), GGAgugaguc (SEQ ID NO: 2227), AGGguaggag (SEQ ID NO: 752), AGGgugggug (SEQ ID NO: 802), AAGgucugag (SEQ ID NO: 313), GAUguaauau (SEQ ID NO: 4042), GGGguaauua (SEQ ID NO: 4043), UAGguaggua (SEQ ID NO: 2524), GAGgcaagua (SEQ ID NO: 1858), GAGguaagga (SEQ ID NO: 1889), UAGguacuac (SEQ ID NO: 4044), UCGgugggug (SEQ ID NO: 4045), AAGgugugga (SEQ ID NO: 401), CAGgucugcc (SEQ ID NO: 1305), UAAgugagcc (SEQ ID NO: 4046), GAAguaaguu (SEQ ID NO: 1820), GAAguaagcc (SEQ ID NO: 1815), UAGgugcgac (SEQ ID NO: 4047), GAGguauggc (SEQ ID NO: 4048), GCAguaagaa (SEQ ID NO: 2145), CAGgugugga (SEQ ID NO: 1438), UUGguaacgu (SEQ ID NO: 4049), GCUguaaaaa (SEQ ID NO: 4050), UUGguuagua (SEQ ID NO: 4051), AUAguaaggg (SEQ ID NO: 4052), UUGguacuag (SEQ ID NO: 4053), CGGgcagccg (SEQ ID NO: 4054), CAGgugcugg (SEQ ID NO: 1389), UAUgugaguu (SEQ ID NO: 2673), CAGgucuggg (SEQ ID NO: 4055), UAAguaagaa (SEQ ID NO: 2415), AAGguuauua (SEQ ID NO: 4056), AGAguaaagc (SEQ ID NO: 4057), AGAgugugag (SEQ ID NO: 4058), UAGgugcgag (SEQ ID NO: 4059), CAAguaaacg (SEQ ID NO: 4060), AAGguacgua (SEQ ID NO: 4061), CUGgugagua (SEQ ID NO: 1759), CCAguaugua (SEQ ID NO: 4062), UUGgugagug (SEQ ID NO: 3006), UGAguaagua (SEQ ID NO: 2772), GAGguuagca (SEQ ID NO: 4063), GUGguaagcc (SEQ ID NO: 4064), CUGguauggc (SEQ ID NO: 1734), AAAguaacac (SEQ ID NO: 8), CAGguacuaa (SEQ ID NO: 1186), UCUguaaguu (SEQ ID NO: 2747), GAGgugaggg (SEQ ID NO: 2024), ACUgugggua (SEQ ID NO: 647), GAUguuugug (SEQ ID NO: 4065), CAGgugucaa (SEQ ID NO: 4066), CAGgucacca (SEQ ID NO: 4067), CCGgugagua (SEQ ID NO: 4068), UUGguaaaua (SEQ ID NO: 4069), CAGgugggggg (SEQ ID NO: 1411), ACUgcaggug (SEQ ID NO: 4070), UAGguauguu (SEQ ID NO: 2554), GGAgcaagug (SEQ ID NO: 4071), UCGgugccuc (SEQ ID NO: 4072), CAAguaacuu (SEQ ID NO: 4073), GAGguaacca (SEQ ID NO: 1879), CAGguaauau (SEQ ID NO: 1151), GGAguaagaa (SEQ ID NO: 4074), GAGguaccuu (SEQ ID NO: 1914), AGGguaagga (SEQ ID NO: 737), CCUgugaguc (SEQ ID NO: 1609), GAGguaaugg (SEQ ID NO: 1900), AUGguguguc (SEQ ID NO: 4075), GGGgugagua (SEQ ID NO: 4076), AGGgucaggu (SEQ ID NO: 4077), UGGguaaggg (SEQ ID NO: 2839), AGGguagguu (SEQ ID NO: 759), AUAgugaguu (SEQ ID NO: 4078), CCCguaggcu (SEQ ID NO: 4079), ACAguaugua (SEQ ID NO: 553), GACgugugua (SEQ ID NO: 4080), GCGgugagga (SEQ ID NO: 4081), CAGgugaccc (SEQ ID NO: 1326), UAAguuuagu (SEQ ID NO: 4082), ACAguugagu (SEQ ID NO: 570), CGGgugaggg (SEQ ID NO: 1639), CAGguggauu (SEQ ID NO: 1398), CGGguagagg (SEQ ID NO: 4083), UAGgugcgug (SEQ ID NO: 2608), GGGguaagaa (SEQ ID NO: 2243), GAGguggggu (SEQ ID NO: 4084), CACgugguu (SEQ ID NO: 4085), ACGguaauug (SEQ ID NO: 4086), AGAgugaguc (SEQ ID NO: 705), UUGgcuccaa (SEQ ID NO: 4087), AAGgugaugc (SEQ ID NO: 355), AAGguugguc (SEQ ID NO: 448), AGCguaaguu (SEQ ID NO: 4088), AUUguaugua (SEQ ID NO: 1006), UCAguuaagu (SEQ ID NO: 4089), CAAguacgug (SEQ ID NO: 4090), CAGgugcgug (SEQ ID NO: 1382), CAGguaggua (SEQ ID NO: 1220), AUGguggggu (SEQ ID NO: 4091), AUGgugaguu (SEQ ID NO: 964), CAGguaauca (SEQ ID NO: 4092), AAGguagggu (SEQ ID NO: 226), CAGgccaagg (SEQ ID NO: 4093), GUGgugagag (SEQ ID NO: 4094), AAGguuggug (SEQ ID NO: 449), CAGguacucu (SEQ ID NO: 1190), UAGgcaugug (SEQ ID NO: 4095), UUGguaccuu (SEQ ID NO: 4096), CUGgugugcc (SEQ ID NO: 4097), ACAguugcca (SEQ ID NO: 4098), UUGguaauau (SEQ ID NO: 4099), GAGgugcaug (SEQ ID NO: 4100), UUGguuugua (SEQ ID NO: 3028), UUGguaagug (SEQ ID NO: 2963), UGUgugugug (SEQ ID NO: 4101), GUGguuugua (SEQ ID NO: 2398), GCGguacaca (SEQ ID NO: 4102), AGAguaugcu (SEQ ID NO: 4103), UUUguaagua (SEQ ID NO: 3038), UCUgugcggg (SEQ ID NO: 4104), AAGgucagug (SEQ ID NO: 295), GAGguaggaa (SEQ ID NO: 1930), GCGguuagca (SEQ ID NO: 4105), AGGgugaggg (SEQ ID NO: 793), GAAgugagua (SEQ ID NO: 4106), CAGgugacag (SEQ ID NO: 4107), AAGgugauua (SEQ ID NO: 357), GAGgccagcc (SEQ ID NO: 4108), GAGgucuccu (SEQ ID NO: 4109), UAGguauuac (SEQ ID NO: 2556), CAUguaagag (SEQ ID NO: 1519), CUGguagggc (SEQ ID NO: 4110), GAAguaagua (SEQ ID NO: 1818), CGGguaagug (SEQ ID NO: 4111), CAGguaaucu (SEQ ID NO: 4112), GUGguaggua (SEQ ID NO: 4113), CAGgugggua (SEQ ID NO: 1413), AAGgccagug (SEQ ID NO: 4114), AAAgugaauc (SEQ ID NO: 4115), ACGguuacgu (SEQ ID NO: 4116), AUGguaggaa (SEQ ID NO: 917), CGGgugagac (SEQ ID NO: 4117), GAGguuggaa (SEQ ID NO: 2099), UGGgugagcc (SEQ ID NO: 2871), CCAgugagua (SEQ ID NO: 1564), CUAguacgag (SEQ ID NO: 4118), CAGguaugac (SEQ ID NO: 1248), GCUgugaggu (SEQ ID NO: 4119), CUGguaugaa (SEQ ID NO: 4120), GGUguacgac (SEQ ID NO: 4121), CUUgugagug (SEQ ID NO: 4122), GUGgugagca (SEQ ID NO: 2380), CUGguaacuu (SEQ ID NO: 1696), CAGguacuau (SEQ ID NO: 1188), AGGguaaggg (SEQ ID NO: 739), UUGguuaguu (SEQ ID NO: 3025), GGUguaagca (SEQ ID NO: 2302), UCGgugagga (SEQ ID NO: 4123), UGGguaaaca (SEQ ID NO: 4124), UCGguacgug (SEQ ID NO: 4125), UAGguagcag (SEQ ID NO: 4126), CUGguaaggc (SEQ ID NO: 1704), GUGguaagga (SEQ ID NO: 2349), UAAguaagca (SEQ ID NO: 2418), GAGguuccaa (SEQ ID NO: 4127), CUGguaugga (SEQ ID NO: 4128), GGGgugggua (SEQ ID NO: 2288), CAGguuuccc (SEQ ID NO: 4129), CAGgucucug (SEQ ID NO: 4130), GAGgugagga (SEQ ID NO: 2022), CUUguggguu (SEQ ID NO: 1805), AUGgugagac (SEQ ID NO: 953), CAGgugaagg (SEQ ID NO: 1319), GCGguagggg (SEQ ID NO: 4131), GUUguuuccc (SEQ ID NO: 4132), AAAgcaucca (SEQ ID NO: 4133), GUGguagguu (SEQ ID NO: 2367), AAGgugugaa (SEQ ID NO: 398), CAGguacagu (SEQ ID NO: 1167), AAGguaccaa (SEQ ID NO: 182), UUGguaauug (SEQ ID NO: 2969), AAGgugcuca (SEQ ID NO: 4134), AAGguucaac (SEQ ID NO: 4135), CAGguuuaca (SEQ ID NO: 4136), GCUguaagug (SEQ ID NO: 2195), AGGguauguc (SEQ ID NO: 769), GAGgucgggg (SEQ ID NO: 1996), AAGgugccug (SEQ ID NO: 363), AAGguaaaaa (SEQ ID NO: 119), GUGgugaguu (SEQ ID NO: 2385), UAGguaagaa (SEQ ID NO: 4137), AGGguauccu (SEQ ID NO: 4138), GUGguaauau (SEQ ID NO: 4139), UCUguaagua (SEQ ID NO: 2744), UGGguaugga (SEQ ID NO: 4140), AUGguaugga (SEQ ID NO: 935), GACgugagcc (SEQ ID NO: 1854), CUGguuuggc (SEQ ID NO: 4141), AUGguauauc (SEQ ID NO: 4142), AAAguaaacu (SEQ ID NO: 4143), AGCgugagug (SEQ ID NO: 721), CUGguauaga (SEQ ID NO: 4144), CAGgugggga (SEQ ID NO: 1409), AGAguauguu (SEQ ID NO: 696), UAGguacuug (SEQ ID NO: 4145), GCAguaggug (SEQ ID NO: 4146), AGUguauguc (SEQ ID NO: 4147), AAGguuaagc (SEQ ID NO: 413), CUGguggccu (SEQ ID NO: 4148), GAAgugaguc (SEQ ID NO: 1839), UUGguguaag (SEQ ID NO: 4149), CAGguaagaa (SEQ ID NO: 1138), CGGgucucgg (SEQ ID NO: 4150), GAGgugcaca (SEQ ID NO: 2035), CUCguuaguu (SEQ ID NO: 4151), AAGgugauca (SEQ ID NO: 352), UAUguaagaa (SEQ ID NO: 2649), GAGgugcuug (SEQ ID NO: 2047), CAGgugguca (SEQ ID NO: 4152), ACGguaaguc (SEQ ID NO: 4153), ACAguaaugu (SEQ ID NO: 4154), CCUguaaggu (SEQ ID NO: 4155), GAGguuaagu (SEQ ID NO: 4156), UCGguaugug (SEQ ID NO: 2725), UGGguauguu (SEQ ID NO: 2863), AAGguauuac (SEQ ID NO: 268), CAGgugaggg (SEQ ID NO: 1343), UUGguaaaca (SEQ ID NO: 4157), AAGguagugu (SEQ ID NO: 4158), GAGguguggc (SEQ ID NO: 4159), CAGguacgga (SEQ ID NO: 4160), AAGgucauca (SEQ ID NO: 4161), CAAguaggca (SEQ ID NO: 4162), CAGgugaaac (SEQ ID NO: 4163), CAGguacugc (SEQ ID NO: 1192), AAUgcaagug (SEQ ID NO: 4164), CAUguaauuc (SEQ ID NO: 4165), AAGguaugcu (SEQ ID NO: 259), CUGgugaguu (SEQ ID NO: 1762), CAGgugguuu (SEQ ID NO: 4166), UGUgugagua (SEQ ID NO: 2922), AAGgucggug (SEQ ID NO: 4167), AUGguaaauu (SEQ ID NO: 883), AGGguauuac (SEQ ID NO: 771), AGUguaugga (SEQ ID NO: 4168), AACguaagau (SEQ ID NO: 4169), GUGguaaggu (SEQ ID NO: 4170), ACUguuagua (SEQ ID NO: 4171), CAGguaucag (SEQ ID NO: 1239), AAGguuaguu (SEQ ID NO: 425), CUGgugagcu (SEQ ID NO: 1754), UUGgugagcu (SEQ ID NO: 4172), UGUguacgua (SEQ ID NO: 4173), GAGgucagcc (SEQ ID NO: 4174), GAGguagaau (SEQ ID NO: 4175), AAGguaugag (SEQ ID NO: 255), UAGguauuuc (SEQ ID NO: 2563), UGUguaacac (SEQ ID NO: 4176), AGUguaaggc (SEQ ID NO: 4177), GAGgucugcu (SEQ ID NO: 4178), AAGguuagca (SEQ ID NO: 418), CAGguaaaug (SEQ ID NO: 1127), AACguaagcu (SEQ ID NO: 4179), CAGgucugca (SEQ ID NO: 4180), CAGguauugu (SEQ ID NO: 1267), GUGguaauuc (SEQ ID NO: 2356), GAGguauaug (SEQ ID NO: 1951), GCCgugagcc (SEQ ID NO: 4181), GAGguaagag (SEQ ID NO: 1883), UGAguaugua (SEQ ID NO: 2787), CAGguaaggg (SEQ ID NO: 1145), GAGguaaauu (SEQ ID NO: 1876), CAGgcaacuu (SEQ ID NO: 4182), UGUguaaguc (SEQ ID NO: 2908), CAGgugcgcu (SEQ ID NO: 4183), CGGguaaacc (SEQ ID NO: 4184), CCGgucaguc (SEQ ID NO: 4185), UAGguggggcg (SEQ ID NO: 4186), GCGgucaguu (SEQ ID NO: 4187), GGGgugggguc (SEQ ID NO: 4188), AGCguaauag (SEQ ID NO: 4189), ACGgugaguc (SEQ ID NO: 4190), CUGguacuug (SEQ ID NO: 1722), CAGguuggua (SEQ ID NO: 4191), AGAguaugug (SEQ ID NO: 695), CUGgugggua (SEQ ID NO: 1771), GAGguggcuu (SEQ ID NO: 4192), AUAguauuga (SEQ ID NO: 4193), UGAgucgucc (SEQ ID NO: 4194), CAGgugcucu (SEQ ID NO: 4195), UACguaauau (SEQ ID NO: 4196), GCUgucccuga (SEQ ID NO: 4197), CAGgcugcac (SEQ ID NO: 4198), CUGgugcgcu (SEQ ID NO: 1766), GCGguaagaa (SEQ ID NO: 4199), UAAguuacuu (SEQ ID NO: 4200), GAAgugagug (SEQ ID NO: 1840), UAGgcaaguc (SEQ ID NO: 2460), UAAguaaaua (SEQ ID NO: 4201), ACGgugagug (SEQ ID NO: 607), CAGguagguu (SEQ ID NO: 1223), GGGguauaac (SEQ ID NO: 4202), GUUgugaguu (SEQ ID NO: 2410), CAUgugagua (SEQ ID NO: 1539), GAGgugcauu (SEQ ID NO: 4203), AAGguuugua (SEQ ID NO: 466), UCGguaaugu (SEQ ID NO: 4204), CGAguaaggg (SEQ ID NO: 1616), GAGgcacgga (SEQ ID NO: 4205), AGGgugugga (SEQ ID NO: 4206), CAGguauggu (SEQ ID NO: 1257), AAGguagaaa (SEQ ID NO: 203), CAGgugccug (SEQ ID NO: 1373), UGGguauaug (SEQ ID NO: 4207), UGAgugagac (SEQ ID NO: 4208), UGGguaauuu (SEQ ID NO: 2847), AUGguaaaua (SEQ ID NO: 881), AAGgcaaagg (SEQ ID NO: 4209), AGUguuuguu (SEQ ID NO: 4210), AUGguauugg (SEQ ID NO: 4211), CUGgugaggc (SEQ ID NO: 1756), UUGguaaaau (SEQ ID NO: 2948), ACAgugaguu (SEQ ID NO: 563), CAGgugcugu (SEQ ID NO: 4212), GAGguuaaga (SEQ ID NO: 2080), AGAguaagaa (SEQ ID NO: 659), GAGguccgcg (SEQ ID NO: 4213), GUGgugagga (SEQ ID NO: 2382), CAGgugagcc (SEQ ID NO: 1338), CAGgugacau (SEQ ID NO:

1324), AUGgcaagcu (SEQ ID NO: 4214), UCGguaauau (SEQ ID NO: 4215), CAGgcaacaa (SEQ ID NO: 4216), GGGguaggga (SEQ ID NO: 2257), CUGgucucgc (SEQ ID NO: 4217), UAGguaacga (SEQ ID NO: 4218), CGGguaaggu (SEQ ID NO: 4219), UAGguaaugc (SEQ ID NO: 4220), CAGgcaagaa (SEQ ID NO: 1099), ACAguaggua (SEQ ID NO: 4221), CAAguaugag (SEQ ID NO: 1049), GCUguucgaa (SEQ ID NO: 4222), AAGguuaugc (SEQ ID NO: 4223), GAUgugaguu (SEQ ID NO: 2136), CAGguggaga (SEQ ID NO: 1396), AGAguuaguu (SEQ ID NO: 4224), UGAgugugcg (SEQ ID NO: 4225), GAGguacagc (SEQ ID NO: 1907), CAGguaagac (SEQ ID NO: 1139), CAUgugcuuu (SEQ ID NO: 4226), AGGguguguu (SEQ ID NO: 4227), ACAguuaagg (SEQ ID NO: 4228), ACAgugaggg (SEQ ID NO: 4229), GAUguauacc (SEQ ID NO: 4230), UUAguaagcu (SEQ ID NO: 4231), CAGguaagau (SEQ ID NO: 1141), AGAgcugcgu (SEQ ID NO: 4232), GAGgcaaguu (SEQ ID NO: 1860), GAAguaagug (SEQ ID NO: 1819), AAGgugaaaa (SEQ ID NO: 4233), AAGguaccua (SEQ ID NO: 4234), GAGguaucag (SEQ ID NO: 4235), AUGguaugua (SEQ ID NO: 4236), AAGguaugaa (SEQ ID NO: 253), UUGgugagcc (SEQ ID NO: 4237), AAGguuagga (SEQ ID NO: 420), AGGguaugua (SEQ ID NO: 768), CAGguaccga (SEQ ID NO: 4238), AGAguaaacu (SEQ ID NO: 4239), AAGgugcaua (SEQ ID NO: 4240), AAGguaaugu (SEQ ID NO: 167), CCGgugugug (SEQ ID NO: 4241), AGGguaaauu (SEQ ID NO: 729), GGGguuuggc (SEQ ID NO: 4242), CAGguacacg (SEQ ID NO: 1164), UUGguaacca (SEQ ID NO: 4243), GAGgucaggu (SEQ ID NO: 1986), UCUguuggua (SEQ ID NO: 4244), CAGguuaguu (SEQ ID NO: 1458), UUGguauguc (SEQ ID NO: 4245), AAGgugcguc (SEQ ID NO: 4246), AGGguaagaa (SEQ ID NO: 733), UUUguaagcc (SEQ ID NO: 4247), AAGgucaggu (SEQ ID NO: 292), CUGguaaacu (SEQ ID NO: 4248), UCGguaauuu (SEQ ID NO: 4249), CUGguaggcu (SEQ ID NO: 4250), GAGgucugua (SEQ ID NO: 4251), GAGguacuuu (SEQ ID NO: 1922), CUGguaaagg (SEQ ID NO: 4252), CGGgugugug (SEQ ID NO: 1650), CAGguguggu (SEQ ID NO: 4253), UCGguacguc (SEQ ID NO: 4254), CAGgugccag (SEQ ID NO: 4255), GGGgugagaa (SEQ ID NO: 2275), ACAgcuagua (SEQ ID NO: 4256), AAGguauagc (SEQ ID NO: 4257), CUGguaggag (SEQ ID NO: 4258), GCUguacgua (SEQ ID NO: 4259), AAGguaaagg (SEQ ID NO: 128), CAAgcacgag (SEQ ID NO: 4260), CUAguaagac (SEQ ID NO: 4261), CCCguaagcg (SEQ ID NO: 4262), CAAgugugag (SEQ ID NO: 1078), AUGguaaggg (SEQ ID NO: 897), AAGgugaggg (SEQ ID NO: 345), CAAguaggua (SEQ ID NO: 1041), GGUguugcug (SEQ ID NO: 2321), GAGguacugu (SEQ ID NO: 1920), UAGguaagau (SEQ ID NO: 2484), CAGgugcgaa (SEQ ID NO: 1374), GAGguccagg (SEQ ID NO: 4263), UUGguauaca (SEQ ID NO: 2982), GGAgugagua (SEQ ID NO: 2226), GAGgugagau (SEQ ID NO: 2017), AAGguggggc (SEQ ID NO: 4264), CAGguaaacg (SEQ ID NO: 4265), UCGguaacuu (SEQ ID NO: 4266), CAGguaaauu (SEQ ID NO: 1128), GAGgugcgca (SEQ ID NO: 4267), ACUgugagua (SEQ ID NO: 643), ACGgugugac (SEQ ID NO: 4268), GUGguaaguc (SEQ ID NO: 2352), CAGguaggca (SEQ ID NO: 1215), CAGgucagca (SEQ ID NO: 1277), GUGguaugug (SEQ ID NO: 4269), AAAguaucug (SEQ ID NO: 4270), CGGguaugua (SEQ ID NO: 4271), AAGguaauaa (SEQ ID NO: 157), GAGgugggga (SEQ ID NO: 2060), GCUguaggug (SEQ ID NO: 2197), GAAgugaguu (SEQ ID NO: 1841), AAAguauuua (SEQ ID NO: 4272), UAUguaagua (SEQ ID NO: 2653), ACGguaugag (SEQ ID NO: 4273), CUGgugagug (SEQ ID NO: 1761), AGAguaaaau (SEQ ID NO: 4274), GCUguauggc (SEQ ID NO: 4275), AUGguaaacc (SEQ ID NO: 879), GCAguaauaa (SEQ ID NO: 4276), UAAguauuua (SEQ ID NO: 4277), AAUgucagug (SEQ ID NO: 515), AUUgcaggag (SEQ ID NO: 4278), CCGguaagaa (SEQ ID NO: 4279), AAGgcaaguu (SEQ ID NO: 101), GAGguuuguc (SEQ ID NO: 4280), AAGguaacug (SEQ ID NO: 139), AAAguaugag (SEQ ID NO: 4281), GAUguuagua (SEQ ID NO: 4282), CAGgugggguc (SEQ ID NO: 1414), AAGguaccga (SEQ ID NO: 4283), CCAguaauua (SEQ ID NO: 4284), GUGguaugcg (SEQ ID NO: 4285), AUGgugcgcu (SEQ ID NO: 4286), CAGgucuaug (SEQ ID NO: 4287), AAGguauuua (SEQ ID NO: 274), CUAguaagau (SEQ ID NO: 4288), AGAguaauuu (SEQ ID NO: 675), GAGguaacgu (SEQ ID NO: 4289), AAGguagcca (SEQ ID NO: 212), CUGgucccgg (SEQ ID NO: 4290), GAGguccuuc (SEQ ID NO: 4291), ACGgucaccc (SEQ ID NO: 4292), AAGguaauac (SEQ ID NO: 158), CAGgugcaug (SEQ ID NO: 1367), AUGguaauag (SEQ ID NO: 4293), UUUguaacac (SEQ ID NO: 4294), UGGguaugau (SEQ ID NO: 4295), CAGgcccccc (SEQ ID NO: 4296), AGAguaguaa (SEQ ID NO: 4297), AGUguaagaa (SEQ ID NO: 814), GAAguauguu (SEQ ID NO: 1833), CAGgugugca (SEQ ID NO: 1434), UUGgugaggg (SEQ ID NO: 3003), UGGguugguu (SEQ ID NO: 4298), CAGguacgua (SEQ ID NO: 1184), GAGgugcggc (SEQ ID NO: 4299), UCUguacggg (SEQ ID NO: 4300), CGGgugcgug (SEQ ID NO: 4301), UACguaagug (SEQ ID NO: 2455), CAUguaagga (SEQ ID NO: 4302), CAGgugacgg (SEQ ID NO: 1329), GAUguaugcu (SEQ ID NO: 4303), UCUgcaauuc (SEQ ID NO: 4304), UGAguaaggc (SEQ ID NO: 2770), GAGguauauu (SEQ ID NO: 1952), AGAgugaguu (SEQ ID NO: 707), AAGguaagcu (SEQ ID NO: 148), UAGgugaagu (SEQ ID NO: 2580), CAGguuagua (SEQ ID NO: 1455), UAUguaagug (SEQ ID NO: 2655), UUGgugggggg (SEQ ID NO: 4305), UGAgcucaaa (SEQ ID NO: 4306), UCGguaugua (SEQ ID NO: 4307), UAAguaugcc (SEQ ID NO: 4308), AAUguaagua (SEQ ID NO: 489), CAGguuugca (SEQ ID NO: 4309), ACGgugagag (SEQ ID NO: 4310), CAGguguuuu (SEQ ID NO: 4311), GUGgugagcc (SEQ ID NO: 4312), AGGguacaua (SEQ ID NO: 4313), UAGguaaccc (SEQ ID NO: 4314), GUGgucagua (SEQ ID NO: 4315), CUGgugagcc (SEQ ID NO: 4316), CAGgugcuua (SEQ ID NO: 1390), AUAgucguga (SEQ ID NO: 4317), AUAgugagug (SEQ ID NO: 862), GAGgucaaaa (SEQ ID NO: 4318), CGUguagcuu (SEQ ID NO: 4319), CAGguguuug (SEQ ID NO: 4320), CAGguuggac (SEQ ID NO: 4321), CAGguaagcu (SEQ ID NO: 4322), AGGgucagaa (SEQ ID NO: 4323), CACguauguc (SEQ ID NO: 4324), CACgugagug (SEQ ID NO: 1098), GGGguacgga (SEQ ID NO: 4325), AAGgcaggac (SEQ ID NO: 4326), GAGgugaagc (SEQ ID NO: 4327), GAGguuugaa (SEQ ID NO: 4328), CAGguaagug (SEQ ID NO: 1148), CAGguaacca (SEQ ID NO: 1131), CAGguacucc (SEQ ID NO: 1189), AAGgugcuuu (SEQ ID NO: 371), GAGguaaaua (SEQ ID NO: 1873), GAGgcaggug (SEQ ID NO: 4329), GAGguucgga (SEQ ID NO: 4330), CAGguauuug (SEQ ID NO: 1270), CAGguaaaua (SEQ ID NO: 1125), CAGgugaugu (SEQ ID NO: 1354), CAGgugauac (SEQ ID NO: 4331), GAGgugaggc (SEQ ID NO: 2023), AGGgugggggg (SEQ ID NO: 4332), UAAguaaguu (SEQ ID NO: 2425), UGGgugaaca (SEQ ID NO: 4333), UAGguacugc (SEQ ID NO: 4334), CAGgcuccug (SEQ ID NO: 4335), AGGguaggca (SEQ ID NO: 753), CAGgugcccg (SEQ ID NO: 1371), GAGguacauc (SEQ ID NO: 4336), AGGgugugug (SEQ ID NO: 804), AAGguaguaa (SEQ ID NO: 231), UGGguaugag (SEQ ID NO: 2859), GGGgugugug (SEQ ID NO: 2294), CUAguaggug (SEQ ID NO: 4337), GAGgcaagga (SEQ ID NO: 4338), AAGgcaagac (SEQ ID NO: 4339), AAAgugcggu (SEQ ID NO: 4340), AAGguugguu (SEQ ID NO: 450), GAGguuaaug (SEQ ID NO: 4341), UUGgugaguc (SEQ ID NO: 3005), UCGguuagcu (SEQ ID NO: 2738), GCAguaagca (SEQ ID NO: 4342), AAGgcaagca (SEQ ID NO: 4343), ACAguaagcu (SEQ ID NO: 4344), GAGguaacag (SEQ ID NO: 1878), AAAguacgua (SEQ ID NO: 4345), GAGguaauac (SEQ ID NO: 1896), UUGguaggug (SEQ ID NO: 2980), CUGguuaguc (SEQ ID NO: 4346), GAGgugacgc (SEQ ID NO: 4347), ACAguaagga (SEQ ID NO: 4348), AAUguacuua (SEQ ID NO: 4349), GGGguacagu (SEQ ID NO: 4350), CGUguaugug (SEQ ID NO: 4351), UCCguagguu (SEQ ID NO: 4352), GAGgugggucg (SEQ ID NO: 4353), UCAgugaguc (SEQ ID NO: 4354), AAAguaagca (SEQ ID NO: 15), GAGgucuggu (SEQ ID NO: 1999), GAGguaauua (SEQ ID NO: 4355), GUAguaagua (SEQ ID NO: 2323), AAGgugggga (SEQ ID NO: 382), UCUgugagca (SEQ ID NO: 4356), GAAguucgug (SEQ ID NO: 4357), ACGgugaggc (SEQ ID NO: 4358), UCAgugagua (SEQ ID NO: 2699), UAGguaguug (SEQ ID NO: 4359), GGUgucuggg (SEQ ID NO: 4360), GGGguaagug (SEQ ID NO: 2252), GAGgugggguu (SEQ ID NO: 2066), UGUgugaguu (SEQ ID NO: 4361), CAUguaagua (SEQ ID NO: 1522), AAGguaggug (SEQ ID NO: 229), AAUguaggag (SEQ ID NO: 4362), GAGgcacguc (SEQ ID NO: 4363), CAAguacauu (SEQ ID NO: 4364), UUGguacaga (SEQ ID NO: 4365), GAGguaguag (SEQ ID NO: 1941), AAAgugaggg (SEQ ID NO: 57), UUGgucagug (SEQ ID NO: 4366), AGGgugaguc (SEQ ID NO: 796), CAGgugaaca (SEQ ID NO: 1317), GGUgugggcc (SEQ ID NO: 4367), CGGgugagcu (SEQ ID NO: 4368), GGGgugaguc (SEQ ID NO: 2283), ACAgugagag (SEQ ID NO: 4369), AGGgugaggu (SEQ ID NO: 794), GCUguaaguc (SEQ ID NO: 2194), AUAguagguu (SEQ ID NO: 4370), CAGgcaugug (SEQ ID NO: 1114), AAGguaaguu (SEQ ID NO: 156), CAGguccgug (SEQ ID NO: 4371), GAGgcaggua (SEQ ID NO: 4372), AUGguggaag (SEQ ID NO: 4373), AUGgugggcg (SEQ ID NO: 4374), GAGgugagaa (SEQ ID NO: 2014), AGUgugagca (SEQ ID NO: 832), UUGguaagua (SEQ ID NO: 2962), CAAguaagca (SEQ ID NO: 4375), GGUgugagcu (SEQ ID NO: 2313), CCCgugggua (SEQ ID NO: 4376), CAGguagaau (SEQ ID NO: 4377), CAGgcugagc (SEQ ID NO: 4378), CUGguggccc (SEQ ID NO: 4379), UGAguaagag (SEQ ID NO: 4380), CACguuagcu (SEQ ID NO: 4381), AAGgugaguc (SEQ ID NO: 348), AAGguagcuc (SEQ ID NO: 4382), UCGgugaguu (SEQ ID NO: 4383), GAGgcccuuc (SEQ ID NO: 4384), CAGguuaugc (SEQ ID NO: 4385), CCUguaagcu (SEQ ID NO: 4386), CAGgucuccu (SEQ ID NO: 4387), UAGguaggcu (SEQ ID NO: 4388), GGGguagggg (SEQ ID NO: 4389), AAGguaguga (SEQ ID NO: 4390), GAGguuguug (SEQ ID NO: 4391), CAGguugguu (SEQ ID NO: 1489), AAAguaagcc (SEQ ID NO: 16), ACAgugagug (SEQ ID NO: 562), UGGgugugau (SEQ ID NO: 4392), CCCguaacua (SEQ ID NO: 4393), AAGguguugc (SEQ ID NO: 408), AAAgcuggug (SEQ ID NO: 4394), GAGguauagu (SEQ ID NO: 4395), ACGguaagag (SEQ ID NO: 4396), AUGguacggu (SEQ ID NO: 913), GAGgccaguu (SEQ ID NO: 4397), GAGguaugcg (SEQ ID NO: 1960), UCGgugggag (SEQ ID NO: 4398), AAGguggaua (SEQ ID NO: 372), CCAguguggc (SEQ ID NO: 4399), AGGguaagug (SEQ ID NO: 742), UCUguaggcu (SEQ ID NO: 4400), CAGgcaagga (SEQ ID NO: 1102), CGGguaauuu (SEQ ID NO: 1628), AUUgugaguc (SEQ ID NO: 1010), CAGguaaacc (SEQ ID NO: 1121), AAGgucaauu (SEQ ID NO: 4401), AAGgugaaua (SEQ ID NO: 327), GUCguaagaa (SEQ ID NO: 4402), GCGguaaguc (SEQ ID NO: 4403), CUGguagagc (SEQ ID NO: 4404), GAGgucgguc (SEQ ID NO: 4405), CAGguaaaca (SEQ ID NO: 1120), AAGgcaagga (SEQ ID NO: 98), CAGgucgucu (SEQ ID NO: 4406), GGGguagggc (SEQ ID NO: 4407), CUGguacuaa (SEQ ID NO: 1721), GAGguagcug (SEQ ID NO: 1929), CUUgucagcu (SEQ ID NO: 4408), UAGguaaggc (SEQ ID NO: 2489), CUGguauuac (SEQ ID NO: 4409), UAAguacguc (SEQ ID NO: 4410), AAGguaagcc (SEQ ID NO: 146), ACGgugaaag (SEQ ID NO: 4411), CCAgccaaua (SEQ ID NO: 4412), CAGguuuguc (SEQ ID NO: 4413), AAGguauaau (SEQ ID NO: 239), AAGgucuuag (SEQ ID NO: 4414), AGGgugagcu (SEQ ID NO: 791), AAGguuaggg (SEQ ID NO: 4415), CGGguaaauu (SEQ ID NO: 4416), CAGguaacgg (SEQ ID NO: 4417), AGAgugugua (SEQ ID NO: 4418), ACAguaaguu (SEQ ID NO: 549), GAUguaauuu (SEQ ID NO: 4419), GAGguaggga (SEQ ID NO: 1934), UUGgcaagug (SEQ ID NO: 2945), AAAgugagga (SEQ ID NO: 4420), AAGguagugc (SEQ ID NO: 234), AGAguaauuc (SEQ ID NO: 674), GGAguaaaua (SEQ ID NO: 4421), GUGguaccca (SEQ ID NO: 4422), CAGguauugc (SEQ ID NO: 4423), GAUgugaggg (SEQ ID NO: 4424), CAAguaaauc (SEQ ID NO: 1017), CAGgugucuc (SEQ ID NO: 1428), AAGguaacag (SEQ ID NO: 4425), UUGguaaaag (SEQ ID NO: 4426), CAGguaucau (SEQ ID NO: 1240), ACGgugagac (SEQ ID NO: 4427), CUGguaugac (SEQ ID NO: 4428), CAGguucacu (SEQ ID NO: 4429), GAGgugauca (SEQ ID NO: 4430), AGUguaaguc (SEQ ID NO: 4431), AACguaagua (SEQ ID NO: 4432), AAAgugagug (SEQ ID NO: 60), GAGguacagg (SEQ ID NO: 4433), CAAguaauga (SEQ ID NO: 4434), GAUguaagga (SEQ ID NO: 4435), UCAguucccc (SEQ ID NO: 4436), GCGguaagga (SEQ ID NO: 4437), UAGguacuaa (SEQ ID NO: 4438), AAGgugaaag (SEQ ID NO: 321), ACUguaagug (SEQ ID NO: 4439), UGGguaugug (SEQ ID NO: 2862), AUGguaacag (SEQ ID NO: 884), CAGguagggu (SEQ ID NO: 1219), ACAguaagug (SEQ ID NO: 548), AAGgugcucc (SEQ ID NO: 366), AAGgugugcu (SEQ ID NO: 4440), AAGgugguga (SEQ ID NO: 4441), ACGgugcgcc (SEQ ID NO: 4442), AAGguauugc (SEQ ID NO: 4443), GGGguaugug (SEQ ID NO: 2267), CAGgugggcu (SEQ ID NO: 1408), GAGguauguu (SEQ ID NO: 1968), AACgugaaua (SEQ ID NO: 4444), CAGguaaugg (SEQ ID NO: 1154), UAGguaugau (SEQ ID NO: 4445), CAGgcaggug (SEQ ID NO: 1108), GGGguugguc (SEQ ID NO: 4446), AAGguauggg (SEQ ID NO: 262), UAAgugaggc (SEQ ID NO: 4447), CAAgugaucg (SEQ ID NO: 4448), AAAguacggg (SEQ ID NO: 4449), AGAgcuacag (SEQ ID NO: 4450), GAGgugggaa (SEQ ID NO: 2054), CAGguacuuu (SEQ ID NO: 1195), GAGgugagag (SEQ ID NO: 2016), CAGguaggguc (SEQ ID NO: 1221), UGGguacagc (SEQ ID NO: 4451), AAGgugucag (SEQ ID NO: 396), AAGgcaagaa (SEQ ID NO: 4452), GAGguaaaca (SEQ ID NO: 4453), AAGguaaagu (SEQ ID NO: 129), AAGguaguca (SEQ ID NO: 4454), CUGguauguc (SEQ ID NO: 4455), GAGguauggg (SEQ ID NO: 1963), AAGguauugu (SEQ ID NO: 273), CUGguacuga (SEQ ID NO: 4456), GAGguaagcu (SEQ ID NO: 1888), UGGgugggua (SEQ ID NO: 2883), CAGguucgug (SEQ ID NO: 4457), AAGguauggu (SEQ ID NO: 4458), CAGgugagca (SEQ ID NO: 1337), UGGguaaauu (SEQ ID NO: 2827), UGUguaggug (SEQ ID NO: 4459), UGUgugagcc (SEQ ID NO: 2921), CUGguaauau (SEQ ID NO: 4460), AAAguauguu (SEQ ID NO: 45), UGUguaagaa (SEQ ID NO: 2903), CUAgugagaa (SEQ ID NO: 4461), AGGguagguc (SEQ ID NO: 757), AAGgugggug (SEQ ID NO: 385), UCGguaagug (SEQ ID NO: 4462), AGUguaaaua (SEQ ID NO: 812), GAUguaagug (SEQ ID NO: 2122), AAGguuagug (SEQ ID NO: 424), UAGguaagca (SEQ ID NO: 2485), CAAgugagaa (SEQ ID NO: 1061), AGUguaagua (SEQ ID NO: 819), CAGgugaauc (SEQ ID NO: 1321), UGGgugagac (SEQ ID NO: 2868), AAGguagggc (SEQ ID NO: 224), CUGguuugug (SEQ ID NO: 1788), GCGguagggc (SEQ ID NO: 4463), GAGguaaucc (SEQ ID NO: 4464), AUUguaauaa (SEQ ID NO: 4465), CUGgugaaua (SEQ ID NO: 1748), AAGguuuaaa (SEQ ID NO: 4466), CCUguacugu (SEQ ID NO: 4467), GCGgugagcg (SEQ ID NO: 4468), AAGguaaucc (SEQ ID NO: 162), UAUgugagua (SEQ ID NO: 2671), CCCgugagug (SEQ ID NO: 1573), CAGgugcaga (SEQ ID NO: 1363), CAGgucaguu (SEQ ID NO: 1284), CAGguaggcu (SEQ ID NO: 4469), AAAguaagug (SEQ ID NO: 23), UAGguugguc (SEQ ID NO: 4470), CAGguugccu (SEQ ID NO: 4471), AAGguaugga (SEQ ID NO: 260), GGUguggacg (SEQ ID NO: 4472), AAAgugagaa (SEQ ID NO: 51), AGGgugagag (SEQ ID NO: 788), GAUguggcau (SEQ ID NO: 4473), UCGguaaggu (SEQ ID NO: 4474), GAGgugcguc (SEQ ID NO: 4475), CGGgugaguc (SEQ ID NO: 4476), AAGguacggg (SEQ ID NO: 190), GAGguucuug (SEQ ID NO: 4477), AAGgugcuug (SEQ ID NO: 4478), UAGguaugua (SEQ ID NO: 2551), AUGgucagca (SEQ ID NO: 4479), CGGguacuca (SEQ ID NO: 4480), AGGgugagga (SEQ ID NO: 792), AUCgugagua (SEQ ID NO: 869), UCAguaagua (SEQ ID NO: 2689), UAGguaaaua (SEQ ID NO: 2469), AAGguaauug (SEQ ID NO: 170), GAAgucagug (SEQ ID NO: 1835), CAGguacaaa (SEQ ID NO: 1160), AAAguuaauc (SEQ ID NO: 4481), AGCgugagcg (SEQ ID NO: 4482), CCGgcuggug (SEQ ID NO: 4483), AGUguaauuu (SEQ ID NO: 4484), UGAgccacuc (SEQ ID NO: 4485), GGGgucugua (SEQ ID NO: 4486), AUGgcauguc (SEQ ID NO: 4487), CGGguaaaga (SEQ ID NO: 4488), AGGguagcau (SEQ ID NO: 4489), CGGguaggag (SEQ ID NO: 1631), GAGguucgug (SEQ ID NO: 4490), UAAguuauuc (SEQ ID NO: 4491), UAUguaagau (SEQ ID NO: 2650), AAGguaguuu (SEQ ID NO: 237), CAGgugguau (SEQ ID NO: 4492), GUGguaauga (SEQ ID NO: 2355), AAGgugauuu (SEQ ID NO: 359), CAGgugaagu (SEQ ID NO: 4493), GUAguaauua (SEQ ID NO: 4494), AUGguuggug (SEQ ID NO: 4495), CCAguaagug (SEQ ID NO: 1557), UAGgugagag (SEQ ID NO: 2589), AUGgugaggc (SEQ ID NO: 959), AAAguuagug (SEQ ID NO: 72), AAGgugccuu (SEQ ID NO: 4496), UAGguaugag (SEQ ID NO: 2546), CAGgugugac (SEQ ID NO: 1431), CUGguggguu (SEQ ID NO: 1774), AUGguaagga (SEQ ID NO: 896), UCUguaagaa (SEQ ID NO: 2740), UCCgugaguu (SEQ ID NO: 4497), AAAgcaggua (SEQ ID NO: 4498), UAUgugagug (SEQ ID NO: 2672), CAGgugguagg (SEQ ID NO: 4499), CAGguuagac (SEQ ID NO: 4500), AUAguaagac (SEQ ID NO: 846), AAGguguugu (SEQ ID NO: 4501), GAGgucugug (SEQ ID NO: 4502), AAGguaagau (SEQ ID NO: 144), CAUguaaguu (SEQ ID NO: 1524), CUGguaauua (SEQ ID NO: 4503), CAGguaggcg (SEQ ID NO: 4504), AGAguaaguc (SEQ ID NO: 669), UGGgugagga (SEQ ID NO: 2872), AAUguaggua (SEQ ID NO: 4505), UAGguuagca (SEQ ID NO: 4506), GGGguaggua (SEQ ID NO: 2258), GAGguauugc (SEQ ID NO: 4507), AUUguacaca (SEQ ID NO: 4508), GAAguaggua (SEQ ID NO: 4509), GGAguaagcu (SEQ ID NO: 2212), UAGguaugug (SEQ ID NO: 2553), GAGgugaaua (SEQ ID NO: 2007), GAGgugggau (SEQ ID NO: 2056), AAGguaaucu (SEQ ID NO: 163), GGUgugaguu (SEQ ID NO: 4510), AACgugaguu (SEQ ID NO: 4511), GAGguaaccg (SEQ ID NO: 4512), UAGguaagga (SEQ ID NO: 2488), AUUguaagaa (SEQ ID NO: 4513), UGGgugagca (SEQ ID NO: 2870), AAGguaaggc (SEQ ID NO: 150), CCAguaucgu (SEQ ID NO: 4514), CCGgugggug (SEQ ID NO: 4515), GAGguagugu (SEQ ID NO: 4516), ACGgugggaa (SEQ ID NO: 4517), GAGgugaccu (SEQ ID NO: 2011), CACguaugua (SEQ ID NO: 4518), AGGgugggga (SEQ ID NO: 799), AAUguaaguc (SEQ ID NO: 490), AAAguuaagu (SEQ ID NO: 70), CAUgugagug (SEQ ID NO: 1541), AGAguauguc (SEQ ID NO: 694), GCGguaugac (SEQ ID NO: 4519), CGGgugaguu (SEQ ID NO: 1643), CCGguauuuu (SEQ ID NO: 4520), GAGguagaac (SEQ ID NO: 4521), UAGguaugaa (SEQ ID NO: 2545), CAGgcgcgug (SEQ ID NO: 4522), CAAguaaguc (SEQ ID NO: 1027), AGUguaagau (SEQ ID NO: 816), AAGguucuac (SEQ ID NO: 4523), CCAguaagua (SEQ ID NO: 1555), GAGguagcag (SEQ ID NO: 4524), CAGgucuguu (SEQ ID NO: 1312), CAGguacaau (SEQ ID NO: 1162), CCGguaaaga (SEQ ID NO: 1574), UAAgugcugu (SEQ ID NO: 4525), AGGgugagaa (SEQ ID NO: 786), CUCguaaggu (SEQ ID NO: 4526), CAGgucagcu (SEQ ID NO: 4527), CAGguaaggc (SEQ ID NO: 1144), AGGgugcagg (SEQ ID NO: 4528), GAGgugaaac (SEQ ID NO: 4529), AGGguaagua (SEQ ID NO: 740), AAUguaugcc (SEQ ID NO: 4530), AAGguaagca (SEQ ID NO: 145), ACGguacggu (SEQ ID NO: 587), AAGguaauga (SEQ ID NO: 164), UCUgcucaau (SEQ ID NO: 4531), ACGguaaugu (SEQ ID NO: 4532), AAGguaguug (SEQ ID NO: 4533), ACGguaagug (SEQ ID NO: 580), CAGgugauga (SEQ ID NO: 4534), GAGguaacac (SEQ ID NO: 4535), GAGguaggua (SEQ ID NO: 1937), CAGguaccuu (SEQ ID NO: 1179), CAGguaauaa (SEQ ID NO: 1150), UUGgugggug (SEQ ID NO: 3016), CUGguaauga (SEQ ID NO: 1710), UAGguaaguc (SEQ ID NO: 2492), AGGgugugac (SEQ ID NO: 4536), GAGgcaauaa (SEQ ID NO: 4537), GUGguaaagc (SEQ ID NO: 4538), CUGgugggcg (SEQ ID NO: 4539), GAUguauguu (SEQ ID NO: 2128), AGGgugagac (SEQ ID NO: 787), UCGgucagca (SEQ ID NO: 4540), AUGgugauua (SEQ ID NO: 4541), CGAgugugua (SEQ ID NO: 4542), CAGguuggug (SEQ ID NO: 1488), AGCgcaagua (SEQ ID NO: 4543), UGGguacguu (SEQ ID NO: 4544), GAGguauuug (SEQ ID NO: 1974), AGUguacaua (SEQ ID NO: 4545), AUGguaagua (SEQ ID NO: 898), ACAguagguu (SEQ ID NO: 4546), AAGgugagag (SEQ ID NO: 337), UUGgugaagu (SEQ ID NO: 4547), AAAguaugua (SEQ ID NO: 43), UGGguaagga (SEQ ID NO: 4548), UAGgugccuu (SEQ ID NO: 4549), and CCUgugggug (SEQ ID NO: 4550).

Additional exemplary gene sequences and splice site sequences (e.g., 5' splice site sequences) include UCCguaaguu (SEQ ID NO: 4551), GUGguaaacg (SEQ ID NO: 4552), CGGgugcggu (SEQ ID NO: 4553), CAUguacuuc (SEQ ID NO: 4554), AGAguaaagg (SEQ ID NO: 4555), CGCgugagua (SEQ ID NO: 4556), AGAgugggca (SEQ ID NO: 4557), AGAguaagcc (SEQ ID NO: 4558), AGAguaaaca (SEQ ID NO: 4559), GUGguuauga (SEQ ID NO: 4560), AGGguaauaa (SEQ ID NO: 4561), UGAguaagac (SEQ ID NO: 4562), AGAguuuguu (SEQ ID NO: 4563), CGGgucugca (SEQ ID NO: 4564), CAGguaaguc (SEQ ID NO: 4565), AAGguagaau (SEQ ID NO: 4566), CAGgucccuc (SEQ ID NO: 4567), AGAguaaugg (SEQ ID NO: 4568), GAGgucuaag (SEQ ID NO: 4569), AGAguagagu (SEQ ID NO: 4570), AUGgucagua (SEQ ID NO: 4571), GAGgccuggg (SEQ ID NO: 4572), AAGguguggc (SEQ ID NO: 4573), AGAgugaucu (SEQ ID NO: 4574), AAGguaucca (SEQ ID NO: 4575), UUCguaagua (SEQ ID NO: 4576), UAAgugggug (SEQ ID NO: 4577), GCCgugaacg (SEQ ID NO: 4578), GAGguugugg (SEQ ID NO: 4579), UAUguaugca (SEQ ID NO: 4580), UGUguaacaa (SEQ ID NO: 4581), AGGguauuag (SEQ ID NO: 4582), UGAguauauc (SEQ ID NO: 4583), AGAguuugug (SEQ ID NO: 4584), GAGgucgcug (SEQ ID NO: 4585), GAGgucaucg (SEQ ID NO: 4586), ACGguaaagc (SEQ ID NO: 4587), UGAguacuug (SEQ ID NO: 4588), CGAgucgccg (SEQ ID NO: 4589), CUGguacguc (SEQ ID NO: 4590), AGGguauugc (SEQ ID NO: 4591), GAAgugaaug (SEQ ID NO: 4592), CAGaugaguc (SEQ ID NO: 4593), UGGguauugg (SEQ ID NO: 4594), UGAguaaaga (SEQ ID NO: 4595), GUGguuccug (SEQ ID NO: 4596), UGAgcaagua (SEQ ID NO: 4597), UAUguaagag (SEQ ID NO: 4598), AAGgucuugc (SEQ ID NO: 4599), AAAgcaugug (SEQ ID NO: 4600), AGAguacagu (SEQ ID NO: 4601), GUGguaaucc (SEQ ID NO: 4602), CAGguagagg (SEQ ID NO: 4603), AAGguacaac (SEQ ID NO: 4604), UGGgcagcau (SEQ ID NO: 4605), CCGgucauca (SEQ ID NO: 4606), CCGguuugua (SEQ ID NO: 4607), UGAguaaggg (SEQ ID NO: 4608), GAAguaugua (SEQ ID NO: 4609), GGGguagcuc (SEQ ID NO: 4610), GCUguacaua (SEQ ID NO: 4611), CUGgucucuu (SEQ ID NO: 4612), GUGguaaaug (SEQ ID NO: 4613), AUCguaagug (SEQ ID NO: 4614), GAGgcaugua (SEQ ID NO: 4615), AAGgucuccc (SEQ ID NO: 4616), UGGgugcguu (SEQ ID NO: 4617), UGUguagguu (SEQ ID NO: 4618), GAAgugagca (SEQ ID NO: 4619), GGUguaauuu (SEQ ID NO: 4620), CUGgugaaau (SEQ ID NO: 4621), AUCguaaguc (SEQ ID NO: 4622), AGAguaaucc (SEQ ID NO: 4623), GGAguagguc (SEQ ID NO: 4624), GAGguaccaa (SEQ ID NO: 4625), CUUguaggug (SEQ ID NO: 4626), AAGguauaag (SEQ ID NO: 4627), AGAguuggua (SEQ ID NO: 4628), AUGguuugug (SEQ ID NO: 4629), UGGgucagau (SEQ ID NO: 4630), AGAguaggac (SEQ ID NO: 4631), AGAguagugu (SEQ ID NO: 4632), AGAguaggag (SEQ ID NO: 4633), CAGgucucua (SEQ ID NO: 4634), AAGguggaug (SEQ ID NO: 4635), UGGguaucaa (SEQ ID NO: 4636), GAUguaugga (SEQ ID NO: 4637), AAGguguuuc (SEQ ID NO: 4638), GCAguguaaa (SEQ ID NO: 4639), UUAguaugua (SEQ ID NO: 4640), UCUguaugca (SEQ ID NO: 4641), AAUguaaaau (SEQ ID NO: 4642), AGAguaaauu (SEQ ID NO: 4643), GGGguacuuu (SEQ ID NO: 4644), GAAguuugau (SEQ ID NO: 4645), AAAguagauu (SEQ ID NO: 4646), UGUguagagu (SEQ ID NO: 4647), UGGguaagcg (SEQ ID NO: 4648), CGGguucagg (SEQ ID NO: 4649), AGGguacgac (SEQ ID NO: 4650), UCGguaagaa (SEQ ID NO: 4651), AGGguuggca (SEQ ID NO: 4652), AAAguacagu (SEQ ID NO: 4653), UAAguuaagg (SEQ ID NO: 4654), AUGguaaugu (SEQ ID NO: 4655), GUGguuuuac (SEQ ID NO: 4656), AGAguaacaa (SEQ ID NO: 4657), AAGguagccc (SEQ ID NO: 4658), GCGgugaggc (SEQ ID NO: 4659), AUGguucagc (SEQ ID NO: 4660), AAGguacuua (SEQ ID NO: 4661), AAGguccgug (SEQ ID NO: 4662), UAGguaagcg (SEQ ID NO: 4663), AUGguaccuu (SEQ ID NO: 4664), GCCguggugg (SEQ ID NO: 4665), CUGgugcguc (SEQ ID NO: 4666), CAGguggaaa (SEQ ID NO: 4667), AAAgucugua (SEQ ID NO: 4668), GAGguaaccc (SEQ ID NO: 4669), AGAguauggg (SEQ ID NO: 4670), UAUgccccug (SEQ ID NO: 4671), AAGgugccag (SEQ ID NO: 4672), ACGgugcggc (SEQ ID NO: 4673), AGGguacuga (SEQ ID NO: 4674), AGAguaagcg (SEQ ID NO: 4675), CUGgcaaggg (SEQ ID NO: 4676), CCAgugugug (SEQ ID NO: 4677), GAGguagacg (SEQ ID NO: 4678), CGGgugcggg (SEQ ID NO: 4679), GAUguaagcu (SEQ ID NO: 4680), AUUguauuua (SEQ ID NO: 4681), UGCgugagug (SEQ ID NO: 4682), CUGgucuaua (SEQ ID NO: 4683), GAGgugcuag (SEQ ID NO: 4684), GAGgugccau (SEQ ID NO: 4685), CAGguacguc (SEQ ID NO: 4686), GAGguucagc (SEQ ID NO: 4687), AACguaagaa (SEQ ID NO: 4688), AGAguaguac (SEQ ID NO: 4689), AAGguaacgg (SEQ ID NO: 4690), UAGgugugac (SEQ ID NO: 4691), CCGguaauag (SEQ ID NO: 4692), CAGguaccag (SEQ ID NO: 4693), UUUguaauug (SEQ ID NO: 4694), AAUguacgaa (SEQ ID NO: 4695), CAGguaauga (SEQ ID NO: 4696), AUCgucaagg (SEQ ID NO: 4697), CUGguagaug (SEQ ID NO: 4698), GGGgugcagu (SEQ ID NO: 4699), AGUgugagaa (SEQ ID NO: 4700), GGGguuuuau (SEQ ID NO: 4701), CCUguccccu (SEQ ID NO: 4702), AUUgugaagu (SEQ ID NO: 4703), AAGguaaacg (SEQ ID NO: 4704), UACgucgugg (SEQ ID NO: 4705), AAGgugccau (SEQ ID NO: 4706), GGGgucccag (SEQ ID NO: 4707), UAUguauggu (SEQ ID NO: 4708), CGGguaauua (SEQ ID NO: 4709), CGGguacucc (SEQ ID NO: 4710), CAGgugacuu (SEQ ID NO: 4711), AGUgugggu (SEQ ID NO: 4712), AGAguauggc (SEQ ID NO: 4713), AAGgccaaca (SEQ ID NO: 4714), AAAgcaagua (SEQ ID NO: 4715), UCAguagguc (SEQ ID NO: 4716), GUGguggcgg (SEQ ID NO: 4717), CAUguauccu (SEQ ID NO: 4718), UCGgugagcc (SEQ ID NO: 4719), AUAguugggu (SEQ ID NO: 4720), AAUguuagcu (SEQ ID NO: 4721), AUGgugaaug (SEQ ID NO: 4722), CGGguaaugu (SEQ ID NO: 4723), UCUguaggug (SEQ ID NO: 4724), CCGgugaggc (SEQ ID NO: 4725), UGAguccacu (SEQ ID NO: 4726), CUAguaagag (SEQ ID NO: 4727), CGGguggggc (SEQ ID NO: 4728), CGAguaagca (SEQ ID NO: 4729), UGUgccaauu (SEQ ID NO: 4730), UCGguaagcc (SEQ ID NO: 4731), UAUguaggug (SEQ ID NO: 4732), UUGgugggcc (SEQ ID NO: 4733), GAGgcugggc (SEQ ID NO: 4734), AGAguaacuu (SEQ ID NO: 4735), ACGguagguc (SEQ ID NO: 4736), CAGgcccaga (SEQ ID NO: 4737), CCGgugggu (SEQ ID NO: 4738), AAGgugacgg (SEQ ID NO: 4739), GGGguacagc (SEQ ID NO: 4740), CAUguaaguc (SEQ ID NO: 4741), AUUgugagaa (SEQ ID NO: 4742), UGUguaagga (SEQ ID NO: 4743), UUUguaagau (SEQ ID NO: 4744), AGGgucauuu (SEQ ID NO: 4745), UGGguuuguu (SEQ ID NO: 4746), CGAguaagcc (SEQ ID NO: 4747), GUGgugugua (SEQ ID NO: 4748), AUGguauaac (SEQ ID NO: 4749), UGGguacgua (SEQ ID NO: 4750), AAAguagagu (SEQ ID NO: 4751), UCGguaacug (SEQ ID NO: 4752), AGAguaauga (SEQ ID NO: 4753), AUGgugggucc (SEQ ID NO: 4754), AGAguaauau (SEQ ID NO: 4755), CAGguacugg (SEQ ID NO: 4756), UAAgucaguu (SEQ ID NO: 4757), GCGguagaga (SEQ ID NO: 4758), AAGgugaugg (SEQ ID NO: 4759), ACAguauguu (SEQ ID NO: 4760), GAUguacguc (SEQ ID NO: 4761), UAGguuucuc (SEQ ID NO: 4762), GAGgcauggg (SEQ ID NO: 4763), AUAgcuaagu (SEQ ID NO: 4764), GUAgucugua (SEQ ID NO: 4765), AAGgugaacg (SEQ ID NO: 4766), GUGgugggucg (SEQ ID NO: 4767), GAGguugauc (SEQ ID NO: 4768), UGAgugggguu (SEQ ID NO: 4769), ACUguacgug (SEQ ID NO: 4770), CUGgugacug (SEQ ID NO: 4771), CAAguuaagc (SEQ ID NO: 4772), GAGguaccca (SEQ ID NO: 4773), AACguaacuu (SEQ ID NO: 4774), CAGguuacua (SEQ ID NO: 4775), AGAguuaguc (SEQ ID NO: 4776), UGGgcacguc (SEQ ID NO: 4777), AGUguauggu (SEQ ID NO: 4778), AAGguugcaa (SEQ ID NO: 4779), CAGguuguua (SEQ ID NO: 4780), AAGgcauccc (SEQ ID NO: 4781), GAUguaaggc (SEQ ID NO: 4782), AGGguacggg (SEQ ID NO: 4783), GAGgucaaag (SEQ ID NO: 4784), CAAgugagcg (SEQ ID NO: 4785), AGAguaaucu (SEQ ID NO: 4786), UCGguagcug (SEQ ID NO: 4787), AAAguaguag (SEQ ID NO: 4788), CAGguucguc (SEQ ID NO: 4789), CGUguaugaa (SEQ ID NO: 4790), AGUguaaaaa (SEQ ID NO: 4791), AAGgucucac (SEQ ID NO: 4792), UAGguggagc (SEQ ID NO: 4793), UGAguaggug (SEQ ID NO: 4794), AGAguaugcc (SEQ ID NO: 4795), GAGguugcau (SEQ ID NO: 4796), CAAguaagag (SEQ ID NO: 4797), UCUgugugcc (SEQ ID NO: 4798), GAGgugaugc (SEQ ID NO: 4799), GGGgugauaa (SEQ ID NO: 4800), CCCgugagcc (SEQ ID NO: 4801), AGAguaacug (SEQ ID NO: 4802), GCGguaagua (SEQ ID NO: 4803), AGAguacauc (SEQ ID NO: 4804), UCGgucuggg (SEQ ID NO: 4805), UAAguaucuc (SEQ ID NO: 4806), GGCguagguu (SEQ ID NO: 4807), AGAguacgcc (SEQ ID NO: 4808), GAUgucuucu (SEQ ID NO: 4809), AGGgcaaggu (SEQ ID NO: 4810), CGAguaugau (SEQ ID NO: 4811), AUGguagagu (SEQ ID NO: 4812), CAAguacgag (SEQ ID NO: 4813), UCGguaugau (SEQ ID NO: 4814), CCGguguguu (SEQ ID NO: 4815), AGGgucugug (SEQ ID NO: 4816), GGAguaggcu (SEQ ID NO: 4817), AAGgucuaug (SEQ ID NO: 4818), GCAgugcgug (SEQ ID NO: 4819), UGGgugagaa (SEQ ID NO: 4820), AGGguaaagu (SEQ ID NO: 4821), GAGguaggac (SEQ ID NO: 4822), CUAguaagca (SEQ ID NO: 4823), UUAguaggcu (SEQ ID NO: 4824), CUGgugggau (SEQ ID NO: 4825), CUGguuagua (SEQ ID NO: 4826), AAGguacgug (SEQ ID NO: 4827), CGGgugagau (SEQ ID NO: 4828), AAGgugcaug (SEQ ID NO: 4829), AAUgugggcu (SEQ ID NO: 4830), CAGguugacu (SEQ ID NO: 4831), CAGguuacag (SEQ ID NO: 4832), GCGguaacau (SEQ ID NO: 4833), AUUgucaguc (SEQ ID NO: 4834), CAAguauaca (SEQ ID NO: 4835), GAUguccgcc (SEQ ID NO: 4836), AAGgugcgga (SEQ ID NO: 4837), AACguaagag (SEQ ID NO: 4838), UGGguuggua (SEQ ID NO: 4839), CAAguguaag (SEQ ID NO: 4840), GUGguaacgu (SEQ ID NO: 4841), CUGgugauca (SEQ ID NO: 4842), AGGgugggggc (SEQ ID NO: 4843), UCGguaaaga (SEQ ID NO: 4844), CAGguacacc (SEQ ID NO: 4845), CGGguaaggg (SEQ ID NO: 4846), CAAguuugcu (SEQ ID NO: 4847), ACAgugcgug (SEQ ID NO: 4848), UUGguauggg (SEQ ID NO: 4849), GAGgcucauc (SEQ ID NO: 4850), CUGguaauag (SEQ ID NO: 4851), AUGguggaua (SEQ ID NO: 4852), UCAgugaauu (SEQ ID NO: 4853), AAUguaauua (SEQ ID NO: 4854), GCAgucuaaa (SEQ ID NO: 4855), AAGguauucu (SEQ ID NO: 4856), GAGgucauca (SEQ ID NO: 4857), UGGguccaug (SEQ ID NO: 4858), AGAguuugua (SEQ ID NO: 4859), AGGguagacu (SEQ ID NO: 4860), AAGguaggac (SEQ ID NO: 4861), UGUguguuga (SEQ ID NO: 4862), UCAguacgug (SEQ ID NO: 4863), AUGgucucuc (SEQ ID NO: 4864), UGAguuagua (SEQ ID NO: 4865), UGAguaaagu (SEQ ID NO: 4866), GAGgugaccg (SEQ ID NO: 4867), GAGguauauc (SEQ ID NO: 4868), CAGgugccau (SEQ ID NO: 4869), AGAgugguga (SEQ ID NO: 4870), GUUguaagaa (SEQ ID NO: 4871), AGAguaaaua (SEQ ID NO: 4872), AGGgugaagg (SEQ ID NO: 4873), CUGguagauu (SEQ ID NO: 4874), GAGguucagg (SEQ ID NO: 4875), AGGgucuuca (SEQ ID NO: 4876), CUGguaaccu (SEQ ID NO: 4877), ACAguacuga (SEQ ID NO: 4878), AGAgugggguc (SEQ ID NO: 4879), AUGguaugag (SEQ ID NO: 4880), AAGguuauau (SEQ ID NO: 4881), AGAguauagu (SEQ ID NO: 4882), AAAguaugaa (SEQ ID NO: 4883), UAGguggcua (SEQ ID NO: 4884), ACCguauggg (SEQ ID NO: 4885), AAAguauaau (SEQ ID NO: 4886), UUUguauggc (SEQ ID NO: 4887), GGGgucgcgu (SEQ ID NO: 4888), GUGgugguuu (SEQ ID NO: 4889), CAGguuugac (SEQ ID NO: 4890), GGAguaggcg (SEQ ID NO: 4891), GAGguacccu (SEQ ID NO: 4892), AUGgugugca (SEQ ID NO: 4893), GUGguuggug (SEQ ID NO: 4894), AAAguaugcu (SEQ ID NO: 4895), UAAguuacau (SEQ ID NO: 4896), ACAguaugag (SEQ ID NO: 4897), GGAguauguu (SEQ ID NO: 4898), UUUgugagaa (SEQ ID NO: 4899), AAUgugcguu (SEQ ID NO: 4900), CAGguagagu (SEQ ID NO: 4901), AUGguguuaa (SEQ ID NO: 4902), CAUgugcguc (SEQ ID NO: 4903), AUAguuggau (SEQ ID NO: 4904), GAGguacgua (SEQ ID NO: 4905), GUUgugagaa (SEQ ID NO: 4906), CAAguacauc (SEQ ID NO: 4907), GAGguaguuu (SEQ ID NO: 4908), ACUguacaga (SEQ ID NO: 4909), CCGguuguga (SEQ ID NO: 4910), UGGgucagug (SEQ ID NO: 4911), GUAguaagaa (SEQ ID NO: 4912), GACguacuuu (SEQ ID NO: 4913), AGAgucaguc (SEQ ID NO: 4914), UAGguuaguu (SEQ ID NO: 4915), AGGgcagcag (SEQ ID NO: 4916), AAGguccuac (SEQ ID NO: 4917), AAUguaauug (SEQ ID NO: 4918), CAGgugcggg (SEQ ID NO: 4919), CUGguaaugg (SEQ ID NO: 4920), CAAguagccc (SEQ ID NO: 4921), GAAgucaguu (SEQ ID NO: 4922), ACAguaauug (SEQ ID NO: 4923), UUAguuagua (SEQ ID NO: 4924), CCUguauuuu (SEQ ID NO: 4925), AUCguaagaa (SEQ ID NO: 4926), CCAgugagca (SEQ ID NO: 4927), GAAguaaggc (SEQ ID NO: 4928), UGAgugggua (SEQ ID NO: 4929), UCAgugguag (SEQ ID NO: 4930), UCUguacagg (SEQ ID NO: 4931), CGAgugagug (SEQ ID NO: 4932), UCCguaugug (SEQ ID NO: 4933), CAUgccguuu (SEQ ID NO: 4934), AAAgugacuu (SEQ ID NO: 4935), AGAguaggca (SEQ ID NO: 4936), GAAguaagag (SEQ ID NO: 4937), CAGgcagguu (SEQ ID NO: 4938), UUGguagagc (SEQ ID NO: 4939), AAGguggaaa (SEQ ID NO: 4940), GAGgcagguc (SEQ ID NO: 4941), AUGguacgac (SEQ ID NO: 4942), AGGguaggaa (SEQ ID NO: 4943), AGGguaggua (SEQ ID NO: 4944), UUGguaaggu (SEQ ID NO: 4945), AUGguacaga (SEQ ID NO: 4946), CAGguagagc (SEQ ID NO: 4947), UAGguaaggu (SEQ ID NO: 4948), GGGguuagag (SEQ ID NO: 4949), AAGguaucaa (SEQ ID NO: 4950), GAGguagccc (SEQ ID NO: 4951), CAGgugccuc (SEQ ID NO: 4952), GCAguaagag (SEQ ID NO: 4953), ACGguagagu (SEQ ID NO: 4954), UGGguaaugg (SEQ ID NO: 4955), CUGgucaguu (SEQ ID NO: 4956), GUGguacauu (SEQ ID NO: 4957), AAAguagguu (SEQ ID NO: 4958), AAGgccaaga (SEQ ID NO: 4959), CGGgugggca (SEQ ID NO: 4960), ACGguccggg (SEQ ID NO: 4961), CGAguaugag (SEQ ID NO: 4962), CUGguaugcc (SEQ ID NO: 4963), GAGguggaug (SEQ ID NO: 4964), CAGgccuuuc (SEQ ID NO: 4965), AAAguacauc (SEQ ID NO: 4966), AAAguaauca (SEQ ID NO: 4967), GAGguaacug (SEQ ID NO: 4968), CUGguaaaga (SEQ ID NO: 4969), CGUguaagca (SEQ ID NO: 4970), UGGgcaagua (SEQ ID NO: 4971), GCGguggcga (SEQ ID NO: 4972), GAGguggccg (SEQ ID NO: 4973), AUUgcaugca (SEQ ID NO: 4974), ACGgugacug (SEQ ID NO: 4975), CAGgucagau (SEQ ID NO: 4976), AGAguaacuc (SEQ ID NO: 4977), UGAguaacag (SEQ ID NO: 4978), AAGguacccg (SEQ ID NO: 4979), AGGguaggcu (SEQ ID NO: 4980), GGGgcaggac (SEQ ID NO: 4981), CCUguaagug (SEQ ID NO: 4982), AUUguaagug (SEQ ID NO: 4983), ACUguacgag (SEQ ID NO: 4984), GUAguagugu (SEQ ID NO: 4985), AGAguaugag (SEQ ID NO: 4986), UCAguguggg (SEQ ID NO: 4987), UGGguauaua (SEQ ID NO: 4988), UAGguagcua (SEQ ID NO: 4989), GGGguaaaga (SEQ ID NO: 4990), AGGguuacuu (SEQ ID NO: 4991), CAUguaaaug (SEQ ID NO: 4992), GGAguaguaa (SEQ ID NO: 4993), CAGgucaauc (SEQ ID NO: 4994), CGGguuagug (SEQ ID NO: 4995), UAGguacaug (SEQ ID NO: 4996), UAGguuaaga (SEQ ID NO: 4997), UGGguaccuu (SEQ ID NO: 4998), CGGgugguaca (SEQ ID NO: 4999), CAGgucuuac (SEQ ID NO: 5000), AAGguggagc (SEQ ID NO: 5001), AUGguaacca (SEQ ID NO: 5002), UCGguaaguu (SEQ ID NO: 5003), UAUguacaaa (SEQ ID NO: 5004), AAUguagauu (SEQ ID NO: 5005), GUAgcuagua (SEQ ID NO: 5006), AAGguauugg (SEQ ID NO: 5007), GAGgucuuug (SEQ ID NO: 5008), GAAguucagg (SEQ ID NO: 5009), UGGguaucac (SEQ ID NO: 5010), AGAguacugg (SEQ ID NO: 5011), CAGguuaaug (SEQ ID NO: 5012), AGGguacgug (SEQ ID NO: 5013), AGGgcacagg (SEQ ID NO: 5014), CUGguuaguu (SEQ ID NO: 5015), UUGguacgag (SEQ ID NO: 5016), ACGgugauca (SEQ ID NO: 5017), CCUgugagag (SEQ ID NO: 5018), GAGgugaagu (SEQ ID NO: 5019), AAGguacauc (SEQ ID NO: 5020), UCUguaugug (SEQ ID NO: 5021), UUGguggaag (SEQ ID NO: 5022), UGGgcagguu (SEQ ID NO: 5023), GAAguggagc (SEQ ID NO: 5024), ACAguaagac (SEQ ID NO: 5025), CGGguaccaa (SEQ ID NO: 5026), CAAguacguc (SEQ ID NO: 5027), AGAgugaggg (SEQ ID NO: 5028), CGGguaagaa (SEQ ID NO: 5029), AAUguaggug (SEQ ID NO: 5030), AUCgugugcu (SEQ ID NO: 5031), UAGgucaugg (SEQ ID NO: 5032), CAGguuuuga (SEQ ID NO: 5033), AAGgcaugca (SEQ ID NO: 5034), GAGgugcugc (SEQ ID NO: 5035), AAGguuaaua (SEQ ID NO: 5036), CAGguucauc (SEQ ID NO: 5037), GCGguaggug (SEQ ID NO: 5038), GACguggagua (SEQ ID NO: 5039), CAGgucuacu (SEQ ID NO: 5040), UUGguaugag (SEQ ID NO: 5041), AGCgugggca (SEQ ID NO: 5042), AUGguaaggu (SEQ ID NO: 5043), AUGguaccuc (SEQ ID NO: 5044), UUGguauggu (SEQ ID NO: 5045), UAUguaugaa (SEQ ID NO: 5046), UGGguauggg (SEQ ID NO: 5047), GAUguaaaua (SEQ ID NO: 5048), CCGguaaguu (SEQ ID NO: 5049), GAGgucugaa (SEQ ID NO: 5050), GAGgugcgag (SEQ ID NO: 5051), CUGgucagcc (SEQ ID NO: 5052), CAGguuuugu (SEQ ID NO: 5053), CGGgugguguu (SEQ ID NO: 5054), UAAguuagua (SEQ ID NO: 5055), UUUgugugug (SEQ ID NO: 5056), CAGguuaacc (SEQ ID NO: 5057), UUGguacuuu (SEQ ID NO: 5058), GCUguaaggc (SEQ ID NO: 5059), AGGguggcug (SEQ ID NO: 5060), GAUguaaaaa (SEQ ID NO: 5061), AAGgucaaaa (SEQ ID NO: 5062), CAGguagcgc (SEQ ID NO: 5063), CAGguuuggc (SEQ ID NO: 5064), GAGgugguuu (SEQ ID NO: 5065), CGGguaaaua (SEQ ID NO: 5066), CUGguucggu (SEQ ID NO: 5067), GGAgugagcc (SEQ ID NO: 5068), AAGgugcgcg (SEQ ID NO: 5069), GAAguacauc (SEQ ID NO: 5070), AGUgucugua (SEQ ID NO: 5071), CCCgugagcu (SEQ ID NO: 5072), GAGguucaca (SEQ ID NO: 5073), CUAgugggua (SEQ ID NO: 5074), GAGguaacua (SEQ ID NO: 5075), UCGguauguc (SEQ ID NO: 5076), UAAguauuug (SEQ ID NO: 5077), CAGguaagcg (SEQ ID NO: 5078), GAGgugguaa (SEQ ID NO: 5079), CGAguaagag (SEQ ID NO: 5080), CCGguaagcu (SEQ ID NO: 5081), GAGgucuugu (SEQ ID NO: 5082), AAGgugggguc (SEQ ID NO: 5083), CACguaagug (SEQ ID NO: 5084), AGUguaauga (SEQ ID NO: 5085), AAAgugugua (SEQ ID NO: 5086), GGAgugccaa (SEQ ID NO: 5087), CACgugaguu (SEQ ID NO: 5088), AAGguuggau (SEQ ID NO: 5089), UAUguaaaua (SEQ ID NO: 5090), CUGguaggaa (SEQ ID NO: 5091), UAUguaaacu (SEQ ID NO: 5092), AAUguauuuu (SEQ ID NO: 5093), CUGgcaagug (SEQ ID NO: 5094), UGUgugguau (SEQ ID NO: 5095), UAUguauguu (SEQ ID NO: 5096), UUGgugacuc (SEQ ID NO: 5097), GGAguaaggu (SEQ ID NO: 5098), AAGguagaug (SEQ ID NO: 5099), UGGguagggu (SEQ ID NO: 5100), AAUguaauuc (SEQ ID NO: 5101), GUGguauggc (SEQ ID NO: 5102), GGAgugggguu (SEQ ID NO: 5103), AGGguaccac (SEQ ID NO: 5104), UAGgugacag (SEQ ID NO: 5105), ACAguaggca (SEQ ID NO: 5106), AUGguuugaa (SEQ ID NO: 5107), GCAguaacua (SEQ ID NO: 5108), CCGguaggua (SEQ ID NO: 5109), AGAguaggcc (SEQ ID NO: 5110), AAGguugaca (SEQ ID NO: 5111), CUGgugugua (SEQ ID NO: 5112), GAAgucuguc (SEQ ID NO: 5113), UGGgcucgga (SEQ ID NO: 5114), CAGguagccu (SEQ ID NO: 5115), AGAguaggua (SEQ ID NO: 5116), UAAguauguc (SEQ ID NO: 5117), CUGguauauc (SEQ ID NO: 5118), GAGguguguu (SEQ ID NO: 5119), AUGgugcaug (SEQ ID NO: 5120), AAGguacgcc (SEQ ID NO: 5121), UGAguaacua (SEQ ID NO: 5122), GAGgugacag (SEQ ID NO: 5123), GUUguccugu (SEQ ID NO: 5124), UUGgugucuu (SEQ ID NO: 5125), AAUgugaagg (SEQ ID NO: 5126), UUGguggaua (SEQ ID NO: 5127), UAGguguguu (SEQ ID NO: 5128), CUGgcaaguu (SEQ ID NO: 5129), GCAguaagau (SEQ ID NO: 5130), GCGguggaaa (SEQ ID NO: 5131), UGCguccagc (SEQ ID NO: 5132), AAAguggagu (SEQ ID NO: 5133), CGUgugagcc (SEQ ID NO: 5134), AGAguacugu (SEQ ID NO: 5135), CAGguauagc (SEQ ID NO: 5136), UACguaagga (SEQ ID NO: 5137), AAGgucuuua (SEQ ID NO: 5138), AAGgugugucu (SEQ ID NO: 5139), GGGguaaauu (SEQ ID NO: 5140), UCAgugagga (SEQ ID NO: 5141), AGAguacguu (SEQ ID NO: 5142), GAGgucguca (SEQ ID NO: 5143), UAGguuugau (SEQ ID NO: 5144), CAUguaaacc (SEQ ID NO: 5145), AAGguggcac (SEQ ID NO: 5146), CAGguagaug (SEQ ID NO: 5147), AACguaaaag (SEQ ID NO: 5148), UAGgucucug (SEQ ID NO: 5149), AUAguaggug (SEQ ID NO: 5150), UAGgcaagag (SEQ ID NO: 5151), UAGgcacggc (SEQ ID NO: 5152), AAGgucuuca (SEQ ID NO: 5153), CCAguaugcu (SEQ ID NO: 5154), CAAgugaguu (SEQ ID NO: 5155), CAGgucucaa (SEQ ID NO: 5156), CAGguuacau (SEQ ID NO: 5157), GGAgugagca (SEQ ID NO: 5158), AGAguacgca (SEQ ID NO: 5159), CUGguguugg (SEQ ID NO: 5160), AAGguacuca (SEQ ID NO: 5161), CUAguaaggg (SEQ ID NO: 5162), AGAguaaaag (SEQ ID NO: 5163), AAGguaacga (SEQ ID NO: 5164), CUGguccccg (SEQ ID NO: 5165), UAAguauggg (SEQ ID NO: 5166), GAGgucgagc (SEQ ID NO: 5167), UUGguauaua (SEQ ID NO: 5168), AAAgucaagg (SEQ ID NO: 5169), AAGgucuagg (SEQ ID NO: 5170), CGAguagguc (SEQ ID NO: 5171), AGGguucguu (SEQ ID NO: 5172), GAGgcaggcc (SEQ ID NO: 5173), CUAguauuac (SEQ ID NO: 5174), ACGguaugug (SEQ ID NO: 5175), UAGgugguuc (SEQ ID NO: 5176), AGAguauaac (SEQ ID NO: 5177), UUGgugcguc (SEQ ID NO: 5178), ACCguuaucu (SEQ ID NO: 5179), CCAgugauga (SEQ ID NO: 5180), GAAguaugca (SEQ ID NO: 5181), GAAguauggc (SEQ ID NO: 5182), CCGguaggac (SEQ ID NO: 5183), AAUguaagca (SEQ ID NO: 5184), AGAguaauug (SEQ ID NO: 5185), AGGguugguu (SEQ ID NO: 5186), GUGguaggag (SEQ ID NO: 5187), AAGgcaguuu (SEQ ID NO: 5188), CAAguaagcc (SEQ ID NO: 5189), CUGgcaagua (SEQ ID NO: 5190), CAGgcaugau (SEQ ID NO: 5191), AGGguaauug (SEQ ID NO: 5192), GGGguaaccu (SEQ ID NO: 5193), AAAguaacua (SEQ ID NO: 5194), UAGgucugcc (SEQ ID NO: 5195), ACGguaugaa (SEQ ID NO: 5196), AGUguauggg (SEQ ID NO: 5197), UGGguuggca (SEQ ID NO: 5198), UAGguaaacu (SEQ ID NO: 5199), AGAguggguga (SEQ ID NO: 5200), AGAguauuug (SEQ ID NO: 5201), AGUguaggaa (SEQ ID NO: 5202), CUUguacgua (SEQ ID NO: 5203), GAUgugagau (SEQ ID NO: 5204), CAGgcagcca (SEQ ID NO: 5205), AAGgucacug (SEQ ID NO: 5206), AAGgucugac (SEQ ID NO: 5207), UAGguuccuu (SEQ ID NO: 5208), CUGgugcuuu (SEQ ID NO: 5209), UGAguuggug (SEQ ID NO: 5210), UUGgugggau (SEQ ID NO: 5211), UGAguagggu (SEQ ID NO: 5212), UCGgugaggu (SEQ ID NO: 5213), AAAguaaaga (SEQ ID NO: 5214), AAGgcaaguc (SEQ ID NO: 5215), CGGguaaagc (SEQ ID NO: 5216), AAAguuaguu (SEQ ID NO: 5217), UUAguaagca (SEQ ID NO: 5218), GAGgucacau (SEQ ID NO: 5219), UAAgugguau (SEQ ID NO: 5220), UAGgugcuuu (SEQ ID NO: 5221), GGAguaggca (SEQ ID NO: 5222), UGAguaagga (SEQ ID NO: 5223), CAGguggagc (SEQ ID NO: 5224), GAUguagaag (SEQ ID NO: 5225), AAUgccugcc (SEQ ID NO: 5226), AUGguaaggc (SEQ ID NO: 5227), UGGguaauau (SEQ ID NO: 5228), CUGguaccuc (SEQ ID NO: 5229), CACgugagcc (SEQ ID NO: 5230), UGAguuugug (SEQ ID NO: 5231), CCGguagugu (SEQ ID NO: 5232), AAAgugacaa (SEQ ID NO: 5233), GAAgugg-guu (SEQ ID NO: 5234), CAGgugcagc (SEQ ID NO: 5235), GAGgugggcc (SEQ ID NO: 5236), UAUgugcguc (SEQ ID NO: 5237), GGGguacugg (SEQ ID NO: 5238), CUGguag-guu (SEQ ID NO: 5239), UUGgcauguu (SEQ ID NO: 5240), AAUguaauac (SEQ ID NO: 5241), UAGgccggug (SEQ ID NO: 5242), AGAgucagua (SEQ ID NO: 5243), UAAguaaauc (SEQ ID NO: 5244), CAGguuccuc (SEQ ID NO: 5245), UAGguacgau (SEQ ID NO: 5246), AGAguuagug (SEQ ID NO: 5247), GCAguaagug (SEQ ID NO: 5248), AGGgugguag (SEQ ID NO: 5249), GGAguaaugu (SEQ ID NO: 5250), GAUguaaguc (SEQ ID NO: 5251), CCAguuucgu (SEQ ID NO: 5252), AAG-guucggg (SEQ ID NO: 5253), AUGguggagu (SEQ ID NO: 5254), AAGguaccgg (SEQ ID NO: 5255), GAAgugcgaa (SEQ ID NO: 5256), UGGgucaguu (SEQ ID NO: 5257), AAGguguaga (SEQ ID NO: 5258), UGGguaggcc (SEQ ID NO: 5259), CCAgugaguc (SEQ ID NO: 5260), AAGguca-cuu (SEQ ID NO: 5261), AGCgugaggc (SEQ ID NO: 5262), UCCgugguaa (SEQ ID NO: 5263), AGAguacuua (SEQ ID NO: 5264), GGGgucagau (SEQ ID NO: 5265), AAG-guggacc (SEQ ID NO: 5266), AGAgugagcg (SEQ ID NO: 5267), AGAgucagau (SEQ ID NO: 5268), UAAguauuac (SEQ ID NO: 5269), AGAguauuuc (SEQ ID NO: 5270), AGAguucagc (SEQ ID NO: 5271), AUGgugaagu (SEQ ID NO: 5272), UAGgugaucc (SEQ ID NO: 5273), GGAguaagau (SEQ ID NO: 5274), UAGguaccaa (SEQ ID NO: 5275), AGAguuggucc (SEQ ID NO: 5276), GAAguga-gac (SEQ ID NO: 5277), AUCguagguu (SEQ ID NO: 5278), GAGguacgcu (SEQ ID NO: 5279), ACGguaaggg (SEQ ID NO: 5280), CAGgcauguc (SEQ ID NO: 5281), UUAguaagau (SEQ ID NO: 5282), UGAguagguu (SEQ ID NO: 5283), AGGguacgaa (SEQ ID NO: 5284), ACGguau-guu (SEQ ID NO: 5285), AGGguacugu (SEQ ID NO: 5286), UUGguaugga (SEQ ID NO: 5287), UAAguaacug (SEQ ID NO: 5288), GCGgucagcc (SEQ ID NO: 5289), UUUguga-guc (SEQ ID NO: 5290), GUGgucagug (SEQ ID NO: 5291), CUGgucugua (SEQ ID NO: 5292), GAGguucuua (SEQ ID NO: 5293), AUGguacuga (SEQ ID NO: 5294), AAUgugc-uuu (SEQ ID NO: 5295), AGGguggcgu (SEQ ID NO: 5296), CCGgcaggaa (SEQ ID NO: 5297), CAUgugggucc (SEQ ID NO: 5298), UUGguuuguu (SEQ ID NO: 5299), CAGguucugu (SEQ ID NO: 5300), ACGguaagcg (SEQ ID NO: 5301), CUGgucagua (SEQ ID NO: 5302), UCAguaggcu (SEQ ID NO: 5303), UGAguaggac (SEQ ID NO: 5304), CAGguuuuaa (SEQ ID NO: 5305), GAGgugu-ccc (SEQ ID NO: 5306), AGGgugguu (SEQ ID NO: 5307), GUGgugagac (SEQ ID NO: 5308), CACguaggga (SEQ ID NO: 5309), GUGguauuuu (SEQ ID NO: 5310), GAGauauccu (SEQ ID NO: 5311), AAGgugaaca (SEQ ID NO: 5312), UAAguagggc (SEQ ID NO: 5313), CUG-gugcggg (SEQ ID NO: 5314), CUGgucaaua (SEQ ID NO: 5315), AGAguaaaaa (SEQ ID NO: 5316), AAGgugcagu (SEQ ID NO: 5317), CGGguaagca (SEQ ID NO: 5318), AAAgugagcc (SEQ ID NO: 5319), AUGguaauca (SEQ ID NO: 5320), GCAguacgug (SEQ ID NO: 5321), AUGgua-caug (SEQ ID NO: 5322), AAGguuaaga (SEQ ID NO: 5323), CGGguaaaug (SEQ ID NO: 5324), GAGguucgca (SEQ ID NO: 5325), GAGgcucugg (SEQ ID NO: 5326), AUGgugggac (SEQ ID NO: 5327), AACgugguag (SEQ ID NO: 5328), AAGgugauag (SEQ ID NO: 5329), GGG-guuugca (SEQ ID NO: 5330), CAUguaaggg (SEQ ID NO: 5331), UCAguugagu (SEQ ID NO: 5332), AAAgugcggc (SEQ ID NO: 5333), AGAgugagcc (SEQ ID NO: 5334), AUGgcaagaa (SEQ ID NO: 5335), ACAguaaggu (SEQ ID NO: 5336), AAGgucucua (SEQ ID NO: 5337), GUG-guaaaaa (SEQ ID NO: 5338), AAAguaggug (SEQ ID NO: 5339), UAGgugcacu (SEQ ID NO: 5340), GUCgugguau (SEQ ID NO: 5341), CAGguauagg (SEQ ID NO: 5342), UGAgugagag (SEQ ID NO: 5343), ACUgugagcc (SEQ ID NO: 5344), AUCguuaguu (SEQ ID NO: 5345), UUUguac-caa (SEQ ID NO: 5346), UGGgugagau (SEQ ID NO: 5347), AGAgugagaa (SEQ ID NO: 5348), AGAguagggg (SEQ ID NO: 5349), AGGgcaagua (SEQ ID NO: 5350), CGGguc-agua (SEQ ID NO: 5351), UUGguaugcc (SEQ ID NO: 5352), CGGguuagau (SEQ ID NO: 5353), GGGgugaagu (SEQ ID NO: 5354), CCCgugugaa (SEQ ID NO: 5355), GCAguuugga (SEQ ID NO: 5356), UGCguaagac (SEQ ID NO: 5357), AGAgucugua (SEQ ID NO: 5358), CACgugagca (SEQ ID NO: 5359), AGGguaaaag (SEQ ID NO: 5360), CAGgcugggu (SEQ ID NO: 5361), GAAguc-uuca (SEQ ID NO: 5362), AAGgcaaaaa (SEQ ID NO: 5363), GUAguaaaua (SEQ ID NO: 5364), CUAgugagag (SEQ ID NO: 5365), GAAguuucug (SEQ ID NO: 5366), CCUguacgua (SEQ ID NO: 5367), GAGgugcgcg (SEQ ID NO: 5368), AAGguguaaa (SEQ ID NO: 5369), CCAguau-guu (SEQ ID NO: 5370), CCGgucagcu (SEQ ID NO: 5371), AUGguuccug (SEQ ID NO: 5372), CAAguuaaau (SEQ ID NO: 5373), AGAguaggcu (SEQ ID NO: 5374), AUG-gugggca (SEQ ID NO: 5375), GGAguaagac (SEQ ID NO: 5376), AGGgucacga (SEQ ID NO: 5377), UAGgugauau (SEQ ID NO: 5378), GAAguaaguc (SEQ ID NO: 5379), CGGguaagau (SEQ ID NO: 5380), CAAguagcua (SEQ ID NO: 5381), UGAguaaaau (SEQ ID NO: 5382), GUCguacgug (SEQ ID NO: 5383), AUGguacgua (SEQ ID NO: 5384), CAGgucucgg (SEQ ID NO: 5385), GAGgcau-guc (SEQ ID NO: 5386), AGAgugggau (SEQ ID NO: 5387), GUGguuagag (SEQ ID NO: 5388), UGGgugguga (SEQ ID NO: 5389), AAGguuaaac (SEQ ID NO: 5390), CUU-guuagcu (SEQ ID NO: 5391), AAAguaggaa (SEQ ID NO: 5392), UAGguuguau (SEQ ID NO: 5393), AGGgugcgcc (SEQ ID NO: 5394), AAGgugggcu (SEQ ID NO: 5395), UAAguaucug (SEQ ID NO: 5396), AAGguaacgu (SEQ ID NO: 5397), AUGgugggc (SEQ ID NO: 5398), CAAgua-cacg (SEQ ID NO: 5399), GGCguaagug (SEQ ID NO: 5400), AUAguaggac (SEQ ID NO: 5401), AGAgugaggu (SEQ ID NO: 5402), UUUguaaaaa (SEQ ID NO: 5403), GAAguuugua (SEQ ID NO: 5404), CUAguaaucu (SEQ ID NO: 5405), AAGguuuuua (SEQ ID NO: 5406), GAG-gugcguu (SEQ ID NO: 5407), UAGgcgagua (SEQ ID NO: 5408), ACCgugagua (SEQ ID NO: 5409), CAGgucccga (SEQ ID NO: 5410), AUGguacugg (SEQ ID NO: 5411), UGAguucagu (SEQ ID NO: 5412), AAUguguggu (SEQ ID NO: 5413), UCCguugguu (SEQ ID NO: 5414), CAGgu-cagag (SEQ ID NO: 5415), CAGgucccua (SEQ ID NO: 5416), UAGguagacu (SEQ ID NO: 5417), CAAguuaagg (SEQ ID NO: 5418), GAGgugugcg (SEQ ID NO: 5419), GAAgcugccc (SEQ ID NO: 5420), CGAguacgug (SEQ ID NO: 5421), CGGguaggua (SEQ ID NO: 5422), UUG-guauuga (SEQ ID NO: 5423), AUUguaugau (SEQ ID NO: 5424), UUGguaugaa (SEQ ID NO: 5425), GAGgugguca (SEQ ID NO: 5426), GCUguaugaa (SEQ ID NO: 5427), CAGguguugc (SEQ ID NO: 5428), CAGguaaaac (SEQ ID NO: 5429), AUAguaaggu (SEQ ID NO: 5430), CUGguua-gag (SEQ ID NO: 5431), AGCgugugag (SEQ ID NO: 5432), AAGguuaucu (SEQ ID NO: 5433), CACgugagua (SEQ ID NO: 5434), AGGgucagua (SEQ ID NO: 5435), GAG-guauaau (SEQ ID NO: 5436), CAGguuauuu (SEQ ID NO: 5437), AGGguggacu (SEQ ID NO: 5438), AUUguaauuc (SEQ ID NO: 5439), UUUgugggguu (SEQ ID NO: 5440), AUGguacgug (SEQ ID NO: 5441), AAGguguucc (SEQ ID NO: 5442), CAGgugacgc (SEQ ID NO: 5443), GAGguac-uaa (SEQ ID NO: 5444), ACAguucagu (SEQ ID NO: 5445), GAGgucacgg (SEQ ID NO: 5446), CAAguaaggc (SEQ ID NO: 5447), AAGguuuggg (SEQ ID NO: 5448), AAAgugggcu (SEQ ID NO: 5449), GCGguucuug (SEQ ID NO: 5450), GAGguggagc (SEQ ID NO: 5451), UGAgucagug (SEQ ID NO: 5452), CAGgucaagg (SEQ ID NO: 5453), AGUguaagcu (SEQ ID NO: 5454), GAGgcagaaa (SEQ ID NO: 5455), AAGgucacac (SEQ ID NO: 5456), GAAguagguu (SEQ ID NO: 5457), GUCguaaguu (SEQ ID NO: 5458), AGAguaugca (SEQ ID NO: 5459), CCUgugcaaa (SEQ ID NO: 5460), ACGgugaaaa (SEQ ID NO: 5461), CAGguacgaa (SEQ ID NO: 5462), CAUgugagga (SEQ ID NO: 5463), AGCgugagua (SEQ ID NO: 5464), GGUguguagg (SEQ ID NO: 5465), AACgugagcu (SEQ ID NO: 5466), GAGgugaacu (SEQ ID NO: 5467), AGAguucagu (SEQ ID NO: 5468), AACgugugua (SEQ ID NO: 5469), CAGguuugugg (SEQ ID NO: 5470), AAGguacuag (SEQ ID NO: 5471), UCAgugaaaa (SEQ ID NO: 5472), AAUgucuggu (SEQ ID NO: 5473), ACGguaaaau (SEQ ID NO: 5474), CUGguguaag (SEQ ID NO: 5475), GAGgugcgaa (SEQ ID NO: 5476), AGGguuucuc (SEQ ID NO: 5477), CAGguagccc (SEQ ID NO: 5478), AUUguauugg (SEQ ID NO: 5479), AUGguacuua (SEQ ID NO: 5480), GAGgcccgac (SEQ ID NO: 5481), UCGguaagac (SEQ ID NO: 5482), CGGgcuguag (SEQ ID NO: 5483), UAUgugugug (SEQ ID NO: 5484), UAGguagaaa (SEQ ID NO: 5485), GUGgucauua (SEQ ID NO: 5486), UAGgugaaag (SEQ ID NO: 5487), ACUguaauuc (SEQ ID NO: 5488), GCAguacagg (SEQ ID NO: 5489), UCGgugaguc (SEQ ID NO: 5490), UAUguaggga (SEQ ID NO: 5491), AUGguauguc (SEQ ID NO: 5492), GUGgugugug (SEQ ID NO: 5493), CUGgugaccu (SEQ ID NO: 5494), AAUgugaaua (SEQ ID NO: 5495), UAGgucucac (SEQ ID NO: 5496), GAGguuauug (SEQ ID NO: 5497), UGAguaggcu (SEQ ID NO: 5498), CGGgcacgua (SEQ ID NO: 5499), GCAguaaaua (SEQ ID NO: 5500), CCGgugagag (SEQ ID NO: 5501), UAAguugguc (SEQ ID NO: 5502), CCGgugagcc (SEQ ID NO: 5503), AAGguuguca (SEQ ID NO: 5504), CUGguauuau (SEQ ID NO: 5505), GGGguauggg (SEQ ID NO: 5506), AAAgucagua (SEQ ID NO: 5507), UUUguaugua (SEQ ID NO: 5508), UAAguacugc (SEQ ID NO: 5509), CAGguaccaa (SEQ ID NO: 5510), GAAguucaga (SEQ ID NO: 5511), AUGgugcggu (SEQ ID NO: 5512), GUGgugaggu (SEQ ID NO: 5513), UGAguaagcc (SEQ ID NO: 5514), UAUguaaggg (SEQ ID NO: 5515), GUGgugggaaa (SEQ ID NO: 5516), GAGgugauug (SEQ ID NO: 5517), GGAguuugua (SEQ ID NO: 5518), AAGgucacga (SEQ ID NO: 5519), GUGguagagg (SEQ ID NO: 5520), UAAguauauc (SEQ ID NO: 5521), AAGgugucca (SEQ ID NO: 5522), UAUgugguau (SEQ ID NO: 5523), GAGguacaau (SEQ ID NO: 5524), AAGguggggg (SEQ ID NO: 5525), GGAguaggug (SEQ ID NO: 5526), and UAGgugacuu (SEQ ID NO: 5527).

In some embodiments, the splice site sequence (e.g., 5' splice site sequence) comprises AGA. In some embodiments, the splice site sequence (e.g., 5' splice site sequence) comprises AAA. In some embodiments, the splice site sequence (e.g., 5' splice site sequence) comprises AAC. In some embodiments, the splice site sequence (e.g., 5' splice site sequence) comprises AAU. In some embodiments, the splice site sequence (e.g., 5' splice site sequence) comprises AAG. In some embodiments, the splice site sequence (e.g., 5' splice site sequence) comprises ACA. In some embodiments, the splice site sequence (e.g., 5' splice site sequence) comprises AUA. In some embodiments, the splice site sequence (e.g., 5' splice site sequence) comprises AUU. In some embodiments, the splice site sequence (e.g., 5' splice site sequence) comprises AUG. In some embodiments, the splice site sequence (e.g., 5' splice site sequence) comprises AUC. In some embodiments, the splice site sequence (e.g., 5' splice site sequence) comprises CAA. In some embodiments, the splice site sequence (e.g., 5' splice site sequence) comprises CAU. In some embodiments, the splice site sequence (e.g., 5' splice site sequence) comprises CAC. In some embodiments, the splice site sequence (e.g., 5' splice site sequence) comprises CAG. In some embodiments, the splice site sequence (e.g., 5' splice site sequence) comprises GAA. In some embodiments, the splice site sequence (e.g., 5' splice site sequence) comprises GAC. In some embodiments, the splice site sequence (e.g., 5' splice site sequence) comprises GAU. In some embodiments, the splice site sequence (e.g., 5' splice site sequence) comprises GAG. In some embodiments, the splice site sequence (e.g., 5' splice site sequence) comprises GGA. In some embodiments, the splice site sequence (e.g., 5' splice site sequence) comprises GCA. In some embodiments, the splice site sequence (e.g., 5' splice site sequence) comprises GGG. In some embodiments, the splice site sequence (e.g., 5' splice site sequence) comprises GGC. In some embodiments, the splice site sequence (e.g., 5' splice site sequence) comprises GUU. In some embodiments, the splice site sequence (e.g., 5' splice site sequence) comprises GGU. In some embodiments, the splice site sequence (e.g., 5' splice site sequence) comprises GUC. In some embodiments, the splice site sequence (e.g., 5' splice site sequence) comprises GUA. In some embodiments, the splice site sequence (e.g., 5' splice site sequence) comprises GUG. In some embodiments, the splice site sequence (e.g., 5' splice site sequence) comprises UCU. In some embodiments, the splice site sequence (e.g., 5' splice site sequence) comprises UCC. In some embodiments, the splice site sequence (e.g., 5' splice site sequence) comprises UCA. In some embodiments, the splice site sequence (e.g., 5' splice site sequence) comprises UCG. In some embodiments, the splice site sequence (e.g., 5' splice site sequence) comprises UUU. In some embodiments, the splice site sequence (e.g., 5' splice site sequence) comprises UUC. In some embodiments, the splice site sequence (e.g., 5' splice site sequence) comprises UUA. In some embodiments, the splice site sequence (e.g., 5' splice site sequence) comprises UUG. In some embodiments, the splice site sequence (e.g., 5' splice site sequence) comprises UGU. In some embodiments, the splice site sequence (e.g., 5' splice site sequence) comprises UAU. In some embodiments, the splice site sequence (e.g., 5' splice site sequence) comprises GGA. In some embodiments, the splice site sequence (e.g., 5' splice site sequence) comprises CUU. In some embodiments, the splice site sequence (e.g., 5' splice site sequence) comprises CUC. In some embodiments, the splice site sequence (e.g., 5' splice site sequence) comprises CUA. In some embodiments, the splice site sequence (e.g., 5' splice site sequence) comprises CUG. In some embodiments, the splice site sequence (e.g., 5' splice site sequence) comprises CCU. In some embodiments, the splice site sequence (e.g., 5' splice site sequence) comprises CCC. In some embodiments, the splice site sequence (e.g., 5' splice site sequence) comprises CCA. In some embodiments, the splice site sequence (e.g., 5' splice site sequence) comprises CCG. In some embodiments, the splice site sequence (e.g., 5' splice site sequence) comprises ACU. In some embodiments, the splice site sequence (e.g., 5' splice site sequence) comprises ACC. In some embodiments, the splice site sequence (e.g., 5' splice site sequence) comprises ACG. In some embodiments, the splice site sequence (e.g., 5' splice site sequence) comprises AGC. In some embodiments, the splice site sequence (e.g., 5' splice site sequence) comprises AGU. In some embodiments, the splice site sequence (e.g., 5' splice site sequence)

comprises AGG. In some embodiments, the splice site sequence (e.g., 5' splice site sequence) comprises CGU. In some embodiments, the splice site sequence (e.g., 5' splice site sequence) comprises UAC. In some embodiments, the splice site sequence (e.g., 5' splice site sequence) comprises UAA. In some embodiments, the splice site sequence (e.g., 5' splice site sequence) comprises UAG. In some embodiments, the splice site sequence (e.g., 5' splice site sequence) comprises CGC. In some embodiments, the splice site sequence (e.g., 5' splice site sequence) comprises CGA. In some embodiments, the splice site sequence (e.g., 5' splice site sequence) comprises CGG. In some embodiments, the splice site sequence comprises AGAguaaggg (SEQ ID NO: 667).

In an embodiment, a gene sequence or splice site sequence provided herein is related to a proliferative disease, disorder, or condition (e.g., cancer, benign neoplasm, or inflammatory disease). In an embodiment, a gene sequence or splice site sequence provided herein is related to a non-proliferative disease, disorder, or condition. In an embodiment, a gene sequence or splice site sequence provided herein is related to a neurological disease or disorder; autoimmune disease or disorder; immunodeficiency disease or disorder; lysosomal storage disease or disorder; cardiovascular condition, disease or disorder; metabolic disease or disorder; respiratory condition, disease, or disorder; renal disease or disorder; or infectious disease in a subject. In an embodiment, a gene sequence or splice site sequence provided herein is related to a neurological disease or disorder (e.g., Huntington's disease). In an embodiment, a gene sequence or splice site sequence provided herein is related to an immunodeficiency disease or disorder. In an embodiment, a gene sequence or splice site sequence provided herein is related to a lysosomal storage disease or disorder. In an embodiment, a gene sequence or splice site sequence provided herein is related to a cardiovascular condition, disease or disorder. In an embodiment, a gene sequence or splice site sequence provided herein is related to a metabolic disease or disorder. In an embodiment, a gene sequence or splice site sequence provided herein is related to a respiratory condition, disease, or disorder. In an embodiment, a gene sequence or splice site sequence provided herein is related to a renal disease or disorder. In an embodiment, a gene sequence or splice site sequence provided herein is related to an infectious disease.

In an embodiment, a gene sequence or splice site sequence provided herein is related to a mental retardation disorder. In an embodiment, a gene sequence or splice site sequence provided herein is related to a mutation in the SETD5 gene. In an embodiment, a gene sequence or splice site sequence provided herein is related to an immunodeficiency disorder. In an embodiment, a gene sequence and splice site sequence provided herein is related to a mutation in the GATA2 gene.

In some embodiments, a compound of Formula (I) described herein interacts with (e.g., binds to) a splicing complex component (e.g., a nucleic acid (e.g., an RNA) or a protein). In some embodiments, the splicing complex component is selected from 9G8, A1 hnRNP, A2 hnRNP, ASD-1, ASD-2b, ASF, BRR2, B1 hnRNP, $C_1$ hnRNP, $C_2$ hnRNP, CBP20, CBP80, CELF, F hnRNP, FBP11, Fox-1, Fox-2, G hnRNP, H hnRNP, hnRNP 1, hnRNP 3, hnRNP C, hnRNP G, hnRNP K, hnRNP M, hnRNP U, Hu, HUR, IhnRNP, K hnRNP, KH-type splicing regulatory protein (KSRP), L hnRNP, LUC7L, M hnRNP, mBBP, muscle-blind like (MBNL), NF45, NFAR, Nova-1, Nova-2, nPTB, P54/SFRS11, polypyrimidine tract binding protein (PTB), a PRP protein (e.g., PRP8, PRP6, PRP31, PRP4, PRP3, PRP28, PRP5, PRP2, PRP19), PRP19 complex proteins, RBM42, R hnRNP, RNPC1, SAD1, SAM68, SC35, SF, SF1/BBP, SF2, SF3A complex, SF3B complex, SFRS10, an Sm protein (such as B, D1, D2, D3, F, E, G), SNU17, SNU66, SNU114, an SR protein, SRm300, SRp20, SRp30c, SRP35C, SRP36, SRP38, SRp40, SRp55, SRp75, SRSF, STAR, GSG, SUP-12, TASR-1, TASR-2, TIA, TIAR, TRA2, TRA2a/b, U hnRNP, U1 snRNP, U11 snRNP, U12 snRNP, U1-70K, U1-A, U1-C, U2 snRNP, U2AF1-RS2, U2AF35, U2AF65, U4 snRNP, U5 snRNP, U6 snRNP, Urp, and YB1.

In some embodiments, the splicing complex component comprises RNA (e.g., snRNA). In some embodiments, a compound described herein binds to a splicing complex component comprising snRNA. The snRNA may be selected from, e.g., U1 snRNA, U2 snRNA, U4 snRNA, U5 snRNA, U6 snRNA, U11 snRNA, U12 snRNA, U4atac snRNA, and any combination thereof.

In some embodiments, the splicing complex component comprises a protein, e.g., a protein associated with an snRNA. In some embodiments, the protein comprises SC35, SRp55, SRp40, SRm300, SFRS10, TASR-1, TASR-2, SF2/ASF, 9G8, SRp75, SRp30c, SRp20 and P54/SFRS11. In some embodiments, the splicing complex component comprises a U2 snRNA auxiliary factor (e.g., U2AF65, U2AF35), Urp/U2AF1-RS2, SF1/BBP, CBP80, CBP 20, SF1 or PTB/hnRNPL. In some embodiments, the splicing complex component comprises a heterogenous ribonucleoprotein particle (hnRNP), e.g., an hnRNP protein. In some embodiments, the hnRNP protein comprises A1, A2/B1, L, M, K, U, F, H, G, R, I or $C_1/C_2$. Human genes encoding hnRNPs include HNRNPA0, HNRNPA1, HNRNPA1L1, HNRNPA1L2, HNRNPA3, HNRNPA2B1, HNRNPAB, HNRNPB1, HNRNPC, HNRNPCL1, HNRNPD, HNRPDL, HNRNPF, HNRNPH1, HNRNPH2, HNRNPH3, HNRNPK, HNRNPL, HNRPLL, HNRNPM, HNRNPR, HNRNPU, HNRNPUL1, HNRNPUL2, HNRNPUL3, and FMR1.

In one aspect, the compounds of Formula (I) and pharmaceutically acceptable salts, solvates, hydrates, tautomers, stereoisomers, and compositions thereof, may modulate (e.g., increase or decrease) a splicing event of a target nucleic acid sequence (e.g., DNA, RNA, or a pre-mRNA), for example, a nucleic acid encoding a gene described herein, or a nucleic acid encoding a protein described herein, or a nucleic acid comprising a splice site described herein. In an embodiment, the splicing event is an alternative splicing event.

In an embodiment, the compound of Formula (I) or a pharmaceutically acceptable salt, solvate, hydrate, tautomer, stereoisomer, and compositions thereof increases splicing at splice site on a target nucleic acid (e.g., an RNA, e.g., a pre-mRNA), by about 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or more, e.g., as determined by a known method in the art, e.g., qPCR. In an embodiment, the compound of Formula (I) or a pharmaceutically acceptable salt, solvate, hydrate, tautomer, stereoisomer, and compositions thereof decreases splicing at splice site on a target nucleic acid (e.g., an RNA, e.g., a pre-mRNA), by about 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or more, e.g., as determined by a known method in the art, e.g., qPCR.

In another aspect, the present disclosure features a method of forming a complex comprising a component of a spliceosome (e.g., a major spliceosome component or a minor spliceosome component), a nucleic acid (e.g., a DNA, RNA, e.g., a pre-mRNA), and a compound of Formula (I) or a pharmaceutically acceptable salt, solvate, hydrate, tautomer, stereoisomer, or composition thereof, comprising contacting the nucleic acid (e.g., a DNA, RNA, e.g., a pre-mRNA) with said compound of Formula (I). In an embodiment, the component of a spliceosome is selected from the U1, U2, U4, U5, U6, U11, U12, U4atac, U6atac small nuclear ribonucleoproteins (snRNPs), or a related accessory factor. In an embodiment, the component of a spliceosome is recruited to the nucleic acid in the presence of the compound of Formula (I), or a pharmaceutically acceptable salt, solvate, hydrate, tautomer, stereoisomer, or composition thereof.

In another aspect, the present disclosure features a method of altering the conformation of a nucleic acid (e.g., a DNA, RNA, e.g., a pre-mRNA) comprising contacting the nucleic acid with a compound of Formula (I) or a pharmaceutically acceptable salt, solvate, hydrate, tautomer, stereoisomer, or composition thereof. In an embodiment, the altering comprises forming a bulge or kink in the nucleic acid. In an embodiment, the altering comprises stabilizing a bulge or a kink in the nucleic acid. In an embodiment, the altering comprises reducing a bulge or a kink in the nucleic acid. In an embodiment, the nucleic acid comprises a splice site. In an embodiment, the compound of Formula (I) interacts with a nucleobase, ribose, or phosphate moiety of a nucleic acid (e.g., a DNA, RNA, e.g., pre-mRNA).

The present disclosure also provides methods for the treatment or prevention of a disease, disorder, or condition. In an embodiment, the disease, disorder or condition is related to (e.g., caused by) a splicing event, such as an unwanted, aberrant, or alternative splicing event. In an embodiment, the disease, disorder or condition comprises a proliferative disease (e.g., cancer, benign neoplasm, or inflammatory disease) or non-proliferative disease. In an embodiment, the disease, disorder, or condition comprises a neurological disease, autoimmune disorder, immunodeficiency disorder, cardiovascular condition, metabolic disorder, lysosomal storage disease, respiratory condition, renal disease, or infectious disease in a subject. In another embodiment, the disease, disorder, or condition comprises a haploinsufficiency disease, an autosomal recessive disease (e.g., with residual function), or a paralogue activation disorder. In another embodiment, the disease, disorder, or condition comprises an autosomal dominant disorder (e.g., with residual function). Such methods comprise the step of administering to the subject in need thereof an effective amount of a compound of Formula (I), or a pharmaceutically acceptable salt, solvate, hydrate, tautomer, stereoisomer thereof, or a pharmaceutical composition thereof. In certain embodiments, the methods described herein include administering to a subject an effective amount of a compound of Formula (I), or a pharmaceutically acceptable salt thereof, or a pharmaceutical composition thereof.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

A proliferative disease, disorder, or condition may also be associated with inhibition of apoptosis of a cell in a biological sample or subject. All types of biological samples described herein or known in the art are contemplated as being within the scope of the disclosure. The compounds of Formula (I) and pharmaceutically acceptable salts, solvates, hydrates, tautomers, stereoisomers, and compositions thereof, may induce apoptosis, and therefore, be useful in treating and/or preventing proliferative diseases, disorders, or conditions.

In certain embodiments, the proliferative disease to be treated or prevented using the compounds of Formula (I) is cancer. As used herein, the term “cancer” refers to a malignant neoplasm (Stedman’s Medical Dictionary, 25th ed.; Hensyl ed.; Williams & Wilkins: Philadelphia, 1990). All types of cancers disclosed herein or known in the art are contemplated as being within the scope of the disclosure. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi’s sarcoma, multiple idiopathic hemorrhagic sarcoma); endometrial cancer (e.g., uterine cancer, uterine sarcoma); esophageal cancer (e.g., adenocarcinoma of the esophagus, Barrett’s adenocarcinoma); Ewing’s sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom’s macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In some embodiments, the proliferative disease is associated with a benign neoplasm. For example, a benign neoplasm may include adenoma, fibroma, hemangioma, tuberous sclerosis, and lipoma. All types of benign neoplasms disclosed herein or known in the art are contemplated as being within the scope of the disclosure.

In some embodiments, the proliferative disease is associated with angiogenesis. All types of angiogenesis disclosed herein or known in the art are contemplated as being within the scope of the disclosure.

In some embodiments, the compound of Formula (I), or a pharmaceutically acceptable salt thereof, or compositions comprising such compound or pharmaceutically acceptable salt thereof, is used to prevent or treat a non-proliferative disease. Exemplary non-proliferative diseases include a neurological disease, autoimmune disorder, immunodeficiency disorder, lysosomal storage disease, cardiovascular condition, metabolic disorder, respiratory condition, inflammatory disease, renal disease, or infectious disease.

In certain embodiments, the non-proliferative disease is a neurological disease. In certain embodiments, the compound of Formula (I), or a pharmaceutically acceptable salt thereof, or compositions comprising such compound or pharmaceutically acceptable salt thereof, is used to prevent or treat a neurological disease, disorder, or condition. A neurological disease, disorder, or condition may include a neurodegenerative disease, a psychiatric condition, or a musculoskeletal disease. A neurological disease may further include a repeat expansion disease, e.g., which may be characterized by the expansion of a nucleic acid sequence in the genome. For example, a repeat expansion disease includes myotonic dystrophy, amyotrophic lateral sclerosis, Huntington's disease, a trinucleotide repeat disease, or a polyglutamine disorder (e.g., ataxia, fragile X syndrome). In some embodiments, the neurological disease comprises a repeat expansion disease, e.g., Huntington's disease. Additional neurological diseases, disorders, and conditions include Alzheimer's disease, Huntington's chorea, a prion disease (e.g., Creutzfeld-Jacob disease, bovine spongiform encephalopathy, Kuru, or scrapie), a mental retardation disorder (e.g., a disorder caused by a SETD5 gene mutation, e.g., intellectual disability-facial dysmorphism syndrome, autism spectrum disorder), Lewy Body disease, diffuse Lewy body disease (DLBD), dementia, progressive supranuclear palsy (PSP), progressive bulbar palsy (PBP), psuedobulbar palsy, spinal and bulbar muscular atrophy (SBMA), primary lateral sclerosis, Pick's disease, primary progressive aphasia, corticobasal dementia, Parkinson's disease, Down's syndrome, multiple system atrophy, spinal muscular atrophy (SMA), progressive spinobulbar muscular atrophy (e.g., Kennedy disease), post-polio syndrome (PPS), spinocerebellar ataxia, pantothenate kinase-associated neurodegeneration (PANK), spinal degenerative disease/motor neuron degenerative diseases, upper motor neuron disorder, lower motor neuron disorder, Hallervorden-Spatz syndrome, cerebral infarction, cerebral trauma, chronic traumatic encephalopathy, transient ischemic attack, Lytigo-bodig (amyotrophic lateral sclerosis-parkinsonism dementia), Guam-Parkinsonism dementia, hippocampal sclerosis, corticobasal degeneration, Alexander disease, Apler's disease, Krabbe's disease, neuroborreliosis, neurosyphilis, Sandhoff disease, Tay-Sachs disease, Schilder's disease, Batten disease, Cockayne syndrome, Kearns-Sayre syndrome, Gerstmann-Straussler-Scheinker syndrome and other transmissible spongiform encephalopathies, hereditary spastic paraparesis, Leigh's syndrome, a demyelinating diseases, neuronal ceroid lipofuscinoses, epilepsy, tremors, depression, mania, anxiety and anxiety disorders, sleep disorders (e.g., narcolepsy, fatal familial insomnia), acute brain injuries (e.g., stroke, head injury), autism, Machado-Joseph disease, or a combination thereof. In some embodiments, the neurological disease comprises Friedrich's ataxia or Sturge Weber syndrome. In some embodiments, the neurological disease comprises Huntington's disease. All types of neurological diseases disclosed herein or known in the art are contemplated as being within the scope of the disclosure.

In certain embodiments, the non-proliferative disease is an autoimmune disorder or an immunodeficiency disorder. In certain embodiments, the compound of Formula (I), or a pharmaceutically acceptable salt thereof, or compositions comprising such compound or pharmaceutically acceptable salt thereof, is used to prevent or treat an autoimmune disease, disorder, or condition, or an immunodeficiency disease, disorder, or condition. Exemplary autoimmune and immunodeficiency diseases, disorders, and conditions include arthritis (e.g., rheumatoid arthritis, osteoarthritis, gout), Chagas disease, chronic obstructive pulmonary disease (COPD), dermatomyositis, diabetes mellitus type 1, endometriosis, Goodpasture's syndrome, Graves' disease, Guillain-Barre syndrome (GBS), Hashiomoto's disease, Hidradenitis suppurativa, Kawasaki disease, ankylosing spondylitis, IgA nephropathy, idiopathic thrombocytopenic purpura, inflammatory bowel disease, Crohn's disease, ulcerative colitis, collagenous colitis, lymphocytic colitis, ischemic colitis, diversion colitis, Behcet's syndrome, infective colitis, indeterminate colitisinterstitial cystitis, lupus (e.g., systemic lupus erythematosus, discoid lupus, drug-induced lupus, neonatal lupus), mixed connective tissue disease, morphea, multiple sclerosis, myasthenia gravis, narcolepsy, neuromyotonia, pemphigus vulgaris, pernicious anemia, psoriasis, psoriatic arthritis, polymyositis, primary biliary cirrhosis, relapsing polychondritis, scleroderma, Sjögren's syndrome, Stiff person syndrome, vasculitis, vitiligo, a disorder caused by a GATA2 mutation (e.g., GATA2 deficiency; GATA2 haploinsufficiency; Emberger syndrome; monocytopenia and *Mycobacterium avium* complex/dendritic cell, monocyte, B and NK lymphocyte deficiency; familial myelodysplastic syndrome; acute myeloid leukemia; chronic myelomonocytic leukemia), neutropenia, aplastic anemia, and Wegener's granulomatosis. In some embodiments, the autoimmune or immunodeficiency disorder comprises chronic mucocutaneous candidiasis. All types of autoimmune disorders and immunodeficiency disorders disclosed herein or known in the art are contemplated as being within the scope of the disclosure.

In certain embodiments, the non-proliferative disease is a cardiovascular condition. In certain embodiments, the compound of Formula (I), or a pharmaceutically acceptable salt thereof, or compositions comprising such compound or pharmaceutically acceptable salt thereof, is used to prevent or treat a cardiovascular disease, disorder, or condition. A cardiovascular disease, disorder, or condition may include a condition relating to the heart or vascular system, such as the arteries, veins, or blood. Exemplary cardiovascular diseases, disorders, or conditions include angina, arrhythmias (atrial or ventricular or both), heart failure, arteriosclerosis, atheroma, atherosclerosis, cardiac hypertrophy, cardiac or vascular aneurysm, cardiac myocyte dysfunction, carotid obstructive disease, endothelial damage after PTCA (percutaneous transluminal coronary angioplasty), hypertension including essential hypertension, pulmonary hypertension and secondary hypertension (renovascular hypertension, chronic glomerulonephritis), myocardial infarction, myocardial ischemia, peripheral obstructive arteriopathy of a limb, an organ, or a tissue; peripheral artery occlusive disease (PAOD), reperfusion injury following ischemia of the brain, heart or other organ or tissue, restenosis, stroke, thrombosis, transient ischemic attack (TIA), vascular occlusion, vasculitis, and vasoconstriction. All types of cardiovascular diseases, disorders, or conditions disclosed herein or known in the art are contemplated as being within the scope of the disclosure.

In certain embodiments, the non-proliferative disease is a metabolic disorder. In certain embodiments, the compound of Formula (I), or a pharmaceutically acceptable salt thereof, or compositions comprising such compound or pharmaceutically acceptable salt thereof, is used to prevent or treat a metabolic disease, disorder, or condition. A metabolic disease, disorder, or condition may include a disorder or condition that is characterized by abnormal metabolism, such as those disorders relating to the consumption of food and water, digestion, nutrient processing, and waste removal. A metabolic disease, disorder, or condition may include an acid-base imbalance, a mitochondrial disease, a wasting syndrome, a malabsorption disorder, an iron metabolism disorder, a calcium metabolism disorder, a DNA repair deficiency disorder, a glucose metabolism disorder, hyperlactatemia, a disorder of the gut microbiota. Exemplary metabolic conditions include obesity, diabetes (Type I or Type II), insulin resistance, glucose intolerance, lactose intolerance, eczema, hypertension, Hunter syndrome, Krabbe disease, sickle cell anemia, maple syrup urine disease, Pompe disease, and metachromatic leukodystrophy. All types of metabolic diseases, disorders, or conditions disclosed herein or known in the art are contemplated as being within the scope of the disclosure.

In certain embodiments, the non-proliferative disease is a respiratory condition. In certain embodiments, the compound of Formula (I), or a pharmaceutically acceptable salt thereof, or compositions comprising such compound or pharmaceutically acceptable salt thereof, is used to prevent or treat a respiratory disease, disorder, or condition. A respiratory disease, disorder, or condition can include a disorder or condition relating to any part of the respiratory system, such as the lungs, alveoli, trachea, bronchi, nasal passages, or nose. Exemplary respiratory diseases, disorders, or conditions include asthma, allergies, bronchitis, allergic rhinitis, chronic obstructive pulmonary disease (COPD), lung cancer, oxygen toxicity, emphysema, chronic bronchitis, and acute respiratory distress syndrome. All types of respiratory diseases, disorders, or conditions disclosed herein or known in the art are contemplated as being within the scope of the disclosure.

In certain embodiments, the non-proliferative disease is a renal disease. In certain embodiments, the compound of Formula (I), or a pharmaceutically acceptable salt thereof, or compositions comprising such compound or pharmaceutically acceptable salt thereof, is used to prevent or treat a renal disease, disorder, or condition. A renal disease, disorder, or condition can include a disease, disorder, or condition relating to any part of the waste production, storage, and removal system, including the kidneys, ureter, bladder, urethra, adrenal gland, and pelvis. Exemplary renal diseases include acute kidney failure, amyloidosis, Alport syndrome, adenovirus nephritis, acute lobar nephronia, tubular necrosis, glomerulonephritis, kidney stones, urinary tract infections, chronic kidney disease, polycystic kidney disease, and focal segmental glomerulosclerosis (FSGS). In some embodiments, the renal disease, disorder, or condition comprises HIV-associated nephropathy or hypertensive nephropathy. All types of renal diseases, disorders, or conditions disclosed herein or known in the art are contemplated as being within the scope of the disclosure.

In certain embodiments, the non-proliferative disease is an infectious disease. In certain embodiments, the compound of Formula (I), or a pharmaceutically acceptable salt thereof, or compositions comprising such compound or pharmaceutically acceptable salt thereof, is used to prevent or treat an infectious disease, disorder, or condition. An infectious disease may be caused by a pathogen such as a virus or bacteria. Exemplary infectious diseases include human immunodeficiency syndrome (HIV), acquired immunodeficiency syndrome (AIDS), meningitis, African sleeping sickness, actinomycosis, pneumonia, botulism, *chlamydia*, Chagas disease, Colorado tick fever, cholera, typhus, giardiasis, food poisoning, ebola hemorrhagic fever, diphtheria, Dengue fever, gonorrhea, streptococcal infection (e.g., Group A or Group B), hepatitis A, hepatitis B, hepatitis C, herpes simplex, hookworm infection, influenza, Epstein-Barr infection, Kawasaki disease, kuru, leprosy, leishmaniasis, measles, mumps, norovirus, meningococcal disease, malaria, Lyme disease, listeriosis, rabies, rhinovirus, rubella, tetanus, shingles, scarlet fever, scabies, Zika fever, yellow fever, tuberculosis, toxoplasmosis, or tularemia. In some embodiments, the infectious disease comprises cytomegalovirus. All types of infectious diseases, disorders, or conditions disclosed herein or known in the art are contemplated as being within the scope of the disclosure.

In certain embodiments, the disease, disorder, or condition is a haploinsufficiency disease. In certain embodiments, the compound of Formula (I), or a pharmaceutically acceptable salt thereof, or compositions comprising such compound or pharmaceutically acceptable salt thereof, is used to prevent or treat a haploinsufficiency disease, disorder, or condition. A haploinsufficiency disease, disorder, or condition may refer to a monogenic disease in which an allele of a gene has a loss-of-function lesion, e.g., a total loss of function lesion. In an embodiment, the loss-of-function lesion is present in an autosomal dominant inheritance pattern or is derived from a sporadic event. In an embodiment, the reduction of gene product function due to the altered allele drives the disease phenotype despite the remaining functional allele (i.e. said disease is haploinsufficient with regard to the gene in question). In an embodiment, a compound of Formula (I) increases expression of the haploinsufficient gene locus. In an embodiment, a compound of Formula (I) increases one or both alleles at the haploinsufficient gene locus. Exemplary haploinsufficiency diseases, disorders, and conditions include Robinow syndrome, cardiomyopathy, cerebellar ataxia, pheochromocytoma, Charcot-Marie-Tooth disease, neuropathy, Takenouchi-Kosaki syndrome, Coffin-Siris syndrome 2, chromosome 1p35 deletion syndrome, spinocerebellar ataxia 47, deafness, seizures, dystonia 9, GLUT1 deficiency syndrome 1, GLUT1 deficiency syndrome 2, stomatin-deficient cryohydrocytosis, basal cell carcinoma, basal cell nevus syndrome, medulloblastoma, somatic, brain malformations, macular degeneration, cone-rod dystrophy, Dejerine-Sottas disease, hypomyelinating neuropathy, Roussy-Levy syndrome, glaucoma, autoimmune lymphoproliferative syndrome, pituitary hormone deficiency, epileptic encephalopathy, early infantile, popliteal pterygium syndrome, van der Woude syndrome, Loeys-Dietz syndrome, Skraban-Deardorff syndrome, erythrocytosis, megalencephaly-polymicrogyria-polydactyly-hydrocephalus syndrome, mental retardation, CINCA syndrome, familial cold inflammatory syndrome 1, keratoendothelitis fugax hereditaria, Muckle-Wells syndrome, Feingold syndrome 1, Acute myeloid leukemia, Heyn-Sproul-Jackson syndrome, Tatton-Brown-Rahman syndrome, Shashi-Pena syndrome, Spastic paraplegia, autosomal dominant, macrophthalmia, colobomatous, with microcornea, holoprosencephaly, schizencephaly, endometrial cancer, familial, colorectal cancer, hereditary nonpolyposis, intellectual developmental disorder with dysmorphic facies and behavioral abnormalities, ovarian hyperstimulation syndrome, schizophrenia, Dias-Logan syndrome, premature ovarian failure, dystonia, dopa-responsive, due to sepiapterin reductase deficiency, Beck-Fahrner syndrome, chromosome 2p12-p11.2 deletion syndrome, neuronopathy, spastic paraplegia, familial adult myoclonic, colorectal cancer, hypothyroidism, Culler-Jones syndrome, holoprosencephaly, myelokathexis, WHIM syndrome, Mowat-Wilson syndrome, mental retardation, an intellectual developmental disorder, autism spectrum disorder, epilepsy, epileptic encephalopathy, Dravet syndrome, migraines, a mental retardation disorder (e.g., a disorder caused by a SETD5 gene mutation, e.g., intellectual disability-facial dysmorphism syndrome, autism spectrum disorder), a disorder caused by a GATA2 mutation (e.g., GATA2 deficiency; GATA2 haploinsufficiency; Emberger syndrome; monocytopenia and *Mycobacterium avium* complex/dendritic cell, monocyte, B and NK lymphocyte deficiency; familial myelodysplastic syndrome; acute myeloid leukemia; chronic myelomonocytic leukemia), and febrile seizures.

In certain embodiments, the disease, disorder, or condition is an autosomal recessive disease, e.g., with residual function. In certain embodiments, the compound of Formula (I), or a pharmaceutically acceptable salt thereof, or compositions comprising such compound or pharmaceutically acceptable salt thereof, is used to prevent or treat an autosomal recessive disease, disorder, or condition. An autosomal recessive disease with residual function may refer to a monogenic disease with either homozygous recessive or compound heterozygous heritability. These diseases may also be characterized by insufficient gene product activity (e.g., a level of gene product greater than 0%). In an embodiment, a compound of Formula (I) may increase the expression of a target (e.g., a gene) related to an autosomal recessive disease with residual function. Exemplary autosomal recessive diseases with residual function include Friedreich's ataxia, Stargardt disease, Usher syndrome, chlorioderma, fragile X syndrome, achromatopsia 3, Hurler syndrome, hemophilia B, alpha-1-antitrypsin deficiency, Gaucher disease, X-linked retinoschisis, Wiskott-Aldrich syndrome, mucopolysaccharidosis (Sanfilippo B), DDC deficiency, epidermolysis bullosa dystrophica, Fabry disease, metachromatic leukodystrophy, and odontochondrodysplasia.

In certain embodiments, the disease, disorder, or condition is an autosomal dominant disease. In certain embodiments, the compound of Formula (I), or a pharmaceutically acceptable salt thereof, or compositions comprising such compound or pharmaceutically acceptable salt thereof, is used to prevent or treat an autosomal dominant disease, disorder, or condition. An autosomal dominant disease may refer to a monogenic disease in which the mutated gene is a dominant gene. These diseases may also be characterized by insufficient gene product activity (e.g., a level of gene product greater than 0%). In an embodiment, a compound of Formula (I) may increase the expression of a target (e.g., a gene) related to an autosomal dominant disease. Exemplary autosomal dominant diseases include Huntington's disease, achondroplasia, antithrombin III deficiency, Gilbert's disease, Ehlers-Danlos syndrome, hereditary hemorrhagic telangiectasia, intestinal polyposis, hereditary elliptosis, hereditary spherocytosis, marble bone disease, Marfan's syndrome, protein C deficiency, Treacher Collins syndrome, Von Willebrand's disease, tuberous sclerosis, osteogenesis imperfecta, polycystic kidney disease, neurofibromatosis, and idiopathic hypoparathyroidism.

In certain embodiments, the disease, disorder, or condition is a paralogue activation disorder. In certain embodiments, the compound of Formula (I), or a pharmaceutically acceptable salt thereof, or compositions comprising such compound or pharmaceutically acceptable salt thereof, is used to prevent or treat a paralogue activation disease, disorder, or condition. A paralogue activation disorder may comprise a homozygous mutation of genetic locus leading to loss-of-function for the gene product. In these disorders, there may exist a separate genetic locus encoding a protein with overlapping function (e.g. developmental paralogue), which is otherwise not expressed sufficiently to compensate for the mutated gene. In an embodiment, a compound of Formula (I) activates a gene connected with a paralogue activation disorder (e.g., a paralogue gene).

The cell described herein may be an abnormal cell. The cell may be in vitro or in vivo. In certain embodiments, the cell is a proliferative cell. In certain embodiments, the cell is a cancer cell. In certain embodiments, the cell is a non-proliferative cell. In certain embodiments, the cell is a blood cell. In certain embodiments, the cell is a lymphocyte. In certain embodiments, the cell is a benign neoplastic cell. In certain embodiments, the cell is an endothelial cell. In certain embodiments, the cell is an immune cell. In certain embodiments, the cell is a neuronal cell. In certain embodiments, the cell is a glial cell. In certain embodiments, the cell is a brain cell. In certain embodiments, the cell is a fibroblast. In certain embodiment, the cell is a primary cell, e.g., a cell isolated from a subject (e.g., a human subject).

In certain embodiments, the methods described herein comprise the additional step of administering one or more additional pharmaceutical agents in combination with the compound of Formula (I), a pharmaceutically acceptable salt thereof, or compositions comprising such compound or pharmaceutically acceptable salt thereof. Such additional pharmaceutical agents include, but are not limited to, anti-proliferative agents, anti-cancer agents, anti-diabetic agents, anti-inflammatory agents, immunosuppressant agents, and a pain-relieving agent. The additional pharmaceutical agent(s) may synergistically augment the modulation of splicing induced by the inventive compounds or compositions of this disclosure in the biological sample or subject. Thus, the combination of the inventive compounds or compositions and the additional pharmaceutical agent(s) may be useful in treating, for example, a cancer or other disease, disorder, or condition resistant to a treatment using the additional pharmaceutical agent(s) without the inventive compounds or compositions.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Reactions can be purified or analyzed according to any suitable method known in the art. For example, product formation can be monitored by spectroscopic means, such as nuclear magnetic resonance (NMR) spectroscopy (e.g., $^1H$ or $^{13}C$), infrared (IR) spectroscopy, spectrophotometry (e.g., UV-visible), mass spectrometry (MS), or by chromatographic methods such as high performance liquid chromatography (HPLC) or thin layer chromatography (TLC).

Proton NMR: $^1H$ NMR spectra were recorded in $CDCl_3$ solution in 5-mm o.d. tubes (Wildmad) at 24° C. and were collected on a BRUKER AVANCE NEO 400 at 400 MHz for $^1H$. The chemical shifts (δ) are reported relative to tetramethylsilane (TMS=0.00 ppm) and expressed in ppm.

LC/MS: Liquid chromatography-mass spectrometry (LC/MS) was performed on Shimadzu-2020EV using column: Shim-pack XR-ODS (C18, Ø4.6×50 mm, 3 μm, 120 Å, 40° C.) operating in ESI(+) ionization mode; flow rate=1.2 mL/min. Mobile phase=0.05% TFA in water or $CH_3CN$; or on Shimadzu-2020EV using column: Poroshell HPH-C18 (C18, Ø4.6×50 mm, 3 μm, 120 Å, 40° C.) operating in ESI(+) ionization mode; flow rate=1.2 mL/min. Mobile phase A: Water/5 mM $NH_4HCO_3$, Mobile phase B: $CH_3CN$.)

Analytical chiral HPLC: Analytical chiral HPLC was performed on a Agilent 1260 using column: CHIRALPAK IG-3, CHIRALPAK IC-3 or CHIRALPAK OJ-3, with flow rate=1.2 mL/min. Mobile phase=MTBE(DEA):EtOH=50:50).

Preparative HPLC purification: prep-HPLC purification was performed using one of the following HPLC conditions:

Condition 1: Shimadzu, Column: XBridge Prep OBD $C_{18}$ Column, 30 Å-150 mm 5 μm; Mobile Phase A: water (10 mmol/L $NH_4HCO_3$) Mobile Phase B: acetonitrile; Flow rate: 60 mL/min; Gradient 1: 3 B to 3 B in 2 min; Gradient 2: 5% B to 35% B in 6 min; Gradient 3: 3 B to 33 B in 6 min; Gradient 4: 5% B up to 45% in 6 min; Gradient 5: 3% B to 23% B in 6 min; Gradient 6: 10% B to 60% B in 8 min; Gradient 7: 5 B to 45 B in 10 min; Gradient 8: 10% B up to 47% B in 10 min; Gradient 9: 10% B up to 50% B in 8 min; Gradient 9: 5% B to 35% B in 8 min; Gradient 10: 10% B to 48% B in 10 min; Gradient 11: 20% B to 52% B in 8 min; Gradient 12: 20% B to 50% B in 6 min; Gradient 13: 20% B to 43% B in 8 min; Gradient 14: 15% B to 45% B in 8 min; Gradient 14: 10% B to 55% B in 8 min; Gradient 15: 5% B to 38% B in 10 min; Gradient 16: 10% B to 35% B in 8 min; Gradient 17: 5% B to 42% B in 8 min; Gradient 18: 5% B to 30% B in 8 min; Gradient 18: 5% B to 40% B in 8 min; Gradient 19: 5% B to 45% B in 8 min; Gradient 21: 5% B to 37% B in 8 min; Gradient 22: 5% B to 65% B in 8 min; Gradient 23: 10% B to 65% B in 8 min; Gradient 24: 5% B to 50% B in 8 min.

Condition 2: Column: Xselect CSH OBD Column 30*150 mm 5 μm, n; Mobile Phase A: water (10 mmol/L $NH_4HCO_3$); Mobile Phase B: acetonitrile; Flow rate: 60 mL/min; Gradient 1: 10 B to 55 B in 8 min; Gradient 2: 5 B to 50 B in 8 min; Gradient 3: 10 B to 60 B in 10 min; Gradient 4: 10 B to 40 B in 8 min; Gradient 5: 5 B to 65 B in 8 min; Gradient 6: 3% B to 63% B in 6 min; Gradient 7: 10% B to 52% B in 8 min; Gradient 8: 5% B to 37% B in 8 min; Gradient 9: 10% B to 38% B in 8 min; Gradient 10: 3% B to 75% B in 8 min; Gradient 11: 10% B to 42% B in 8 min; Gradient 12: 15% B to 40% B in 10 min; Gradient 13: 10% B to 60% B in 8 min; Gradient 14: 5% B to 35% B in 8 min; Gradient 15: 15% B to 36% B in 8 min.

Condition 3: Column: EP-$C_{18}$M 10 μm 120 A; Mobile Phase A: water (1 mmol/L HCl); Mobile Phase B: acetonitrile; Flow rate: 100 mL/min; Gradient: 40% B to 70% B in 35 min.

Condition 4: Column: Poroshell HPH-C18, 3.0*50 mm, 2.7 um; Mobile Phase A: water (5 mM $NH_4HCO_3$); Mobile Phase B: acetonitrile; Flow rate: 1.2 mL/min; Gradient 1:10% B to 95% B in 1.2 min, hold 0.5 min.

Condition 5: Column: X Select CSH OBD 30×150 mm 5 μm; Mobile phase A: water (0.1% formic acid); Mobile phase B: acetonitrile; Gradient 1: 3% phase B up to 18% in 6 min.

Condition 6: Column: X Select CSH OBD 30×150 mm 5 μm; Mobile phase A: water (0.05% HCl); Mobile phase B: acetonitrile; Flow rate: 60 mL/min; Gradient 1: 3% phase B up to 3% in 2 min; Gradient 2: 3% B to 18% B in 8 min.

Condition 7: Column: X Select CSH OBD 30×150 mm 5 μm; Mobile phase A: water (0.05% formic acid);

Mobile phase B: acetonitrile; Flow rate: 60 mL/min; Gradient 1: 3% phase B up to 20% in 8 min.

Condition 8: Column: YMC-Actus Triart C18, 30 mm×150 mm, 5 μm; Mobile phase A: water (0.05% HCl); Mobile phase B: acetonitrile; Gradient 1: 5% B to 35% B in 8 min.

Condition 9: Column: YMC-Actus Triart C18, 30 mm×150 mm, 5 μm; Mobile phase A: water (10 mmol/L $NH_4HCO_3$); Mobile phase B: acetonitrile; Flow rate: 60 mL/min Gradient 1: 10% B to 70% B in 8 min; Gradient 2: 15% B to 55% B in 8 min; Gradient 3: 5% B to 65% B in 8 min; Gradient 4: 5% B to 45% B in 8 min; Gradient 5:15% B to 45% B in 10 min; Gradient 6: 15% B to 70% B in 8 min; Gradient 7: 5% B to 50% B in 8 min; Gradient 8: 15% B to 50% B in 8 min; Gradient 9: 20% B to 44% B in 10 min.

Preparative chiral HPLC: purification by chiral HPLC was performed on a Gilson-GX 281 using column: CHIRALPAK IG-3, CHIRALPAK IC-3 or CHIRALPAK OJ-3.

Condition 1: Column: CHIRALPAK IG, 3×25 cm, 5 μm; Mobile Phase A: MTBE (0.1% DEA), Mobile Phase B: ethanol; Flow rate: 20 mL/min; Gradient 1: 50 B to 50 B in 18 min.

Reverse flash chromagraphy: purification by reverse flash chromatography was performed using one of the following conditions:

Condition 1: Column, $C_{18}$; Mobile phase: MeOH in water; Gradient 1, 10% to 50% in 1 0 min; Detector, UV 254 nm.

Condition 2: Column, silica gel; Mobile phase: MeOH in water; Gradient 1: 10% to 50% in 10 min; Detector, UV 254 nm.

General Synthetic Schemes

Compounds of the present disclosure may be prepared using a synthetic protocol illustrated in one of Schemes A, B, or C.

Scheme A:

Scheme A.

Steps 1 and 2

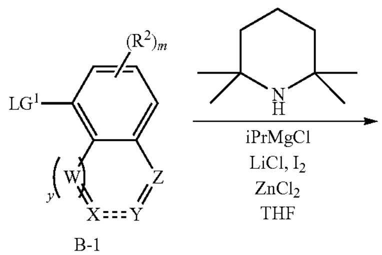

B-1

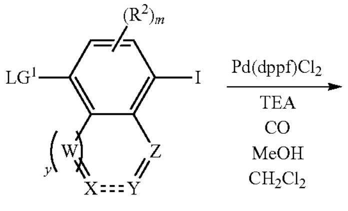

B-2

-continued

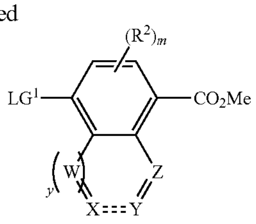

B-3

Steps 3 and 4

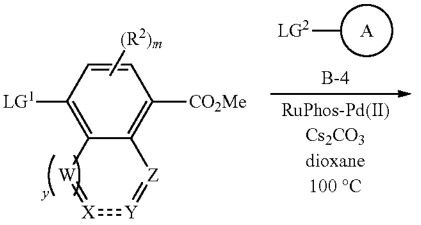

B-3

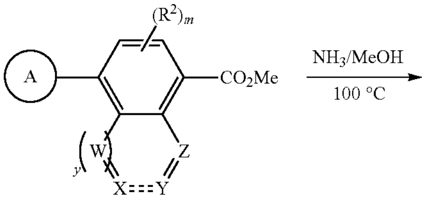

B-5

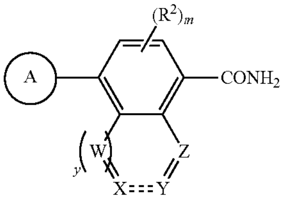

B-6

Step 5

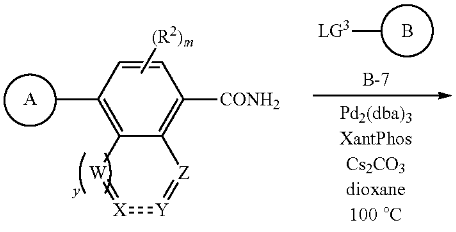

B-6

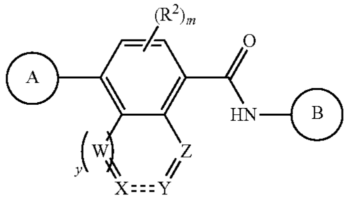

(II-I)

An exemplary method of preparing a compound of Formula (I); wherein A, B, W, X, Y, Z, $R^2$, and m are as defined herein; and $LG^1$, $LG^2$, and $LG^3$ are each independently a leaving group (e.g., halo, —$B(OR^{12})_2$). In some embodiments of the application, y is 0.

An exemplary method of preparing a compound described herein, e.g., a compound of Formula (II-I) is provided in Scheme A. In Step 1, B-2 is prepared by treating B-1 with a mixture of 2,2,6,6-tetramethylpiperidine, isopropylmagnesium chloride (iPrMgCl), lithium chloride (LiCl), iodine ($I_2$), and zinc chloride ($ZnCl_2$) in tetrahydrofuran (THF), or with a similar combination of reagents or solvent. In Step 2, B-3 is prepared by incubating B2 with 1,1'-bis(diphenylphosphino)ferrocene)palladium(II) dichloride (Pd(dppf) $Cl_2$), carbon monoxide (CO), and triethylamine (TEA), in a mixture of methanol (MeOH) and dichloromethane ($CH_2Cl_2$) or a similar mixture of solvents. Alternative catalysts to Pd(dppf)$Cl_2$ may also be used, such as a suitable palladium catalyst, and/or using alternative reagents sufficient to provide B-3.

In Step 3, B-5 is prepared by incubating B-3 with B-4 in the presence of RuPhos-Pd(II) (e.g., RuPhos-Pd(II)-G2 or RuPhos-Pd(II)-G3), and cesium carbonate ($Cs_2CO_3$) or a similar reagent. Step 3 may also be carried out using an alternative catalyst to RuPhos-Pd(II), such as another ruthenium catalyst. The reaction may be conducted in dioxane or a similar solvent, at 100° C. or a temperature sufficient to provide B-5. B-5 is then converted to B-6 by treatment with a mixture of ammonia and methanol, at 100° C. or a temperature sufficient to provide B-6.

B-6 and B-7 are coupled to provide a compound of Formula (II-I) in Step 5. This coupling reaction may be conducted in the presence of tris(dibenzylideneacetone) dipalladium(0) ($Pd_2(dba)_3$, XantPhos, and cesium carbonate or a suitable alternative. Step 5 may also be carried out using an alternative catalyst to $Pd_2(dba)_3$, such as another palladium catalyst, and/or an alternative ligand to XantPhos (e.g., a different phosphine ligand). The reaction may be conducted in dioxane or a similar solvent, at 100° C. or a temperature sufficient to provide the compound of Formula (II-I). Each starting material and/or intermediate in Scheme B may be protected and deprotected using standard protecting group methods. In addition, purification and characterization of each intermediate as well as the final compound of Formula (II) may be afforded by any accepted procedure.

-continued

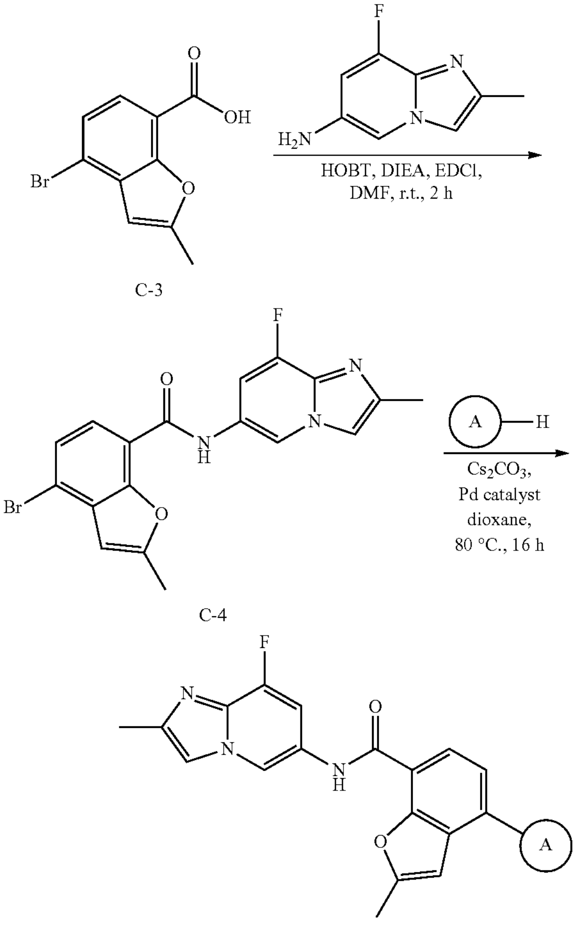

C-3

C-4

(II-I)

An exeplary method of preparing a compound of Formula (I); where A is as defined herein.

Scheme B.

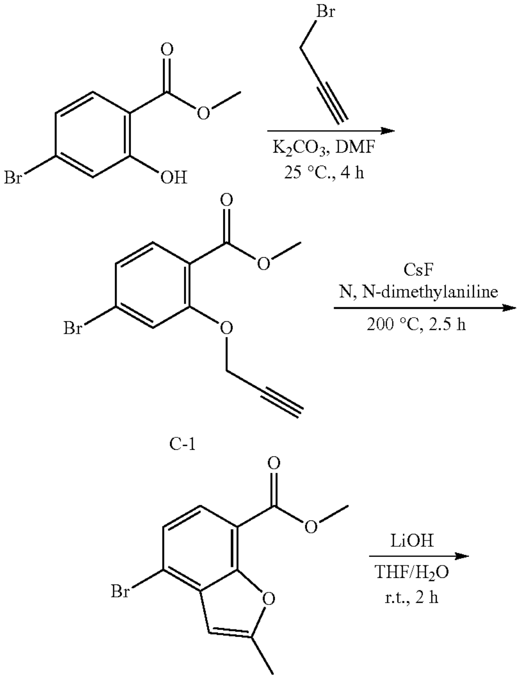

C-1

C-2

Scheme C.

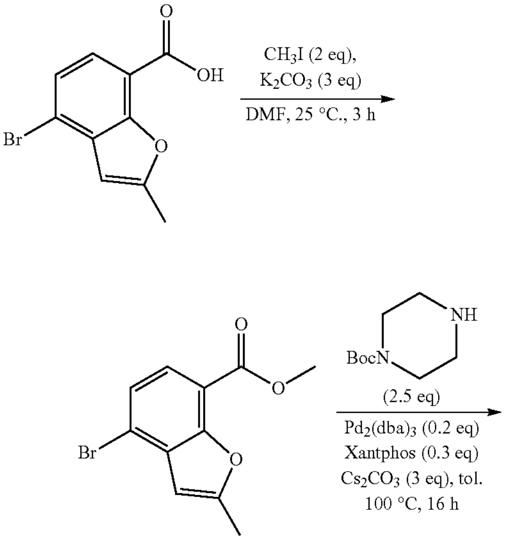

D-1

-continued

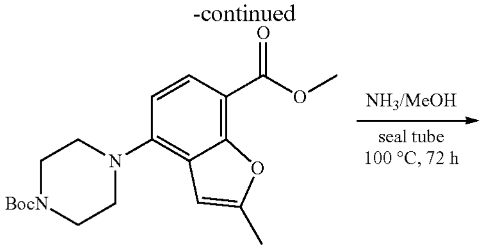

D-2

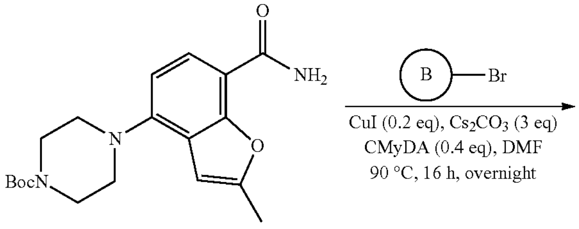

D-3

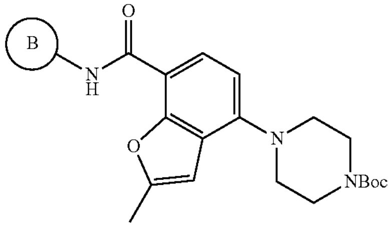

(II-I)

An exemplary method of preparing a compound of Formula (I); where B is as defined herein.

Example 1: Synthesis of Compound 118

Synthesis of Intermediate B72

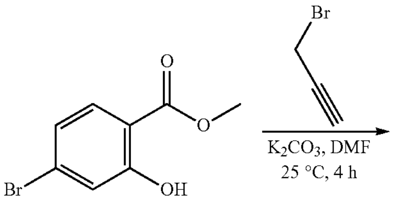

B71

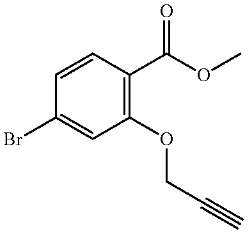

B72

A mixture of methyl 4-bromo-2-hydroxybenzoate (10 g, 43 mmol) and $K_2CO_3$ (18 g, 130 mmol) in dimethylformamide (200 mL) was stirred for 15 min at room temperature under a nitrogen atmosphere. Propargyl bromide (7.2 g, 61 mmol) was then added dropwise, and the resulting mixture was stirred for 4 h. The mixture was then diluted with water (1 L) and extracted with ethyl acetate (2×200 mL). The combined organic layers were washed with brine (2×200 mL), dried over anhydrous $Na_2SO_4$, filtered, and concentrated under reduced pressure, to afford methyl 4-bromo-2-(prop-2-yn-1-yloxy) benzoate (B72; 11.3 g) as a solid. LCMS (ES, m/z): 269 $[M+H]^+$.

Synthesis of Intermediate B73

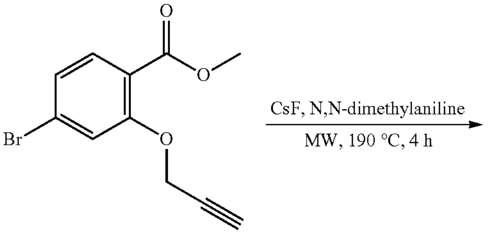

B72

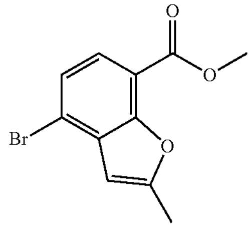

B73

A mixture of methyl 4-bromo-2-(prop-2-yn-1-yloxy) benzoate (B72; 1.13 g, 4.2 mmol) and cesium fluoride (0.64 g, 4.2 mmol) in N,N-dimethylaniline (10 mL) was irradiated with microwave radiation for 4 h at 190° C. The process was repeated 10 times, after which each of the 10 reaction mixtures were combined and dissolved in ethyl acetate (300 mL). The resulting mixture was washed with 4N HCl (3×200 mL), and brine (200 mL), then dried over anhydrous $Na_2SO_4$, filtered, and concentrated under reduced pressure. The crude product was purified by preparative HPLC (Condition 3) to afford methyl 4-bromo-2-methyl-1-benzofuran-7-carboxylate (1.3 g, 11.50%) as an off-white solid. LCMS (ES, m/z): 269 $[M+H]^+$

Synthesis of Intermediate B74

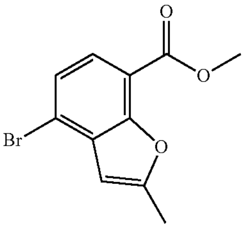

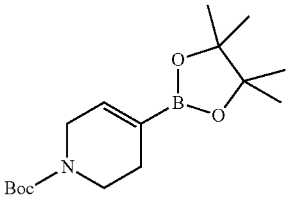

B27

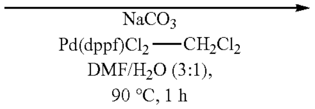

B73

-continued

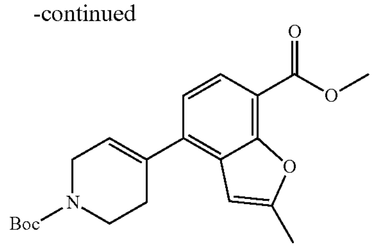

B74

A mixture of methyl 4-bromo-2-methyl-1-benzofuran-7-carboxylate (B73; 450 mg, 1.67 mmol), tert-butyl 4-(4,4,5,5-tetramethyl-1,3,2-dioxaborolan-2-yl)-3,6-dihydro-2H-pyridine-1-carboxylate (B27; 621 mg, 2 mmol), and $Na_2CO_3$ (532 mg, 5 mmol) in dimethylformamide (9 mL) and $H_2O$ (3 mL) was degassed with nitrogen, and then, $Pd(dppf)Cl_2$—$CH_2Cl_2$ (137 mg, 0.17 mmol) was added, and the mixture was stirred for 1 h at 90° C. The resulting mixture was poured into water (50 mL) and extracted with ethyl acetate (2×20 mL). The combined organic layers were dried over anhydrous $Na_2SO_4$, filtered, and concentrated under reduced pressure. The residue was purified by silica gel column chromatography, eluting with petroleum ether/ethyl acetate (20:1-4:1) to afford tert-butyl 4-[7-(methoxycarbonyl)-2-methyl-1-benzofuran-4-yl]-3,6-dihydro-2H-pyridine-1-carboxylate (B74; 620 mg) as an oil. LCMS (ES, m/z): 316 $[M+H-56]^+$, 357 $[M+H-56+ACN]^+$.

Synthesis of Intermediate B75

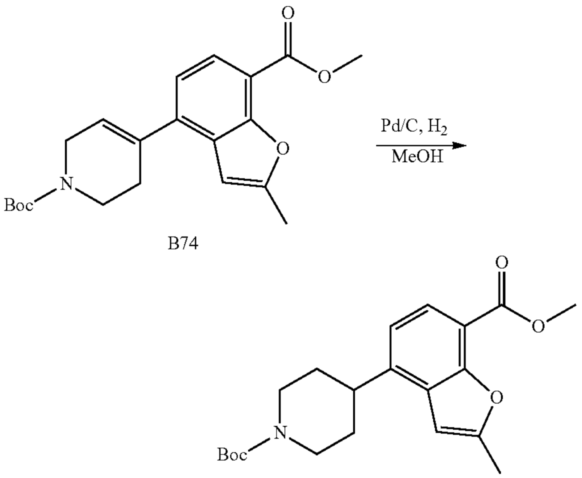

B74

B75

A mixture of tert-butyl 4-[7-(methoxycarbonyl)-2-methyl-1-benzofuran-4-yl]-3,6-dihydro-2H-pyridine-1-carboxylate (B74; 600 mg, 1.62 mmol) and palladium on carbon (100 mg, 0.94 mmol) in methanol (20 mL) was stirred for 1 h at room temperature under a hydrogen atmosphere. The resulting mixture was filtered, the filter cake was washed with methanol, and the filtrate was concentrated under reduced pressure to afford tert-butyl 4-[7-(methoxycarbonyl)-2-methyl-1-benzofuran-4-yl]piperidine-1-carboxylate (B75; 600 mg) as a solid. LCMS (ES, m/z): 318 $[M+H-56]^+$.

Synthesis of Intermediate B76

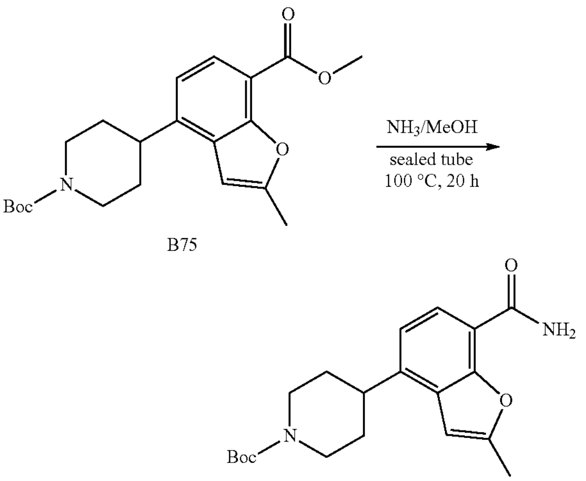

B75

B76

A mixture of tert-butyl 4-[7-(methoxycarbonyl)-2-methyl-1-benzofuran-4-yl]piperidine-1-carboxylate (B75; 600 mg, 1.61 mmol) and ammonia in methanol (60 mL, 2.9 mol) was stirred overnight at 100° C. in a sealed tube. The resulting mixture was concentrated under reduced pressure to afford tert-butyl 4-(7-carbamoyl-2-methyl-1-benzofuran-4-yl)piperidine-1-carboxylate (B76; 570 mg) as a solid. LCMS (ES, m/z): 303 $[M+H-56]^+$.

Synthesis of Intermediate B77

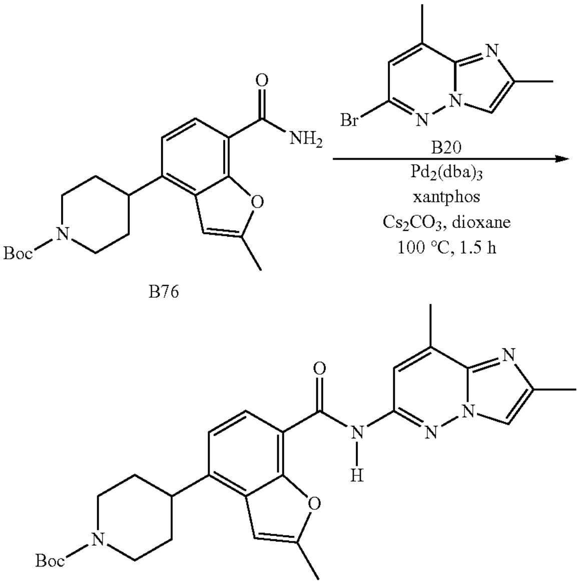

B76

B77

A mixture of tert-butyl 4-(7-carbamoyl-2-methyl-1-benzofuran-4-yl)piperidine-1-carboxylate (B76; 150 mg, 0.42 mmol), 6-bromo-2,8-dimethylimidazo[1,2-b]pyridazine (B20; 95 mg, 0.42 mmol), $Cs_2CO_3$ (409 mg, 1.26 mmol), and XantPhos (24.2 mg, 0.042 mmol) in dioxane (5 mL) was degassed with nitrogen 3 times, then $Pd_2(dba)_3$ (19.2 mg, 0.021 mmol, 0.05 equiv) was added, and the mixture was degassed 3 more times, then stirred for 1.5 h at 100° C. under a nitrogen atmosphere. The resulting mixture was filtered, the filtrate was concentrated under reduced pressure and purified by silica gel column chromatography, eluting with petroleum ether/ethyl acetate (10:1-1:1) to afford tert-butyl 4-[7-([2,8-dimethylimidazo[1,2-b]pyridazin-6-yl]carbamoyl)-2-methyl-1-benzofuran-4-yl]piperidine-1-carboxylate (B77; 170 mg) as a solid. LCMS (ES, m/z): 504 $[M+H]^+$.

Synthesis of Compound 118

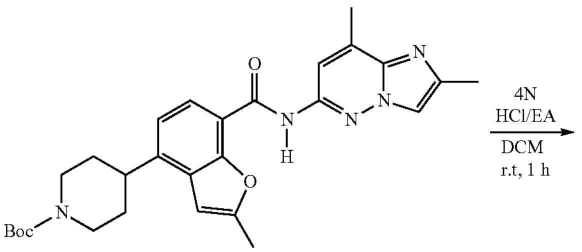

B77

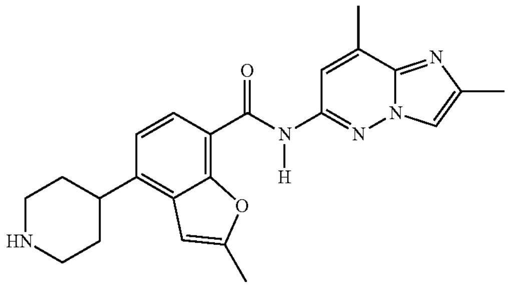

118

A solution of HCl in ethyl acetate (3 mL) was added in portions to a mixture of tert-butyl 4-[7-([2,8-dimethylimidazo[1,2-b]pyridazin-6-yl]carbamoyl)-2-methyl-1-benzofuran-4-yl]piperidine-1-carboxylate (B77; 170 mg, 0.39 mmol) in dichloromethane (3 mL) at room temperature. The resulting mixture was stirred for 1 h at room temperature under nitrogen atmosphere, and then concentrated under reduced pressure. The crude product was purified by preparative HPLC (Condition 2, Gradient 3) to afford N-[2,8-dimethylimidazo[1,2-b]pyridazin-6-yl]-2-methyl-4-(piperidin-4-yl)-1-benzofuran-7-carboxamide (Compound 118; 68.9 mg) as a solid. LCMS (ES, m/z): 404 $[M+H]^+$. $^1H$ NMR (400 MHz, DMSO-d6) δ 10.57 (s, 1H), 7.92 (s, 1H), 7.81 (d, J=1.3 Hz, 1H), 7.69 (d, J=7.9 Hz, 1H), 7.20 (d, J=7.9 Hz, 1H), 6.89 (d, J=1.3 Hz, 1H), 3.07 (d, J=11.9 Hz, 2H), 2.99 (s, 1H), 2.73-2.63 (m, 2H), 2.58 (d, J=1.1 Hz, 3H), 2.53 (d, J=1.1 Hz, 3H), 2.39 (s, 3H), 1.78-1.61 (m, 4H).

Example 2: Synthesis of Compound 149

Synthesis of Intermediate B103

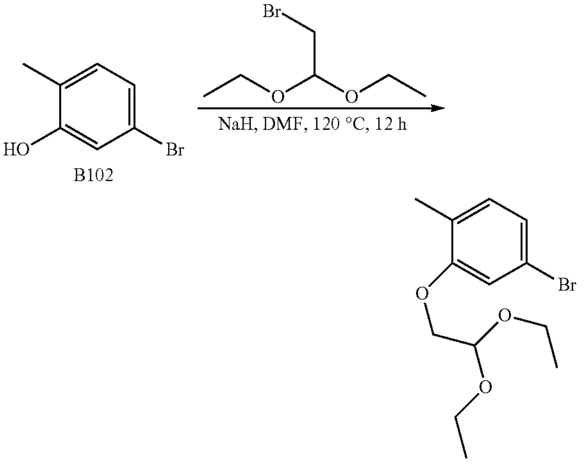

B103

A mixture of 5-bromo-2-methylphenol (B102; 10 g, 53.5 mmol), sodium hydride (2.36 g, 98.4 mmol), and 2-bromo-1,1-diethoxyethane (15.8 g, 80.2 mmol) in dimethylformamide (150 mL) was stirred for 12 h at 120° C. The reaction was then quenched with 500 mL of water/ice, and the pH of the solution was adjusted to 7. The resulting solution was extracted with ethyl acetate (3×200 mL) and dried over anhydrous sodium sulfate. The residue was purified by silica gel column chromatography eluting with ethyl acetate/petroleum ether (1:10), to afford 4-bromo-2-(2,2-diethoxyethoxy)-1-methylbenzene (B103; 9.8 g) as a solid. LCMS (ES, m/z): 303 $[M+H]^+$.

Synthesis of Intermediate B104

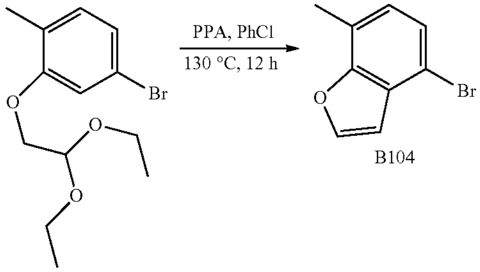

B103

A mixture of 4-bromo-2-(2,2-diethoxyethoxy)-1-methylbenzene (B103; 8.6 g, 26.4 mmol), and polyphosphoric acid (13 g, 113 mmol) in chlorobenzene (200 mL) was stirred for 12 h at 130° C. The resulting mixture was concentrated under reduced pressure and purified by silica gel column chromatography eluting with ethyl acetate/petroleum ether (1:10), to afford 4-bromo-7-methyl-1-benzofuran (B104; 2.40 g) as a solid. LCMS (ES, m/z): 211 $[M+H]^+$.

Synthesis of Intermediate B105

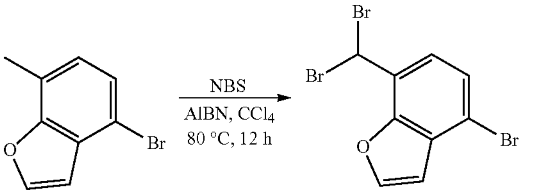

B104 B105

A mixture of 4-bromo-7-methyl-1-benzofuran (B104; 1.5 g, 7.1 mmol), N-bromosuccinimide (3 g, 17 mmol), and azobisisobutyronitrile (187 mg, 1.1 mmol), in carbon tetrachloride (30 mL) was stirred for 12 h at 80° C. The resulting solution was extracted with ethyl acetate (3×50 mL) and dried over anhydrous sodium sulfate. The residue was purified by silica gel column chromatography eluting with ethyl acetate/petroleum ether (1:10), to afford 4-bromo-7-(dibromomethyl)-1-benzofuran (B105; 1.70 g) as a solid. LCMS (ES, m/z): 367 $[M+H]^+$.

Synthesis of Intermediate B106

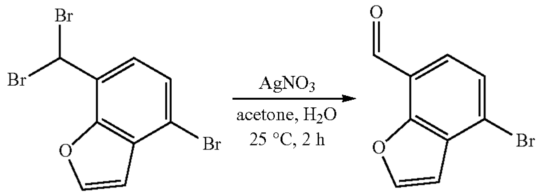

B105 B106

A mixture of 4-bromo-7-(dibromomethyl)-1-benzofuran (B105; 1.56 g, 4.3 mmol) and silver nitrate (2.9 g, 16.9 mmol) in a mixture of acetone (25 mL) and $H_2O$ (5 mL) was stirred for 2 h at 25° C., then filtered. The pH of the solution was adjusted to 8, and the solution was extracted with ethyl acetate (3×100 mL), dried over anhydrous sodium sulfate, and concentrated, to afford 4-bromo-1-benzofuran-7-carbaldehyde (B106; 900 mg) as a solid. LCMS (ES, m/z): 225 $[M+H]^+$.

Synthesis of Intermediate B107

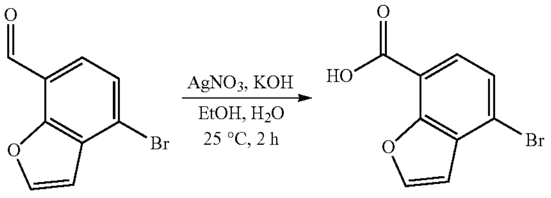

B106 B107

A mixture of 4-bromo-1-benzofuran-7-carbaldehyde (B106; 900 mg, 4 mmol), ethanol (20 mL), silver nitrate (1.4 g, 8 mmol), and potassium hydroxide (898 mg, 16 mmol) in water (20 mL) was stirred for 2 h at 25° C., and then filtered. The pH of the solution was adjusted to 4, and the solution was extracted with ethyl acetate (3×10 mL), dried over anhydrous sodium sulfate, and concentrated, to afford 4-bromo-1-benzofuran-7-carboxylic acid (B107; 900 mg) as a solid. LCMS (ES, m/z): 241 $[M+H]^+$.

Synthesis of Intermediate B108

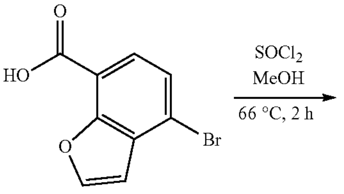

B107

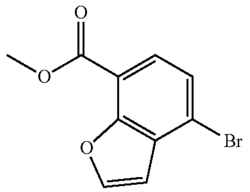

B108

A mixture of 4-bromo-1-benzofuran-7-carboxylic acid (B107; 850 mg, 3.5 mmol) and thionyl chloride (839 mg, 7 mmol) in methanol (18 mL) was stirred for 2 h at 66° C. The reaction was then quenched with methanol, and the residue was purified by silica gel column chromatography eluting with ethyl acetate/petroleum ether (1:10), to afford methyl 4-bromo-1-benzofuran-7-carboxylate (B108; 800 mg) as a solid. LCMS (ES, m/z): 255 $[M+H]^+$.

Synthesis of Intermediate B109

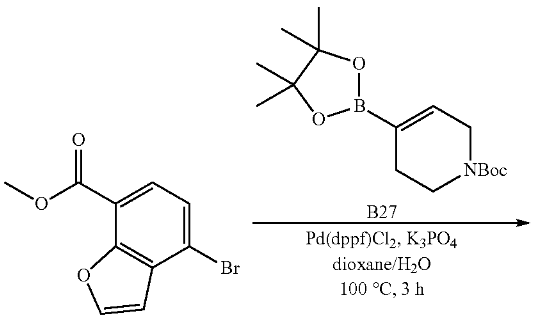

B108

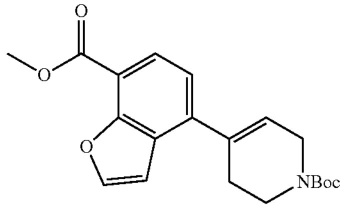

B109

A mixture of methyl 4-bromo-1-benzofuran-7-carboxylate (B108; 260 mg, 1 mmol), tert-butyl 4-(4,4,5,5-tetramethyl-1,3,2-dioxaborolan-2-yl)-3,6-dihydro-2H-pyridine-1-carboxylate (B27; 473 mg, 1.5 mmol), $Pd(dppf)Cl_2$ (75 mg, 0.1 mmol), and $K_3PO_4$ (649 mg, 3 mmol), in dimethylformamide (6 mL) was stirred for 3 h at 100° C. The resulting solution was extracted with ethyl acetate (3×10 mL) and dried over anhydrous sodium sulfate. The residue was purified by silica gel column chromatography eluting with ethyl acetate/petroleum ether (1:4), to afford tert-butyl 4-[7-(methoxycarbonyl)-1-benzofuran-4-yl]-3,6-dihydro-2H-pyridine-1-carboxylate (B109; 400 mg) as a solid. LCMS (ES, m/z): 358 $[M+H]^+$.

Synthesis of Intermediate B110

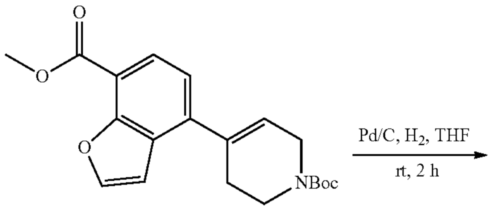

B109

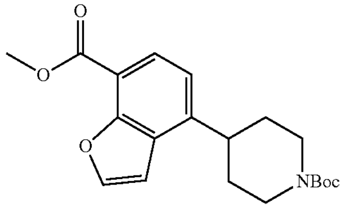

B110

Palladium on carbon (30 mg, 0.28 mmol) was added to a solution of tert-butyl 4-[7-(methoxycarbonyl)-1-benzofuran-4-yl]-3,6-dihydro-2H-pyridine-1-carboxylate (B109; 350 mg, 0.98 mmol) in tetrahydrofuran (15 mL), and the mixture was maintained under a hydrogen atmosphere using a balloon, for 2 h. The mixture was then filtered through a Celite pad and concentrated under reduced pressure, and the residue was purified by reverse phase flash chromatography on a $C_{18}$ column, eluting with acetonitrile/water (10 mmol/L $NH_4HCO_3$), with a gradient of 50% acetonitrile up to 80% over 20 min, to afford tert-butyl 4-[7-(methoxycarbonyl)-1-benzofuran-4-yl]piperidine-1-carboxylate (B110; 280 mg) as an oil. LCMS (ES, m/z): 360 $[M+H]^+$.

Synthesis of Intermediate B111

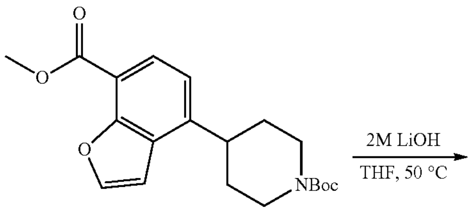

B110

-continued

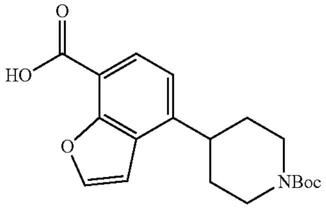

B111

A solution of tert-butyl 4-[7-(methoxycarbonyl)-1-benzofuran-4-yl]piperidine-1-carboxylate (B110; 200 mg, 0.56 mmol) and aqueous lithium hydroxide (2M, 1 mL) in tetrahydrofuran (1 mL) was stirred for 3 h at 50° C. under a nitrogen atmosphere. The resulting mixture was diluted with water (10 mL), and the pH was adjusted to 5 with aqueous HCl. The resulting mixture was extracted with ethyl acetate (3×5 mL), and the combined organic layers were washed with brine (5 mL), dried over anhydrous sodium sulfate, filtered, and concentrated under reduced pressure, to afford 4-[1-(tert-butoxycarbonyl) piperidin-4-yl]-1-benzofuran-7-carboxylic acid (B111; 160 mg) as a solid. LCMS (ES, m/z): 346 $[M+H]^+$.

Synthesis of Intermediate B112

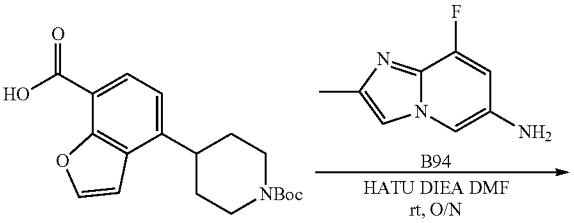

B111

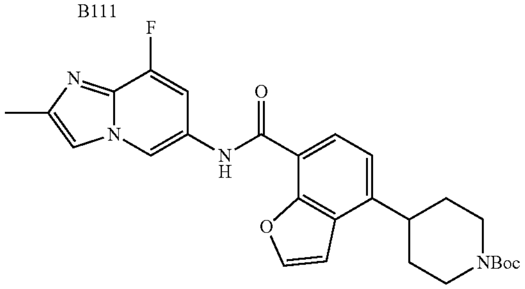

B112

A mixture of 4-[1-(tert-butoxycarbonyl) piperidin-4-yl]-1-benzofuran-7-carboxylic acid (B111; 50 mg, 0.15 mmol) 8-fluoro-2-methylimidazo[1,2-a]pyridin-6-amine (B94; 36 mg, 0.22 mmol), hexafluorophosphate azabenzotriazole tetramethyl uronium (83 mg, 0.22 mmol) and diisopropylethylamine (56 mg, 0.43 mmol) in dimethylformamide (1 mL) was stirred overnight at room temperature under a nitrogen atmosphere. The resulting mixture was diluted with water (10 mL) and extracted with ethyl acetate (3×10 mL). The combined organic layers were washed with brine (10 mL), dried over anhydrous sodium sulfate, filtered, and concentrated under reduced pressure, to afford tert-butyl 4-[7-([8-fluoro-2-methylimidazo[1,2-a]pyridin-6-yl]carbamoyl)-1-benzofuran-4-yl]piperidine-1-carboxylate (B112; 70 mg) as a solid. The crude product was used in the next step directly without further purification. LCMS (ES, m/z): 493 $[M+H]^+$.

Synthesis of Compound 149

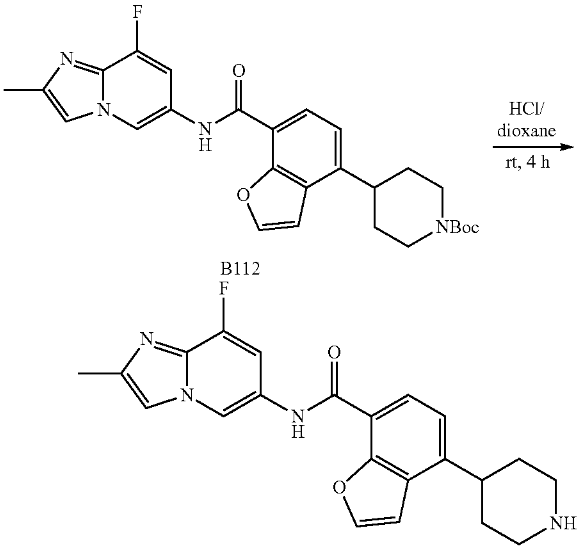

B112

149

A mixture of tert-butyl 4-[7-([8-fluoro-2-methylimidazo[1,2-a]pyridin-6-yl]carbamoyl)-1-benzofuran-4-yl]piperidine-1-carboxylate (B112; 70 mg), HCl in 1,4-dioxane (1 mL), and dioxane (1 mL) was stirred for 4 h at room temperature under a nitrogen atmosphere. The resulting mixture was concentrated under reduced pressure, and purified by preparative HPLC (Condition 2, Gradient 4), to afford N-[8-fluoro-2-methylimidazo[1,2-a]pyridin-6-yl]-4-(piperidin-4-yl)-1-benzofuran-7-carboxamide hydrochloride (Compound 149; 3.9 mg) as a solid. LCMS (ES, m/z): 393 $[M+H]^+$. $^1H$ NMR (400 MHz, DMSO-$d_6$, ppm) δ 10.79 (s, 1H), 9.47 (d, J=1.5 Hz, 1H), 9.15 (d, J=11.3 Hz, 1H), 9.00 (d, J=11.3 Hz, 1H), 8.23 (dd, J=17.9, 2.4 Hz, 2H), 7.85 (d, J=11.9 Hz, 1H), 7.77 (d, J=7.7 Hz, 1H), 7.45 (d, J=2.3 Hz, 1H), 7.26 (d, J=7.9 Hz, 1H), 3.39-3.27 (m, 3H), 3.12 (d, J=12.1 Hz, 1H), 3.06 (d, J=12.0 Hz, 1H), 2.48 (d, J=1.0 Hz, 3H), 2.14 (qd, J=13.3, 4.0 Hz, 2H), 2.01-1.93 (m, 2H).

Example 3: Synthesis of Compound 119

Synthesis of Intermediate B113

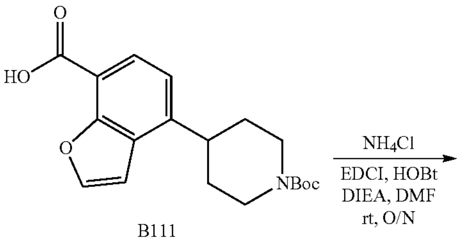

B111

-continued

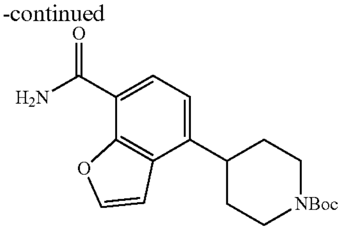

B113

A mixture of 4-[1-(tert-butoxycarbonyl) piperidin-4-yl]-1-benzofuran-7-carboxylic acid (B111 from Example 6, 75 mg, 0.22 mmol), ammonium chloride (17 mg, 0.33 mmol), hydroxybenzotriazole (38 mg, 0.28 mmol), 1-ethyl-3-(3-dimethylaminopropyl)carbodiimide (54 mg, 0.28 mmol) and diisopropylethylamine (84 mg, 0.65 mmol) in dimethylformamide (1 mL) was stirred overnight at room temperature under a nitrogen atmosphere. The resulting mixture was diluted with water (10 mL) and extracted with ethyl acetate (3×5 mL). The combined organic layers were washed with brine (3×5 mL), dried over anhydrous sodium sulfate, filtered, concentrated under reduced pressure, to afford tert-butyl 4-(7-carbamoyl-1-benzofuran-4-yl) piperidine-1-carboxylate (B113; 75 mg) as a solid. LCMS (ES, m/z): 345 $[M+H]^+$.

Synthesis of Intermediate B114

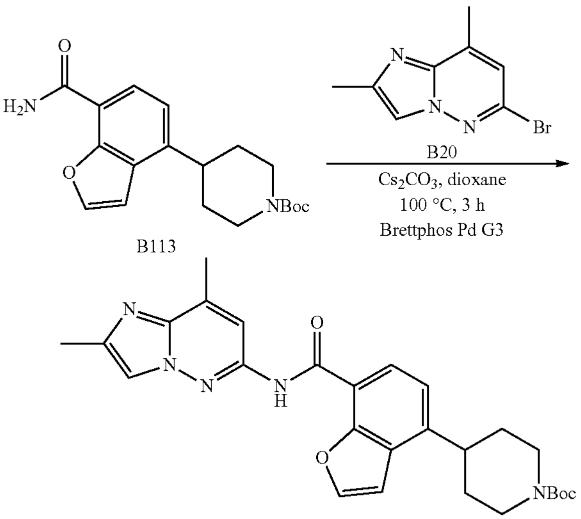

B113

B114

A mixture of tert-butyl 4-(7-carbamoyl-1-benzofuran-4-yl) piperidine-1-carboxylate (B113; 75 mg, 0.22 mmol), BrettPhos Pd G3 (0.66 mg, 0.001 mmol), cesium carbonate (14 mg, 0.044 mmol) and 6-bromo-2,8-dimethylimidazo[1,2-b]pyridazine (B20; 74 mg, 0.33 mmol) in dioxane (0.5 mL) was stirred for 3 h at 100° C. under a nitrogen atmosphere. The resulting mixture was then concentrated under reduced pressure and purified by preparative TLC eluting with dichloromethane/methanol (5:1), to afford tert-butyl 4-[7-([2,8-dimethylimidazo[1,2-b]pyridazin-6-yl]carbamoyl)-1-benzofuran-4-yl]piperidine-1-carboxylate (B114; 90 mg) as a solid. LCMS (ES, m/z): 490 $[M+H]^+$.

Synthesis of Compound 119

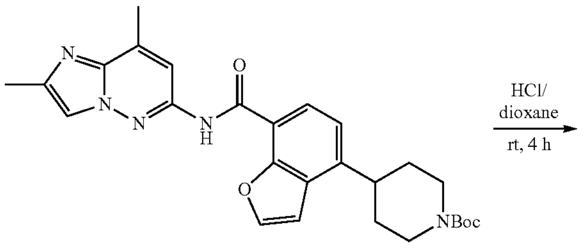

B114

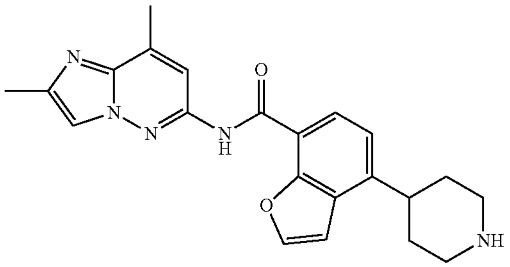

119

A solution of tert-butyl 4-[7-([2,8-dimethylimidazo[1,2-b]pyridazin-6-yl]carbamoyl)-1-benzofuran-4-yl]piperidine-1-carboxylate (B114; 90 mg, 0.18 mmol) and HCl in 1,4-dioxane (0.5 mL, 2 mmol), in dioxane (0.5 mL), was stirred for 4 h at room temperature under a nitrogen atmosphere. The resulting mixture was concentrated under reduced pressure, and purified by preparative HPLC (Condition 1, Gradient 7), to afford N-[2,8-dimethylimidazo[1,2-b]pyridazin-6-yl]-4-(piperidin-4-yl)-1-benzofuran-7-carboxamide (Compound 119; 15.4 mg) as a solid. LCMS (ES, m/z): 390 $[M+H]^+$. $^1$HNMR (400 MHz, DMSO-$d_6$, ppm) δ 8.20 (d, J=2.3 Hz, 1H), 7.93 (s, 1H), 7.86 (d, J=1.3 Hz, 1H), 7.80 (d, J=7.8 Hz, 1H), 7.32-7.25 (m, 2H), 3.11-3.03 (m, 3H), 2.92 (s, 1H), 2.75-2.65 (m, 2H), 2.59 (d, J=1.1 Hz, 3H), 2.39 (s, 3H), 1.79-1.62 (m, 4H).

Example 4: Synthesis of Compound 148

Synthesis of Intermediate B130

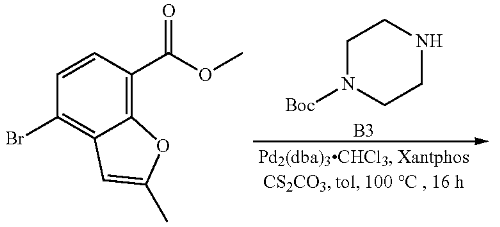

B73

-continued

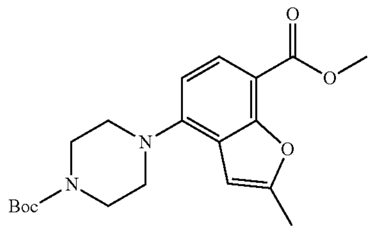

B130

A mixture of methyl 4-bromo-2-methyl-1-benzofuran-7-carboxylate (B73 from Example 18; 700 mg, 2.5 mmol), tert-butyl piperazine-1-carboxylate (B2; 570 mg, 3 mmol), $Pd_2(dba)_3 \cdot CHCl_3$ (132 mg, 0.13 mmol), XantPhos (148 mg, 0.26 mmol) and cesium carbonate (2.5 g, 7.6 mmol) in toluene (10 mL) was stirred for 16 h at 100° C. under a nitrogen atmosphere. The mixture was then cooled to 25° C. and concentrated under vacuum. The residue was purified by silica gel column chromatography eluting with petroleum ether/ethyl acetate (1:1), to afford tert-butyl 4-[7-(methoxycarbonyl)-2-methyl-1-benzofuran-4-yl]piperazine-1-carboxylate (B130; 800 mg) as a solid. LCMS (ES, m/z): 375 $[M+H]^+$.

Synthesis of Intermediate B131

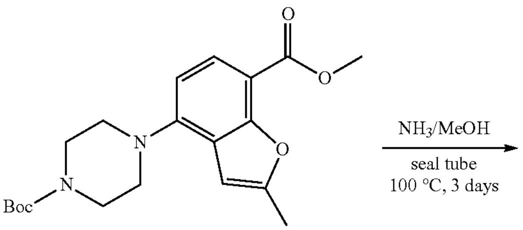

B130

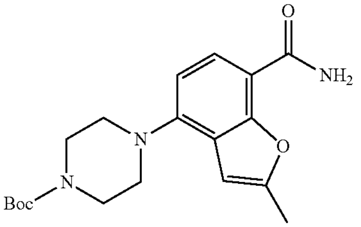

B131

A solution of tert-butyl 4-[7-(methoxycarbonyl)-2-methyl-1-benzofuran-4-yl]piperazine-1-carboxylate (B130; 800 mg, 2 mmol) and ammonia in methanol (80 mL) was stirred for 3 days at 100° C. in a sealed tube. The mixture was then cooled to 25° C. and concentrated under reduced pressure. The residue was purified by silica gel column chromatography eluting with petroleum ether/ethyl acetate (1:1), to afford tert-butyl 4-(7-carbamoyl-2-methyl-1-benzofuran-4-yl)piperazine-1-carboxylate (B131; 600 mg) as a solid. LCMS (ES, m/z): 360 $[M+H]^+$.

Synthesis of Intermediate B132

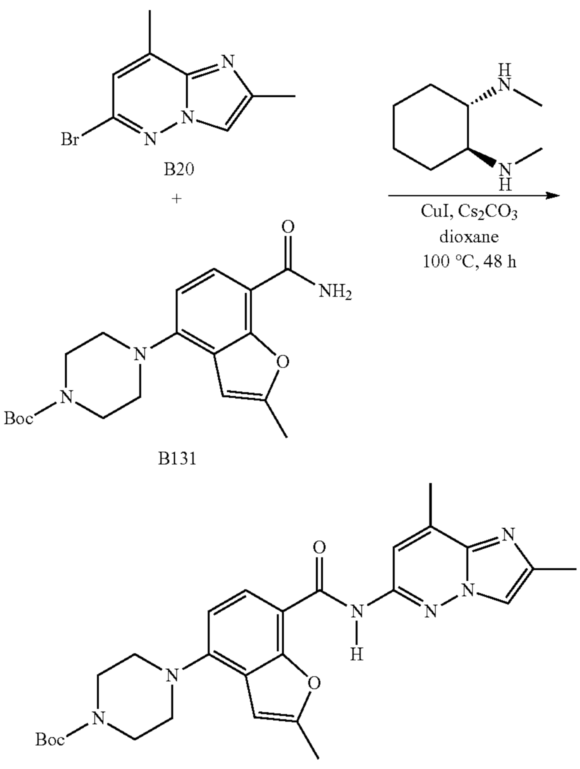

B20
+
B131
B132

A mixture of tert-butyl 4-(7-carbamoyl-2-methyl-1-benzofuran-4-yl)piperazine-1-carboxylate (B131; 150 mg, 0.4 mmol), 6-bromo-2,8-dimethylimidazo[1,2-b]pyridazine (B20; 110 mg, 0.5 mmol), copper(I) iodide (8 mg, 0.04 mmol), $N_1$,$N_2$-dimethylcyclohexane-1,2-diamine (12 mg, 0.08 mmol) and cesium carbonate (400 mg, 1.3 mmol) in 1,4-dioxane (7.5 mL) was stirred for 48 h at 100° C. under an argon atmosphere. The mixture was then cooled to 25° C. and concentrated under vacuum. The residue was purified by silica gel column chromatography, eluting with petroleum ether/ethyl acetate (1:2) to afford tert-butyl 4-[7-([2,8-dimethylimidazo[1,2-b]pyridazin-6-yl]carbamoyl)-2-methyl-1-benzofuran-4-yl]piperazine-1-carboxylate (B132; 20 mg) as a solid. LCMS (ES, m/z): 505 $[M+H]^+$.

Synthesis of Compound 148

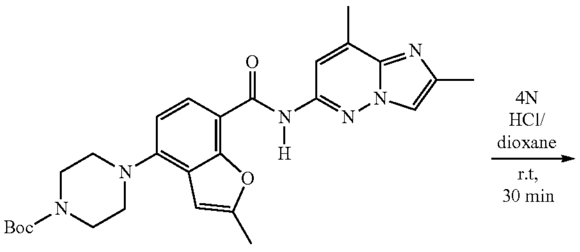

B132

-continued

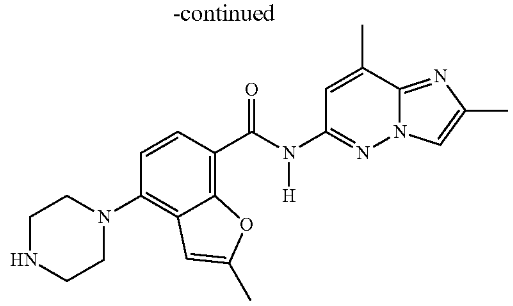

148

A solution of tert-butyl 4-[7-([2,8-dimethylimidazo[1,2-b]pyridazin-6-yl]carbamoyl)-2-methyl-1-benzofuran-4-yl] piperazine-1-carboxylate (B132; 100 mg, 0.19 mmol) and HCl in 1,4-dioxane (5 mL, 88 mmol) was stirred for 30 min at room temperature. The resulting mixture was concentrated under reduced pressure, and purified by preparative HPLC (Condition 1, Gradient 6), to afford N-[2,8-dimethylimidazo[1,2-b]pyridazin-6-yl]-2-methyl-4-(piperazin-1-yl)-1-benzofuran-7-carboxamide (Compound 148; 35.3 mg) as a solid. LCMS (ES, m/z): 405 $[M+H]^+$. $^1H$ NMR (400 MHz, DMSO-$d_6$) δ 10.25 (s, 1H), 7.91 (s, 1H), 7.84 (d, J=1.3 Hz, 1H), 7.72 (d, J=8.4 Hz, 1H), 6.75 (d, J=9.0 Hz, 2H), 3.21 (dd, J=6.1, 3.5 Hz, 4H), 2.92 (t, J=4.8 Hz, 4H), 2.57 (d, J=1.1 Hz, 3H), 2.50 (s, 3H), 2.38 (s, 3H).

Example 5: Synthesis of Compound 142

Synthesis of Intermediate B133

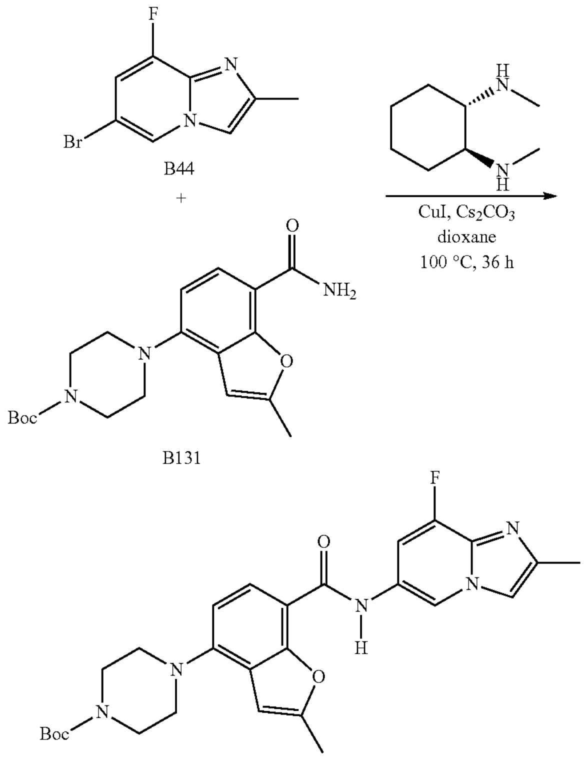

B44
+
B131
B133

A mixture of tert-butyl 4-(7-carbamoyl-2-methyl-1-benzofuran-4-yl)piperazine-1-carboxylate (B131 from Example 30; 150 mg, 0.42 mmol), 6-bromo-8-fluoro-2-methylimidazo[1,2-a]pyridine (B44; 115 mg, 0.5 mmol), copper(I) iodide (8 mg, 0.041 mmol), $N_1$,$N_2$-dimethylcyclohexane-1,2-diamine (12 mg, 0.082 mmol) and cesium carbonate (400 mg, 1.23 mmol) in 1,4-dioxane (7.5 mL) was stirred for 48 h at 100° C. under an argon atmosphere. The mixture was then cooled to 25° C. and concentrated under vacuum. The residue was purified by silica gel column chromatography eluting with petroleum ether/ethyl acetate (1:2), to afford tert-butyl 4-[7-([8-fluoro-2-methylimidazo[1,2-a]pyridin-6-yl]carbamoyl)-2-methyl-1-benzofuran-4-yl]piperazine-1-carboxylate (B133; 20 mg) as a solid. LCMS (ES, m/z): 508 $[M+H]^+$.

Synthesis of Compound 142

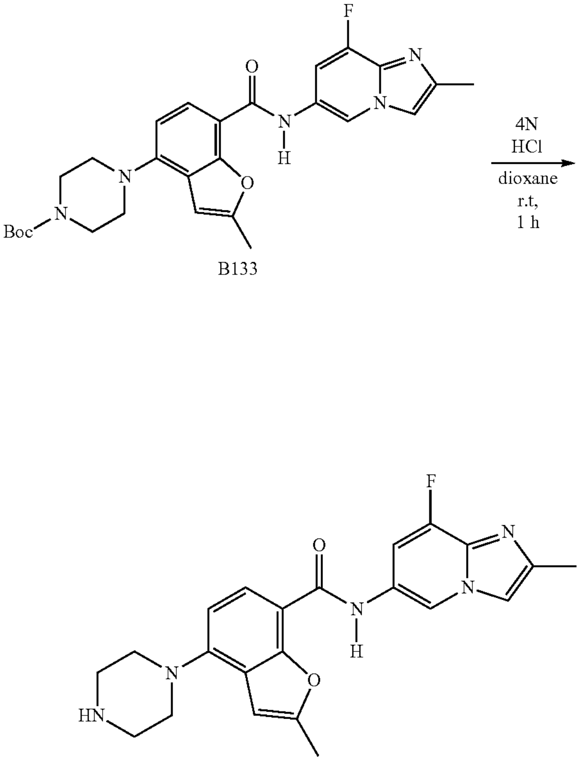

B133

142

A mixture of tert-butyl 4-[7-([8-fluoro-2-methylimidazo[1,2-a]pyridin-6-yl]carbamoyl)-2-methyl-1-benzofuran-4-yl]piperazine-1-carboxylate (B133; 20 mg, 0.04 mmol) and HCl in 1,4-dioxane (1 mL) was stirred for 1 h at 25° C., and the mixture was then concentrated under reduced pressure. The crude product was purified by preparative HPLC (Condition 5, Gradient 1), to afford N-[8-fluoro-2-methylimidazo[1,2-a]pyridin-6-yl]-2-methyl-4-(piperazin-1-yl)-1-benzofuran-7-carboxamide (Compound 142; 4.9 mg) as a solid. LCMS (ES, m/z): 408 $[M+H]^+$. $^1H$ NMR (400 MHz, DMSO-$d_6$) δ 10.04 (d, J=2.2 Hz, 1H), 9.15 (d, J=1.7 Hz, 1H), 8.22 (s, 1H), 7.91 (d, J=3.0 Hz, 1H), 7.61 (d, J=8.3 Hz, 1H), 7.32 (dd, J=12.6, 1.7 Hz, 1H), 6.81-6.74 (m, 2H), 3.27-3.21 (m, 4H), 3.02 (s, 4H), 2.51 (s, 3H), 2.35 (s, 3H).

Example 6: Synthesis of Compound 187

Synthesis of Intermediate B135

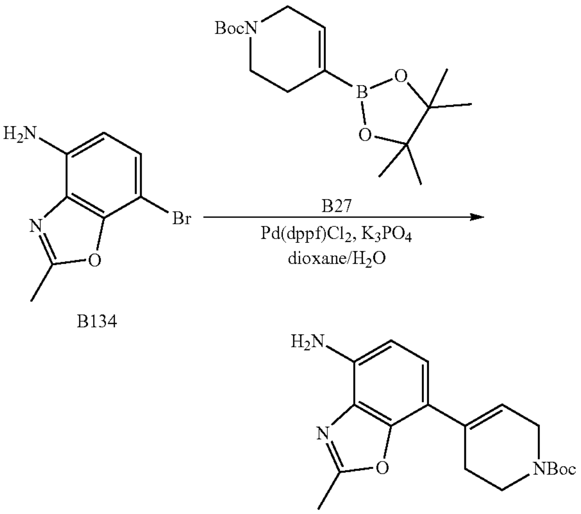

B134

B135

A solution of 7-bromo-2-methyl-1,3-benzoxazol-4-amine (B134; 1 g, 4.32 mmol), tert-butyl 4-(4,4,5,5-tetramethyl-1,3,2-dioxaborolan-2-yl)-3,6-dihydro-2H-pyridine-1-carboxylate (B27; 1.6 g, 5.2 mmol), Pd(dppf)$Cl_2$ $CH_2Cl_2$ (352 mg, 0.43 mmol) and $K_3PO_4$ (2.75 g, 13 mmol) in 1,4-dioxane (12 mL) and $H_2O$ (3 mL) was stirred for 2 h at 80° C. under a nitrogen atmosphere. The mixture was then cooled to 25° C. and concentrated under reduced pressure. The mixture was then poured onto water (100 mL) and extracted with ethyl acetate (3×100 mL), dried over anhydrous sodium sulfate, filtered, and concentrated under reduced pressure. The residue was purified by silica gel column chromatography, eluting with hexane/ethyl acetate (5:1), to afford tert-butyl 4-(4-amino-2-methyl-1,3-benzoxazol-7-yl)piperidine-1-carboxylate (B135; 1.1 g) as a solid. LCMS (ES, m/z): 330 $[M+H]^+$.

Synthesis of Intermediate B136

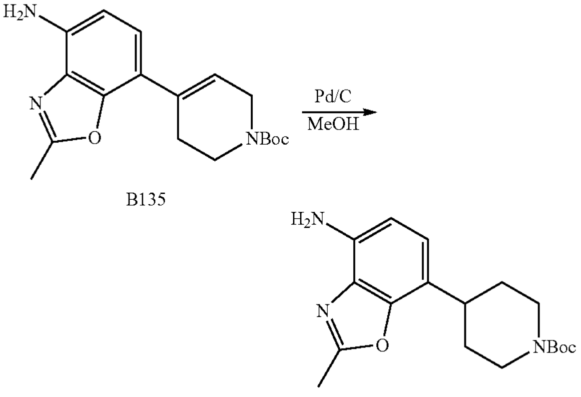

B135

B136

A mixture of tert-butyl 4-(4-amino-2-methyl-1,3-benzoxazol-7-yl)piperidine-1-carboxylate (B135; 1.1 g, 3 mmol) and palladium on carbon (108 mg, 1 mmol) in methanol (30 mL) was stirred for 4 h at 50° C. under a hydrogen atmosphere. The mixture was then cooled to 25° C. and concentrated under vacuum, to afford tert-butyl 4-(4-amino-2-methyl-1,3-benzoxazol-7-yl)piperidine-1-carboxylate (B136; 1.05 g) as a solid. LCMS (ES, m/z): 332 [M+H]$^+$.

Synthesis of Intermediate B137

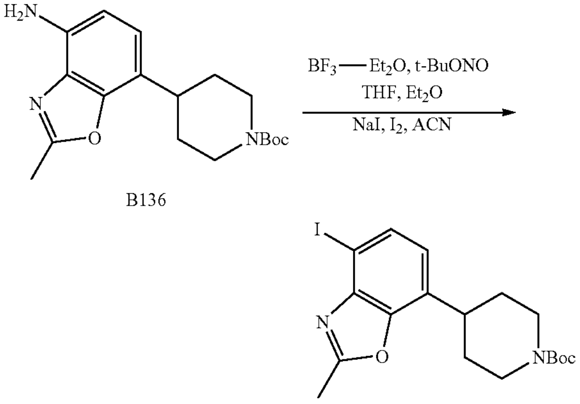

B136

B137

To a solution of tert-butyl 4-(4-amino-2-methyl-1,3-benzoxazol-7-yl)piperidine-1-carboxylate (800 mg, 2.2 mmol) in tetrahydrofuran (16 mL) was added boron trifluoride diethyl etherate (1.37 mL, 9.7 mmol) dropwise at 25° C. A solution of tert-butyl nitrite (851 mg, 8.23 mmol) in tetrahydrofuran (16 mL) was then added dropwise at −50° C., and the mixture was warmed to −5° C. Next, diethyl ether (32 mL) was added and the mixture was stirred for 15 min until a solid precipitated, which was collected and dissolved in acetonitrile (15 mL). Sodium iodide (456 mg, 3 mmol) and iodine (386 mg, 1.5 mmol) were then added, and the resulting mixture was stirred for 15 min at 25° C. The mixture was then partitioned between aqueous sodium sulfite solution and dichloromethane, and the combined organic layers were separated, dried over anhydrous sodium sulfate, filtered, and concentrated under reduced pressure, to afford tert-butyl 4-(4-iodo-2-methyl-1,3-benzoxazol-7-yl) piperidine-1-carboxylate (B137; 700 mg) as a solid. LCMS (ES, m/z): 443 [M+H]$^+$.

Synthesis of Intermediate B138

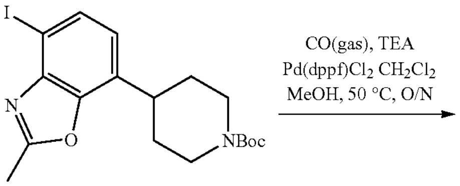

B137

-continued

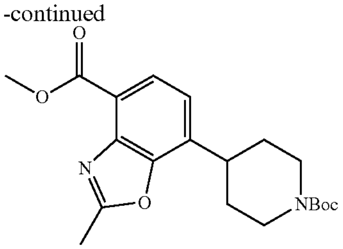

B138

A solution of tert-butyl 4-(4-iodo-2-methyl-1,3-benzoxazol-7-yl)piperidine-1-carboxylate (B137; 650 mg, 1.4 mmol), triethylamine (437 mg, 4.3 mmol) and Pd(dppf)$Cl_2$ $CH_2Cl_2$ (117 mg, 0.14 mmol) in methanol (10 mL) was stirred for 6 h at 50° C. under a carbon monoxide atmosphere. The resulting mixture was concentrated under reduced pressure, and purified by silica gel column chromatography eluting with hexane/ethyl acetate (5:1), to afford methyl 7-[1-(tert-butoxycarbonyl)piperidin-4-yl]-2-methyl-1,3-benzoxazole-4-carboxylate (B138; 350 mg) as a solid. LCMS (ES, m/z): 375 [M+H]$^+$.

Synthesis of Intermediate B139

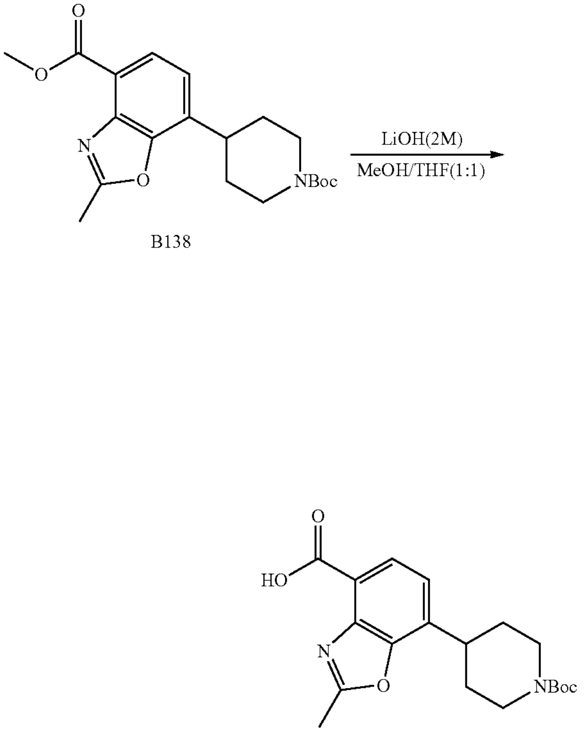

B138

B139

A solution of methyl 7-[1-(tert-butoxycarbonyl)piperidin-4-yl]-2-methyl-1,3-benzoxazole-4-carboxylate (B138; 150 mg, 0.39 mmol) and lithium hydroxide (2M, 393 µL, 0.79 mmol) in methanol (2 mL) and tetrahydrofuran (2 mL) was stirred for 2 h at 40° C. The resulting mixture was concentrated under vacuum, and the crude product (B139; 130 mg) was used in the next step directly without further purification. LCMS (ES, m/z): 361 [M+H]$^+$.

Synthesis of Intermediate B140

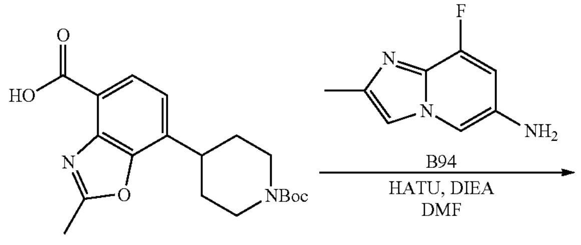

B139

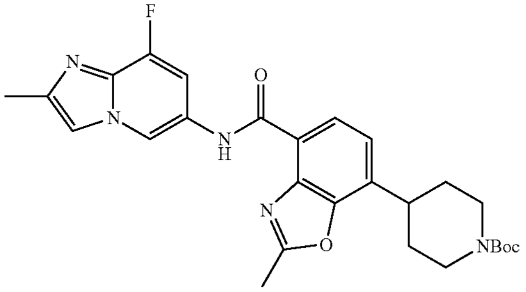

B140

A solution of 7-[1-(tert-butoxycarbonyl)piperidin-4-yl]-2-methyl-1,3-benzoxazole-4-carboxylic acid (B139; 130 mg, 0.4 mmol), 8-fluoro-2-methylimidazo[1,2-a]pyridin-6-amine (B94; 61 mg, 0.4 mmol), hexafluorophosphate azabenzotriazole tetramethyl uronium (161 mg, 0.4 mmol) and diisopropylethylamine (137 mg, 1.0 mmol) in dimethylformamide (2 mL) was stirred for 30 min at 25° C. The resulting mixture was poured into water (20 mL) and extracted with ethyl acetate (2×20 mL). The combined organic layers were washed with brine (2×20 mL), dried over anhydrous sodium sulfate, filtered, and concentrated under reduced pressure. The residue was purified by silica gel column chromatography, eluting with hexane/ethyl acetate (1:1) to afford tert-butyl 4-[4-([8-fluoro-2-methylimidazo[1,2-a]pyridin-6-yl]carbamoyl)-2-methyl-1,3-benzoxazol-7-yl]piperidine-1-carboxylate (B140; 50 mg) as a solid. LCMS (ES, m/z): 508 $[M+H]^+$.

Synthesis of Compound 187

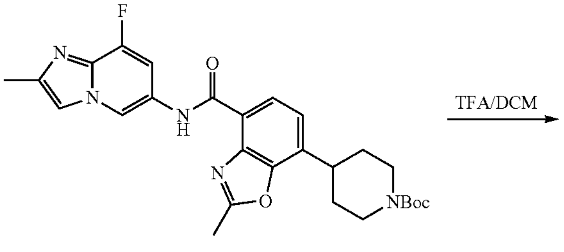

B140

-continued

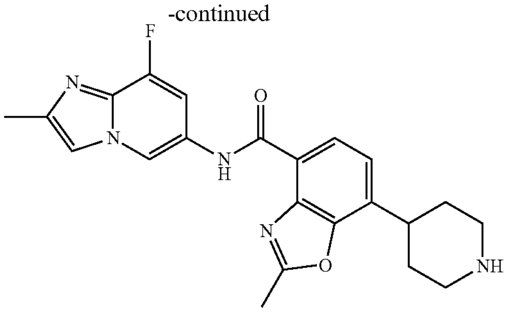

187

A solution of tert-butyl 4-[4-([8-fluoro-2-methylimidazo[1,2-a]pyridin-6-yl]carbamoyl)-2-methyl-1,3-benzoxazol-7-yl]piperidine-1-carboxylate (B140; 50 mg, 0.1 mmol) and trifluoroacetic acid (0.5 mL) in dichloromethane (0.5 mL) was stirred for 30 min at 25° C., and then concentrated under reduced pressure. The crude product was purified by preparative HPLC (Condition 1, Gradient 7), to afford N-[8-fluoro-2-methylimidazo[1,2-a]pyridin-6-yl]-2-methyl-7-(piperidin-4-yl)-1,3-benzoxazole-4-carboxamide (Compound 187; 12.5 mg) as a solid. LCMS (ES, m/z): 408 $[M+H]^+$. $^1H$ NMR (400 MHz, DMSO-$d_6$, ppm) δ 10.79 (s, 1H), 9.18 (d, J=1.7 Hz, 1H), 7.96-7.89 (m, 2H), 7.42 (d, J=8.0 Hz, 1H), 7.33 (dd, J=12.3, 1.7 Hz, 1H), 3.10 (dd, J=10.0, 6.3 Hz, 3H), 2.81 (s, 3H), 2.68 (td, J=11.8, 3.5 Hz, 2H), 2.36 (s, 3H), 1.85-1.69 (m, 4H).

Example 7: Synthesis of Compound 188

Synthesis of Intermediate B141

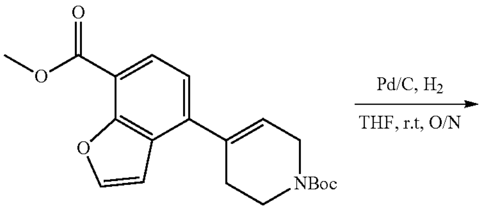

B109

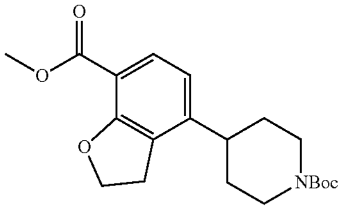

B141

A mixture of tert-butyl 4-[7-(methoxycarbonyl)-1-benzofuran-4-yl]-3,6-dihydro-2H-pyridine-1-carboxylate (B109 from Example 26; 150 mg) in tetrahydrofuran (10 mL) and palladium on carbon (15 mg) was hydrogenated at room temperature overnight using a hydrogen balloon, and was then filtered through a Celite pad and concentrated under reduced pressure, to afford tert-butyl 4-[7-(methoxycarbonyl)-2,3-dihydro-1-benzofuran-4-yl]piperidine-1-carboxylate (B141; 150 mg) as an oil. LCMS (ES, m/z): 362 $[M+H]^+$.

Synthesis of Intermediate B142

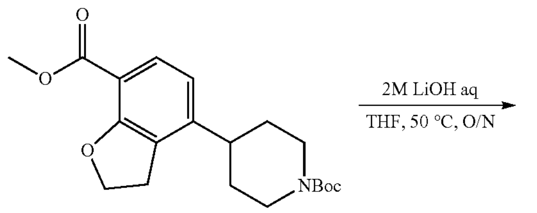

B141

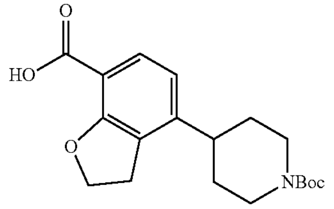

B142

A solution of tert-butyl 4-[7-(methoxycarbonyl)-2,3-dihydro-1-benzofuran-4-yl]piperidine-1-carboxylate (B141; 150 mg), and aqueous lithium hydroxide (2M, 1 mL) was stirred overnight at 50° C. under a nitrogen atmosphere. The pH of the mixture was then adjusted to 5 using aqueous HCl, and the resulting mixture was extracted with ethyl acetate (3×10 mL). The combined organic layers were washed with brine, dried over anhydrous sodium sulfate, filtered, and concentrated under reduced pressure, to afford 4-[1-(tert-butoxycarbonyl) piperidin-4-yl]-2,3-dihydro-1-benzofuran-7-carboxylic acid (B142; 130 mg) as a solid. LCMS (ES, m/z): 348[M+H]$^+$.

Synthesis of Intermediate B143

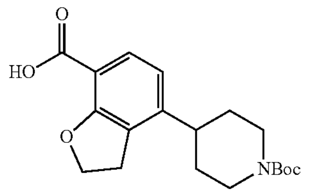

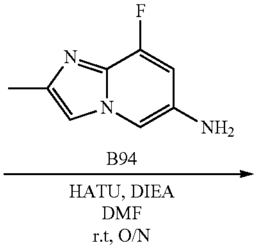

B142

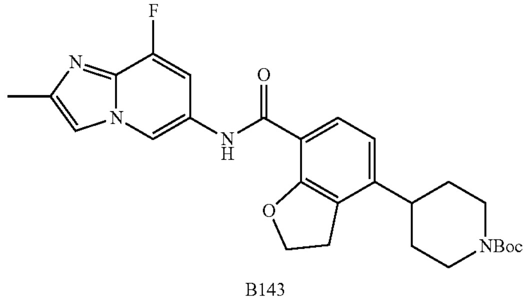

B143

A mixture of 4-[1-(tert-butoxycarbonyl) piperidin-4-yl]-2,3-dihydro-1-benzofuran-7-carboxylic acid (B94; 120 mg, 0.35 mmol), 8-fluoro-2-methylimidazo[1,2-a]pyridin-6-amine (86 mg, 0.5 mmol), hexafluorophosphate azabenzotriazole tetramethyl uronium (197 mg, 0.5 mmol) and diisopropylethylamine (134 mg, 1 mmol) in dimethylformamide (2 mL) was stirred overnight at room temperature under a nitrogen atmosphere. The resulting mixture was diluted with water (10 mL), and the precipitated solids were collected by filtration and washed with water (2×5 mL), to afford tert-butyl 4-[7-([8-fluoro-2-methylimidazo[1,2-a]pyridin-6-yl]carbamoyl)-2,3-dihydro-1-benzofuran-4-yl]piperidine-1-carboxylate (B143; 80 mg) as a solid. LCMS (ES, m/z): 495 [M+H]$^+$.

Synthesis of Compound 188

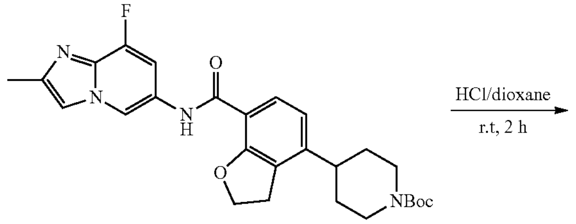

B143

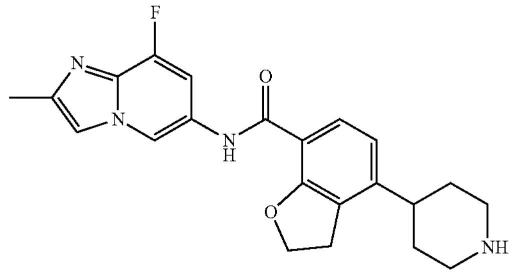

188

A mixture of tert-butyl 4-[7-([8-fluoro-2-methylimidazo[1,2-a]pyridin-6-yl]carbamoyl)-2,3-dihydro-1-benzofuran-4-yl]piperidine-1-carboxylate (B143; 80 mg), HCl in 1,4-dioxane (0.5 mL), and dioxane (0.5 mL) was stirred for 2 h at room temperature under a nitrogen atmosphere. The resulting mixture was then concentrated under reduced pressure and purified by preparative HPLC (Condition 1, Gradient 7), to afford N-[8-fluoro-2-methylimidazo[1,2-a]pyridin-6-yl]-4-(piperidin-4-yl)-2,3-dihydro-1-benzofuran-7-carboxamide (Compound 188; 29.1 mg) as a solid. LCMS (ES, m/z): 395 [M+H]$^+$. $^1$H NMR (400 MHz, DMSO-$d_6$, ppm) δ 9.74 (s, 1H), 9.10 (d, J=1.6 Hz, 1H), 7.90 (dd, J=3.1, 1.0 Hz, 1H), 7.58 (d, J=8.1 Hz, 1H), 7.29 (dd, J=12.6, 1.7 Hz, 1H), 6.90 (d, J=8.1 Hz, 1H), 4.76 (t, J=8.7 Hz, 2H), 3.27 (t, J=8.7 Hz, 3H), 3.04 (d, J=12.4 Hz, 2H), 2.83 (s, 1H), 2.61 (qd, J=11.8, 10.2, 3.0 Hz, 2H), 2.34 (s, 3H), 1.66 (d, J=12.3 Hz, 2H), 1.55 (qd, J=12.1, 3.9 Hz, 2H).

Example 8: Synthesis of Compound 141

Synthesis of Intermediate B201

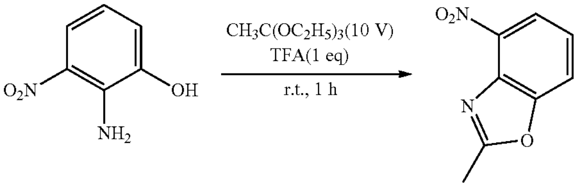

B201

To a stirred solution of 2-amino-3-nitro-phenol (20 g, 127.170 mmol) in triethyl orthoacetate (200 mL) was added TFA (9.45 mL, 82.841 mmol) dropwise at room temperature. The reaction mixture was stirred for 1 h at room temperature, then poured into water (500 mL), extracted with ethyl acetate (3×300 mL). The combined organic layers were washed with brine (2×500 mL), dried over anhydrous $Na_2SO_4$, and filtered. The filtrate was concentrated in vacuo. The residue was purified by silica gel column chromatography, eluted with PE/EA (5:1) to afford 2-methyl-4-nitro-1,3-benzoxazole (6 g, 25.95%) as a solid. LCMS (ES, m/z): 179 $[M+H]^+$.

Synthesis of Intermediate B202

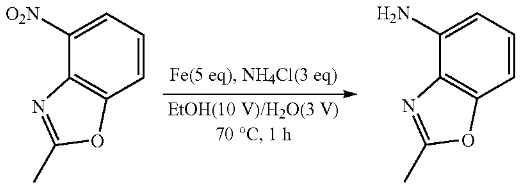

B201 B202

To a stirred solution of 2-methyl-4-nitro-1,3-benzoxazole (5 g, 27.505 mmol) and $NH_4Cl$ (4.41 g, 82.515 mmol) in a mixture of ethanol (50 mL) and $H_2O$ (15.00 mL) was added Fe (7.68 g, 137.525 mmol) portionwise at 70° C. The reaction mixture was stirred at 70° C. for 1 h, then filtered, and the filter cake washed with ethanol (3×50 mL). The filtrate was concentrated in vacuo to afford 2-methyl-1,3-benzoxazol-4-amine (4.2 g, 92.75%) as a solid. LCMS (ES, m/z): 149 $[M+H]^+$.

Synthesis of Intermediate B203

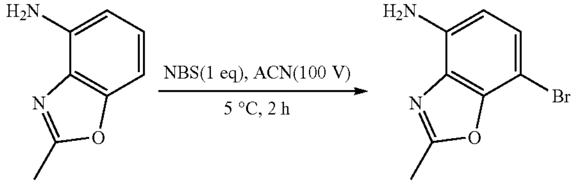

B202 B203

To a stirred solution of 2-methyl-1,3-benzoxazol-4-amine (4 g, 26.457 mmol) in acetonitrile (380 mL) was added NBS (4.71 g, 26.463 mmol) in acetonitrile (20 mL) dropwise at 5° C. The reaction mixture was stirred at 5° C. for 2 h, then poured into water (400 mL), extracted with ethyl acetate (3×400 mL). The combined organic layers were washed with a saturated solution of sodium bicarbonate (2×500 mL), dried over anhydrous $Na_2SO_4$, and filtered. The filtrate was concentrated in vacuo and the residue was purified by silica gel column chromatography, eluted with PE/EA (1:1) to afford 7-bromo-2-methyl-1,3-benzoxazol-4-amine (6 g, 97.88%) as a solid. LCMS (ES, m/z): 227/229 $[M+H]^+$.

Synthesis of Intermediate B204

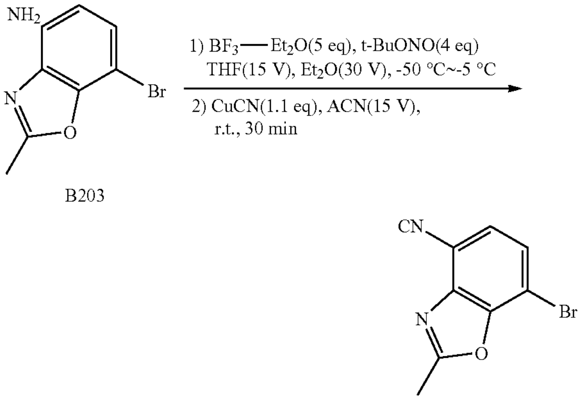

B203

B204

To a stirred solution of 7-bromo-2-methyl-1,3-benzoxazol-4-amine (950 mg, 4.1 mmol) in THF (12.25 mL) was added $BF_3 \cdot Et_2O$ (2.91 g, 20.503 mmol) dropwise at 25° C., followed by t-$BuNO_2$ (1.69 g, 16.389 mmol) in THF (2 mL) dropwise at −50° C. The reaction was then allowed to warm to −5° C. Diethyl ether (28.5 mL) was added and the reaction mixture was stirred at −5° C. for 15 min until a solid precipitated. The solid was collected and dissolved in acetonitrile (14.25 mL). CuCN (403.95 mg, 4.510 mmol) was added into the solution, and the resulting mixture was stirred for 15 min at 25° C. The mixture was partitioned between aqueous sodium sulfite solution and DCM. The combined organic layers were separated, dried over anhydrous $Na_2SO_4$, and filtered. The filtrate was concentrated in vacuo to afford 7-bromo-2-methyl-1,3-benzoxazole-4-carbonitrile (350 mg, 35.29%) as a solid. LCMS (ES, m/z): 237/239 $[M+H]^+$.

Synthesis of Intermediate B205

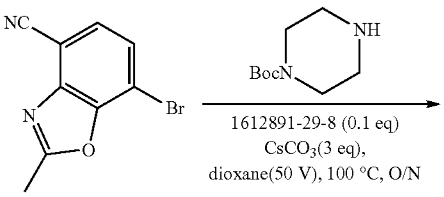

B204

-continued

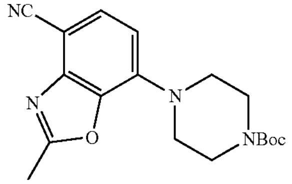

B205

A solution of 7-bromo-2-methyl-1,3-benzoxazole-4-carbonitrile (300 mg, 1.240 mmol), tert-butyl piperazine-1-carboxylate (277 mg, 1.488 mmol), $Cs_2CO_3$ (1.21 g, 3.714 mmol) and Pd-PEPPSI-IPentCl 2-methylpyridine (o-picoline (104 mg, 0.124 mmol) in 1,4-dioxane (15 mL) was stirred at 100° C. overnight under a nitrogen atmosphere. The mixture was allowed to cool to room temperature. The reaction mixture was concentrated in vacuo and the residue was purified by silica gel column chromatography, eluted with PE/EA (1:1) to afford tert-butyl 4-(4-cyano-2-methyl-1,3-benzoxazol-7-yl)piperazine-1-carboxylate (310 mg, 71.54%) as a solid. LCMS (ES, m/z): 343 $[M+H]^+$.

Synthesis of Intermediate B206

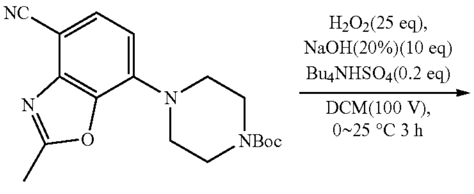

B205

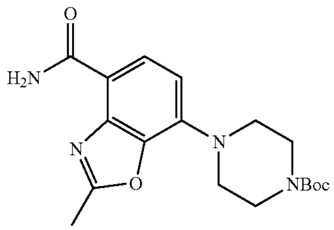

B206

To a stirred solution of tert-butyl 4-(4-cyano-2-methyl-1,3-benzoxazol-7-yl)piperazine-1-carboxylate (130 mg, 0.372 mmol) and $Bu_4NHSO_4$ (25 mg, 0.074 mmol) in DCM (13 mL) was added $H_2O_2$ (30%) (316.41 mg, 9.302 mmol) and sodium hydroxide (20%, aq) (0.60 mL, 3.721 mmol) dropwise at 0° C. The reaction mixture was stirred at 25° C. for 3 h, then extracted with DCM (2×30 mL). The combined organic layers were washed with brine (2×50 mL), dried over anhydrous $Na_2SO_4$, and filtered. The filtrate was concentrated in vacuo and the residue was purified by silica gel column chromatography, eluted with PE/EA (1:1) to afford tert-butyl 4-(4-carbamoyl-2-methyl-1,3-benzoxazol-7-yl) piperazine-1-carboxylate (45 mg, 32.89%) as a solid. LCMS (ES, m/z): 361 $[M+H]^+$.

Synthesis of Intermediate B207

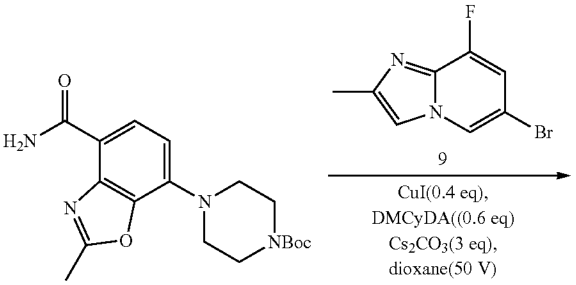

B206

9

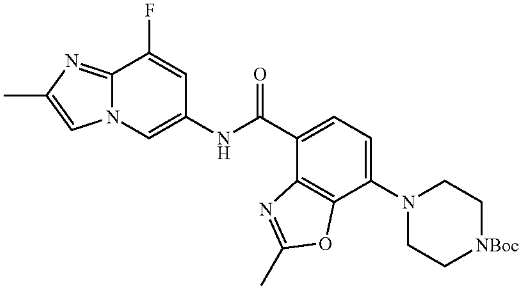

B207

A solution of tert-butyl 4-(4-carbamoyl-2-methyl-1,3-benzoxazol-7-yl)piperazine-1-carboxylate (35 mg, 0.095 mmol), 6-bromo-8-fluoro-2-methylimidazo[1,2-a]pyridine (26 mg, 0.114 mmol), CuI (7 mg, 0.038 mmol), (1R,2R)-1-N,2-N-dimethylcyclohexane-1,2-diamine (8 mg, 0.057 mmol) and $Cs_2CO_3$ (93 mg, 0.285 mmol) in 1,4-dioxane (1.75 mL) was stirred for overnight at 120° C. under a nitrogen atmosphere. The reaction mixture was filtered, the filter cake washed with 1,4-dioxane (2×10 mL), and the filtrate was concentrated in vacuo. The residue was purified by silica gel column chromatography, eluted with DCM/MeOH (10:1) to afford tert-butyl 4-[4-([8-fluoro-2-methylimidazo[1,2-a]pyridin-6-yl]carbamoyl)-2-methyl-1,3-benzoxazol-7-yl]piperazine-1-carboxylate (6 mg, 12.15%) as a brown solid. LCMS (ES, m/z): 509 $[M+H]^+$.

Synthesis of Compound 141

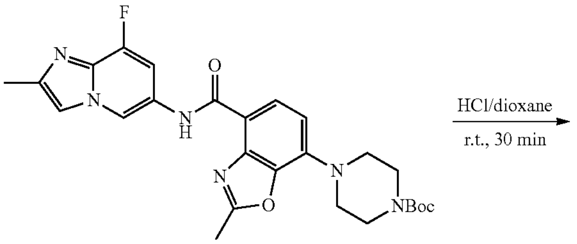

B207

-continued

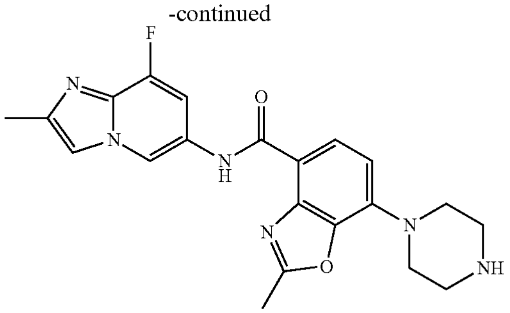

141

A solution of tert-butyl 4-[4-([8-fluoro-2-methylimidazo[1,2-a]pyridin-6-yl]carbamoyl)-2-methyl-1,3-benzoxazol-7-yl]piperazine-1-carboxylate (6 mg, 0.012 mmol) and HCl (gas) in 1,4-dioxane (1 mL) was stirred at 25° C. for 30 min. The reaction mixture was concentrated in vacuo and the crude product was purified by Prep-HPLC (Condition 8, Gradient 1) to afford N-[8-fluoro-2-methylimidazo[1,2-a]pyridin-6-yl]-2-methyl-7-(piperazin-1-yl)-1,3-benzoxazole-4-carboxamide hydrochloride (3.5 mg, 72.63%) as a solid. LCMS (ES, m/z): 409 [M+H]$^+$. $^1$H NMR (400 MHz, DMSO-$d_6$) δ 11.06 (s, 1H), 9.63 (s, 2H), 9.56 (d, J=1.5 Hz, 1H), 8.31 (d, J=2.3 Hz, 1H), 8.12 (dd, J=11.7, 1.6 Hz, 1H), 7.91 (d, J=8.6 Hz, 1H), 7.07 (d, J=8.7 Hz, 1H), 3.79 (t, J=5.2 Hz, 4H), 3.28 (dd, J=16.4, 11.9 Hz, 4H), 2.81 (s, 3H), 2.54 (s, 3H).

Example 9: Synthesis of Compound 208

Synthesis of Intermediate B217

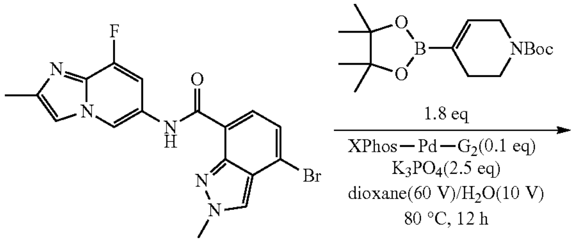

B216

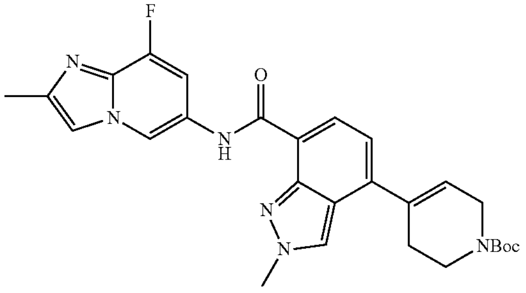

B217

A solution of 4-bromo-N-[8-fluoro-2-methylimidazo[1,2-a]pyridin-6-yl]-2-methylindazole-7-carboxamide (500 mg, 1.24 mmol), tert-butyl 4-(4,4,5,5-tetramethyl-1,3,2-dioxaborolan-2-yl)-3,6-dihydro-2H-pyridine-1-carboxylate (691.8 mg, 2.23 mmol), $K_3PO_4$ (659.6 mg, 3.10 mmol) and XPhos palladium(II) biphenyl-2-amine chloride (97.8 mg, 0.12 mmol) in a mixture of dioxane (30 mL) and $H_2O$ (5 mL) was stirred for 12 h at 80° C. under a nitrogen atmosphere. The reaction mixture was diluted with $H_2O$ (100 mL), extracted with DCM (3×100 mL). The combined organic layers were washed with saturated NaCl (1×100 mL), dried over anhydrous $Na_2SO_4$, and filtered. The filtrate was concentrated in vacuo and the residue was purified by silica gel column chromatography, eluted with DCM/MeOH (97/3) to afford tert-butyl 4-[7-([8-fluoro-2-methylimidazo[1,2-a]pyridin-6-yl]carbamoyl)-2-methylindazol-4-yl]-3,6-dihydro-2H-pyridine-1-carboxylate (590 mg, 94%) as a solid. LCMS (ES, m/z): 505 [M+H]$^+$.

Synthesis of Intermediate B218

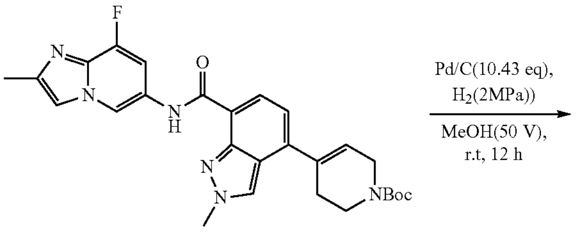

B217

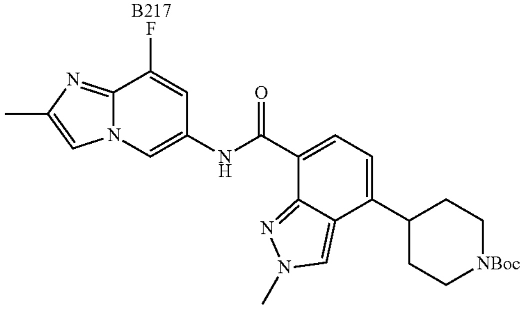

B218

To a solution of tert-butyl 4-[7-([8-fluoro-2-methylimidazo[1,2-a]pyridin-6-yl]carbamoyl)-2-methylindazol-4-yl]-3,6-dihydro-2H-pyridine-1-carboxylate (530.0 mg, 1.05 mmol) in MeOH (30 mL) was added Pd/C (1165.9 mg, 10.95 mmol) in a pressure tank. The mixture was hydrogenated at room temperature under 20 psi of hydrogen pressure for 12 h, filtered through a Celite pad and concentrated in vacuo to afford tert-butyl 4-[7-([8-fluoro-2-methylimidazo[1,2-a]pyridin-6-yl]carbamoyl)-2-methylindazol-4-yl]piperidine-1-carboxylate (306 mg, 57.5%) as a solid. LCMS (ES, m/z): 507 [M+H]$^+$.

Synthesis of Compound 208

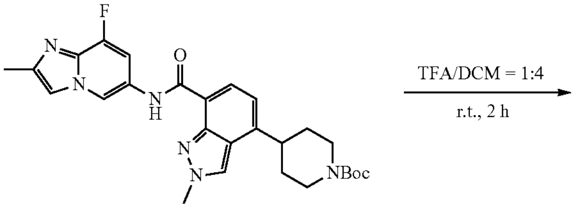

B218

-continued

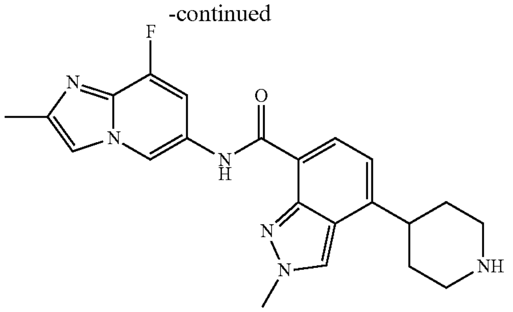

208

A solution of tert-butyl 4-[7-([8-fluoro-2-methylimidazo[1,2-a]pyridin-6-yl]carbamoyl)-2-methylindazol-4-yl]piperidine-1-carboxylate (40 mg, 0.08 mmol) in a mixture of DCM (1.6 mL) and TFA (0.4 mL) was stirred for 1 h at room temperature. The reaction mixture was concentrated in vacuo and the crude product (70 mg) was purified by Prep-HPLC (Condition 9, Gradient 3) to afford N-[8-fluoro-2-methylimidazo[1,2-a]pyridin-6-yl]-2-methyl-4-(piperidin-4-yl)indazole-7-carboxamide (5.1 mg, 15.7%) as a solid. LCMS (ES, m/z): 407 $[M+H]^+$. $^1H$ NMR (400 MHz, DMSO-$d_6$) δ 11.14 (s, 1H), 9.24 (d, J=1.6 Hz, 1H), 8.88 (s, 1H), 8.04 (d, J=7.4 Hz, 1H), 7.93 (d, J=3.0 Hz, 1H), 7.38 (dd, J=12.3, 1.7 Hz, 1H), 7.10 (d, J=7.4 Hz, 1H), 4.35 (s, 3H), 3.08 (dd, J=9.4, 6.3 Hz, 3H), 2.75-2.65 (m, 2H), 2.36 (s, 3H), 1.86-1.78 (m, 2H), 1.72 (tt, J=12.7, 6.4 Hz, 2H). $^{19}F$ NMR (376 MHz, DMSO) δ −131.87.

Example 10: Synthesis of Compound

Synthesis of Intermediate B219

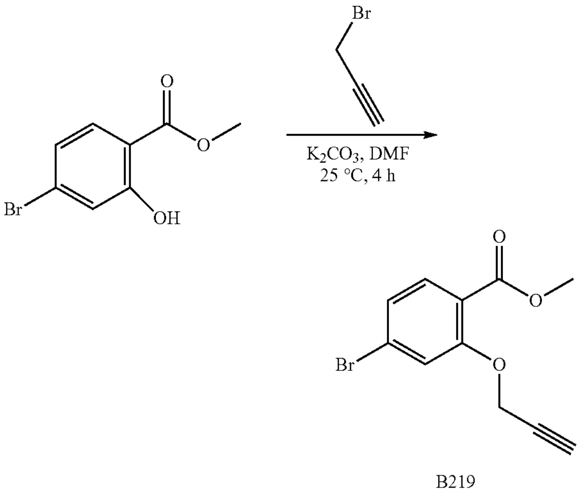

B219

A mixture of methyl 1-(2-hydroxy-4-methylphenyl)acetate (30 g, 165.553 mmol), propargyl bromide (27.57 g, 0.232 mmol), and $K_2CO_3$ (68.64 g, 0.497 mmol) in DMF (300 mL) was stirred for 4 h at 25° C. The reaction mixture was diluted with water, extracted with ethyl acetate (1:1, 3×1 L), and the combined aqueous layers were concentrated in vacuo to afford methyl 1-[4-methyl-2-(prop-2-yn-1-yloxy)phenyl]acetate (23 g, 63.36%) as a solid. LCMS (ES, m/z): 268 $[M+H]^+$.

Synthesis of Intermediate B220

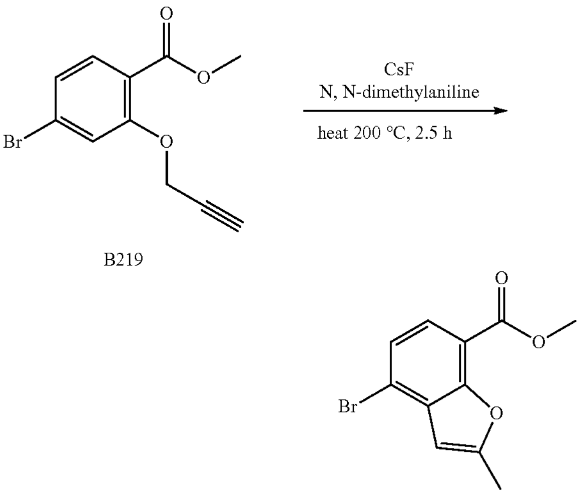

B219

B220

A mixture of methyl 1-[4-bromo-2-(prop-2-yn-1-yloxy)phenyl]acetate (1.00 g, 3.52 mmol) and CsF (0.53 mg, 0.004 mmol) in N,N-dimethylaniline (9 mL) was stirred for 2.5 h at 200° C. The reaction mixture was diluted with water, extracted with ethyl acetate (1:1, 3×1 L), and concentrated in vacuo to afford methyl 1-(4-bromo-2-methyl-1-benzofuran-7-yl)acetate (700 mg, 70%) as a solid. LCMS (ES, m/z): 268 $[M+H]^+$.

Synthesis of Intermediate B221

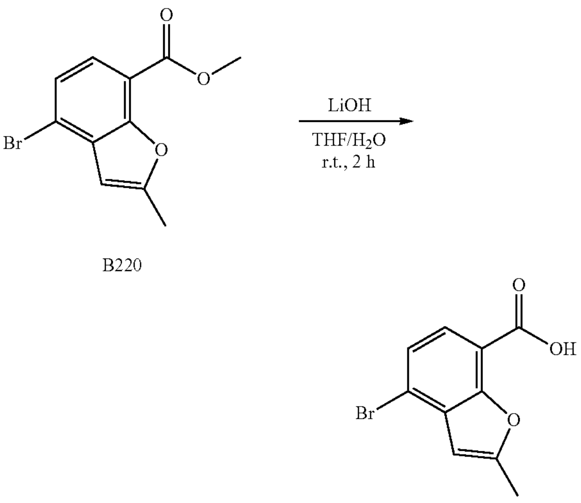

B220

B221

To a stirred solution of methyl 4-bromo-2-methyl-1-benzofuran-7-carboxylate (11.52 g, 42.81 mmol) in THF (440 mL) was added LiOH (2.05 mg, 0.086 mmol) and $H_2O$ (60 mL) in portionwise. The reaction mixture was stirred for 2 h at 25° C., then acidified to pH 5 with HCl (1M), and extracted with ethyl acetate (3×300 mL). The combined organic layers were concentrated in vacuo and the residue was purified by reverse flash chromatography (Condition 2, Gradient 1) to afford 4-bromo-2-methyl-1-benzofuran-7-carboxylic acid (4.5 g, 41%) as a solid. LCMS (ES, m/z): 254 [M+H]$^+$.

Synthesis of Intermediate B222

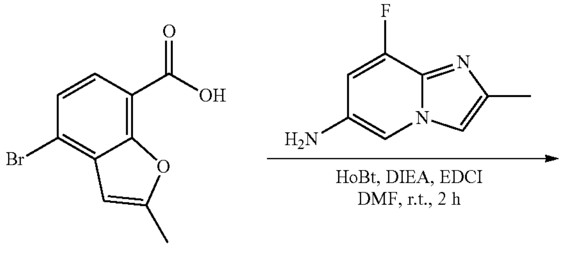

B221

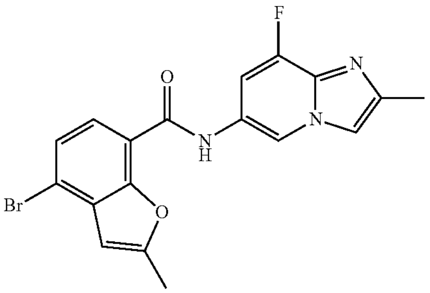

B222

To a stirred solution of 4-bromo-2-methyl-1-benzofuran-7-carboxylic acid (3.5 g, 13.722 mmol) and 8-fluoro-2-methylimidazo[1,2-a]pyridin-6-amine (2.72 g, 0.017 mmol) in DMF (15 mL) were added HoBt (2.22 g, 16.466 mmol), EDCI (3.945 g, 20.583 mmol) and DIEA (7.09 g, 54.888 mmol) portionwise. The reaction mixture was stirred for 2 h at 25° C., then diluted with water, and extracted with ethyl acetate (1:1, 3×20 mL). The combined organic layers were concentrated in vacuo and the crude product (7 g) was purified by Prep-TLC (DCM:MeOH=9:1) to afford 4-bromo-N-[8-fluoro-2-methylimidazo[1,2-a]pyridin-6-yl]-2-methyl-1-benzofuran-7-carboxamide (3.5 g) as a solid. LCMS (ES, m/z): 401 [M+H]$^+$.

Synthesis of Compound 189

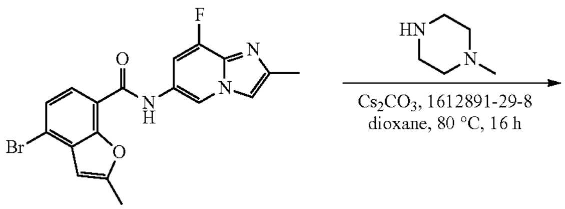

B222

-continued

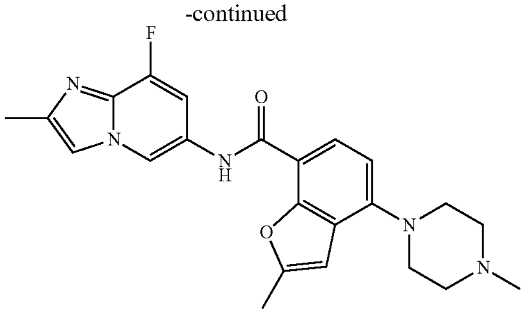

189

A mixture of 4-bromo-N-[8-fluoro-2-methylimidazo[1,2-a]pyridin-6-yl]-2-methyl-1-benzofuran-7-carboxamide (100 mg, 0.249 mmol), 1-methyl-piperazine (29.88 mg, 0.299 mmol), Pd-PEPPSI-IPentCl 2-methylpyridine (o-picoline (20.91 mg, 0.025 mmol), and $Cs_2CO_3$ (243 mg, 0.747 mmol) in dioxane (10.00 mL) was stirred for 16 h at 80° C. under a $N_2$ atmosphere. The mixture was allowed to cool to 25° C., then purified by reverse flash chromatography (Condition 1, Gradient 1) to afford N-[8-fluoro-2-methylimidazo [1,2-a] pyridin-6-yl]-2-methyl-4-(4-methylpiperazin-1-yl)-1-benzofuran-7-carboxamide (37.1 mg, 35.41%) as a solid. LCMS (ES, m/z): 421 [M+H]$^+$. $^1$H NMR (400 MHz, DMSO-$d_6$) δ 10.02 (s, 1H), 9.15 (d, J=1.6 Hz, 1H), 7.91 (dd, J=3.2, 1.0 Hz, 1H), 7.60 (d, J=8.3 Hz, 1H), 7.32 (dd, J=12.7, 1.7 Hz, 1H), 6.80-6.72 (m, 2H), 3.26 (t, J=4.9 Hz, 4H), 2.54 (d, J=4.9 Hz, 4H), 2.52 (s, 3H), 2.37-2.33 (m, 3H), 2.27 (s, 3H). $^{19}$F NMR (376 MHz, DMSO-$d_6$) δ −−132.18.

Example 11: Synthesis of Compound 204

Synthesis of Compound 204

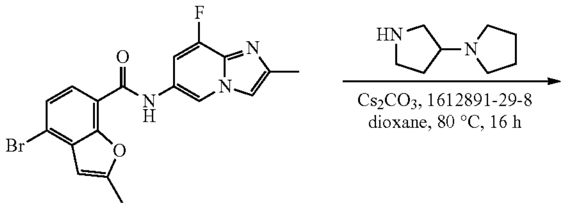

B222

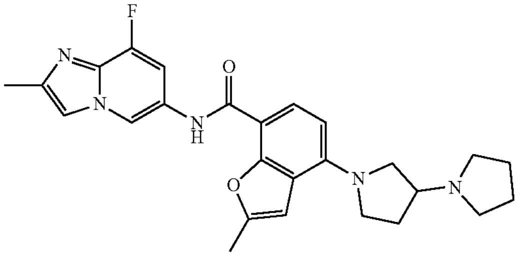

204

A mixture of 4-bromo-N-[8-fluoro-2-methylimidazo[1,2-a]pyridin-6-yl]-2-methyl-1-benzofuran-7-carboxamide (100 mg, 0.249 mmol), 1,3'-bipyrrolidine (41.84 mg, 0.299 mmol), Pd-PEPPSI-IPentCl 2-methylpyridine (o-picoline) (20.91 mg, 0.025 mmol), and $Cs_2CO_3$ (243.01 mg, 0.747 mmol) in dioxane (10 mL) was stirred for 16 h at 80° C.

under a $N_2$ atmosphere. The reaction mixture was allowed to cool to 25° C., then concentrated in vacuo, and purified by reverse flash chromatography (Condition 1, Gradient 1) to afford 4-[[1,3'-bipyrrolidin]-1'-yl]-N-[8-fluoro-2-methylimidazo[1,2-a]pyridin-6-yl]-2-methyl-1-benzofuran-7-carboxamide (25.6 mg, 22.31%) as a solid. LCMS (ES, m/z): 461 $[M+H]^+$. $^1$H NMR (400 MHz, DMSO-$d_6$) δ 9.70 (s, 1H), 9.13 (d, J=1.6 Hz, 1H), 7.89 (dd, J=3.2, 1.0 Hz, 1H), 7.61 (d, J=8.6 Hz, 1H), 7.36 (dd, J=12.8, 1.7 Hz, 1H), 6.94 (d, J=1.2 Hz, 1H), 6.35 (d, J=8.6 Hz, 1H), 3.75-3.70 (dd, J=9.5, 6.6 Hz, 2H), 3.61 (q, J=9.0, 8.6 Hz, 1H), 3.51-3.42 (m, 1H), 2.88 (p, J=6.9 Hz, 1H), 2.56 (d, J=6.4 Hz, 4H), 2.49 (d, J=0.9 Hz, 3H), 2.35 (d, J=0.9 Hz, 3H), 2.15 (m, 1H), 2.01-1.87 (m, 1H), 1.73 (s, 4H). $^{19}$F NMR (376 MHz, DMSO-$d_6$) δ −132.43.

Example 12: Synthesis of Compound 203

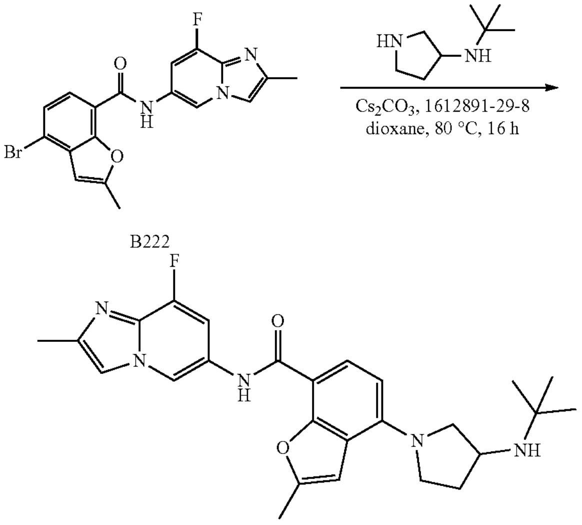

B222

203

To a stirred solution of 4-bromo-N-[8-fluoro-2-methylimidazo[1,2-a]pyridin-6-yl]-2-methyl-1-benzofuran-7-carb oxamide (100 mg, 0.249 mmol) and N-tert-butylpyrrolidin-3-amine (53.05 mg, 0.374 mmol) in dioxane (10 mL) was added $Cs_2CO_3$ (243.01 mg, 0.747 mmol) and Pd-PEPPSI-IPentCl 2-methylpyridine (o-picoline) (41.83 mg, 0.050 mmol) portionwise. The reaction mixture was stirred for 16 h at 80° C. under a $N_2$ atmosphere, then allowed to cool to 25° C., diluted with water, and extracted with ethyl acetate (3×20 mL). The combined organic layers were concentrated under reduced pressure, and the residue was purified by reverse flash chromatography (Condition 1, Gradient 1) to afford 4-[3-(tert-butylamino)pyrrolidin-1-yl]-N-[8-fluoro-2-methylimidazo[1,2-a]pyridin-6-yl]-2-methyl-1-benzofuran-7-carboxamide (56.3 mg, 48.85%) as a solid. LCMS (ES, m/z): 463 $[M+H]^+$. $^1$H NMR (400 MHz, DMSO-$d_6$) δ 9.68 (s, 1H), 9.13 (d, J=1.7 Hz, 1H), 7.89 (dd, J=3.2, 1.0 Hz, 1H), 7.61 (d, J=8.6 Hz, 1H), 7.36 (dd, J=12.8, 1.6 Hz, 1H), 6.87 (d, J=1.2 Hz, 1H), 6.31 (d, J=8.7 Hz, 1H), 3.78 (dd, J=9.4, 6.8 Hz, 1H), 3.64 (s, 1H), 3.56 (q, J=8.6 Hz, 2H), 3.20 (m, 1H), 2.49 (d, J=1.0 Hz, 3H), 2.35 (d, J=0.9 Hz, 3H), 2.17 (d, J=9.6 Hz, 1H), 1.76 (s, 1H), 1.10 (s, 9H). $^{19}$F NMR (376 MHz, DMSO-$d_6$) δ −132.44.

Example 13: Synthesis of Compound 199

Synthesis of Compound 199

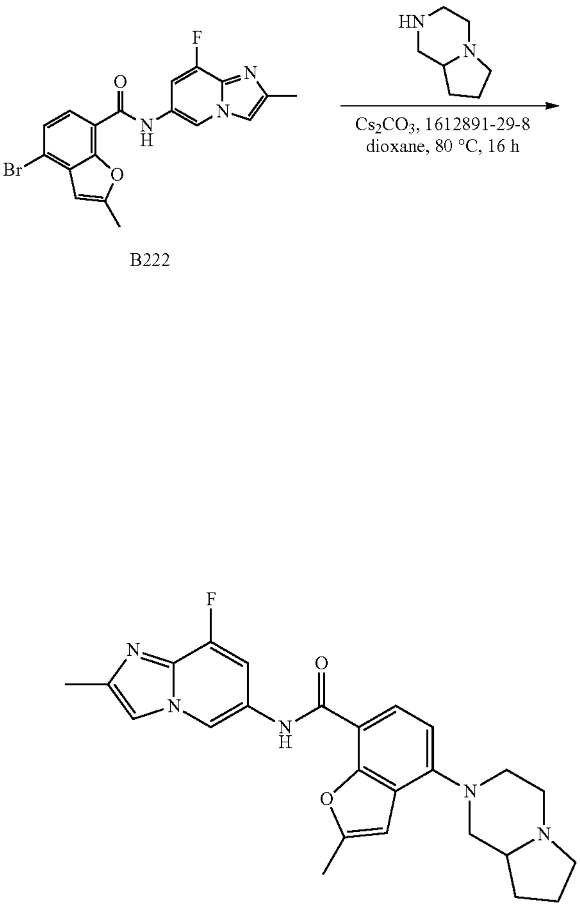

B222

199

A mixture of 4-bromo-N-[8-fluoro-2-methylimidazo[1,2-a]pyridin-6-yl]-2-methyl-1-benzofuran-7-carboxamide (100 mg, 0.249 mmol), octahydropyrrolo[1,2-a]pyrazine (47.06 mg, 0.374 mmol), Pd-PEPPSI-IPentCl 2-methylpyridine (o-picoline) (20.9 mg, 0.025 mmol), and $Cs_2CO_3$ (243 mg, 0.747 mmol) in dioxane (10 mL) was stirred for 16 h at 100° C. under a $N_2$ atmosphere. The reaction mixture was allowed to cool to 25° C., concentrated in vacuo, and the residue purified by reverse flash chromatography (Condition 1, Gradient 1) to afford N-[8-fluoro-2-methylimidazo[1,2-a]pyridin-6-yl]-4-[hexahydro-1H-pyrrolo[1,2-a]pyrazin-2-yl]-2-methyl-1-benzofuran-7-carboxamide (63.4 mg, 56.98%) as a solid. LCMS (ES, m/z): 447 $[M+H]^+$. $^1$H NMR (400 MHz, DMSO-$d_6$) δ 10.01 (s, 1H), 9.15 (d, J=1.6 Hz, 1H), 7.91 (dd, J=3.2, 1.0 Hz, 1H), 7.60 (d, J=8.3 Hz, 1H), 7.32 (dd, J=12.6, 1.6 Hz, 1H), 6.81-6.73 (m, 2H), 3.79 (d, J=11.3 Hz, 1H), 3.67 (d, J=11.8 Hz, 1H), 3.12-3.00 (m, 2H), 2.95 (td, J=11.7, 3.0 Hz, 1H), 2.64 (dd, J=11.5, 10.0 Hz, 1H), 2.51 (d, J=7.5 Hz, 3H), 2.37-2.31 (m, 4H), 2.18 (d, J=8.5 Hz, 1H), 2.11 (dd, J=17.0, 8.4 Hz, 1H), 1.92-1.80 (m, 1H), 1.72 (s, 2H), 1.39 (td, J=11.0, 6.7 Hz, 1H). $^{19}$F NMR (376 MHz, DMSO-$d_6$) δ −132.19.

Example 14: Synthesis of Compound 198

Synthesis of Compound 198

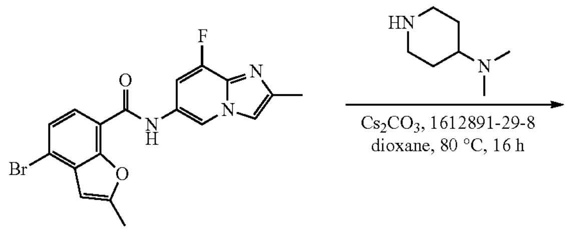

B222

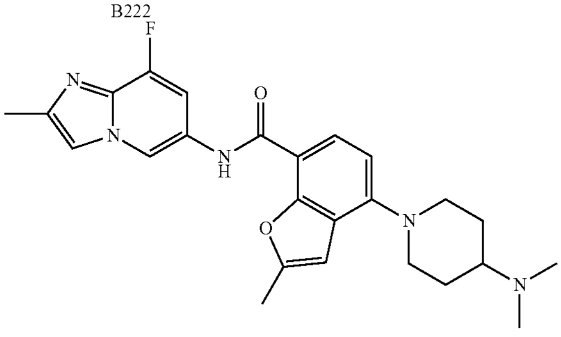

198

A mixture of 4-bromo-N-[8-fluoro-2-methylimidazo[1,2-a]pyridin-6-yl]-2-methyl-1-benzofuran-7-carboxamide (100 mg, 0.249 mmol), N,N-dimethylpiperidin-4-amine (38.25 mg, 0.299 mmol), Pd-PEPPSI-IPentCl 2-methylpyridine (o-picoline) (20.91 mg, 0.025 mmol), and $Cs_2CO_3$ (243 mg, 0.747 mmol) in dioxane (10 mL) was stirred for 16 h at 80° C. under a $N_2$ atmosphere. The reaction mixture was allowed to cool to 25° C., then concentrated in vacuo, and the residue purified by reverse flash chromatography (Condition 1, Gradient 1) to afford 4-[4-(dimethylamino)piperidin-1-yl]-N-[8-fluoro-2-methylimidazo[1,2-a]pyridin-6-yl]-2-methyl-1-benzofuran-7-carboxamide (32.1 mg, 28.72%) as a solid. LCMS (ES, m/z): 449 $[M+H]^+$. $^1$H NMR (400 MHz, DMSO-$d_6$) δ 10.00 (s, 1H), 9.15 (d, J=1.6 Hz, 1H), 7.91 (dd, J=3.1, 1.0 Hz, 1H), 7.59 (d, J=8.3 Hz, 1H), 7.32 (dd, J=12.7, 1.7 Hz, 1H), 6.79-6.70 (m, 2H), 3.74 (d, J=12.3 Hz, 2H), 2.83 (td, J=12.3, 2.3 Hz, 2H), 2.52 (m, 3H), 2.35 (d, J=0.8 Hz, 3H), 2.29 (s, 1H), 2.23 (s, 6H), 1.94-1.85 (m, 2H), 1.60 (qd, J=12.0, 3.8 Hz, 2H). $^{19}$F NMR (376 MHz, DMSO-$d_6$) δ −132.19.

Example 15: Synthesis of Compound 197

Synthesis of Compound 197

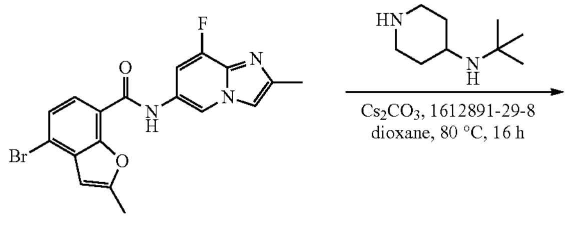

B222

-continued

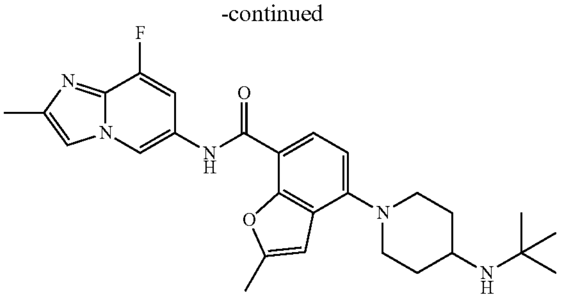

197

A mixture of 4-bromo-N-[8-fluoro-2-methylimidazo[1,2-a]pyridin-6-yl]-2-methyl-1-benzofuran-7-carboxamide (100 mg, 0.249 mmol), N-tert-butylpiperidin-4-amine (52.45 mg, 0.336 mmol), Pd-PEPPSI-IPentCl 2-methylpyridine (o-picoline) (20.91 mg, 0.025 mmol), and $Cs_2CO_3$ (243.01 mg, 0.747 mmol) in dioxane (10 mL) was stirred for 16 h at 80° C. under a $N_2$ atmosphere. The reaction mixture was allowed to cool to 25° C., then concentrated in vacuo. The residue was purified by reverse flash chromatography (Condition 1, Gradient 1) to afford 4-[4-(tert-butylamino)piperidin-1-yl]-N-[8-fluoro-2-methylimidazo [1,2-a]pyridin-6-yl]-2-methyl-1-benzofuran-7-carboxamide (17.3 mg) as a solid. LCMS (ES, m/z): 477 $[M+H]^+$. $^1$H NMR (400 MHz, DMSO-$d_6$) δ 9.98 (s, 1H), 9.15 (d, J=1.6 Hz, 1H), 7.94-7.88 (m, 1H), 7.59 (d, J=8.3 Hz, 1H), 7.32 (dd, J=12.7, 1.7 Hz, 1H), 6.74 (d, J=8.4 Hz, 1H), 6.69 (d, J=1.2 Hz, 1H), 3.63 (d, J=12.3 Hz, 2H), 2.92 (t, J=11.7 Hz, 2H), 2.70 (m, 1H), 2.50 (s, 3H), 2.37 (s, 3H), 1.85 (d, J=12.4 Hz, 2H), 1.48 (d, J=11.7 Hz, 2H), 1.08 (s, 9H). $^{19}$F NMR (376 MHz, DMSO-$d_6$) δ −132.20.

Example 16: Synthesis of Compound 196

Synthesis of Intermediate B223

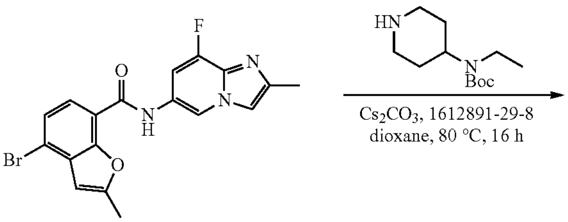

B222

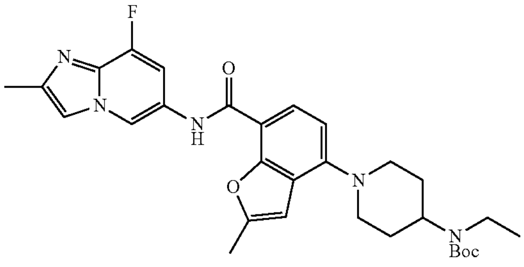

B223

A mixture of 4-bromo-N-[8-fluoro-2-methylimidazo[1,2-a]pyridin-6-yl]-2-methyl-1-benzofuran-7-carboxamide (100 mg, 0.249 mmol), tert-butyl N-ethyl-N-(piperidin-4-yl)carbamate (85.15 mg, 0.374 mmol), Pd-PEPPSI-IPentCl 2-methylpyridine (o-picoline) (41.83 mg, 0.050 mmol), and $Cs_2CO_3$ (243.01 mg, 0.747 mmol) in dioxane (10 mL) was stirred for 16 h at 80° C. under a $N_2$ atmosphere. The reaction mixture was allowed to cool to 25° C., then concentrated in vacuo. The residue was purified by reverse flash chromatography (Condition 1, Gradient 1) to afford tert-butyl N-ethyl-N-[1-[7-([8-fluoro-2-methylimidazo [1,2-a]pyridin-6-yl]carbamoyl)-2-methyl-1-benzofuran-4-yl]piperidin-4-yl]carbamate (105 mg) as a solid. LCMS (ES, m/z): 549 $[M+H]^+$.

Synthesis of Compound 196

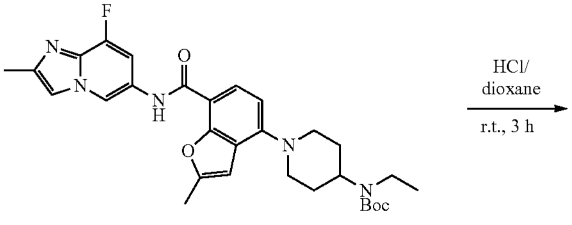

B223

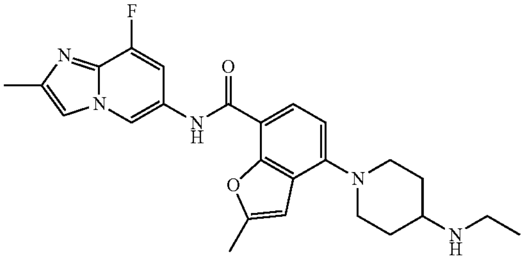

196

To a mixture of tert-butyl N-ethyl-N-[1-[7-([8-fluoro-2-methylimidazo[1,2-a]pyridin-6-yl]carbamoyl)-2-methyl-1-benzofuran-4-yl]piperidin-4-yl]carbamate (95 mg, 0.173 mmol) in dioxane (9 mL) was added HCl (3 mL) in portions. The reaction mixture was stirred for 3 h at 25° C. The resulting mixture was concentrated in vacuo and the residue purified by reverse flash chromatography (Condition 1, Gradient 1) to afford 4-[4-(ethylamino)piperidin-1-yl]-N-[8-fluoro-2-methylimidazo[1,2-a]pyridin-6-yl]-2-methyl-1-benzofuran-7-carboxamide (22 mg, 28.32%) as a solid. LCMS (ES, m/z): 449 $[M+H]^+$. $^1H$ NMR (400 MHz, DMSO-$d_6$) δ 9.99 (s, 1H), 9.15 (d, J=1.6 Hz, 1H), 7.91 (dd, J=3.2, 1.0 Hz, 1H), 7.59 (d, J=8.3 Hz, 1H), 7.32 (dd, J=12.7, 1.7 Hz, 1H), 6.75 (d, J=8.4 Hz, 1H), 6.70 (d, J=1.3 Hz, 1H), 3.66 (d, J=12.6 Hz, 2H), 2.95-2.84 (m, 2H), 2.62 (q, J=7.0 Hz, 3H), 2.50 (s, 3H), 2.35 (s, 3H), 1.99-1.92 (m, 2H), 1.48 (d, J=11.1 Hz, 1H), 1.43 (d, J=11.4 Hz, 1H), 1.05 (t, J=7.1 Hz, 3H). $^{19}F$ NMR (376 MHz, DMSO-$d_6$) δ −132.20.

Example 17: Synthesis of Compound 209

Synthesis of Compound 209

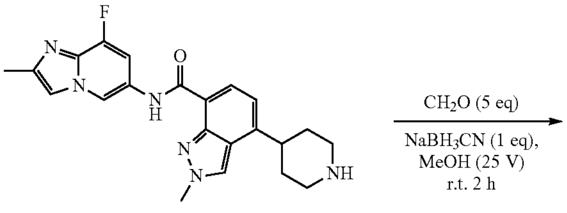

208

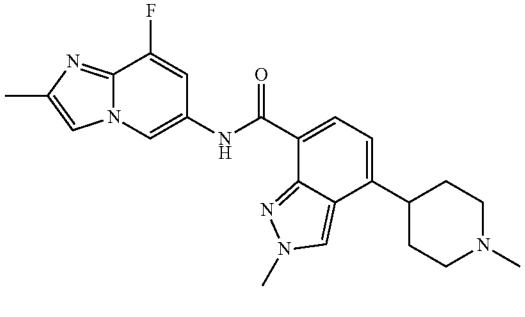

209

To a stirred solution of N-[8-fluoro-2-methylimidazo[1,2-a]pyridin-6-yl]-2-methyl-4-(piperidin-4-yl)indazole-7-carboxamide (270.0 mg, 0.66 mmol) and $CH_2O$ (99.6 mg, 3.32 mmol) in methanol (7 mL) was added $NaBH_3CN$ (41.7 mg, 0.66 mmol) dropwise at 0° C. The reaction mixture was stirred for 2 h at room temperature, then filtered, and the filter cake washed with methanol (3×5 mL). The filtrate was concentrated in vacuo and the residue purified by Prep-HPLC (Condition 2, Gradient 1) to afford N-[8-fluoro-2-methylimidazo[1,2-a]pyridin-6-yl]-2-methyl-4-(1-methylpiperidin-4-yl)indazole-7-carboxamide (7.3 mg, 2.5%) as a solid. LCMS (ES, m/z): 421 $[M+H]^+$. $^1H$ NMR (400 MHz, DMSO-$d_6$) δ 11.13 (s, 1H), 9.23 (d, J=1.7 Hz, 1H), 8.87 (s, 1H), 8.03 (d, J=7.3 Hz, 1H), 7.92 (dd, J=3.2, 1.1 Hz, 1H), 7.37 (dd, J=12.3, 1.7 Hz, 1H), 7.12 (d, J=7.4 Hz, 1H), 4.34 (s, 3H), 2.97-2.85 (m, 3H), 2.38-2.33 (m, 3H), 2.24 (s, 3H), 2.06 (dt, J=13.3, 8.4 Hz, 2H), 1.87 (dt, J=8.8, 4.1 Hz, 4H). $^{19}F$ NMR (376 MHz, DMSO) δ −132.27.

Example 18: Synthesis of Compound 210

Synthesis of Compound 210

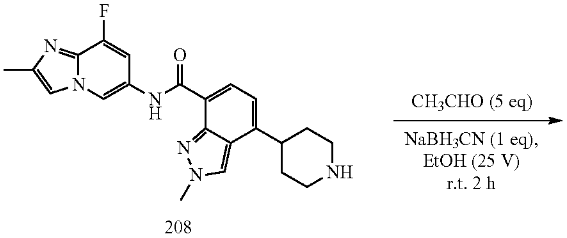

208

-continued

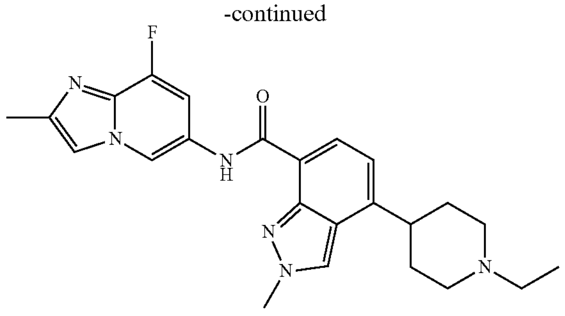

210

To a mixture solution of N-[8-fluoro-2-methylimidazo[1,2-a]pyridin-6-yl]-2-methyl-4-(piperidin-4-yl)indazole-7-carboxamide (270.0 mg, 0.66 mmol) and $CH_3CHO$ (146.1 mg, 3.32 mmol) in ethanol (7 mL) was added $NaBH_3CN$ (41.7 mg, 0.66 mmol) dropwise at 0° C. The reaction mixture was stirred for 2 h at room temperature, then filtered, and the filter cake washed with ethanol (3×5 mL). The filtrate was concentrated in vacuo and the residue purified by Prep-HPLC (Condition 2, Gradient 13) to afford 4-(1-ethylpiperidin-4-yl)-N-[8-fluoro-2-methylimidazo[1,2-a]pyridin-6-yl]-2-methylindazole-7-carboxamide (26.0 mg, 8.9%) as a solid. LCMS (ES, m/z): 435 $[M+H]^+$. $^1H$ NMR (400 MHz, DMSO-$d_6$) δ 11.13 (s, 1H), 9.25 (d, J=1.6 Hz, 1H), 8.88 (s, 1H), 8.03 (d, J=7.3 Hz, 1H), 7.93 (dd, J=3.2, 1.1 Hz, 1H), 7.37 (dd, J=12.2, 1.7 Hz, 1H), 7.13 (d, J=7.4 Hz, 1H), 4.35 (s, 3H), 3.04 (d, J=10.8 Hz, 2H), 2.94 (td, J=10.4, 9.8, 5.5 Hz, 1H), 2.41 (q, J=7.1 Hz, 2H), 2.36 (s, 3H), 2.07 (t, J=10.5 Hz, 2H), 1.93-1.77 (m, 4H), 1.05 (t, J=7.2 Hz, 3H). $^{19}F$ NMR (376 MHz, DMSO) δ −132.28.

Example 19: Synthesis of Compound 211

Synthesis of Intermediate B224

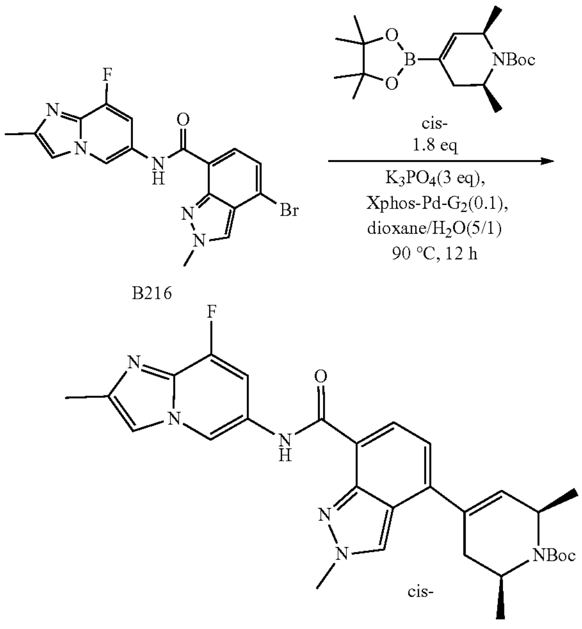

B216

B224

A mixture of 4-bromo-N-[8-fluoro-2-methylimidazo[1,2-a]pyridin-6-yl]-2-methylindazole-7-carboxamide (80.0 mg, 0.20 mmol), tert-butyl (cis-)-2,6-dimethyl-4-(4,4,5,5-tetramethyl-1,3,2-dioxaborolan-2-yl)-5,6-dihydro-2H-pyridine-1-carboxylate (120.7 mg, 0.35 mmol), $K_3PO_4$ (126.6 mg, 0.59 mmol), and XPhos palladium(II) biphenyl-2-amine chloride (15.6 mg, 0.02 mmol) in dioxane (3 mL) and $H_2O$ (0.6 mL) was stirred for 12 h at 90° C. under a $N_2$ atmosphere. The reaction mixture was diluted with $H_2O$ (20 mL) and extracted with DCM (3×20 mL). The combined organic layers were washed with saturated NaCl (1×20 mL), dried over anhydrous $Na_2SO_4$, and filtered. The filtrate was concentrated in vacuo and the residue was purified by Prep-TLC (DCM/MeOH=10/1) to afford tert-butyl (cis-)-4-[7-([8-fluoro-2-methylimidazo[1,2-a]pyridin-6-yl]carbamoyl)-2-methylindazol-4-yl]-2,6-dimethyl-5,6-dihydro-2H-pyridine-1-carboxylate (55.0 mg, 48.2%) as a solid. LCMS (ES, m/z): 533 $[M+H]^+$.

Synthesis of Intermediate B225

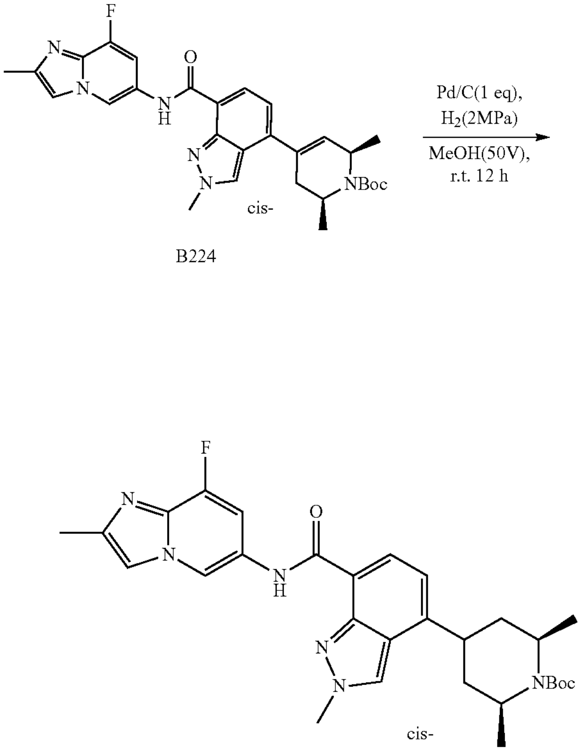

B224

B225

To a solution of tert-butyl (cis-)-4-[7-([8-fluoro-2-methylimidazo[1,2-a]pyridin-6-yl]carbamoyl)-2-methylindazol-4-yl]-2,6-dimethyl-5,6-dihydro-2H-pyridine-1-carboxylate (45.0 mg, 0.08 mmol) in methanol (2.25 mL) in a pressure tank was added Pd/C (10%, 98.9 mg). The mixture was hydrogenated at room temperature under 30 psi of hydrogen pressure for 12 h, filtered through a Celite pad and concentrated in vacuo to afford tert-butyl (cis-)-4-[7-([8-fluoro-2-methylimidazo[1,2-a]pyridin-6-yl]carbamoyl)-2-methylindazol-4-yl]-2,6-dimethylpiperidine-1-carboxylate (34.0 mg, 75.2%) as a solid. LCMS (ES, m/z): 535 $[M+H]^+$.

Synthesis of Compound 211

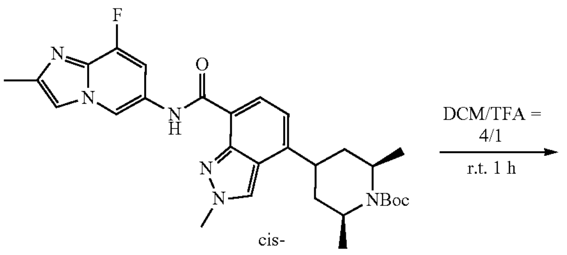

B225

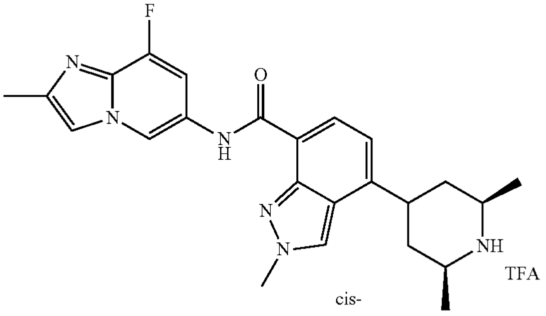

211

A solution of tert-butyl (cis-)-4-[7-([8-fluoro-2-methylimidazo[1,2-a]pyridin-6-yl]carbamoyl)-2-methylindazol-4-yl]-2,6-dimethylpiperidine-1-carboxylate (34.0 mg, 0.06 mmol) in a mixture of DCM (1.20 mL) and TFA (0.30 mL) was stirred for 1 h at room temperature. The reaction mixture was concentrated in vacuo and purified by Prep-HPLC (Condition 9, Gradient 4) to afford 4-[(cis-)-2,6-dimethylpiperidin-4-yl]-N-[8-fluoro-2-methylimidazo[1,2-a]pyridin-6-yl]-2-methylindazole-7-carboxamide trifluoroacetic acid (2.7 mg, 9.7%) as a solid. LCMS (ES, m/z): 435 $[M+H]^+$. $^1H$ NMR (400 MHz, DMSO-$d_6$) δ 11.14 (s, 1H), 9.24 (d, J=1.7 Hz, 1H), 8.87 (s, 1H), 8.05 (d, J=7.3 Hz, 1H), 7.93 (d, J=3.0 Hz, 1H), 7.38 (dd, J=12.3, 1.7 Hz, 1H), 7.09 (d, J=7.4 Hz, 1H), 4.36 (s, 3H), 3.18 (s, 1H), 2.97 (s, 2H), 2.36 (s, 3H), 1.88 (s, 2H), 1.41 (s, 2H), 1.13 (s, 6H). $^{19}F$ NMR (376 MHz, DMSO) δ −73.41, −131.86.

Example 20: Synthesis of Compound 212

Synthesis of Intermediate B226

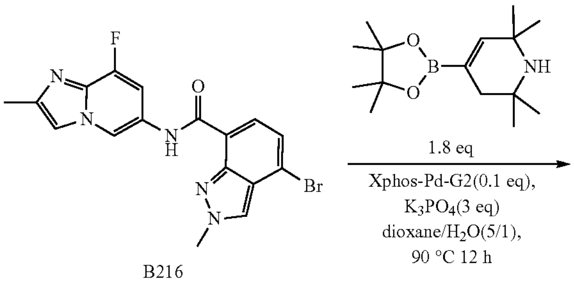

B216

-continued

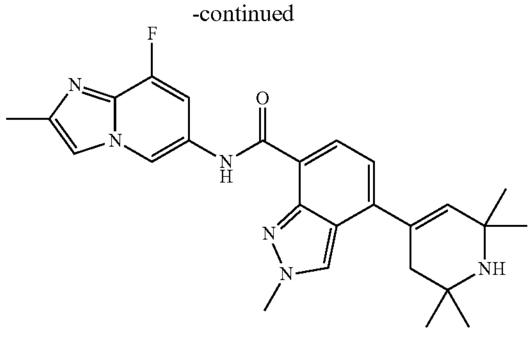

B226

A mixture of 4-bromo-N-[8-fluoro-2-methylimidazo[1,2-a]pyridin-6-yl]-2-methylindazole-7-carboxamide (80.0 mg, 0.20 mmol), 2,2,6,6-tetramethyl-4-(4,4,5,5-tetramethyl-1,3,2-dioxaborolan-2-yl)-1,3-dihydropyridine (94.9 mg, 0.35 mmol), $K_3PO_4$ (126.6 mg, 0.59 mmol), and XPhos palladium(II) biphenyl-2-amine chloride (15.6 mg, 0.02 mmol) in dioxane (3 mL) and $H_2O$ (0.6 mL) was stirred for 12 h at 90° C. under a $N_2$ atmosphere, then diluted with $H_2O$ (20 mL) and extracted with DCM (20 mL×3). The combined organic layers were washed with saturated NaCl (1×20 mL), dried over anhydrous $Na_2SO_4$, and filtered. The filtrate was concentrated in vacuo and the residue was purified by Prep-TLC (DCM/MeOH=10/1) to afford N-[8-fluoro-2-methylimidazo[1,2-a]pyridin-6-yl]-2-methyl-4-(2,2,6,6-tetramethyl-1,3-dihydropyridin-4-yl)indazole-7-carboxamide (60.0 mg, 62.8%) as a solid. LCMS (ES, m/z): 461 $[M+H]^+$.

Synthesis of Compound 212

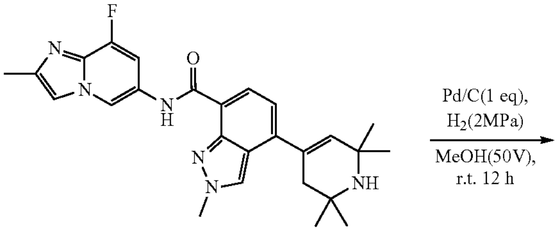

B226

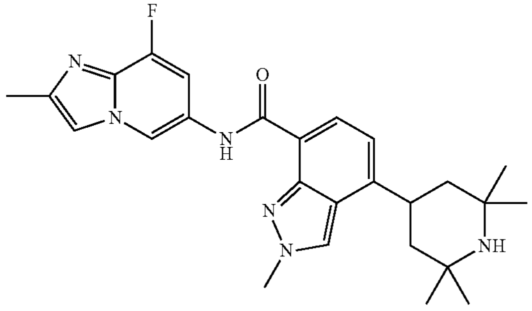

212

To a solution of N-[8-fluoro-2-methylimidazo[1,2-a]pyridin-6-yl]-2-methyl-4-(2,2,6,6-tetramethyl-1,3-dihydropyridin-4-yl)indazole-7-carboxamide (50.0 mg, 0.11 mmol) in methanol (2.5 mL) in a pressure tank was added Pd/C (10%, 115.5 mg). The reaction mixture was hydrogenated at room temperature under 20 psi of hydrogen pressure for 12 h, filtered through a Celite pad, and the filtrate concentrated in vacuo. The residue was purified by Prep-HPLC (Condition 2, Gradient 14) to afford N-[8-fluoro-2-methylimidazo[1,2-a]pyridin-6-yl]-2-methyl-4-(2,2,6,6-tetramethylpiperidin-4-yl)indazole-7-carboxamide (9.7 mg, 19.2%) as a solid. LCMS (ES, m/z): 463 $[M+H]^+$. $^1H$ NMR (400 MHz, DMSO-$d_6$) δ 11.15 (s, 1H), 9.24 (d, J=1.7 Hz, 1H), 8.85 (s, 1H), 8.05 (d, J=7.4 Hz, 1H), 7.93 (dd, J=3.2, 1.1 Hz, 1H), 7.38 (dd, J=12.3, 1.7 Hz, 1H), 7.12 (d, J=7.4 Hz, 1H), 4.37 (s, 3H), 3.48 (t, J=12.6 Hz, 1H), 2.39-2.34 (m, 3H), 1.78-1.69 (m, 2H), 1.48 (t, J=12.6 Hz, 2H), 1.32 (s, 6H), 1.11 (s, 6H). $^{19}F$ NMR (376 MHz, DMSO) δ −131.87.

Example 21: Synthesis of Compound 217

Synthesis of Intermediate B227

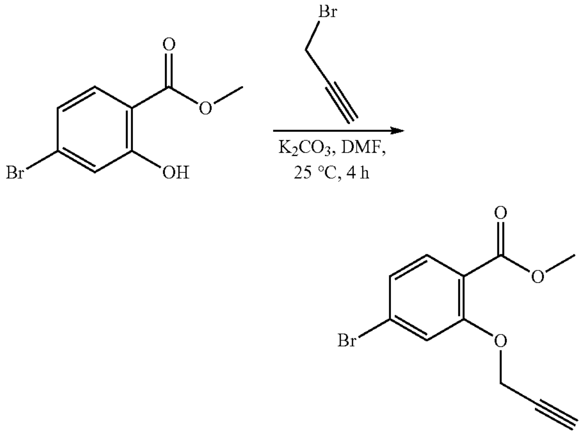

B227

A solution of methyl 1-(2-hydroxy-4-methylphenyl)acetate (30.00 g, 165.553 mmol, 1.00 equiv) and propargyl bromide (27.57 g, 0.232 mmol, 1.4 equiv) and $K_2CO_3$ (68.64 g, 0.497 mmol, 3 equiv) in DMF (300.00 mL) was stirred for 4 h at 25° C. The aqueous layer was extracted with EA and $H_2O$(1:1, 3×1 L). The resulting mixture was concentrated under reduced pressure. This resulted in methyl 1-[4-methyl-2-(prop-2-yn-1-yloxy) phenyl]acetate (23 g, 63.36%) as a solid. LCMS (ES, m/z): 268 $[M+H]^+$.

Synthesis of Intermediate B228

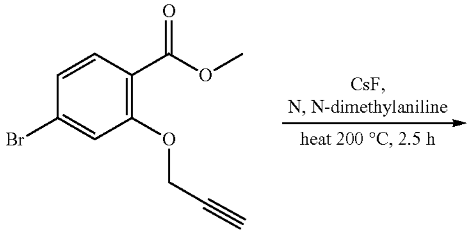

B227

-continued

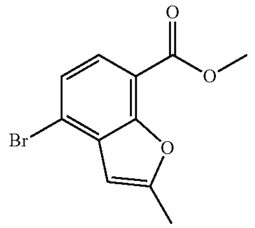

B228

A solution of methyl 1-[4-bromo-2-(prop-2-yn-1-yloxy) phenyl]acetate (1.00 g, 3.520 mmol) and CsF (0.53 mg, 0.004 mmol) in N,N-dimethylaniline (9.00 mL) was stirred for 2.5 h at 200° C. The reaction mixture was diluted with water and extracted with ethyl acetate (1:1, 3×1 L). The combined organic layers were concentrated in vacuo to afford methyl 1-(4-bromo-2-methyl-1-benzofuran-7-yl)acetate (700 mg, 70%) as a solid. LCMS (ES, m/z): 268 $[M+H]^+$.

Synthesis of Intermediate B229

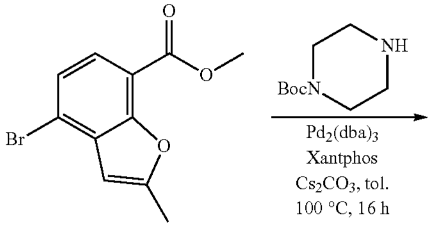

B228

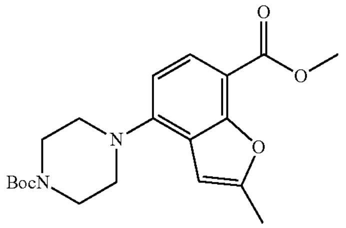

B229

To a mixture of methyl 4-bromo-2-methyl-1-benzofuran-7-carboxylate (2.00 g, 7.432 mmol) and tert-butyl piperazine-1-carboxylate (2.08 g, 11.149 mmol) in toluene (200 mL) was added Xantphos (1.290 g, 2.230 mmol), $Pd(dba)_2$ (854.72 mg, 1.486 mmol), and $Cs_2CO_3$ (7.26 g, 22.297 mmol). The reaction mixture was stirred for 16 h at 100° C. under a $N_2$ atmosphere, then allowed to cool to 25° C., diluted with water and extracted with ethyl acetate (1:1, 3×100 mL). The combined organic layers were concentrated in vacuo and the residue was purified by Prep-HPLC, eluted with EA:PE=1:3, to afford tert-butyl4-[7-(methoxycarbonyl)-2-methyl-1-benzofuran-4-yl]piperazine-1-carboxylate (1.45 g, 52.10%) as a solid. LCMS (ES, m/z): 374 $[M+H]^+$.

Synthesis of Intermediate B230

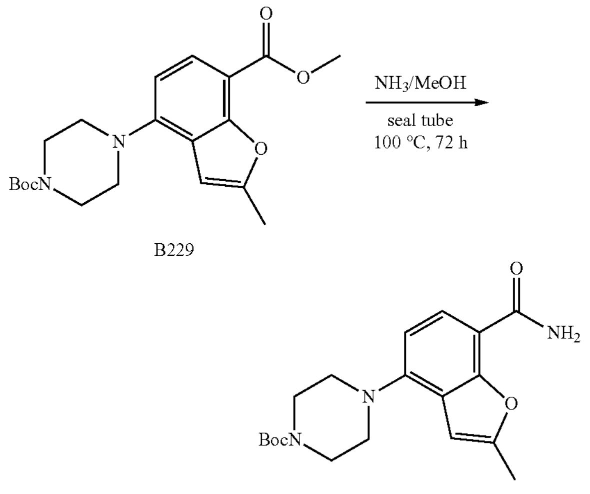

B229

B230

Tert-butyl 4-[7-(methoxycarbonyl)-2-methyl-1-benzofuran-4-yl]piperazine-1-carboxylate (1.40 g, 3.739 mmol) and $NH_3$ (191.03 mg, 11.217 mmol) were combined in methanol (150 mL) in a sealed tube. The reaction mixture was stirred for 72 h at 100° C., then concentrated in vacuo to afford tert-butyl 4-(7-carbamoyl-2-methyl-1-benzofuran-4-yl)piperazine-1-carboxylate (1.3 g, 96.74%) as a solid. LCMS (ES, m/z): 359 $[M+H]^+$.

Synthesis of Intermediate B231

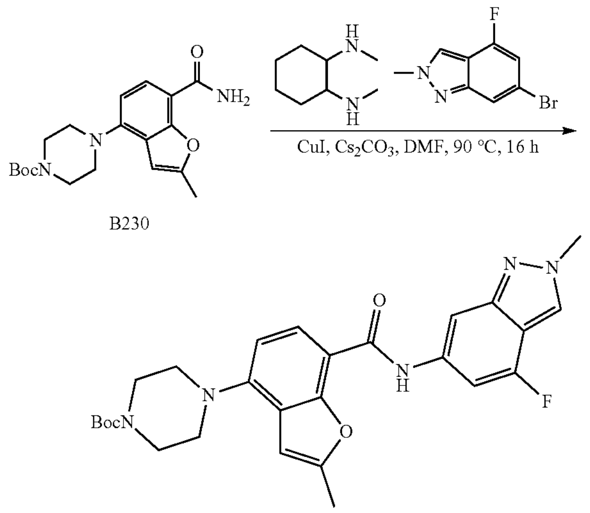

B230

B231

To a stirred solution of tert-butyl 4-(7-carbamoyl-2-methyl-1-benzofuran-4-yl)piperazine-1-carboxylate (100 mg, 0.278 mmol) and 6-bromo-4-fluoro-2-methylindazole (95.59 mg, 0.417 mmol) in DMF (10 mL) was added N1,N2-dimethylcyclohexane-1,2-diamine (7.92 mg, 0.056 mmol), CuI (21.19 mg, 0.111 mmol), and $Cs_2CO_3$ (271.95 mg, 0.834 mmol). The reaction mixture was stirred for 16 h at 90° C. under $N_2$ a atmosphere, then allowed to cool to 25° C., diluted with water, and extracted with ethyl acetate (1:1, 3×30 mL). The reaction mixture was concentrated in vacuo and the residue was purified by Prep-HPLC, eluted with PE:EA=3:1, to afford tert-butyl4-[7-[(4-fluoro-2-methylindazol-6-yl)carbamoyl]-2-methyl-1-benzofuran-4-yl]piperazine-1-carboxylate (75 mg, 53.11%) as a solid. LCMS (ES, m/z): 507 $[M+H]^+$.

Synthesis of Compound 217

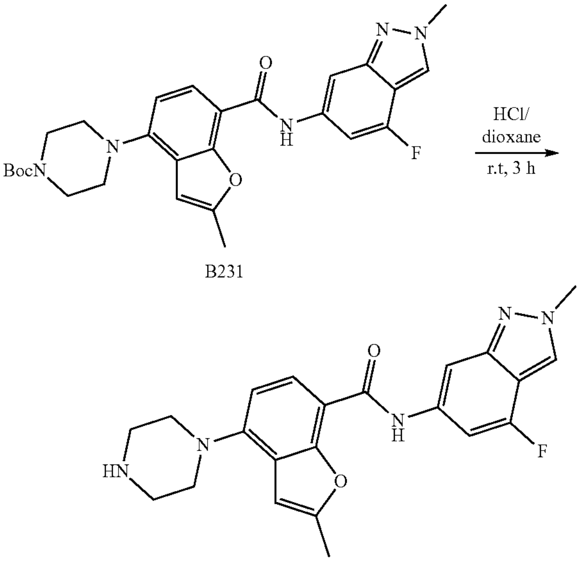

B231

217

To a stirred solution of tert-butyl4-[7-[(4-fluoro-2-methylindazol-6-yl)carbamoyl]-2-methyl-1-benzofuran-4-yl]piperazine-1-carboxylate (70.0 mg) in dioxane (9 mL) was added HCl (3 mL) dropwise at 25° C. The reaction mixture was concentrated in vacuo and the residue was purified by reverse flash chromatography (Condition 1, Gradient 1) to afford N-(4-fluoro-2-methylindazol-6-yl)-2-methyl-4-(piperazin-1-yl)-1-benzofuran-7-carboxamide (41.7 mg) as a white solid. LCMS (ES, m/z): 407 $[M+H]^+$. $^1H$ NMR (400 MHz, DMSO-$d_6$) δ 10.02 (s, 1H), 8.47 (s, 1H), 8.03 (d, J=1.4 Hz, 1H), 7.60 (d, J=8.3 Hz, 1H), 7.20 (dd, J=12.5, 1.4 Hz, 1H), 6.78-6.70 (m, 2H), 4.16 (s, 3H), 3.20-3.13 (m, 4H), 2.95-2.88 (m, 4H), 2.52 (d, J=2.3 Hz, 3H). $^{19}F$ NMR (376 MHz, DMSO-$d_6$) δ −116.97.

Example 22: Synthesis of Compound 218

Synthesis of Intermediate B232

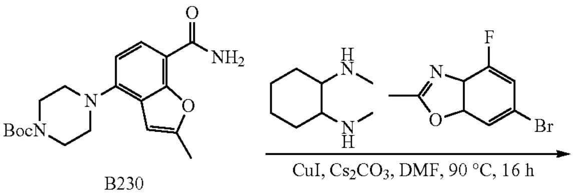

B230

-continued

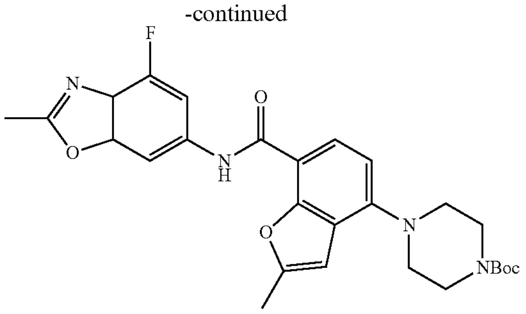

B232

To a stirred solution of tert-butyl 4-(7-carbamoyl-2-methyl-1-benzofuran-4-yl)piperazine-1-carboxylate (100 mg, 0.278 mmol) and 6-bromo-4-fluoro-2-methyl-3a,7a-dihydro-1,3-benzoxazole (96.84 mg, 0.417 mmol) in DMF (10 mL) were added N1,N2-dimethylcyclohexane-1,2-diamine (7.92 mg, 0.056 mmol), CuI (21.19 mg, 0.111 mmol), and $Cs_2CO_3$ (271.95 mg, 0.834 mmol). The reaction mixture was stirred for 16 h at 90° C. under a $N_2$ atmosphere, then allowed to cool to 25° C., diluted with water, and extracted with ethyl acetate (1:1, 3x30 mL). The combined organic layers were concentrated in vacuo and the residue was purified by Prep-HPLC, eluted with PE:EA=3:1, to afford tert-butyl 4-[7-[(4-fluoro-2-methyl-2,7a-dihydro-1,3-benzoxazol-6-yl)carbamoyl]-2-methyl-1-benzofuran-4-yl]piperazine-1-carboxylate (90 mg, 63.36%) as a solid. LCMS (ES, m/z): 510 $[M+H]^+$.

Synthesis of Compound 218

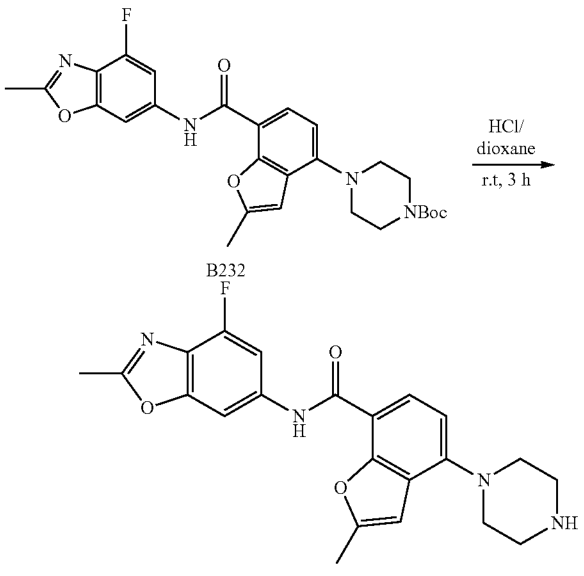

B232

218

To a stirred solution of tert-butyl 4-[7-[(4-fluoro-2-methyl-2,7a-dihydro-1,3-benzoxazol-6-yl)carbamoyl]-2-methyl-1-benzofuran-4-yl]piperazine-1-carboxylate (85 mg, 0.166 mmol) in dioxane (9 mL) was added HCl (3.00 mL, 0.044 mmol) dropwise. The reaction mixture was stirred for 3 h at 25° C., then concentrated in vacuo. The residue was purified by reverse flash chromatography (Condition 1, Gradient 1) to afford N-(4-fluoro-2-methyl-2,7a-dihydro-1,3-benzoxazol-6-yl)-2-methyl-4-(piperazin-1-yl)-1-benzofuran-7-carboxamide (25.7 mg, 37.61%) as a solid. LCMS (ES, m/z): 408 $[M+H]^+$. $^1H$ NMR (400 MHz, DMSO-$d_6$) δ 10.25 (s, 1H), 8.08 (d, J=1.6 Hz, 1H), 7.66-7.57 (m, 2H), 6.78-6.71 (m, 2H), 3.21-3.14 (m, 4H), 2.95-2.88 (m, 4H), 2.63 (s, 3H), 2.52 (s, 3H). $^{19}F$ NMR (376 MHz, DMSO-$d_6$) δ -126.16.

Example 23: Synthesis of Compound 219

Synthesis of Intermediate B233

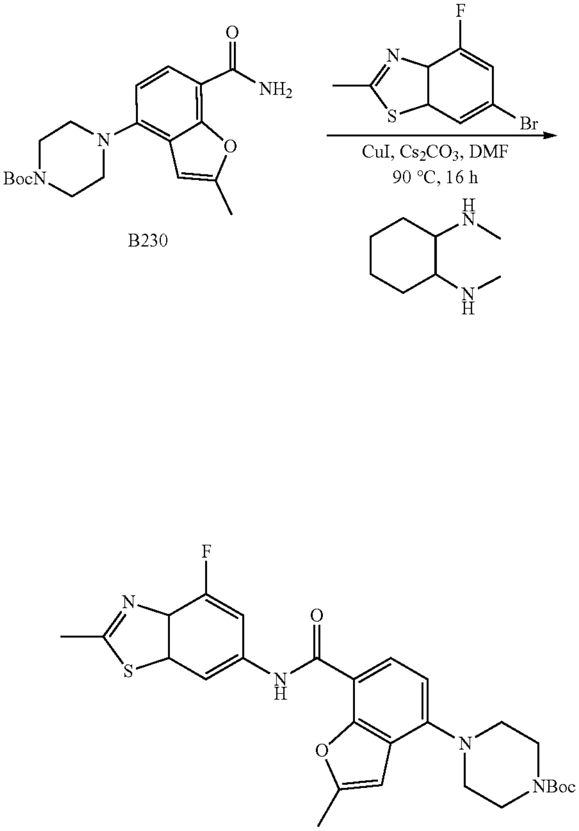

B230

B233

To a stirred solution of tert-butyl 4-(7-carbamoyl-2-methyl-1-benzofuran-4-yl)piperazine-1-carboxylate (100 mg, 0.278 mmol) and 6-bromo-4-fluoro-2-methyl-3a,7a-dihydro-1,3-benzothiazole (103.54 mg, 0.417 mmol) in DMF (10 mL) was added N1,N2-dimethylcyclohexane-1,2-diamine (7.92 mg, 0.056 mmol), CuI (21.19 mg, 0.111 mmol), and $Cs_2CO_3$ (271.95 mg, 0.834 mmol). The reaction mixture was stirred for 16 h at 90° C. under a $N_2$ atmosphere, then allowed to cool to 25° C., diluted with water, and extracted with ethyl acetate (1:1, 3x30 mL). The combined organic layers were concentrated in vacuo and the residue purified by Prep-HPLC, eluted with PE:EA=3:1, to afford tert-butyl 4-[7-[(4-fluoro-2-methyl-2,7a-dihydro-1,3-benzothiazol-6-yl)carbamoyl]-2-methyl-1-benzofuran-4-yl]piperazine-1-carboxylate (50.4 mg, 34.40%) as a solid. LCMS (ES, m/z): 526 $[M+H]^+$.

Synthesis of Compound 219

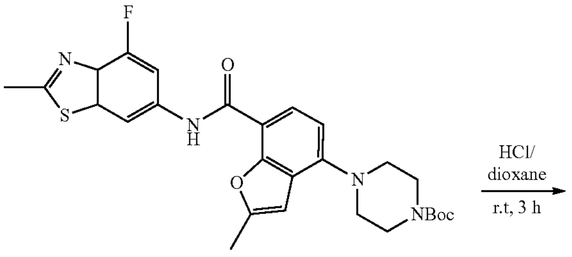

PH-RMT-2020-0457-5

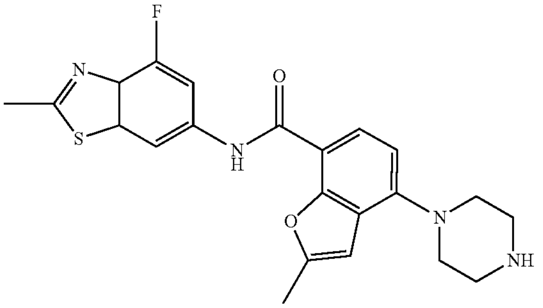

PH-RMT-2020-0457

To a stirred solution of tert-butyl 4-[7-[(4-fluoro-2-methyl-2,7a-dihydro-1,3-benzothiazol-6-yl) carbamoyl]-2-methyl-1-benzofuran-4-yl]piperazine-1-carboxylate (95 mg, 0.180 mmol) in dioxane (9 mL) was added HCl (3.00 mL, 0.044 mmol) dropwise. The reaction mixture was stirred for 3 h at 25° C., then concentrated in vacuo. The residue was purified by reverse flash chromatography (Condition 1, Gradient 1) to afford N-(4-fluoro-2-methyl-2,7a-dihydro-1,3-benzothiazol-6-yl)-2-methyl-4-(piperazin-1-yl)-1-benzofuran-7-carboxamide (50.4 mg, 65.51%) as a solid. LCMS (ES, m/z): 426 $[M+H]^+$. $^1H$ NMR (400 MHz, DMSO-$d_6$) δ 10.23 (s, 1H), 8.33 (d, J=1.9 Hz, 1H), 7.76 (dd, J=12.9, 1.9 Hz, 1H), 7.61 (d, J=8.3 Hz, 1H), 6.78-6.71 (m, 2H), 3.17 (dd, J=6.3, 3.4 Hz, 4H), 2.91 (t, J=4.9 Hz, 4H), 2.81 (s, 3H), 2.52 (s, 3H). $^{19}F$ NMR (376 MHz, DMSO-$d_6$) δ −122.33

Example 24: Synthesis of Compounds 190-195, 200-202, 205-206, and 255

Compounds 190-195, 200-202, 205-206, and 255 were prepared according to General Scheme C. The full synthesis of compound 190 is provided here as an exemplary procedure.

Synthesis of Intermediate B238

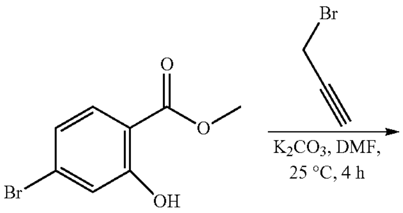

-continued

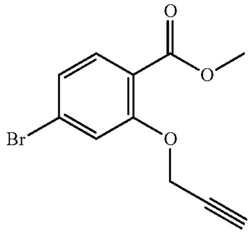

B238

A mixture of methyl 1-(2-hydroxy-4-methylphenyl)acetate (30 g, 165.553 mmol, 1.00 equiv), propargyl bromide (27.57 g, 0.232 mmol, 1.4 equiv), and $K_2CO_3$ (68.64 g, 0.497 mmol, 3 equiv) in DMF (300.00 mL) was stirred for 4 h at 25° C. The reaction mixture was partitioned between water and ethyl acetate, and the aqueous layer was extracted with EA (3×1 L). The combined organic layers were concentrated under reduced pressure to afford methyl 1-[4-methyl-2-(prop-2-yn-1-yloxy) phenyl]acetate (23 g, 63.36%) as a solid. LCMS (ES, m/z): 268 $[M+H]^+$.

Synthesis of Intermediate B239

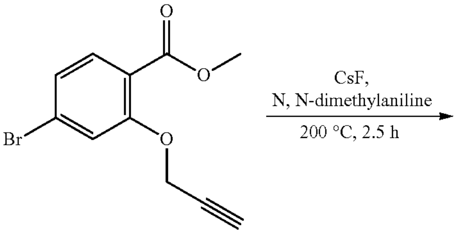

B238

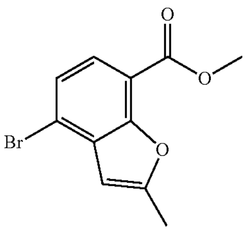

B239

A mixture of methyl 1-[4-bromo-2-(prop-2-yn-1-yloxy) phenyl]acetate (1.00 g, 3.520 mmol, 1.00 equiv) and CsF (0.53 mg, 0.004 mmol, 1 equiv) in N,N-dimethylaniline (9.00 mL) was stirred for 2.5 h at 200° C. under microwave radiation. The reaction mixture was partitioned between water and ethyl acetate, and the aqueous layer was extracted with ethyl acetate (3×1 L). The combined organic layers were concentrated under reduced pressure to afford methyl 1-(4-bromo-2-methyl-1-benzofuran-7-yl)acetate (700 mg, 70.00%) as a solid. LCMS (ES, m/z): 268 $[M+H]^+$.

Synthesis of Intermediate 240

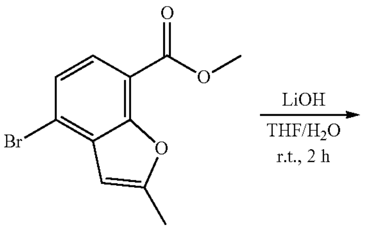

B239

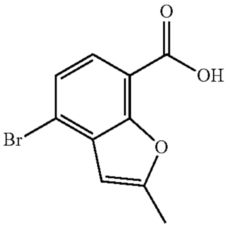

B240

To a solution of methyl 4-bromo-2-methyl-1-benzofuran-7-carboxylate (11.52 g, 42.810 mmol, 1.00 equiv) in THF (440 mL) was added LiOH (2050. mg, 0.086 mmol, 2.00 equiv) and $H_2O$ (60 mL) in portions. The reaction mixture was stirred for 2 h at 25° C., then adjusted to pH 5 with HCl (1M). The aqueous layer was extracted with ethyl acetate (3×300 mL). The combined organic layers were concentrated under vacuum to give a residue. The residue was purified by reverse flash chromatography (Column: $C_{18}$ silica gel column; Mobile Phase: acetonitrile in water (10 mmoL/L $NH_4HCO_3$); Gradient: 10% to 50% gradient in 10 min; detector, UV 254 nm) to afford 4-bromo-2-methyl-1-benzofuran-7-carboxylic acid (4.5 g, 41.21%) as a solid. LCMS (ES, m/z): 254 $[M+H]^+$.

Synthesis of Intermediate B241

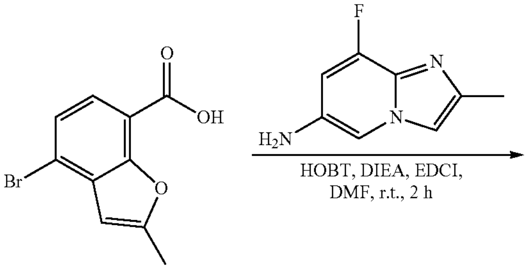

B240

-continued

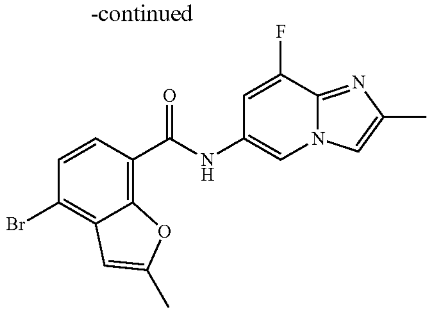

B241

To a mixture of 4-bromo-2-methyl-1-benzofuran-7-carboxylic acid (3.50 g, 13.722 mmol, 1.00 equiv) and 8-fluoro-2-methylimidazo[1,2-a]pyridin-6-amine (2719.75 mg, 0.017 mmol, 1.20 equiv) in DMF (15.00 mL) was added HOBT (2225 mg, 16.466 mmol, 1.20 equiv), EDCI (3946 mg, 20.583 mmol, 1.50 equiv), and DIEA (7094 mg, 54.888 mmol, 4.00 equiv) in portions. The reaction mixture was stirred for 2 h at 25° C., then partitioned between ethyl acetate and water. The aqueous layer was extracted with ethyl acetate (3×20 mL), and the combined organic layers concentrated under vacuum to give a residue. The residue was purified by silica gel column, eluted with DCM:MeOH (9:1), to afford 4-bromo-N-[8-fluoro-2-methylimidazo[1,2-a]pyridin-6-yl]-2-methyl-1-benzofuran-7-carboxamide (3.5 g) as a solid. LCMS (ES, m/z): 401 $[M+H]^+$.

Synthesis of Intermediate B242

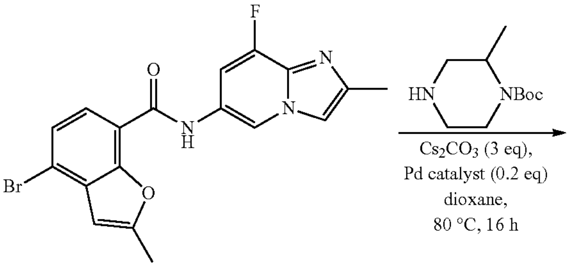

B241

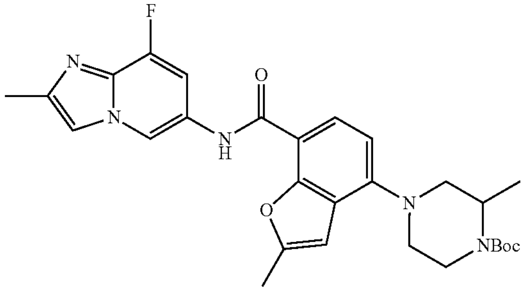

B242

To a mixture of 4-bromo-N-{8-fluoro-2-methylimidazo[1,2-a]pyridin-6-yl}-2-methyl-1-benzofuran-7-carboxamide (100 mg, 0.249 mmol, 1.00 equiv) and tert-butyl 2-methylpiperazine-1-carboxylate (74.69 mg, 0.373 mmol, 1.5 equiv) in 1,4-dioxane (5 mL) was added $Cs_2CO_3$ (243.01 mg, 0.747 mmol, 3 equiv) and Pd-PEPPSI-IPentCl 2-methylpyridine (o-picoline) (41.83 mg, 0.050 mmol, 0.2 equiv). The reaction mixture was stirred for 16 h at 100° C. under $N_2$ atmosphere, then allowed to cool to 25° C. The resulting mixture was extracted with ethyl acetate (15 mL). The combined organic layers were washed with $H_2O$ (20 mL), dried over anhydrous $Na_2SO_4$, and filtered. After filtration, the filtrate was concentrated under reduced pressure to give a residue. The residue was purified by silica gel column chromatography, eluted with PE:EA (5:1), to afford tert-butyl 4-[7-({8-fluoro-2-methylimidazo[1,2-a]pyridin-6-yl}carbamoyl)-2-methyl-1-benzofuran-4-yl]-2-methylpiperazine-1-carboxylate (75 mg, 52.05%) as a solid. LCMS (ES, m/z): 522 $[M+H]^+$.

Synthesis of Compound 190

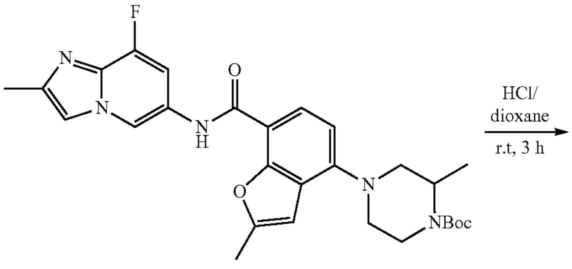

B242

-continued

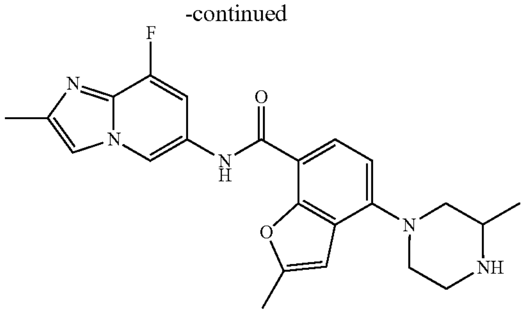

190

A mixture of tert-butyl 4-[7-({8-fluoro-2-methylimidazo[1,2-a]286yridine-6-yl}carbamoyl)-2-methyl-1-benzofuran-4-yl]-2-methylpiperazine-1-carboxylate (90 mg, 0.173 mmol, 1.00 equiv) and HCl (2 mL) in dioxane (4 mL) was stirred for 3 h at 25° C. The resulting mixture was concentrated under reduced pressure to give a residue. The residue was purified by reverse flash chromatography (Column: silica gel; Mobile Phase: acetonitrile in water (10 mmoL/L $NH_4HCO_3$); Gradient: 10% to 50% in 10 min; detector, UV 254 nm) to afford N-{8-fluoro-2-methylimidazo[1,2-a]pyridin-6-yl}-2-methyl-4-(3-methylpiperazin-1-yl)-1-benzofuran-7-carboxamide (65.3 mg, 85.30%) as a solid. LCMS: (ES, m/z): 422 $[M+H]^+$. $^1H$ NMR: (400 MHz, DMSO-$d_6$) δ 10.00 (s, 1H), 9.14 (d, J=1.6 Hz, 1H), 7.91 (dd, J=3.2, 1.0 Hz, 1H), 7.60 (d, J=8.3 Hz, 1H), 7.32 (dd, J=12.7, 1.6 Hz, 1H), 6.77-6.71 (m, 2H), 3.58-3.50 (m, 2H), 3.02-2.95 (m, 1H), 2.90 (td, J=11.8, 11.2, 2.6 Hz, 2H), 2.76 (td, J=11.3, 3.2 Hz, 1H), 2.55 (s, 3H), 2.52 (s, 1), 2.35 (d, J=0.9 Hz, 3H), 1.05 (d, J=6.3 Hz, 3H).

| Compound | A-H | LCMS (ES, m/z) $[M + H]^+$ | $^1H$ NMR (400 MHz, DMSO-$d_6$) δ |
|---|---|---|---|
| 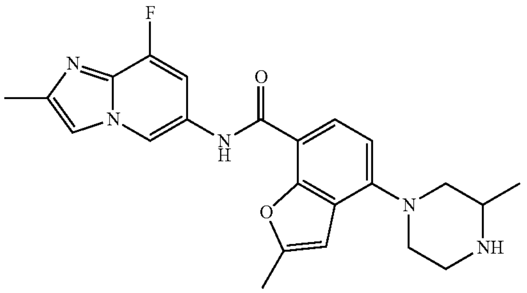 190 | 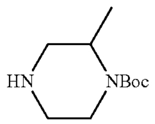 | 422 | 10.00 (s, 1H), 9.14 (d, J = 1.6 Hz, 1H), 7.91 (dd, J = 3.2, 1.0 Hz, 1H), 7.60 (d, J = 8.3 Hz, 1H), 7.32 (dd, J = 12.7, 1.6 Hz, 1H), 6.77-6.71 (m, 2H), 3.58-3.50 (m, 2H), 3.02-2.95 (m, 1H), 2.90 (td, J = 11.8, 11.2, 2.6 Hz, 2H), 2.76 (td, J = 11.3, 3.2 Hz, 1H), 2.55 (s, 3H), 2.52 (s, 1H), 2.35 (d, J = 0.9 Hz, 3H), 1.05 (d, J = 6.3 Hz, 3H) |
| 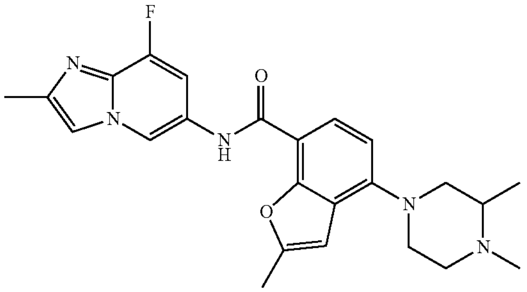 191 | 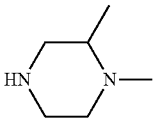 | 436 | 10.01 (s, 1H), 9.14 (d, J = 1.6 Hz, 1H), 7.91 (dd, J = 3.2, 1.1 Hz, 1H), 7.60 (d, J = 8.3 Hz, 1H), 7.32 (dd, J = 12.7, 1.6 Hz, 1H), 6.78-6.72 (m, 2H), 3.61-3.47 (m, 2H), 2.96 (td, J = 11.4, 2.8 Hz, 1H), 2.89-2.81 (m, 1H), 2.61 (dd, J = 11.9, 9.8 Hz, 1H), 2.50 (s, 3H), 2.42-2.33 (m, 4H), 2.26 (m, 4H), 1.08 (d, J = 6.2 Hz, 3H). |

-continued

| Compound | A-H | LCMS (ES, m/z) [M + H]+ | $^1$H NMR (400 MHz, DMSO-$d_6$) δ |
|---|---|---|---|
| 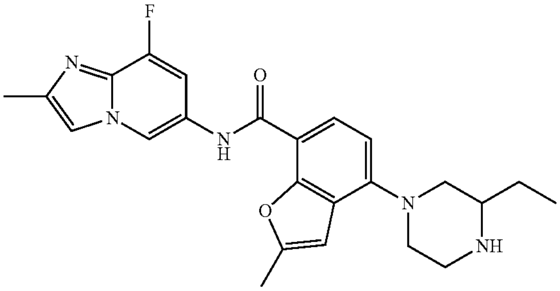 [SMILES: CCC1CN(c2ccc(C(=O)Nc3cc(F)c4nc(C)cn4c3)c3oc(C)cc23)CCN1] 192 | 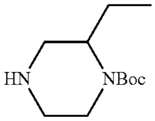 | 436 | 9.99 (s, 1H), 9.14 (d, J = 1.6 Hz, 1H), 7.91 (dd, J = 3.2, 1.0 Hz, 1H), 7.60 (d, J = 8.3 Hz, 1H), 7.32 (dd, J = 12.7, 1.6 Hz, 1H), 6.75 (d, J = 8.4 Hz, 1H), 6.70 (d, J = 1.3 Hz, 1H), 3.55 (d, J = 11.3 Hz, 2H), 3.00 (d, J = 11.9 Hz, 1H), 2.89 (t, J = 11.1 Hz, 1H), 2.83-2.73 (m, 1H), 2.70 (s, 1H), 2.53 (s, 1H), 2.52 (s, 3H), 2.35 (d, J = 0.8 Hz, 3H), 1.47-1.32 (m, 2H), 0.95 (t, J = 7.5 Hz, 3H) |
| 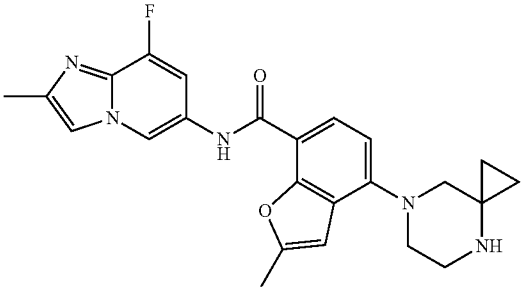 [SMILES: Cc1cn2cc(NC(=O)c3ccc(N4CCNC5(CC5)C4)c4cc(C)oc34)cc(F)c2n1] 194 | 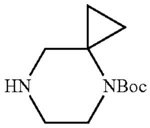 | 434 | 9.99 (s, 1H), 9.14 (d, J = 1.6 Hz, 1H), 7.91 (dd, J = 3.2, 1.0 Hz, 1H), 7.60 (d, J = 8.3 Hz, 1H), 7.32 (dd, J = 12.7, 1.6 Hz, 1H), 6.73 (d, J = 8.4 Hz, 1H), 6.66 (d, J = 1.2 Hz, 1H), 3.20 (dd, J = 6.4, 3.5 Hz, 2H), 3.07 (s, 2H), 2.96 (t, J = 4.9 Hz, 2H), 2.51 (s, 3H), 2.35 (d, J = 0.8 Hz, 3H), 0.62-0.54 (m, 2H), 0.57-0.50 (m, 2H) |
| 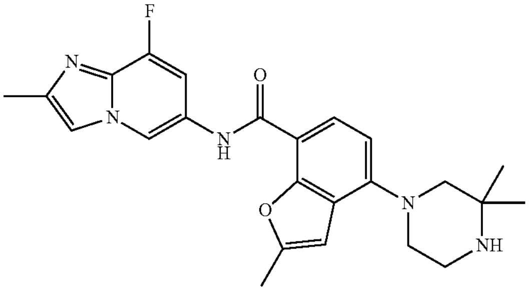 193 | 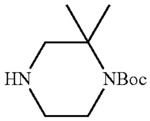 | 437 | 9.99 (s, 1H), 9.14 (d, J = 1.6 Hz, 1H), 7.91 (dd, J = 3.2, 1.0 Hz, 1H), 7.60 (d, J = 8.4 Hz, 1H), 7.32 (dd, J = 12.7, 1.7 Hz, 1H), 6.73 (d, J = 8.4 Hz, 1H), 6.66 (q, J = 1.0 Hz, 1H), 3.11 (t, J = 5.1 Hz, 2H), 2.95 (d, J = 7.5 Hz, 4H), 2.50 (s, 3H), 2.35 (d, J = 0.8 Hz, 3H), 1.19 (s, 6H) |
| 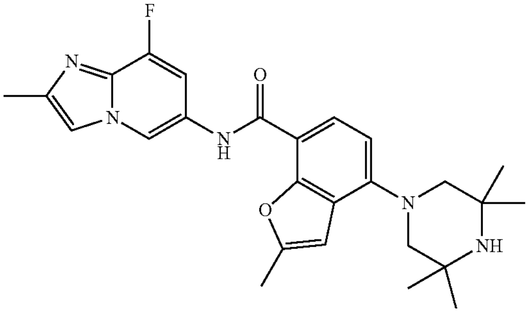 195 | 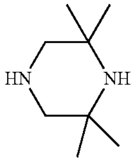 | 464 | 9.99 (s, 1H), 9.14 (d, J = 1.6 Hz, 1H), 7.91 (dd, J = 3.2, 1.0 Hz, 1H), 7.61 (d, J = 8.3 Hz, 1H), 7.32 (dd, J = 12.7, 1.6 Hz, 1H), 6.77 (d, J = 8.5 Hz, 1H), 6.63 (d, J = 1.2 Hz, 1H), 2.95 (s, 4H), 2.50 (s, 3H), 2.35 (d, J = 0.9 Hz, 3H), 1.22 (s, 12H) |

-continued
| Compound | A-H | LCMS (ES, m/z) [M + H]+ | $^{1}$H NMR (400 MHz, DMSO-$d_6$) δ |
|---|---|---|---|
| 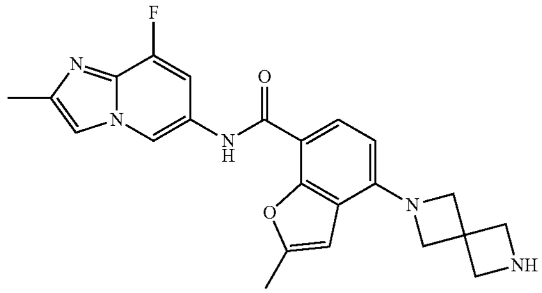 [SMILES: Cc1cn2cc(NC(=O)c3ccc(N4CC5(CNC5)C4)c4cc(C)oc34)cc(F)c2n1] 205 | 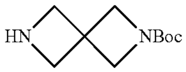 | 420 | 9.77 (s, 1H), 9.12 (d, J = 1.6 Hz, 1H), 7.89 (d, J = 3.1 Hz, 1H), 7.59 (d, J = 8.3 Hz, 1H), 7.34 (dd, J = 12.7, 1.7 Hz, 1H), 6.70 (s, 1H), 6.20 (d, J = 8.4 Hz, 1H), 4.28 (s, 1H), 4.23 (s, 4H), 4.05 (s, 1H), 3.66 (d, J = 3.1 Hz, 3H), 2.49 (d, J = 1.0 Hz, 3H), 2.35 (s, 3H) |
| 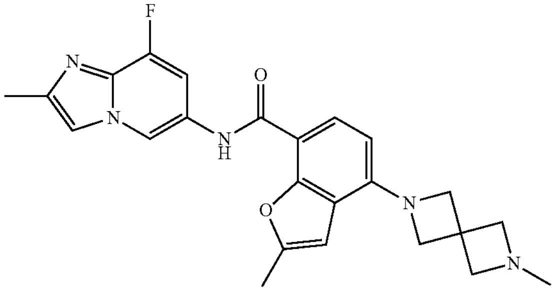 206 | 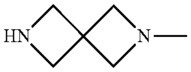 | 432 | 9.76 (s, 1H), 9.12 (d, J = 1.6 Hz, 1H), 7.92-7.86 (m, 1H), 7.58 (d, J = 8.4 Hz, 1H), 7.34 (dd, J = 12.8, 1.6 Hz, 1H), 6.69 (d, J = 1.2 Hz, 1H), 6.19 (d, J = 8.4 Hz, 1H), 4.21 (s, 4H), 2.52 (s, 3H), 2.49 (d, J = 1.1 Hz, 4H), 2.35 (d, J = 0.8 Hz, 3H), 2.21 (s, 3H) |
| 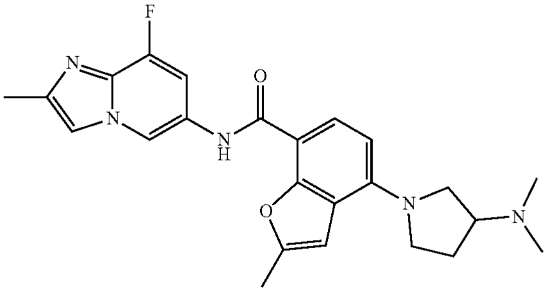 202 | 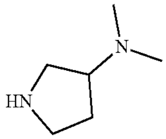 | 436 | 9.70 (s, 1H), 9.13 (d, J = 1.6 Hz, 1H), 7.89 (dd, J = 3.2, 1.0 Hz, 1H), 7.61 (d, J = 8.5 Hz, 1H), 7.36 (dd, J = 12.8, 1.6 Hz, 1H), 6.94 (d, J = 1.3 Hz, 1H), 6.36 (d, J = 8.7 Hz, 1H), 3.80-3.66 (m, 2H), 3.66-3.56 (m, 1H), 3.40 (t, J = 8.8 Hz, 1H), 2.82 (p, J = 7.5 Hz, 1H), 2.49 (d, J = 1.0 Hz, 3H), 2.35 (d, J = 0.9 Hz, 3H), 2.25 (s, 6H), 2.20 (s, 1H), 1.92-1.78 (m, 1H) |
| 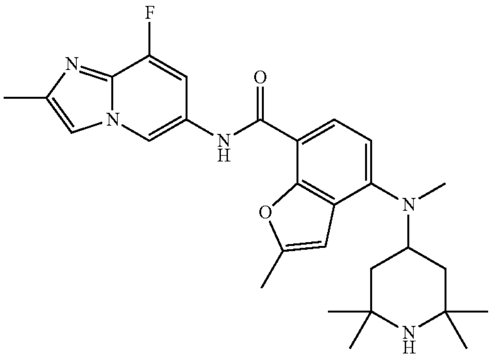 201 | 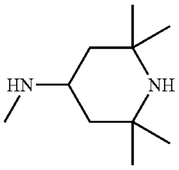 | 492 | 9.91 (s, 1H), 9.15 (d, J = 1.6 Hz, 1H), 7.91 (dd, J = 3.1, 1.0 Hz, 1H), 7.60 (d, J = 8.4 Hz, 1H), 7.33 (dd, J = 12.7, 1.7 Hz, 1H), 6.69-6.59 (m, 2H), 4.19 (d, J = 11.7 Hz, 1H), 2.86 (s, 3H), 2.50 (s, 3H), 2.35 (d, J = 0.8 Hz, 3H), 1.57 (s, 2H), 1.47 (t, J = 12.2 Hz, 2H), 1.17 (s, 6H), 1.09 (s, 6H) |

-continued

| Compound | A-H | LCMS (ES, m/z) [M + H]+ | $^1$H NMR (400 MHz, DMSO-$d_6$) δ |
|---|---|---|---|
| 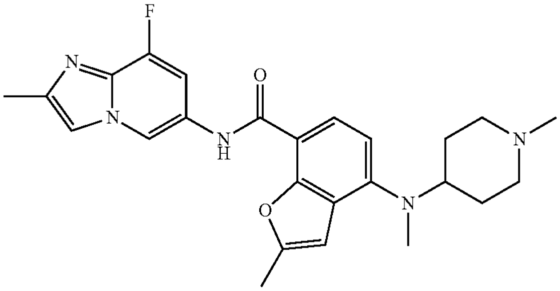 200 | 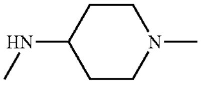 | 450 | 9.87 (s, 1H), 9.14 (d, J = 1.6 Hz, 1H), 7.90 (dd, J = 3.2, 1.0 Hz, 1H), 7.59 (d, J = 8.5 Hz, 1H), 7.33 (dd, J = 12.7, 1.6 Hz, 1H), 6.65 (d, J = 8.6 Hz, 2H), 3.68 (tt, J = 11.4, 3.8 Hz, 1H), 2.89 (s, 5H), 2.52 (s, 3H), 2.35 (d, J = 0.9 Hz, 3H), 2.19 (s, 3H), 2.04-1.97 (m, 1H), 1.96 (t, J = 11.5 Hz, 1H), 1.94-1.87 (m, 1H), 1.85 (dd, J = 12.0, 3.7 Hz, 1H), 1.65 (d, J = 11.8 Hz, 2H) |
| 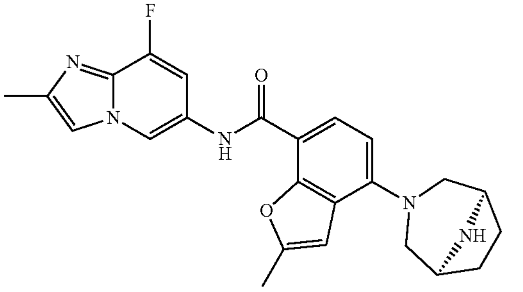 [SMILES: Cc1cn2cc(NC(=O)c3ccc(N4C[C@H]5CC[C@@H](C4)N5)c4cc(C)oc34)cc(F)c2n1] 255 | 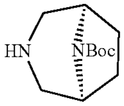 | 434 | 9.93 (s, 1H), 9.14 (d, J = 1.6 Hz, 1H), 7.90 (dd, J = 3.2, 0.9 Hz, 1H), 7.58 (d, J = 8.5 Hz, 1H), 7.32 (dd, J = 12.7, 1.6 Hz, 1H), 6.78 (d, J = 1.2 Hz, 1H), 6.65 (d, J = 8.5 Hz, 1H), 3.49 (d, J = 9.8 Hz, 4H), 2.99 (d, J = 9.9 Hz, 2H), 2.50 (s, 3H), 2.35 (d, J = 0.8 Hz, 3H), 1.84 (q, J = 6.6, 5.8 Hz, 2H), 1.72 (s, 2H) |

Example 25: Synthesis of Compounds 261

Synthesis of Intermediate B243

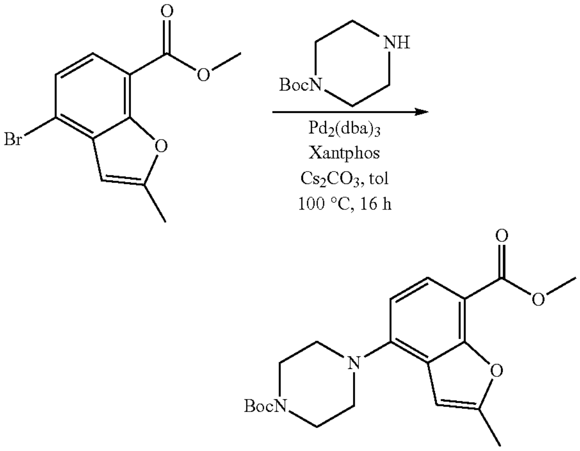

B243

To a mixture of methyl 4-bromo-2-methyl-1-benzofuran-7-carboxylate (2.00 g, 7.432 mmol, 1.00 equiv) and tert-butyl piperazine-1-carboxylate (2076 mg, 11.149 mmol, 1.50 equiv) in toluene (200 mL) was added Xantphos (1290 mg, 2.230 mmol, 0.30 equiv), $Pd(dba)_2$ (854.7 mg, 1.486 mmol, 0.20 equiv), and $Cs_2CO_3$ (7264.8 mg, 22.297 mmol, 3.00 equiv). The reaction mixture was stirred for 16 h at 100° C. under $N_2$ atmosphere, then allowed to cool to 25° C. and partitioned between water and ethyl acetate. The aqueous layer was extracted with ethyl acetate (3×100 mL). The combined organic layers were concentrated under reduced pressure to give a residue. The residue was purified by silica gel chromatography, eluted with EA:PE (1:3), to afford tert-butyl 4-[7-(methoxycarbonyl)-2-methyl-1-benzofuran-4-yl]piperazine-1-carboxylate (1.45 g, 52.10%) as a solid. LCMS (ES, m/z): 374 [M+H]+.

Synthesis of Intermediate B244

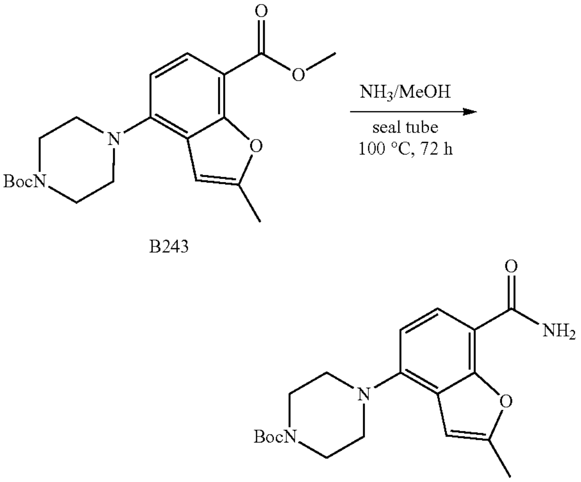

B243

B244

Tert-butyl 4-[7-(methoxycarbonyl)-2-meth yl-1-benzofuran-4-yl]piperazine-1-carboxylate (1.40 g, 3.739 mmol, 1.00 equiv) and $NH_3$ (191.03 mg, 11.217 mmol, 3.00 equiv) were combined in MeOH (150.00 mL) in a sealed tube. The reaction mixture was stirred for 72 h at 100° C., then concentrated under reduced pressure to afford tert-butyl 4-(7-carbamoyl-2-methyl-1-benzofuran-4-yl) piperazine-1-carboxylate (1.3 g, 96.74%) as a solid. LCMS (ES, m/z): 359 $[M+H]^+$.

Synthesis of Intermediate B245

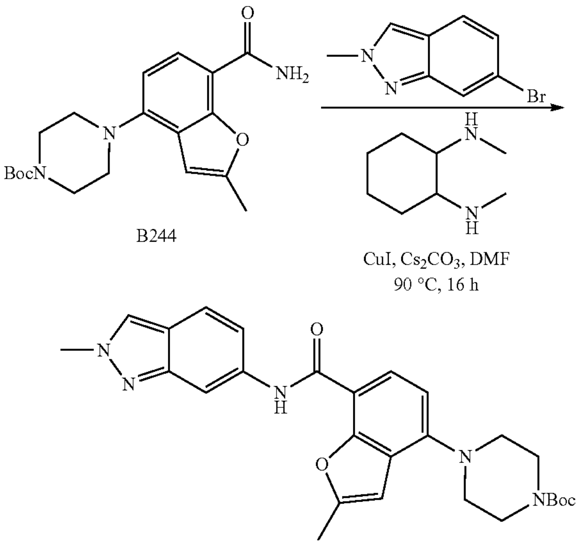

B244

B245

To a mixture of tert-butyl 4-(7-carbamoyl-2-methyl-1-benzofuran-4-yl)piperazine-1-carboxylate (100 mg, 0.278 mmol, 1.00 equiv) and 6-bromo-2-methylindazole (88.08 mg, 0.417 mmol, 1.5 equiv) in DMF (10 mL) was added N1,N2-dimethylcyclohexane-1,2-diamine (15.83 mg, 0.111 mmol, 0.4 equiv), $Cs_2CO_3$ (271.95 mg, 0.834 mmol, 3 equiv), and CuI (15.90 mg, 0.083 mmol, 0.3 equiv). The reaction mixture was stirred for 16 h at 90° C. under $N_2$ atmosphere, then allowed to cool to 25° C. The resulting mixture was extracted with ethyl acetate (15 mL). The organic layer was washed with $H_2O$ (3×20 mL), dried over anhydrous $Na_2SO_4$, and filtered. After filtration, the filtrate was concentrated under reduced pressure to give a residue. The residue was purified by Prep-HPLC, eluted with PE:EA (3:1), to afford tert-butyl 4-{2-methyl-7-[(2-methylindazol-6-yl)carbamoyl]-1-benzofuran-4-yl}piperazine-1-carboxylate (60 mg, 41.85%) as a solid. LCMS (ES, m/z): 490 $[M+H]^+$.

Synthesis of Compound 261

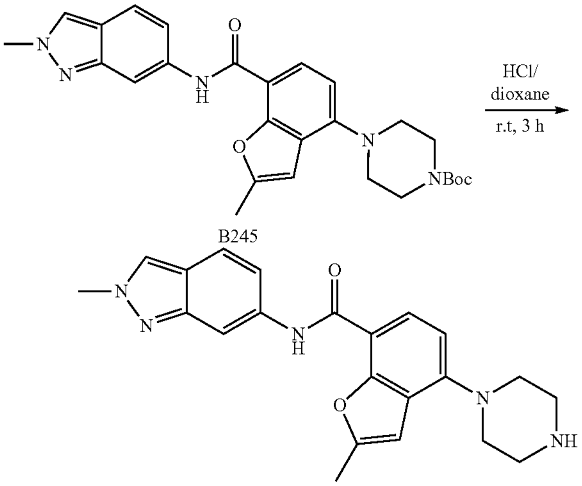

B245

261

A mixture of tert-butyl 4-{2-methyl-7-[(2-methylindazol-6-yl)carbamoyl]-1-benzofuran-4-yl}piperazine-1-carboxylate (110 mg, 0.225 mmol, 1.00 equiv) and HCl (5.5 mL) in dioxane (11.0 mL) was stirred for 3 h at 25° C., then concentrated under reduced pressure to give a residue. The residue was purified by reverse flash chromatography (Column: silica gel; Mobile Phase: acetonitrile in water (10 mmoL/L $NH_4HCO_3$): Gradient: 10% to 50% in 10 min; detector, UV 254 nm) to afford 2-methyl-N-(2-methylindazol-6-yl)-4-(piperazin-1-yl)-1-benzofuran-7-carboxamide (67 mg, 76.57%) as a solid. LCMS: (ES, W/z): $390[M+H]^+$. $^1H$ NMR: $^1H$ NMR (400 MHz, DMSO-$d_6$) δ9.91 (s, 1H), 8.25 (d, J=15.1 Hz, 2H), 7.64 (dd, J=15.3, 8.6 Hz, 2H), 7.26 (dd, J=8.9, 1.8 Hz, 1H), 6.78-6.65 (m, 2H), 4.14 (s, 3H), 3.16 (dd, J=6.2, 3.5 Hz, 4H), 2.91 (dd, J=6.0, 3.5 Hz, 4H), 2.52 (s, 3H).

Compounds 261-268 were prepared according to General Scheme D and the general protocol outlined above for Compound 261, with specific details outlined in the table below.

| Compound | B-Br | LCMS (ES, m/z) $[M + H]^+$ | $^1H$ NMR (400 MHz, DMSO-$d_6$) δ |
|---|---|---|---|
| 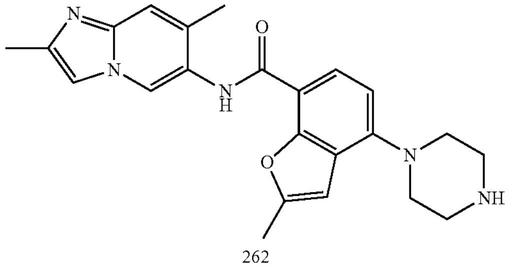 262 | 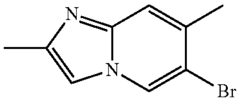 | 404 | 9.41 (s, 1H), 9.09 (s, 1H), 7.74 (d, J = 8.4 Hz, 1H), 7.68 (s, 1H), 7.37 (s, 1H), 6.81-6.75 (m, 2H), 3.19 (s, 4H), 2.91 (s, 4H), 2.53 (s, 3H), 2.46 (s, 3H), 2.31 (s, 3H) |

-continued
| Compound | B-Br | LCMS (ES, m/z) $[M + H]^+$ | $^1H$ NMR (400 MHz, DMSO-$d_6$) δ |
| --- | --- | --- | --- |
| 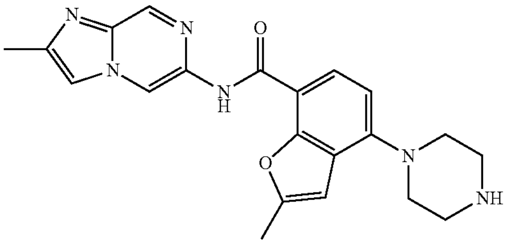 [SMILES: Cc1cn2cc(NC(=O)c3ccc(N4CCNCC4)c4cc(C)oc34)ncc2n1] 263 | 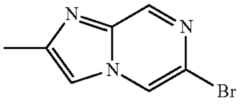 | 390 | 9.93 (s, 1H), 9.41 (d, J = 1.4 Hz, 1H), 8.85 (d, J = 1.5 Hz, 1H), 8.06 (s, 1H), 7.78 (d, J = 8.5 Hz, 1H), 6.82-6.75 (m, 2H), 3.20 (dd, J = 6.5, 3.3 Hz, 4H), 2.90 (dd, J = 5.8, 3.6 Hz, 4H), 2.55 (d, J = 1.0 Hz, 3H), 2.42 (s, 3H) |
| 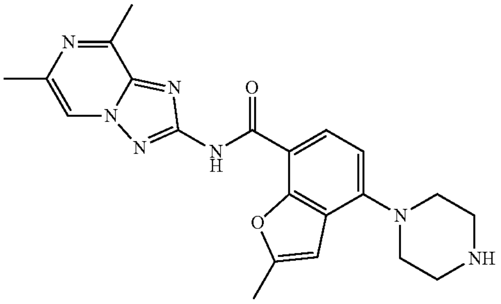 [SMILES: Cc1cn2nc(NC(=O)c3ccc(N4CCNCC4)c4cc(C)oc34)nc2c(C)n1] 264 | 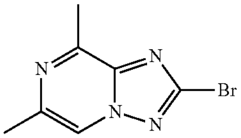 | 406 | 10.70 (s, 1H), 8.74 (s, 1H), 7.68 (d, J = 8.3 Hz, 1H), 6.78-6.69 (m, 2H), 3.22 (dd, J = 6.3, 3.5 Hz, 4H), 2.96 (dd, J = 6.1, 3.7 Hz, 4H), 2.76 (s, 3H), 2.52 (s, 3H), 2.50 (s, 3H) |
| 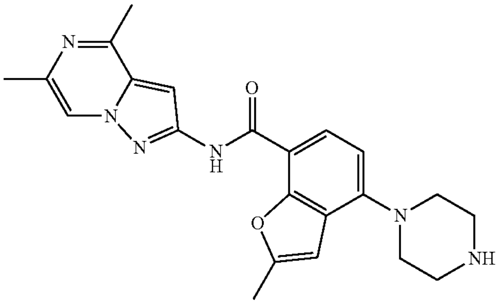 [SMILES: Cc1cn2nc(NC(=O)c3ccc(N4CCNCC4)c4cc(C)oc34)cc2c(C)n1] 265 | 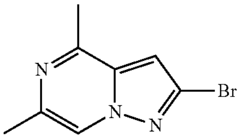 | 405 | 10.49 (s, 1H), 8.41-8.36 (m, 1H), 7.73 (d, J = 8.4 Hz, 1H), 7.26 (d, J = 1.0 Hz, 1H), 6.75 (dd, J = 4.8, 3.7 Hz, 2H), 3.19 (t, J = 4.6 Hz, 4H), 2.91 (d, J = 4.9 Hz, 4H), 2.67 (s, 3H), 2.53 (d, J = 1.0 Hz, 3H), 2.41 (d, J = 1.0 Hz, 3H) |
| 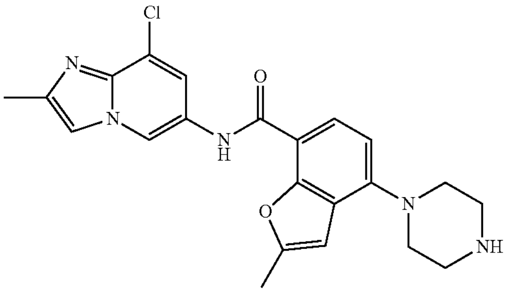 266 | 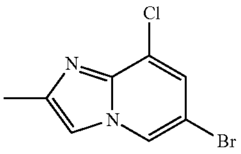 | 424 | 10.00 (s, 1H), 9.26 (d, J = 1.7 Hz, 1H), 7.91 (d, J = 1.0 Hz, 1H), 7.64-7.57 (m, 2H), 6.78-6.71 (m, 2H), 3.30 (s, 4H), 3.17 (d, J = 5.0 Hz, 4H), 2.90 (s, J = 4.9 Hz, 3H), 2.36 (d, J = 0.8 Hz, 3H) |
| 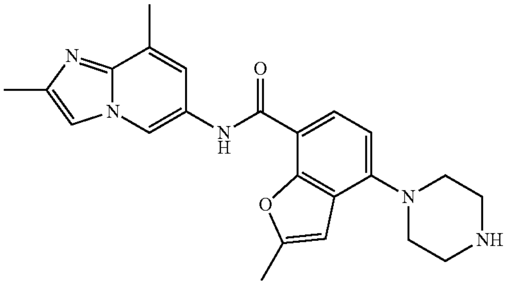 [SMILES: Cc1cn2cc(NC(=O)c3ccc(N4CCNCC4)c4cc(C)oc34)cc(C)c2n1] 267 | 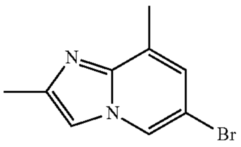 | 404 | 9.85 (s, 1H), 9.10 (d, J = 2.0 Hz, 1H), 7.73 (d, J = 1.0 Hz, 1H), 7.61 (d, J = 8.3 Hz, 1H), 7.15 (dd, J = 2.0, 1.1 Hz, 1H), 6.77-6.70 (m, 2H), 3.16 (dd, J = 6.3, 3.5 Hz, 4H), 2.90 (t, J = 4.8 Hz, 4H), 2.52 (s, 3H), 2.46 (t, J = 0.9 Hz, 3H), 2.33 (d, J = 0.9 Hz, 3H) |

-continued

| Compound | B-Br | LCMS (ES, m/z) $[M + H]^+$ | $^1H$ NMR (400 MHz, DMSO-$d_6$) δ |
|---|---|---|---|
| 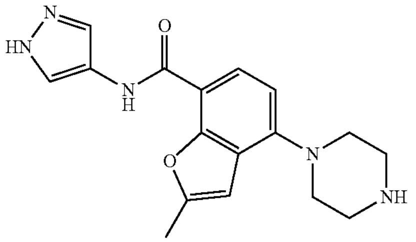 [SMILES: Cc1cc2c(N3CCNCC3)ccc(C(=O)Nc3cn[nH]c3)c2o1] 268 | 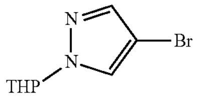 | 326 | 9.92 (s, 1H), 7.86 (s, 2H), 7.58 (d, J = 8.3 Hz, 1H), 6.71 (d, J = 8.3 Hz, 2H), 3.14 (t, J = 4.7 Hz, 4H), 2.90 (t, J = 4.8 Hz, 4H), 2.52 (s, 3H) |

Example 26: Synthesis of Compound 143

Synthesis of Intermediate B246

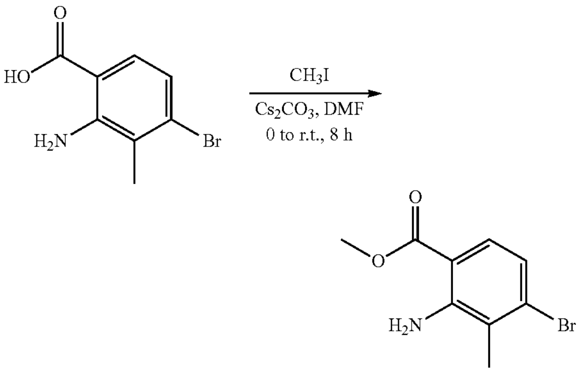

B246

To a mixture of 2-amino-4-bromo-3-methylbenzoic acid (10.00 g, 43.467 mmol, 1.00 equiv) and $Cs_2CO_3$ (21.24 g, 65.201 mmol, 1.50 equiv) in DMF (100 mL) was added methyl iodide (7.40 g, 52.160 mmol, 1.20 equiv) dropwise at 0° C. under nitrogen atmosphere. The reaction mixture was stirred for 8 h at room temperature under nitrogen atmosphere, then quenched with water. The resulting mixture was extracted with ethyl acetate (3×100 mL), dried over anhydrous $Na_2SO_4$, and filtered. After filtration, the filtrate was concentrated under reduced pressure to afford methyl 2-amino-4-bromo-3-methylbenzoate (10 g, 94.25%) as a solid. LCMS (ES, m/z): 244 $[M+H]^+$.

Synthesis of Intermediate B247

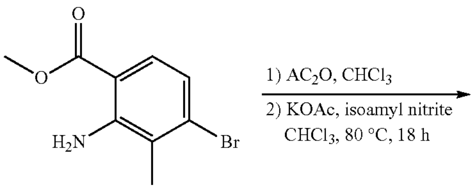

B246

-continued

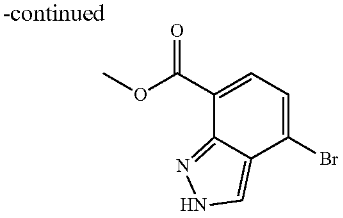

B247

To a mixture of methyl 2-amino-4-bromo-3-methylbenzoate (10.00 g, 40.969 mmol, 1.00 equiv) and $AC_2O$ in chloroform (100 mL) was added KOAC and isoamyl nitrite in portions over 1 h at room temperature under nitrogen atmosphere. The reaction mixture was stirred for an additional 18 h at 80° C. The resulting mixture was extracted with dichloromethane (3×100 mL), dried over anhydrous $Na_2SO_4$, and filtered. After filtration, the filtrate was concentrated under reduced pressure to afford methyl 4-bromo-2H-indazole-7-carboxylate (9.1 g, 87.08%) as a solid. LCMS (ES, m/z): $254[M+H]^+$.

Synthesis of Intermediate B248

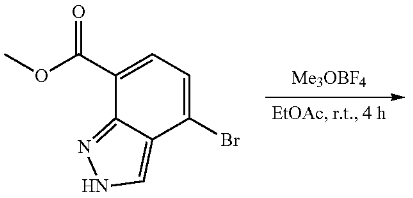

B247

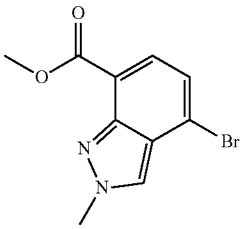

B248

A mixture of methyl 4-bromo-2H-indazole-7-carboxylate (2.00 g) and $Me_3OBF_4$ (2.10 g, 1.30 equiv) in ethyl acetate (20 mL) was stirred at room temperature for 4 h under nitrogen atmosphere. The reaction mixture was basified to pH 8 with saturated $NaHCO_3$ aqueous, then resulting mixture was extracted with ethyl acetate (3×50 mL), dried over anhydrous $Na_2SO_4$, and filtered. After filtration, the filtrate was concentrated under reduced pressure to afford methyl 4-bromo-2-methylindazole-7-carboxylate (1.9 g, 90.04%) as a solid. LCMS (ES, m/z): 269 $[M+H]^+$.

Synthesis of Intermediate B249

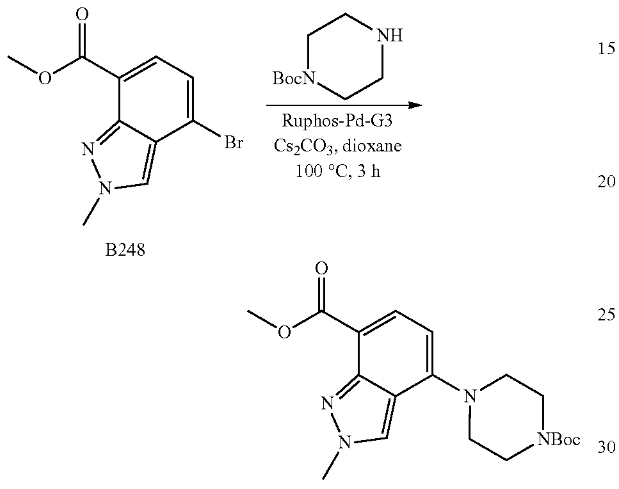

B248

B249

To a mixture of methyl 4-bromo-2-methylindazole-7-carboxylate (1.80 g, 6.689 mmol, 1.00 equiv) and tert-butyl piperazine-1-carboxylate (1.50 g, 8.027 mmol, 1.20 equiv) in 1,4-dioxane was added RuPhos Palladacycle Gen.3 (0.56 g, 0.669 mmol, 0.10 equiv) and $Cs_2CO_3$ (6.54 g, 20.067 mmol, 3.00 equiv) in portions at room temperature under nitrogen atmosphere. The reaction mixture was stirred overnight at 100° C. under nitrogen atmosphere. The resulting mixture was quenched with water and extracted with ethyl acetate (3×50 mL), washed with saturated NaCl (1×50 mL). The organic layers were combined, dried over anhydrous $Na_2SO_4$, and filtered. After filtration, the filtrate was concentrated under reduced pressure to give a residue. The residue was purified by silica gel column chromatography, eluted with PE/EA (1:1), to afford methyl 4-[4-(tert-butoxycarbonyl) piperazin-1-yl]-2-methylindazole-7-carboxylate (1.2 g, 47.91%) as a solid. LCMS (ES, m/z): 375 $[M+H]^+$.

Synthesis of Intermediate B250

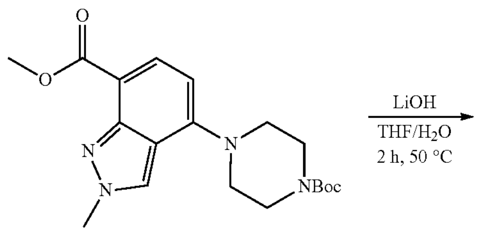

B249

-continued

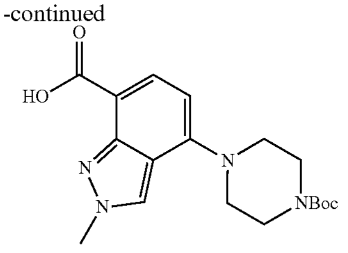

B250

To methyl 4-[4-(tert-butoxycarbonyl) piperazin-1-yl]-2-methylindazole-7-carboxylate (200.00 mg, 0.534 mmol, 1.00 equiv) in a mixture of THF (2 mL) and $H_2O$ (2 mL) was added LiOH (0.05 g, 2.136 mmol, 4.00 equiv). The reaction mixture was stirred for 2 h at 50° C. under nitrogen atmosphere. The resulting mixture was adjusted to pH 4 with 1 N HCl, extracted with ethyl acetate (3×10 mL), dried over anhydrous $Na_2SO_4$, and filtered. After filtration, the filtrate was concentrated under reduced pressure to afford 4-[4-(tert-butoxycarbonyl)piperazin-1-yl]-2-methylindazole-7-carboxylic acid (190 mg, 98.70%) as a solid. LCMS (ES, m/z): 361 $[M+H]^+$.

Synthesis of Intermediate B251

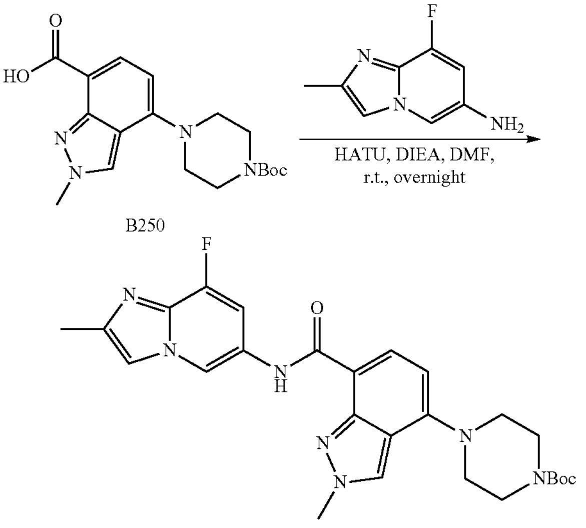

B250

B251

To a mixture of 4-[4-(tert-butoxycarbonyl)piperazin-1-yl]-2-methylindazole-7-carboxylic acid (170 mg, 0.472 mmol, 1.00 equiv) and 8-fluoro-2-methylimidazo[1,2-a] pyridin-6-amine (93.49 mg, 0.000 mmol, 1.20 equiv) in DMF (2 mL) was added HATU (269.02 mg, 0.708 mmol, 1.50 equiv) and DIEA (300.02 mg, 0.708 mmol, 3.00 equiv) in portions at room temperature under nitrogen atmosphere. The reaction mixture was stirred for overnight, then quenched with water (10 mL), extracted with ethyl acetate (3×10 mL), dried over anhydrous $Na_2SO_4$, and filtered. After filtration, the filtrate was concentrated under reduced pressure to afford tert-butyl 4-[7-([8-fluoro-2-methylimidazo[1,2-a]pyridin-6-yl]carbamoyl)-2-methylindazol-4-yl]piperazine-1-carboxylate (201 mg, 83.96%) as a solid. LCMS (ES, m/z): 508$[M+H]^+$.

Synthesis of Compound 143

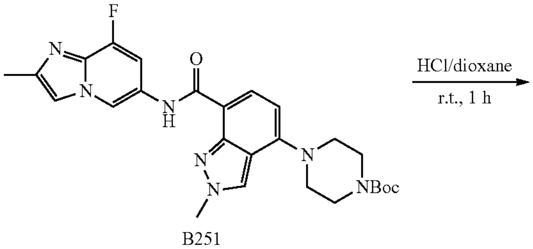

B251

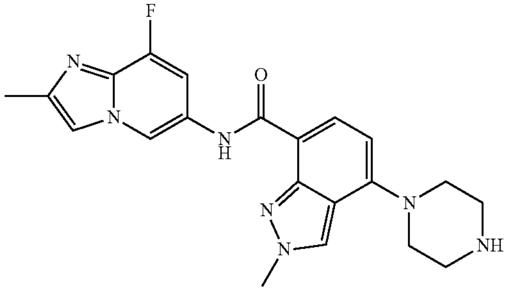

143

A mixture of tert-butyl 4-[7-([8-fluoro-2-methylimidazo[1,2-a]pyridin-6-yl]carbamoyl)-2-methylindazol-4-yl]piperazine-1-carboxylate (201 mg) and HCl (gas)/dioxane in 1,4-dioxane (2 mL) was stirred for 1 h at room temperature under nitrogen atmosphere. The resulting mixture was concentrated under reduced pressure to give a residue. The residue was purified by Prep-HPLC (Condition 2, Gradient 15) to afford N-[8-fluoro-2-methylimidazo[1,2-a]pyridin-6-yl]-2-methyl-4-(piperazin-1-yl) indazole-7-carboxamide (42.2 mg) as a solid. LCMS (ES, m/z): 408$[M+H]^+$. $^1H$ NMR (400 MHz, DMSO-$d_6$) δ 11.07 (s, 1H), 9.22 (d, J=1.7 Hz, 1H), 8.88 (s, 1H), 8.01 (d, J=8.0 Hz, 1H), 7.91 (d, J=3.1 Hz, 1H), 7.36 (dd, J=12.4, 1.7 Hz, 1H), 6.58 (d, J=8.1 Hz, 1H), 4.32 (s, 3H), 3.54 (dd, J=6.8, 3.6 Hz, 4H), 3.22 (dd, J=6.4, 3.6 Hz, 4H), 2.36 (s, 3H).

Example 27: Synthesis of Compound 145

Synthesis of Intermediate B252

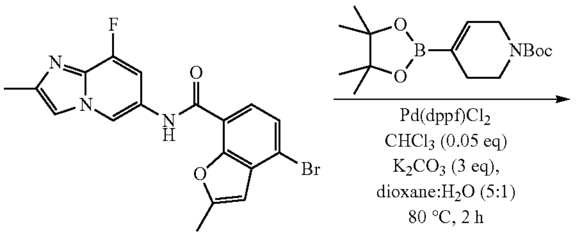

B222

-continued

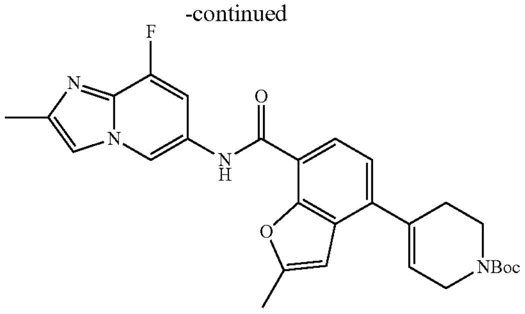

B252

To a mixture of 4-bromo-N-[8-fluoro-2-methylimidazo[1,2-a]pyridine-6-yl]-2-methyl-1-benzofuran-7-carboxamide (200.00 mg, 0.497 mmol, 1.00 equiv) and tert-butyl 4-(4,4,5,5-tetramethyl-1,3,2-dioxaborolan-2-yl)-3,6-dihydro-2H-pyridine-1-carboxylate (153.75 mg, 0.497 mmol, 1 equiv) in 1,4-dioxane (20 ml) and water (4 ml) was added Pd(dppf)$Cl_2$ (40.51 mg, 0.050 mmol, 0.1 equiv) and $K_2CO_3$ (206.16 mg, 1.492 mmol, 3.00 equiv). The reaction mixture was stirred for 2 h at 80° C. under a nitrogen atmosphere, then quenched with water at room temperature. The resulting mixture was extracted with DCM (3×20 mL). The combined organic layers were washed with brine (2×10 mL), dried over anhydrous $Na_2SO_4$, and filtered. After filtration, the filtrate was concentrated under reduced pressure to give a residue. The residue was purified by Prep-TLC/silica gel column chromatography, eluted with DCM/MeOH (10:1), to afford tert-butyl 4-[7-([8-fluoro-2-methylimidazo[1,2-a]pyridin-6-yl]carbamoyl)-2-methyl-1-benzofuran-4-yl]-3,6-dihydro-2H-pyridine-1-carboxylate (160 mg, 63.77%) as a solid. LCMS (ES, m/z): 505 $[M+H]^+$.

Synthesis of Intermediate B253

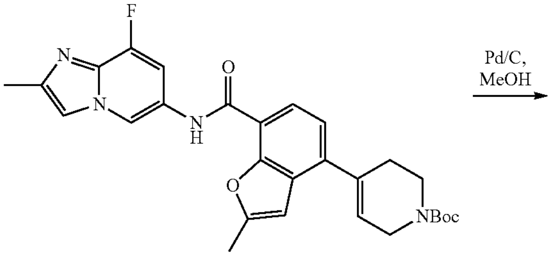

B252

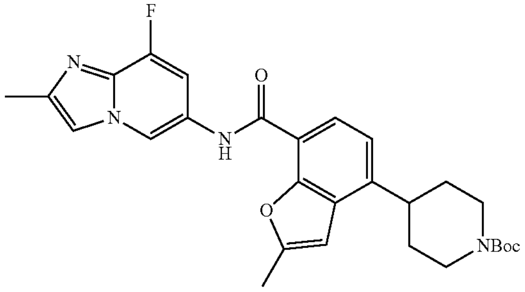

B253

To a solution of tert-butyl 4-[7-([8-fluoro-2-methylimidazo[1,2-a]pyridine-6-yl]carbamoyl)-2-methyl-1-benzofuran-4-yl]-3,6-dihydro-2H-pyridine-1-carboxylate (150 mg) in methanol (15 mL) was added Pd/C (10%, 15 mg) under nitrogen atmosphere in a 100 mL sealed tube. The reaction mixture was hydrogenated at room temperature for 6 h under a hydrogen atmosphere using a hydrogen balloon, then filtered through a Celite pad, and concentrated under reduced pressure to afford tert-butyl 4-[7-([8-fluoro-2-methylimidazo[1,2-a]pyridin-6-yl]carbamoyl)-2-methyl-1-benzofuran-4-yl]piperidine-1-carboxylate (120 mg) as a solid. LCMS (ES, m/z): 507 [M+H]$^+$.

Synthesis of Compound 145

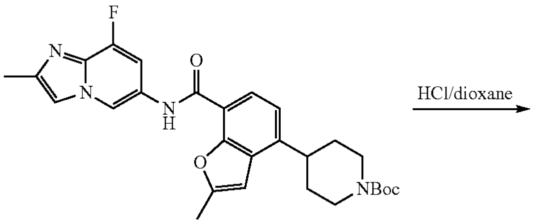

B253

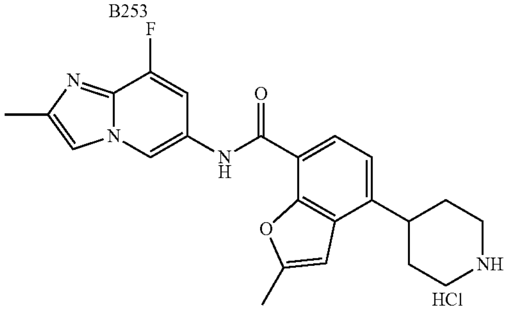

145

A mixture of tert-butyl 4-[7-([8-fluoro-2-methylimidazo[1,2-a]pyridine-6-yl]carbamoyl)-2-methyl-1-benzofuran-4-yl]piperidine-1-carboxylate (110.00 mg), HCl (gas) in 1,4-dioxane (2 mL), and methanol (2 mL) was stirred for 30 min at room temperature, then concentrated under reduced pressure to give a residue. The residue was purified by reverse flash chromatography (Column: silica gel; Mobile Phase: acetonitrile in water; Gradient: 10% to 50% in 10 min; detector, UV 254 nm), followed by prep-HPLC (Condition 1, Gradient 23) to afford N-[8-fluoro-2-methylimidazo[1,2-a]pyridin-6-yl]-2-methyl-4-(piperidin-4-yl)-1-benzofuran-7-carboxamide (90 mg) as a solid. LCMS (ES, m/z): 407 [M+H]$^+$.

Example 28: Synthesis of Compound 256

Synthesis of Compound 256

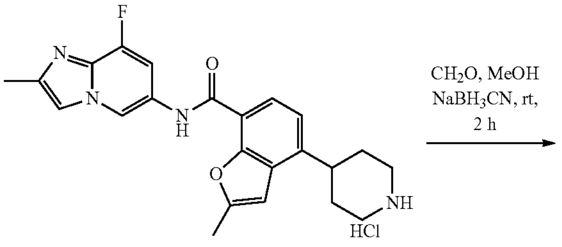

145

-continued

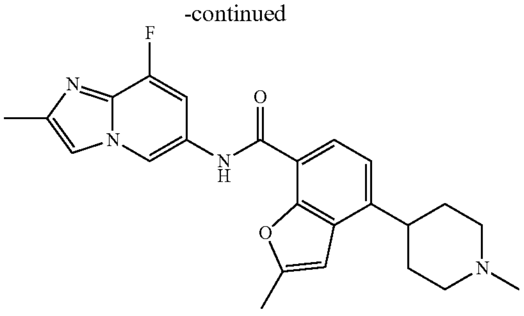

256

A mixture of N-[8-fluoro-2-methylimidazo[1,2-a]pyridin-6-yl]-2-methyl-4-(piperidin-4-yl)-1-benzofuran-7-carboxamide (45.00 mg, 0.111 mmol, 1.00 equiv), HCHO (2.00 mL, 54.619 mmol, 493.35 equiv), and methanol (4 mL) was stirred for 1 h at room temperature. To the reaction mixture was added NaBH$_3$CN (10.00 mg, 0.159 mmol, 1.44 equiv) dropwise at room temperature. The resulting mixture was stirred for an additional 30 min at room temperature, then concentrated in vacuo to give a residue. The residue was purified by reverse flash chromatography (Column: silica gel; Mobile Phase: acetonitrile in water; Gradient: 10% to 50% in 10 min; detector, UV 254 nm) followed by prep-HPLC (Condition 1, Gradient 23) to afford N-[8-fluoro-2-methylimidazo[1,2-a]pyridin-6-yl]-2-methyl-4-(1-methylpiperidin-4-yl)-1-benzofuran-7-carboxamide (17.1 mg, 36.73%) as a solid. LCMS (ES, m/z): 421 [M+H]$^+$. $^1$H NMR (400 MHz, DMSO-d$_6$) δ 10.28 (s, 1H), 9.17 (d, J=1.6 Hz, 1H), 7.93 (dd, J=3.2, 1.0 Hz, 1H), 7.58 (d, J=7.8 Hz, 1H), 7.28 (dd, J=12.6, 1.6 Hz, 1H), 7.21 (d, J=7.9 Hz, 1H), 6.85 (d, J=1.3 Hz, 1H), 2.92 (dd, J=8.9, 5.6 Hz, 2H), 2.84 (dq, J=10.6, 4.9 Hz, 1H), 2.5 (m, 3H), 2.35 (s, 3H), 2.24 (s, 3H), 2.06 (dt, J=11.0, 5.6 Hz, 2H), 1.81 (td, J=10.6, 9.8, 3.7 Hz, 4H).

Example 29: Synthesis of Compound 257

Synthesis of Compound 257

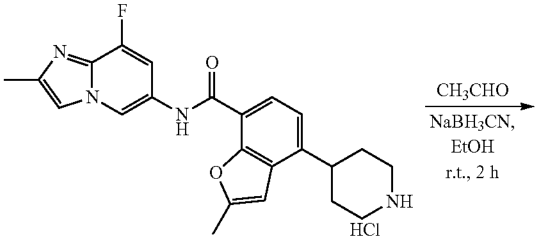

145

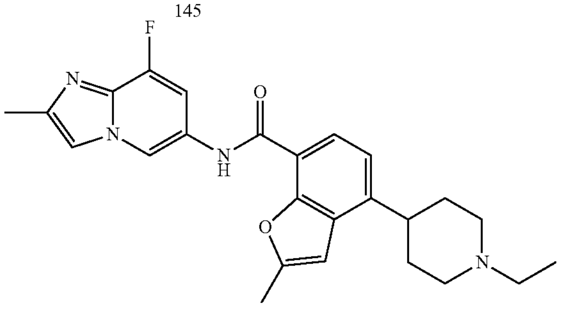

257

A mixture of N-[8-fluoro-2-methylimidazo[1,2-a]pyridin-6-yl]-2-methyl-4-(piperidin-4-yl)-1-benzofuran-7-carboxamide (45.00 mg), $CH_3CHO$ (2.00 mL), and ethanol (4 mL) was stirred for 1 h at room temperature. To the reaction mixture was added $NaBH_3CN$ (10.00 mg). The resulting mixture was stirred for an additional 1 h at room temperature, then concentrated under reduced pressure to give a residue. The residue was purified by reverse flash chromatography (Column: silica gel; Mobile Phase: acetonitrile in water; Gradient: 10% to 50% in 10 min; detector, UV 254 nm), followed by prep-HPLC (Condition 1, Gradient 23) to afford 4-(1-ethylpiperidin-4-yl)-N-[8-fluoro-2-methylimidazo[1,2-a]pyridin-6-yl]-2-methyl-1-benzofuran-7-carboxamide (16.7 mg) as a solid. LCMS (ES, m/z): 435 $[M+H]^+$. $^1H$ NMR (400 MHz, DMSO-$d_6$) δ 10.28 (s, 1H), 9.17 (d, J=1.6 Hz, 1H), 7.93 (d, J=3.1 Hz, 1H), 7.58 (d, J=7.8 Hz, 1H), 7.28 (dd, J=12.6, 1.7 Hz, 1H), 7.22 (d, J=7.8 Hz, 1H), 6.85 (s, 1H), 3.02 (dd, J=8.8, 5.4 Hz, 2H), 2.89 (q, J=7.7, 7.2 Hz, 1H), 2.51 (s, 3H), 2.44-2.33 (m, 5H), 2.11-1.98 (m, 2H), 1.80 (dt, J=9.2, 4.5 Hz, 4H), 1.05 (t, J=7.2 Hz, 3H).

Example 30: Synthesis of Compound 271

Synthesis of Intermediate B254

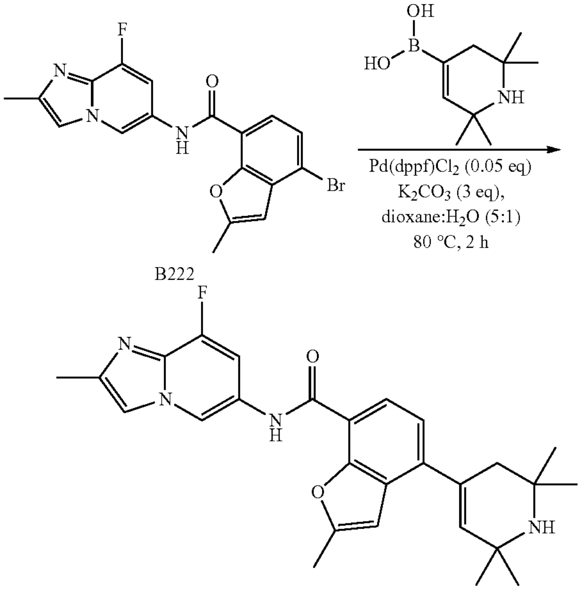

B222

B254

To a mixture of 4-bromo-N-[8-fluoro-2-methylimidazo[1,2-a]pyridin-6-yl]-2-methyl-1-benzofuran-7-carboxamide (100.00 mg, 0.249 mmol, 1.00 equiv) and 2,2,6,6-tetramethyl-1,3-dihydropyridin-4-ylboronic acid (45.51 mg, 0.249 mmol, 1 equiv) in 1,4-dioxane (20 mL) and water (4 ml) was added Pd(dppf)$Cl_2$ (20.25 mg, 0.025 mmol, 0.1 equiv) and $K_2CO_3$ (103.08 mg, 0.746 mmol, 3.00 equiv). The reaction mixture as stirred for 2 h at 80° C. under a nitrogen atmosphere, then concentrated under reduced pressure to give a residue. The residue was purified by Prep-TLC/silica gel column chromatography, eluted with $CH_2Cl_2$/methanol (10:1), to afford N-[8-fluoro-2-methylimidazo[1,2-a]pyridin-6-yl]-2-methyl-4-(2,2,6,6-tetramethyl-1,3-dihydropyridin-4-yl)-1-benzofuran-7-carboxamide (64 mg, 55.89%) as a solid. LCMS (ES, m/z): 461 $[M+H]^+$.

Synthesis of Compound 271

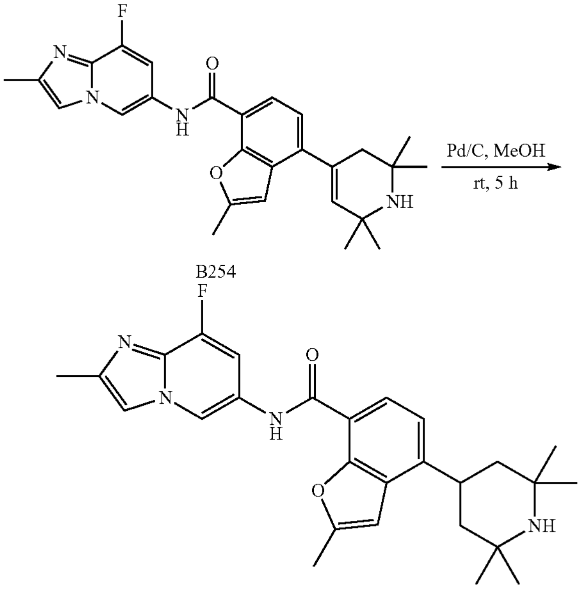

B254

271

A mixture of N-[8-fluoro-2-methylimidazo[1,2-a]pyridin-6-yl]-2-methyl-4-(2,2,6,6-tetramethyl-1,3-dihydropyridin-4-yl)-1-benzofuran-7-carboxamide (54 mg), Pd/C (1.00 mg), and methanol (1.00 mL) was stirred for 5 h at room temperature. The resulting mixture was filtered and the filter cake was washed with methanol (3×10 mL). The filtrate was concentrated under reduced pressure to give a residue. The residue was purified by reverse flash chromatography (Column: silica gel; Mobile Phase: acetonitrile in water; Gradient: 10% to 50% in 10 min; detector, UV 254 nm), followed by prep-HPLC (Condition 1, Gradient 23) to afford N-[8-fluoro-2-methylimidazo[1,2-a]pyridin-6-yl]-2-methyl-4-(2,2,6,6-tetramethylpiperidin-4-yl)-1-benzofuran-7-carboxamide (5 mg) as a solid. LCMS (ES, m/z): 463 $[M+H]^+$. $^1H$ NMR (400 MHz, DMSO-d6) δ 10.31 (s, 1H), 9.17 (d, J=1.6 Hz, 1H), 8.36 (s, 2H), 7.94 (d, J=3.1 Hz, 1H), 7.61 (d, J=7.9 Hz, 1H), 7.30 (dd, J=12.5, 1.7 Hz, 1H), 7.21 (d, J=7.9 Hz, 1H), 6.92 (d, J=1.3 Hz, 1H), 3.53-3.42 (m, 1H), 2.53 (d, J=1.1 Hz, 3H), 2.36 (s, 3H), 1.73-1.66 (s, 2H), 1.61-1.52 (m, 2H), 1.40 (s, 6H), 1.24 (s, 6H).

Example 31: Synthesis of Compound 277

Synthesis of Intermediate 255

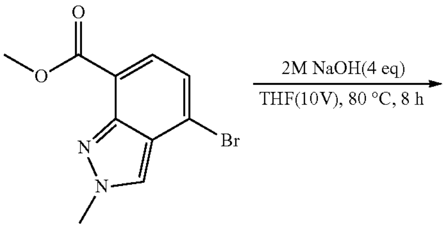

-continued

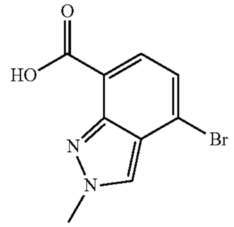

B255

A mixture of methyl 4-bromo-2-methylindazole-7-carboxylate (1.5 g, 5.57 mmol, 1.00 equiv) and NaOH (2 M) (10 mL, 4.00 equiv) in THF (10 mL) was stirred for 8 h at 80° C. The reaction mixture was acidified to pH 4 with HCl (aq.), then extracted with diethyl ether (3×20 mL). The combined organic layers were washed with saturated NaCl aq (1×20 mL), dried over anhydrous $MgSO_4$, and filtered. After filtration, the filtrate was concentrated under reduced pressure to afford 4-bromo-2-methylindazole-7-carboxylic acid (1.1 g, 77.3%) as a solid. LCMS (ES, m/z): 255 $[M+H]^+$.

Synthesis of Intermediate B256

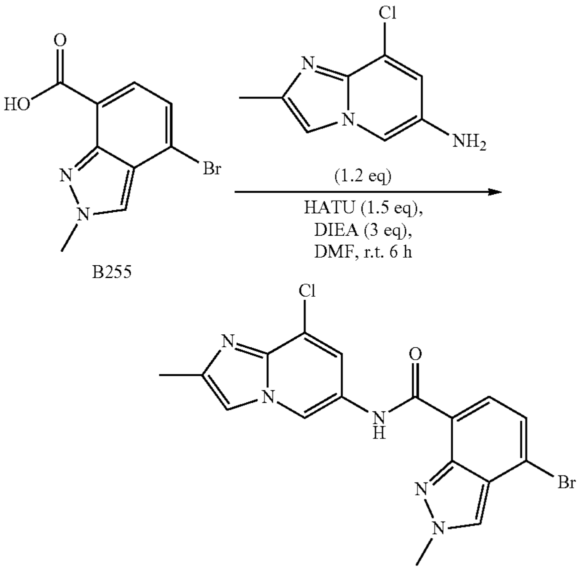

B255

B256

To a mixture of 4-bromo-2-methylindazole-7-carboxylic acid (1.1 g, 4.31 mmol, 1.00 equiv) and 8-chloro-2-methylimidazo[1,2-a]pyridin-6-amine (1.1 g, 6.47 mmol, 1.50 equiv) in DMF (30 ml) was added HATU (2.4 g, 6.47 mmol, 1.50 equiv) and DIEA (1.6 g, 12.94 mmol, 3.00 equiv) in portions. The reaction mixture was stirred for 6 h at room temperature, then extracted with diethyl ether (3×20 mL). The combined organic layers were washed with saturated NaCl (1×20 mL), dried over anhydrous $Na_2SO_4$, and filtered. After filtration, the filtrate was concentrated under reduced pressure to give a residue. The residue was purified by silica gel column chromatography, eluted with $CH_2Cl_2$/PE (5:01), to afford 4-bromo-N-{8-chloro-2-methylimidazo[1,2-a]-pyridin-6-yl}-2-methylindazole-7-carboxamide (1.20 g, 66.4%) as a solid. LCMS (ES, m/z): 418 $[M+H]^+$.

Synthesis of Intermediate B257

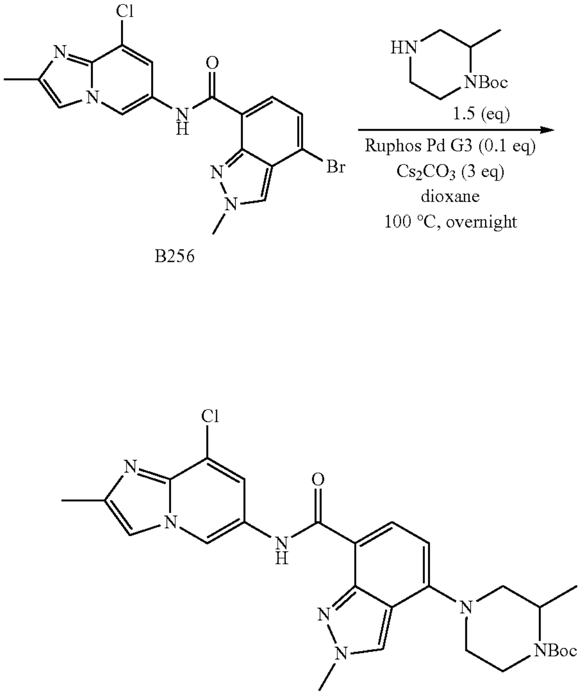

B256

B257

To a stirred mixture of 4-bromo-N-{8-chloro-2-methylimidazo[1,2-a]pyridin-6-yl}-2-methylindazole-7-carboxamide (100.0 mg, 0.24 mmol, 1.00 equiv) and tert-butyl 2-methylpiperazine-1-carboxylate (71.7 mg, 0.36 mmol, 1.50 equiv) in 1,4-dioxane (3 mL) was added $Cs_2CO_3$ (233.4 mg, 0.72 mmol, 3.00 equiv) and RuPhos Palladacycle Gen.3 (19.98 mg, 0.02 mmol, 0.10 equiv) in portions. The reaction mixture was stirred for 10 h at 100° C. under nitrogen atmosphere, then extracted with diethyl ether (3×10 mL). The combined organic layers were washed with saturated NaCl (1×10 mL), dried over anhydrous $Na_2SO_4$, and filtered. After filtration, the filtrate was concentrated under reduced pressure to give a residue. The residue was purified by silica gel column chromatography, eluted with PE/EA (1:4), to afford tert-butyl 4-[7-({8-chloro-2-methy-limidazo[1,2-a]pyridin-6-yl}carbamoyl)-2-methylindazol-4-yl]-2-methylpiperazine-1-carboxylate as a solid. LCMS (ES, m/z): 538 $[M+H]^+$.

Synthesis of Compound 277

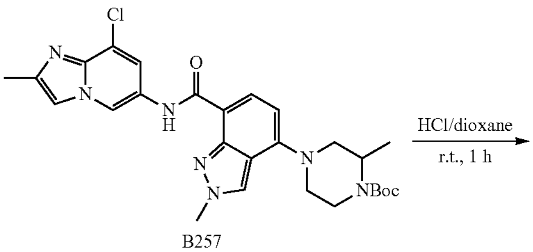

B257

-continued

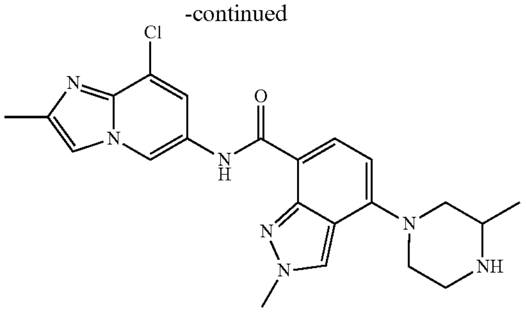

277

A solution of tert-butyl 4-[7-({8-chloro-2-methylimidazo[1,2-a]pyridin-6-yl}carbamoyl)-2-methylinda-zol-4-yl]-2-methylpiperazine-1-carboxylate (70.0 mg, 0.13 mmol, 1.00 equiv) in HCl/dioxane (4 mol/L, 10 mL) was stirred for 1 h at room temperature. The resulting mixture was concentrated under reduced pressure to give a residue. The residue was purified by reverse flash chromatography (Condition 1, Gradient 24) to afford N-{8-chloro-2-methylimidazo[1,2-a]pyridine-6-yl}-2-methyl-4-(3-methylpiperazin-1-yl)indazole-7-carboxamide as a solid (11.8 mg). LCMS (ES, m/z): 438 $[M+H]^+$. $^1H$ NMR (400 MHz, DMSO-$d_6$) δ 11.06 (s, 1H), 9.33 (d, J=1.7 Hz, 1H), 8.80 (s, 1H), 7.97 (d, J=8.1 Hz, 1H), 7.90 (s, 1H), 7.58 (d, J=1.8 Hz, 1H), 6.49 (d, J=8.2 Hz, 1H), 4.30 (s, 3H), 3.81-3.73 (m, 2H), 3.04-2.94 (m, 1H), 2.90 (t, J=9.7 Hz, 3H), 2.58-2.51 (m, 1H), 2.36 (s, 4H), 1.07 (d, J=6.3 Hz, 3H).

Example 32: Synthesis of Compound 278

Synthesis of Compound 278

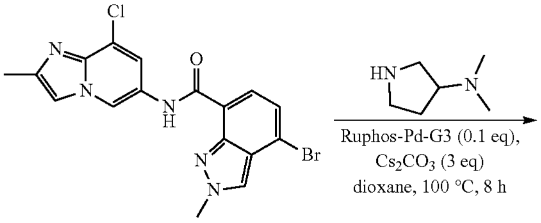

B256

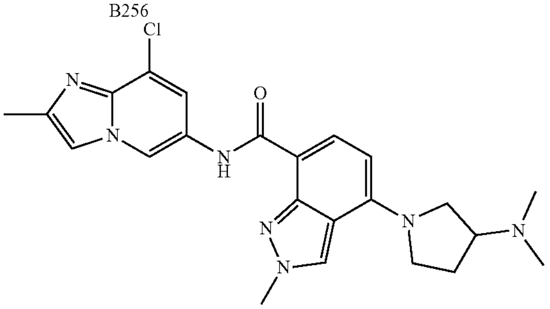

278

To a stirred mixture of 4-bromo-N-{8-chloro-2-methylimidazo[1,2-a]pyridin-6-yl}-2-methylindazole-7-carboxamide (200.00 mg, 0.49 mmol, 1.00 equiv) and N,N-dimethylpyrrolidin-3-amine (81.82 mg, 0.72 mmol, 1.50 equiv) in 1,4-dioxane was added RuPhos Palladacycle Gen.3 (39.95 mg, 0.05 mmol, 0.10 equiv) and $Cs_2CO_3$ (466.92 mg, 1.43 mmol, 3.00 equiv). The resulting mixture was stirred for 8 h at 100° C. under nitrogen atmosphere. The aqueous layer was extracted with diethyl ether (3×10 mL). The combined organic layers were washed with saturated NaCl (1×10 mL), dried over anhydrous $Na_2SO_4$, and filtered. After filtration, the filtrate was concentrated under reduced pressure to give a residue. The residue was purified by silica gel column chromatography, eluted with $CH_2Cl_2$/MeOH (1:4), followed by prep-HPLC (Condition 9, Gradient 6) to afford N-{8-chloro-2-methylimidazo[1,2-a]pyridin-6-yl}-4-[3-(dimethylamino)pyrrolidin-1-yl]-2-methylindazole-7-carboxamide (31.90 mg) as a solid. LCMS (ES, m/z): 452 $[M+H]^+$. $^1H$ NMR (400 MHz, DMSO-$d_6$) δ 10.99 (s, 1H), 9.30 (d, J=1.7 Hz, 1H), 8.85 (s, 1H), 7.93 (d, J=8.2 Hz, 1H), 7.88 (s, 1H), 7.52 (d, J=1.7 Hz, 1H), 6.04 (d, J=8.4 Hz, 1H), 4.28 (s, 3H), 3.83 (t, J=8.4 Hz, 1H), 3.76 (t, J=9.4 Hz, 1H), 3.68-3.57 (m, 1H), 3.45 (t, J=9.1 Hz, 1H), 2.91 (d, J=8.1 Hz, 1H), 2.35 (s, 3H), 2.29 (s, 6H), 2.27-2.20 (m, 1H), 1.92 (q, J=10.3 Hz, 1H).

Example 33: Synthesis of Compound 285

Synthesis of Intermediate B258

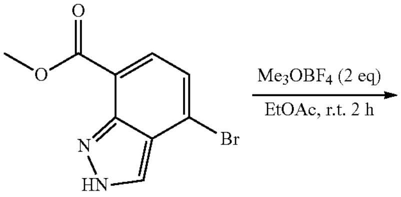

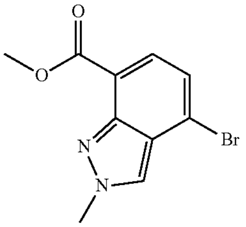

B258

A mixture of methyl 4-bromo-2H-indazole-7-carboxylate (500.0 mg, 1.96 mmol, 1.00 equiv) and tetrafluoroboranuide; trimethyloxidanium (579.8 mg, 3.92 mmol, 2.00 equiv) in ethyl acetate (10.00 mL, 102.14 mmol, 52.11 equiv) was stirred for 16 h at room temperature. The resulting mixture was partitioned between water and ethyl acetate, and extracted with ethyl acetate (3×10 mL). The combined organic layers were washed with saturated NaCl (1×10 mL), dried over anhydrous $Na_2SO_4$, and filtered. After filtration, the filtrate was concentrated under reduced pressure to afford methyl 4-bromo-2-methylindazole-7-carboxylate (500.0 mg, 94.7%) as a solid. LCMS (ES, m/z): 269 $[M+H]^+$.

Synthesis of Intermediate B259

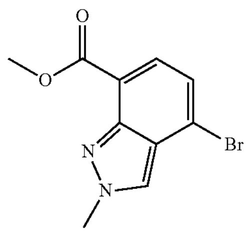

B258

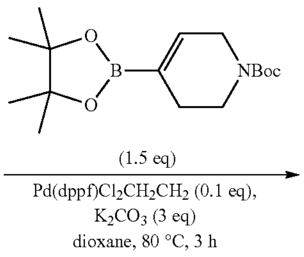

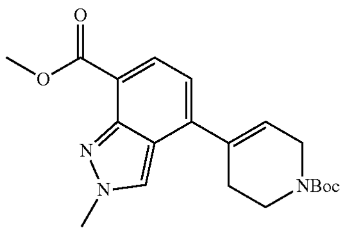

B259

To a stirred mixture of methyl 4-bromo-2-methylindazole-7-carboxylate (170.0 mg, 0.63 mmol, 1.00 equiv) and tert-butyl 4-(4,4,5,5-tetramethyl-1,3,2-dioxaborolan-2-yl)-3,6-dihydro-2H-pyridine-1-carboxylate (293.0 mg, 0.95 mmol, 1.50 equiv) in 1,4-dioxane (5 mL) was added Pd(dppf)$Cl_2CH_2Cl_2$ (51.4 mg, 0.06 mmol, 0.10 equiv) and $K_2CO_3$ (261.9 mg, 1.90 mmol, 3.00 equiv). The reaction mixture was stirred for 3 h at 80° C. under nitrogen atmosphere, then extracted with ethyl acetate (3×10 mL). The combined organic layers were washed with saturated NaCl (1×10 mL), dried over anhydrous $Na_2SO_4$, and filtered. After filtration, the filtrate was concentrated under reduced pressure to give a residue. The residue was purified by silica gel column chromatography, eluted with $CH_2Cl_2$/PE (5:01), to afford methyl 4-[1-(tert-butoxycarbonyl)-3,6-dihydro-2H-pyridin-4-yl]-2-methylindazole-7-carboxylate (180.0 mg, 76.7%) as a solid. LCMS (ES, m/z): 371 $[M+H]^+$.

Synthesis of Intermediate B260

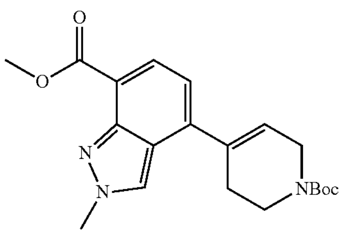

B259

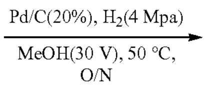

-continued

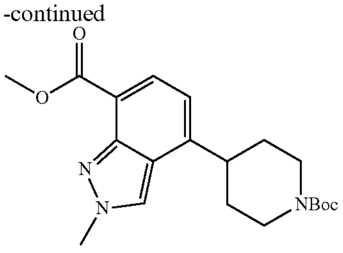

B260

To a stirred mixture of methyl 4-[1-(tert-butoxycarbonyl)-3,6-dihydro-2H-pyridin-4-yl]-2-methy lindazole-7-carboxylate (180.0 mg, 0.49 mmol, 1.00 equiv) and Pd/C (36.00 mg) in MeOH was added $H_2$ (4 MPa). The reaction mixture was stirred for 2 days at 50° C. The resulting mixture was filtered, and the filter cake washed with MeOH (3×5 mL). The filtrate was concentrated under reduced pressure to afford methyl 4-[1-(tert-butoxycarbonyl)-piperidin-4-yl]-2-methylindazole-7-carboxylate (180.0 mg, 99.4%) as an oil. LCMS (ES, m/z): 374 $[M+H]^+$.

Synthesis of Intermediate B261

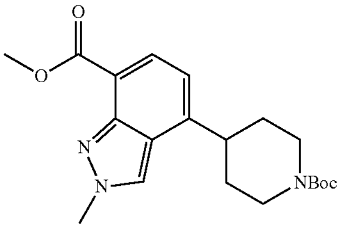

B260

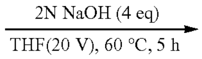

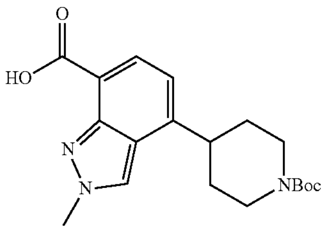

B261

A mixture of methyl 4-[1-(tert-butoxycarbonyl)piperidin-4-yl]-2-methylindazole-7-carboxylate (180.0 mg, 0.48 mmol, 1.00 equiv) and NaOH (2M) (9.6 mL, 4.00 equiv) in THF (10 mL) was stirred for 5 h at 50° C. The reaction mixture was acidified to pH 4 with HCl (aq.). The resulting mixture was extracted with ethyl acetate (3×10 mL). The combined organic layers were washed with saturated NaCl (1×10 mL), dried over anhydrous $Na_2SO_4$, and filtered. After filtration, the filtrate was concentrated under reduced pressure to afford 4-[1-(tert-butoxycarbonyl)-piperidin-4-yl]-2-methylindazole-7-carboxylic acid (160.0 mg, 92.3%) as a solid. LCMS (ES, m/z): 360 $[M+H]^+$.

Synthesis of Intermediate B262

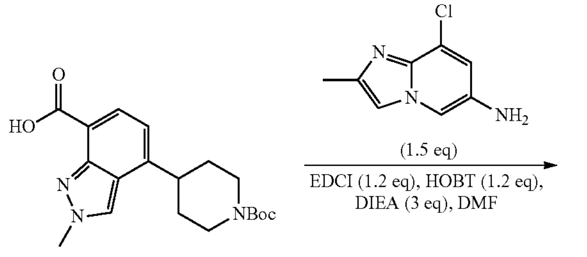

B261

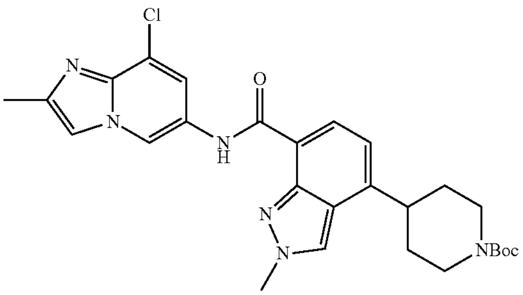

B262

To a stirred mixture of 4-[1-(tert-butoxycarbonyl)piperidin-4-yl]-2-methylindazole-7-carboxylic acid (80.00 mg, 0.22 mmol, 1.00 equiv) and 8-chloro-2-methylimidazo[1,2-a]pyridin-6-amine (48.51 mg, 0.27 mmol, 1.20 equiv) in DMF (5 ml) was added HOBT (36.09 mg, 0.27 mmol, 1.20 equiv), DIEA (86.30 mg, 0.67 mmol, 3.00 equiv) and EDCI (51.20 mg, 0.27 mmol, 1.20 equiv). The reaction mixture was stirred for 6 h at 40° C. The resulting mixture was extracted with ethyl acetate (3x10 mL). The combined organic layers were washed with saturated NaCl (1x10 mL), dried over anhydrous $Na_2SO_4$, and filtered. After filtration, the filtrate was concentrated under reduced pressure to afford tert-butyl 4-[7-({8-chloro-2-methylimidazo[1,2-a]pyridin-6-yl}carbamoyl)-2-methylindazol-4-yl]piperidine-1-carboxylate (100.00 mg, 85.90%) as a solid. LCMS (ES, m/z): 523 [M+H]+.

Synthesis of Compound 285

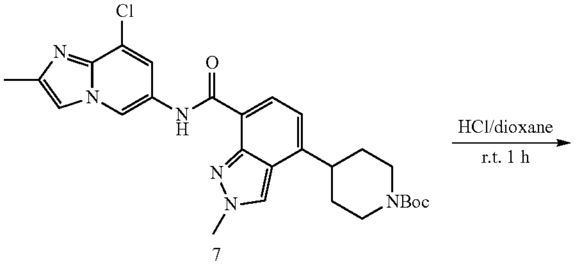

7
B262

-continued

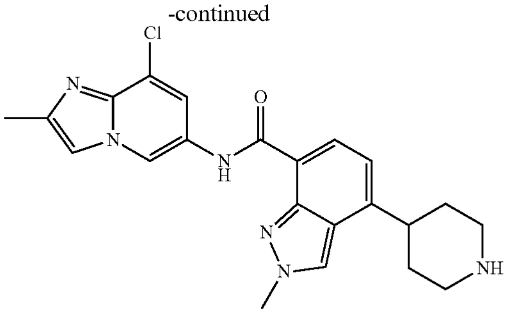

285

A solution of tert-butyl 4-[7-({8-chloro-2-methylimidazo[1,2-a]pyridin-6-yl}carbamoyl)-2-methy-lindazol-4-yl]piperidine-1-carboxylate (100.00 mg, 0.19 mmol, 1.00 equiv) in HCl/dioxane (5 mL) was stirred for 1 h at room temperature. The resulting mixture was concentrated under reduced pressure to give a residue. The residue was purified by prep-HPLC (Condition 9, Gradient 7) to afford N-{8-chloro-2-methylimidazo[1,2-a]pyridin-6-yl}-2-methyl-4-(piperidin-4-yl) indazole-7-carboxamide (24.3 mg, 30.05%) as a solid. LCMS (ES, m/z): 423 [M+H]+. $^1$H NMR (400 MHz, DMSO-$d_6$) δ 11.12 (s, 1H), 9.36 (d, J=1.8 Hz, 1H), 8.88 (s, 1H), 8.04 (d, J=7.3 Hz, 1H), 7.92 (s, 1H), 7.60 (d, J=1.7 Hz, 1H), 7.10 (d, J=7.4 Hz, 1H), 4.35 (s, 3H), 3.08 (t, J=11.3 Hz, 3H), 2.71 (d, J=11.2 Hz, 2H), 2.36 (s, 3H), 1.82 (d, J=12.3 Hz, 2H), 1.74 (dd, J=11.6, 3.6 Hz, 2H).

Example 34: Synthesis of Compound 286

Synthesis of Intermediate B263

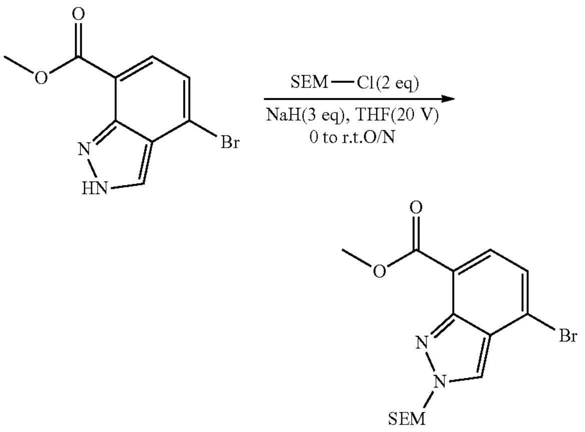

B263

To a stirred mixture of methyl 4-bromo-2H-indazole-7-carboxylate (2.0 g, 7.84 mmol, 1.00 equiv) and NaH (0.56 g, 23.52 mmol, 3.00 equiv) in THF (40 mL) was added SEM-Cl (2.61 g, 15.68 mmol, 2.00 equiv). The reaction mixture was stirred for 4 h at 0° C., then partitioned between water and ethyl acetate and extracted with ethyl acetate (3x20 mL). The combined organic layers were washed with saturated NaCl (1x40 mL), dried over anhydrous $Na_2SO_4$, and filtered. After filtration, the filtrate was concentrated under reduced pressure to afford methyl 4-bromo-2-{[2-(trimethylsilyl)ethoxy]methyl}indazole-7-carboxylate (1.50 g, 49.65%) as a solid. LCMS (ES, m/z): 385 [M+H]+.

Synthesis of Intermediate B264

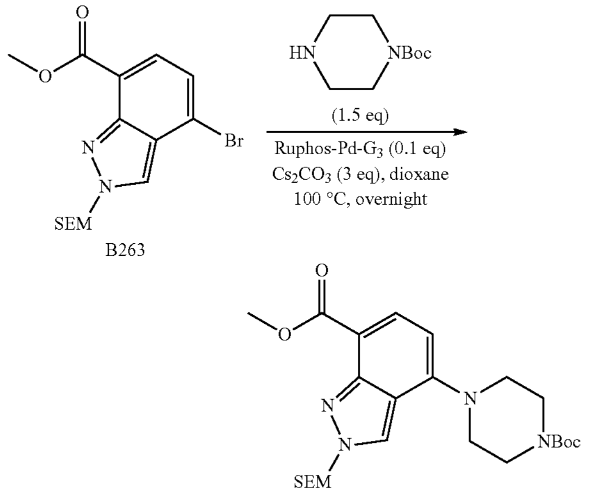

B263

B264

To a stirred mixture of methyl 4-bromo-2-{[2-(trimethylsilyl)ethoxy]methyl}indazole-7-carboxylate (1.50 g, 3.89 mmol, 1.00 equiv) and tert-butyl piperazine-1-carboxylate (1.09 g, 5.84 mmol, 1.50 equiv) in 1,4-dioxane (100 mL) was added RuPhos Palladacycle Gen.3 (0.33 g, 0.39 mmol, 0.10 equiv) and $Cs_2CO_3$ (3.80 g, 11.68 mmol, 3.00 equiv). The reaction mixture was stirred for 8 h at 100° C. under nitrogen atmosphere. The resulting mixture was extracted with ethyl acetate (3×50 mL). The combined organic layers were washed with saturated NaCl (lx 50 mL), dried over anhydrous $Na_2SO_4$, and filtered. After filtration, the filtrate was concentrated under reduced pressure. The residue was purified by silica gel column chromatography, eluted with $CH_2Cl_2$/MeOH (10:01), to afford methyl 4-[4-(tert-butoxycarbonyl)piperazin-1-yl]-2-{[2-(trimethylsilyl)-ethoxy]methyl}indazole-7-carboxylate (0.95 g, 49.74%) as a solid. LCMS (ES, m/z): 491 $[M+H]^+$.

Synthesis of Intermediate B265

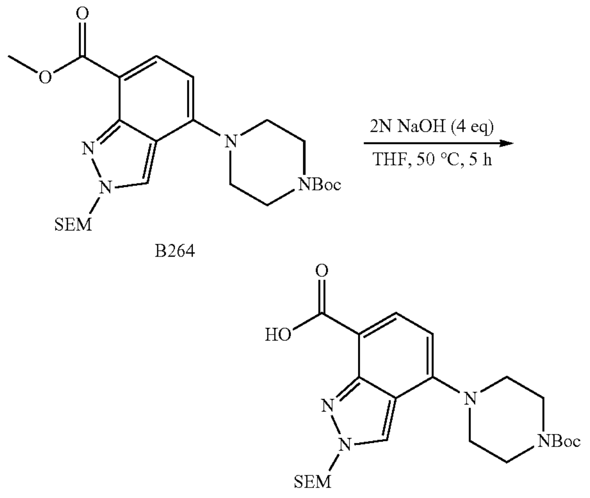

B264

B265

A mixture of methyl 4-[4-(tert-butoxycarbonyl)piperazin-1-yl]-2-{[2-(trimethylsilyl) ethoxy]methyl}indazole-7-carboxylate (500.00 mg, 1.02 mmol, 1.00 equiv) and NaOH (2M) (20 mL, 4.00 equiv) in THF (20 mL) was stirred for 5 h at 50° C. The reaction mixture was acidified to pH 4 with HCl (aq.). The resulting mixture was extracted with ethyl acetate (3×20 mL). The combined organic layers were washed with saturated NaCl (1×20 mL), dried over anhydrous $Na_2SO_4$, and filtered. After filtration, the filtrate was concentrated under reduced pressure to afford 4-[4-(tert-butoxycarbonyl)piperazin-1-yl]-2-{[2-(trimethylsilyl) ethoxy]methyl}indazole-7-carboxylic acid (450 mg, 92.65%) as a solid. LCMS (ES, m/z): 477 $[M+H]^+$.

Synthesis of Intermediate B266

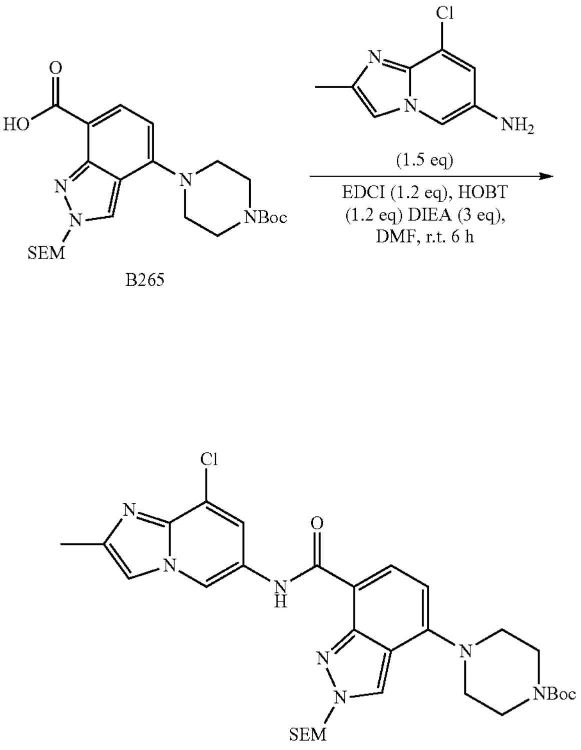

B265

B266

To a stirred mixture of 4-[4-(tert-butoxycarbonyl)piperazin-1-yl]-2-{[2-(trimethylsilyl)ethoxy]methyl}indazole-7-carboxylic acid (450.0 mg, 0.94 mmol, 1.00 equiv) and 8-chloro-2-methylimidazo [1,2-a]pyridin-6-amine (257.2 mg, 1.42 mmol, 1.50 equiv) in DMF (10 mL) was added HOBT (153.0 mg, 1.13 mmol, 1.20 equiv), DIEA (146.4 mg, 1.13 mmol, 1.20 equiv), and EDCI (542.9 mg, 2.83 mmol, 3.00 equiv). The reaction mixture was stirred for 8 h at 40° C., then extracted with ethyl acetate (3×10 mL). The combined organic layers were washed with saturated NaCl (1×10 mL), dried over anhydrous $Na_2SO_4$, and filtered. After filtration, the filtrate was concentrated under reduced pressure to afford tert-butyl 4-[7-({8-chloro-2-methylimidazo[1,2-a]pyridine-6-yl}carbamoyl)-2-{[2-(trimethyl silyl) ethoxy]methyl}-indazol-4-yl]piperazine-1-carboxylate (560.0 mg, 92.6%) as a solid. LCMS (ES, m/z): 640 $[M+H]^+$.

Synthesis of Compound 286

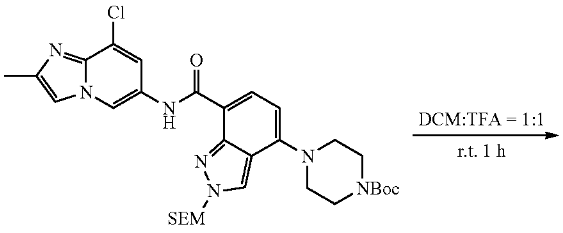

B266

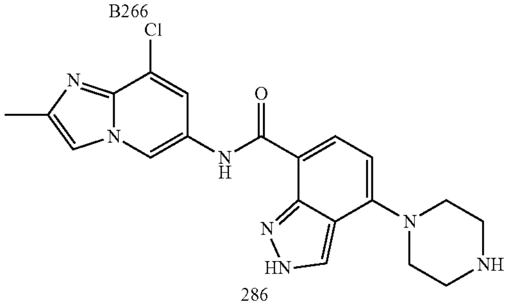

286

A solution of tert-butyl 4-[7-({8-chloro-2-methylimidazo [1,2-a]pyridine-6-yl}carbamoyl)-2-{[2-(tri methylsilyl) ethoxy]methyl}indazol-4-yl]piperazine-1-carboxylate (100.00 mg, 0.16 mmol, 1.00 equiv) in TFA/DCM (1:1) (5 mL) was stirred for 2 h at room temperature. The resulting mixture was concentrated under reduced pressure to give a residue. The residue was purified by prep-HPLC (Condition 1, Gradient 19) to afford N-{8-chloro-2-methylimidazo[1,2-a]pyridin-6-yl}-4-(piperazin-1-yl)-2H-indazole-7-carboxamide (25.5 mg, 36.55%) as a solid. LCMS (ES, m/z): 410 $[M+H]^+$. $^1$H-NMR (400 MHz, DMSO-$d_6$) δ 13.01 (s, 1H), 10.21 (s, 1H), 9.15 (d, J=1.7 Hz, 1H), 8.24 (s, 1H), 7.99 (d, J=8.2 Hz, 1H), 7.91 (s, 1H), 7.68 (d, J=1.7 Hz, 1H), 6.55 (d, J=8.3 Hz, 1H), 3.40 (dd, J=6.3, 3.6 Hz, 4H), 2.96-2.89 (m, 4H), 2.36 (s, 3H).

Example 35: Synthesis of Compound 284

Synthesis of Intermediate B267

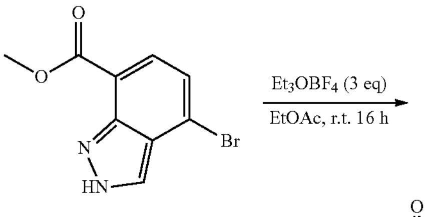

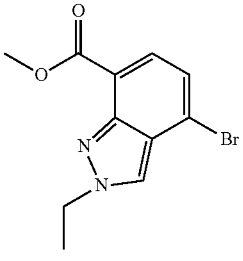

B267

A mixture of methyl 4-bromo-2H-indazole-7-carboxylate (500.00 mg, 1.96 mmol, 1.00 equiv) and tetrafluoroboranuide; triethyloxidanium (1117.26 mg, 5.88 mmol, 3.00 equiv) in AcOH (5 ml) was stirred for 20 h at room temperature. The resulting mixture was extracted with ethyl acetate (3×10 mL). The combined organic layers were washed with saturated NaCl (1×10 mL), dried over anhydrous $Na_2SO_4$, and filtered. After filtration, the filtrate was concentrated under reduced pressure to afford methyl 4-bromo-2-ethylindazole-7-carboxylate (480.0 mg, 86.4%) as a solid. LCMS (ES, m/z): 283 $[M+H]^+$.

Synthesis of Intermediate B268

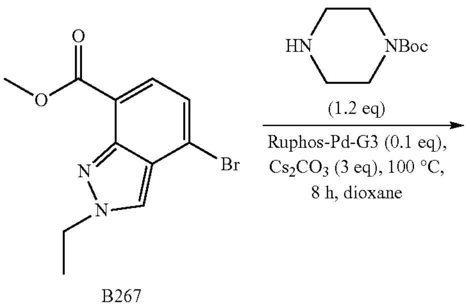

B267

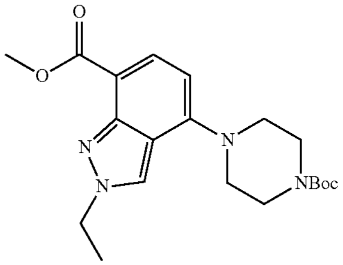

B268

To a stirred mixture of methyl 4-bromo-2-ethylindazole-7-carboxylate (480.00 mg, 1.70 mmol, 1.00 equiv) and tert-butyl piperazine-1-carboxylate (378.92 mg, 2.03 mmol, 1.20 equiv) in 1,4-dioxane (10 ml) was added RuPhos Palladacycle Gen.3 (141.80 mg, 0.17 mmol, 0.10 equiv), and $Cs_2CO_3$ (1657.15 mg, 5.09 mmol, 3.00 equiv) at 100° C. under nitrogen atmosphere. The resulting mixture was extracted with ethyl acetate (3×20 mL). The combined organic layers were washed with saturated NaCl (1×10 mL), dried over anhydrous $Na_2SO_4$, and filtered. After filtration, the filtrate was concentrated under reduced pressure to give a residue. The residue was purified by silica gel column chromatography, eluted with $CH_2Cl_2$/MeOH (10:01) to afford methyl 4-[4-(tert-butoxycarbonyl)piperazin-1-yl]-2-ethylindazole-7-carboxylate (390.00 mg, 59.22%) as a solid. LCMS (ES, m/z): 389 $[M+H]^+$ Synthesis of Intermediate B269

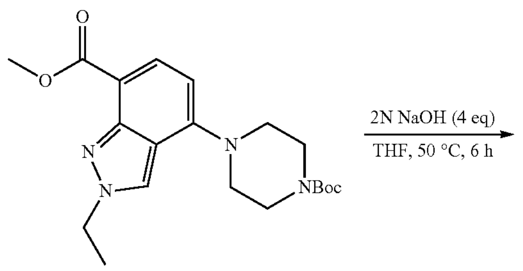

B268

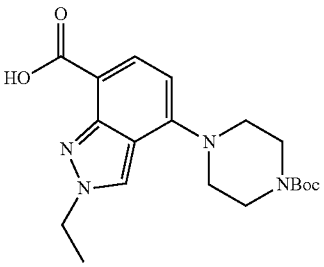

B269

A mixture of methyl 4-[4-(tert-butoxycarbonyl)piperazin-1-yl]-2-ethylindazole-7-carboxylate (390.00 mg, 1.00 mmol, 1.00 equiv) and NaOH (2M) (2 mL, 4.00 equiv) in THF (5 ml) was stirred for 5 h at 50° C. The reaction mixture was acidified to pH 4 with HCl (aq.). The resulting mixture was extracted with ethyl acetate (3×10 mL). The combined organic layers were washed with saturated NaCl (1×10 mL), dried over anhydrous $Na_2SO_4$, and filtered. After filtration, the filtrate was concentrated under reduced pressure to afford 4-[4-(tert-butoxycarbonyl)piperazin-1-yl]-2-ethylindazole-7-carboxylic acid (340.0 mg, 90.4%) as a solid. LCMS (ES, m/z): 375 $[M+H]^+$ Synthesis of Intermediate B270

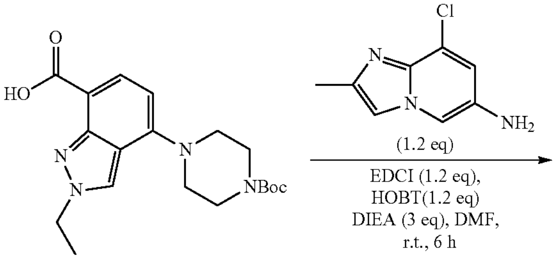

B269

-continued

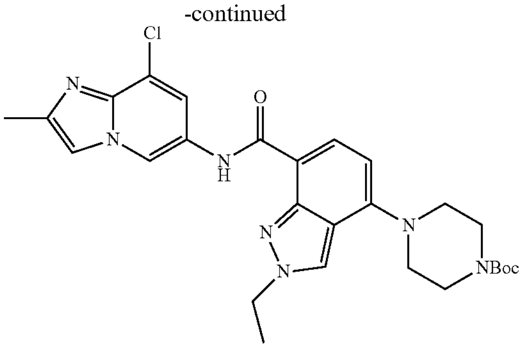

B270

To a stirred mixture of 4-[4-(tert-butoxycarbonyl)piperazin-1-yl]-2-ethylindazole-7-carboxylic acid (340.00 mg, 0.91 mmol, 1.00 equiv) and 8-chloro-2-methylimidazo[1,2-a]pyridin-6-amine (197.90 mg, 1.09 mmol, 1.20 equiv) in DMF (10 ml) was added HOBT (147.23 mg, 1.09 mmol, 1.20 equiv), DIEA (352.07 mg, 2.72 mmol, 3.00 equiv), and EDCI (208.88 mg, 1.09 mmol, 1.20 equiv). The reaction mixture was stirred for 6 h at 40° C., then extracted with ethyl acetate (3×10 mL). The combined organic layers were washed with saturated NaCl (1×10 mL), dried over anhydrous $Na_2SO_4$, and filtered. After filtration, the filtrate was concentrated under reduced pressure to afford tert-butyl 4-[7-({8-chloro-2-methylimidazo[1,2-a]pyridin-6-yl}carbamoyl)-2-ethylindazol-4-yl]piperazine-1-carboxylate (380.0 mg, 77.7%) as a solid. LCMS (ES, m/z): 538 $[M+H]^+$ Synthesis of Compound 284

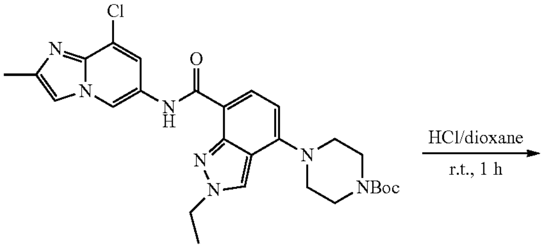

B270

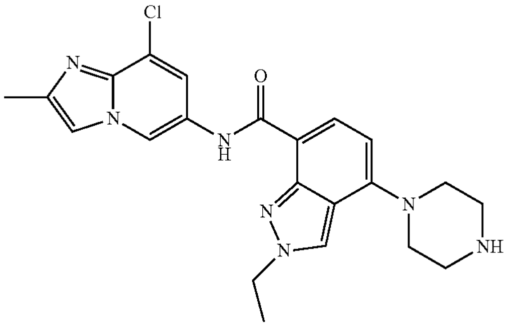

284

A solution of tert-butyl 4-[7-({8-chloro-2-methylimidazo[1,2-a]pyridin-6-yl}carbamoyl)-2-ethylinda-zol-4-yl]piperazine-1-carboxylate (100.00 mg, 0.19 mmol, 1.00 equiv) in HCl/dioxane (5 mL) was stirred for 1 h at room temperature. The resulting mixture was concentrated under reduced pressure to give a residue. The residue was purified by prep-HPLC (Condition 9, Gradient 8) to afford N-{8-chloro-2-methylimidazo[1,2-a]pyridin-6-yl}-2-ethyl-4-(piperazin-1-yl)indazole-7-carboxamide (26.1 mg, 32.0%) as a solid. LCMS (ES, m/z): 438 [M+H]$^+$. $^1$H-NMR (400 MHz, DMSO-$d_6$) δ 9.18 (d, J=1.7 Hz, 1H), 8.73 (s, 1H), 7.97 (d, J=8.0 Hz, 1H), 7.82 (s, 1H), 7.53 (d, J=1.7 Hz, 1H), 6.50 (d, J=8.1 Hz, 1H), 4.55 (q, J=7.3 Hz, 2H), 3.40 (dd, J=6.5, 3.6 Hz, 4H), 3.02-2.95 (m, 4H), 2.33 (s, 3H), 1.58 (t, J=7.3 Hz, 3H).

Example 36: Synthesis of Compound 283

Synthesis of Intermediate B271

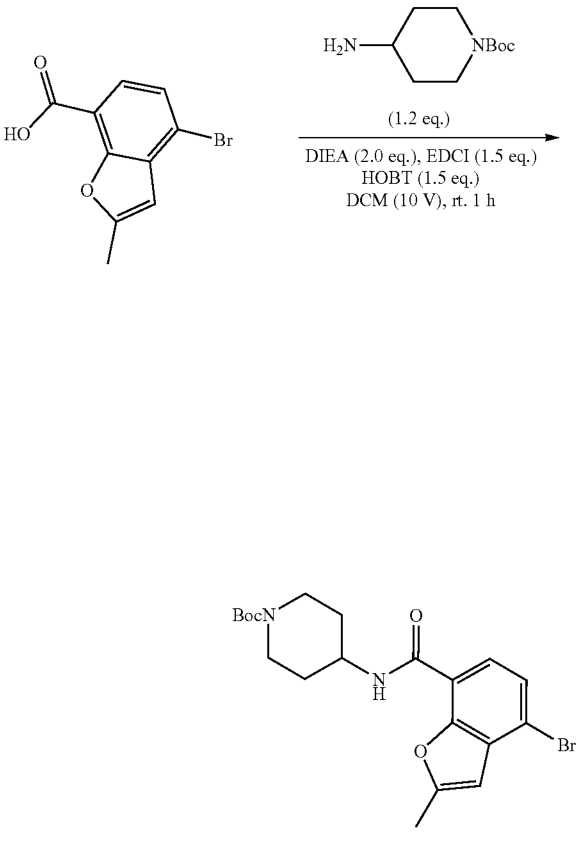

B271

4-bromo-2-methyl-1-benzofuran-7-carboxylic acid (300.00 mg, 1.10 mmol, 1.00 equiv), tert-butyl 4-aminopiperidine-1-carboxylate (282.0 mg, 1.40 mmol, 1.20 equiv), DIEA (304.0 mg, 2.30 mmol, 2.00 equiv), EDCI (338.0 mg, 1.70 mmol, 1.50 equiv), and HOBT (238.0 mg, 1.70 mmol, 1.50 equiv) were combined in DCM (3.0 mL) at room temperature. The reaction mixture was stirred for 1 h at room temperature, then concentrated under reduced pressure to a residue. The residue was purified by silica gel column chromatography, eluted with PE/EA (3:1), to afford tert-butyl 4-(4-bromo-2-methyl-1-benzofuran-7-amido) piperidine-1-carboxylate (300.0 mg, 58.3%) as a solid. LCMS (ES, m/z): 437 [M+H]$^+$.

Synthesis of Intermediate B272

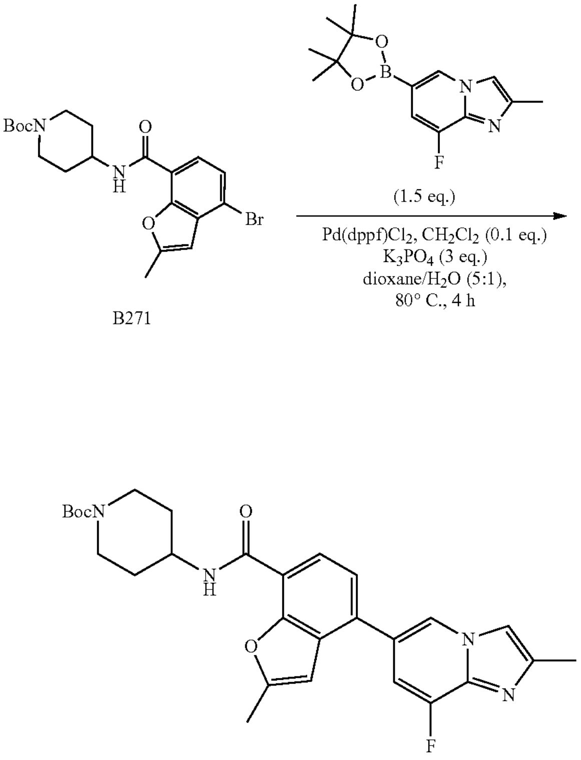

B271

B272

To a solution of tert-butyl 4-(4-bromo-2-methyl-1-benzofuran-7-amido) piperidine-1-carboxylate (100.0 mg, 0.20 mmol, 1.00 equiv) and 8-fluoro-2-methyl-6-(4,4,5,5-tetramethyl-1,3,2-dioxaborolan-2-yl) imidazo-[1,2-a]pyridine (75.0 mg, 0.20 mmol, 1.20 equiv) in a mixture of dioxane (5.0 mL) and water (1.0 mL) was added $K_3PO_4$ (145.0 mg, 0.60 mmol, 3.00 equiv) and Pd(dppf)$C_{12}$·$CH_2Cl_2$ (18.0 mg, 0.02 mmol, 0.10 equiv). After stirring for 3 h at 80° C. under a nitrogen atmosphere, the resulting mixture was concentrated under reduced pressure to give a residue. The residue was purified by Prep-TLC/silica gel column chromatography, eluted with PE/EA (1:1), to afford tert-butyl 4-(4-{8-fluoro-2-methylimidazo[1,2-a]pyridin-6-yl}-2-methyl-1-benzofuran-7-amido) piperidine-1-carboxylate (100.0 mg, 86.3%) as an oil. LCMS (ES, m/z): 507 [M+H]$^+$.

Synthesis of Compound 283

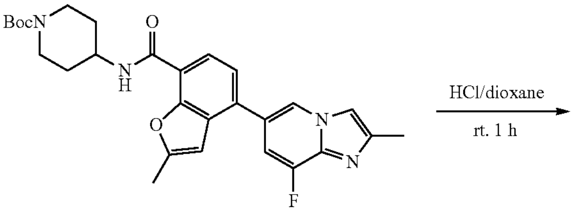

B272

-continued

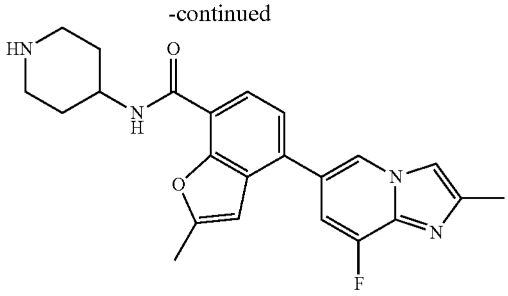

283

A mixture of tert-butyl 4-(4-{8-fluoro-2-methylimidazo[1,2-a]pyridin-6-yl}-2-methyl-1-benzofuran-7-amido) piperidine-1-carboxylate (50.0 mg, 0.10 mmol, 1.00 equiv) and HCl (gas) in 1,4-dioxane (1 mL) was stirred for 1 h at room temperature, then concentrated under reduced pressure to give a residue. The residue was purified by prep-HPLC (Condition 1, Gradient 18) to afford 4-{8-fluoro-2-methylimidazo[1,2-a]pyridin-6-yl}-2-methyl-N-(piperidin-4-yl)-1-benzofuran-7-carboxamide (14.9 mg, 37.2%) as a white solid. LCMS (ES, m/z): 407 $[M+H]^+$. $^1$H-NMR (400 MHz, DMSO-$d_6$) δ 8.71 (d, J=1.4 Hz, 1H), 8.08 (d, J=7.8 Hz, 1H), 7.91 (dd, J=3.1, 1.0 Hz, 1H), 7.66 (d, J=7.9 Hz, 1H), 7.47 (d, J=7.9 Hz, 1H), 7.40 (dd, J=12.1, 1.5 Hz, 1H), 6.96 (t, J=1.1 Hz, 1H), 3.98-3.86 (m, 1H), 3.02-2.92 (m, 2H), 2.58 (dd, J=12.0, 2.5 Hz, 2H), 2.54 (d, J=1.1 Hz, 3H), 2.40 (d, J=0.9 Hz, 3H), 1.84 (dd, J=11.7, 4.0 Hz, 2H), 1.55-1.40 (m, 2H).

Example 37: Synthesis of Compound 282

Synthesis of Intermediate B273

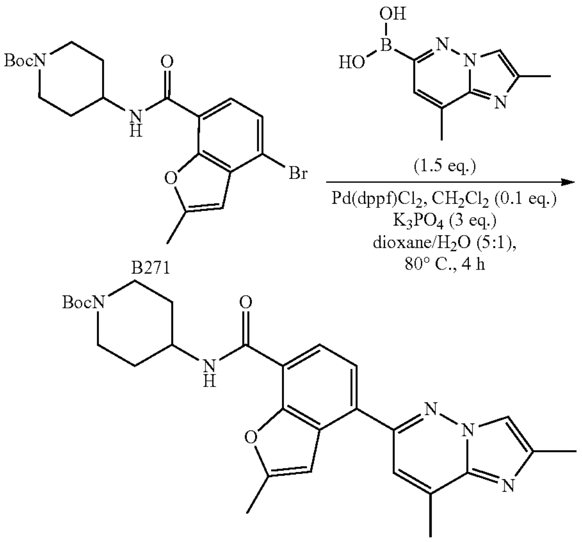

B271

B273

To a mixture of tert-butyl 4-(4-bromo-2-methyl-1-benzofuran-7-amido) piperidine-1-carboxylate (100.0 mg, 0.20 mmol, 1.00 equiv) and 2,8-dimethylimidazo[1,2-b]pyridazin-6-ylboronic acid (65.0 mg, 0.30 mmol, 1.50 equiv) in a mixture of dioxane (5 mL) and water (1 mL) was added $K_3PO_4$ (145.0 mg, 0.60 mmol, 3.00 equiv) and $Pd(dppf)Cl_2{\cdot}CH_2Cl_2$ (18.0 mg, 0.02 mmol, 0.10 equiv). The reaction mixture was stirred for 4 h at 80° C. under a nitrogen atmosphere, then concentrated under reduced pressure to give a residue. The residue was purified by Prep-TLC/silica gel column chromatography, eluted with PE/EA (1:1), to afford tert-butyl 4-(4-{2,8-dimethylimidazo[1,2-b]pyridazin-6-yl}-2-methyl-1-benzofuran-7-amido) piperidine-1-carboxylate (100.0 mg, 86.8%) as an oil. LCMS (ES, m/z): 504 $[M+H]^+$.

Synthesis of Compound 282

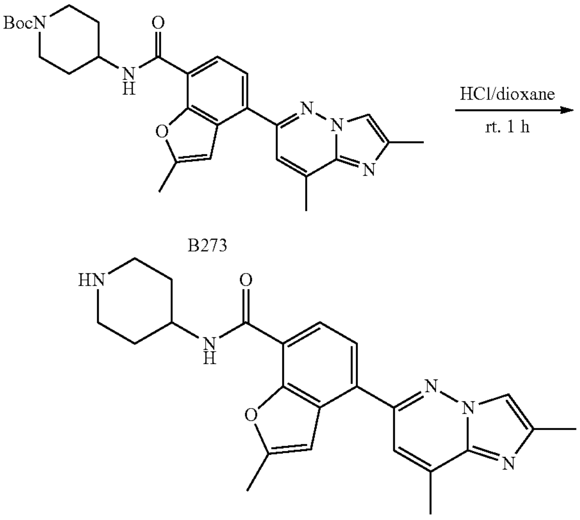

B273

282

A mixture of tert-butyl 4-(4-{2,8-dimethylimidazo[1,2-b]pyridazin-6-yl}-2-methyl-1-benzofuran-7-amido) piperidine-1-carboxylate (100.0 mg, 0.20 mmol, 1.00 equiv) and HCl/dioxane (1 mL) was stirred for 1 h at room temperature. The reaction mixture was concentrated under pressure to give a residue. The residue was purified by prep-HPLC (Condition 1, Gradient 18) to afford 4-{2,8-dimethylimidazo[1,2-b]pyridazin-6-yl}-2-methyl-N-(piperidin-4-yl)-1-benzofuran-7-carboxamide (10.6 mg, 13.3%) as a solid. LCMS (ES, m/z): 404 $[M+H]^+$. $^1$H-NMR (400 MHz, DMSO-$d_6$) δ 8.15 (d, J=7.9 Hz, 2H), 7.84 (d, J=8.0 Hz, 1H), 7.70-7.63 (m, 2H), 7.26 (d, J=1.3 Hz, 1H), 3.97-3.89 (m, 1H), 2.98 (dt, J=12.3, 3.7 Hz, 2H), 2.66-2.61 (m, 3H), 2.60-2.53 (m, 5H), 2.43 (s, 3H), 1.84 (dd, J=12.7, 3.8 Hz, 2H), 1.47 (qd, J=11.5, 4.0 Hz, 2H).

Example 38: Synthesis of Compound 280

Synthesis of Intermediate B274

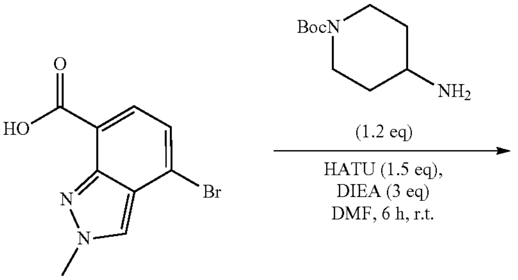

-continued

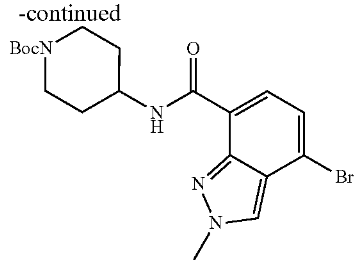

B274

To a stirred mixture of 4-bromo-2-methylindazole-7-carboxylic acid (650.00 mg, 2.55 mmol, 1.00 equiv) and tert-butyl 4-aminopiperidine-1-carboxylate (765.57 mg, 3.82 mmol, 1.50 equiv) in DMF was added HATU (1453.42 mg, 3.82 mmol, 1.50 equiv) and DIEA (988.06 mg, 7.64 mmol, 3.00 equiv) in portions at room temperature. The resulting mixture was stirred for 8 h at room temperature. The resulting mixture was extracted with diethyl ether (3x20 mL). The combined organic layers were washed with saturated NaCl (aq) (1x20 mL), dried over anhydrous $Na_2SO_4$, and filtered. After filtration, the filtrate was concentrated under reduced pressure to give a residue. The residue was purified by silica gel column chromatography, eluted with PE/EA (1:01), to afford tert-butyl 4-(4-bromo-2-methylindazole-7-amido)piperidine-1-carboxylate (700.00 mg, 62.81%) as a solid. LCMS (ES, m/z): 437 $[M+H]^+$.

Synthesis of Intermediate B275

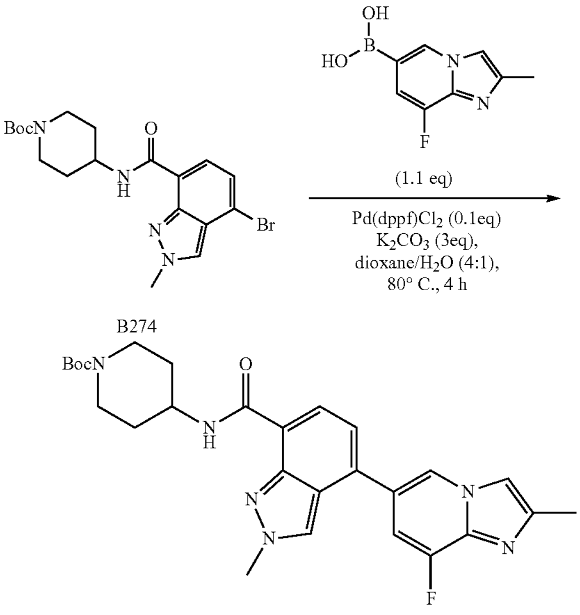

B274

B275

To a stirred mixture of tert-butyl 4-(4-bromo-2-methylindazole-7-amido)piperidine-1-carboxylate (200.00 mg, 0.46 mmol, 1.00 equiv) and 8-fluoro-2-methylimidazo[1,2-a]pyridin-6-ylboronic acid (133.06 mg, 0.69 mmol, 1.50 equiv) in dioxane/$H_2O$ (4:1) was added Pd(dppf)$Cl_2$·$CH_2Cl_2$ (37.25 mg, 0.05 mmol, 0.10 equiv) and $K_2CO_3$ (189.61 mg, 1.37 mmol, 3.00 equiv) in portions. The reaction mixture was stirred for 4 h at 80° C. under nitrogen atmosphere, then extracted with diethyl ether (3x10 mL). The combined organic layers were washed with saturated NaCl (aq) (1x10 mL), dried over anhydrous $Na_2SO_4$, and filtered. After filtration, the filtrate was concentrated under reduced pressure to give a residue. The residue was purified by silica gel column chromatography, eluted with $CH_2Cl_2$/MeOH (10:1), to afford tert-butyl 4-(4-{8-fluoro-2-methylimidazo[1,2-a]pyridin-6-yl}-2-methylindazole-7-amido)piperidine-1-carboxylate (120.00 mg, 51.80%) as a solid. LCMS (ES, m/z): 507 $[M+H]^+$ Synthesis of Compound 280

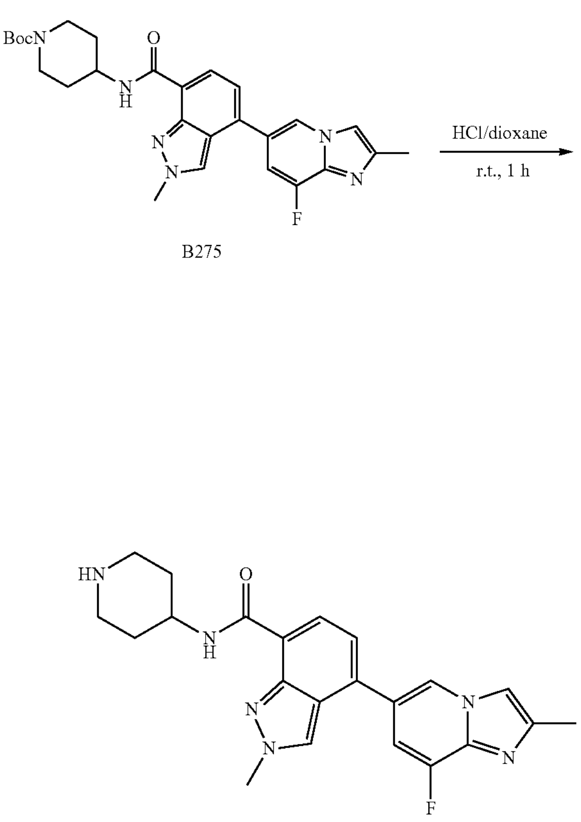

B275

280

A mixture of tert-butyl 4-(4-{8-fluoro-2-methylimidazo[1,2-a]pyridin-6-yl}-2-methylindazole-7-amido)piperidine-1-carboxylate (120.00 mg, 0.24 mmol, 1.00 equiv) and HCl/dioxane (5.00 mL) was stirred for 1 h at room temperature. The resulting mixture was concentrated under reduced pressure to give a residue. The residue was purified by Prep-HPLC (Condition 1, Gradient 18) to afford 4-{8-fluoro-2-methylimidazo[1,2-a]pyridin-6-yl}-2-methyl-N-(piperidin-4-yl)indazole-7-carboxamide (28.30 mg, 35.27%) as a solid. LCMS (ES, m/z): 407 $[M+H]^+$. $^1H$ NMR (400 MHz, DMSO-$d_6$) δ 9.19 (d, J=7.7 Hz, 1H), 8.93 (s, 1H), 8.83 (d, J=1.4 Hz, 1H), 8.08 (d, J=7.4 Hz, 1H), 7.90 (d, J=3.1 Hz, 1H), 7.53 (dd, J=12.2, 1.4 Hz, 1H), 7.42 (d, J=7.4 Hz, 1H), 4.30 (s, 3H), 4.01 (s, 1H), 2.98 (dt, J=12.6, 4.1 Hz, 2H), 2.67-2.56 (m, 2H), 2.41 (s, 3H), 1.96-1.87 (m, 2H), 1.47 (dd, J=10.3, 3.6 Hz, 2H).

Example 39: Synthesis of Compound 281

Synthesis of Intermediate B276

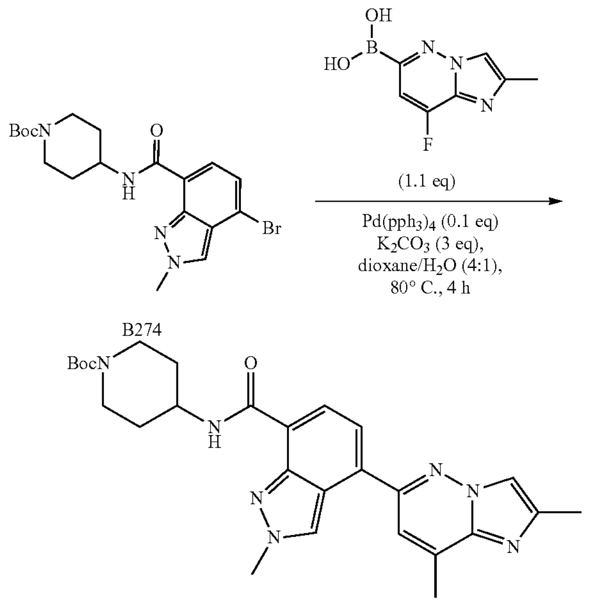

B274

B276

To a stirred mixture of tert-butyl 4-(4-bromo-2-methylindazole-7-amido) piperidine-1-carboxylate (200.00 mg, 0.46 mmol, 1.00 equiv) and 2,8-dimethylimidazo[1,2-b]pyridazin-6-ylboronic acid (131.02 mg, 0.69 mmol, 1.50 equiv) in dioxane/$H_2O$ (4:1, 5.00 ml) was added $Pd(PPh_3)_4$ (52.85 mg, 0.05 mmol, 0.10 equiv) and $K_2CO_3$ (189.61 mg, 1.37 mmol, 3.00 equiv) in portions. The reaction mixture was stirred at 80° C. under nitrogen atmosphere. The resulting mixture was extracted with diethyl ether (3×10 mL). The combined organic layers were washed with saturated NaCl aq (1×10 mL), dried over anhydrous $Na_2SO_4$, and filtered. After filtration, the filtrate was concentrated under reduced pressure to give a residue. The residue was purified by silica gel column chromatography, eluted with $CH_2Cl_2$/MeOH (10:01), to afford tert-butyl 4-(4-{2,8-dimethylimidazo[1,2-b]pyridazin-6-yl}-2-methylindazole-7-amido)piperidine-1-carboxylate (100 mg, 43.42%) as a solid. LCMS (ES, m/z): 504 $[M+H]^+$.

Synthesis of Compound 281

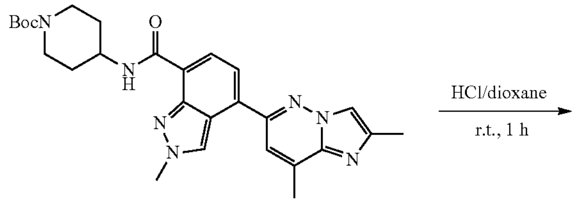

B276

-continued

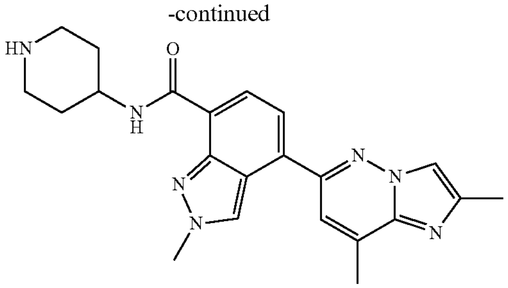

281

A mixture of tert-butyl 4-(4-{2,8-dimethylimidazo[1,2-b]pyridazin-6-yl}-2-methylindazole-7-amido)piperidine-1-carboxylate (120.00 mg, 0.24 mmol, 1.00 equiv) and HCl/dioxane (5.00 mL) was stirred for 1 h at room temperature. The resulting solution was concentrated under reduced pressure to give a residue. The residue was purified by Prep-HPLC (Condition 1, Gradient 18) to afford 4-{2,8-dimethylimidazo[1,2-b]pyridazin-6-yl}-2-methyl-N-(piperidin-4-yl)indazole-7-carboxamide (61.10 mg, 63.55%) as a solid. LCMS (ES, m/z): 404 $[M+H]^+$. $^1H$ NMR (400 MHz, DMSO-$d_6$) δ 9.26 (d, J=7.6 Hz, 1H), 9.16 (s, 1H), 8.15 (s, 1H), 8.11 (d, J=7.4 Hz, 1H), 7.90 (d, J=7.5 Hz, 1H), 7.79 (d, J=5.5 Hz, 1H), 4.33 (s, 3H), 4.02 (d, J=10.6 Hz, 1H), 2.98 (d, J=12.0 Hz, 2H), 2.65 (s, 1H), 2.54-2.48 (m, 4H), 2.44 (s, 3H), 1.92 (dd, J=12.8, 5.0 Hz, 2H), 1.52-1.38 (m, 2H).

Example 40: Synthesis of Compound 279

Synthesis of Intermediate B277

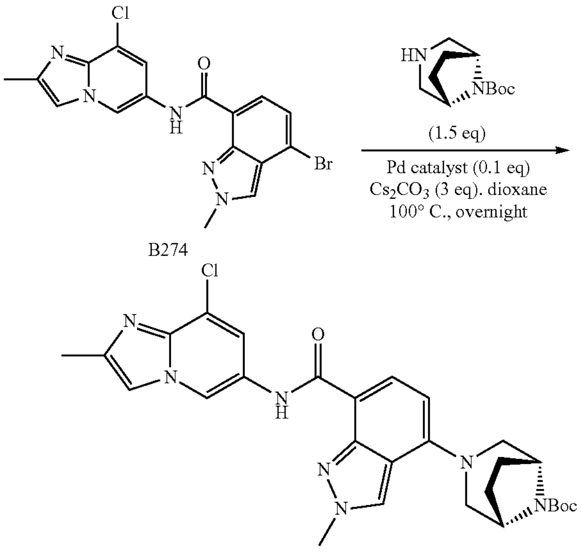

B274

B277

To a stirred mixture of 4-bromo-N-{8-chloro-2-methylimidazo[1,2-a]pyridin-6-yl}-2-methylindazole-7-carboxamide (100.00 mg, 0.24 mmol, 1.00 equiv) and tert-butyl (1R,5S)-3,8-diazabicyclo[3.2.1]octane-8-carboxylate (76.06 mg, 0.36 mmol, 1.50 equiv) in 1,4-dioxane was added RuPhos Palladacycle Gen.3 (19.98 mg, 0.02 mmol, 0.100 equiv) and $Cs_2CO_3$ (233.46 mg, 0.72 mmol, 3.00 equiv).

The reaction mixture was stirred for 10 h at 100° C. under nitrogen atmosphere, then extracted with diethyl ether (3×10 mL). The combined organic layers were washed with saturated NaCl (aq) (1×10 mL), dried over anhydrous $Na_2SO_4$, and filtered. After filtration, the filtrate was concentrated under reduced pressure to give a residue. The residue was purified by silica gel column chromatography, eluted with PE/EA (1:4), to afford tert-butyl (1R,5S)-3-[7-({8-chloro-2-methylimidazo[1,2-a]pyridin-6-yl}carbamoyl)-2-methylindazol-4-yl]-3,8-diazabicyclo[3.2.1]octane-8-carboxylate (60.00 mg, 45.67%) as a solid. LCMS (ES, m/z): 550 $[M+H]^+$.

Synthesis of Compound 279

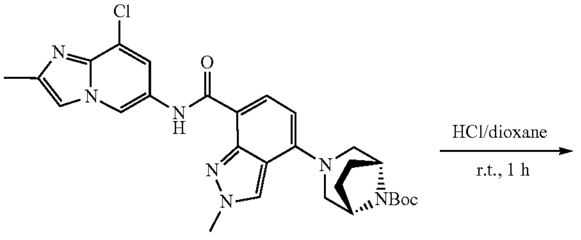

B277

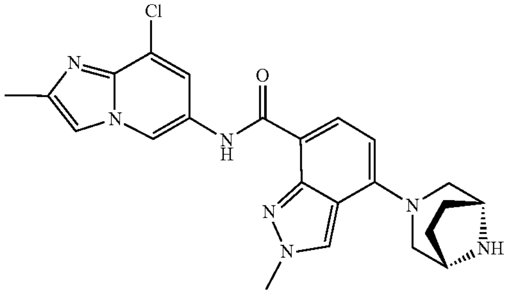

279

A solution of tert-butyl (1R,5S)-3-[7-({8-chloro-2-methylimidazo[1,2-a]pyridin-6-yl}carbamoyl)-2-methylindazol-4-yl]-3,8-diazabicyclo[3.2.1]octane-8-carboxylate (60.00 mg, 0.11 mmol, 1.00 equiv) in HCl/dioxane (10 mL) was stirred for 1 h at room temperature. The resulting mixture was concentrated under reduced pressure to give a residue. The residue was purified by prep-HPLC (Condition 9, Gradient 9) to afford N-{8-chloro-2-methylimidazo[1,2-a]pyridin-6-yl}-4-[(1R,5S)-3,8-diazabicyclo[3.2.1]octan-3-yl]-2-methylindazole-7-carboxamide (6.10 mg, 12.43%) as a solid. LCMS (ES, m/z): 450 $[M+H]^+$. $^1$H NMR (400 MHz, DMSO-$d_6$) δ 11.10 (s, 1H), 9.34 (d, J=1.8 Hz, 1H), 8.86 (s, 1H), 7.94 (d, J=8.3 Hz, 1H), 7.90 (s, 1H), 7.57 (d, J=1.7 Hz, 1H), 6.37 (d, J=8.4 Hz, 1H), 4.29 (s, 3H), 3.71 (dd, J=11.3, 2.3 Hz, 2H), 3.56 (s, 2H), 3.15 (dd, J=11.2, 2.3 Hz, 2H), 2.36 (s, 3H), 1.76 (dt, J=12.0, 8.2 Hz, 4H).

Example 41: Synthesis of Compound 287

Synthesis of Compound 287

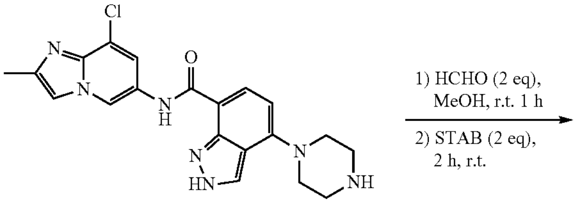

286

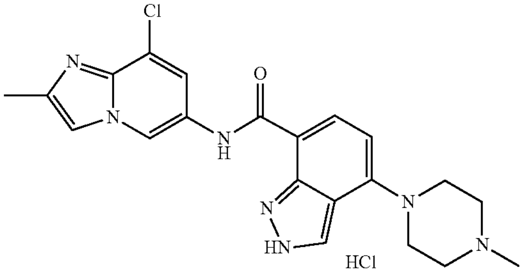

287

A mixture of N-{8-chloro-2-methylimidazo[1,2-a]pyridin-6-yl}-4-(piperazin-1-yl)-2H-indazole-7-carboxamide (80.00 mg, 0.20 mmol, 1.00 equiv) and formaldehyde (11.72 mg, 0.39 mmol, 2.00 equiv) in methanol (5 mL, 123.50 mmol, 632.72 equiv) was stirred for 1 h at room temperature. To the reaction mixture was added STAB (82.73 mg, 0.39 mmol, 2.00 equiv). The resulting mixture was stirred for an additional 2 h at room temperature, then extracted with ethyl acetate (3×10 mL). The combined organic layers were washed with saturated NaCl (1×10 mL), dried over anhydrous $Na_2SO_4$, and filtered. After filtration, the filtrate was concentrated under reduced pressure to give a residue. The residue was purified by prep-HPLC (Condition 6, Gradient 1, Gradient 2) to afford N-{8-chloro-2-methylimidazo[1,2-a]pyridin-6-yl}-4-(4-methyl-piperazin-1-yl)-2H-indazole-7-carboxamide (1.9 mg, 2.30%) as a solid. LCMS (ES, m/z): 424 $[M+H]^+$. $^1$H-NMR (400 MHz, DMSO-$d_6$) δ 13.12 (s, 1H), 11.25 (s, 1H), 11.05 (s, 1H), 9.56 (d, J=1.6 Hz, 1H), 8.56 (s, 1H), 8.39 (s, 1H), 8.36 (m, 1H), 8.27 (m, 1H), 6.68 (d, J=8.3 Hz, 1H), 4.12 (d, J=13.2 Hz, 2H), 3.44 (d, J=12.6 Hz, 3H), 3.44 (d, J=12.6 Hz, 4H) 3.30 (dt, J=12.7, 9.2 Hz, 2H), 2.86 (d, J=4.2 Hz, 3H).

Example 42: Exemplary Splicing Assay for Monitoring Expression Levels of Splice Variants Compounds described herein were used to modulate RNA transcript abundance in cells. The expression of a target mRNA was measured by detecting the formation of an exon-exon junction in the canonical transcript (CJ). A compound mediated exon-inclusion event was detected by observing an increase in formation of a new junction with an alternative exon (AJ). Real-time qPCR assays were used to detect these splicing switches and interrogate the potency of various compounds towards different target genes. A high-throughput real time quantitative PCR (RT-qPCR) assay was developed to measure these two isoforms of the mRNA (CJ and AJ) for an exemplary gene, HTT, together with a control housekeeping gene, GAPDH or GUSB or PPIA, used for normalization. Briefly, the A673 or K562 cell line was treated with various compounds described herein (e.g., compounds of Formula (I)). After treatment, the levels of the HTT mRNA targets were determined from each sample of cell lysate by cDNA synthesis followed by qPCR.

Materials

Cells-to-$C_T$ 1-step kit: ThermoFisher A25602, Cells-to-CT lysis reagent: ThermoFisher 4391851C, TaqMan™ Fast Virus 1-Step Master Mix: ThermoFisher 4444436

GAPDH: VIC-PL, ThermoFisher 4326317E (Assay: Hs99999905_m1)—used for K562/suspension cell lines GUSB: VIC-PL, ThermoFisher 4326320E (Assay: Hs99999908_m1)—used for K562/suspension cell lines PPIA: VIC-PL, ThermoFisher 4326316E (Assay: Hs99999904_m1)—used for A673/adherent cell lines Probe/Primer Sequences

```
Canonical junction (CJ)
HTT Primer 1:
                                (SEQ ID NO: 5528)
TCCTCCTGAGAAAGAGAAGGAC

HTT Primer 2:
                                (SEQ ID NO: 5529)
GCCTGGAGATCCAGACTCA

HTT CY5-Probe:
                                (SEQ ID NO: 5530)
/5Cy5/TGGCAACCCTTGAGGCCCTGTCCT/
3IAbRQSp/

Alternative junction (AJ)
HTT Primer 1:
                                (SEQ ID NO: 5531)
TCCTGAGAAAGAGAAGGACATTG

HTT Primer 2:
                                (SEQ ID NO: 5532)
CTGTGGGCTCCTGTAGAAATC

HTT FAM-Probe:
                                (SEQ ID NO: 5533)
/56-FAM/TGGCAACCC/ZEN/
TTGAGAGGCAAGCCCT/3IABKFQ/
```

Description

The A673 cell line was cultured in DMEM with 10% FBS. Cells were diluted with full growth media and plated in a 96-well plate (15,000 cells in 100 ul media per well). The plate was incubated at 37° C. with 5% $CO_2$ for 24 hours to allow cells to adhere. An 11-point 3-fold serial dilution of the compounds was made in DMSO then diluted in media in an intermediate plate. Compounds were transferred from the intermediate plate to the cell plate with the top dose at a final concentration of 10 uM in the well. Final DMSO concentration was kept at or below 0.25%. The cell plate was returned to the incubator at 37° C. with 5% $CO_2$ for an additional 24 hours.

The K562 cell line was cultured in IMDM with 10% FBS. For K562, cells were diluted with full growth media and plated in either a 96-well plate (50,000 cells in 50 uL media per well) or a 384-well plate (8,000-40,000 cells in 45 uL media per well). An 11-point 3-fold serial dilution of the compounds were made in DMSO then diluted in media in an intermediate plate. Compound was transferred from the intermediate plate to the cell plate with the top dose at a final concentration of 10 uM in the well. Final DMSO concentration was kept at or below 0.25%. Final volume was 100 uL for 96-well plate and 50 uL for 384-well plate. The cell plate was then placed in an incubator at 37° C. with 5% CO2 for 24 hours.

The cells were then gently washed with 50 uL-100 uL cold PBS before proceeding to addition of lysis buffer. 30 uL-50 μL of room temperature lysis buffer with DNAse I (and optionally RNAsin) was added to each well. Cells were shaken/mixed thoroughly at room temperature for 5-10 minutes for lysis to take place and then 3 uL-5 μL of room temperature stop solution was added and wells were shaken/mixed again. After 2-5 minutes, the cell lysate plate was transferred to ice for RT-qPCR reaction setup. The lysates could also be frozen at −80° C. for later use.

In some cases, a direct lysis buffer was used. An appropriate volume of 3× lysis buffer (10 mM Tris, 150 mM NaCl, 1.5%-2.5% Igepal and 0.1-1 U/uL RNAsin, pH 7.4) was directly added to either K562 or A673 cells in media and mixed by pipetting 3 times. The plates were then incubated at room temperature with shaking/rocking for 20-50 minutes to allow for lysis to take place. After this time, the cell lysate plate was transferred to ice to set up for the RT-qPCR reactions. The lysates could also be frozen at −80° C. for later use.

To set up 10 uL RT-qPCR reactions, cell lysates were transferred to 384-well qPCR plates containing the master mix according to the table below. The plates were sealed, gently vortexed, and spun down before the run. The volumes were adjusted accordingly in some instances where the reaction was carried in 20 μL. The table below summarizes the components of the RT-qPCR reactions:

| Component | 1X |
|---|---|
| Taqman 1-step RT-qPCR mix (4X) | 2.5 |
| 20X AJ Primers + Probe (FAM) | 0.5 |
| 20X CJ Primers + Probe (CY5) | 0.5 |
| 20X PPIA Control (VIC) | 0.5 |
| Cell lysate (1X) | 1-2 |
| $H_2O$ | 4-5 |
| Total volume | 10 |

The RT-qPCR reaction was performed using a QuantStudio (ThermoFisher) under the following fast cycling conditions. All samples and standards were analyzed at least in duplicate. In some instances, bulk room temperature (RT) step of 5-10 minutes was completed for all plates before proceeding with qPCR. The table below summarizes the PCR cycle:

| Step | # cycles | Temp. | Time |
|---|---|---|---|
| RT step | 1 | 50° C. | 5 min |
| RT inactivation/initial denaturation | 1 | 95° C. | 20 sec |
| Amplification | 40 | 95° C. | 3 sec |
| | | 60° C. | 30 sec |

The data analysis was performed by first determining the ΔCt vs the housekeeper gene. This ΔCt was then normalized against the DMSO control (ΔΔCt) and converted to RQ (relative quantification) using the 2^(−ΔΔCt) equation. The RQ were then converted to a percentage response by arbitrarily setting an assay window of 3.5 ΔCt for HTT-CJ and an assay window of 9 ΔCt for HTT-AJ. These assay windows correspond to the maximal modulation observed at high concentration of the most active compounds. The percentage response was then fitted to the 4 parametric logistic equation to evaluate the concentration dependence of compound treatment. The increase in AJ mRNA is reported as $AC_{50}$ (compound concentration having 50% response in AJ increase) while the decrease in CJ mRNA levels is reported as $IC_{50}$ (compound concentration having 50% response in CJ decrease).

A summary of these results is illustrated in Table 2, wherein "A" represents an $AC_{50}/IC_{50}$ of less than 100 nM; "B" represents an $AC_{50}/IC_{50}$ of between 100 nM and 1 μM; and "C" represents an $AC_{50}/IC_{50}$ of between 1 μM and 10 μM; and "D" represents an $AC_{50}/IC_{50}$ of greater than 10 μM.

TABLE 2

Modulation of RNA Splicing by Exemplary Compounds

| Compound No. | HTT AJ $AC_{50}$ (nM) | HTT CJ $AC_{50}$ (nM) |
|---|---|---|
| 118 | C | C |
| 119 | D | C |
| 140 | C | C |
| 141 | A | A |
| 142 | C | C |
| 143 | B | B |
| 145 | C | C |
| 148 | C | C |
| 149 | C | C |
| 187 | B | B |
| 188 | D | D |
| 189 | C | C |
| 190 | C | C |
| 191 | C | B |
| 193 | C | C |
| 194 | C | C |
| 196 | C | C |
| 197 | D | D |
| 198 | C | B |
| 199 | B | B |
| 200 | C | C |
| 201 | D | D |
| 202 | C | D |
| 203 | C | C |
| 204 | C | C |
| 205 | C | B |
| 206 | C | C |
| 207 | B | B |
| 208 | B | B |
| 209 | B | B |
| 210 | B | B |
| 211 | C | C |
| 212 | D | C |
| 217 | C | C |
| 218 | D | D |
| 219 | D | D |
| 228 | B | B |
| 229 | B | B |
| 230 | D | D |
| 231 | D | D |
| 234 | B | C |
| 235 | C | C |
| 238 | C | C |
| 239 | B | B |
| 240 | B | B |
| 241 | C | C |
| 242 | C | B |
| 243 | B | B |
| 244 | D | D |
| 245 | B | B |
| 246 | C | C |
| 247 | D | D |
| 249 | D | D |
| 250 | B | B |
| 251 | B | B |
| 252 | B | B |
| 253 | D | D |
| 255 | C | C |
| 256 | C | C |
| 257 | C | C |
| 258 | B | C |
| 259 | C | C |
| 260 | B | B |
| 261 | C | C |
| 262 | D | D |
| 263 | C | C |
| 264 | D | D |
| 265 | D | D |
| 266 | C | C |
| 267 | C | D |
| 268 | D | D |
| 269 | B | B |
| 270 | D | D |
| 271 | D | D |
| 272 | B | B |
| 273 | D | D |
| 274 | D | C |
| 275 | C | C |
| 277 | B | B |
| 278 | C | C |
| 279 | C | C |
| 280 | C | C |
| 281 | C | C |
| 282 | C | C |
| 283 | D | C |
| 284 | D | C |
| 285 | B | B |
| 286 | D | D |

Additional studies were carried out for a larger panel of genes using the protocol provided above. The junction between flanking upstream and downstream exons was used to design canonical junction qPCR assays. At least one of the forward primer, reverse primer or the CY5-labeled 5' nuclease probe (with 3' quencher such as ZEN/Iowa Black FQ) was designed to overlap with the exon junction to capture the CJ mRNA transcript. BLAST was used to confirm the specificity of the probeset and parameters such as melting temperature, GC content, amplicon size, and primer dimer formation are considered during their design. Data for the decrease in CJ mRNA levels for three exemplary genes (HTT, SMN2, and Target C) analyzed in this panel are reported as $IC_{50}$ (compound concentration having 50% response in CJ decrease).

A summary of the results from the panel is illustrated in Table 3, wherein "A" represents an $IC_{50}$ of less than 100 nM; "B" represents an $IC_{50}$ of between 100 nM and 1 μM; and "C" represents an $IC_{50}$ of between 1 M and 10 μM; and "D" represents an $IC_{50}$ of greater than 10 μM.

TABLE 3

| Modulation of RNA Splicing by Exemplary Compounds | | | |
|---|---|---|---|
| Compound No. | HTT | SMN2 | Target C |
| 118 | C | — | D |
| 119 | C | B | D |
| 140 | C | B | — |
| 141 | A | A | B |
| 142 | C | A | B |
| 143 | B | A | A |
| 145 | C | A | B |
| 148 | C | B | C |
| 149 | C | A | D |
| 187 | B | A | B |
| 188 | D | B | C |
| 189 | C | A | C |
| 190 | C | B | C |
| 191 | B | A | C |
| 192 | C | A | C |
| 193 | C | A | D |
| 194 | C | A | D |
| 195 | D | A | D |
| 196 | C | A | C |
| 197 | D | B | D |
| 198 | B | A | C |
| 199 | B | A | C |
| 200 | C | A | C |
| 201 | D | C | D |
| 202 | D | A | D |
| 203 | C | B | C |
| 204 | C | A | C |
| 205 | B | A | C |
| 206 | C | A | D |
| 207 | B | A | C |
| 208 | B | A | C |
| 209 | B | D | C |
| 210 | B | A | C |
| 211 | C | A | D |
| 212 | C | B | D |
| 217 | C | C | D |
| 218 | D | A | D |
| 219 | D | B | D |
| 228 | B | A | B |
| 229 | B | A | C |
| 230 | D | D | D |
| 231 | D | D | D |
| 234 | C | A | C |
| 235 | C | A | D |
| 238 | C | A | D |
| 239 | B | A | C |
| 240 | B | A | C |
| 241 | C | A | C |
| 242 | B | A | C |
| 243 | B | A | C |
| 244 | D | B | D |
| 245 | B | A | B |
| 246 | C | A | D |
| 247 | D | D | D |
| 249 | D | A | D |
| 250 | B | A | C |
| 251 | B | A | C |
| 252 | B | A | B |
| 253 | D | C | D |

TABLE 3-continued

| Modulation of RNA Splicing by Exemplary Compounds | | | |
|---|---|---|---|
| Compound No. | HTT | SMN2 | Target C |
| 255 | C | A | D |
| 256 | C | A | D |
| 257 | C | A | D |
| 258 | C | A | C |
| 259 | C | A | C |
| 260 | B | A | D |
| 261 | C | C | D |
| 262 | D | A | D |
| 263 | C | A | C |
| 264 | D | D | D |
| 265 | D | C | D |
| 266 | C | A | D |
| 267 | D | A | D |
| 268 | D | D | D |
| 269 | B | A | C |
| 270 | D | D | D |
| 271 | D | B | D |
| 272 | B | A | B |
| 273 | D | A | D |
| 274 | C | A | D |
| 275 | C | A | D |
| 277 | B | A | C |
| 278 | C | A | C |
| 279 | C | A | D |
| 280 | C | C | D |
| 281 | C | B | C |

EQUIVALENTS AND SCOPE

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, FIGURES, or Examples but rather is as set forth in the appended claims. Those of ordinary skill in the art will appreciate that various changes and modifications to this description may be made without departing from the spirit or scope of the present invention, as defined in the following claims.

SEQUENCE LISTING

The patent contains a lengthy sequence listing. A copy of the sequence listing is available in electronic form from the USPTO web site (https://seqdata.uspto.gov/docdetail?docId=US12774281B2). An electronic copy of the sequence listing will also be available from the USPTO upon request and payment of the fee set forth in 37 CFR 1.19(b)(3).

The invention claimed is:

1. A compound of Formula (I-a):

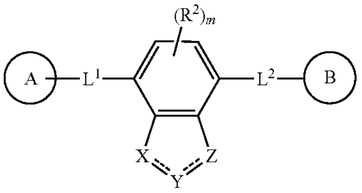

(I-a)

or a pharmaceutically acceptable salt, solvate, hydrate, tautomer, or stereoisomer thereof, wherein:

A is a nitrogen-containing heterocyclyl optionally substituted with one or more $R^1$;

B is a nitrogen-containing heteroaryl optionally substituted with one or more $R^1$;

X and Y are each independently $C(R^{3a})$, $C(R^{3a})(R^{3b})$, N, $N(R^{3c})$, or O, and the bonds in the ring comprising X, Y, and Z may be single or double bonds as valency permits;

Z is N, $N(R^{3c})$, or O;

$L^1$ is absent;

$L^2$ is —C(O)N($R^4$)—;

each $R^1$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, $C_1$-$C_6$ alkylene-aryl, $C_1$-$C_6$ alkenylene-aryl, $C_1$-$C_6$ alkylene-heteroaryl, heteroaryl, halo, cyano, oxo, —$OR^A$, —$NR^BR^C$, —$NR^BC(O)R^D$, —$NO_2$, —C(O)$NR^BR^C$, —C(O)$R^D$, —C(O)O$R^D$, —$SR^E$, or —$S(O)_x$ $R^D$, wherein each alkyl, alkylene, alkenyl, alkynyl, heteroalkyl, haloalkyl, cycloalkyl, heterocyclyl, aryl, and heteroaryl is optionally substituted with one or more $R^6$; or two $R^1$ groups, together with the atoms to which they are attached, form a 3-7-membered cycloalkyl, heterocyclyl, aryl, or heteroaryl, wherein each cycloalkyl, heterocyclyl, aryl, and heteroaryl is optionally substituted with one or more $R^6$;

each $R^2$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, halo, cyano, or —$OR^A$;

$R^{3a}$ and $R^{3b}$ are each independently hydrogen, $C_1$-$C_6$-alkyl, $C_1$-$C_6$-heteroalkyl, $C_1$-$C_6$-haloalkyl, halo, cyano, —$OR^A$, —$NR^BR^C$, —C(O)$R^D$, or —C(O)O$R^D$; or each of $R^{3a}$ and $R^{3b}$, together with the carbon atom to which they are attached, form an oxo group;

$R^{3c}$ is hydrogen or $C_1$-$C_6$-alkyl;

each $R^4$ is independently hydrogen, $C_1$-$C_6$-alkyl, or $C_1$-$C_6$-haloalkyl;

each $R^6$ is independently $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, heteroaryl, halo, cyano, oxo, —$OR^A$, —$NR^BR^C$, —$NR^BC(O)R^D$, —$NO_2$, —C(O)$NR^BR^C$, —C(O)$R^D$, —C(O)O$R^D$, —$SR^E$, or —$S(O)_xR^D$, wherein each alkyl, alkenyl, alkynyl, heteroalkyl, haloalkyl, cycloalkyl, heterocyclyl, aryl, and heteroaryl is optionally substituted with one or more $R^{11}$;

each $R^7$ is $C_1$-$C_6$-alkyl, halo, cyano, oxo, or —$OR^{A1}$;

each $R^{11}$ is independently $C_1$-$C_6$-alkyl, $C_1$-$C_6$-heteroalkyl, $C_1$-$C_6$-haloalkyl, cycloalkyl, heterocyclyl, aryl, heteroaryl, halo, cyano, oxo, or —$OR^A$;

each $R^A$ is independently hydrogen, $C_1$-$C_6$ alkyl, $C_1$-$C_6$ haloalkyl, aryl, heteroaryl, $C_1$-$C_6$ alkylene-aryl, $C_1$-$C_6$ alkylene-heteroaryl, —C(O)$R^D$, or —$S(O)_x$ $R^D$;

each of $R^B$ and $R^C$ is independently hydrogen, $C_1$-$C_6$ alkyl, $C_1$-$C_6$ heteroalkyl, cycloalkyl, heterocyclyl, or —$OR^A$; or $R^B$ and $R^C$ together with the atom to which they are attached form a 3-7-membered heterocyclyl ring optionally substituted with one or more $R^7$;

each $R^D$ and $R^E$ is independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, heteroaryl, $C_1$-$C_6$ alkylene-aryl, or $C_1$-$C_6$ alkylene-heteroaryl;

each $R^{A1}$ is hydrogen or $C_1$-$C_6$-alkyl;

m is 0, 1, or 2; and x is 0, 1, or 2.

2. The compound of claim 1, wherein A is a monocyclic or bicyclic heterocyclyl.

3. The compound of claim 1, wherein A is selected from

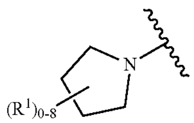,
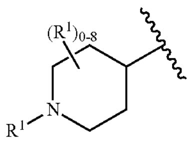,
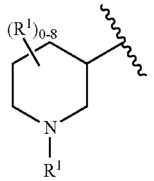,
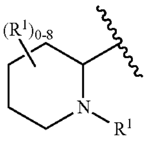,
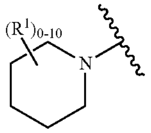,
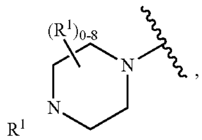,
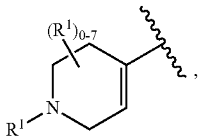,
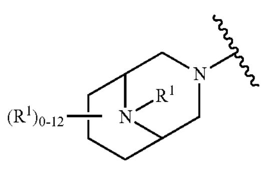,
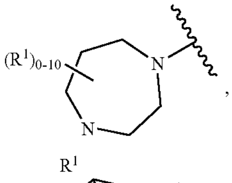,
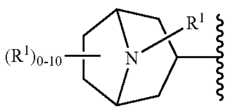,
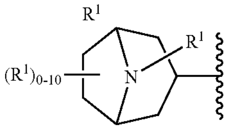,
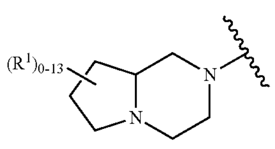, and
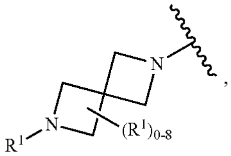, wherein $R^1$ is as defined in claim 1.

4. The compound of claim 1, wherein A is selected from

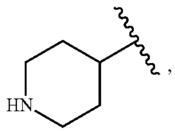, 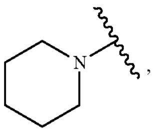, 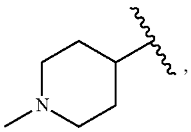, 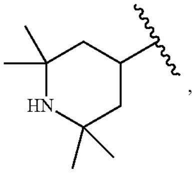, 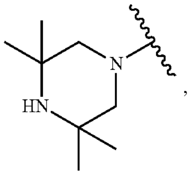, 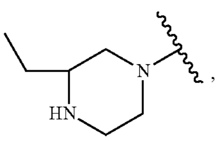, 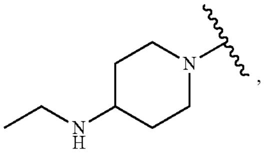, 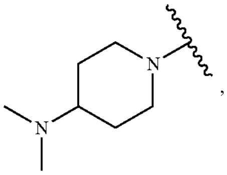, 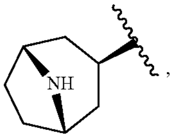, 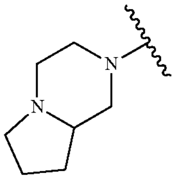, 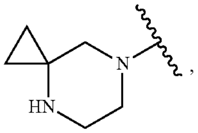, 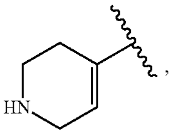, 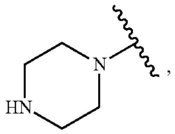, 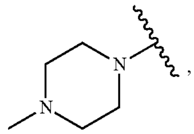, 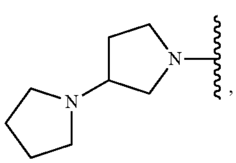, and 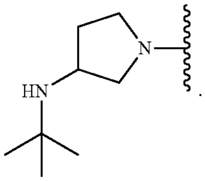.

5. The compound of claim 1, wherein B is selected from

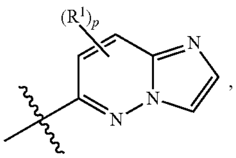, 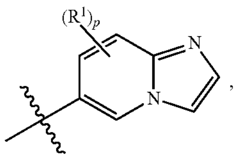, 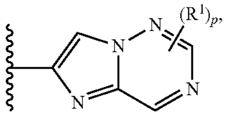 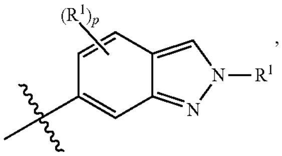,

-continued

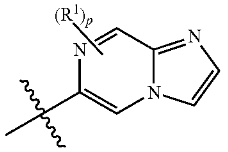, 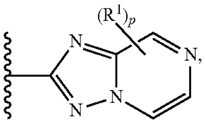 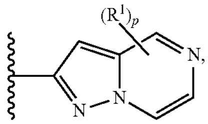 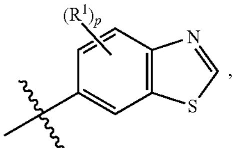, and 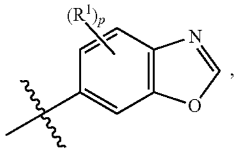, wherein $R^1$ is as defined in claim 1; and, p is 0, 1, 2, 3, or 4.

6. The compound of claim 1, wherein B is selected from

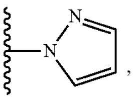, 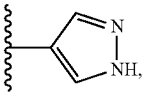 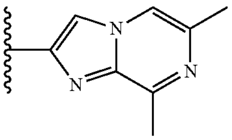, 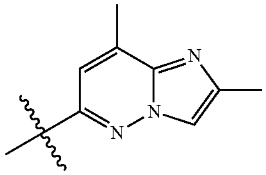, 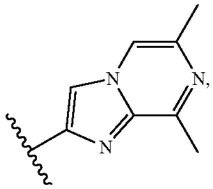 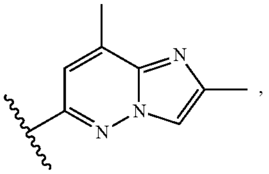, 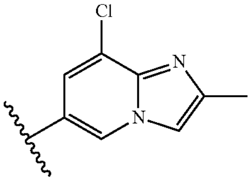, 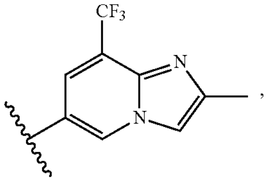, and 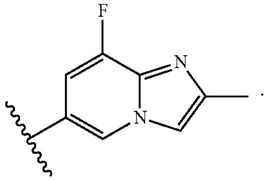.

7. The compound of claim 1, wherein one of X, Y, and Z is $C(R^{3a})$ and the others of X, Y, and Z are each independently O, N or $N(R^{3c})$.

8. The compound of claim 1, wherein at least one of X, Y, and Z is O.

9. The compound of claim 1, wherein Z and Y are each independently N or $N(R^{3c})$, and X is $C(R^{3a})$.

10. The compound of claim 1, wherein

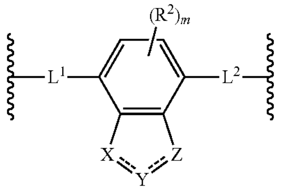

is selected from

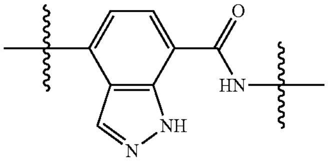
,

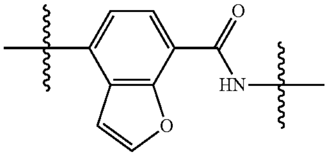
,

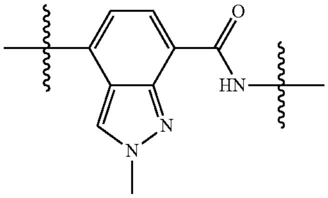
,

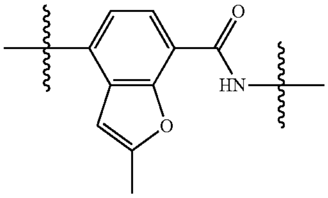
,

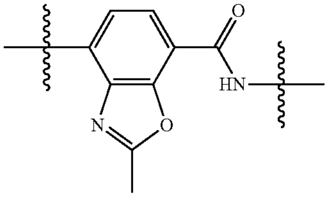
,

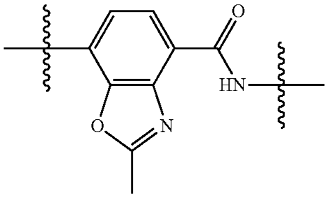
,

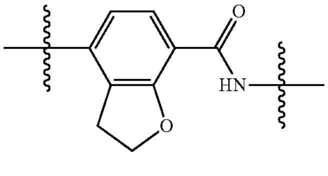
, and

-continued

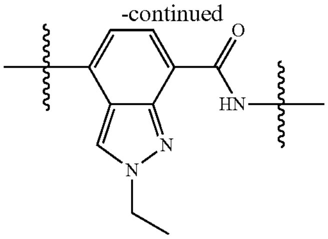
.

11. The compound of claim 1, wherein the compound of Formula (I-a) is Formula (I-b):

(I-b)

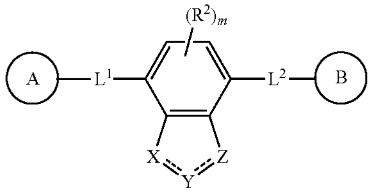

or a pharmaceutically acceptable salt, solvate, hydrate, tautomer, or stereoisomer thereof, wherein:

A is a nitrogen-containing heterocyclyl optionally substituted with one or more $R^1$;

B is a nitrogen-containing heteroaryl optionally substituted with one or more $R^1$;

X and Y are each independently $C(R^{3a})$, $C(R^{3a})(R^{3b})$, N, $N(R^{3c})$, or O, and the bonds in the ring comprising X, Y, and Z may be single or double bonds as valency permits;

Z is N, $N(R^{3c})$, or O;

$L^2$ is $C(O)N(R^4)$—;

each $R^1$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, $C_1$-$C_6$ alkylene-aryl, $C_1$-$C_6$ alkenylene-aryl, $C_1$-$C_6$ alkylene-heteroaryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_x$ $R^D$, wherein each alkyl, alkylene, alkenyl, alkynyl, heteroalkyl, haloalkyl, cycloalkyl, heterocyclyl, aryl, and heteroaryl is optionally substituted with one or more $R^6$; or two $R^1$ groups, together with the atoms to which they are attached, form a 3-7-membered cycloalkyl, heterocyclyl, aryl, or heteroaryl, wherein each cycloalkyl, heterocyclyl, aryl, and heteroaryl is optionally substituted with one or more $R^6$;

each $R^2$ is independently hydrogen, $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, halo, cyano, or —$OR^A$;

$R^{3a}$ and $R^{3b}$ are each independently hydrogen, $C_1$-$C_6$-alkyl, $C_1$-$C_6$-heteroalkyl, $C_1$-$C_6$-haloalkyl, halo, cyano, —$OR^A$, —$NR^BR^C$, —$C(O)R^D$, or —$C(O)OR^D$; or each of $R^{3a}$ and $R^{3b}$, together with the carbon atom to which they are attached, form an oxo group;

$R^{3c}$ is hydrogen or $C_1$-$C_6$-alkyl;

each $R^4$ is independently hydrogen, $C_1$-$C_6$-alkyl, or $C_1$-$C_6$-haloalkyl;

each $R^5$ is independently hydrogen, $C_1$-$C_6$-alkyl, $C_1$-$C_6$-heteroalkyl, $C_1$-$C_6$-haloalkyl, cycloalkyl, halo, cyano, oxo, —$OR^A$, —$NR^BR^C$, —$C(O)R^D$, or —$C(O)OR^D$;

each $R^6$ is independently $C_1$-$C_6$-alkyl, $C_2$-$C_6$-alkenyl, $C_2$-$C_6$-alkynyl, $C_1$-$C_6$-heteroalkyl, $C_1$-$C_6$-haloalkyl, cycloalkyl, heterocyclyl, aryl, heteroaryl, halo, cyano, oxo, —$OR^A$, —$NR^BR^C$, —$NR^BC(O)R^D$, —$NO_2$, —$C(O)NR^BR^C$, —$C(O)R^D$, —$C(O)OR^D$, —$SR^E$, or —$S(O)_xR^D$, wherein each alkyl, alkenyl, alkynyl, heteroalkyl, haloalkyl, cycloalkyl, heterocyclyl, aryl, and heteroaryl is optionally substituted with one or more $R^{11}$;

each $R^7$ is $C_1$-$C_6$-alkyl, halo, cyano, oxo, or —$OR^{A1}$;

each $R^{11}$ is independently $C_1$-$C_6$-alkyl, $C_1$-$C_6$-heteroalkyl, $C_1$-$C_6$-haloalkyl, cycloalkyl, heterocyclyl, aryl, heteroaryl, halo, cyano, oxo, or —$OR^A$;

each $R^A$ is independently hydrogen, $C_1$-$C_6$ alkyl, $C_1$-$C_6$ haloalkyl, aryl, heteroaryl, $C_1$-$C_6$ alkylene-aryl, $C_1$-$C_6$ alkylene-heteroaryl, —$C(O)R^D$, or —$S(O)_x$ $R^D$;

each of $R^B$ and $R^C$ is independently hydrogen, $C_1$-$C_6$ alkyl, $C_1$-$C_6$ heteroalkyl, cycloalkyl, heterocyclyl, or —$OR^A$; or $R^B$ and $R^C$ together with the atom to which they are attached form a 3-7-membered heterocyclyl ring optionally substituted with one or more $R^7$;

each $R^D$ and $R^E$ is independently hydrogen, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, heteroaryl, $C_1$-$C_6$ alkylene-aryl, or $C_1$-$C_6$ alkylene-heteroaryl;

each $R^{A1}$ is hydrogen or $C_1$-$C_6$-alkyl;

m is 0, 1, or 2; and x is 0, 1, or 2.

12. The compound of claim 1, wherein the compound of Formula (I) is a compound of Formula (I-c):

(I-c)

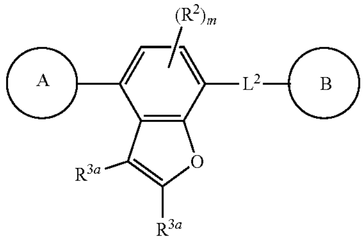

or a pharmaceutically acceptable salt, solvate, hydrate, tautomer, or stereoisomer thereof, wherein each of A, B, $L^2$, $R^2$, $R^{3a}$, m, and subvariables thereof are defined as in claim 1.

13. The compound of claim 1, wherein the compound of Formula (I-a) is a compound of Formula (I-d):

(I-d)

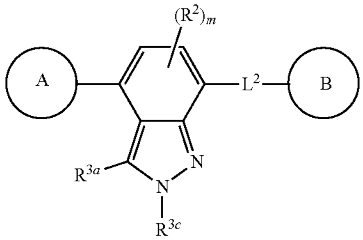

or a pharmaceutically acceptable salt, solvate, hydrate, tautomer, or stereoisomer thereof, wherein each of A, B, $L^2$, $R^2$, $R^{3a}$, $R^{3c}$, m, and subvariables thereof are defined as in claim 1.

14. The compound of claim 1, wherein the compound of Formula (I-a) is a compound of Formula (I-e):

(I-e)

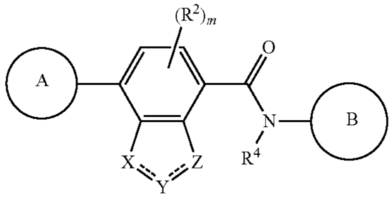

or a pharmaceutically acceptable salt, solvate, hydrate, tautomer, or stereoisomer thereof, wherein each of A, B, X, Y, Z, $L^2$, $R^2$, $R^4$, m, and subvariables thereof are defined as in claim 1.

15. The compound of claim 1, wherein the compound of Formula (I) is a compound of Formula (I-h):

(I-h)

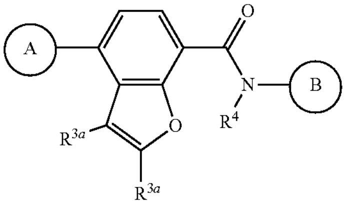

or a pharmaceutically acceptable salt, solvate, hydrate, tautomer, or stereoisomer thereof, wherein each of A, B, $L^2$, $R^{3a}$, $R^4$, m, and subvariables thereof are defined as in claim 1.

16. The compound of claim 1, wherein the compound is selected from:

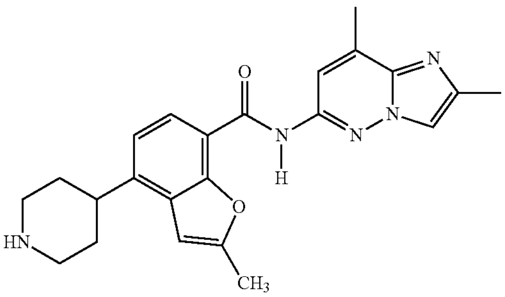

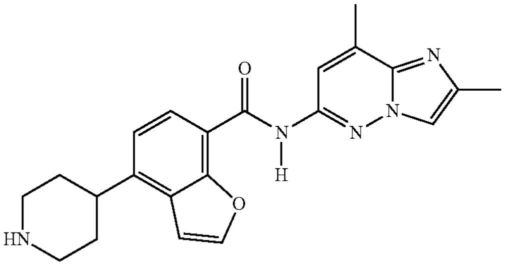

-continued
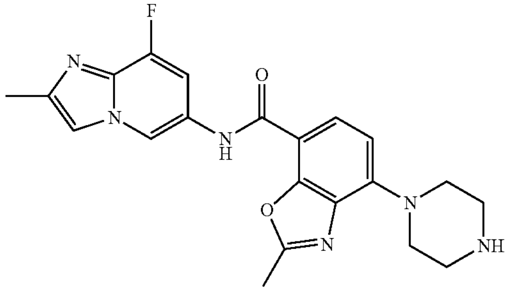
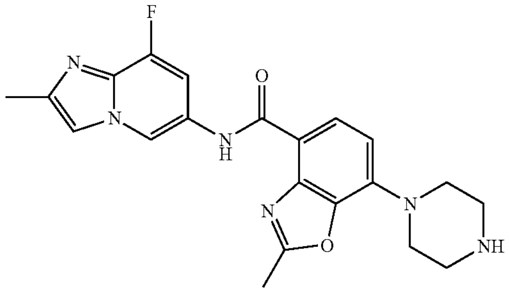
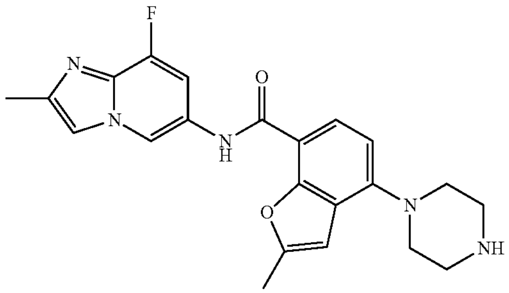
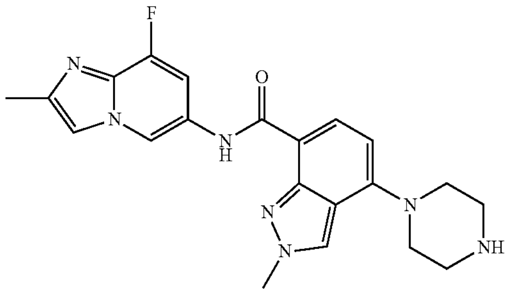
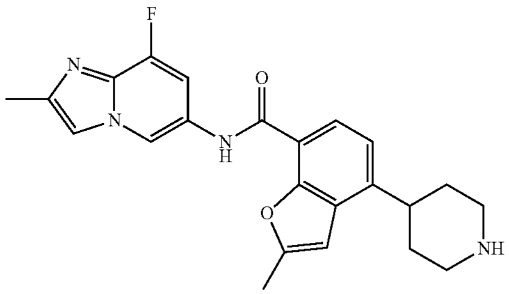
-continued
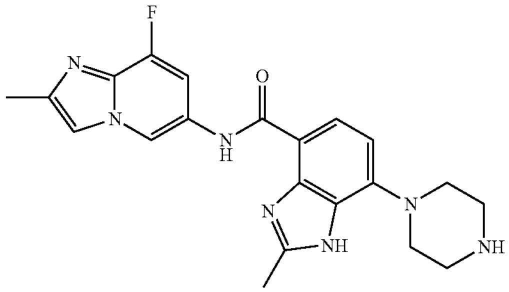
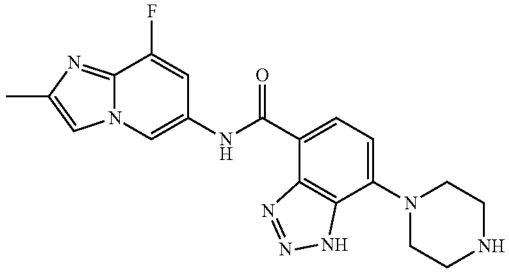
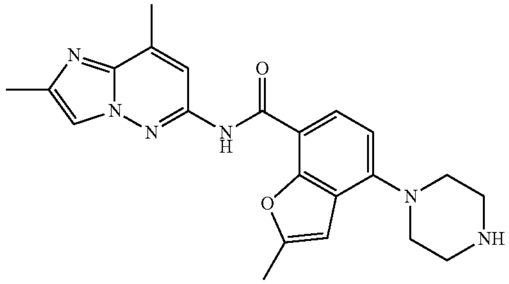
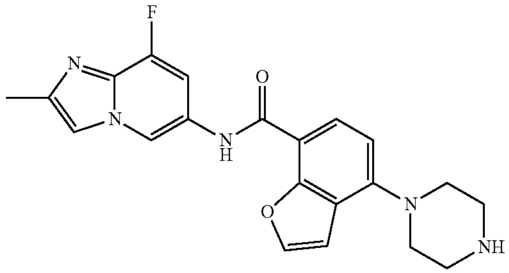
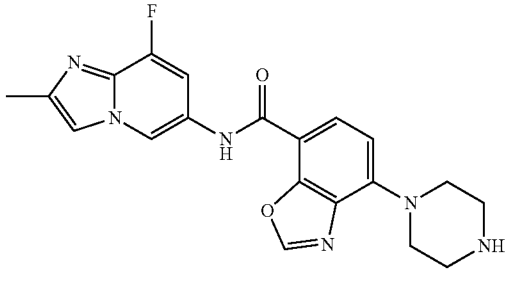
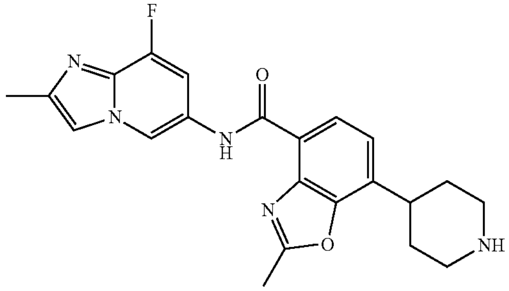

-continued
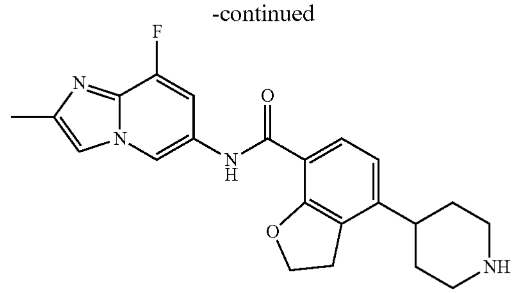
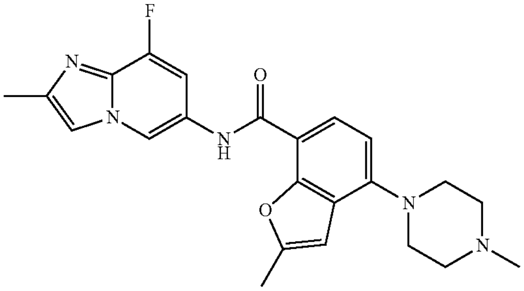
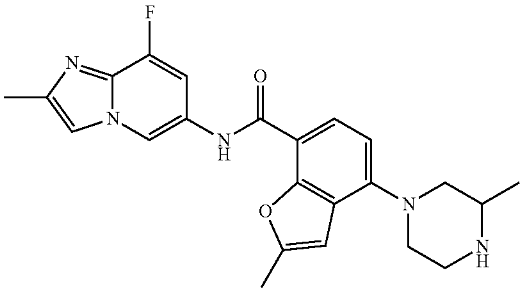
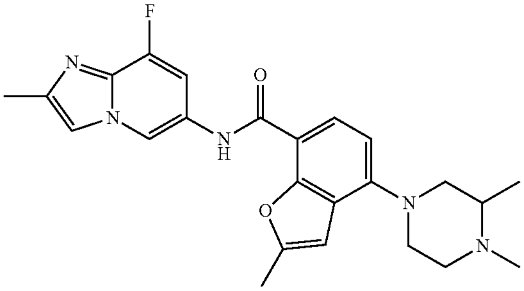
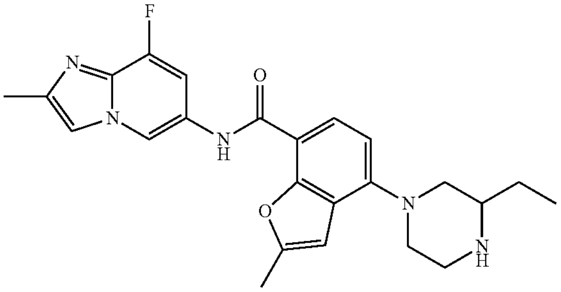
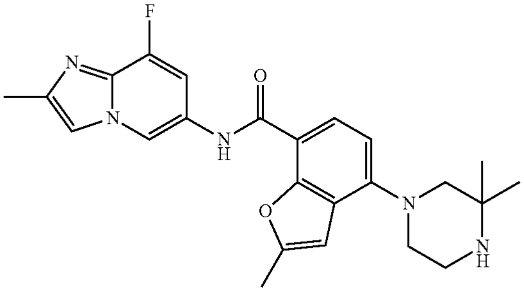
-continued
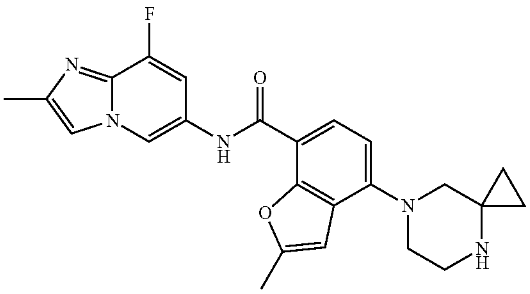
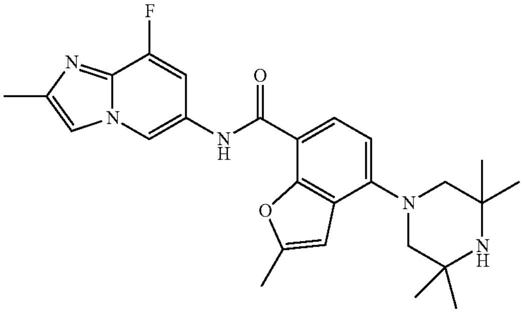
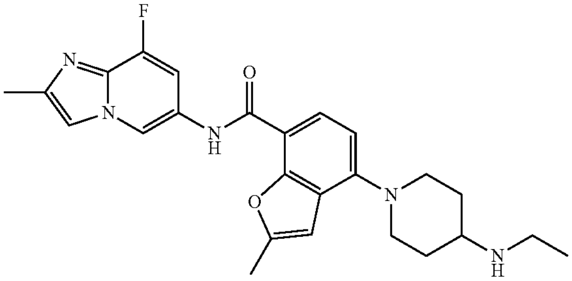
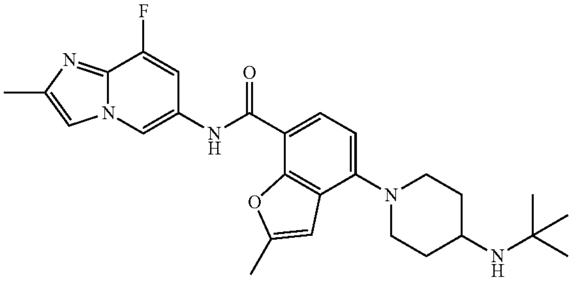
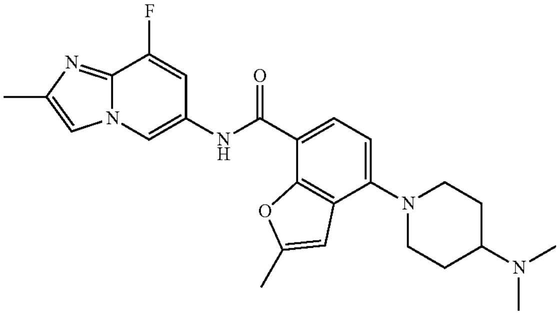

-continued
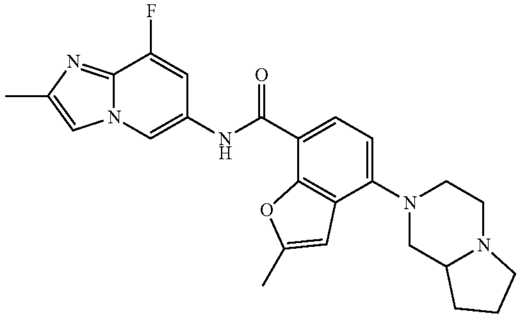
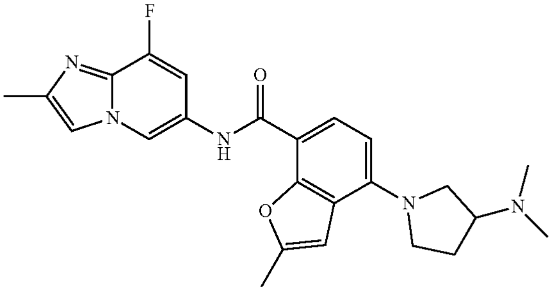
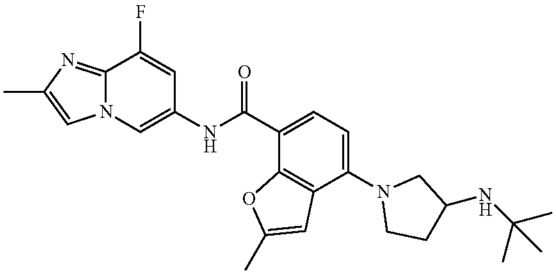
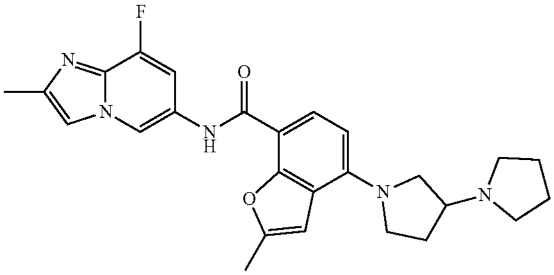
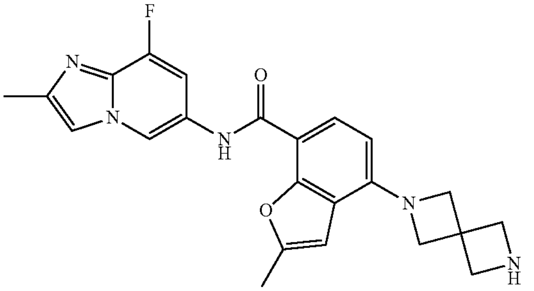
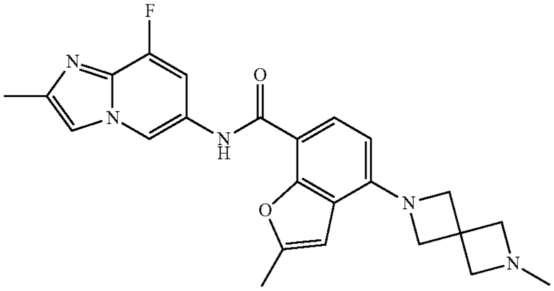
-continued
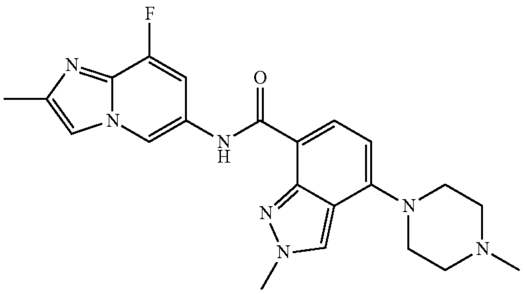
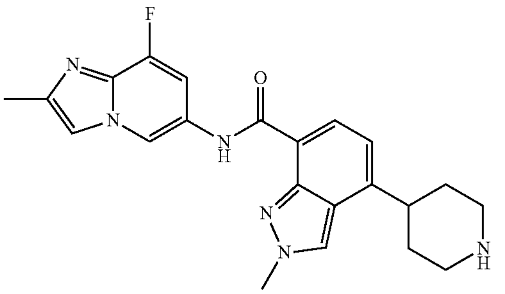
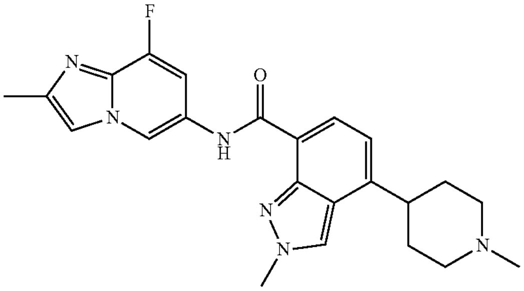
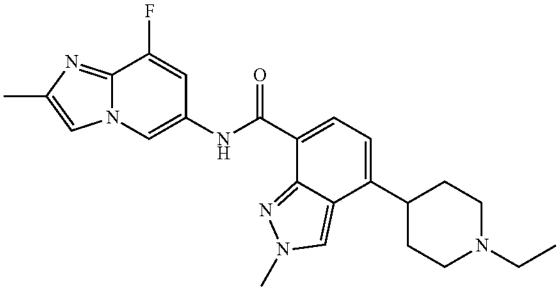
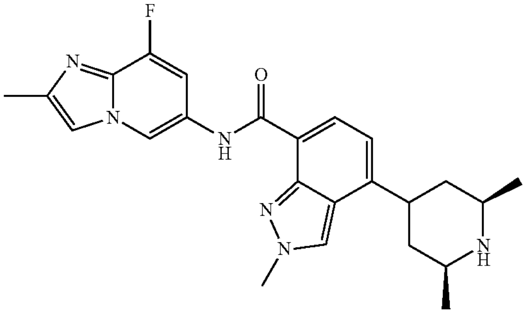

-continued
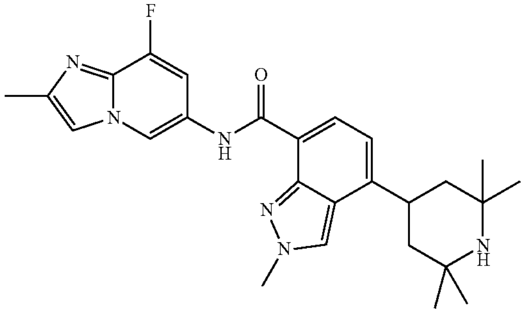
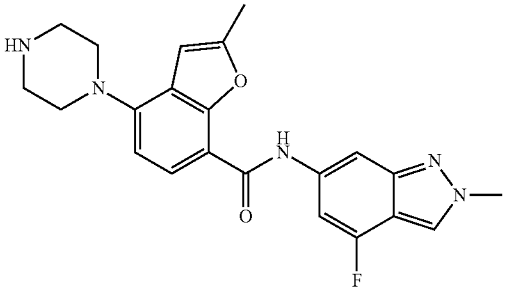
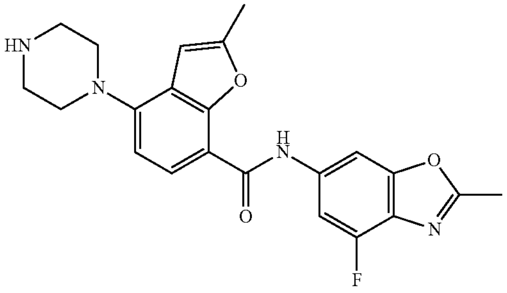
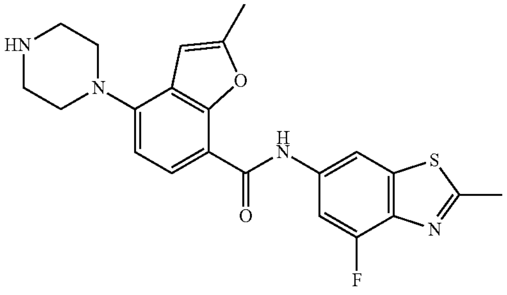
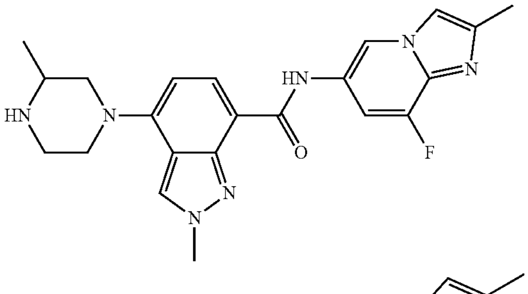
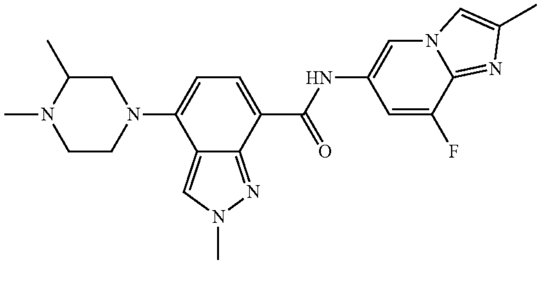
-continued
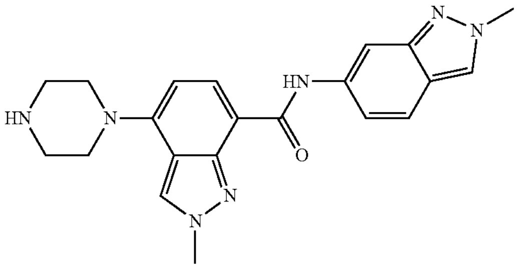
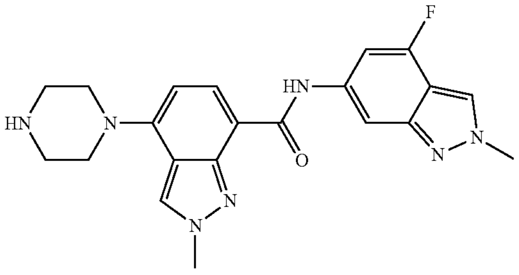
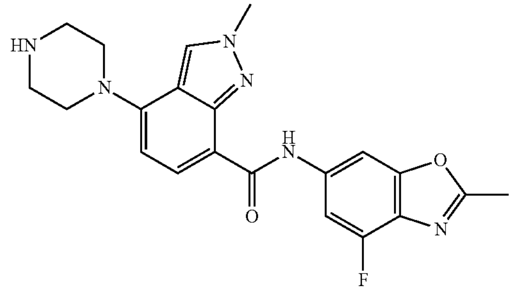
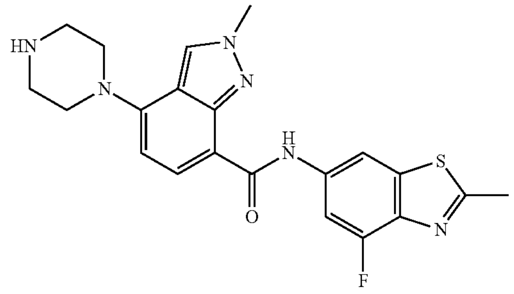
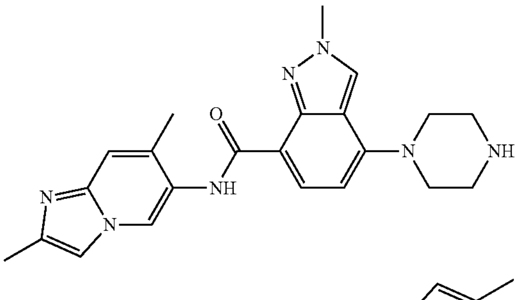
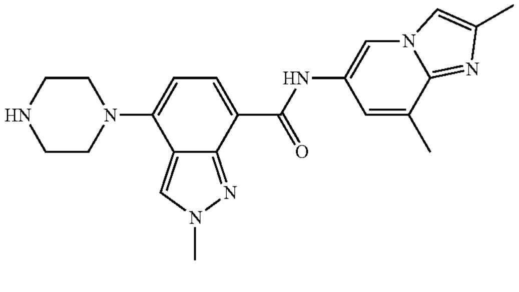

-continued
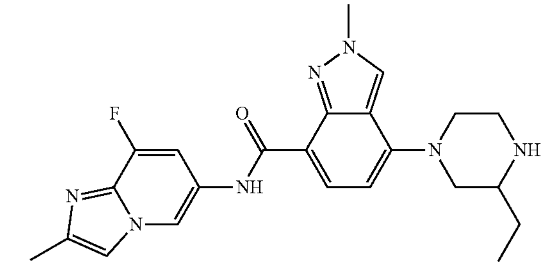
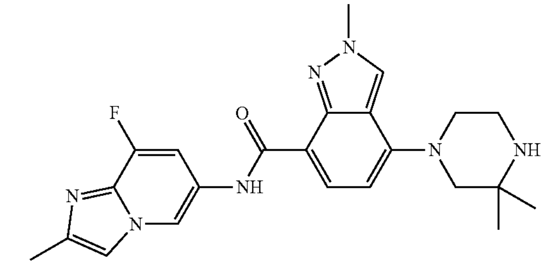
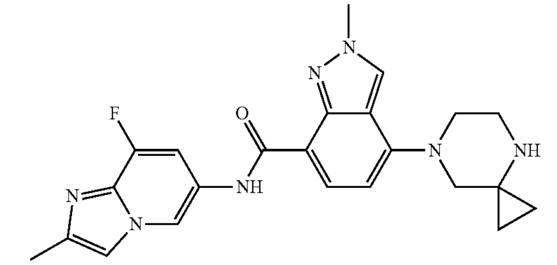
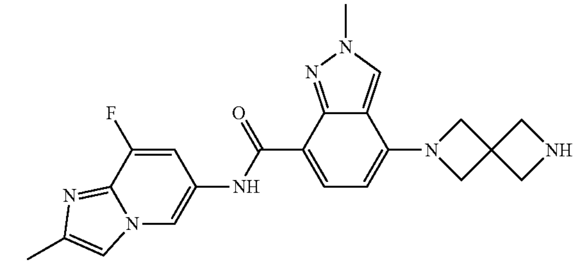
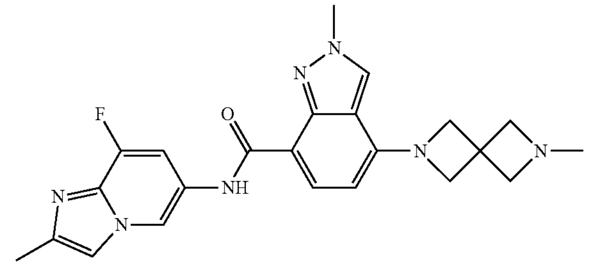
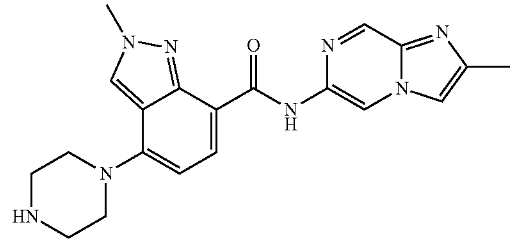
-continued
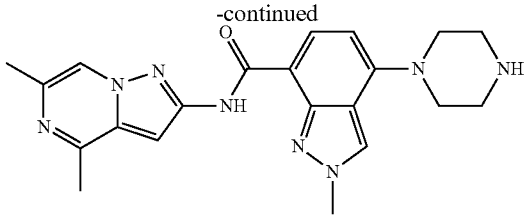
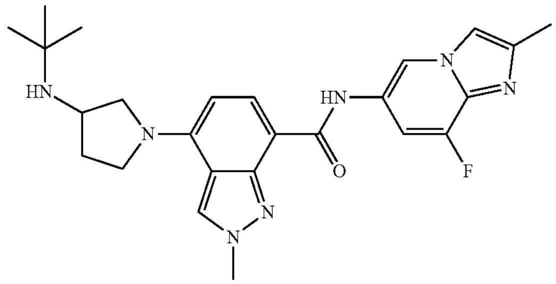
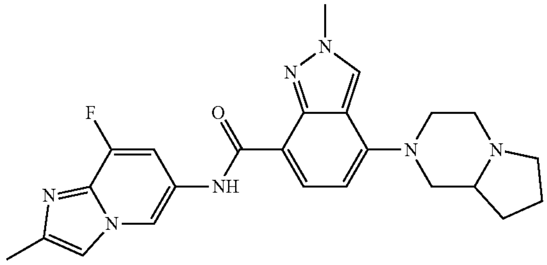
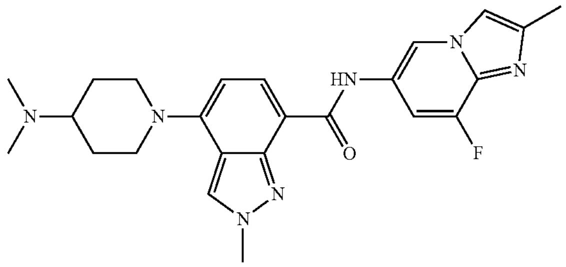
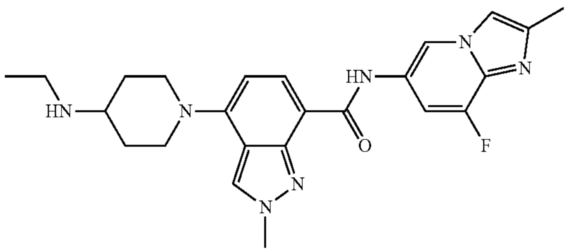
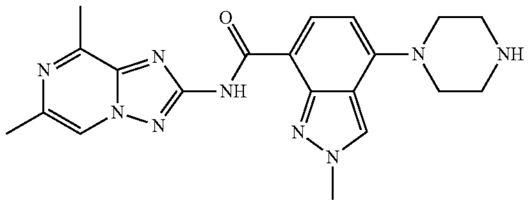

-continued
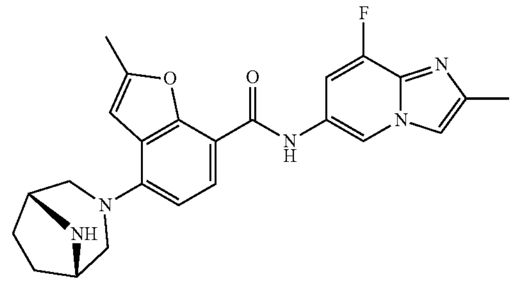
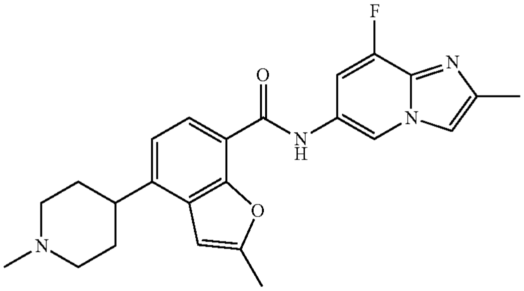
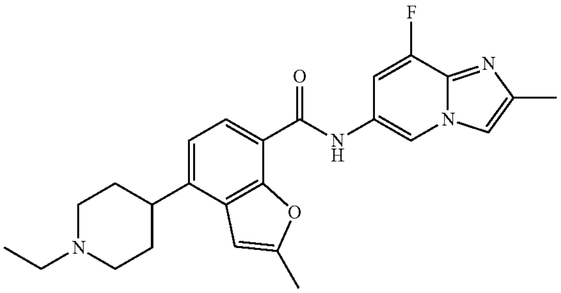
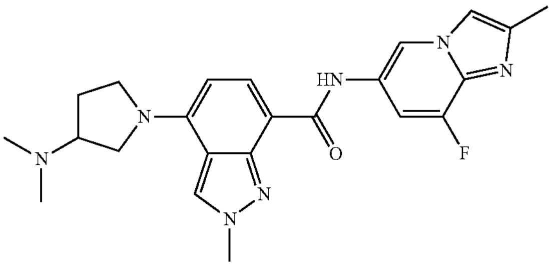
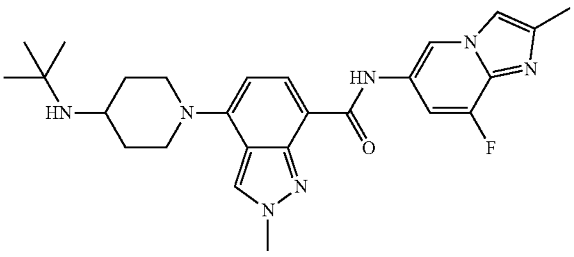
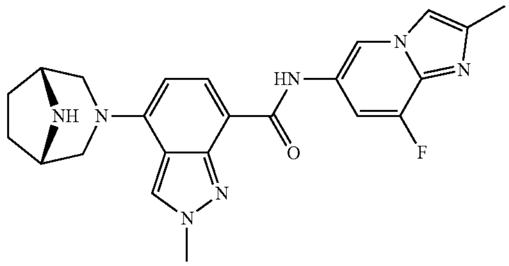
-continued
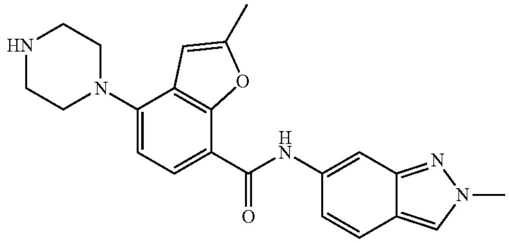
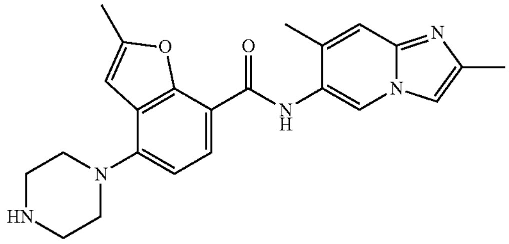
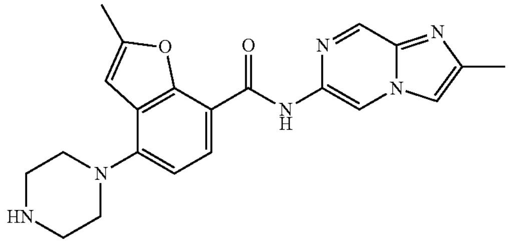
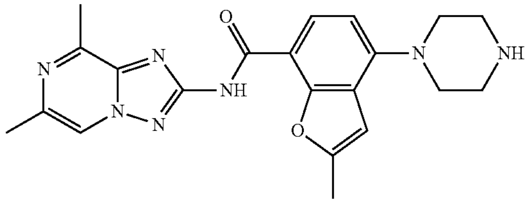
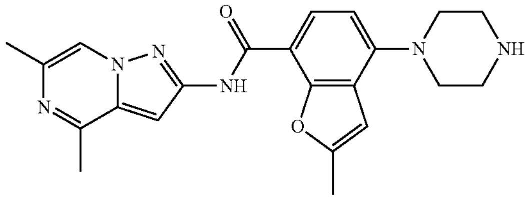
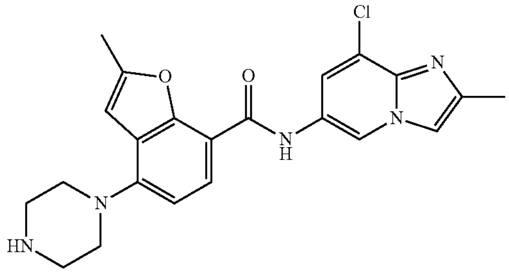
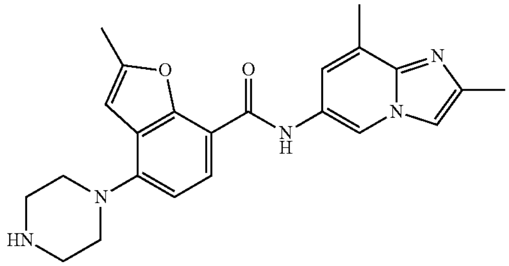

-continued
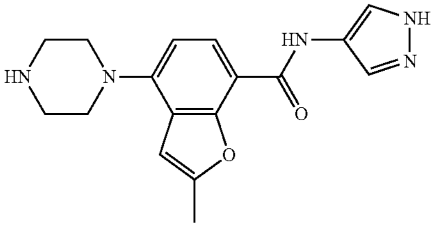
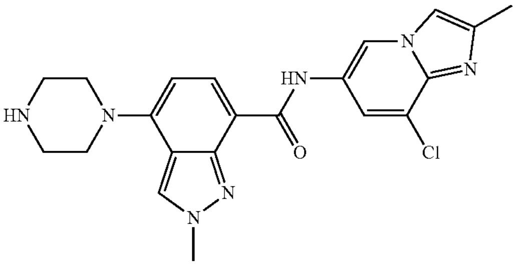
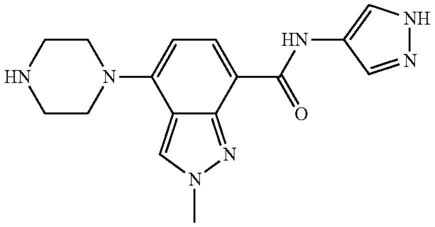
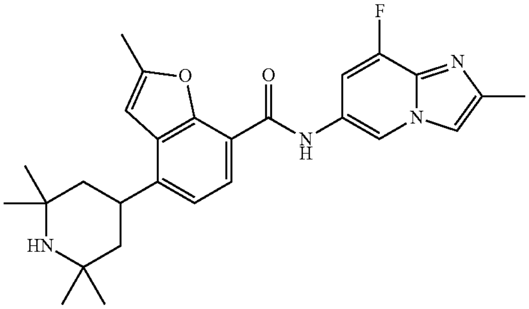
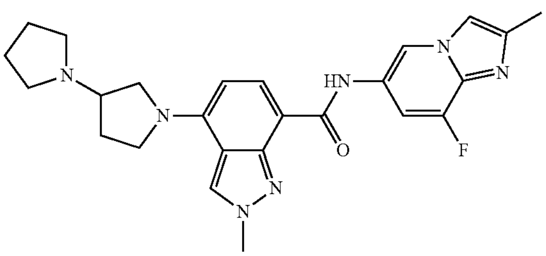
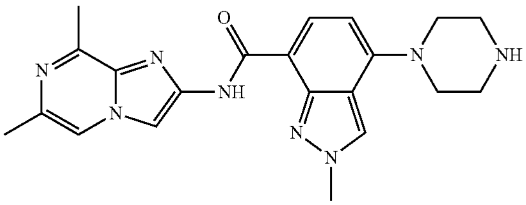
-continued
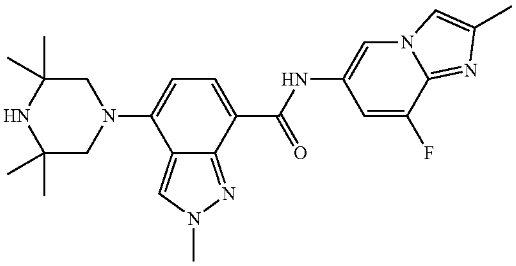
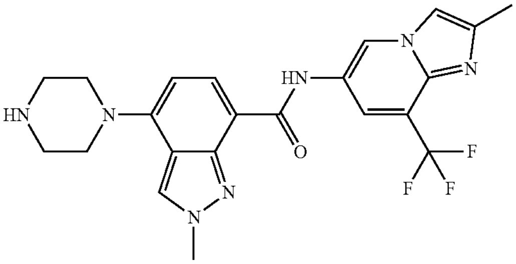
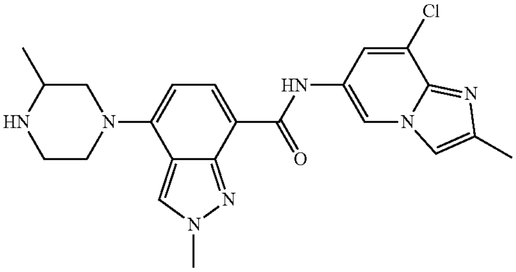
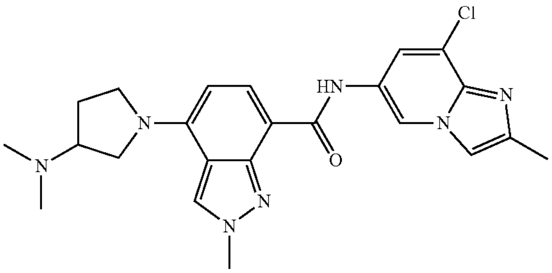
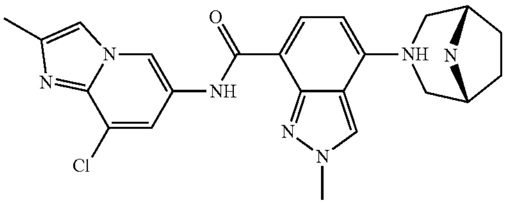
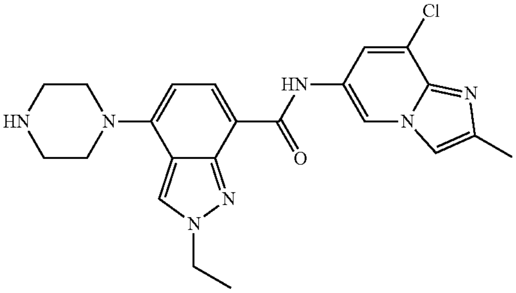

-continued

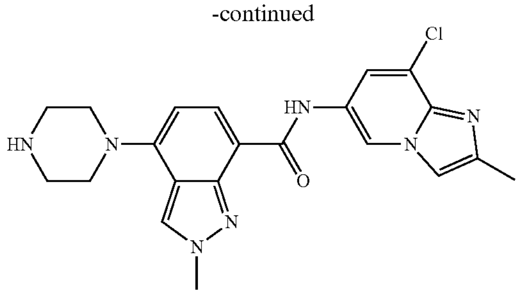

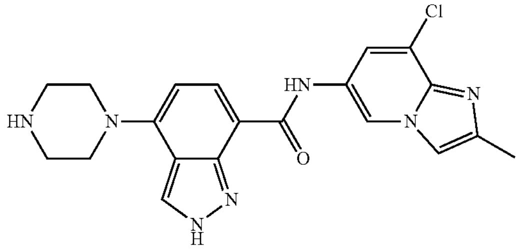

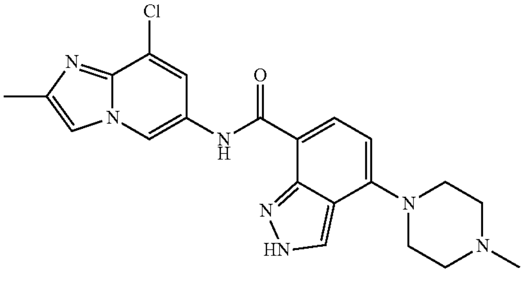

or a pharmaceutically acceptable salt, solvate, hydrate, tautomer, or stereoisomer thereof.

17. The compound of claim 1, wherein:

(a) the compound alters a target nucleic acid;

(b) the compound binds to a target nucleic acid; or (c) the compound stabilizes a target nucleic acid.

18. The compound of claim 1, wherein:

(a) the compound increases splicing at splice site on a target nucleic acid, by 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or more, as determined by qPCR; or (b) the compound decreases splicing at splice site on a target nucleic acid, by 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or more, as determined by qPCR.

19. A pharmaceutical composition comprising a compound of claim 1 and a pharmaceutically acceptable excipient.

20. A composition for use in treating a disease or disorder in a subject comprising administering to the subject a compound of Formula (I-a) according to claim 1.

21. The composition for use of claim 20, wherein the disease or disorder comprises a proliferative disease.

22. The composition for use of claim 20, wherein the disease or disorder comprises a neurological disease or disorder, autoimmune disease or disorder, immunodeficiency disease or disorder, lysosomal storage disease or disorder, cardiovascular disease or disorder, metabolic disease or disorder, respiratory disease or disorder, renal disease or disorder, or infectious disease.

* * * * *